US011661451B2

(12) United States Patent
Fukuchi et al.

(10) Patent No.: US 11,661,451 B2
(45) Date of Patent: May 30, 2023

(54) ANTI-CD147 ANTIBODY

(71) Applicant: DAIICHI SANKYO COMPANY, LIMITED, Tokyo (JP)

(72) Inventors: Keisuke Fukuchi, Tokyo (JP); Kayoko Nanai, Tokyo (JP); Masato Amano, Tokyo (JP); Kozo Yoneda, Tokyo (JP); Yusuke Totoki, Tokyo (JP); Shoji Yamamoto, Tokyo (JP)

(73) Assignee: DAIICHI SANKYO COMPANY, LIMITED, Tokyo (JP)

(*) Notice: Subject to any disclaimer, the term of this patent is extended or adjusted under 35 U.S.C. 154(b) by 436 days.

(21) Appl. No.: 16/633,565

(22) PCT Filed: Jul. 26, 2018

(86) PCT No.: PCT/JP2018/028047

§ 371 (c)(1),
(2) Date: Jan. 23, 2020

(87) PCT Pub. No.: WO2019/022187

PCT Pub. Date: Jan. 31, 2019

(65) Prior Publication Data

US 2020/0362033 A1 Nov. 19, 2020

(30) Foreign Application Priority Data

Jul. 27, 2017 (JP) ............................ JP2017-145701

(51) Int. Cl.

| | |
|---|---|
| ***C07K 16/28*** | (2006.01) |
| ***A61K 47/68*** | (2017.01) |
| ***A61P 35/00*** | (2006.01) |
| ***A61K 39/395*** | (2006.01) |
| ***A61K 45/06*** | (2006.01) |
| ***G01N 33/574*** | (2006.01) |
| *A61K 39/00* | (2006.01) |

(52) U.S. Cl.

CPC ...... *C07K 16/2803* (2013.01); *A61K 39/3955* (2013.01); *A61K 45/06* (2013.01); *A61K 47/6803* (2017.08); *A61K 47/6849* (2017.08); *A61P 35/00* (2018.01); *G01N 33/57484* (2013.01); *A61K 2039/505* (2013.01); *C07K 2317/21* (2013.01); *C07K 2317/24* (2013.01); *C07K 2317/31* (2013.01); *C07K 2317/33* (2013.01); *C07K 2317/622* (2013.01); *C07K 2317/732* (2013.01); *C07K 2317/734* (2013.01)

(58) Field of Classification Search

CPC ............ C07K 16/2803; C07K 2317/21; C07K 2317/24; C07K 2317/31; C07K 2317/33; C07K 2317/622; C07K 2317/732; C07K 2317/734; A61K 39/3955; A61K 45/06; A61K 47/6803; A61K 47/6849; A61K 2039/505; A61P 35/00; G01N 33/57484

See application file for complete search history.

(56) References Cited

U.S. PATENT DOCUMENTS

| | | | |
|---|---|---|---|
| 2011/0200627 A1 | 8/2011 | Cunningham et al. | |
| 2015/0110797 A1 | 4/2015 | Rahat et al. | |
| 2017/0037129 A1 | 2/2017 | Gros et al. | |

FOREIGN PATENT DOCUMENTS

| | | | | |
|---|---|---|---|---|
| CN | 104086654 A | 10/2014 | | |
| JP | 2012-506369 A | 3/2012 | | |
| JP | 2017-513857 A | 6/2017 | | |
| RU | 2014131097 A | 2/2016 | | |
| WO | WO-99/45031 A2 | 9/1999 | | |
| WO | WO-2009/086320 A1 | 7/2009 | | |
| WO | WO-201 0/036460 A2 | 4/2010 | | |
| WO | WO 2016/042050 | * | 3/2016 | ............ C07K 16/22 |
| WO | WO-201 6/094566 A2 | 6/2016 | | |
| WO | WO-2017/061602 A1 | 4/2017 | | |

OTHER PUBLICATIONS

Weidle et al. (Cancer Genomics & Proteomics, 7: 157-170, 2010).*
McCarthy et al. (J. Immunol. Methods, 251(1-2): 137-149, 2001).*
Lin et al. (African Journal of Biotechnology, 10(79):18294-18302, 2011).*
Bifang He et al.: "Epitope Mapping of Metuximab on CD147 Using Phage Display and Molecular Docking", Computational and Mathematical Methods in Medicine; vol. 2013; Jun. 3, 2013; pp. 1-6.
C. Koch et al: "T cell activation-associated epitopes of CD147 in regulation of the T cell response, and their definition by antibody affinity and antigen density", International Immunology; vol. 11; No. 5; May 1, 1999; pp. 777-786.
Chiampanichayakul S. et al: "CD147 contains different bioactive epitopes involving the regulation of cell adhesion and lymphocyte activation", Immunobilogy, Urban Und Fischer Verlag, DE; vol. 211, No. 3; Apr. 3, 2006; pp. 167-178.
Extended European Search Report dated Mar. 5, 2021 for corresponding European Patent Application No. 18838397.0.
X-M Ku et al.: "Epitope mapping of series of monoclonal antibodies against the hepatocellular carcinoma-associated antigen HAb18G/CD147"; Scandinavian Journal of Immunology, Blackwell Science Publ., Oxford, GB; Biosciences Information Service, Philadelphia, PA, US; vol. 65, No. 5, May 1, 2007; pp. 435-443.

(Continued)

*Primary Examiner* — Nelson B Moseley, II
(74) *Attorney, Agent, or Firm* — Foley & Lardner LLP

(57) ABSTRACT

An object of the present invention is to provide a novel anti-CD147 antibody exhibiting potent antitumor efficacy and having excellent safety. Another object of the present invention is to provide a pharmaceutical product comprising such an antibody. Another object of the present invention is to provide a method for treating tumors using the antibody or the pharmaceutical product, for example. The present invention provides a CD147-specific antibody that activates CD147 and exhibits high antitumor efficacy. The present invention provides the anti-CD147 antibody that exhibits high antitumor efficacy independent of effector functions. The present invention provides a pharmaceutical composition comprising such an anti-CD147 antibody. The present invention provides a method for treating tumors using such an anti-CD147 antibody and/or pharmaceutical composition.

60 Claims, 49 Drawing Sheets

Specification includes a Sequence Listing.

(56) References Cited

OTHER PUBLICATIONS

Office Action issued in Colombia Application No. NC2020/0001112 dated Oct. 29, 2021, (16 pages).
Qin et al., "CD147-induced cell proliferation is associated with Smad4 signal inhibition," Experimental Cell Research, vol. 358, Issue 2, Sep. 15, 2017, pp. 279-289.
Deeg et al., "Treatment of steroid-refractory acute graft-versus-host disease with anti-CD147 monoclonal antibody ABX-CBL," Blood, vol. 98, Issue 7, Oct. 1, 2001, pp. 2052-2058.
Chen et al., "Targeting radioimmunotherapy of hepatocellular carcinoma with iodine ($^{131}$I) metuximab injection: Clinical Phase I/II trials," International Journal of Radiation Oncology*Biology*Physics, vol. 65, Issue 2, Jun. 1, 2006, pp. 435-444.
Xu et al., "A randomized controlled trial of licartin for preventing hepatoma recurrence after liver transplantation," Hepatology, vol. 45, Issue 2, Feb. 2007, pp. 269-276.
Koch et al., "T cell activation-associated epitopes of CD147 in regulation of the T cell response, and their definition by antibody affinity and antigen density," International Immunology, vol. 11, Issue 5, May 1999, pp. 777-786.
International Searching Authority, "International Search Report," issued in connection with International Patent Application No. PCT/JP2018/028047, dated Oct. 9, 2018.
International Searching Authority, "Written Opinion," issued in connection with International Patent Application No. PCT/JP2018/028047, dated Oct. 9, 2018.
Office Action and Search Report issued in corresponding Russian Patent Application No. 2020108219 dated Apr. 6, 2022.
Office Action issued in corresponding Chinese Patent Application No. 201880049502X, dated Mar. 1, 2023.

* cited by examiner

[Figure 2-1]
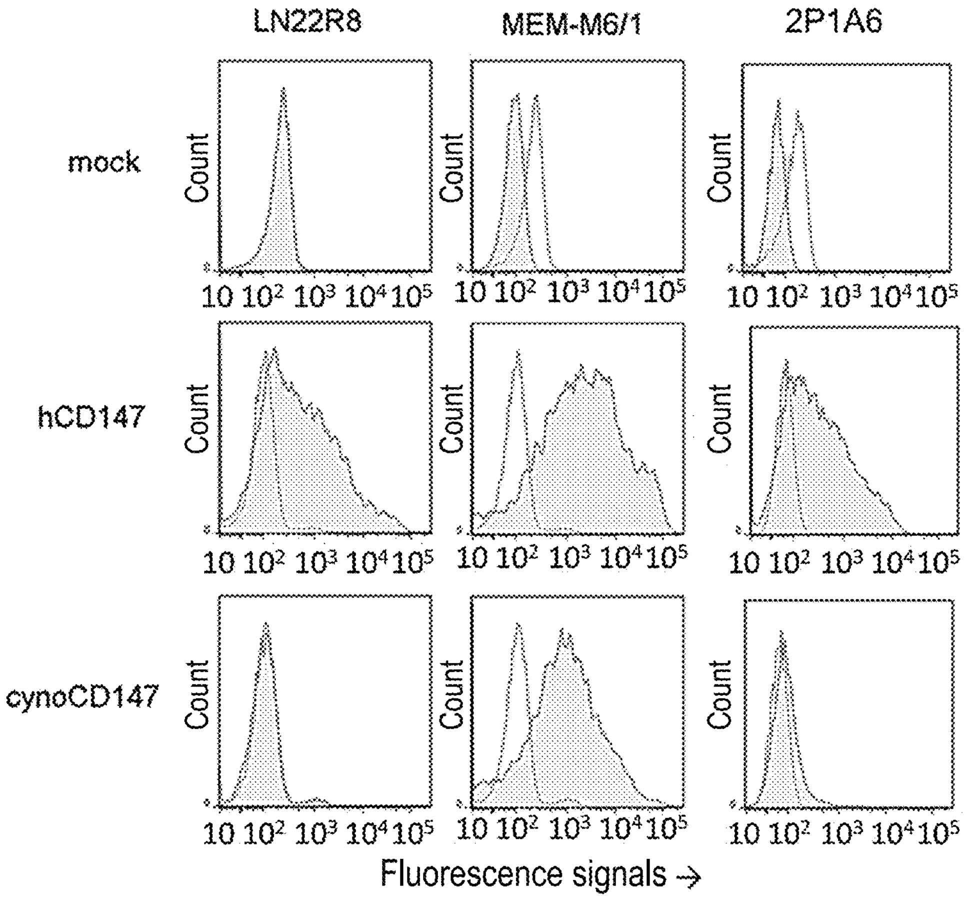

[Figure 2-2]
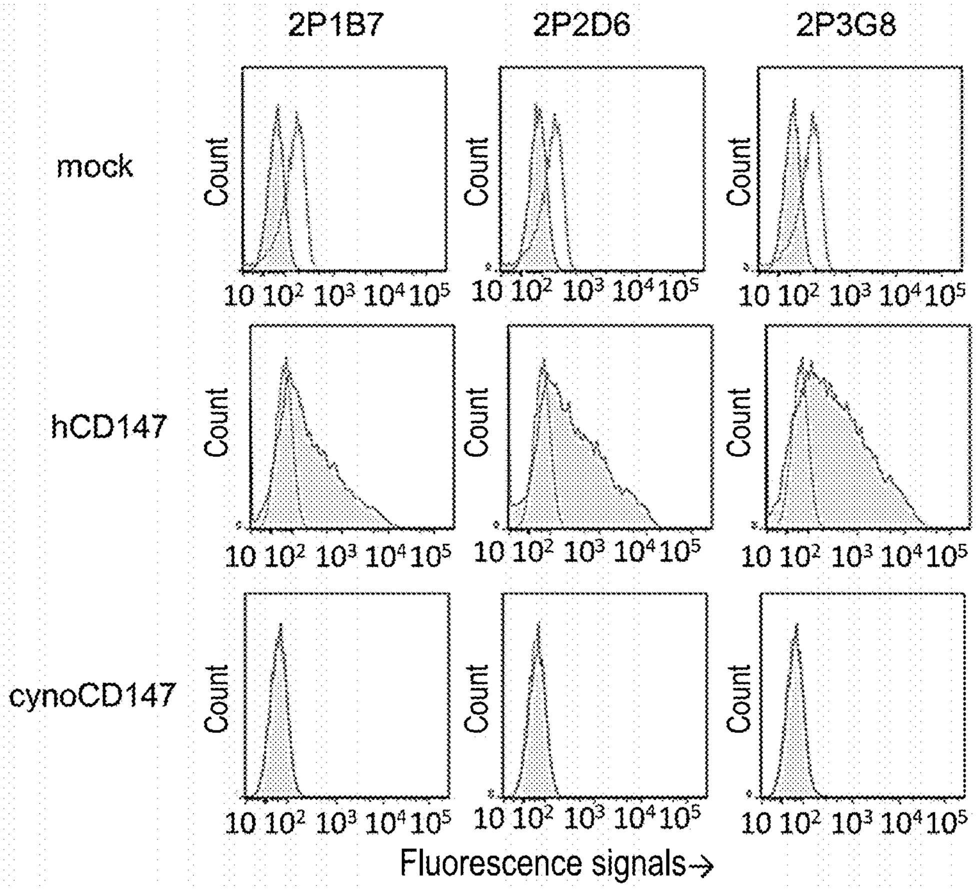

[Figure 2-3]
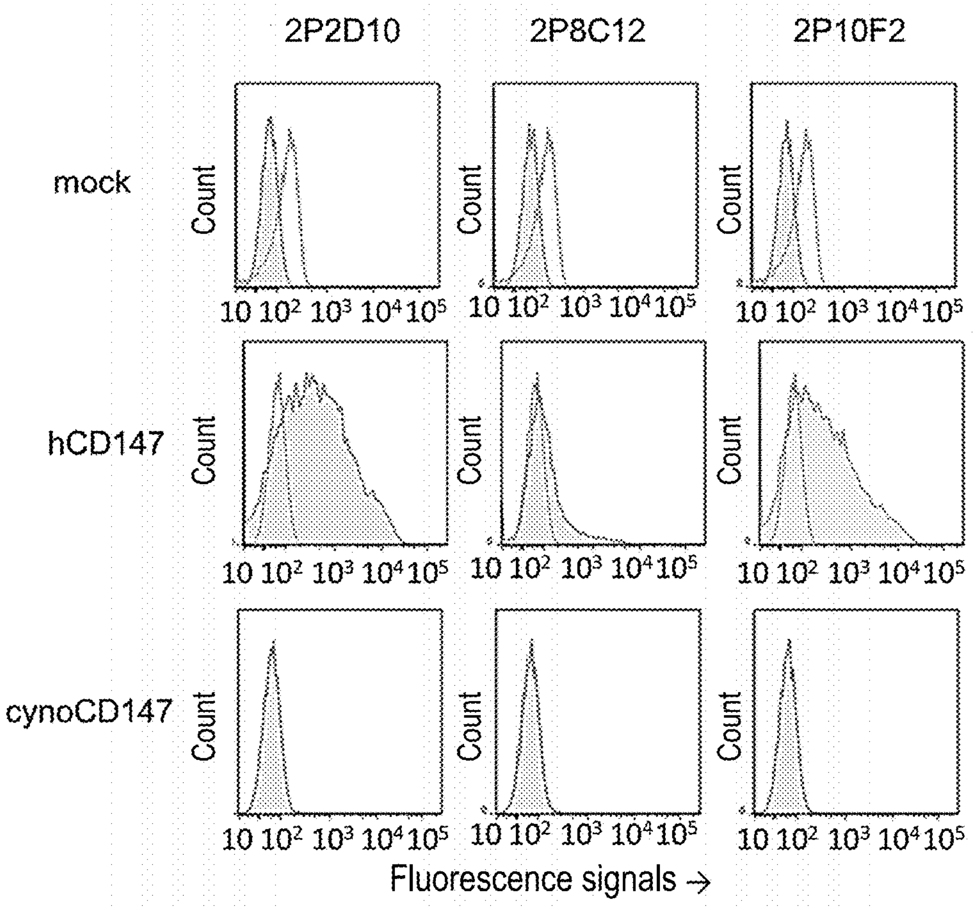

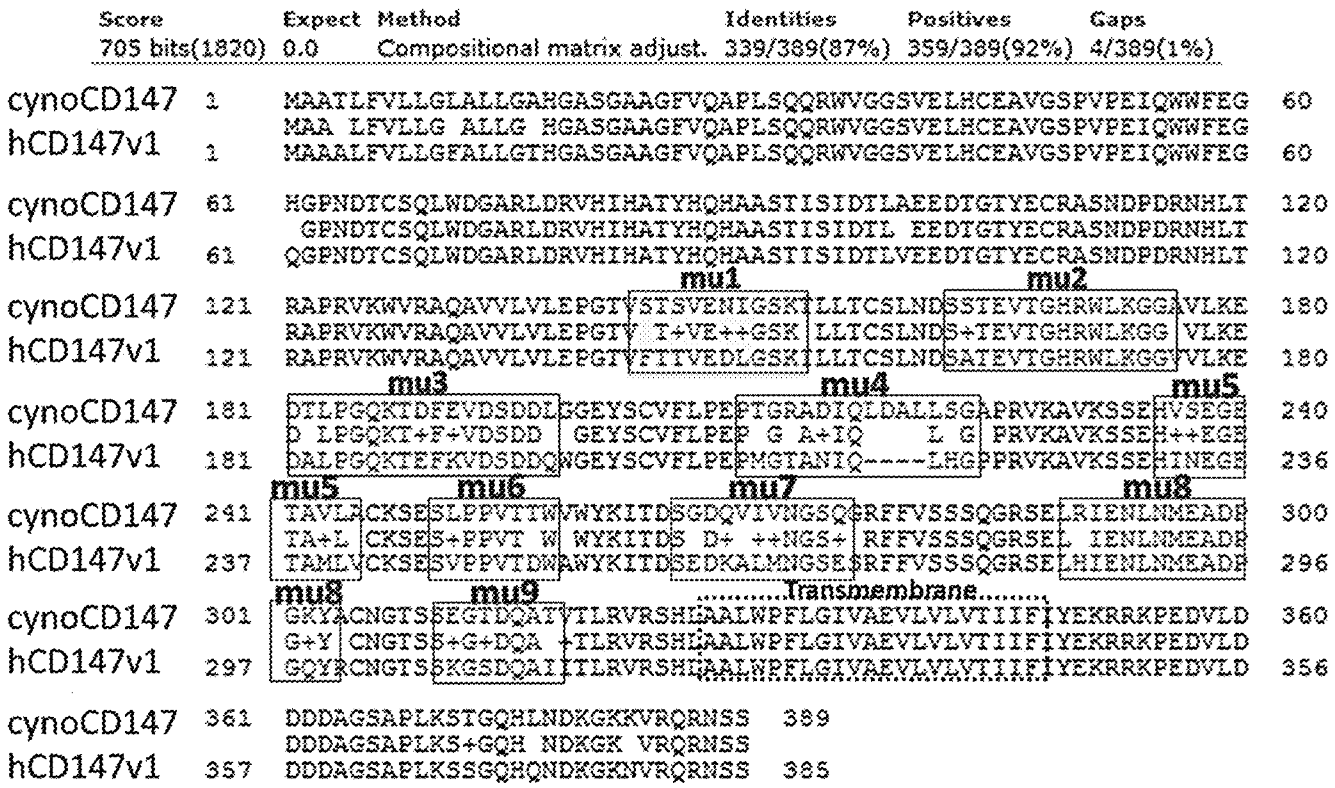

Figure 3

```
Score      Expect  Method                                 Identities      Positives       Gaps
705 bits(1820)  0.0  Compositional matrix adjust.  339/389(87%)  359/389(92%)  4/389(1%)

cynoCD147    1    MAATLFVLLGLALLGARGASGAAGFVQAPLSQQRWVGGSVELHCEAVGSPVFEIQWWFEG    60
hCD147v1     1    MAA LFVLLG ALLG RGASGAAGFVQAPLSQQRWVGGSVELHCEAVGSPVFEIQWWFEG    60
                  MAAALFVLLGFALLGTHGASGAAGFVQAPLSQQRWVGGSVELHCEAVGSPVFEIQWWFEG

cynoCD147   61    HGPNDTCSQLWDGARLDRVHIHATYHQAASTISIDTLAEEDTGIYECRASNDPDRNHLI    120
hCD147v1    61     GPNDTCSQLWDGARLDRVHIHATYHQAASTISIDIL EEDTGIYECRASNDPDRNHLI    120
                  QGPNDTCSQLWDGARLDRVHIHATYHQAASTISIDILVEEDTGIYECRASNDPDRNHLI
                                                              mu1
cynoCD147  121    RAPRVKWVRAQAVVLVLEPGTYSTSVENIGSKLLITCSLNDSTEVTGHRWLKGGAVLKE    180
hCD147v1   121    RAPRVKWVRAQAVVLVLEPGTY  T+VE++GSK LLITCSLNDS+TEVTGHRWLKGG VLKE    180
                  RAPRVKWVRAQAVVLVLEPGTFTTVEDLGSKLLITCSLNDSATEVTGHRWLKGGVLKE
                                              mu2
cynoCD147  181    DTLPGQKTDFEVDSDDLEGEYSCVFLPEFTGRADIQLDALLSGAPRVKAVKSSEHVSEGE    240
hCD147v1   181    D LPGQK+ +F+VDSDD  GEYSCVFLPEF  G  A+IQ       L G PRVKAVKSSE++EGH    236
                  DALPGQKIEFKVDSDDQWGEYSCVFLPEMGTANIQ-----LHGPRVKAVKSSEHINEGE
                         mu3                        mu4                    mu5
cynoCD147  241    TAVLCKSESLPVTTMTWYKITDSGDQVIVNGSQRFFVSSSQGRSELRIENLNMEADP    300
hCD147v1   237    TA+L CKSE+ PVT W  WYKITDS D+  ++NGS+ RFFVSSSQGRSEL IENLNMEADP    296
                  TAMLNCKSESVPPVTDWANWYKITDSEDKALMNGSESRFFVSSSQGRSELHIENLNMEADP
                         mu6                mu7           Transmembrane......,
cynoCD147  301    GKYRCNGTSEGIDQATTLRVRSHIAALWPFLGIVAEVLVLVTIIFIYEKRRKPEDVLD    360
hCD147v1   297    G+Y CNGTS+G+DQA +TLRVRSHIAALWPFLGIVAEVLVLVTIIFIYEKRRKPEDVLD    356
                  GQYRCNGTSRKGSDQAIFTLRVRSHIAALWPFLGIVAEVLVLVTIIFIYEKRRKPEDVLD
                         mu8
cynoCD147  361    DDDAGSAPLKSTGQHLNDKGKRVRQRNSS    389
hCD147v1   357    DDDAGSAPLKS+GQH  NDKGK VRQRNSS    385
                  DDDAGSAPLKSSGQHQNDKGKNVRQRNSS
```

[Figure 4-1]

SEQ ID NO: 7: Nucleotide sequence of LN22R8 light chain variable region
GACATCCAGATGACCCAGTCTCCATCCTCCTTATCTGCCTCTCTGGGAGAAAGAGTCAGTCTCACTTGTCGGGCAAGTCTGGAAATT
AGTGGTTTCTTAAGTTGGCTTCAGCAGAAACCAGATGGAACTATTAAACGCCTGATCTACGCCGCATCCATTTTAGATTCTGGTGTC
CCAAAAAGGTTCAGTGGCAGTAGGTCTGGGTCAGATTATTCTCTCACCATCAGCAGCCTTGAGTCTGAAGATTTTGCAGACTATTAC
TGTCTACAATATGCTAGTTATCCGTGGACGTTCGGTGGAGGCACCAAGCTGGAAATCAAACGG SEQ ID NO: 8: Amino acid sequence of LN22R8 light chain variable region (each CDR is underlined)
DIQMTQSPSSLSASLGERVSLTCRASLEISGFLSWLQQKPDGTIKRLIYAASILDSGVPKRFSGSRSGSDYSLTISSLESEDFADYY
CLQYASYPWTFGGGTKLEIKR SEQ ID NO: 11: Amino acid sequence of CDRL1 of LN22R8
RASLEISGFLS SEQ ID NO: 12: Amino acid sequence of CDRL2 of LN22R8
AASILDS SEQ ID NO: 13: Amino acid sequence of CDRL3 of LN22R8
LQYASYPWT

[Figure 4-2]

SEQ ID NO: 9: Nucleotide sequence of LN22R8 heavy chain variable region
CAGATCCAGTTGGTGCAGTCTGGACCTGAGCTGAAGAAGCCTGGAGAGACAGTCAAGATCTCCTGCAAGGCTTCTGGGTATACCTTC
ACAAACTATGGAATGAACTGGGTGAAGCAGGCTCCAGGAAAGGGTTTAAAGTGGATGGGCTGGATAAACACCTACACTGGAGAGCCA
ACATATGCTGATGACTTCAAGGGACGGTTTGCCTTCTCTTTGGAAACCTCTGCCAGCACTGCCTATTTGCAGATCAACAACCTCAAA
AATGAGGACACGGCTACATATTTCTGTGCAAGAGGGGGGTATGGTAACTACGGGGCGGGGGCTATGGACTACTGGGGTCAAGGTACC
TCAGTCACCGTCTCCTCA SEQ ID NO: 10: Amino acid sequence of LN22R8 heavy chain variable region (each CDR is underlined)
QIQLVQSGPELKKPGETVKISCKASGYTFTNYGMNWVKQAPGKGLKWMGWINTYTGEPTYADDFKGRFAFSLETSASTAYLQINNLK
NEDTATYFCARGGYGNYGAGAMDYWGQGTSVTVSS SEQ ID NO: 14: Amino acid sequence of CDRH1 of LN22R8
GYTFTNYGMN SEQ ID NO: 15: Amino acid sequence of CDRH2 of LN22R8
WINTYTGEPT SEQ ID NO: 16: Amino acid sequence of CDRH3 of LN22R8
GGYGNYGAGAMDY

[Figure 5-1]

SEQ ID NO: 17: Nucleotide sequence of 2P10F2 light chain variable region
GACATCCAGATGACACAGTCTCCAGCTTCCCTGTCTGCATCTCTGGGAGAAACTGTCTCCATCGAATGTCTTGCAAGTGAGGGCATT
TCCAATAGTTTAGCGTGGTATCAGCAGAAGCCAGGGAAATCTCCTCAGCTCCTGATCTATGGTGCAAGTAGCTTGCAAGACGGGGTC
CCATCACGGTTCAGTGGCAGTGGATCTGGCACACAGTATTCTCTCAAGATCAGCGGCATGCAACCTGAAGATGAAGGGGTTTATTAC
TGTCAACAGGGTTACAAGTATCCATTCACGTTCGGCTCAGGGACGAAGTTGGAAATAAAACGG SEQ ID NO: 18: Amino acid sequence of 2P10F2 light chain variable region (each CDR is underlined)
DIQMTQSPASLSASLGETVSIECLASEGISNSLAWYQQKPGKSPQLLIYGASSLQDGVPSRFSGSGSGTQYSLKISGMQPEDEGVYY
CQQGYKYPFTFGSGTKLEIKR SEQ ID NO: 21: Amino acid sequence of CDRL1 of 2P10F2
LASEGISNSLA SEQ ID NO: 22: Amino acid sequence of CDRL2 of 2P10F2
GASSLQD SEQ ID NO: 23: Amino acid sequence of CDRL3 of 2P10F2
QQGYKYPFT

[Figure 5-2]

SEQ ID NO: 19: Nucleotide sequence of 2P10F2 heavy chain variable region
GAGGTGCAGCTTCAGGAGTCAGGACCTGGCCTTGTGAAACCCTCACAGTCACTCTCCCTCACCTGTTCTGTCACTGGTTACTCCATC
ACTAGTAATTACTGGGGCTGGATCCGGAAGTTCCCAGGAAATAAAATGGAGTGGATGGGATGCATAACCTACAGTGGTGGCACTAGC
TACAACCCATCTCTCAAAAGTCGAATCTCCATTACTAGAGACACATCAAAGAATCAGTTCTTCCTGCAGTTGAACTCTGTAACTACT
GAGGACACAGCCACATATTACTGTGCAAGTTCCTATACCAGTGGTGACGTCGATTACTGGGGCCAAGGAGTCATGGTCACAGTCTCC
TCA SEQ ID NO: 20: Amino acid sequence of 2P10F2 heavy chain variable region (each CDR is underlined)
EVQLQESGPGLVKPSQSLSLTCSVTGYSITSNYWGWIRKFPGNKMEWMGCITYSGGTSYNPSLKSRISITRDTSKNQFFLQLNSVTT
EDTATYYCASSYTSGDVDYWGQGVMVTVSS SEQ ID NO: 24: Amino acid sequence of CDRH1 of 2P10F2
GYSITSNYWG SEQ ID NO: 25: Amino acid sequence of CDRH2 of 2P10F2
CITYSGGTS SEQ ID NO: 26: Amino acid sequence of CDRH3 of 2P10F2
SYTSGDVDY

[Figure 6]
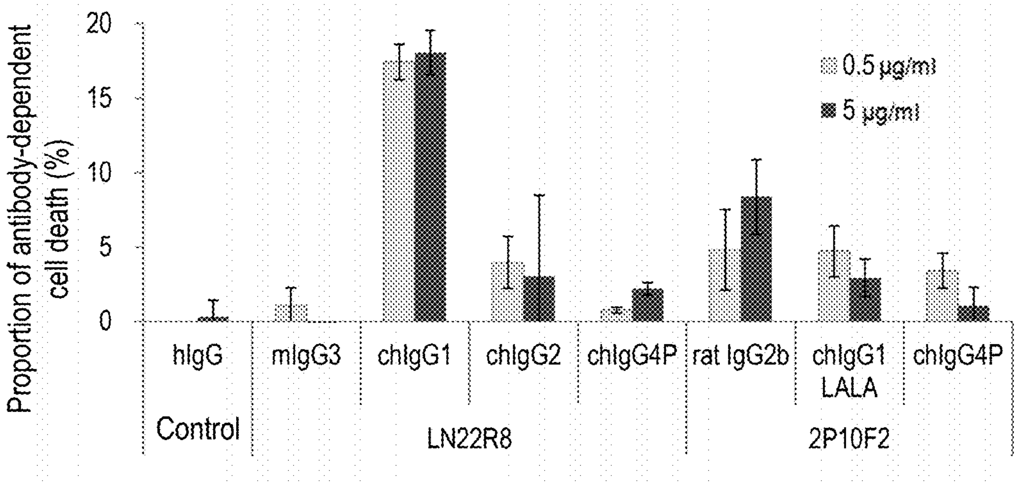
[Figure 7]
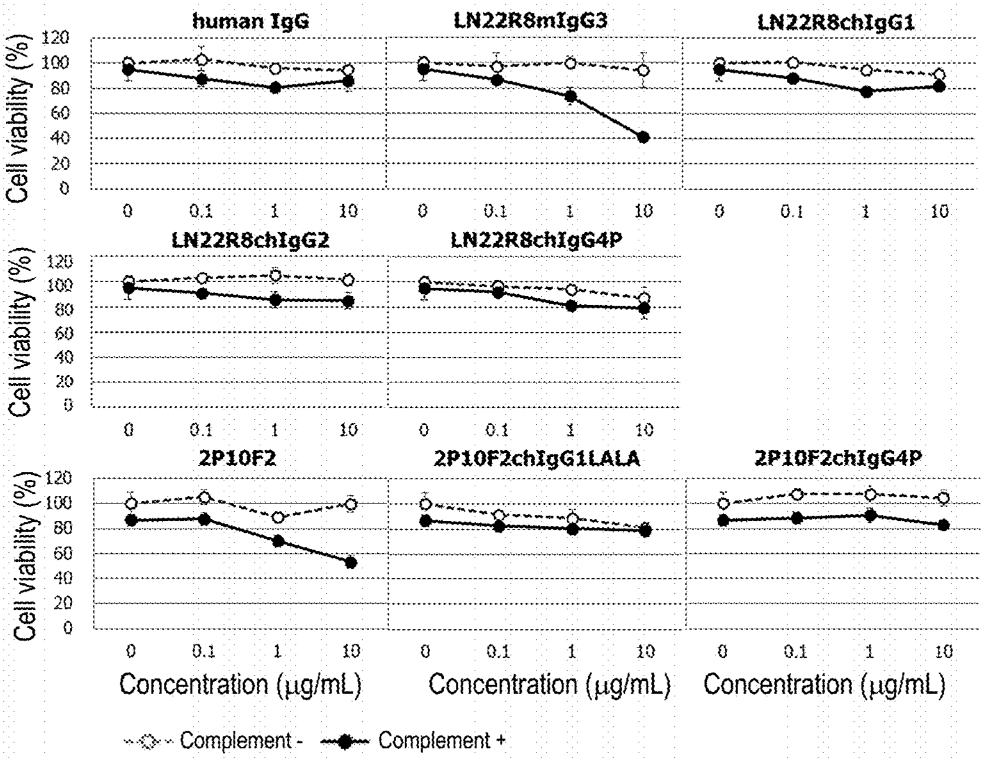

[Figure 10]
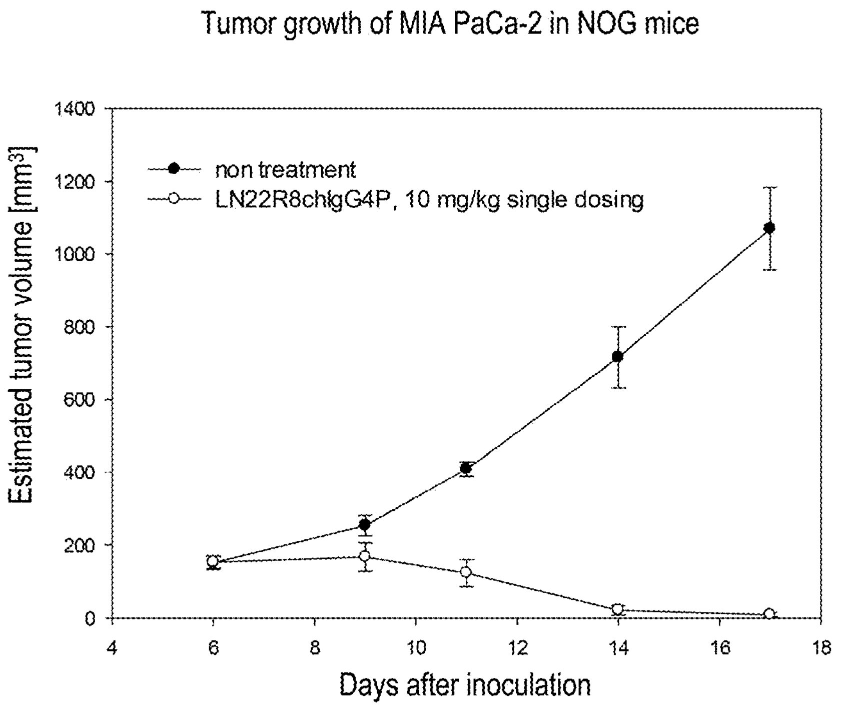

[Figure 12]
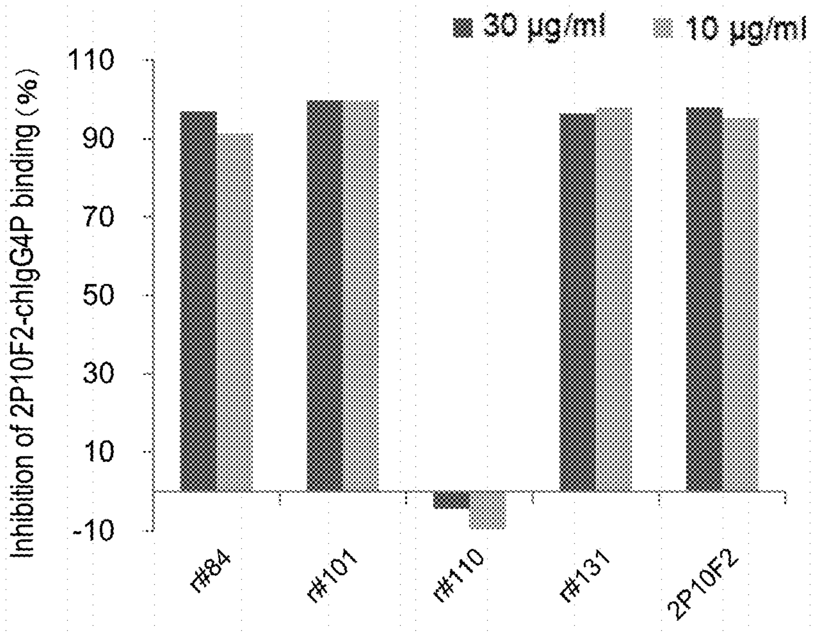

Figure 14(a)

Design of #84H1h variable region

```
rat_CD147_#84 HC   1 EVQLVESGGGLVQPGRSLKLSCAASGFTFSNYYMAWVRQAPKKGLEWVATITTSGSRPYY 60
#84H1h             1 ...............G..R.......................G.....S........... 60

rat_CD147_#84 HC  61 PDSVKGRFTISRDNAKSSLYLQMNSLKSEDTATYYCARHIYYYDGYPFAYWGQGTLVTVS 120
#84H1h            61 A.............S.NT........RA....V........................... 120

rat_CD147_#84 HC 121 S                                                            121
#84H1h           121 .                                                            121
```

Figure 14(b)

Design of #84L2h variable region

```
rat_CD147_#84 LC   1 DVQMTQSPSYLAASPGESVSISCKASKSISNNLAWYQEKPGKANKLLIHSGSTLQSGTPS 60
#84L2h             1 .........S.S..V.DR.T.T...............Q...................... 60

rat_CD147_#84 LC  61 RFSGSGSGTDFTLTIRSLEPEDFAVYYCQQYNEYPLTFGSGTKLEIKR             108
#84L2h            61 ...............S..QP...T...............Q...V....             108
```

Figure 15(a)

Design of #101H1h variable region

```
rat_CD147_#101 HC   1 EVQLVESDGGLVQPGRSLKLSCAASGFTFSDYYMAWVRQAPTKGLEWVATISYDGSNTYY 60
#101H1h             1 .......G..........R......................G.................. 60

rat_CD147_#101 HC  61 RDSVKGRFTISRDNAKSTLYLQMDSLRSGDTATYYCARFYNNYYFDYWGQGVMVTVSS   118
#101H1h            61 ..............S........N...A....V..................TL.....   118
```

Figure 15(b)

Design of #101L2h variable region

```
rat_CD147_#101 LC   1 DIQMTQSPSLLSASVGGRITLNCKASQNLYKNLAWYQQKLGEAPKLLIDNANSLQTGIPS 60
#101L2h             1 .........S......D.V.I..................P.K.................. 60

rat_CD147_#101 LC  61 RFSGSGSGTDFTLTISSLQPEDVATYFCQQYYSGSYTFGAGTKLELKR             108
#101L2h            61 ......................F................Q...V.I..             108
```

Figure 16(a)

(a) Design of #110H1h variable region

```
rat_CD147_#110 HC   1 QVQLQQSGAELVKPGSSVKISCKASGYTFTSDFMHWIKQQPGNGLEWIGWIYPGDGDTEY 60
#110H1h             1 ....V.....VK...A...V................VR.A..Q....M............ 60

rat_CD147_#110 HC  61 NQKFNGKATLTADKSSSTAYMQLSSLTSEDSAVYFCARGRGYVMDAWGQGASVTVSS    117
#110H1h            61 ....Q.RV...R.T.I.....E..R.R.D.T...Y..............TT.....    117
```

Figure 16(b)

(b) Design of #110H13h variable region

```
rat_CD147_#110 HC   1 QVQLQQSGAELVKPGSSVKISCKASGYTFTSDFMHWIKQQPGNGLEWIGWIYPGDGDTEY 60
#110H13h            1 ....V.....VK...A...V................VR.A..Q....M............ 60

rat_CD147_#110 HC  61 NQKFNGKATLTADKSSSTAYMQLSSLTSEDSAVYFCARGRGYVMDAWGQGASVTVSS    117
#110H13h           61 A...Q.RV.M.R.T.I.....E..R.R.D.T...Y..............TT.....    117
```

Figure 16(c)

(c) Design of #110L4h variable region

```
rat_CD147_#110 LC   1 DIQMTQTPSSMPASLGERVTISCRASQGISNYLNWYQQKPDGTIKPLIYYTSNLQSGVPS 60
#110L4h             1 ......S...LS..V.D....T..................GKA................. 60

rat_CD147_#110 LC  61 RFSGSGSGTDYSLTISSLEPEDFAMYFCQQYDSSPRTFGGGTKLELKR             108
#110L4h            61 ...........T......Q.....T.................V.I..              108
```

Figure 16(d)

(d) Design of #110L2h variable region

```
rat_CD147_#110 LC   1 DIQMTQTPSSMPASLGERVTISCRASQGISNYLNWYQQKPDGTIKPLIYYTSNLQSGVPS 60
#110L2h             1 ......S...LS..V.D....T..................GKAP................ 60

rat_CD147_#110 LC  61 RFSGSGSGTDYSLTISSLEPEDFAMYFCQQYDSSPRTFGGGTKLELKR             108
#110L2h            61 ...........T......Q.....T.Y...............V.I..              108
```

Figure 16(e)

(e) Design of #110L12h variable region

```
rat_CD147_#110 LC   1 DIQMTQTPSSMPASLGERVTISCRASQGISNYLNWYQQKPDGTIKPLIYYTSNLQSGVPS 60
#110L12h            1 ......S...LS..V.D....T..................GKAP................ 60

rat_CD147_#110 LC  61 RFSGSGSGTDYSLTISSLEPEDFAMYFCQQYDSSPRTFGGGTKLELKR             108
#110L12h           61 ..........FT......Q.....T.Y...............V.I..              108
```

Figure 17(a)

(a) Design of #131H2h variable region

```
rat_CD147_#131 HC   1 EVQLVESGGGLVQPGRSLKLSCGASGFTFNNYWMTWVRQAPGKGLEWVASITKAGGSTYY 60
#131H2h             1 Q.........V.......R...A..................................... 60

rat_CD147_#131 HC  61 RDSVKGRFTISRDNAKSTLYLQMNSLRSEDTATYYCTRELGEFYVMDAWGQGASVTVSS  119
#131H2h            61 A.............S............A.G..V....................TT.....  119
```

Figure 17(b)

(b) Design of #131L2h variable region

```
rat_CD147_#131 LC   1 DVQMTQSPSYLAASPGESVSISCKASKSINTYLAWYQEKPGKTNKLLIYSGSTLQSGTPS 60
#131L2h             1 .........S.S..V.DR.T.T...................................... 60

rat_CD147_#131 LC  61 RFSGSGSGTDFTLTIRSLEPEDFAVYYCQQHNEYPFTFGSGTKLEIKR             108
#131L2h            61 ................S..Q.....T...............Q........           108
```

[Figure 19]
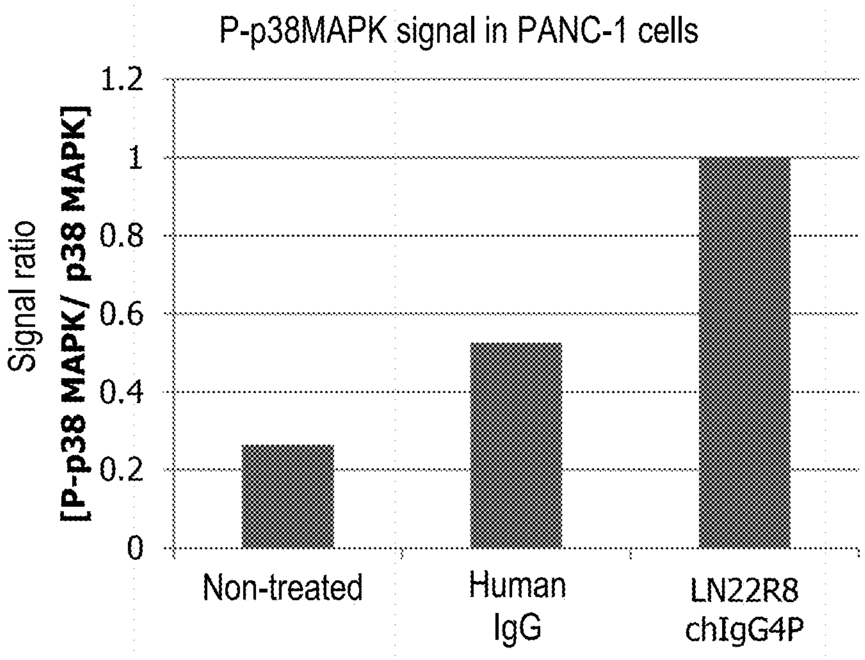

[Figure 24]
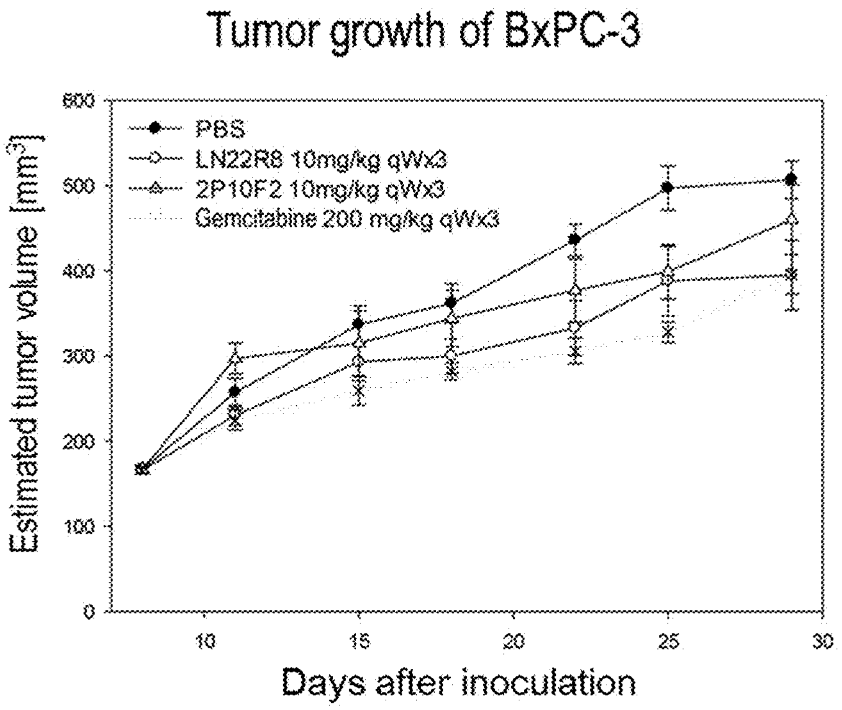

[Figure 27]
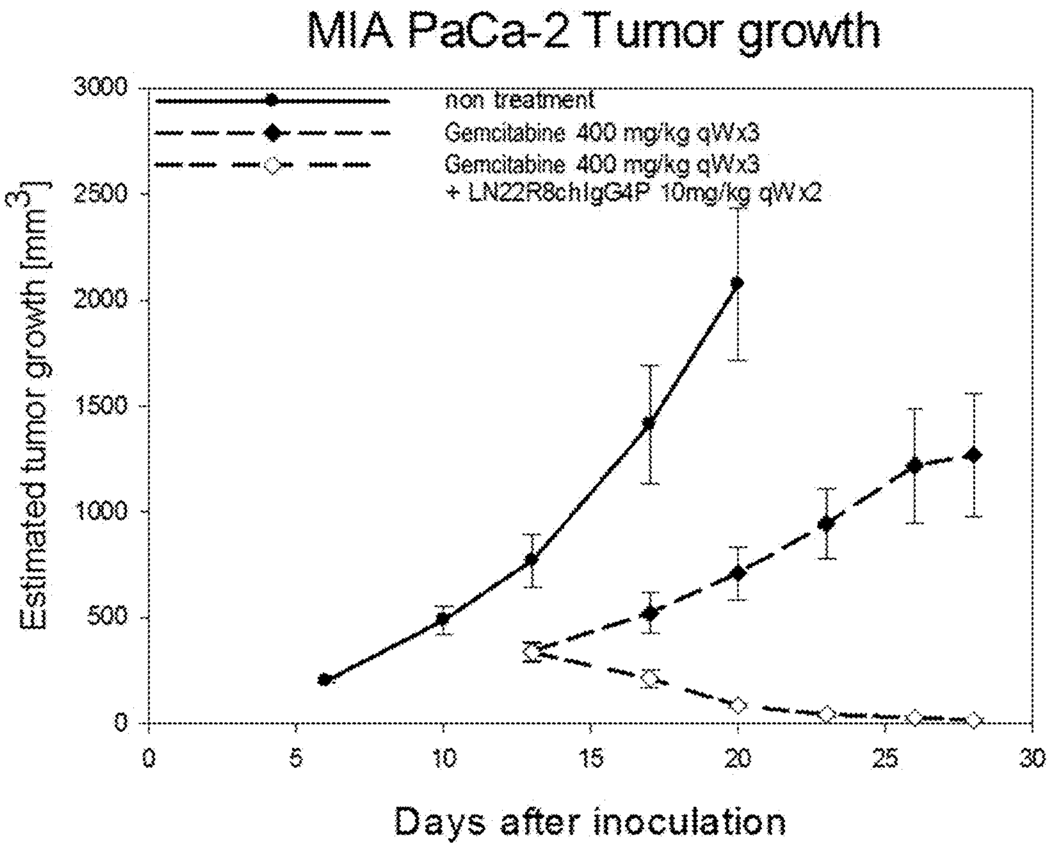

[Figure 30]
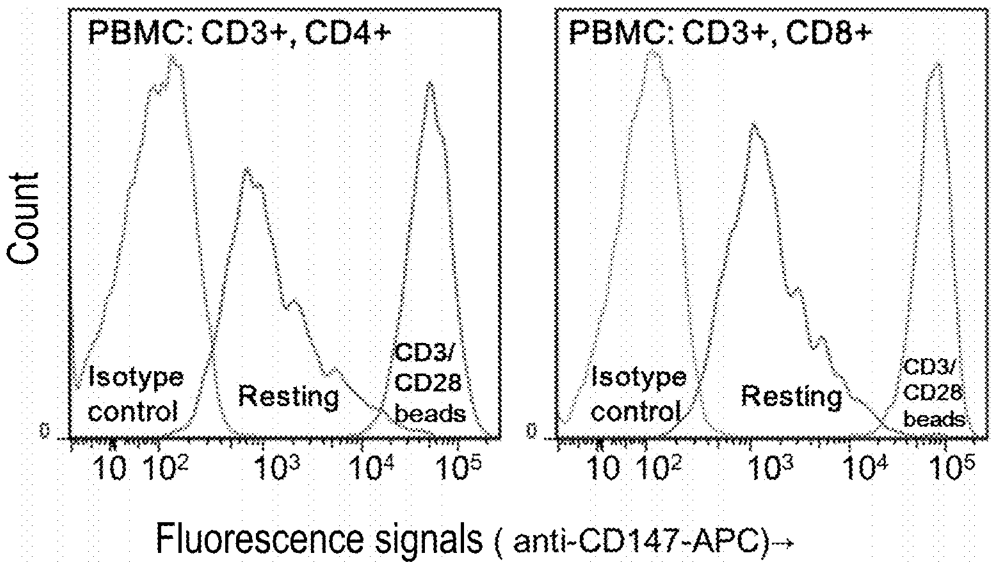
[Figure 31]
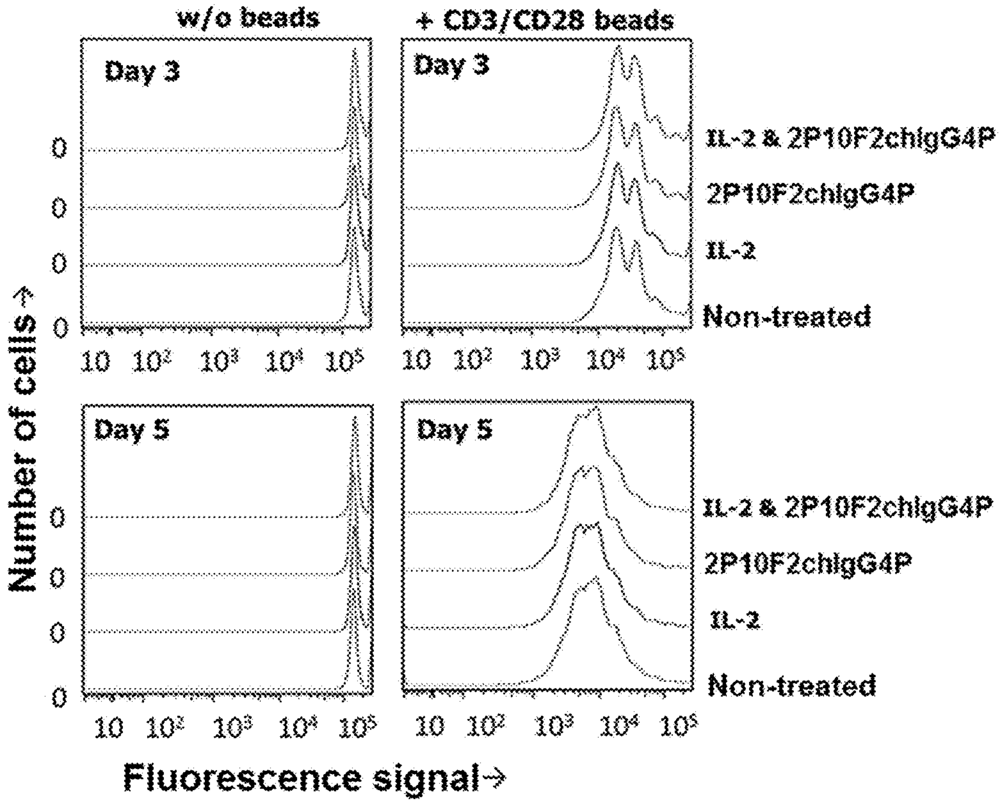

[Figure 32]

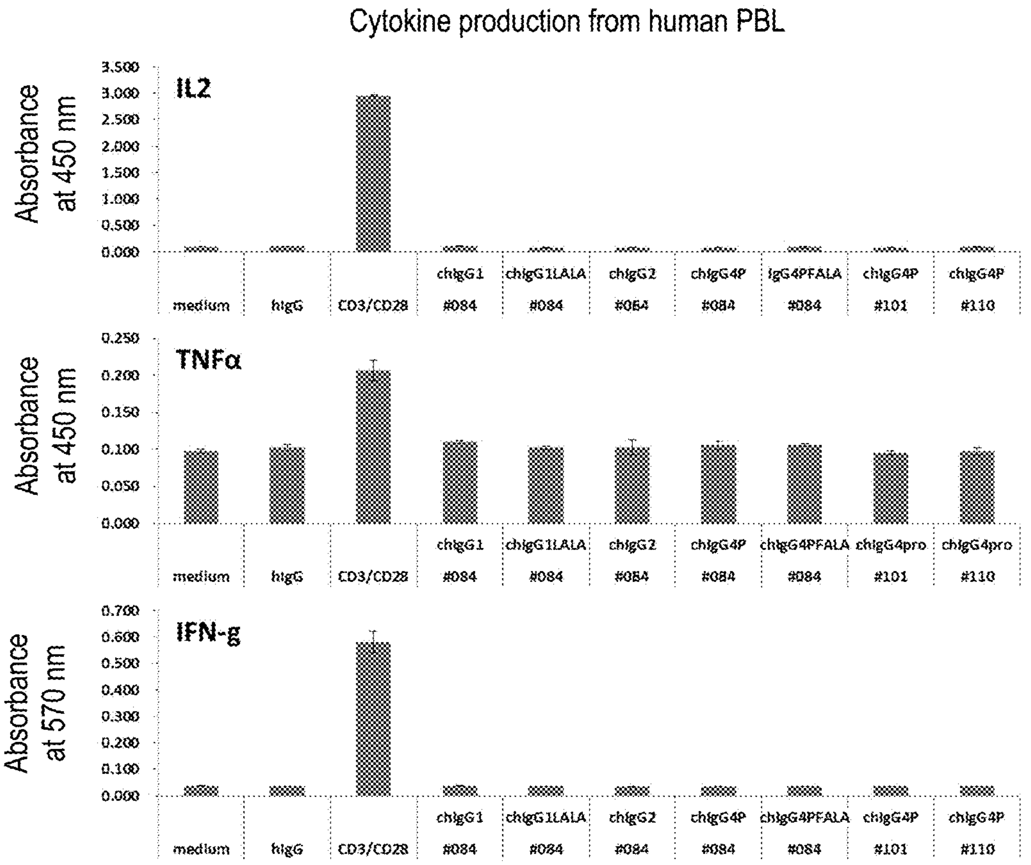

[Figure 33-1]

SEQ ID NO: 48: Nucleotide sequence of rat_CD147_#84 light chain variable region

GATGTCCAGATGACCCAGTCTCCATCTTATCTTGCTGCGTCTCCTGGAGAAAGTGTTTCCATCAGTTGCAAGGCAAGTAAGAGCATTAGCAATAA
TTTAGCCTGGTATCAGGAGAAACCTGGGAAAGCAAATAAGCTTCTTATTCACTCTGGGTCAACTTTGCAATCTGGAACTCCATCGAGGTTCAGTG
GCAGTGGATCTGGTACAGATTTCACGCTCACCATCAGAAGCCTGGAGTTTGAAGATTTTGCAGTCTATTACTGTCAACAGTATAATGAATACCCA
CTCACGTTCGGTTCTGGGACCAAGCTGGAGATCAAACGG

SEQ ID NO: 49: Amino acid sequence of rat_CD147_#84 light chain variable region (each CDR is underlined)

DVQMTQSPSYLAASPGESVSISC<u>KASKSISNNLA</u>WYQEKPGKANKLLIH<u>SGSTLQS</u>GTPSRFSGSGSGTDFTLTIRSLEFEDFAVYYC<u>QQYNEYP</u>
<u>LT</u>FGSGTKLEIKR

SEQ ID NO: 52: Amino acid sequence of CDRL1 of rat_CD147_#84

KASKSISNNLA

SEQ ID NO: 53: Amino acid sequence of CDRL2 of rat_CD147_#84

SGSTLQS

SEQ ID NO: 54: Amino acid sequence of CDRL3 of rat_CD147_#84

QQYNEYPLT

[Figure 33-2]

SEQ ID NO: 50: Nucleotide sequence of rat_CD147_#84 heavy chain variable region

GAGGTGCAGCTGGTGGAGTCTGGGGGAGGCCTAGTGCAGCCTGGAAGGTCCCTGAAACTCTCCTGTGCAGCCTCAGGATTCACTTTCAGTAACTA
TTACATGGCCTGGGTCCGCCAGGCTCCAAAGAAGGGTCTGGAGTGGGTCGCAACCATTACTACCAGTGGTAGCAGACCTTACTATCCAGACTCCG
TGAAAGGCCGATTCACTATCTCCAGAGATAATGCAAAAAGCAGCCTATACCTGCAAATGAACAGTCTGAAGTCTGAGGACACGGCCACTTATTAC
TGTGCAAGACATATTTATTACTATGATGGTTACCCCTTTGCTTACTGGGGCCAAGGCACTCTGGTCACTGTCTCTTCA

SEQ ID NO: 51: Amino acid sequence of rat_CD147_#84 heavy chain variable region (each CDR is underlined)

EVQLVESGGGLVQPGRSLKLSCAASGFTFSNYYMAWVRQAPKKGLEWVATITTSGSRPYYPDSVKGRFTISRDNAKSSLYLQMNSLKSEDTATYY
CARHIYYYDGYPFAYWGQGTLVTVSS

SEQ ID NO: 55: Amino acid sequence of CDRH1 of rat_CD147_#84

GFTFSNYYMA

SEQ ID NO: 56: Amino acid sequence of CDRH2 of rat_CD147_#84

TITTSGSRPY

SEQ ID NO: 57: Amino acid sequence of CDRH3 of rat_CD147_#84

HIYYYDGYPFAY

[Figure 34-1]

SEQ ID NO: 58: Nucleotide sequence of rat_CD147_#101 light chain variable region GACATCCAGATGACCCAGTCTCCTTCACTCCTGTCTGCATCTGTGGGAGGCAGAATCACTCTCAACTGCAAAGCAAGTCAGAATCTCTATAAGAA
CTTAGCCTGGTATCAGCAGAAGCTTGGAGAAGCTCCCAAACTCCTGATTGATAATGCAAACAGTTTGCAAACGGGCATCCCATCAAGGTTCAGTG
GCAGTGGATCTGGTACAGATTTCACACTCACCATCAGCAGCCTGCAGCCTGAAGATGTTGCCACATATTTCTGCCAGCAGTATTATAGCGGGTCG
TACACGTTTGGAGCTGGGACCAAGCTGGAACTGAAACGG SEQ ID NO: 59: Amino acid sequence of rat_CD147_#101 light chain variable region (each CDR is underlined)

DIQMTQSPSLLSASVGGRITLNCKASQNLYKNLAWYQQKLGEAPKLLIDNANSLQTGIPSRFSGSGSGTDFTLTISSLQPEDVATYFCQQYYSGS
YTFGAGTKLELKR

SEQ ID NO: 62: Amino acid sequence of CDRL1 of rat_CD147_#101

KASQNLYKNLA

SEQ ID NO: 63: Amino acid sequence of CDRL2 of rat_CD147_#101

NANSLQT

SEQ ID NO: 64: Amino acid sequence of CDRL3 of rat_CD147_#101

QQYYSGSYT

[Figure 34-2]

SEQ ID NO: 60: Nucleotide sequence of rat_CD147_#101 heavy chain variable region GAGGTGCAGCTGGTGGAGTCTGATGGAGGCTTAGTGCAGCCTGGAAGGTCCCTAAAACTCTCCTGTGCAGCCTCAGGATTCACTTTCAGTGACTA
TTACATGGCCTGGGTCCGCCAGGCTCCAACGAAGGGGCTGGAGTGGGTCGCAACCATTAGTTATGATGGTAGTAACACTTACTATCGAGACTCCG
TGAAGGGCCGATTCACTATCTCCAGAGATAATGCAAAAAGCACCCTATACCTGCAAATGGACAGTCTGAGGTCTGGGGACACGGCCACTTATTAC
TGTGCAAGATTTTACAACAACTACTACTTTGATTACTGGGGCCAAGGAGTCATGGTCACAGTCTCCTCA SEQ ID NO: 61: Amino acid sequence of rat_CD147_#101 heavy chain variable region (each CDR is underlined)

EVQLVESDGGLVQPGRSLKLSCAASGFTFSDYYMAWVRQAPTKGLEWVATISYDGSNTYYRDSVKGRFTISRDNAKSTLYLQMDSLRSGDTATYY
CARFYNNYYFDYWGQGVMVTVSS

SEQ ID NO: 65: Amino acid sequence of CDRH1 of rat_CD147_#101

GFTFSDYYMA

SEQ ID NO: 66: Amino acid sequence of CDRH2 of rat_CD147_#101

TISYDGSNTY

SEQ ID NO: 67: Amino acid sequence of CDRH3 of rat_CD147_#101

FYNNYYFDY

[Figure 35-1]

SEQ ID NO: 68: Nucleotide sequence of rat_CD147_#110 light chain variable region
GACATCCAGATGACCCAGACTCCATCCTCCATGCCTGCATCTCTGGGAGAGAGAGTCACCATCAGTTGCAGAGCAAGTCAGGGTATTAGCAATTA
TCTAAACTGGTATCAGCAGAAACCAGATGGAACGATTAAACCCCTGATCTACTACACATCCAATTTACAATCTGGTGTCCCATCAAGGTTCAGTG
GCAGTGGGTCTGGGACAGATTATTCTCTCACCATCAGCAGCCTGGAGCCTGAAGATTTTGCAATGTATTTCTGCCAACAGTATGATAGTTCTCCT
CGGACGTTCGGTGGAGGCACCAAGCTGGAATTGAAACGG SEQ ID NO: 69: Amino acid sequence of rat_CD147_#110 light chain variable region (each CDR is underlined)
DIQMTQTPSSMPASLGERVTISCRASQGISNYLNWYQQKPDGTIKPLIYYTSNLQSGVPSRFSGSGSGTDYSLTISSLEPEDFAMYFCQQYDSSP
RTFGGGTKLELKR SEQ ID NO: 72: Amino acid sequence of CDRL1 of rat_CD147_#110
RASQGISNYLN SEQ ID NO: 73: Amino acid sequence of CDRL2 of rat_CD147_#110
YTSNLQS SEQ ID NO: 74: Amino acid sequence of CDRL3 of rat_CD147_#110
QQYDSSPRT

[Figure 35-2]

SEQ ID NO: 70: Nucleotide sequence of rat_CD147_#110 heavy chain variable region
CAGGTACAGCTGCAGCAATCTGGGGCTGAACTGGTGAAGCCTGGGTCCTCAGTGAAAATTTCCTGCAAGGCTTCTGGCTACACCTTCACCAGTGA
CTTTATGCACTGGATAAAACAGCAGCCTGGAAATGGCCTTGAGTGGATTGGGTGGATTTATCCTGGAGATGGTGATACAGAGTACAATCAAAAGT
TCAATGGGAAGGCAACACTCACTGCAGACAAATCCTCCAGCACAGCCTATATGCAGCTCAGCAGCCTGACATCTGAGGACTCTGCAGTCTATTTC
TGTGCAAGGGGACGGGGGTATGTTATGGATGCCTGGGGTCAAGGAGCTTCAGTCACTGTCTCCTCA SEQ ID NO: 71: Amino acid sequence of rat_CD147_#110 heavy chain variable region (each CDR is underlined)
QVQLQQSGAELVKPGSSVKISCKASGYTFTSDFMHWIKQQPGNGLEWIGWIYPGDGDTEYNQKFNGKATLTADKSSSTAYMQLSSLTSEDSAVYF
CARGRGYVMDAWGQGASVTVSS SEQ ID NO: 75: Amino acid sequence of CDRH1 of rat_CD147_#110
GYTFTSDFMH SEQ ID NO: 76: Amino acid sequence of CDRH2 of rat_CD147_#110
WIYPGDGDTE SEQ ID NO: 77: Amino acid sequence of CDRH3 of rat_CD147_#110
GRGYVMDA

[Figure 36-1]

SEQ ID NO: 78: Nucleotide sequence of rat_CD147_#131 light chain variable region
GATGTCCAGATGACCCAGTCTCCATCTTATCTTGCTGCGTCTCCTGGAGAAAGTGTTTCCATCAGTTGCAAGGCAAGTAAAAGCATTAACACATA
CTTAGCCTGGTATCAGGAGAAACCTGGGAAAACGAATAAGCTTCTTATCTACTCTGGGTCAACTTTGCAATCTGGAACTCCATCGAGATTCAGTG
GCAGTGGATCTGGTACAGATTTCACGCTCACCATCAGAAGCCTGGAGCCTGAAGATTTTGCAGTCTACTACTGTCAACAGCATAATGAATACCCC
TTCACGTTCGGCTCAGGGACGAAGTTGGAAATAAAACGG SEQ ID NO: 79: Amino acid sequence of rat_CD147_#131 light chain variable region (each CDR is underlined)
DVQMTQSPSYLAASPGESVSISCKASKSINTYLAWYQEKPGKTNKLLIYSGSTLQSGTPSRFSGSGSGTDFTLTIRSLEPEDFAVYYCQQHNEYP
FTFGSGTKLEIKR SEQ ID NO: 82: Amino acid sequence of CDRL1 of rat_CD147_#131
KASKSINTYLA SEQ ID NO: 83: Amino acid sequence of CDRL2 of rat_CD147_#131
SGSTLQS SEQ ID NO: 84: Amino acid sequence of CDRL3 of rat_CD147_#131
QQHNEYPFT

[Figure 36-2]

SEQ ID NO: 80: Nucleotide sequence of rat_CD147_#131 heavy chain variable region
GAGGTGCAGCTGGTGGAGTCTGGGGGAGGCCTAGTGCAGCCTGGAAGGTCTCTGAAACTATCCTGTGGAGCCTCTGGATTCACATTCAATAACTA
CTGGATGACCTGGGTCCGCCAGGCTCCAGGGAAGGGGCTGGAGTGGGTTGCATCCATTACTAAAGCTGGTGGTAGCACTTACTATCGAGACTCTG
TGAAGGGCCGATTCACTATCTCCAGAGATAATGCAAAAAGCACCCTATATCTGCAAATGAACAGTCTGAGGTCTGAGGACACGGCCACTTATTAC
TGTACAAGAGAACTGGGAGAGTTCTATGTTATGGATGCCTGGGGTCAAGGAGCTTCAGTCACTGTCTCCTCA SEQ ID NO: 81: Amino acid sequence of rat_CD147_#131 heavy chain variable region (each CDR is underlined)
EVQLVESGGGLVQPGRSLKLSCGASGFTFNNYWMTWVRQAPGKGLEWVASITKAGGSTYYRDSVKGRFTISRDNAKSTLYLQMNSLRSEDTATYY
CTRELGEFYVMDAWGQGASVTVSS SEQ ID NO: 85: Amino acid sequence of CDRH1 of rat_CD147_#131
GFTFNNYWMT SEQ ID NO: 86: Amino acid sequence of CDRH2 of rat_CD147_#131
SITKAGGSTY SEQ ID NO: 87: Amino acid sequence of CDRH3 of rat_CD147_#131
ELGEFYVMDA

[Figure 37-1]

SEQ ID NO: 123: Amino acid sequence of #84H1hIgG2 (each CDR is underlined)
MKHLWFFLLLVAAPRWVLSEVQLVESGGGLVQPGGSLRLSCAASGFTFSNYYMAWVRQAPGKGLEWVSTITTSGSRPYYADSVKGRFTISRDNSK
NTLYLQMNSLRAEDTAVYYCARHIYYYDGYPFAYWGQGTLVTVSSASTKGPSVFPLAPCSRSTSESTAALGCLVKDYFPEPVTVSWNSGALTSGV
HTFPAVLQSSGLYSLSSVVTVPSSNFGTQTYTCNVDHKPSNTKVDKTVERKCCVECPPCPAPPVAGPSVFLFPPKPKDTLMISRTPEVTCVVVDV
SHEDPEVQFNWYVDGVEVHNAKTKPREEQFNSTFRVVSVLTVVHQDWLNGKEYKCKVSNKGLPAPIEKTISKTKGQPREPQVYTLPPSREEMTKN
QVSLTCLVKGFYPSDIAVEWESNGQPENNYKTTPPMLDSDGSFFLYSKLTVDKSRWQQGNVFSCSVMHEALHNHYTQKSLSLSPGK
Signal sequence1-19, Variable region20-140, Constant region141-466

SEQ ID NO: 124: Nucleotide sequence of #84H1hIgG2
ATGAAACACCTGTGGTTCTTCCTCCTGCTGGTGGCAGCTCCCAGATGGGTGCTGAGCGAAGTGCAGCTGGTTGAGTCTGGCGGAGGACTGGTTCA
ACCTGGCGGAAGCCTGAGACTGTCTTGTGCCGCCAGCGGCTTCACCTTCAGCAACTACTATATGGCCTGGGTCCGACAGGCCCCTGGCAAAGGAC
TTGAATGGGTGTCCACCATCACCACCAGCGGCAGCAGACCTTACTACGCCGATAGCGTGAAGGGCAGATTCACCATCAGCCGGGACAACAGCAAG
AACACCCTGTACCTGCAGATGAACAGCCTGAGAGCCGAGGACACCGCCGTGTACTATTGCGCCAGACACATCTACTACTACGACGGCTACCCCTT
CGCCTATTGGGGCCAGGGAACACTGGTCACAGTTAGCTCAGCCTCCACCAAGGGCCCTTCCGTGTTCCCTCTGGCCCCTTGTAGCCGTTCCACCA
GCGAGTCCACCGCCGCCCTTGGCTGTCTGGTGAAGGACTACTTCCCTGAGCCTGTGACCGTGAGCTGGAACTCCGGAGCCCTTACCAGCGGCGTG
CACACCTTCCCTGCCGTGCTGCAGTCCAGCGGCCTTTACTCCCTGAGCTCCGTGGTGACCGTGCCTAGCTCCAACTTCGGCACCCAAACCTACAC
CTGTAACGTGGACCACAAGCCTAGCAACACCAAGGTGGACAAGACCGTGGAGCGTAAGTGTTGTGTGGAGTGTCCTCCTTGTCCTGCCCCTCCTG
TGGCCGGACCTTCCGTGTTCCTTTTCCCTCCTAAGCCTAAGGACACCCTGATGATCAGCCGTACCCCTGAGGTGACCTGTGTGGTGGTGGACGTG
TCCCACGAGGACCCTGAGGTGCAGTTCAACTGGTACGTGGACGGCGTGGAGGTGCACAACGCCAAGACCAAGCCTCGTGAGGAGCAATTCAACAG
CACCTTCCGTGTGGTGTCCGTGCTTACCGTGGTGCACCAAGACTGGCTGAACGGCAAGGAGTACAAGTGTAAGGTGAGCAACAAGGGACTTCCTG
CCCCTATCGAGAAGACCATCTCCAAGACCAAGGGCCAACCTCGTGAGCCTCAAGTGTACACCCTTCCTCCTAGCCGTGAGGAGATGACCAAGAAC
CAAGTGTCCCTTACCTGTCTGGTGAAGGGCTTCTACCCTAGCGACATCGCCGTGGAGTGGGAGTCCAACGGACAACCTGAGAACAACTACAAGAC
CACCCCTCCTATGCTTGACAGCGACGGCTCCTTCTTCCTGTACAGCAAGCTgACCGTGGACAAGTCCCGTTGGCAACAAGGCAACGTGTTCAGCT
GTTCCGTGATGCACGAGGCCCTGCACAACCACTACACCCAAAAGAGCCTTTCCCTGAGCCCTGGAAAG
Signal sequence1-57, Variable region58-420, Constant region421-1398

[Figure 37-2]

SEQ ID NO: 125: Amino acid sequence of #84H1hIgG4P (each CDR is underlined)

MKHLWFFLLLVAAPRWVLSEVQLVESGGGLVQPGGSLRLSCAASGFTFSNYYMAWVRQAPGKGLEWVSTITTSGSRPYYADSVKGRFTISRDNSK
NTLYLQMNSLRAEDTAVYYCARHIYYYDGYPFAYWGQGTLVTVSSASTKGPSVFPLAPCSRSTSESTAALGCLVKDYFPEPVTVSWNSGALTSGV
HTFPAVLQSSGLYSLSSVVTVPSSSLGTKTYTCNVDHKPSNTKVDKRVESKYGPPCPPCPAPEFLGGPSVFLFPPKPKDTLMISRTPEVTCVVVD
VSQEDPEVQFNWYVDGVEVHNAKTKPREEQFNSTYRVVSVLTVLHQDWLNGKEYKCKVSNKGLPSSIEKTISKAKGQPREPQVYTLPPSQEEMTK
NQVSLTCLVKGFYPSDIAVEWESNGQPENNYKTTPPVLDSDGSFFLYSRLTVDKSRWQEGNVFSCSVMHEALHNHYTQKSLSLSLGK

Signal sequence1-19, Variable region20-140, Constant region141-467

SEQ ID NO: 126: Nucleotide sequence of #84H1hIgG4P

ATGAAACACCTGTGGTTCTTCCTCGTGCTGGTGGCAGCTCCCAGATGGGTGCTGAGCGAAGTGCAGCTGGTTGAGTCTGGCGGAGGACTGGTTCA
ACCTGGCGGAAGCCTGAGACTGTCTTGTGCCGCCAGCGGCTTCACCTTCAGCAACTACTATATGGCCTGGGTCCGACAGGCCCCTGGCAAAGGAC
TTGAATGGGTGTCCACCATCACCACCAGCGGCAGCAGACCTTACTACGCCGATAGCGTGAAGGGCAGATTCACCATCAGCCGGGACAACAGCAAG
AACACCCTGTACCTGCAGATGAACAGCCTGAGAGCCGAGGACACCGCCGTGTACTATTGCGCCAGACACATCTACTACTACGACGGCTACCCCTT
CGCCTATTGGGGCCAGGGAACACTGGTCACAGTTAGCTCAGCCTCCACCAAGGGCCCTAGCGTGTTCCCTCTGGCCCCTTGTAGCAGAAGCACCA
GCGAGTCTACAGCCGCCCTGGGCTGCCTCGTGAAGGACTACTTTCCCGAGCCCGTGACCGTGTCCTGGAACTCTGGCGCTCTGACAAGCGGCGTG
CACACCTTTCCAGCCGTGCTGCAGAGCAGCGGCCTGTACTCTCTGTCCAGCGTCGTGACTGTGCCCAGCAGCTCTCTGGGCACCAAGACCTACAC
CTGTAACGTGGACCACAAGCCCAGCAACACCAAGGTGGACAAGCGGGTGGAATCTAAGTACGGCCCTCCCTGCCCTCCTTGCCCAGCCCCTGAAT
TTCTGGGCGGACCCTCCGTGTTCCTGTTCCCCCCAAAGCCCAAGGACACCCTGATGATCAGCCGGACCCCCGAAGTGACCTGCGTGGTGGTGGAT
GTGTCCCAGGAAGATCCCGAGGTGCAGTTCAATTGGTACGTGGACGGCGTGGAAGTGCACAACGCCAAGACCAAGCCTAGAGAGGAACAGTTCAA
CAGCACCTACCGGGTGGTGTCCGTGCTGACAGTGCTGCACCAGGACTGGCTGAACGGCAAAGAGTACAAGTGCAAGGTGTCCAACAAGGGCCTGC
CCAGCTCCATCGAGAAAACCATCAGCAAGGCCAAGGGCCAGCCCCGCGAACCCCAGGTGTACACACTGCCTCCAAGCCAGGAAGAGATGACCAAG
AATCAGGTGTCCCTGACCTGTCTCGTGAAAGGCTTCTACCCCTCCGATATCGCCGTGGAATGGGAGAGCAACGGCCAGCCCGAGAACAACTACAA
GACCACCCCCCCTGTGCTGGACTCCGATGGCTCATTCTTCCTGTACAGCAGACTGACCGTGGACAAGAGCCGGTGGCAGGAAGGCAACGTGTTCA
GCTGCTCCGTGATGCACGAGGCCCTGCACAACCACTACACCCAGAAGTCCCTGTCTCTGAGCCTGGGCAAA

Signal sequence1-57, Variable region58-420, Constant region421-1401

[Figure 37-3]

SEQ ID NO: 127: Amino acid sequence of #84L2h (each CDR is underlined)

MVLQTQVFISLLLWISGAYGDVQMTQSPSSLSASVGDRVTITCKASKSISNNLAWYQQKPGKANKLLIHSGSTLQSGTPSRFSGSGSGTDFTLTI
SSLQPEDFATYYCQQYNEYPLTFGQGTKVEIKRTVAAPSVFIFPPSDEQLKSGTASVVCLLNNFYPREAKVQWKVDNALQSGNSQESVTEQDSKD
STYSLSSTLTLSKADYEKHKVYACEVTHQGLSSPVTKSFNRGEC

Signal sequence1-20, Variable region21-128, Constant region129-234

SEQ ID NO: 128: Nucleotide sequence of #84L2h

ATGGTGCTGCAGACCCAGGTGTTCATCTCCCTGCTGCTGTGGATCTCCGGCGCGTACGGCGACGTTCAGATGACACAGAGCCCTAGCAGCCTGTC
TGCCAGCGTGGGAGACAGAGTGACCATCACATGCAAGGCCAGCAAGAGCATCAGCAACAACCTGGCCTGGTATCAGCAGAAGCCCGGAAAGGCCA
ACAAGCTGCTGATCCACAGCGGCAGCACACTGCAGTCTGGCACCCCTAGCAGATTTTCCGGCTCTGGCAGCGGCACCGATTTCACCCTGACCATA
TCTAGCCTGCAGCCTGAGGACTTCGCCACCTACTACTGCCAGCAGTACAACGAGTACCCTCTGACCTTTGGCCAGGGCACCAAGGTGGAAATCAA
GCGTACGGTGGCCGCCCCCTCCGTGTTCATCTTCCCCCCCTCCGACGAGCAGCTGAAGTCCGGCACCGCCTCCGTGGTGTGCCTGCTGAATAACT
TCTACCCCAGAGAGGCCAAGGTGCAGTGGAAGGTGGACAACGCCCTGCAGTCCGGGAACTCCCAGGAGAGCGTGACCGAGCAGGACAGCAAGGAC
AGCACCTACAGCCTGAGCAGCACCCTGACCCTGAGCAAAGCCGACTACGAGAAGCACAAGGTGTACGCCTGCGAGGTGACCCACCAGGGCCTGAG
CTCCCCCGTCACCAAGAGCTTCAACAGGGGGGAGTGT

Signal sequence1-60, Variable region61-384, Constant region385-702

[Figure 38-1]

SEQ ID NO: 129: Amino acid sequence of #101H1hIgG2 (each CDR is underlined)

MKHLWFFLLLVAAPRWVLSEVQLVESGGGLVQPGRSLRLSCAASGFTFSDYYMAWVRQAPGKGLEWVATISYDGSNTYYRDSVKGRFTISRDNSK
STLYLQMNSLRAGDTAVYYCARFYNNYYFDYWGQGTLVTVSSASTKGPSVFPLAPCSRSTSESTAALGCLVKDYFPEPVTVSWNSGALTSGVHTF
PAVLQSSGLYSLSSVVTVPSSNFGTQTYTCNVDHKPSNTKVDKTVERKCCVECPPCPAPPVAGPSVFLFPPKPKDTLMISRTPEVTCVVVDVSHE
DPEVQFNWYVDGVEVHNAKTKPREEQFNSTFRVVSVLTVVHQDWLNGKEYKCKVSNKGLPAPIEKTISKTKGQPREPQVYTLPPSREEMTKNQVS
LTCLVKGFYPSDIAVEWESNGQPENNYKTTPPMLDSDGSFFLYSKLTVDKSRWQQGNVFSCSVMHEALHNHYTQKSLSLSPGK

Signal sequence1-19, Variable region20-137, Constant region138-463

SEQ ID NO: 130: Nucleotide sequence of #101H1hIgG2

ATGAAACACCTGTGGTTCTTCCTCCTGCTGGTGGCAGCTCCCAGATGGGTGCTGAGCGAAGTGCAGCTGGTTGAGTCTGGCGGAGGACTGGTTCA
GCCTGGCAGAAGCCTGAGACTGTCTTGTGCCGCCAGCGGCTTCACCTTCAGCGACTACTATATGGCCTGGGTCCGACAGGCCCCTGGCAAAGGAC
TTGAATGGGTCGCCACCATCAGCTACGACGGCAGCAACACCTACTACCGGGACAGCGTGAAGGGCAGATTCACCATCTCCAGAGACAACAGCAAG
AGCACCCTGTACCTGCAGATGAACAGCCTGAGAGCCGGCGATACCGCCGTGTACTACTGCGCCAGATTCTACAACAACTACTACTTCGACTACTG
GGGCCAGGGCACCCTGGTCACAGTTAGCTCAGCCTCCACCAAGGGCCCTTCCGTGTTCCCTCTGGCCCCTTGTAGCCGTTCCACCAGCGAGTCCA
CCGCCGCCCTTGGCTGTCTGGTGAAGGACTACTTCCCTGAGCCTGTGACCGTGAGCTGGAACTCCGGAGCCCTTACCAGCGGCGTGCACACCTTC
CCTGCCGTGCTGCAGTCCAGCGGCCTTTACTCCCTGAGCTCCGTGGTGACCGTGCCTAGCTCCAACTTCGGCACCCAAACCTACACCTGTAACGT
GGACCACAAGCCTAGCAACACCAAGGTGGACAAGACCGTGGAGCGTAAGTGTTGTGTGGAGTGTCCTCCTTGTCCTGCCCCTCCTGTGGCCGGAC
CTTCCGTGTTCCTTTTCCCTCCTAAGCCTAAGGACACCCTGATGATCAGCCGTACCCCTGAGGTGACCTGTGTGGTGGTGGACGTGTCCCACGAG
GACCCTGAGGTGCAGTTCAACTGGTACGTGGACGGCGTGGAGGTGCACAACGCCAAGACCAAGCCTCGTGAGGAGCAATTCAACAGCACCTTCCG
TGTGGTGTCCGTGCTTACCGTGGTGCACCAAGACTGGCTGAACGGCAAGGAGTACAAGTGTAAGGTGAGCAACAAGGGACTTCCTGCCCCTATCG
AGAAGACCATCTCCAAGACCAAGGGCCAACCTCGTGAGCCTCAAGTGTACACCCTTCCTCCTAGCCGTGAGGAGATGACCAAGAACCAAGTGTCC
CTTACCTGTCTGGTGAAGGGCTTCTACCCTAGCGACATCGCCGTGGAGTGGGAGTCCAACGGACAACCTGAGAACAACTACAAGACCACCCCTCC
TATGCTTGACAGCGACGGCTCCTTCTTCCTGTACAGCAAGCTgACCGTGGACAAGTCCCGTTGGCAACAAGGCAACGTGTTCAGCTGTTCCGTGA
TGCACGAGGCCCTGCACAACCACTACACCCAAAAGAGCCTTTCCCTGAGCCCTGGAAAG

Signal sequence1-57, Variable region58-411, Constant region412-1389

[Figure 38-2]

SEQ ID NO: 131: Amino acid sequence of #101H1hIgG4P (each CDR is underlined)

MKHLWFFLLLVAAPRWVLSEVQLVESGGGLVQPGRSLRLSCAASGFTFSDYYMAWVRQAPGKGLEWVATISYDGSNTYYRDSVKGRFTISRDNSK
STLYLQMNSLRAGDTAVYYCARFYNNYYFDYWGQGTLVTVSSASTKGPSVFPLAPCSRSTSESTAALGCLVKDYFPEPVTVSWNSGALTSGVHTF
PAVLQSSGLYSLSSVVTVPSSSLGTKTYTCNVDHKPSNTKVDKRVESKYGPPCPPCPAPEFLGGPSVFLFPPKPKDTLMISRTPEVTCVVVDVSQ
EDPEVQFNWYVDGVEVHNAKTKPREEQFNSTYRVVSVLTVLHQDWLNGKEYKCKVSNKGLPSSIEKTISKAKGQPREPQVYTLPPSQEEMTKNQV
SLTCLVKGFYPSDIAVEWESNGQPENNYKTTPPVLDSDGSFFLYSRLTVDKSRWQEGNVFSCSVMHEALHNHYTQKSLSLSLGK

Signal sequence1-19, Variable region20-137, Constant region138-464

SEQ ID NO: 132: Nucleotide sequence of #101H1hIgG4P

ATGAAACACCTGTGGTTCTTCCTCCTGCTGGTGGCAGCTCCCAGATGGGTGCTGAGCGAAGTGCAGCTGGTTGAGTCTGGCGGAGGACTGGTTCA
GCCTGGCAGAAGCCTGAGACTGTCTTGTGCCGCCAGCGGCTTCACCTTCAGCGACTACTATATGGCCTGGGTCCGACAGGCCCCTGGCAAAGGAC
TTGAATGGGTCGCCACCATCAGCTACGACGGCAGCAACACCTACTACCGGGACAGCGTGAAGGGCAGATTCACCATCTCCAGAGACAACAGCAAG
AGCACCCTGTACCTGCAGATGAACAGCCTGAGAGCCGGCGATACCGCCGTGTACTACTGCGCCAGATTCTACAACAACTACTACTTCGACTACTG
GGGCCAGGGCACCCTGGTCACAGTTAGCTCAGCCTCCACCAAGGGCCCTAGCGTGTTCCCTCTGGCCCCTTGTAGCAGAAGCACCAGCGAGTCTA
CAGCCGCCCTGGGCTGCCTCGTGAAGGACTACTTTCCCGAGCCCGTGACCGTGTCCTGGAACTCTGGCGCTCTGACAAGCGGCGTGCACACCTTT
CCAGCCGTGCTGCAGAGCAGCGGCCTGTACTCTCTGTCCAGCGTCGTGACTGTGCCCAGCAGCTCTCTGGGCACCAAGACCTACACCTGTAACGT
GGACCACAAGCCCAGCAACACCAAGGTGGACAAGCGGGTGGAATCTAAGTACGGCCCTCCCTGCCCTCCTTGCCCAGCCCCTGAATTTCTGGGCG
GACCCTCCGTGTTCCTGTTCCCCCCAAAGCCCAAGGACACCCTGATGATCAGCCGGACCCCCGAAGTGACCTGCGTGGTGGTGGATGTGTCCCAG
GAAGATCCCGAGGTGCAGTTCAATTGGTACGTGGACGGCGTGGAAGTGCACAACGCCAAGACCAAGCCTAGAGAGGAACAGTTCAACAGCACCTA
CCGGGTGGTGTCCGTGCTGACAGTGCTGCACCAGGACTGGCTGAACGGCAAAGAGTACAAGTGCAAGGTGTCCAACAAGGGCCTGCCCAGCTCCA
TCGAGAAAACCATCAGCAAGGCCAAGGGCCAGCCCCGCGAACCCCAGGTGTACACACTGCCTCCAAGCCAGGAAGAGATGACCAAGAATCAGGTG
TCCCTGACCTGTCTCGTGAAAGGCTTCTACCCCTCCGATATCGCCGTGGAATGGGAGAGCAACGGCCAGCCCGAGAACAACTACAAGACCACCCC
CCCTGTGCTGGACTCCGATGGCTCATTCTTCCTGTACAGCAGACTGACCGTGGACAAGAGCCGGTGGCAGGAAGGCAACGTGTTCAGCTGCTCCG
TGATGCACGAGGCCCTGCACAACCACTACACCCAGAAGTCCCTGTCTCTGAGCCTGGGCAAA

Signal sequence1-57, Variable region58-411, Constant region412-1392

[Figure 38-3]

SEQ ID NO: 133: Amino acid sequence of #101L2h (each CDR is underlined)

MVLQTQVFISLLLWISGAYGDIQMTQSPSSLSASVGDRVTINCKASQNLYKNLAWYQQKPGKAPKLLIDNANSLQTGIPSRFSGSGSGTDFTLTI
SSLQPEDFATYFCQQYYSGSYTFGQGTKVEIKRTVAAPSVFIFPPSDEQLKSGTASVVCLLNNFYPREAKVQWKVDNALQSGNSQESVTEQDSKD
STYSLSSTLTLSKADYEKHKVYACEVTHQGLSSPVTKSFNRGEC

Signal sequence1-20, Variable region21-128, Constant region129-234

SEQ ID NO: 134: Nucleotide sequence of #101L2h

ATGGTGCTGCAGACCCAGGTGTTCATCTCCCTGCTGCTGTGGATCTCCGGCGCGTACGGCGATATCCAGATGACACAGAGCCCTAGCAGCCTGTC
TGCCAGCGTGGGAGATAGAGTGACCATCAACTGCAAGGCCAGCCAGAACCTGTACAAGAACCTGGCCTGGTATCAGCAGAAGCCCGGCAAGGCTC
CTAAGCTGCTGATCGACAACGCCAACAGCCTGCAGACCGGCATTCCCAGCAGATTTTCTGGCAGCGGCTCCGGCACCGATTTCACCCTGACCATA
TCTAGCCTGCAGCCTGAGGACTTCGCCACCTACTTTTGCCAGCAGTACTACAGCGGCAGCTACACCTTTGGCCAGGGCACCAAGGTGGAAATCAA
GCGTACGGTGGCCGCCCCCTCCGTGTTCATCTTCCCCCCCTCCGACGAGCAGCTGAAGTCCGGCACCGCCTCCGTGGTGTGCCTGCTGAATAACT
TCTACCCCAGAGAGGCCAAGGTGCAGTGGAAGGTGGACAACGCCCTGCAGTCCGGGAACTCCCAGGAGAGCGTGACCGAGCAGGACAGCAAGGAC
AGCACCTACAGCCTGAGCAGCACCCTGACCCTGAGCAAAGCCGACTACGAGAAGCACAAGGTGTACGCCTGCGAGGTGACCCACCAGGGCCTGAG
CTCCCCCGTCACCAAGAGCTTCAACAGGGGGGAGTGT

Signal sequence1-60, Variable region61-384, Constant region385-702

[Figure 39-1]

SEQ ID NO: 135: Amino acid sequence of #110H1hIgG4P (each CDR is underlined)

MKHLWFFLLLVAAPRWVLSQVQLVQSGAEVKKPGASVKVSCKASGYTFTSDFMHWVRQAPGQGLEWMGWIYPGDGDTEYNQKFQGRVTLTRDTSI
STAYMELSRLRSDDTAVYYCARGRGYVMDAWGQGTTVTVSSASTKGPSVFPLAPCSRSTSESTAALGCLVKDYFPEPVTVSWNSGALTSGVHTFP
AVLQSSGLYSLSSVVTVPSSSLGTKTYTCNVDHKPSNTKVDKRVESKYGPPCPPCPAPEFLGGPSVFLFPPKPKDTLMISRTPEVTCVVVDVSQE
DPEVQFNWYVDGVEVHNAKTKPREEQFNSTYRVVSVLTVLHQDWLNGKEYKCKVSNKGLPSSIEKTISKAKGQPREPQVYTLPPSQEEMTKNQVS
LTCLVKGFYPSDIAVEWESNGQPENNYKTTPPVLDSDGSFFLYSRLTVDKSRWQEGNVFSCSVMHEALHNHYTQKSLSLSLGK

Signal sequence1-19, Variable region20-136, Constant region137-463

SEQ ID NO: 136: Nucleotide sequence of #110H1hIgG4P

ATGAAACACCTGTGGTTCTTCCTCCTGCTGGTGGCAGCTCCCAGATGGGTGCTGAGCCAGGTTCAGCTGGTTCAGTCTGGCGCCGAAGTGAAGAA
ACCTGGCGCCTCTGTGAAGGTGTCCTGCAAGGCCAGCGGCTACACCTTTACCAGCGACTTCATGCACTGGGTCCGACAGGCTCCAGGACAGGGAC
TTGAATGGATGGGCTGGATCTATCCCGGCGACGGCGACACCGAGTACAACCAGAAATTCCAGGGCAGAGTGACCCTGACCAGAGACACCAGCATC
AGCACCGCCTACATGGAACTGAGCCGGCTGAGATCCGATGACACCGCCGTGTACTACTGCGCCAGAGGCAGAGGCTATGTGATGGATGCTTGGGG
CCAGGGCACCACCGTTACAGTTAGCTCAGCCTCCACCAAGGGCCCTAGCGTGTTCCCTCTGGCCCCTTGTAGCAGAAGCACCAGCGAGTCTACAG
CCGCCCTGGGCTGCCTCGTGAAGGACTACTTTCCCGAGCCCGTGACCGTGTCCTGGAACTCTGGCGCTCTGACAAGCGGCGTGCACACCTTTCCA
GCCGTGCTGCAGAGCAGCGGCCTGTACTCTCTGTCCAGCGTCGTGACTGTGCCCAGCAGCTCTCTGGGCACCAAGACCTACACCTGTAACGTGGA
CCACAAGCCCAGCAACACCAAGGTGGACAAGCGGGTGGAATCTAAGTACGGCCCTCCCTGCCCTCCTTGCCCAGCCCCTGAATTTCTGGGCGGAC
CCTCCGTGTTCCTGTTCCCCCCAAAGCCCAAGGACACCCTGATGATCAGCCGGACCCCCGAAGTGACCTGCGTGGTGGTGGATGTGTCCCAGGAA
GATCCCGAGGTGCAGTTCAATTGGTACGTGGACGGCGTGGAAGTGCACAACGCCAAGACCAAGCCTAGAGAGGAACAGTTCAACAGCACCTACCG
GGTGGTGTCCGTGCTGACAGTGCTGCACCAGGACTGGCTGAACGGCAAAGAGTACAAGTGCAAGGTGTCCAACAAGGGCCTGCCCAGCTCCATCG
AGAAAACCATCAGCAAGGCCAAGGGCCAGCCCCGCGAACCCCAGGTGTACACACTGCCTCCAAGCCAGGAAGAGATGACCAAGAATCAGGTGTCC
CTGACCTGTCTCGTGAAAGGCTTCTACCCCTCCGATATCGCCGTGGAATGGGAGAGCAACGGCCAGCCCGAGAACAACTACAAGACCACCCCCCC
TGTGCTGGACTCCGATGGCTCATTCTTCCTGTACAGCAGACTGACCGTGGACAAGAGCCGGTGGCAGGAAGGCAACGTGTTCAGCTGCTCCGTGA
TGCACGAGGCCCTGCACAACCACTACACCCAGAAGTCCCTGTCTCTGAGCCTGGGCAAA

Signal sequence1-57, Variable region58-408, Constant region409-1389

[Figure 39-2]

SEQ ID NO: 147: Amino acid sequence of #110H13hIgG4P (each CDR is underlined)

MKHLWFFLLLVAAPRWVLSQVQLVQSGAEVKKPGASVKVSCKASGYTFTSDFMHWVRQAPGQGLEWMGWIYPGDGDTEYAQKFQGRVTMTRDTSI
STAYMELSRLRSDDTAVYYCARGRGYVMDAWGQGTTVTVSSASTKGPSVFPLAPCSRSTSESTAALGCLVKDYFPEPVTVSWNSGALTSGVHTFP
AVLQSSGLYSLSSVVTVPSSSLGTKTYTCNVDHKPSNTKVDKRVESKYGPPCPPCPAPEFLGGPSVFLFPPKPKDTLMISRTPEVTCVVVDVSQE
DPEVQFNWYVDGVEVHNAKTKPREEQFNSTYRVVSVLTVLHQDWLNGKEYKCKVSNKGLPSSIEKTISKAKGQPREPQVYTLPPSQEEMTKNQVS
LTCLVKGFYPSDIAVEWESNGQPENNYKTTPPVLDSDGSFFLYSRLTVDKSRWQEGNVFSCSVMHEALHNHYTQKSLSLSLGK

Signal sequence1-19, Variable region20-136, Constant region137-463

SEQ ID NO: 148: Nucleotide sequence of #110H13hIgG4P

ATGAAACACCTGTGGTTCTTCCTCCTGCTGGTGGCAGCTCCCAGATGGGTGCTGAGCCAGGTTCAGCTGGTTCAGTCTGGCGCCGAAGTGAAGAA
ACCTGGCGCCTCTGTGAAGGTGTCCTGCAAGGCCAGCGGCTACACCTTTACCAGCGACTTCATGCACTGGGTCCGACAGGCTCCAGGACAGGGAC
TTGAATGGATGGGCTGGATCTATCCCGGCGACGGCGATACAGAGTACGCCCAGAAATTCCAGGGCAGAGTGACCATGACCAGAGACACCAGCATC
AGCACCGCCTACATGGAACTGAGCCGGCTGAGATCCGATGACACCGCCGTGTACTACTGCGCCAGAGGCAGAGGCTATGTGATGGATGCTTGGGG
CCAGGGCACCACCGTTACAGTTAGCTCAGCCTCCACCAAGGGCCCTAGCGTGTTCCCTCTGGCCCCTTGTAGCAGAAGCACCAGCGAGTCTACAG
CCGCCCTGGGCTGCCTCGTGAAGGACTACTTTCCCGAGCCCGTGACCGTGTCCTGGAACTCTGGCGCTCTGACAAGCGGCGTGCACACCTTTCCA
GCCGTGCTGCAGAGCAGCGGCCTGTACTCTCTGTCCAGCGTCGTGACTGTGCCCAGCAGCTCTCTGGGCACCAAGACCTACACCTGTAACGTGGA
CCACAAGCCCAGCAACACCAAGGTGGACAAGCGGGTGGAATCTAAGTACGGCCCTCCCTGCCCTGCTTGCCCAGCCCCTGAATTTCTGGGCGGAC
CCTCCGTGTTCCTGTTCCCCCCAAAGCCCAAGGACACCCTGATGATCAGCCGGACCCCCGAAGTGACCTGCGTGGTGGTGGATGTGTCCCAGGAA
GATCCCGAGGTGCAGTTCAATTGGTACGTGGACGGCGTGGAAGTGCACAACGCCAAGACCAAGCCTAGAGAGGAACAGTTCAACAGCACCTACCG
GGTGGTGTCCGTGCTGACAGTGCTGCACCAGGACTGGCTGAACGGCAAAGAGTACAAGTGCAAGGTGTCCAACAAGGGCCTGCCCAGCTCCATCG
AGAAAACCATCAGCAAGGCCAAGGGCCAGCCCCGCGAACCCCAGGTGTACACACTGCCTCCAAGCCAGGAAGAGATGACCAAGAATCAGGTGTCC
CTGACCTGTCTCGTGAAAGGCTTCTACCCCTCCGATATCGCCGTGGAATGGGAGAGCAACGGCCAGCCCGAGAACAACTACAAGACCACCCCCCC
TGTGCTGGACTCCGATGGCTCATTCTTCCTGTACAGCAGACTGACCGTGGACAAGAGCCGGTGGCAGGAAGGCAACGTGTTCAGCTGCTCCGTGA
TGCACGAGGCCCTGCACAACCACTACACCCAGAAGTCCCTGTCTCTGAGCCTGGGCAAA

Signal sequence1-57, Variable region58-408, Constant region409-1389

[Figure 39-3]

SEQ ID NO: 137: Amino acid sequence of #110L4h (each CDR is underlined)

MVLQTQVFISLLLWISGAYGDIQMTQSPSSLSASVGDRVTITCRASQGISNYLNWYQQKPGKAIKPLIYYTSNLQSGVPSRFSGSGSGTDYTLTI
SSLQPEDFATYFCQQYDSSPRTFGGGTKVEIKRTVAAPSVFIFPPSDEQLKSGTASVVCLLNNFYPREAKVQWKVDNALQSGNSQESVTEQDSKD
STYSLSSTLTLSKADYEKHKVYACEVTHQGLSSPVTKSFNRGEC

Signal sequence1-20, Variable region21-128, Constant region129-234

SEQ ID NO: 138: Nucleotide sequence of #110L4h

ATGGTGCTGCAGACCCAGGTGTTCATCTCCCTGCTGCTGTGGATCTCCGGCGCGTACGGCGATATCCAGATGACACAGAGCCCTAGCAGCCTGTC
TGCCAGCGTGGGAGACAGAGTGACCATCACCTGTAGAGCCAGCCAGGGCATCAGCAACTACCTGAACTGGTATCAGCAGAAGCCCGGCAAGGCCA
TCAAGCCCCTGATCTACTACACCAGCAACCTGCAGAGCGGCGTGCCCAGCAGATTTTCTGGCTCTGGCAGCGGCACCGACTACACCCTGACCATA
TCTAGCCTGCAGCCTGAGGACTTCGCCACCTACTTTTGCCAGCAGTACGACAGCAGCCCCAGAACCTTTGGCGGCGGAACAAAGGTGGAAATCAA
GCGTACGGTGGCCGCCCCCTCCGTGTTCATCTTCCCCCCCTCCGACGAGCAGCTGAAGTCCGGCACCGCCTCCGTGGTGTGCCTGCTGAATAACT
TCTACCCCAGAGAGGCCAAGGTGCAGTGGAAGGTGGACAACGCCCTGCAGTCCGGGAACTCCCAGGAGAGCGTGACCGAGCAGGACAGCAAGGAC
AGCACCTACAGCCTGAGCAGCACCCTGACCCTGAGCAAAGCCGACTACGAGAAGCACAAGGTGTACGCCTGCGAGGTGACCCACCAGGGCCTGAG
CTCCCCCGTCACCAAGAGCTTCAACAGGGGGGAGTGT

Signal sequence1-60, Variable region61-384, Constant region385-702

[Figure 39-4]

SEQ ID NO: 149: Amino acid sequence of #110L2h (each CDR is underlined)

MVLQTQVFISLLLWISGAYGDIQMTQSPSSLSASVGDRVTITCRASQGISNYLNWYQQKPGKAPKPLIYYTSNLQSGVPSRFSGSGSGTDYTLTI
SSLQPEDFATYYCQQYDSSPRTFGGGTKVEIKRTVAAPSVFIFPPSDEQLKSGTASVVCLLNNFYPREAKVQWKVDNALQSGNSQESVTEQDSKD
STYSLSSTLTLSKADYEKHKVYACEVTHQGLSSPVTKSFNRGEC

Signal sequence1-20, Variable region21-128, Constant region129-234

SEQ ID NO: 150: Nucleotide sequence of #110L2h

ATGGTGCTGCAGACCCAGGTGTTCATCTCCCTGCTGCTGTGGATCTCCGGCGCGTACGGCGATATCCAGATGACACAGAGCCCTAGCAGCCTGTC
TGCCAGCGTGGGAGACAGAGTGACCATCACCTGTAGAGCCAGCCAGGGCATCAGCAACTACCTGAACTGGTATCAGCAGAAGCCCGGCAAGGCCC
CTAAGCCTCTGATCTACTACACCAGCAACCTGCAGAGCGGCGTGCCCAGCAGATTTTCTGGCTCTGGCAGCGGCACCGACTACACCCTGACCATA
TCTAGCCTGCAGCCTGAGGACTTCGCCACCTACTACTGCCAGCAGTACGACAGCAGCCCCAGAACATTTGGCGGAGGCACCAAGGTGGAAATCAA
GCGTACGGTGGCCGCCCCCTCCGTGTTCATCTTCCCCCCCTCCGACGAGCAGCTGAAGTCCGGCACCGCCTCCGTGGTGTGCCTGCTGAATAACT
TCTACCCCAGAGAGGCCAAGGTGCAGTGGAAGGTGGACAACGCCCTGCAGTCCGGGAACTCCCAGGAGAGCGTGACCGAGCAGGACAGCAAGGAC
AGCACCTACAGCCTGAGCAGCACCCTGACCCTGAGCAAAGCCGACTACGAGAAGCACAAGGTGTACGCCTGCGAGGTGACCCACCAGGGCCTGAG
CTCCCCCGTCACCAAGAGCTTCAACAGGGGGGAGTGT

Signal sequence1-60, Variable region61-384, Constant region385-702

[Figure 39-5]

SEQ ID NO: 151: Amino acid sequence of #110L12h (each CDR is underlined)
MVLQTQVFISLLLWISGAYGDIQMTQSPSSLSASVGDRVTITCRASQGISNYLNWYQQKPGKAPKPLIYYTSNLGSGVPSRFSGSGSGTDFTLTI
SSLQPEDFATYYCQQYDSSPRTFGGGTKVEIKRTVAAPSVFIFPPSDEQLKSGTASVVCLLNNFYPREAKVQWKVDNALQSGNSQESVTEQDSKD
STYSLSSTLTLSKADYEKHKVYACEVTHQGLSSPVTKSFNRGEC
Signal sequence1-20, Variable region21-128, Constant region129-234

SEQ ID NO: 152: Nucleotide sequence of #110L12h
ATGGTGCTGCAGACCCAGGTGTTCATCTCCCTGCTGCTGTGGATCTCCGGCGCGTACGGCGATATCCAGATGACACAGAGCCCTAGCAGCCTGTC
TGCCAGCGTGGGAGACAGAGTGACCATCACCTGTAGAGCCAGCCAGGGCATCAGCAACTACCTGAACTGGTATCAGCAGAAGCCCGGCAAGGCCC
CTAAGCCTCTGATCTACTACACCAGCAACCTGCAGAGCGGCGTGCCCAGCAGATTTTCTGGCTCTGGCAGCGGCACCGACTTCACCCTGACCATA
TCTAGCCTGCAGCCTGAGGACTTCGCCACCTACTACTGCCAGCAGTACGACAGCAGCCCCAGAACATTTGGCGGAGGCACCAAGGTGGAAATCAA
GCGTACGGTGGCCGCCCCCTCCGTGTTCATCTTCCCCCCCTCCGACGAGCAGCTGAAGTCCGGCACCGCCTCCGTGGTGTGCCTGCTGAATAACT
TCTACCCCAGAGAGGCCAAGGTGCAGTGGAAGGTGGACAACGCCCTGCAGTCCGGGAACTCCCAGGAGAGCGTGACCGAGCAGGACAGCAAGGAC
AGCACCTACAGCCTGAGCAGCACCCTGACCCTGAGCAAAGCCGACTACGAGAAGCACAAGGTGTACGCCTGCGAGGTGACCCACCAGGGCCTGAG
CTCCCCCGTCACCAAGAGCTTCAACAGGGGGGAGTGT
Signal sequence1-60, Variable region61-384, Constant region385-702

[Figure 40-1]

SEQ ID NO: 139: Amino acid sequence of #131H2hIgG2 (each CDR is underlined)
MKHLWFFLLLVAAPRWVLSQVQLVESGGGVVQPGRSLRLSCAASGFTFNNYWMTWVRQAPGKGLEWVASITKAGGSTYYADSVKGRFTISRDNSK
STLYLQMNSLRAEGTAVYYCTRELGEFYVMDAWGQGTTVTVSSASTKGPSVFPLAPCSRSTSESTAALGCLVKDYFPEPVTVSWNSGALTSGVHT
FPAVLQSSGLYSLSSVVTVPSSNFGTQTYTCNVDHKPSNTKVDKTVERKCCVECPPCPAPPVAGPSVFLFPPKPKDTLMISRTPEVTCVVVDVSH
EDPEVQFNWYVDGVEVHNAKTKPREEQFNSTFRVVSVLTVVHQDWLNGKEYKCKVSNKGLPAPIEKTISKTKGQPREPQVYTLPPSREEMTKNQV
SLTCLVKGFYPSDIAVEWESNGQPENNYKTTPPMLDSDGSFFLYSKLTVDKSRWQQGNVFSCSVMHEALHNHYTQKSLSLSPGK
Signal sequence1-19, Variable region20-138, Constant region139-464

SEQ ID NO: 140: Nucleotide sequence of #131H2hIgG2
ATGAAACACCTGTGGTTCTTCCTCCTGCTGGTGGCAGCTCCCAGATGGGTGCTGAGCCAGGTTCAGCTGGTTGAATCTGGTGGCGGAGTGGTGCA
GCCTGGCAGATCTCTGAGACTGTCTTGTGCCGCCAGCGGCTTCACCTTCAACAACTACTGGATGACCTGGGTCCGACAGGCCCCTGGCAAAGGAC
TTGAATGGGTCGCCAGCATCACCAAGGCTGGCGGCTCTACCTACTACGCCGATAGCGTGAAGGGCAGATTCACCATCAGCCGGGACAACAGCAAG
AGCACCCTGTACCTGCAGATGAACAGCCTGAGAGCCGAGGGCACAGCCGTGTACTACTGTACAAGAGAGCTGGGCGAGTTCTACGTGATGGATGC
CTGGGGCCAGGGCACCACAGTTACAGTTAGCTCAGCCTCCACCAAGGGCCCTTCCGTGTTCCCTCTGGCCCCTTGTAGCCGTTCCACCAGCGAGT
CCACCGCCGCCCTTGGCTGTCTGGTGAAGGACTACTTCCCTGAGCCTGTGACCGTGAGCTGGAACTCCGGAGCCCTTACCAGCGGCGTGCACACC
TTCCCTGCCGTGCTGCAGTCCAGCGGCCTTTACTCCCTGAGCTCCGTGGTGACCGTGCCTAGCTCCAACTTCGGCACCCAAACCTACACCTGTAA
CGTGGACCACAAGCCTAGCAACACCAAGGTGGACAAGACCGTGGAGCGTAAGTGTTGTGTGGAGTGTCCTCCTTGTCCTGCCCCTCCTGTGGCCG
GACCTTCCGTGTTCCTTTTCCCTCCTAAGCCTAAGGACACCCTGATGATCAGCCGTACCCCTGAGGTGACCTGTGTGGTGGTGGACGTGTCCCAC
GAGGACCCTGAGGTGCAGTTCAACTGGTACGTGGACGGCGTGGAGGTGCACAACGCCAAGACCAAGCCTCGTGAGGAGCAATTCAACAGCACCTT
CCGTGTGGTGTCCGTGCTTACCGTGGTGCACCAAGACTGGCTGAACGGCAAGGAGTACAAGTGTAAGGTGAGCAACAAGGGACTTCCTGCCCCTA
TCGAGAAGACCATCTCCAAGACCAAGGGCCAACCTCGTGAGCCTCAAGTGTACACCCTTCCTCCTAGCCGTGAGGAGATGACCAAGAACCAAGTG
TCCCTTACCTGTCTGGTGAAGGGCTTCTACCCTAGCGACATCGCCGTGGAGTGGGAGTCCAACGGACAACCTGAGAACAACTACAAGACCACCCC
TCCTATGCTTGACAGCGACGGCTCCTTCTTCCTGTACAGCAAGCTgACCGTGGACAAGTCCCGTTGGCAACAAGGCAACGTGTTCAGCTGTTCCG
TGATGCACGAGGCCCTGCACAACCACTACACCCAAAAGAGCCTTTCCCTGAGCCCTGGAAAG
Signal sequence1-57, Variable region58-414, Constant region415-1392

[Figure 40-2]

SEQ ID NO: 141: Amino acid sequence of #131L2h (each CDR is underlined)
MVLQTQVFISLLLWISGAYGDVQMTQSPSSLSASVGDRVTITCKASKSINTYLAWYQEKPGKTNKLLIYSGSTLQSGTPSRFSGSGSGTDFTLTI
SSLQPEDFATYYCQQHNEYPFTFGQGTKLEIKRTVAAPSVFIFPPSDEQLKSGTASVVCLLNNFYPREAKVQWKVDNALQSGNSQESVTEQDSKD
STYSLSSTLTLSKADYEKHKVYACEVTHQGLSSPVTKSFNRGEC
Signal sequence1-20, Variable region21-128, Constant region129-234

SEQ ID NO: 142: Nucleotide sequence of #131L2h
ATGGTGCTGCAGACCCAGGTGTTCATCTCCCTGCTGCTGTGGATCTCCGGCGCGTACGGCGACGTTCAGATGACACAGAGCCCTAGCAGCCTGTC
TGCCAGCGTGGGAGACAGAGTGACCATCACATGCAAGGCCAGCAAGAGCATCAACACCTACCTGGCCTGGTATCAAGAGAAGCCCGGCAAGACCA
ACAAGCTGCTGATCTACAGCGGCAGCACACTGCAGAGCGGCACCCCTTCTAGATTTTCCGGCTCTGGCAGCGGCACCGACTTCACCCTGACCATA
TCTAGCCTGCAGCCTGAGGACTTCGCCACCTACTACTGCCAGCAGCACAACGAGTACCCCTTCACCTTTGGCCAGGGCACCAAGCTGGAAATCAA
GCGTACGGTGGCCGCCCCCTCCGTGTTCATCTTCCCCCCCTCCGACGAGCAGCTGAAGTCCGGCACCGCCTCCGTGGTGTGCCTGCTGAATAACT
TCTACCCCAGAGAGGCCAAGGTGCAGTGGAAGGTGGACAACGCCCTGCAGTCCGGGAACTCCCAGGAGAGCGTGACCGAGCAGGACAGCAAGGAC
AGCACCTACAGCCTGAGCAGCACCCTGACCCTGAGCAAAGCCGACTACGAGAAGCACAAGGTGTACGCCTGCGAGGTGACCCACCAGGGCCTGAG
CTCCCCCGTCACCAAGAGCTTCAACAGGGGGGAGTGT
Signal sequence1-60, Variable region61-384, Constant region385-702

[Figure 41]
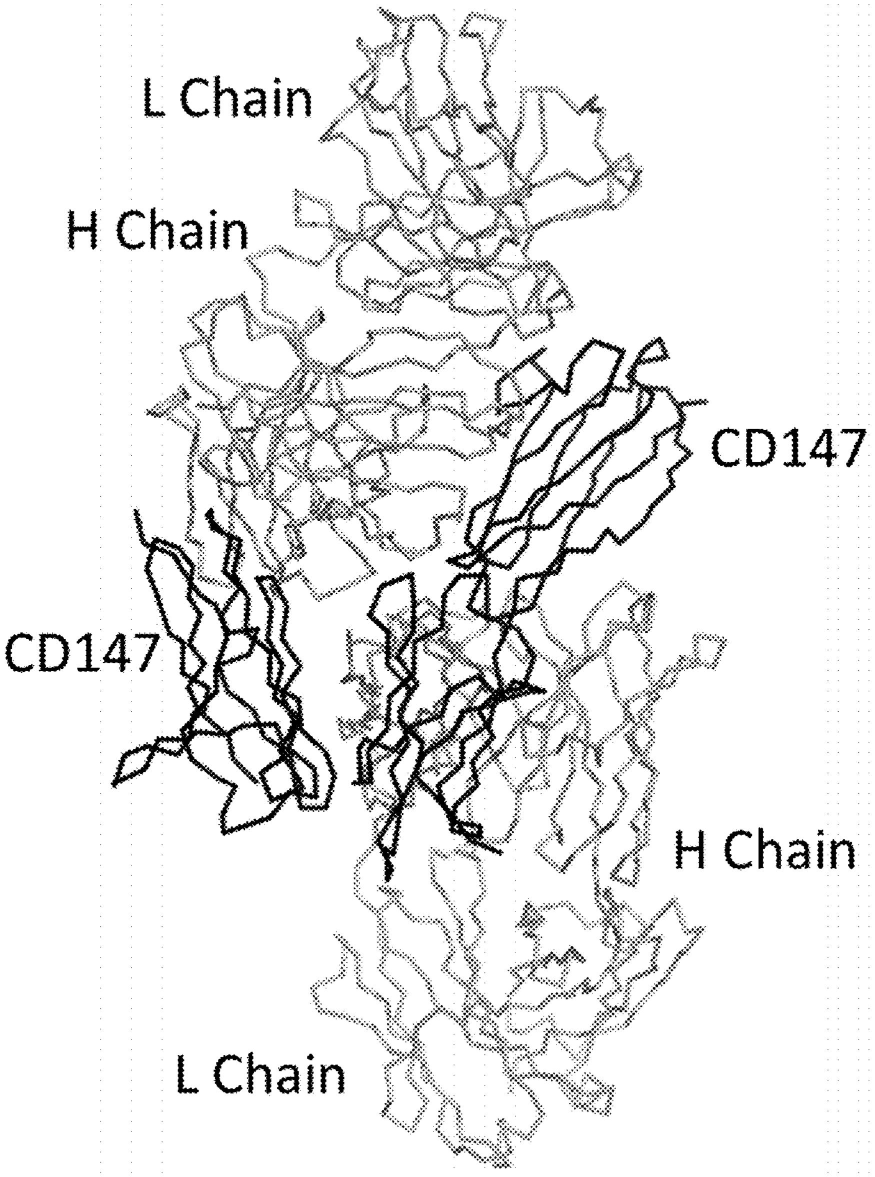

[Figure 42]
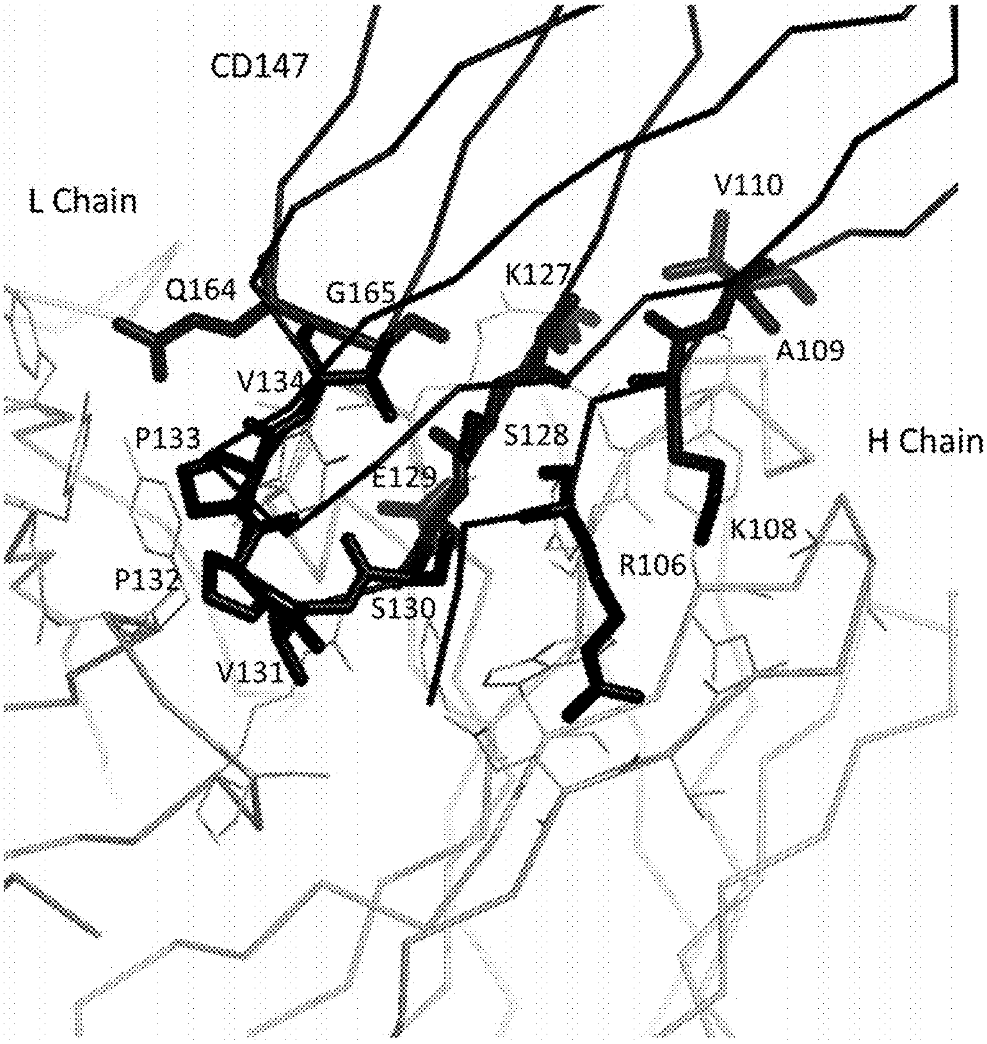

[Figure 43]
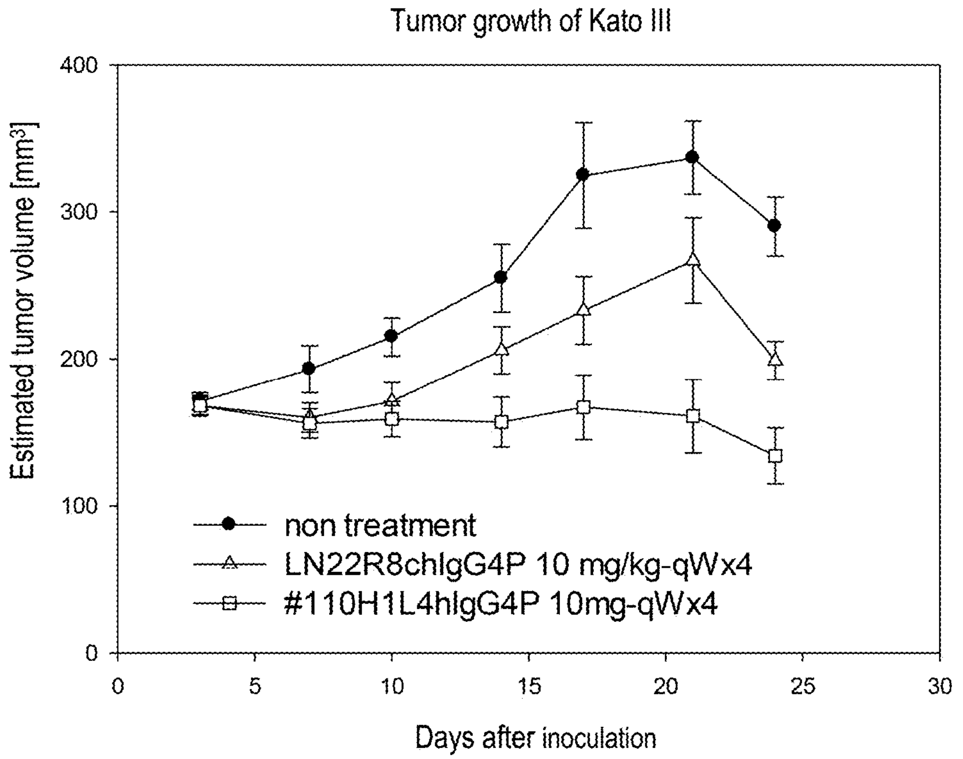
[Figure 44]
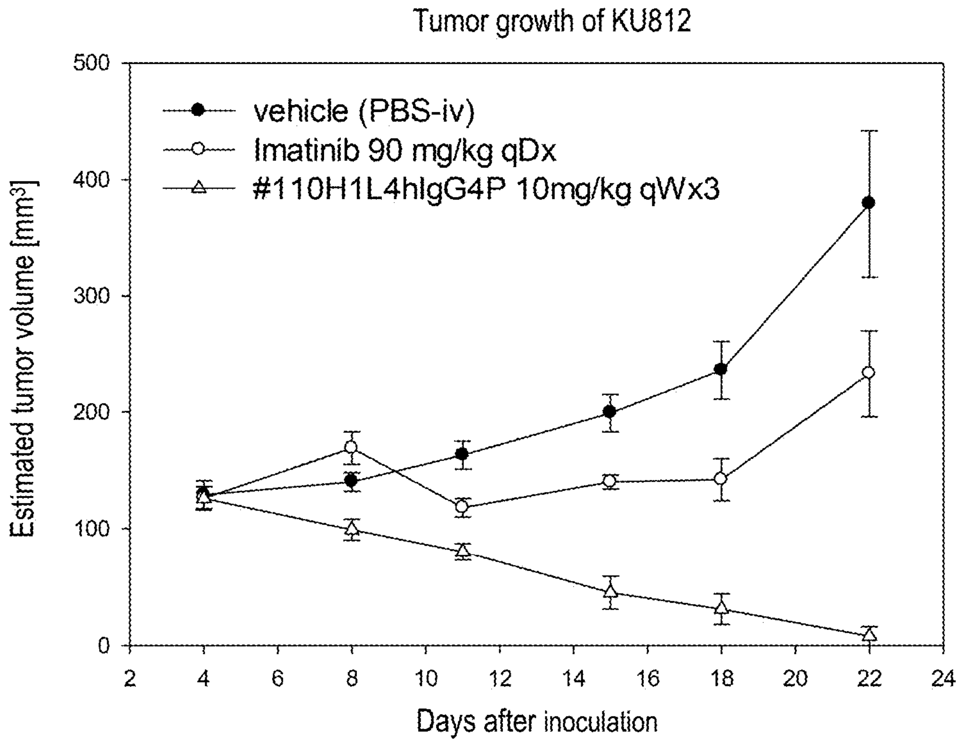

[Figure 45]
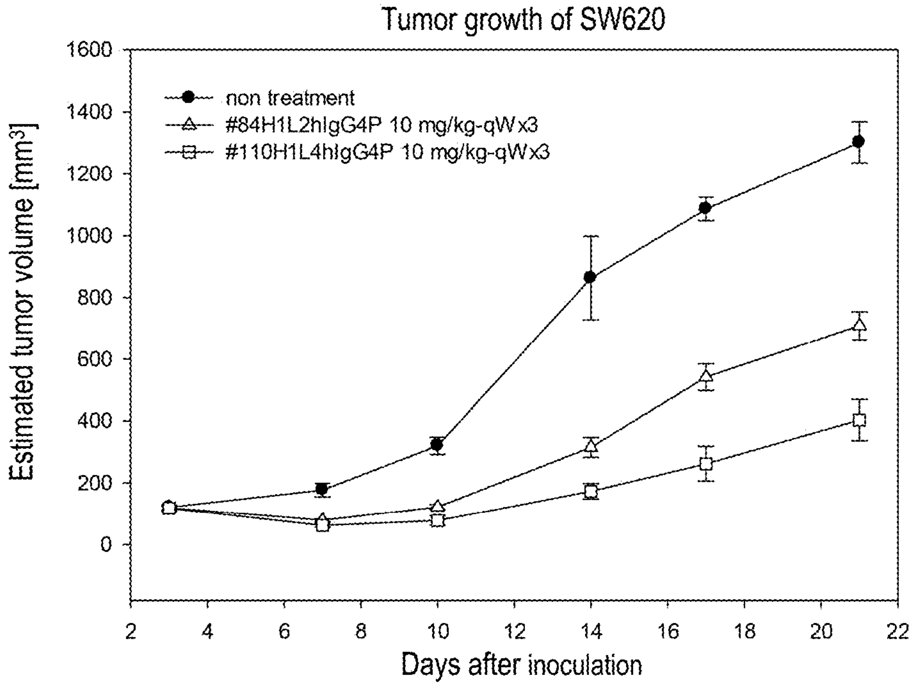
[Figure 46]
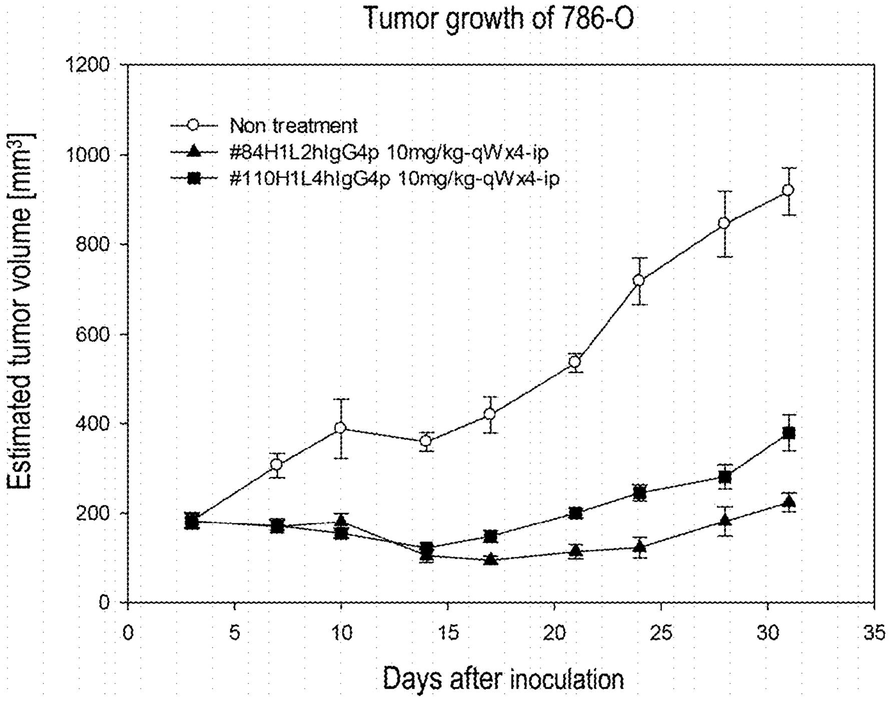

[Figure 47]
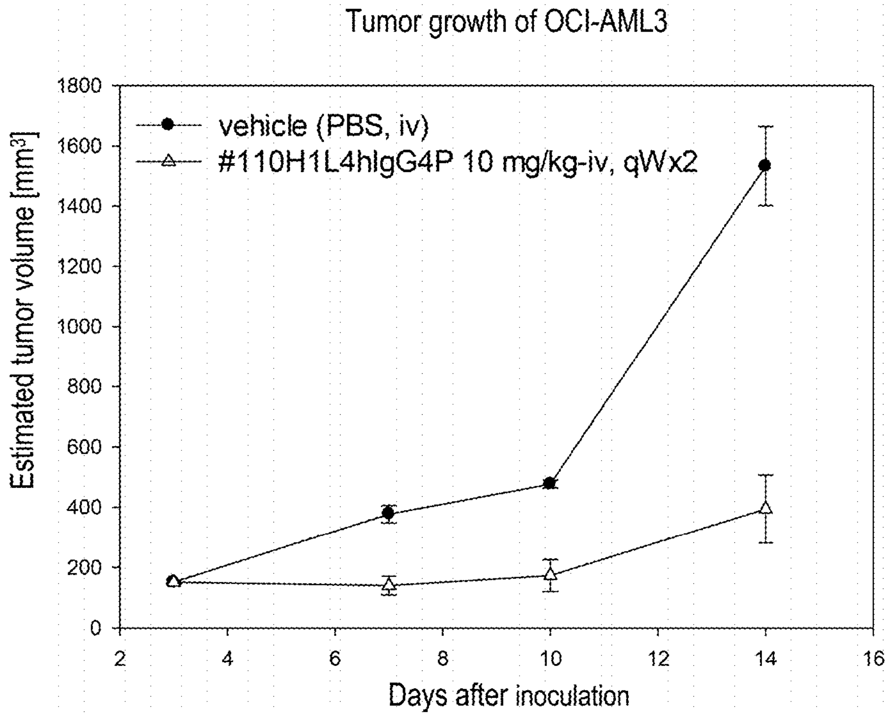
[Figure 48]
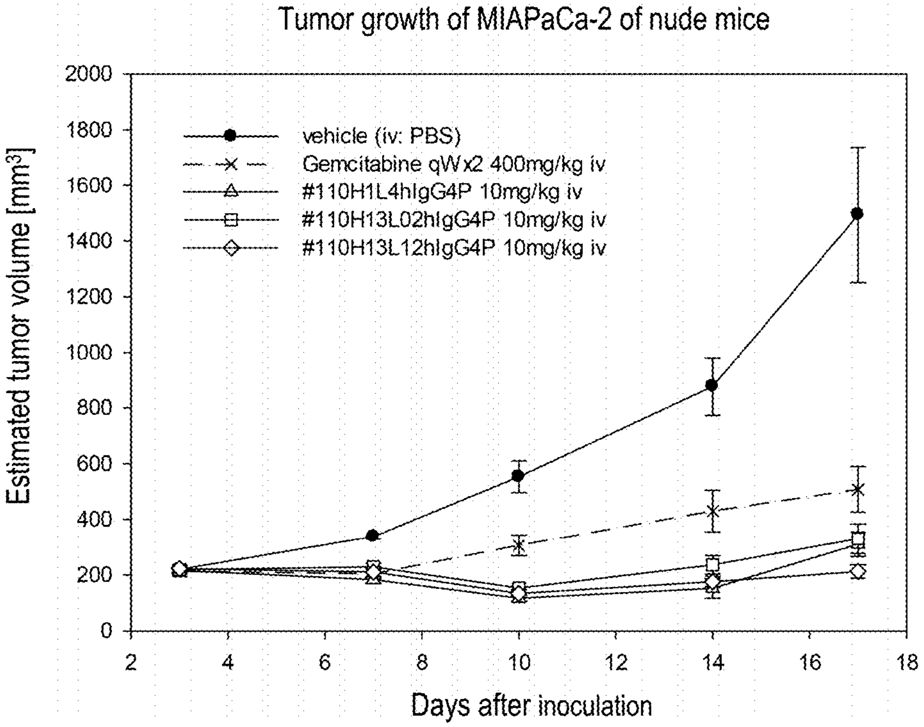

ANTI-CD147 ANTIBODY

CROSS-REFERENCE TO RELATED APPLICATIONS

The present application claims priority under 37 U.S.C. § 371 to International Patent Application No. PCT/JP2018/028047, filed Jul. 26, 2018, which claims priority to and the benefit of Japanese Patent Application No. 2017-145701, filed on Jul. 27, 2017. The contents of these applications are hereby incorporated by reference in their entireties.

SEQUENCE LISTING

The instant application contains a Sequence Listing which has been submitted in ASCII format via EFS-Web and is hereby incorporated by reference in its entirety. Said ASCII copy, is named 098065-0255_SL.txt and is 106 kb in size.

TECHNICAL FIELD

The present invention relates to an anti-CD147 antibody exhibiting potent antitumor efficacy, a method for producing the anti-CD147 antibody, and an antitumor agent comprising the anti-CD147 antibody.

BACKGROUND ART

Advances in methods and remedies for treating cancers have revealed that cancers previously considered to be incurable are treatable and completely curable. A CTLA4 antibody and a PD1 antibody, which have been developed as antibody drugs exhibiting particularly excellent drug stability and specificity, exhibit high objective response rates against, and occasionally cure, melanoma and some solid cancers through activation of immune cells including T cells, bringing good news to cancer patients. Treatments of most intractable solid cancers with these remedies have been attempted. However, most pancreatic cancers and liver cancers, etc., do not show sensitivity to these drugs, and exhibit high recurrence rates even when treated by surgical extraction or treated based on the use of conventional anticancer agents. Hence, treatments and remedies by which cancers can be completely cured are earnestly sought.

CD147 is a single-pass transmembrane protein having 2 to 3 immunoglobulin-like domains, and is known to activate downstream signal-related molecules, such as FAK, MEK, Erk, JAK/STAT, AKT and MAPK family molecules through interactions between multiple CD147 proteins, or through interactions with extracellular or cell membrane surface molecules, such as CD44, Integrin family molecules, CD98, VEGFR, CypA/B, and MCT1/3/4 which are involved in growth, invasion, and inflammation, thereby accelerating the production of proteases such as MMPs, and cancer growth, metastasis, and invasion. Moreover, it has been reported that a high CD147 expression level leads to a short survival period and a poor prognosis. Hence, CD147 is considered as one of the target molecules for cancer treatment.

Antibodies targeting CD147, ABX-CBL and Licartin have, in fact, been administered clinically to humans. ABX-CBL inhibits binding between CD147 and cyclophilin A, and not only suppresses T cell activity, but also exhibits cytotoxic activity against normal cells including CD147-positive T cells in a complement-dependent manner in blood. Clinical trials performed for GVHD as a target disease have revealed insufficient efficacy and have resulted in observations of severe muscle pains, and thus this antibody has not been approved as a drug (Patent Literature 1, Non Patent Literature 1).

Licartin is a biopharmaceutical prepared by adding a radioactive isotope, iodine I 131, to the Fab'2 portion of a HAb18 antibody, and has been approved as a drug in China, the relevant type of cancer being liver cancer (Non Patent Literature 2, Non Patent Literature 3). Licartin lacks the Fc portion of the antibody for activating immune cells and complements, and has not been reported to have immune-mediated toxicity and has not been reported clinically to cure liver cancer completely.

As to other antibodies targeting CD147, an anti-CD147 monoclonal antibody blocking biological activity related to CD147, such as vascularization or VEGF-producing matrix metalloprotease production (Patent Literature 2), an anti-CD147 monoclonal antibody inhibiting T cell activation (Non Patent Literature 4), and an antibody specifically binding to the CD147 molecule characterized by having ADCC activity and CDC activity (Patent Literature 3) are known. However, a CD147 antibody lacking effector functions and exhibiting antitumor efficacy is unknown. Moreover, the association between activation of the cell signal transduction system through CD147 and antitumor efficacy is unknown.

CITATION LIST

Patent Literature

Patent Literature 1: WO1999/045031
Patent Literature 2: WO2010/036460
Patent Literature 3: WO2017/061602

Non Patent Literature

Non Patent Literature 1: Deeg H, et al., J. Blood., 2052-2058, 2001
Non Patent Literature 2: Chen Z, et al., Int. J. Radiation Oncology Biol. Phys., 435-444, 2006
Non Patent Literature 3: Xu J, et al., Hepatology, 269-276, 2007
Non Patent Literature 4: Koch C, et al., International Immunology, 777-786, 1999

SUMMARY OF INVENTION

Problem to be Solved by the Invention

An object of the present invention is to provide a novel anti-CD147 antibody having novel pharmacologic effects, excellent safety, and high antitumor efficacy, a pharmaceutical product comprising the antibody, and a method for treating tumors using the antibody or the pharmaceutical product and the like.

Solution

As a result of intensive studies to achieve the above object, the present inventors have discovered for the first time that the activation of signal-related molecules through CD147 is associated with antitumor efficacy. The present inventors have successfully obtained a CD147-specific antibody activating CD147 and exhibiting high antitumor efficacy. The antibody of the present invention has the feature of exhibiting high antitumor efficacy in a manner independent of effector functions. Antibodies exhibiting antitumor efficacy in an effector function-dependent manner have been reported. However, the antibody of the present invention has the feature of not acting on T cells and PBMC, and exhibiting high antitumor efficacy in a manner independent of effector functions, and thus is an excellent antibody expected to be safe as a pharmaceutical product. The antibody of the present invention exhibits efficacy in liver cancer cells which is remarkably more strong than that of sorafenib that is used as one of the standard care drugs for liver cancer. The antibody of the present invention exhibits efficacy in pancreatic cancer cells which is remarkably more strong than that of gemcitabine that is used as one of the standard of care drugs for pancreatic cancer. The antibody of the present invention exhibits efficacy in chronic myeloid leukemia cells which is remarkably more strong than that of imatinib that is used as one of the standard of care drugs for chronic myeloid leukemia. The present inventors have identified that the CD147 antibody of the present invention activates the p38MAPK and SMAD signal transduction system in cancer cells. The present inventors have identified that the CD147 antibody of the present invention exhibits excellent antitumor efficacy in SMAD4-positive cells.

The invention of the present application encompasses the following aspects.

[1]

An antibody against human CD147 or an antigen-binding fragment thereof, which competes with at least one antibody selected from the group consisting of the following (A) to (F) for binding to human CD147 and which activates signal transduction through CD147:

(A) an antibody comprising a heavy chain variable region consisting of an amino acid sequence represented by SEQ ID NO: 71 and a light chain variable region consisting of an amino acid sequence represented by SEQ ID NO: 69;

(B) an antibody comprising a heavy chain variable region consisting of an amino acid sequence represented by SEQ ID NO: 51 and a light chain variable region consisting of an amino acid sequence represented by SEQ ID NO: 49;

(C) an antibody comprising a heavy chain variable region consisting of an amino acid sequence represented by SEQ ID NO: 61 and a light chain variable region consisting of an amino acid sequence represented by SEQ ID NO: 59, (D) an antibody comprising a heavy chain variable region consisting of an amino acid sequence represented by SEQ ID NO: 81 and a light chain variable region consisting of an amino acid sequence represented by SEQ ID NO: 79;

(E) an antibody comprising a heavy chain variable region consisting of an amino acid sequence represented by SEQ ID NO: 10 and a light chain variable region consisting of an amino acid sequence represented by SEQ ID NO: 8; and (F) an antibody comprising a heavy chain variable region consisting of an amino acid sequence represented by SEQ ID NO: 20 and a light chain variable region consisting of an amino acid sequence represented by SEQ ID NO: 18.

[2]

An antibody against human CD147 or an antigen-binding fragment thereof, which binds to an epitope to which at least one antibody selected from the group consisting of the following (A) to (F) binds, and which activates signal transduction through CD147:

(A) an antibody comprising a heavy chain variable region consisting of an amino acid sequence represented by SEQ ID NO: 71 and a light chain variable region consisting of an amino acid sequence represented by SEQ ID NO: 69;

(B) an antibody comprising a heavy chain variable region consisting of an amino acid sequence represented by SEQ ID NO: 51 and a light chain variable region consisting of an amino acid sequence represented by SEQ ID NO: 49;

(C) an antibody comprising a heavy chain variable region consisting of an amino acid sequence represented by SEQ ID NO: 61 and a light chain variable region consisting of an amino acid sequence represented by SEQ ID NO: 59;

(D) an antibody comprising a heavy chain variable region consisting of an amino acid sequence represented by SEQ ID NO: 81 and a light chain variable region consisting of an amino acid sequence represented by SEQ ID NO: 79;

(E) an antibody comprising a heavy chain variable region consisting of an amino acid sequence represented by SEQ ID NO: 10 and a light chain variable region consisting of an amino acid sequence represented by SEQ ID NO: 8; and (F) an antibody comprising a heavy chain variable region consisting of an amino acid sequence represented by SEQ ID NO: 20 and a light chain variable region consisting of an amino acid sequence represented by SEQ ID NO: 18.

[3]

The antibody against human CD147 or the antigen-binding fragment thereof according to [1] or [2], which has decreased ADCC activity or lacks ADCC activity.

[4]

The antibody against human CD147 or the antigen-binding fragment thereof according to any one of [1] to [3], which has decreased CDC activity or lacks CDC activity.

[5]

The antibody against human CD147 or the antigen-binding fragment thereof according to any one of [1] to [4], which has decreased ADCP activity or lacks ADCP activity.

[6]

The antibody or the antigen-binding fragment thereof according to any one of [1] to [5], which binds to an epitope comprising residues of arginine (Arg) at position 106 to glycine (Gly) at position 165 in SEQ ID NO: 3.

[7]

The antibody or the antigen-binding fragment thereof according to any one of [1] to [6], which binds to an epitope comprising residues of arginine (Arg) at position 106, lysine (Lys) at position 108, alanine (Ala) at position 109, valine (Val) at position 110, lysine (Lys) at position 127, serine (Ser) at position 128, glutamic acid (Glu) at position 129, serine (Ser) at position 130, valine (Val) at position 131, proline (Pro) at position 132, proline (Pro) at position 133, valine (Val) at position 134, glutamine (Gln) at position 164 and glycine (Gly) at position 165 in the amino acid sequence set forth in SEQ ID NO: 3.

[8]

The antibody or the antigen-binding fragment thereof according to any one of [1] to [7], wherein:

in the heavy chain sequence, which comprises a variable region having CDRH1, CDRH2 and CDRH3, the CDRH1 consists of an amino acid sequence represented by SEQ ID NO: 75, the CDRH2 consists of an amino acid sequence represented by SEQ ID NO: 76, and the CDRH3 consists of an amino acid sequence represented by SEQ ID NO: 77; and in the light chain sequence, which comprises a variable region having CDRL1, CDRL2 and CDRL3, the CDRL1 consists of an amino acid sequence represented by SEQ ID NO: 72, the CDRL2 consists of an amino acid sequence represented by SEQ ID NO: 73, and the CDRL3 consists of an amino acid sequence represented by SEQ ID NO: 74.

[9]

The antibody or the antigen-binding fragment thereof according to any one of [1] to [5], which binds to an epitope comprising an amino acid sequence set forth in SEQ ID NO:

143 or an amino acid sequence in which one or several amino acids are deleted, substituted or added in the sequence of SEQ ID NO: 143.

[10]

The antibody or the antigen-binding fragment thereof according to any one of [1] to [5] or [9], wherein:

in the heavy chain sequence, which comprises a variable region having CDRH1, CDRH2 and CDRH3, the CDRH1 consists of an amino acid sequence represented by SEQ ID NO: 55, the CDRH2 consists of an amino acid sequence represented by SEQ ID NO: 56, and the CDRH3 consists of an amino acid sequence represented by SEQ ID NO: 57; and in the light chain sequence, which comprises a variable region having CDRL1, CDRL2 and CDRL3, the CDRL1 consists of an amino acid sequence represented by SEQ ID NO: 52, the CDRL2 consists of an amino acid sequence represented by SEQ ID NO: 53, and the CDRL3 consists of an amino acid sequence represented by SEQ ID NO: 54.

[11]

The antibody or the antigen-binding fragment thereof according to any one of [1] to [5] or [9], wherein:

in the heavy chain sequence, which comprises a variable region having CDRH1, CDRH2 and CDRH3, the CDRH1 consists of an amino acid sequence represented by SEQ ID NO: 65, the CDRH2 consists of an amino acid sequence represented by SEQ ID NO: 66, and the CDRH3 consists of an amino acid sequence represented by SEQ ID NO: 67; and in the light chain sequence, which comprises a variable region having CDRL1, CDRL2 and CDRL3, the CDRL1 consists of an amino acid sequence represented by SEQ ID NO: 62, the CDRL2 consists of an amino acid sequence represented by SEQ ID NO: 63, and the CDRL3 consists of an amino acid sequence represented by SEQ ID NO: 64.

[12]

The antibody or the antigen-binding fragment thereof according to any one of [1] to [5] or [9], wherein:

in the heavy chain sequence, which comprises a variable region having CDRH1, CDRH2 and CDRH3, the CDRH1 consists of an amino acid sequence represented by SEQ ID NO: 85, the CDRH2 consists of an amino acid sequence represented by SEQ ID NO: 86, and the CDRH3 consists of an amino acid sequence represented by SEQ ID NO: 87; and in the light chain sequence, which comprises a variable region having CDRL1, CDRL2 and CDRL3, the CDRL1 consists of an amino acid sequence represented by SEQ ID NO: 82, the CDRL2 consists of an amino acid sequence represented by SEQ ID NO: 83, and the CDRL3 consists of an amino acid sequence represented by SEQ ID NO: 84.

[13]

The antigen-binding fragment of the antibody according to any one of [1] to [12], which is selected from the group consisting of Fab, F(ab')2, Fab' and Fv.

[14]

The antibody according to any one of [1] to [12], which is scFv.

[15]

The antibody or the antigen-binding fragment thereof according to any one of [1] to [12], which is a chimeric antibody.

[16]

The antibody or the antigen-binding fragment thereof according to any one of [1] to [12], which is humanized.

[17]

The antibody according to any one of [1] to [16], wherein the heavy chain comprises a human immunoglobulin G1 heavy chain constant region, a human immunoglobulin G2 heavy chain constant region or a human immunoglobulin G4 heavy chain constant region, and the light chain comprises a human immunoglobulin κ light chain constant region.

[18]

The antibody according to [17], wherein the heavy chain comprises the human immunoglobulin G4 heavy chain constant region.

[19]

The antibody according to [18], wherein within the human immunoglobulin G4 heavy chain constant region, the serine (Ser) at position 228 as indicated by the EU index is substituted with a proline (Pro).

[20]

The antibody according to [18], wherein within the human immunoglobulin G4 heavy chain constant region, the phenylalanine (Phe) at position 234 as indicated by the EU index is substituted with an alanine (Ala), and the leucine (Leu) at position 235 as indicated by the EU index is substituted with an alanine (Ala).

[21]

The antibody according to [18], wherein within the human immunoglobulin G4 heavy chain constant region, the serine (Ser) at position 228 as indicated by the EU index is substituted with a proline (Pro), the phenylalanine (Phe) at position 234 as indicated by the EU index is substituted with an alanine (Ala), and the leucine (Leu) at position 235 as indicated by the EU index is substituted with an alanine (Ala).

[22]

The antibody according to [17], wherein the heavy chain comprises the human immunoglobulin G2 heavy chain constant region.

[23]

An antibody against human CD147 or an antigen-binding fragment thereof, which comprises the following (c) and (d), and activates signal transduction through CD147:

(c) a heavy chain variable region selected from the group consisting of the following (c1) to (c4):

(c1) a heavy chain variable region consisting of amino acid residues at positions 20 to 136 in an amino acid sequence represented by SEQ ID NO: 135;

(c2) a heavy chain variable region consisting of amino acid residues at positions 20 to 136 in an amino acid sequence represented by SEQ ID NO: 147;

(c3) an amino acid sequence having at least 95% or more sequence identity with the sequence of a framework region outside each CDR sequence in the sequence of (c1) or (c2); and (c4) an amino acid sequence in which one or several amino acids are deleted, substituted, or added in the sequence of a framework region outside each CDR sequence in the sequence according to any one of (c1) to (c3); and (d) a light chain variable region selected from the group consisting of the following (d1) to (d5):

(d1) a light chain variable region consisting of amino acid residues at positions 21 to 128 in an amino acid sequence represented by SEQ ID NO: 137;

(d2) a light chain variable region consisting of amino acid residues at positions 21 to 128 in an amino acid sequence represented by SEQ ID NO: 149;

(d3) a light chain variable region consisting of amino acid residues at positions 21 to 128 in an amino acid sequence represented by SEQ ID NO: 151;

(d4) an amino acid sequence having at least 95% or more sequence identity with the sequence of a framework region outside each CDR sequence in the sequence according to any one of (d1) to (d3); and (d5) an amino acid sequence in which one or several amino acids are deleted, substituted, or added in the sequence of a framework region outside each CDR sequence in the sequence according to any one of (d1) to (d4).

[24]

The antibody or the antigen-binding fragment thereof according to [23], which comprises:

the heavy chain variable region consisting of amino acid residues at positions 20 to 136 in the amino acid sequence represented by SEQ ID NO: 135; and the light chain variable region consisting of amino acid residues at positions 21 to 128 in the amino acid sequence represented by SEQ ID NO: 137.

[25]

The antibody or the antigen-binding fragment thereof according to [23], which comprises:

the heavy chain consisting of amino acid residues at positions 20 to 463 in the amino acid sequence represented by SEQ ID NO: 135; and the light chain consisting of amino acid residues at positions 21 to 234 in the amino acid sequence represented by SEQ ID NO: 137.

[26]

The antibody or the antigen-binding fragment thereof according to [23], which comprises:

the heavy chain variable region consisting of amino acid residues at positions 20 to 136 in the amino acid sequence represented by SEQ ID NO: 147; and the light chain variable region consisting of amino acid residues at positions 21 to 128 in the amino acid sequence represented by SEQ ID NO: 149.

[27]

The antibody or the antigen-binding fragment thereof according to [23], which comprises:

the heavy chain consisting of amino acid residues at positions 20 to 463 in the amino acid sequence represented by SEQ ID NO: 147; and the light chain consisting of amino acid residues at positions 21 to 234 in the amino acid sequence represented by SEQ ID NO: 149.

[28]

The antibody or the antigen-binding fragment thereof according to [23], which comprises:

the heavy chain variable region consisting of amino acid residues at positions 20 to 136 in the amino acid sequence represented by SEQ ID NO: 147; and the light chain variable region consisting of amino acid residues at positions 21 to 128 in the amino acid sequence represented by SEQ ID NO: 151.

[29]

The antibody or the antigen-binding fragment thereof according to [23], which comprises:

the heavy chain consisting of amino acid residues at positions 20 to 463 in the amino acid sequence represented by SEQ ID NO: 147; and the light chain consisting of amino acid residues at positions 21 to 234 in the amino acid sequence represented by SEQ ID NO: 151.

[30]

An antibody against human CD147 or an antigen-binding fragment thereof, which comprises the following (a) and (b), and activates signal transduction through CD147:

(a) a heavy chain variable region selected from the group consisting of the following (a1) to (a4):

(a1) a heavy chain variable region consisting of amino acid residues at positions 20 to 140 in an amino acid sequence represented by SEQ ID NO: 123;

(a2) a heavy chain variable region consisting of amino acid residues at positions 20 to 140 in an amino acid sequence represented by SEQ ID NO: 125;

(a3) an amino acid sequence having at least 95% or more sequence identity with the sequence of a framework region outside each CDR sequence in the sequence of (a1) or (a2); and (a4) an amino acid sequence in which one or several amino acids are deleted, substituted, or added in the sequence of a framework region outside each CDR sequence in the sequence according to any one of (a1) to (a3); and (b) a light chain variable region selected from the group consisting of the following (b1) to (b3):

(b1) a light chain variable region consisting of amino acid residues at positions 21 to 128 in an amino acid sequence represented by SEQ ID NO: 127;

(b2) an amino acid sequence having at least 95% or more sequence identity with the sequence of a framework region outside each CDR sequence in the sequence of (b1); and (b3) an amino acid sequence in which one or several amino acids are deleted, substituted, or added in the sequence of a framework region outside each CDR sequence in the sequence of (b1) or (b2).

[31]

The antibody or the antigen-binding fragment thereof according to [30], which comprises:

the heavy chain variable region consisting of amino acid residues at positions 20 to 140 in the amino acid sequence represented by SEQ ID NO: 123 or the heavy chain variable region consisting of amino acid residues at positions 20 to 140 in the amino acid sequence represented by SEQ ID NO: 125; and the light chain variable region consisting of amino acid residues at positions 21 to 128 in the amino acid sequence represented by SEQ ID NO: 127.

[32]

The antibody or the antigen-binding fragment thereof according to [30], which comprises:

the heavy chain consisting of amino acid residues at positions 20 to 466 in the amino acid sequence represented by SEQ ID NO: 123 or the heavy chain consisting of amino acid residues at positions 20 to 467 in the amino acid sequence represented by SEQ ID NO: 125; and the light chain consisting of amino acid residues at positions 21 to 234 in the amino acid sequence represented by SEQ ID NO: 127.

[33]

An antibody against human CD147 or an antigen-binding fragment thereof, which comprises the following (e) and (f), and activates signal transduction through CD147:

(e) a heavy chain variable region selected from the group consisting of the following (e1) to (e4):

(e1) a heavy chain variable region consisting of amino acid residues at positions 20 to 137 in an amino acid sequence represented by SEQ ID NO: 129;

(e2) a heavy chain variable region consisting of amino acid residues at positions 20 to 137 in an amino acid sequence represented by SEQ ID NO: 131;

(e3) an amino acid sequence having at least 95% or more sequence identity with the sequence of a framework region outside each CDR sequence in the sequence of (e1) or (e2); and (e4) an amino acid sequence in which one or several amino acids are deleted, substituted, or added in the sequence of a framework region outside each CDR sequence in the sequence according to any one of (e1) to (e3); and (f) a light chain variable region selected from the group consisting of the following (f1) to (f3):

(f1) a light chain variable region consisting of amino acid residues at positions 21 to 128 in an amino acid sequence represented by SEQ ID NO: 133;

(f2) an amino acid sequence having at least 95% or more sequence identity with the sequence of a framework region outside each CDR sequence in the sequence of (f1); and (f3) an amino acid sequence in which one or several amino acids are deleted, substituted, or added in the sequence of a framework region outside each CDR sequence in the sequence of (f1) or (f2).

[34]

The antibody or the antigen-binding fragment thereof according to [33], which comprises:

the heavy chain variable region consisting of amino acid residues at positions 20 to 137 in the amino acid sequence represented by SEQ ID NO: 129 or the heavy chain variable region consisting of amino acid residues at positions 20 to 137 in the amino acid sequence represented by SEQ ID NO: 131; and the light chain variable region consisting of amino acid residues at positions 21 to 128 in the amino acid sequence represented by SEQ ID NO: 133.

[35]

The antibody or the antigen-binding fragment thereof according to [33], which comprises:

the heavy chain consisting of amino acid residues at positions 20 to 463 in the amino acid sequence represented by SEQ ID NO: 129 or the heavy chain consisting of amino acid residues at positions 20 to 464 in the amino acid sequence represented by SEQ ID NO: 131; and the light chain consisting of amino acid residues at positions 21 to 234 in the amino acid sequence represented by SEQ ID NO: 133.

[36]

An antibody against human CD147 or an antigen-binding fragment thereof, which comprises the following (g) and (h), and activates signal transduction through CD147:

(g) a heavy chain variable region selected from the group consisting of the following (g1) to (g3):

(g1) a heavy chain variable region consisting of amino acid residues at positions 20 to 138 in an amino acid sequence represented by SEQ ID NO: 139;

(g2) an amino acid sequence having at least 95% or more sequence identity with the sequence of a framework region outside each CDR sequence in the sequence of (g1); and (g3) an amino acid sequence in which one or several amino acids are deleted, substituted, or added in the sequence of a framework region outside each CDR sequence in the sequence of (g1) or (g2); and (h) a light chain variable region selected from the group consisting of the following (h1) to (h3):

(h1) a light chain variable region consisting of amino acid residues at positions 21 to 128 in an amino acid sequence represented by SEQ ID NO: 141;

(h2) an amino acid sequence having at least 95% or more sequence identity with the sequence of a framework region outside each CDR sequence in the sequence of (h1); and (h3) an amino acid sequence in which one or several amino acids are deleted, substituted, or added in the sequence of a framework region outside each CDR sequence in the sequence of (h1) or (h2).

[37]

The antibody or the antigen-binding fragment thereof according to [36], which comprises:

the heavy chain variable region consisting of amino acid residues at positions 20 to 138 in the amino acid sequence represented by SEQ ID NO: 139; and the light chain variable region consisting of amino acid residues at positions 21 to 128 in the amino acid sequence represented by SEQ ID NO: 141.

[38]

The antibody or the antigen-binding fragment thereof according to [36], which comprises:

the heavy chain consisting of amino acid residues at positions 20 to 464 in the amino acid sequence represented by SEQ ID NO: 139; and the light chain consisting of amino acid residues at positions 21 to 234 in the amino acid sequence represented by SEQ ID NO: 141.

[39]

The antibody against human CD147 or the antigen-binding fragment thereof according to any one of [23] to [38], which has decreased ADCC activity or lacks ADCC activity.

[40]

The antibody against human CD147 or the antigen-binding fragment thereof according to any one of [23] to [39], which has decreased CDC activity or lacks CDC activity.

[41]

The antibody against human CD147 or the antigen-binding fragment thereof according to any one of [23] to [40], which has decreased ADCP activity or lacks ADCP activity.

[42]

A pharmaceutical composition comprising at least one of the antibodies or antigen-binding fragments thereof according to any one of [1] to [41].

[43]

The pharmaceutical composition according to [42], which is an antitumor agent.

[44]

The pharmaceutical composition according to [43], wherein the tumor is a tumor expressing CD147.

[45]

The pharmaceutical composition according to [43] or [44], wherein the tumor is pancreatic cancer, liver cancer, gastric cancer, colon cancer, renal cancer, breast cancer, uterine cancer, ovarian cancer, lung cancer, lymphoma, thyroid cancer, skin cancer, head and neck cancer, sarcoma, prostate cancer, bladder cancer, brain tumor, gastrointestinal stromal tumor (GIST), leukemia, acute myeloid leukemia (AML), chronic myeloid leukemia (CML), chronic lymphocytic leukemia (CLL), acute lymphocytic leukemia (ALL), malignant lymphoma, B-cell lymphoma, non-Hodgkin's lymphoma or diffuse large B-cell lymphoma (DLBCL).

[46]

The pharmaceutical composition according to any one of [43] to [45], wherein the tumor is pancreatic cancer, liver cancer, gastric cancer, colon cancer, renal cancer, leukemia, acute myeloid leukemia (AML), chronic myeloid leukemia (CML), chronic lymphocytic leukemia (CLL), acute lymphocytic leukemia (ALL), malignant lymphoma, B-cell lymphoma, non-Hodgkin's lymphoma or diffuse large B-cell lymphoma (DLBCL).

[47]

The pharmaceutical composition according to any one of [43] to [46], wherein the tumor is a SMAD4-positive tumor or a tumor having a decreased expression level of or lacking the expression of KLF5.

[48]

The pharmaceutical composition according to any one of [42] to [47], further comprising another antitumor agent.

[49]

A method for treating a tumor, comprising administering the antibody or the antigen-binding fragment thereof according to any one of [1] to [41] or the pharmaceutical composition according to any one of [42] to [48] to a patient.

[50]

The method according to [49], wherein the tumor is a tumor expressing CD147.

[51]

The method according to any one of [49] or [50], wherein the tumor is pancreatic cancer, liver cancer, gastric cancer, colon cancer, renal cancer, breast cancer, uterine cancer, ovarian cancer, lung cancer, lymphoma, thyroid cancer, skin cancer, head and neck cancer, sarcoma, prostate cancer, bladder cancer, brain tumor, gastrointestinal stromal tumor (GIST), leukemia, acute myeloid leukemia (AML), chronic myeloid leukemia (CML), chronic lymphocytic leukemia (CLL), acute lymphocytic leukemia (ALL), malignant lymphoma, B-cell lymphoma, non-Hodgkin's lymphoma or diffuse large B-cell lymphoma (DLBCL).

[52]

The method according to any one of [49] to [51], wherein the tumor is pancreatic cancer, liver cancer, gastric cancer, colon cancer, renal cancer, leukemia, acute myeloid leukemia(AML), chronic myeloid leukemia (CML), chronic lymphocytic leukemia (CLL), acute lymphocytic leukemia (ALL), malignant lymphoma, B-cell lymphoma, non-Hodgkin's lymphoma or diffuse large B-cell lymphoma (DLBCL).

[53]

The method according to any one of [49] to [52], wherein the tumor is a SMAD4-positive tumor or a tumor having a decreased expression level of or lacking the expression of KLF5.

[54]

The method according to any one of [49] to [53], wherein the antibody or the antigen-binding fragment thereof, or the pharmaceutical composition is administered in combination with another antitumor agent.

[55]

A polynucleotide which encodes the antibody or the antigen-binding fragment thereof according to any one of [1] to [41].

[56]

The polynucleotide according to [55], which comprises a polynucleotide selected from the group consisting of the following (j1) to (j3):

(j1) a polynucleotide encoding CDRH1 consisting of an amino acid sequence represented by SEQ ID NO: 75, CDRH2 consisting of an amino acid sequence represented by SEQ ID NO: 76 and CDRH3 consisting of an amino acid sequence represented by SEQ ID NO: 77, and a polynucleotide encoding CDRL1 consisting of an amino acid sequence represented by SEQ ID NO: 72, CDRL2 consisting of an amino acid sequence represented by SEQ ID NO: 73 and CDRL3 consisting of an amino acid sequence represented by SEQ ID NO: 74;

(j2) a polynucleotide having at least 95% sequence identity with the nucleotide sequence according to (j1); and (j3) a polynucleotide in which one to several nucleotides are substituted, deleted or added in the polynucleotide according to (j1) or (j2).

[57]

The polynucleotide according to [55], which comprises a polynucleotide selected from the group consisting of the following (i1) to (i3):

(i1) a polynucleotide encoding CDRH1 consisting of an amino acid sequence represented by SEQ ID NO: 55, CDRH2 consisting of an amino acid sequence represented by SEQ ID NO: 56 and CDRH3 consisting of an amino acid sequence represented by SEQ ID NO: 57, and a polynucleotide encoding CDRL1 consisting of an amino acid sequence represented by SEQ ID NO: 52, CDRL2 consisting of an amino acid sequence represented by SEQ ID NO: 53 and CDRL3 consisting of an amino acid sequence represented by SEQ ID NO: 54;

(i2) a polynucleotide having at least 95% sequence identity with the nucleotide sequence according to (i1); and (i3) a polynucleotide in which one to several nucleotides are substituted, deleted or added in the polynucleotide according to (i1) or (i2).

[58]

The polynucleotide according to [55], which comprises a polynucleotide selected from the group consisting of the following (k1) to (k3):

(k1) a polynucleotide encoding CDRH1 consisting of an amino acid sequence represented by SEQ ID NO: 65, CDRH2 consisting of an amino acid sequence represented by SEQ ID NO: 66 and CDRH3 consisting of an amino acid sequence represented by SEQ ID NO: 67, and a polynucleotide encoding CDRL1 consisting of an amino acid sequence represented by SEQ ID NO: 62, CDRL2 consisting of an amino acid sequence represented by SEQ ID NO: 63 and CDRL3 consisting of an amino acid sequence represented by SEQ ID NO: 64;

(k2) a polynucleotide having at least 95% sequence identity with the nucleotide sequence according to (k1); and (k3) a polynucleotide in which one to several nucleotides are substituted, deleted or added in the polynucleotide according to (k1) or (k2).

[59]

The polynucleotide according to [55], which comprises a polynucleotide selected from the group consisting of the following (m1) to (m3):

(m1) a polynucleotide encoding CDRH1 consisting of an amino acid sequence represented by SEQ ID NO: 85, CDRH2 consisting of an amino acid sequence represented by SEQ ID NO: 86 and CDRH3 consisting of an amino acid sequence represented by SEQ ID NO: 87, and a polynucleotide encoding CDRL1 consisting of an amino acid sequence represented by SEQ ID NO: 82, CDRL2 consisting of an amino acid sequence represented by SEQ ID NO: 83 and CDRL3 consisting of an amino acid sequence represented by SEQ ID NO: 84;

(m2) a polynucleotide having at least 95% sequence identity with the nucleotide sequence according to (m1); and (m3) a polynucleotide in which one to several nucleotides are substituted, deleted or added in the polynucleotide according to (m1) or (m2).

[60]

An expression vector comprising the polynucleotide according to any one of [55] to [59].

[61]

A host cell transformed with the expression vector according to [60].

[62]

A method for producing the antibody or the antigen-binding fragment thereof according to any one of [1] to [41], comprising a step of culturing the host cell according to [61] and collecting a target antibody or an antigen-binding fragment thereof from a culture supernatant.

[63]

The antibody or the antigen-binding fragment thereof according to any one of [1] to [41], wherein the activation of signal transduction through CD147 is an activation of p38 and/or an activation of SMAD4.

[64]

The antibody or the antigen-binding fragment thereof according to [63], wherein the activation of p38MAPK and/or the activation of SMAD4 is an increase in p38MAPK expression level, the phosphorylation of p38MAPK, the phosphorylation of HSP27, an increase in CXCL8 expression level, an increase in rhoB expression level, a decrease in KLF5 mRNA or a decrease in KLF5 protein expression level.

[65]

A method for treating a tumor, comprising administering the antibody or the antigen-binding fragment thereof according to [63] or [64].

[66]

A method for predicting responsiveness to cancer treatment, comprising:

detecting the expression of SMAD4 or the expression of KLF5 in a biological sample derived from a cancer patient; and determining a patient's responsiveness to cancer treatment with the antibody or the antigen-binding fragment thereof according to any one of [1] to [41] or the pharmaceutical composition according to any one of [42] to [48] to be positive, when SMAD4 expression is detected in the patient, or a decrease in KLF5 expression level or a lack of KLF5 expression is detected in the patient.

[67]

A method for selecting subjects for cancer treatment, comprising:

detecting the expression of SMAD4 or the expression of KLF5 in a biological sample derived from a cancer patient; and selecting a patient as a subject of cancer treatment with the antibody or the antigen-binding fragment thereof according to any one of [1] to [41] or the pharmaceutical composition according to any one of [42] to [48], when SMAD4 expression is detected in the patient or a decrease in KLF5 expression level or a lack of KLF5 expression is detected in the patient.

[68]

A method for treating cancer, comprising:

using a biological sample derived from a cancer patient to detect the presence or the absence of the expression of SMAD4 or to detect the expression of KLF5 in the biological sample; and administering the antibody or the antigen-binding fragment thereof according to any one of [1] to [41] or the pharmaceutical composition according to any one of [42] to [48] to a patient in whom SMAD4 expression is detected or to a patient in whom a decrease in KLF5 expression level or a lack of KLF5 expression is detected.

[69]

A kit for determining responsiveness to cancer treatment with the antibody or the antigen-binding fragment thereof according to any one of [1] to [41] or the pharmaceutical composition according to any one of [42] to [48], the kit comprising at least one means for detecting the expression of SMAD4 or the expression of KLF5 in a biological sample derived from a cancer patient.

[70]

An antibody-drug complex comprising the antibody or the antigen-binding fragment thereof according to any one of [1] to [41] conjugated to another drug.

[71]

A bispecific antibody comprising: the antigen-binding fragment of the antibody according to any one of [1] to [41]; and an antigen-binding fragment which binds to an antigen other than CD147.

Advantageous Effects of Invention

The antibody of the present invention is an antibody that specifically recognizes CD147, and is characterized by activating signal-related molecules through CD147, and having high antitumor efficacy. CD147 is expressed not only in tumor cells, but also in blood cells. However, the antibody of the present invention does not act on T cells or PBMC and is independent of effector functions, and thus has an advantage of posing fewer safety concerns in development thereof as an antitumor agent. The antibody of the present invention exhibits extremely high antitumor efficacy. The antibody of the present invention exhibits efficacy in liver cancer cells which is remarkably more strong than that of sorafenib that is used as one of the standard of care drugs for liver cancer. The antibody of the present invention exhibits efficacy in pancreatic cancer cells which is remarkably more strong than that of gemcitabine that is used as one of the standard of care drugs for pancreatic cancer. The antibody of the present invention exhibits efficacy in chronic myeloid leukemia cells which is remarkably more strong than that of imatinib that is used as one of the standard of care drugs for chronic myeloid leukemia.

BRIEF DESCRIPTION OF DRAWINGS

FIG. 2-1 shows the binding activity to human CD147 or monkey CD147.

FIG. 2-2 shows the binding activity to human CD147 or monkey CD147.

FIG. 2-3 shows the binding activity to human CD147 or monkey CD147.

FIG. 3 shows a comparison of the amino acid sequences between human CD147 and cynomolgus monkey CD147 and the positions of mu1 to mu9 in human CD147 and cynomolgus monkey CD147.

FIG. 4-1 shows the nucleotide sequence and the amino acid sequence of the LN22R8 light chain variable region and the amino acid sequences of CDRL1, CDRL2, and CDRL3 of the LN22R8 light chain.

FIG. 4-2 shows the nucleotide sequence and the amino acid sequence of the LN22R8 heavy chain variable region and the amino acid sequences of CDRH1, CDRH2, and CDRH3 of the LN22R8 heavy chain.

FIG. 5-1 shows the nucleotide sequence and the amino acid sequence of the 2P10F2 light chain variable region and the amino acid sequences of CDRL1, CDRL2, and CDRL3 of the 2P10F2 light chain.

FIG. 5-2 shows the nucleotide sequence and the amino acid sequence of 2P10F2 heavy chain variable region and the amino acid sequences of CDRH1, CDRH2, and CDRH3 of the 2P10F2 heavy chain.

FIG. 6 shows the ADCC activities of human chimeric antibodies.

FIG. 7 shows the CDC activities of human chimeric antibodies.

FIGS. 9-1(*a*) to (*d*) show the antitumor efficacy of antibodies in a MIA PaCa-2 subcutaneous implantation model using NOD-scid mice.

FIGS. 9-2(*e*) to (*g*) show the antitumor efficacy of antibodies in MIA PaCa-2 subcutaneous implantation model using NOD-scid mice.

FIG. 10 shows the antitumor efficacy of LN22R8chIgG4P in a MIA PaCa-2 subcutaneous implantation model using NOG mice.

FIG. 12 shows a competition assay of 2P10F2 with r #84, r #101, r #110, and r #131.

FIGS. 13-1(*a*) to (*d*) show the antitumor efficacy of chimeric antibodies in a MIA PaCa-2 subcutaneous implantation model.

FIGS. 13-2(*e*) to (*h*) show the antitumor efficacy of chimeric antibodies in a MIA PaCa-2 subcutaneous implantation model.

FIGS. 13-3(*i*) to (*l*) show the antitumor efficacy of chimeric antibodies in a MIA PaCa-2 subcutaneous implantation model.

FIG. 13-4(*m*) and (*n*) show the antitumor efficacy of chimeric antibodies in a MIA PaCa-2 subcutaneous implantation model.

FIG. 14(*a*) shows the design of the variable region of humanized antibody heavy chain #84H1h, and FIG. 14(*b*) shows the design of the variable region of humanized antibody light chain #84L2h.

FIG. 15(*a*) shows the design of the variable region of humanized antibody heavy chain #101H1h, and FIG. 15(*b*) shows the design of the variable region of humanized antibody light chain #101L2h.

FIG. 16(*a*) shows the design of the variable region of humanized antibody heavy chain #110H1h, FIG. 16(*b*) shows the design of the variable region of humanized antibody heavy chain #110H13h, FIG. 16(*c*) shows the design of the variable region of humanized antibody light chain #110L4h, FIG. 16(*d*) shows the design of the variable region of humanized antibody light chain #110L2h, and FIG. 16(*e*) shows the design of the variable region of humanized antibody light chain #110L12h.

FIG. 17(*a*) shows the design of the variable region of humanized antibody heavy chain #131H2h, and FIG. 17(*b*) shows the design of the variable region of humanized antibody light chain #131L2h.

FIG. 19 shows p38MAPK phosphorylation by an anti-human CD147 human chimeric antibody.

FIG. 24 shows the results of evaluating the antitumor efficacy of anti-CD147 antibodies and gemcitabine using SMAD4-negative pancreatic cancer cells BxPC-3.

FIG. 27 shows the antitumor efficacy of an anti-CD147 human chimeric antibody in a gemcitabine-resistant pancreatic cancer tumor model.

FIG. 28(*b*) shows p38MAPK activation by humanized CD147 antibodies in liver cancer cells.

FIG. 30 shows CD147-APC binding in CD3- and CD4-positive cells and CD3- and CD8-positive cells.

FIG. 31 shows evaluation of the influence of anti-human CD147 antibodies on the growth of human peripheral blood mononuclear cells.

FIG. 32 shows evaluation of the influence of anti-human CD147 antibodies on cytokine production by human peripheral blood lymphocytes.

FIG. 33-1 shows the nucleotide sequence and the amino acid sequence of the rat_CD147_#84 light chain variable region, and the amino acid sequences of CDRL1, CDRL2, and CDRL3 of the rat_CD147_#84 light chain.

FIG. 33-2 shows the nucleotide sequence and the amino acid sequence of the rat_CD147_#84 heavy chain variable region and the amino acid sequences of CDRH1, CDRH2, and CDRH3 of the rat_CD147_#84 heavy chain.

FIG. 34-1 shows the nucleotide sequence and the amino acid sequence of the rat_CD147_#101 light chain variable region, and the amino acid sequences of CDRL1, CDRL2, and CDRL3 of the rat_CD147_#101 light chain.

FIG. 34-2 shows the nucleotide sequence and the amino acid sequence of the rat_CD147_#101 heavy chain variable region and the amino acid sequences of CDRH1, CDRH2, and CDRH3 of the rat_CD147_#101 heavy chain.

FIG. 35-1 shows the nucleotide sequence and the amino acid sequence of the rat_CD147_#110 light chain variable region, and the amino acid sequences of CDRL1, CDRL2, and CDRL3 of the rat_CD147_#110 light chain.

FIG. 35-2 shows the nucleotide sequence and the amino acid sequence of the rat_CD147_#110 heavy chain variable region and the amino acid sequences of CDRH1, CDRH2, and CDRH3 of the rat_CD147_#110 heavy chain.

FIG. 36-1 shows the nucleotide sequence and the amino acid sequence of the rat_CD147_#131 light chain variable region, and the amino acid sequences of CDRL1, CDRL2, and CDRL3 of the rat_CD147_#131 light chain.

FIG. 36-2 shows the nucleotide sequence and the amino acid sequence of the rat_CD147_#131 heavy chain variable region and the amino acid sequences of CDRH1, CDRH2, and CDRH3 of the rat_CD147_#131 heavy chain.

FIG. 37-1 shows the amino acid sequence and the nucleotide sequence of #84H1hIgG2.

FIG. 37-2 shows the amino acid sequence and the nucleotide sequence of #84H1hIgG4P.

FIG. 37-3 shows the amino acid sequence and the nucleotide sequence of #84L2h.

FIG. 38-1 shows the amino acid sequence and the nucleotide sequence of #101H1hIgG2.

FIG. 38-2 shows the amino acid sequence and the nucleotide sequence of #101H1hIgG4P.

FIG. 38-3 shows the amino acid sequence and the nucleotide sequence of #101L2h.

FIG. 39-1 shows the amino acid sequence and the nucleotide sequence of #110H1hIgG4P.

FIG. 39-2 shows the amino acid sequence and the nucleotide sequence of #110H13hIgG4P.

FIG. 39-3 shows the amino acid sequence and the nucleotide sequence of #110L4h.

FIG. 39-4 shows the amino acid sequence and the nucleotide sequence of #110L2h.

FIG. 39-5 shows the amino acid sequence and the nucleotide sequence of #110L12h.

FIG. 40-1 shows the amino acid sequence and the nucleotide sequence of #131H2hIgG2.

FIG. 40-2 shows the amino acid sequence and the nucleotide sequence of #131L2h.

FIG. 41 shows a ribbon diagram showing two complexes contained in the asymmetric unit. CD147 is shown in black, and the heavy chain (H CHAIN) and the light chain (L CHAIN) of the antibody are shown in gray.

FIG. 42 shows the interaction surface between CD147 and the antibody. The amino acids of CD147 in the vicinity of the antibody are represented by stick models and are labeled with characters. The other parts of CD147 are represented by black ribbon models. Meanwhile, the amino acids of the antibody in the vicinity of CD147 are represented by thin line models, and the other parts of the antibody are represented by gray ribbon models.

FIG. 43 shows the antitumor efficacy of chimeric and humanized CD147 antibodies in a gastric cancer model.

FIG. 44 shows the antitumor efficacy of a humanized CD147 antibody in a chronic myeloid leukemia (CML) model.

FIG. 45 shows the antitumor efficacy of humanized CD147 antibodies in a colon cancer model.

FIG. 46 shows the antitumor efficacy of humanized CD147 antibodies in a renal cancer model.

FIG. 47 shows the antitumor efficacy of a humanized CD147 antibody in an acute myeloid leukemia (AML) model.

FIG. 48 shows the antitumor efficacy of humanized CD147 antibodies in a pancreatic cancer model.

DESCRIPTION OF EMBODIMENTS

Figure 1A:
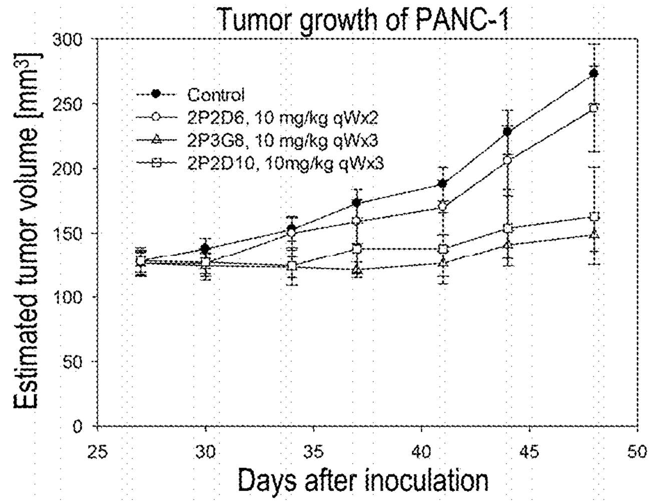
FIGS. 1(*a*) to (*c*) show changes in tumor volume in a PANC-1 xenograft model.
Figure 1B:
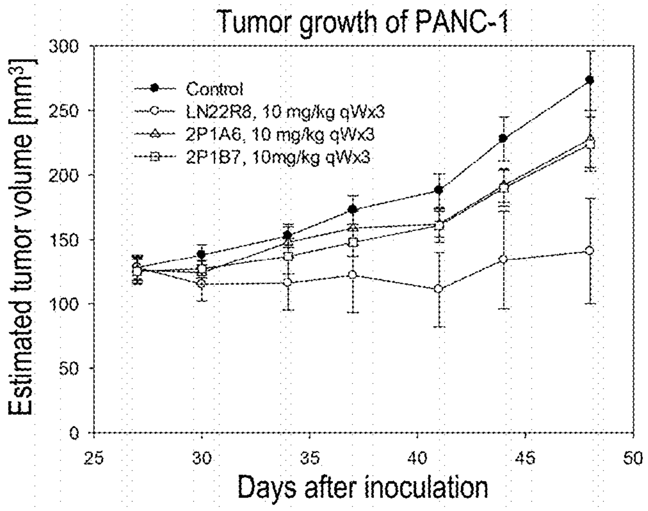
Figure 1C:
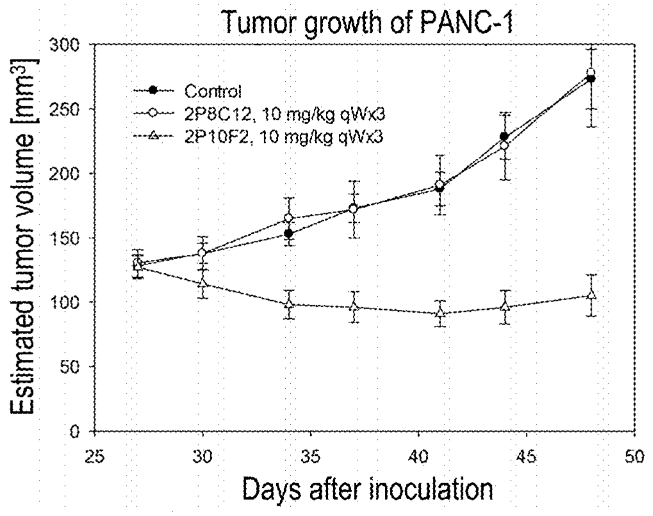

Preferred embodiments of the present invention are as described below with reference to the drawings. The embodiments described as follows illustrate examples of representative embodiments of the invention, and the scope of the invention is not to be narrowly interpreted by the embodiments.

(Definition) The terms "cancer(s)" and "tumor(s)" as used herein are used as synonyms, and each term is used to refer to, unless otherwise specifically limited, solid cancer, non-solid cancer, or both of them.

Examples of the term "gene(s)" as used herein include not only DNA, but also mRNA thereof, and cDNA and cRNA thereof.

The term "polynucleotide(s)" or "nucleotide(s)" as used herein is used synonymously with "nucleic acid" and examples thereof include DNA, RNA, probes, oligonucleotides, and primers.

The terms "polypeptide(s)" and "protein(s)" are used herein indistinguishably.

Examples of the term "cells" as used herein include cells within an individual animal and cultured cells.

The term "CD147" as used herein is used synonymously with "CD147 protein".

The term "functional fragment of an antibody" also called "antigen-binding fragment of an antibody" as used herein refers to a partial fragment of an antibody having binding activity to an antigen. Examples thereof include Fab, F(ab')2, Fv, scFv, a diabody, a linear antibody and a multi-specific antibody formed of antibody fragments. Examples of an antigen-binding fragment of an antibody also include Fab', which is a monovalent fragment of an antibody variable region, and is prepared by treating F(ab')2 under reducing conditions. However, examples thereof are not limited to these molecules as long as they are capable of binding to antigens. Examples of these antigen-binding fragments include not only fragments prepared by treating the full-length antibody protein molecules with appropriate enzymes, but also proteins produced by appropriate host cells using antibody genes modified by genetic engineering techniques.

The term "effector activity" as used herein refers to either one or more of antibody-dependent cellular cytotoxicity (hereinafter, referred to as "ADCC") activity, complement-dependent cytotoxicity (hereinafter, referred to as "CDC") activity, and antibody-dependent cellular phagocytosis (hereinafter, referred to as "ADCP") activity.

The term "effector functions" used herein refers to exhibition of one or more "effector activity".

Antibody-dependent cellular cytotoxicity (ADCC) activity can be measured by a $^{51}Cr$ release assay method, which measures cell death caused when immune cells having effector activity, an antibody and $^{51}Cr$-labeled target cells are brought into contact. The ADCC activity of the anti-human CD147 antibody of the present invention is measured as follows. Regarding the ADCC activity of the anti-human CD147 antibody, human peripheral blood mononuclear cells (PBMC) are used as effector cells, and a CD147-positive human cancer cell line (for example, pancreatic cancer cell line MIA PaCa-2) is used as ADCC target cells. Cancer cells labeled with a radioisotope, $^{51}Cr$, and the antibody to be evaluated are treated at a concentration of 0.5 or 5 μg/ml at 4° C. for 30 minutes, PBMC separated from human peripheral blood is added at 20 times the proportion of cancer cells, and then cells are cultured for 4 hours at 37° C. in the presence of 5% $CO_2$. A Total release value is obtained by measuring $^{51}Cr$ released in the supernatant using TopCount NXT v2.53. The measured value of $^{51}Cr$ released from $^{51}Cr$-labeled cancer cells treated with Triton-100 is designated as a "Maximum release value" and the measured value of $^{51}Cr$ released from $^{51}Cr$-labeled cancer cells treated with antibody in the absence of PBMC is designated as a "Spontaneous release value". With these values, % Specific release is calculated from the following formula. As a negative control sample, human IgG (hIgG, ChromPure Human IgG, Jackson ImmunoResearch Laboratories, Cat. 009-000-003)

is used. The measurement is performed three times, and then the average value and the standard deviation are calculated.

% specific release=(Total release−Spontaneous release)/Maximum release

Complement-dependent cytotoxicity (CDC) activity can be evaluated by measuring cell death caused when complement contained in blood, an antibody and target cells are brought into contact. The CDC activity of the anti-human CD147 antibody of the present invention is measured as follows. The complement-dependent cytotoxicity activity (CDC activity) of the anti-human CD147 antibody is evaluated using human pancreatic cell line MIA PaCa-2 as target cells. Commercially available rabbit complement (Low Tox-M Rabbit Complement, CEDARLANE LABORATORIES LIMITED, Cat. CL3051) is used as the complement. Human IgG (hIgG, ChromPureHuman IgG, Jackson ImmunoResearch Laboratories, Cat. 009-000-003) is used as a CDC-negative control antibody. Target cells are treated with the antibody to be evaluated and the negative control antibody at concentrations of 0, 0.1, 1 or 10 μg/ml for 1 hour at 4° C., the rabbit complement is added in such a manner that the final concentration is 7.5%, the resultant mixture is heated at 37° C. in the presence of 5% $CO_2$ for 3 hours, and then intracellular ATP contained in living cells is measured using the CellTiter-Glo Lumimescent Cell Viability Assay (Promega, Cat. G7572). Luminescent signals obtained using the CellTiter-Glo Lumimescent Cell Viability Assay are quantitatively determined using an EnVision 2104 Multilabel Reader (Perkin Elmer). The measurement is performed three times and the average value and the standard deviation are calculated. Luminescent signals obtained from untreated cells are designated as 100%, and decreased luminescent signals which are dependent on the antibody and the complement are designated as CDC activity.

Antibody-dependent cellular phagocytosis (ADCP) activity can be evaluated by measuring phagocytosis caused when immune cells capable of phagocytosis, an antibody and target cells are brought into contact by a double fluorescent labeling method.

The ADCP activity of the anti-human CD147 antibody of the present invention is measured as follows. It has been reported that a human IgG antibody exhibits cytotoxic activity against cancer cells through induction of antibody-dependent cellular phagocytosis (ADCP) by monocytes and macrophages via interaction with mouse Fcγ receptor (Overdijk et al., Journal of Immunology, 1-9, 2012). The ADCP activity of the human chimeric antibody of the present invention is evaluated using RAW264.7 (ATCC, TIB-71) as effector cells and human pancreatic cell line PANC-1 or MIA PaCa-2 as ADCP target cells. After 1 hour of treatment of ADCP target cells labeled using a PKH67 Green Fluorescent Cell Linker Mini Kit for General Cell Membrane Labeling (SIGMA, Cat. MINI67-1KIT) with an antibody to be evaluated having a concentration of 20 μg/ml at 4° C., RAW264.7 cells labeled using a PKH26 Red Fluorescent Cell Linker Kit for General Cell Membrane Labeling (SIGMA, Cat. PKH26GL-1KT) are added in an amount 5 times that of the ADCP target cells, followed by 3 hours of heating at 37° C. in the presence of 5% $CO_2$. With the use of a flow cytometer (BD (Becton, Dickinson and Company), CantoII), the proportion of PKH26-positive cells, which are transferred to a PKH67 signal positive status due to phagocytosis, is measured. As a negative control sample, the same measurement is performed for a sample treated with human IgG (hIgG, ChromPure Human IgG, Jackson ImmunoResearch Laboratories, Cat. 009-000-003). The measurement is performed three times and the average value and the standard deviation are calculated.

The expression "substantially lacking effector activity" or "having decreased effector activity or lacking effector activity" as used herein means that the antibody does not exhibit at least one of ADCC activity, CDC activity or ADCP activity, or that the levels of these activities are so low that the functions are not sufficiently exhibited. The expression "substantially lacking effector activity" or "having decreased effector activity or lacking effector activity" means, for example, that the activity of an antibody to be evaluated is at the same level as that of a negative control as determined by one of the above methods for evaluating activity.

The expression "having decreased ADCC activity or lacking ADCC activity" as used herein means that an antibody to be evaluated does not exhibit ADCC activity, or that the ADCC activity is at a low level such that it is not exhibited sufficiently. The expression "having decreased ADCC activity or lacking ADCC activity" means, for example, that the activity of an antibody to be evaluated is at the same level as that of a negative control as determined by the above method for evaluating activity.

The expression "having decreased CDC activity or lacking CDC activity" means that an antibody to be evaluated does not exhibit CDC activity, or, that the CDC activity is at a low level such that it is not exhibited sufficiently. The expression "having decreased CDC activity or lacking CDC activity" means, for example, that the activity of an antibody to be evaluated is at the same level as that of a negative control as determined by the above method for evaluating activity.

The expression "having decreased ADCP activity or lacking ADCP activity" means that an antibody to be evaluated does not exhibit ADCP activity, or, that the ADCP activity is at a low level such that it is not exhibited sufficiently. The expression "having decreased ADCP activity or lacking ADCP activity" means, for example, that the activity of an antibody to be evaluated is at the same level as that of a negative control as determined by the above method for evaluating activity.

The expression "having decreased ADCC activity or lacking ADCC activity", "having decreased CDC activity or lacking CDC activity" or "having decreased ADCP activity or lacking ADCP activity" means, for example, that the activity of each antibody to be evaluated is at the same level as that of a negative control as determined by the above methods for evaluating activity.

The expression "activates signal transduction through CD147", "activation of signal-related molecules through CD147", "activation of CD147" or "activates CD147" as used herein refers to the activation of one or more cellular signal transduction systems through CD147 and means that at least one of the signal-related molecules located downstream of CD147 is activated. The activation of signal transduction through CD147 means that the expression of a gene located downstream of the CD147 signal is accelerated or decreased, the expression of the protein is accelerated or decreased, or the phosphorylation of the protein is accelerated or decreased. Examples of the signal-related molecules which are located downstream of CD147 include, FAK, MEK, Erk, JAK/STAT, AKT or MAP kinase (MAPK), or activation of signal molecules located further downstream thereof. Examples of MAPK include ERK1/2, JNK or p38MAPK, and more preferably p38MAPK. Examples of signal molecules located further downstream of MAPK include HSP27, cxcl8 or SMAD (for example, SMAD2, SMAD3 and/or SMAD4). Examples of the "activation of CD147" include increased p38MAPK mRNA expression level, increased p38MAPK protein expression level, phosphorylation of p38MAPK, phosphorylation of HSP27 (for example, phosphorylation of Ser82 of HSP27 or phosphorylation of Ser15 of HSP27), increased cxcl8 mRNA expression level, increased cxcl8 protein expression level, increased rhoB mRNA expression level or increased rhoB protein expression level through SMAD signal activation, or, decreased KLF5 mRNA or decreased KLF5 protein expression level.

The term "epitope" used herein refers to a partial peptide of, or a partial three-dimensional structure of, CD147, to which a specific anti-CD147 antibody binds. The above epitope that is a partial peptide of CD147 can be determined by a method well known by persons skilled in the art, such as an immunoassay method. First, various partial structures of antigens are prepared. Upon preparation of the partial structures, known oligonucleotide synthesis techniques can be employed. For example, a series of polypeptides are prepared by gene recombination techniques known by persons skilled in the art in such a manner that lengths of polypeptides from the C-terminus or the N-terminus of CD147 are sequentially shortened, the reactivity of the antibody to these polypeptides is examined, recognition sites are roughly determined, peptides that are even shorter than the polypeptides are synthesized, and then the reactivity to these peptides is examined, so that an epitope can be determined. Further, when the epitope of an antibody, which binds to a membrane protein consisting of plurality of extracellular domains, is a three-dimensional structure consisting of a plurality of domains, the amino acid sequence of a specific extracellular domain can be modified to modify the three-dimensional structure, so that the specific domain to which the antibody binds can be determined. An epitope that is a partial three-dimensional structure of an antigen, to which a specific antibody binds, can also be determined by specifying the amino acid residues of an antigen adjacent to the above antibody by X-ray structure analysis.

If a second antibody binds to a partial peptide or a partial three-dimensional structure, to which a first antibody binds, it can be determined that the first antibody and the second antibody share a common epitope. Through confirmation of a second antibody cross-competing with a first antibody in terms of its binding to the antigen (specifically, the second antibody inhibits the binding of the first antibody to the antigen), it can be determined that the first antibody and the second antibody bind to the same epitope, even if the specific sequence or structure of the epitope has not determined. When a first antibody and a second antibody bind to the same epitope, and the first antibody has a special effect such as antitumor efficacy, the second antibody can be expected to have a similar activity.

Each of the heavy chains and the light chains of an antibody molecule is known to have 3 complementarity determining regions (CDRs). The complementarity determining regions are also referred to as hypervariable regions (hypervariable domains), are located in the heavy chain and the light chain variable regions of an antibody, are sites where the variability of the primary structure is particularly high, and are located separately in the primary structure of the polypeptide chains of the heavy chains and the light chains. Regarding the term "complementarity determining regions of an antibody" as used herein, the heavy chain complementarity determining regions are denoted as CDRH1, CDRH2, and CDRH3 from the amino terminal side of the heavy chain amino acid sequence, and the light chain complementarity determining regions are denoted as CDRL1, CDRL2, and CDRL3 from the amino terminal side of the light chain amino acid sequence. These sites are adjacent to each other on the three-dimensional structure, and determine the specificity to an antigen to which the antibody binds.

The term "several" as used herein in the expressions "1 to several" and "1 or several" refers to 2 to 10, preferably, 10 or less, more preferably, 5 or 6 or less, further more preferably, 2 or 3.

(CD147)

CD147 is a single-pass transmembrane protein having 2 to 3 immunoglobulin-like domains, and is known to activate downstream signal-related molecules, such as FAK, MEK, Erk, JAK/STAT, AKT and MAPK family molecules through interactions between multiple CD147 proteins, or through interactions with extracellular or cell membrane surface molecules involved in growth, invasion, and inflammation, such as CD44, Integrin family molecules, CD98, VEGFR, CypA/B, and MCT1/3/4, thereby accelerating the production of proteases such as MMP, and cancer growth, metastasis, and invasion.

Three variants of human CD147 are known. Variant 1 is expressed in a retina-specific manner and is a single-pass transmembrane protein having 3 immunoglobulin-like domains (these domains may be referred to as D0, D1 and D2, respectively herein.). Variant 2 is expressed in T cells or various normal cells, and, is a single-pass transmembrane protein having 2 immunoglobulin-like domains (D1, D2), the increased expression of which in various cancer tissues has been reported. Variant 3 is a single-pass transmembrane protein having 1 immunoglobulin-like domain.

The amino acid sequence and the nucleotide sequence of variant 1 of human CD147 are available with reference to GenBank Accession Nos. NP_001719.2 and NM_001728.3, and, the amino acid sequence is disclosed herein as SEQ ID NO: 1, and the nucleotide sequence is disclosed herein as SEQ ID NO: 2. The three immunoglobulin-like domains of variant 1 range from amino acid number 22 to 138 (D0), amino acid number 140 to 218 (D1), and amino acid number 223 to 323 (D2), respectively, in SEQ ID NO: 1, (Redzic, J., J. Mol. Biol., 2011, 68-82) (Grass et al., Biosol. Rep, 2016, 1-16). The transmembrane region of variant 1 ranges from amino acid number 324 to 344 in SEQ ID NO: 1.

The amino acid sequence and the nucleotide sequence of variant 2 of human CD147 are available with reference to GenBank Accession Nos. NP_940991.1 and NM_198589.2, and the amino acid sequence is disclosed herein as SEQ ID NO: 3, and the nucleotide sequence is disclosed herein as SEQ ID NO: 4. The two immunoglobulin-like domains (D1, D2) of variant 2 range from amino acid number 24 to 102 (D1) and amino acid number 107 to 207 (D2), respectively, in SEQ ID NO: 3. The transmembrane region of variant 2 ranges from amino acid number 208 to 228 in SEQ ID NO: 3 (Grass et al., Biosol. Rep, 2016, 1-16).

The amino acid sequence and the nucleotide sequence of variant 3 of human CD147 are available with reference to GenBank Accession Nos. NP_940992.1 and NM_198590.2. The human CD147 gene is also available from a commercial source.

The amino acid sequence and the nucleotide sequence of cynomolgus monkey CD147 (also referred to as monkey CD147 herein) are available with reference to GenBank Accession Nos. XP_005587354.1 and XM_005587297.1. The monkey CD147 gene is also available from a commercial source. The amino acid sequence and the nucleotide sequence of mouse CD147 are available with reference to GenBank Accession Nos. NP_001070652.1 and NM_001077184. 1. The mouse CD147 gene is also available from a commercial source.

CD147 to be used in the present invention can be obtained by synthesizing CD147 in vitro, or by using genetically engineered host cells to produce CD147. Specifically, CD147 cDNA is incorporated into a vector capable of expressing it, and then CD147 is synthesized in a solution containing an enzyme, a substrate and energy substances required for transcription and translation, or host cells of other prokaryotes or eukaryotes are transformed to express CD147, so that the protein can be obtained.

The cDNA of CD147 can be obtained by a polymerase chain reaction (hereinafter, referred to as "PCR"), namely, a PCR method, using a cDNA library expressing the cDNA of CD147 as a template, and primers for specific amplification of the cDNA of CD147 (Saiki, R. K., et al., Science, (1988)239, 487-49), for example.

Examples of the cDNA of CD147 include a polynucleotide hybridizing under stringent conditions to a polynucleotide consisting of a nucleotide sequence complementary to a nucleotide sequence encoding human, monkey or mouse CD147, and, encoding a protein having biological activity equivalent to that of CD147. Further, examples of the cDNA of CD147 include a polynucleotide that is a splicing variant transcribed from the human, monkey or mouse CD147 gene locus or a polynucleotide hybridizing under stringent conditions thereto, and, encodes a protein having biological activity equivalent to that of CD147.

Examples of CD147 further include a protein: consisting of the amino acid sequence of human, monkey or mouse CD147, or an amino acid sequence in which one or several amino acids are substituted, deleted, or added in the amino acid sequence of human, monkey or mouse CD147 from which a signal sequence is removed; and having biological activity equivalent to that of CD147. Further, examples of CD147 include a protein: consisting of an amino acid sequence encoded by a splicing variant transcribed from the human, monkey or mouse CD147 gene locus, or the amino acid sequence in which one or several amino acids are substituted, deleted, or added; and having biological activity equivalent to that of CD147.

(Production of Anti-CD147 Antibody)

The antibody against CD147 of the present invention can be obtained as follows. Specifically, a non-human animal is immunized with an antigen of interest, a lymph, a lymphatic tissue, a hemocyte sample or bone marrow-derived cells are collected from the animal after establishment of immunity, and then according to a known method (for example, Kohler and Milstein, Nature (1975)256, p. 495-497, Kennet, R. ed., Monoclonal Antibodies, p. 365-367, Plenum Press, N. Y. (1980)), antibody-producing cells, which produce an antibody against CD147, and myeloma cells are fused to establish hybridomas, and thus a monoclonal antibody can be obtained. Specific examples of such a method are described in WO2009/48072 (disclosed on Apr. 16, 2009) and WO2010/117011 (disclosed on Oct. 14, 2010). Examples of the thus obtained monoclonal antibody can include LN22R8, 2P10F2, rat_CD147_#84, rat_CD147_#101, rat_CD147_#110 and rat_CD147_#131. However, methods for obtaining a monoclonal antibody fall under the category of an already established field, and examples thereof are not limited to the above listed specific examples.

Examples of the antibody of the present invention include, in addition to the above monoclonal antibody against CD147, a gene recombinant antibody, which is artificially modified in order to lower heterologous antigenicity against humans, for example, a chimeric antibody, a humanized antibody, and a human antibody. These antibodies can be produced using known methods.

Examples of a chimeric antibody can include antibodies in which the antibody variable regions and constant regions are heterologous to each other, for example, a chimeric antibody, in which a mouse or rat-derived antibody variable region is joined to a human-derived constant region (see Proc. Natl. Acad. Sci. USA., 81, 6851-6855, (1984)). An example of an LN22R8-derived chimeric antibody is an antibody consisting of a heavy chain having an amino acid sequence consisting of amino acid residues at positions 20 to 471 of SEQ ID NO: 33, a heavy chain having an amino acid sequence consisting of amino acid residues at positions 20 to 467 of SEQ ID NO: 35 or a heavy chain having an amino acid sequence consisting of amino acid residues at positions 20 to 468 of SEQ ID NO: 37, and a light chain having an amino acid sequence consisting of amino acid residues at positions 21 to 234 of SEQ ID NO: 31 in the sequence listing. An example of a 2P10F2-derived chimeric antibody is an antibody consisting of a heavy chain having an amino acid sequence consisting of amino acid residues at positions 20 to 466 of SEQ ID NO: 43, a heavy chain having an amino acid sequence consisting of amino acid residues at positions 20 to 462 of SEQ ID NO: 45 or a heavy chain having an amino acid sequence consisting of amino acid residues at positions 20 to 463 of SEQ ID NO: 47, and a light chain having an amino acid sequence consisting of amino acid residues at positions 21 to 234 of SEQ ID NO: 41 in the sequence listing.

An example of a rat_CD147_#84-derived chimeric antibody is an antibody consisting of a heavy chain having an amino acid sequence consisting of amino acid residues at positions 20 to 470 of SEQ ID NO: 92, a heavy chain having an amino acid sequence consisting of amino acid residues at positions 20 to 466 of SEQ ID NO: 94, and a heavy chain having an amino acid sequence consisting of amino acid residues at positions 20 to 467 of SEQ ID NO: 96, a heavy chain having an amino acid sequence consisting of amino acid residues at positions 20 to 470 of SEQ ID NO: 98 or a heavy chain having an amino acid sequence consisting of amino acid residues at positions 20 to 467 of SEQ ID NO: 100, and, a light chain having an amino acid sequence consisting of amino acid residues at positions 21 to 234 of SEQ ID NO: 90 in the sequence listing.

An example of a rat_CD147_#101-derived chimeric antibody is an antibody consisting of a heavy chain having an amino acid sequence consisting of amino acid residues at positions 20 to 463 of SEQ ID NO: 104, a heavy chain having an amino acid sequence consisting of amino acid residues at positions 20 to 464 of SEQ ID NO: 106 or a heavy chain having an amino acid sequence consisting of amino acid residues at positions 20 to 464 of SEQ ID NO: 108, and, a light chain having an amino acid sequence consisting of amino acid residues at positions 21 to 234 of SEQ ID NO: 102 in the sequence listing.

An example of a rat_CD147_#110-derived chimeric antibody is an antibody consisting of a heavy chain having an amino acid sequence consisting of amino acid residues at positions 20 to 462 of SEQ ID NO: 112, a heavy chain having an amino acid sequence consisting of amino acid residues at positions 20 to 463 of SEQ ID NO: 114 or a heavy chain having an amino acid sequence consisting of amino acid residues at positions 20 to 463 of SEQ ID NO: 116, and, a light chain having an amino acid sequence consisting of amino acid residues at positions 21 to 234 of SEQ ID NO: 110 in the sequence listing.

An example of a rat_CD147_#131-derived chimeric antibody is an antibody consisting of a heavy chain having an amino acid sequence consisting of amino acid residues at positions 20 to 464 of SEQ ID NO: 120 or a heavy chain having an amino acid sequence consisting of amino acid residues at positions 20 to 465 of SEQ ID NO: 122, and, a light chain having an amino acid sequence consisting of amino acid residues at positions 21 to 234 of SEQ ID NO: 118 in the sequence listing.

Examples of a humanized antibody can include, an antibody in which only CDRs are incorporated into a human-derived antibody (see Nature (1986)321, p. 522-525), an antibody in which amino acid residues of a partial framework in addition to a CDR sequence are also incorporated into a human antibody by a CDR grafting method (International Publication WO90/07861).

Examples of the antibody of the present invention include any rat_CD147_#84 antibody-derived humanized antibody, as long as it retains all the 6 types of CDR sequence of rat_CD147_#84, has binding activity to CD147, and, is an antibody activating CD147. Note that the heavy chain variable region of the rat_CD147_#84 antibody comprises CDRH1 consisting of the amino acid sequence represented by SEQ ID NO: 55, CDRH2 consisting of the amino acid sequence represented by SEQ ID NO: 56, and CDRH3 consisting of the amino acid sequence represented by SEQ ID NO: 57. The light chain variable region of the rat_CD147_#84 antibody comprises CDRL1 consisting of the amino acid sequence represented by SEQ ID NO: 52, CDRL2 consisting of the amino acid sequence represented by SEQ ID NO: 53, and CDRL3 consisting of the amino acid sequence represented by SEQ ID NO: 54. The amino acid sequence and the nucleotide sequence of the light chain variable region or the heavy chain variable region of the rat_CD147_#84 antibody, and the amino acid sequences of the CDRs are also described in FIG. 33-1 and FIG. 33-2.

Examples of the antibody of the present invention include a rat_CD147_#101 antibody-derived humanized antibody, as long as it retains all the 6 types of CDR sequence of rat_CD147_#101, has binding activity to CD147, and, is an antibody activating CD147. Note that the heavy chain variable region of the rat_CD147_#101 antibody comprises CDRH1 consisting of the amino acid sequence represented by SEQ ID NO: 65, CDRH2 consisting of the amino acid sequence represented by SEQ ID NO: 66, and CDRH3 consisting of the amino acid sequence represented by SEQ ID NO: 67. The light chain variable region of the rat_CD147_#101 antibody comprises CDRL1 consisting of the amino acid sequence represented by SEQ ID NO: 62, CDRL2 consisting of the amino acid sequence represented by SEQ ID NO: 63, and CDRL3 consisting of the amino acid sequence represented by SEQ ID NO: 64. The amino acid sequence and the nucleotide sequence of the light chain variable region or the heavy chain variable region of the rat_CD147_#101 antibody, and the amino acid sequences of CDRs are also described in FIG. 34-1 and FIG. 34-2.

Examples of the antibody of the present invention include a rat_CD147_#110 antibody-derived humanized antibody, as long as it retains all the 6 types of CDR sequence of rat_CD147_#110, has binding activity to CD147, and, is an antibody activating CD147. Note that the heavy chain variable region of the rat_CD147_#110 antibody comprises CDRH1 consisting of the amino acid sequence represented by SEQ ID NO: 75, CDRH2 consisting of the amino acid sequence represented by SEQ ID NO: 76, and CDRH3 consisting of the amino acid sequence represented by SEQ ID NO: 77. The light chain variable region of the rat_CD147_#110 antibody comprises CDRL1 consisting of the amino acid sequence represented by SEQ ID NO: 72, CDRL2 consisting of the amino acid sequence represented by SEQ ID NO: 73, and CDRL3 consisting of the amino acid sequence represented by SEQ ID NO: 74. The amino acid sequence and the nucleotide sequence of the light chain variable region or the heavy chain variable region of the rat_CD147_#110 antibody and the amino acid sequences of the CDRs are also described in FIG. 35-1 and FIG. 35-2.

Examples of the antibody of the present invention include a rat_CD147_#131 antibody-derived humanized antibody, as long as it retains all the 6 types of CDR sequence of rat_CD147_#131, has binding activity to CD147, and, is an antibody activating CD147. Note that the heavy chain variable region of the rat_CD147_#131 antibody comprises CDRH1 consisting of the amino acid sequence represented by SEQ ID NO: 85, CDRH2 consisting of the amino acid sequence represented by SEQ ID NO: 86, and CDRH3 consisting of the amino acid sequence represented by SEQ ID NO: 87. The light chain variable region of the rat_CD147_#131 antibody comprises CDRL1 consisting of the amino acid sequence represented by SEQ ID NO: 82, CDRL2 consisting of the amino acid sequence represented by SEQ ID NO: 83, and CDRL3 consisting of the amino acid sequence represented by SEQ ID NO: 84. The amino acid sequence and the nucleotide sequence of the light chain variable region or the heavy chain variable region of the rat_CD147_#131 antibody and the amino acid sequences of CDRs are also described in FIG. 36-1 and FIG. 36-2.

Examples of the antibody of the present invention further include a CDR-modified humanized antibody in which 1 to 3 amino acid residues in each CDR are substituted with other amino acid residues, as long as it has binding activity to CD147, and, is an antibody activating CD147. Examples of a rat_CD147_#84 antibody-derived humanized antibody include a humanized anti-CD147 antibody or an antigen-binding fragment of the antibody, having the following (a) and (b):

(a) a heavy chain variable region selected from the group consisting of the following (a1) to (a4):

(a1) a heavy chain variable region consisting of amino acid residues at positions 20 to 140 in an amino acid sequence represented by SEQ ID NO: 123;

(a2) a heavy chain variable region consisting of amino acid residues at positions 20 to 140 in an amino acid sequence represented by SEQ ID NO: 125;

(a3) an amino acid sequence having at least 95% or more sequence identity with the sequence of a framework region outside each CDR sequence in the sequence of (a1) or (a2); and (a4) an amino acid sequence in which one or several amino acids are deleted, substituted, or added in the sequence of a framework region outside each CDR sequence in the sequence according to any one of (a1) to (a3); and (b) a light chain variable region selected from the group consisting of the following (b1) to (b3):

(b1) a light chain variable region consisting of amino acid residues at positions 21 to 128 in an amino acid sequence represented by SEQ ID NO: 127;

(b2) an amino acid sequence having at least 95% or more sequence identity with the sequence of a framework region outside each CDR sequence in the sequence of (b1); and (b3) an amino acid sequence in which one or several amino acids are deleted, substituted, or added in the sequence of a framework region outside each CDR sequence in the sequence of (b1) or (b2).

Preferred examples of a rat_CD147_#84 antibody-derived humanized antibody include an antibody comprising the heavy chain variable region consisting of amino acid residues at positions 20 to 140 in the amino acid sequence represented by SEQ ID NO: 125 and the light chain variable region consisting of amino acid residues at positions 21 to 128 in the amino acid sequence represented by SEQ ID NO: 127, or, an antibody comprising the heavy chain variable region consisting of amino acid residues at positions 20 to 140 in the amino acid sequence represented by SEQ ID NO: 123 and the light chain variable region consisting of amino acid residues at positions 21 to 128 in the amino acid sequence represented by SEQ ID NO: 127.

Preferred examples of a rat_CD147_#84 antibody-derived humanized antibody include an antibody comprising a heavy chain consisting of amino acid residues at positions 20 to 467 in the amino acid sequence represented by SEQ ID NO: 125 and a light chain consisting of amino acid residues at positions 21 to 234 in the amino acid sequence represented by SEQ ID NO: 127, or, an antibody comprising a heavy chain consisting of amino acid residues at positions 20 to 466 in the amino acid sequence represented by SEQ ID NO: 123 and a light chain consisting of amino acid residues at positions 21 to 234 in the amino acid sequence represented by SEQ ID NO: 127.

Examples of a rat_CD147_#101 antibody-derived humanized antibody include the humanized anti-CD147 antibody or an antigen-binding fragment of the antibody, having the following (e) and (f):

(e) a heavy chain variable region selected from the group consisting of the following (e1) to (e4):

(e1) a heavy chain variable region consisting of amino acid residues at positions 20 to 137 in an amino acid sequence represented by SEQ ID NO: 129;

(e2) a heavy chain variable region consisting of amino acid residues at positions 20 to 137 in an amino acid sequence represented by SEQ ID NO: 131;

(e3) an amino acid sequence having at least 95% or more sequence identity with the sequence of a framework region outside each CDR sequence in the sequence of (e1) or (e2); and (e4) an amino acid sequence in which one or several amino acids are deleted, substituted, or added in the sequence of a framework region outside each CDR sequence in the sequence according to any one of (e1) to (e3); and (f) a light chain variable region selected from the group consisting of the following (f1) to (f3):

(f1) a light chain variable region consisting of amino acid residues at positions 21 to 128 in an amino acid sequence represented by SEQ ID NO: 133;

(f2) an amino acid sequence having at least 95% or more sequence identity with the sequence of a framework region outside each CDR sequence in the sequence of (f1); and (f3) an amino acid sequence in which one or several amino acids are deleted, substituted, or added in the sequence of a framework region outside each CDR sequence in the sequence of (f1) or (f2).

Preferred examples of a rat_CD147_#101 antibody-derived humanized antibody include an antibody comprising the heavy chain variable region consisting of amino acid residues at positions 20 to 137 in the amino acid sequence represented by SEQ ID NO: 129 and the light chain variable region consisting of amino acid residues at positions 21 to 128 in the amino acid sequence represented by SEQ ID NO: 133, or, an antibody comprising the heavy chain variable region consisting of amino acid residues at positions 20 to 137 in the amino acid sequence represented by SEQ ID NO: 131 and the light chain variable region consisting of amino acid residues at positions 21 to 128 in the amino acid sequence represented by SEQ ID NO: 133.

Preferred examples of a rat_CD147_#101 antibody-derived humanized antibody include an antibody comprising the heavy chain consisting of amino acid residues at positions 20 to 463 in the amino acid sequence represented by SEQ ID NO: 129 and the light chain consisting of amino acid residues at positions 21 to 234 in the amino acid sequence represented by SEQ ID NO: 133, or, an antibody comprising the heavy chain consisting of amino acid residues at positions 20 to 464 in the amino acid sequence represented by SEQ ID NO: 131 and the light chain consisting of amino acid residues at positions 21 to 234 in the amino acid sequence represented by SEQ ID NO: 133.

Examples of a rat_CD147_#110 antibody-derived humanized antibody include the humanized anti-CD147 antibody or an antigen-binding fragment of the antibody, having the following (c) and (d):

(c) a heavy chain variable region selected from the group consisting of the following (c1) to (c4):

(c1) a heavy chain variable region consisting of amino acid residues at positions 20 to 136 in an amino acid sequence represented by SEQ ID NO: 135;

(c2) a heavy chain variable region consisting of amino acid residues at positions 20 to 136 in an amino acid sequence represented by SEQ ID NO: 147;

(c3) an amino acid sequence having at least 95% or more sequence identity with the sequence of a framework region outside each CDR sequence in the sequence of (c1) or (c2); and (c4) an amino acid sequence in which one or several amino acids are deleted, substituted, or added in the sequence of a framework region outside each CDR sequence in the sequence according to any one of (c1) to (c3), (d) a light chain variable region selected from the group consisting of the following (d1) to (d5):

(d1) a light chain variable region consisting of amino acid residues at positions 21 to 128 in an amino acid sequence represented by SEQ ID NO: 137;

(d2) a light chain variable region consisting of amino acid residues at positions 21 to 128 in an amino acid sequence represented by SEQ ID NO: 149;

(d3) a light chain variable region consisting of amino acid residues at positions 21 to 128 in an amino acid sequence represented by SEQ ID NO: 151;

(d4) an amino acid sequence having at least 95% or more sequence identity with the sequence of a framework region outside each CDR sequence in the sequence according to any one of (d1) to (d3); and (d5) an amino acid sequence in which one or several amino acids are deleted, substituted, or added in the sequence of a framework region outside each CDR sequence in the sequence according to any one of (d1) to (d4).

Preferred examples of a rat_CD147_#110 antibody-derived humanized antibody include: an antibody comprising the heavy chain variable region consisting of amino acid residues at positions 20 to 136 in the amino acid sequence represented by SEQ ID NO: 135 and the light chain variable region consisting of amino acid residues at positions 21 to 128 in the amino acid sequence represented by SEQ ID NO: 137; an antibody comprising the heavy chain variable region consisting of amino acid residues at positions 20 to 136 in the amino acid sequence represented by SEQ ID NO: 147 and the light chain variable region consisting of amino acid residues at positions 21 to 128 in the amino acid sequence represented by SEQ ID NO: 149; or, an antibody comprising the heavy chain variable region consisting of amino acid residues at positions 20 to 136 in the amino acid sequence represented by SEQ ID NO: 147 and the light chain variable region consisting of amino acid residues at positions 21 to 128 in the amino acid sequence represented by SEQ ID NO: 151.

Preferred examples of a rat_CD147_#110 antibody-derived humanized antibody include: an antibody comprising the heavy chain consisting of amino acid residues at positions 20 to 463 in the amino acid sequence represented by SEQ ID NO: 135 and the light chain consisting of amino acid residues at positions 21 to 234 in the amino acid sequence represented by SEQ ID NO: 137; an antibody comprising the heavy chain consisting of amino acid residues at positions 20 to 463 in the amino acid sequence represented by SEQ ID NO: 147, and, the light chain consisting of amino acid residues at positions 21 to 234 in the amino acid sequence represented by SEQ ID NO: 149; or, an antibody comprising the heavy chain consisting of amino acid residues at positions 20 to 463 in the amino acid sequence represented by SEQ ID NO: 147, and, the light chain consisting of amino acid residues at positions 21 to 234 in the amino acid sequence represented by SEQ ID NO: 151.

Examples of a rat_CD147_#131 antibody-derived humanized antibody include the humanized anti-CD147 antibody or an antigen-binding fragment of the antibody, having the following (g) and (h):

(g) a heavy chain variable region selected from the group consisting of the following (g1) to (g3):

(g1) a heavy chain variable region consisting of amino acid residues at positions 20 to 138 in an amino acid sequence represented by SEQ ID NO: 139;

(g2) an amino acid sequence having at least 95% or more sequence identity with the sequence of a framework region outside each CDR sequence in the sequence of (g1); and (g3) an amino acid sequence in which one or several amino acids are deleted, substituted, or added in the sequence of a framework region outside each CDR sequence in the sequence of (g1) or (g2), and, (h) a light chain variable region selected from the group consisting of the following (h1) to (h3):

(h1) a light chain variable region consisting of amino acid residues at positions 21 to 128 in an amino acid sequence represented by SEQ ID NO: 141;

(h2) an amino acid sequence having at least 95% or more sequence identity with the sequence of a framework region outside each CDR sequence in the sequence of (h1); and (h3) an amino acid sequence in which one or several amino acids are deleted, substituted, or added in the sequence of a framework region outside each CDR sequence in the sequence of (h1) or (h2).

Preferred examples of a rat_CD147_#131 antibody-derived humanized antibody include: an antibody comprising the heavy chain variable region consisting of amino acid residues at positions 20 to 138 in the amino acid sequence represented by SEQ ID NO: 139 and the light chain variable region consisting of amino acid residues at positions 21 to 128 in the amino acid sequence represented by SEQ ID NO: 141.

Preferred examples of a rat_CD147_#131 antibody-derived humanized antibody include an antibody comprising the heavy chain consisting of amino acid residues at positions 20 to 464 in the amino acid sequence represented by SEQ ID NO: 139 and the light chain consisting of amino acid residues at positions 21 to 234 in the amino acid sequence represented by SEQ ID NO: 141.

The above rat_CD147_#84 antibody-derived humanized antibody, rat_CD147_#101 antibody-derived humanized antibody, rat_CD147_#110 antibody-derived humanized antibody or rat_CD147_#131 antibody-derived humanized antibody preferably activates p38MAPK signal transduction and/or SMAD4 signal transduction through CD147.

Examples of the antibody of the present invention can further include human antibodies. The term "anti-CD147 human antibody" refers to a human antibody having only the gene sequence of a human chromosome-derived antibody. Such an anti-CD147 human antibody can be obtained by, for example, a method using mice producing a human antibody having a human chromosome fragment comprising the genes of the heavy chains and the light chains of a human antibody (see Tomizuka, K. et al., Nature Genetics (1997)16, p. 133-143; Kuroiwa, Y. et al., Nucl. Acids Res. (1998) 26, p. 3447-3448; Yoshida, H. et al., Animal Cell Technology: Basic and Applied Aspects vol. 10, p. 69-73 (Kitagawa, Y., Matsuda, T. and Iijima, S. eds.), Kluwer Academic Publishers, 1999; Tomizuka, K. et al., Proc. Natl. Acad. Sci. USA (2000) 97, p. 722-727 etc.).

Specifically, such human antibody-producing mice can be obtained by: producing gene-recombinant animals through disruption of the gene loci of the endogenous immunoglobulin heavy chain and light chain, and then introducing the gene loci of the human immunoglobulin heavy chain and light chain via a vector such as a human artificial chromosome (HAC) vector or a mouse artificial chromosome (MAC) vector in place of the disrupted loci; and recombinant animals are then created by crossing these animals.

Eukaryotic cells are transformed by gene recombination techniques with cDNA encoding each of such a human antibody heavy chain and light chain, preferably a vector comprising the cDNA, and then the transformed cells producing the gene-recombinant human monoclonal antibody are cultured, so that the antibody can be obtained from the culture supernatant. Here, as host cells, eukaryotic cells, preferably CHO cells, mammalian cells such as lymphocytes and myeloma cells can be used.

Methods for obtaining a phage display-derived human antibody selected from a human antibody library (see Wormstone, I. M. et al., Investigative Ophthalmology & Visual Science. (2002) 43(7), p. 2301-2308; Carmen, S. et al., Briefings in Functional Genomics and Proteomics (2002), 1(2), p. 189-203; Siriwardena, D. et al., Ophthalmology (2002) 109(3), p. 427-431, etc.) are also known.

For example, a phage display method can be employed whereby a human antibody variable region is expressed on the phage surface as a single-chain antibody (scFv), and then phage binding to the antigen is selected (Nature Biotechnology (2005), 23, (9), p. 1105-1116). The gene of the phage selected based on its binding to an antigen is analyzed, so that the DNA sequence encoding the human antibody variable region binding to the antigen can be determined. Once the DNA sequence of scFv binding to the antigen is revealed, an expression vector having the sequence is prepared, and then introduced into an appropriate host for expression, and thus a human antibody can be obtained (WO92/01047, WO92/20791, WO93/06213, WO93/11236, WO93/19172, WO95/01438, WO95/15388, Annu. Rev. Immunol. (1994) 12, p. 433-455, Nature Biotechnology (2005) 23(9), p. 1105-1116).

Examples of the antibody of the present invention also include an antibody having the same epitope as that of an antibody provided by the present invention. Examples thereof include an antibody having the same epitope as that of at least one of LN22R8, 2P10F2, rat_CD147_#84, rat_CD147_#101, rat_CD147_#110 and rat_CD147_#131.

LN22R8 and 2P10F2 of the present invention recognized an epitope denoted as mu3 in FIG. 3 (human CD147v1: DALPGQKTEFKVDSDDQ (SEQ ID NO: 143), monkey CD147: DTLPGQKTDFEVDSDDL (SEQ ID NO: 144)). Examples of the antibody of the present invention also include an antibody that recognizes or binds to a sequence comprising an amino acid sequence in which 1 or several, preferably 1 to 3, more preferably 1 or 2 amino acids are deleted, substituted, or added in the sequence of SEQ ID NO: 143 or SEQ ID NO: 144, or SEQ ID NO: 143 or SEQ ID NO: 144. The antibody preferably activates signal transduction through CD147.

Examples of the antibody of the present invention include an antibody that recognizes the same epitope as that of rat_CD147_#110, preferably, humanized #110H1L4. The antibody preferably activates signal transduction through CD147. The results of the analysis of the epitope of humanized #110H1L4 are described in Example 17.

A suitable antibody can be selected through evaluation of the binding activity to an antigen as known by persons skilled in the art. The dissociation constant of an antibody and the antigen (CD147) can be measured using Biacore T200 (GE Healthcare Bioscience) with surface plasmon resonance (SPR) as the detection principle. For example, an antibody at an appropriate concentration and an analyte are reacted to an antigen immobilized as a ligand, the binding and dissociation thereof are measured, and thus the association rate constant ka1, the dissociation rate constant kd1 and the dissociation constant (KD; KD=kd1/ka1) can be obtained.

A device to be used for the evaluation of binding activity to CD147 is not limited to Biacore T200. Binding activity to CD147 can also be evaluated using an instrument with surface plasmon resonance (SPR) as the detection principle, KinExA (Sapidyne Instruments) with kinetic exclusion assay as the detection principle, BLItz system (Pall) with bio-layer interferometry as the detection principle, or ELISA (Enzyme-Linked ImmunoSorbent Assay), for example.

An example of another indicator for comparison of the properties of antibodies can be the stability of antibodies. Differential scanning calorimetry (DSC) is a method capable of quickly and accurately measuring the thermal unfolding midpoint (Tm), serving as a good indicator of the relative structural stability of proteins. Tm values are measured using DSC, the Tm values are compared, and then differences in thermal stability can be compared. The storage stability of an antibody is known to be correlated with the thermal stability of the antibody to some extent (Lori Burton, et al., Pharmaceutical Development and Technology (2007) 12, p. 265-273). Hence, a suitable antibody can be selected with thermal stability as an indicator. Examples of other indicators for selection of an antibody can include a high yield in appropriate host cells, and low aggregability in an aqueous solution. For example, since an antibody exhibiting the highest yield does not always exhibit the highest thermal stability, an optimum antibody for administration to humans should be selected through a comprehensive determination based on the above indicators.

A method for obtaining a single chain immunoglobulin, which involves linking the full-length sequences of an antibody heavy chain and light chain with an appropriate linker, is also known (Lee, H-S, et al., Molecular Immunology (1999) 36, p. 61-71; Shirrmann, T. et al., mAbs (2010), 2, (1) p. 1-4). Such a single chain immunoglobulin can retain the structure and activity analogous to those of an antibody that is originally a tetramer through dimerization. The antibody of the present invention may also be an antibody having a single heavy chain variable region, but lacking a light chain sequence. Such an antibody is referred to as a single domain antibody (sdAb) or a nanobody, and has been actually observed among camels or lamas and reported as retaining antigen binding ability (Muyldemans S. et al., Protein Eng. (1994) 7(9), 1129-35, Hamers-Casterman C. et al., Nature (1993) 363 (6428) 446-8). The above antibody can also be construed as a type of an antigen-binding fragment of the antibody in accordance with the present invention.

Antibody-dependent cellular cytotoxic activity can be enhanced by regulating the glycosylation of the sugar chain binding to the antibody of the present invention. Examples of known techniques for regulating the glycosylation of antibodies include, but are not limited to, WO99/54342, WO2000/61739, and WO2002/31140.

When an antibody is prepared by isolating an antibody gene and then introducing the isolated gene into an appropriate host, such an appropriate host and an expression vector can be used in combination.

Specific examples of an antibody gene can include combinations of genes encoding antibody heavy chain sequences and genes encoding light chain sequences described herein. Upon transformation of host cells, a heavy chain sequence gene and a light chain sequence gene can be inserted into the same expression vector, or can be inserted into different expression vectors. When eukaryotic cells are used as host cells, animal cells, plant cells, and eukaryotic microorganisms can be used. Examples of animal cells can include mammalian cells, for example, monkey cells; that is, COS cells (Gluzman, Y. Cell (1981) 23, p. 175-182, ATCC CRL-1650), dihydrofolate reductase deficient cell lines of mouse fibroblasts NIH3T3 (ATCC, CRL-1658) or Chinese hamster ovary cells (CHO cells, ATCC CCL-61) (Urlaub, G. and Chasin, L. A. Proc. Natl. Acad. Sci. USA. (1980) 77, p. 4126-4220). When prokaryotic cells are used, examples thereof can include *Escherichia coli* and *Bacillus subtilis*. An antibody gene of interest is introduced into these cells by transformation, and then the thus transformed cells are cultured in vitro, thereby obtaining the antibody. The above culture methods may vary in yield depending on the sequence of an antibody. Hence, an antibody that would be easy to produce as a drug can be selected by using the yield as an indicator by which to select between antibodies having equivalent binding activity.

An isotype of the antibody of the present invention is not limited and examples thereof can include IgG (IgG1, IgG2, IgG3, IgG4), IgM, IgA (IgA1, IgA2), IgD or IgE. Such an isotype is preferably IgG or IgM, and another example thereof is preferably IgG.

Human IgG1 exhibits very strong effector functions including CDC activity through mediation of complement fixation and antibody-dependent cellular cytotoxic activity out of the existing 4 types of human IgG subclass (Bruggemann et al., J. Exp. Med., 1351-1361, 1987). When a molecule that is highly expressed in cancer is targeted by a therapeutic antibody, human IgG1 is used as it is an IgG isotype that exhibits therapeutic effects by promoting the induction of cancer-cell death due to cytotoxicity mediated by effector functions (e.g., trastuzumab and rituximab). However, it has been reported that a human IgG1 antibody targeting HLA-DR with its original CDC activity, led to cynomolgus monkeys dying after administration thereof. The use of such an antibody as an antibody drug which targets a molecule that is also expressed in normal organs causes a concern that the effector functions could induce a severe adverse reaction (Tawara, T., J. Immunology, 2008, 2294-2298). When IgG1 is used as an isotype of the antibody of the present invention, the IgG1 antibody may have a mutation, and specifically, effector functions can be adjusted by substitution of some of the amino acid residues of the constant regions (see WO88/007089, WO94/28027, WO94/29351). Examples of a variant of IgG1 with attenuated effector functions include IgG1 LALA (IgG1-L234A, L235A), and 1gG1 LAGA (IgG1-L235A, G237A).

Human IgG2 has very weak effector functions including CDC activity through complement fixation and antibody-dependent cellular cytotoxic activity among the existing 4 types of human IgG subclass (Bruggemann et al., J. Exp. Med., 1351-1361, 1987). When a molecule that is expressed in normal organs is targeted by a therapeutic antibody, IgG2 is used as one of the IgG formats to avoid toxicity due to cytotoxicity mediated by effector functions (Denosumab, Evolocumab, Brodalumab).

Human IgG4 has very weak effector functions including CDC activity through complement fixation and antibody-dependent cellular cytotoxic activity among the existing 4 types of human IgG subclass (Bruggemann et al., J. Exp. Med., 1351-1361, 1987). When a molecule that is expressed in normal organs is targeted by a therapeutic antibody, IgG4 is used as one of the IgG formats to avoid toxicity due to cytotoxicity mediated by effector functions (Opdivo). When IgG4 is used as an isotype of the antibody of the present invention, splitting, a distinct feature of IgG4, is suppressed and the half-life can be extended by substitution of some of amino acid residues of the constant regions (see Molecular Immunology, 30, 1 105-108 (1993)).

When IgG4 is used as an isotype of the antibody of the present invention, the IgG4 antibody may have a mutation. Examples of a mutation of an IgG4 variant include (Proc Natl Acad Sci USA. 1969, 63(1), 78-85; Kabat et al., Sequences of proteins of immunological interest, 1991 Fifth edition) a substitution (F234A) of phenylalanine at position 234 according to the EU Index with alanine and substitution (L235A) of leucine at position 235 according to the EU Index with alanine (Parekh et al., mAbs, 310-318, 2012). Such a mutation of an antibody is referred to as FALA mutation. IgG4P FALA further attenuates effector functions through substitution of two amino acid residues required for interaction with FcγRs (for example, FcγRI, FcγRII or FcγRIII) existing in the CH2 domain with alanine. Since S—S bond formation between antibody heavy chains is unstable in IgG4, a mutation for accelerating S—S bond formation between antibody heavy chains is introduced into IgG4 in order to increase the stability. Examples of such a mutation include a substitution (S228P) of serine at position 228 according to the EU Index with proline (ANGAL et al., Molecular Immunology, 105-108, 1993). Such mutation of an antibody is referred to as Pro mutation. Into the constant region of the antibody of the present invention, both FALA mutation and Pro mutation described above may be introduced simultaneously (Vafa et al., Methods, 65, 114-126, 2014). An IgG4 heavy chain having the FALA mutation is referred to as "IgG4FALA"-type heavy chain, an IgG4 heavy chain having the Pro mutation is referred to as "IgG4P"-type heavy chain, and an IgG4 heavy chain having both FALA mutation and Pro mutation is referred to as "IgG4PFALA"-type heavy chain.

An antibody heavy chain constant region consists of CH1, hinge, CH2 and CH3 regions, wherein CH1 is defined as ranging from EU Index No. 118 to 215, the hinge is defined as ranging from EU Index No. 216 to 230, CH2 is defined as ranging from EU Index No. 231 to 340, and CH3 is defined as ranging from EU Index No. 341 to 446. According to the EU Index, proline resulting from substitution of serine at position 228, alanine resulting from substitution of phenylalanine at position 234, and alanine resulting from substitution of leucine at position 235 correspond to: proline at position 248, alanine at position 254 and alanine at position 255, respectively, in SEQ ID NO: 100 representing the amino acid sequence of human chimeric rat_CD147_#84 heavy chain IgG4PFALA; proline at position 245, alanine at position 251, and alanine at position 252, respectively, in SEQ ID NO: 108 representing the amino acid sequence of human chimeric rat_CD147_#101 heavy chain IgG4PFALA; and proline at position 244, alanine at position 250, and alanine at position 251, respectively, in SEQ ID NO: 108 representing the amino acid sequence of human chimeric rat_CD147_#110 heavy chain IgG4PFALA.

Preferred examples of an isotype of the antibody of the present invention include IgG1, IgG2, IgG4, IgG4P or IgG4PFALA, particularly preferred examples thereof include IgG2, IgG4P or IgG4PFALA, and even more preferred examples thereof include IgG2 or IgG4P.

The antibody of the present invention may also be an antigen-binding fragment of an antibody, which has an antigen-binding site of the antibody or a modified product thereof. An antibody is treated with protease such as papain or pepsin, or, an antibody gene is modified by genetic engineering techniques and then the resultant is expressed in appropriate cultured cells, so that a fragment of the antibody can be obtained. Of these antibody fragments, fragments retaining all or part of functions of the full-length antibody molecule can be referred to as an antigen-binding fragment of the antibody. An example of the functions of an antibody is activation of antigen-related signal transduction.

CD147 is also expressed in blood cells including erythrocytes and normal organs essential for survival (Spring, et al., Eur. J. Immunol., 1997, 891-897), and thus antitumor efficacy exerted using effector functions accompanying an antibody has a high risk for adverse reaction. It has been actually reported that erythrocytes are sensitive to effector functions (ADCC, CDC, ADCP) resulting from antibody binding (Flegel, W., Transfusion, 2015, S47-S58), and the thus increased antibody in vivo against erythrocytes is known to cause autoimmune hemolytic anemia (Gibson, J., Aust. N. Z. J. Med., 1988. 625-637). The antibody of the present invention as a therapeutic antibody targeting CD147 that is also expressed in normal cells is characterized in that any one of or all of ADCC activity, ADCP activity and CDC activity, which cause serious adverse reaction, are detected at low levels or none of these activities are detected.

The present inventors have discovered for the first time that the anti-human CD147 antibody exhibits antitumor efficacy independent of the antibody's effector functions by activating cell signal transduction through CD147. In the present invention, the antibody retains the functions of binding activity to CD147 and/or activating CD147. The antibody of the present invention activates preferably downstream signal-related molecules mediating CD147, for example, FAK, MEK, Erk, JAK/STAT, AKT or MAP kinase (MAPK) or activates signal-related signal located further downstream thereof. The antibody of the present invention activates more preferably, molecules located downstream of MAPK or MAPK. An example of MAPK is, preferably, p38MAPK. Examples of signal molecules located further downstream of MAPK include HSP27, cxcl8 and SMAD (for example, SMAD2, SMAD3 or SMAD4, preferably, SMAD4). Examples of the "activation of CD147" include increased p38MAPK mRNA expression level, increased p38MAPK protein expression level, phosphorylation of p38MAPK, phosphorylation of HSP27 (for example, phosphorylation of Ser82 of HSP27 or phosphorylation of Ser15 of HSP27), increased cxcl8 mRNA expression level, increased cxcl8 protein expression level, increased rhoB mRNA expression level or increased rhoB protein expression level through SMAD signal activation. Examples of the "activation of CD147" include preferably, increased p38MAPK protein expression level, phosphorylation of p38MAPK, phosphorylation of HSP27 (for example, phosphorylation of Ser82 of HSP27 or phosphorylation of Ser15 of HSP27), increased cxcl8 mRNA expression level, and increased rhoB mRNA expression level through SMAD signal activation.

SMAD2 or SMAD3 is known to be phosphorylated by the TGFβ receptor when TGFβ binds to the TGFβ receptor (TGFBR1/2), so as to form a heterotrimer with SMAD4. After nuclear import thereof, the heterotrimer is known to bind to a transcriptional regulatory domain having a SMAD DNA binding sequence on the chromosome (Smad binding element: SBE), and then positively or negatively controls the mRNA expression of downstream genes (Miyazono, The Official Journal of the Japan Geriatrics Society, 1999, 162-166). Therefore, it is considered that the activation of SMAD4 requires the presence of SMAD2 or SMAD3. SMAD2, SMAD3 and SMAD4 negatively control KLF5 expression level in a TGFβ-dependent manner (David et al., Cell, 2016, 164(5), 1015-1030). In SMAD4-deficient pancreatic cancer cells, signals for suppressing the expression of the KLF5 gene through SMAD2, SMAD3 and SMAD4 are canceled, and thus KLF5 protein is expressed. It is known that when SMAD4 is lost and KLF5 is expressed, TGFβ-dependent cell death signaling (SOX4-dependent) is suppressed (above-mentioned David et al, Cell).

Figure 21B:
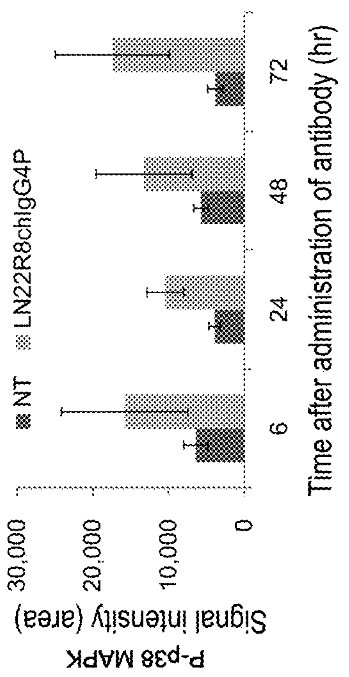
FIGS. 21(*a*) to (*c*) show p38MAPK phosphorylation by an anti-human CD147 human chimeric antibody in tumors.
Figure 21A:
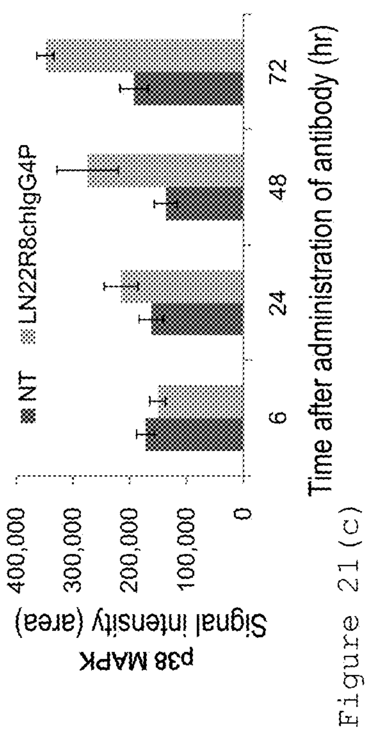
Figure 21C:
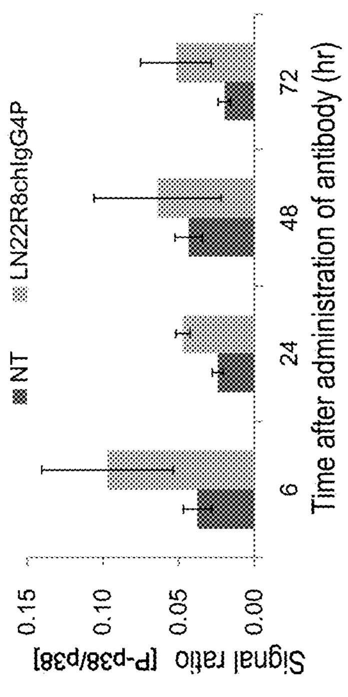
Figure 22A:
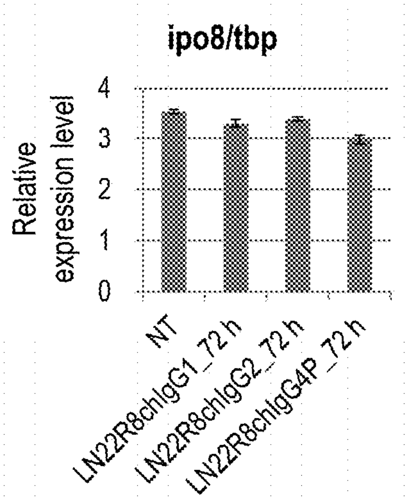
FIGS. 22(*a*) to (*c*) show expression of ipo8, cxcl8 and rhoB by anti-human CD147 human chimeric antibodies.
Figure 22B:
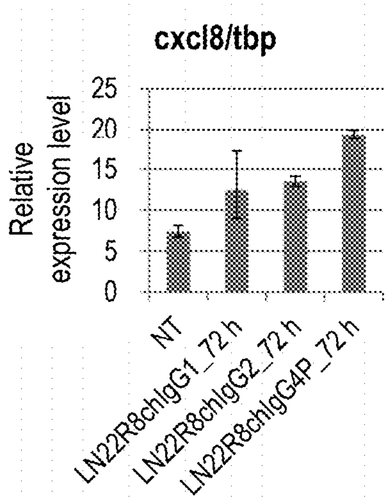
Figure 22C:
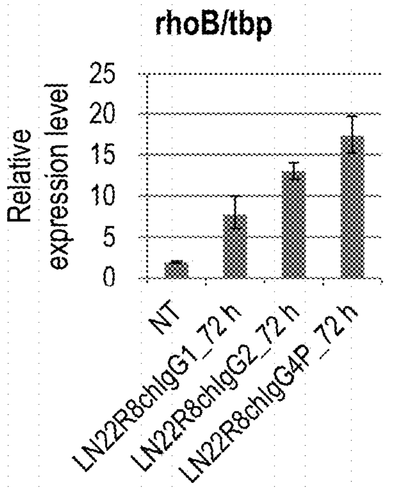
Figure 23A:
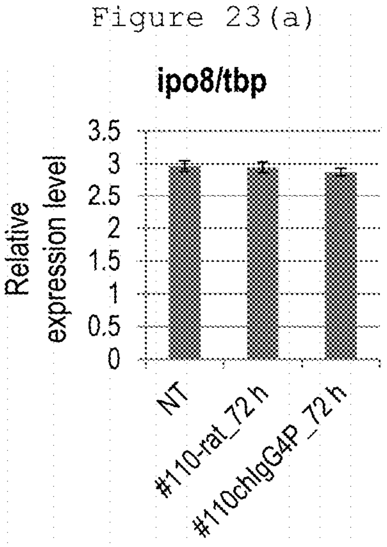
FIGS. 23(*a*) to (*c*) show expression of ipo8, cxcl8 and rhoB by an anti-human CD147 rat antibody and its human chimeric antibody.
Figure 23B:
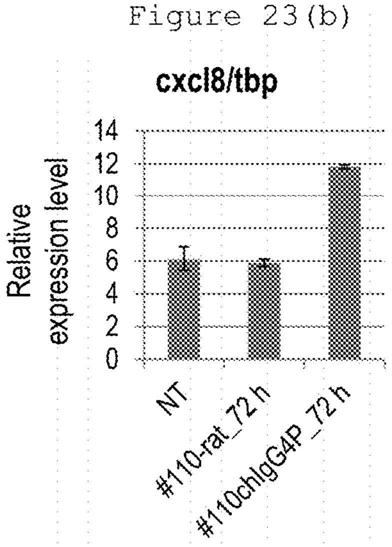
Figure 23C:
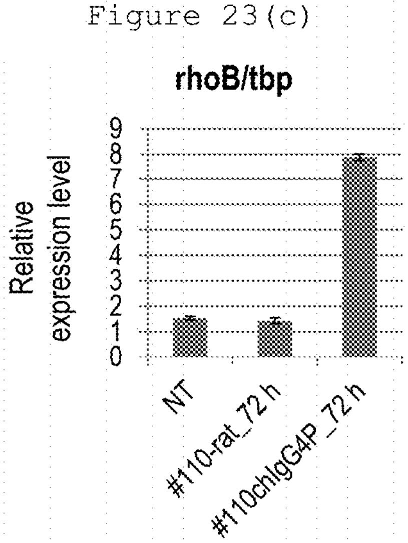

The present inventors have discovered that the anti-human CD147 antibody of the present invention phosphorylates p38MAPK (FIG. 21), phosphorylates HSP27 (FIG. 20), and increases the expression of cxcl8 (FIG. 22(*b*) and FIG. 23(*b*)). Therefore, activation of CD147 by the antibody of the present invention can be confirmed by confirming a change in gene expression, protein expression or phosphorylation of at least one of these molecules before and after the administration of the antibody.

The present inventors have discovered that: the anti-human CD147 antibody of the present invention exhibits efficacy on a pancreatic cancer model expressing SMAD4 protein (FIG. 25); the anti-human CD147 antibody of the present invention exhibited partial (up to about 30%) anti-tumor efficacy in a pancreatic cancer model such as BxPC-3 having a gene mutation in SMAD4 and expressing no SMAD4 (FIG. 24); and downstream molecules of SMAD2, SMAD3 and SMAD4 (rhoB, FIG. 22(*c*) and FIG. 23(*c*)) are induced in tumors after administration of the anti-human CD147 antibody of the present invention. Therefore, before and after administration of the antibody of the present invention, the presence or the absence of a change in rhoB gene expression or rhoB protein expression is confirmed, so that if the antibody of the present invention mediates the activation of CD147, this can be confirmed. The genome sequence, gene expression or protein expression of SMAD4 in patient samples is measured using a method known by persons skilled in the art, patients in which SMAD4 is expressed are selected as subject patients to which the antibody of the present invention is to be administered, and thus the antibody of the present invention can be administered to them.

The level of KLF5 expression is known to be high in a SMAD4-negative model such as BxPC-3 (David et al., Cell, 2016, 164(5), 1015-1030). Sensitivity to the anti-human CD147 antibody of the present invention was decreased from 91% to 20% in the KLF5-expressing MIA PaCa-2 model (Example 26). Accordingly, the present inventors consider that KLF5 expression suppresses SMAD2-, SMAD3- and SMAD4-dependent cell death signaling induced by the CD147 antibody. Since KLF5 expression levels are low in liver cancer, ALL, lymphoma, gastrointestinal stromal tumor (GIST), skin cancer, sarcoma, AML or renal cancer, the anti-human CD147 antibody of the present invention is expected to be effective for many patients with these cancers. The gene expression or the protein expression of KLF5 in patient samples is measured using a method known by persons skilled in the art, patients exhibiting decreased KLF5 expression levels or lacking KLF5 expression are selected as subject patients to which the antibody of the present invention is to be administered, and thus the antibody of the present invention can be administered to them. The degree of a decrease in KLF5 expression in this case can be determined by a method known by persons skilled in the art and performing appropriate clinical trials. For example, patients for which effects can be obtained and patients for which no effect can be obtained are compared for KLF5 expression level, thereby determining an appropriate threshold.

Examples of antibody fragments can include Fab, $F(ab')_2$, Fv, or single-chain Fv (scFv) in which heavy chain Fv and light chain Fv are connected with an appropriate linker, a diabody (diabodies), a linear antibody, and a multi-specific antibody formed of antibody fragments. Examples of antibody fragments include Fab', which is a monovalent fragment of an antibody variable region, and prepared by treating $F(ab')_2$ under reducing conditions.

Moreover, the antibody of the present invention may also be a multi-specific antibody having specificity to at least two different types of antigens. Such a molecule generally binds to two types of antigens (i.e., bispecific antibody), and examples of the "multispecific antibody" in the present invention include an antibody having specificity to three or more (for example, 3 types) antigens.

The multispecific antibody of the present invention may be a full-length antibody, or fragments of such an antibody (for example, $F(ab')_2$ bispecific antibody). A bispecific antibody can be prepared by binding a heavy chain and a light chain (HL pair) of two types of antibodies, or, fusing hybridomas producing different monoclonal antibodies to each other, so as to prepare bispecific antibody-producing fused cells (Millstein et al., Nature (1983) 305, P. 537-539).

The antibody of the present invention may be a single chain antibody (also described as scFv). A single chain antibody is obtained by connecting an antibody heavy chain variable region and a light chain variable region with a polypeptide linker (Pluckthun, The Pharmacology of Monoclonal Antibodies, 113 (Ed., Rosenberg and Moore, Springer Verlag, New York, p. 269-315 (1994), Nature Biotechnology (2005), 23, p. 1126-1136). BiscFv fragment prepared by connecting two scFvs with a polypeptide linker can also be used as a bispecific antibody.

Methods for preparing a single chain antibody are known in the art (for example, see U.S. Pat. Nos. 4,946,778, 5,260,203, 5,091,513, and 5,455,030.). In the scFv, a heavy chain variable region and a light chain variable region are connected via a linker that does not form a conjugate, preferably a polypeptide linker (Huston, J. S. et al., Proc. Natl. Acad. Sci. USA. (1988), 85, p. 5879-5883). A heavy chain variable region and a light chain variable region in scFv may be derived from the same antibody or different antibodies. As a polypeptide linker for connecting variable regions, for example, an arbitrary single chain peptide consisting of 12 to 19 residues is used.

DNA encoding scFv can be obtained by amplifying by the PCR method using as a template, one selected out of: DNA encoding the above antibody heavy chain or heavy chain variable region, and DNA encoding the light chain or light chain variable region, DNA encoding the full-length sequence of each region or a DNA portion encoding a desired amino acid sequence thereof, and a primer pair specifying each end thereof, and then amplifying using DNA encoding a polypeptide linker portion, and a primer pair specifying end so that the ends are connected to a heavy chain and a light chain, respectively, in combination.

Once DNA encoding scFv is prepared, an expression vector containing the DNA and a host transformed with the expression vector can be obtained according to a standard method, and, scFv can be obtained according to a standard method using the host. These antibody fragments can be produced by a host after obtainment of the gene thereof and expression of the gene in the same manner as described above.

The antibody of the present invention may be polymerized to have enhanced affinity for an antigen. An antibody to be polymerized may be a single type of antibody or a plurality of antibodies recognizing a plurality of epitopes of the same antigen. Examples of a method for polymerization of an antibody can include, binding of an IgG CH3 domain with two scFvs, binding with streptavidin, and introduction of a helix-turn-helix motif.

The antibody of the present invention may also be a polyclonal antibody that is a mixture of multiple types of anti-CD147 antibody differing in amino acid sequence. An example of a polyclonal antibody can be a mixture of multiple types of antibody differing in CDR. As such a polyclonal antibody, a mixture of cells producing different antibodies is cultured and an antibody purified from the culture can be used (see WO2004/061104).

The antibody of the present invention may be an antibody having 80% to 99% identity (or homology) with the above antibody heavy chain and/or light chain. Through combination of sequences exhibiting high homology with the above heavy chain amino acid sequence and light chain amino acid sequence, an antibody having antigen binding ability, activation of CD147, preferably, activation of MAPK, and activation of downstream signal molecules of MAPK equivalent to those of each antibody above can be selected. Such homology is generally 80% or more homology, preferably 90% or more homology, more preferably 95% or more homology, and most preferably 99% or more homology. Through combination of the heavy chain and/or the light chain amino acid sequence with an amino acid sequence in which 1 to several amino acid residues are substituted, deleted and/or added, an antibody having various effects equivalent to those of each antibody above can be selected. The number of amino acid residues to be substituted, deleted and/or added is generally 10 or less amino acid residues, preferably 5 to 6 or less amino acid residues, more preferably 2 to 3 or less amino acid residues, and most preferably 1 amino acid residue. In addition, it is known that the carboxyl terminal lysine residue of an antibody heavy chain produced by cultured mammalian cells is deleted (Tsubaki et al., Int. J. Biol. Macromol, 139-147, 2013). However, deletion and modification of these heavy chain sequences do not affect the antibody's binding ability to an antigen and effector functions (e.g., activation of complement and antibody-dependent cellular cytotoxicity). Therefore, the present invention includes an antibody subjected to a modification, and examples thereof can include an antibody in which 1 or 2 amino acids are deleted at the heavy chain carboxyl terminus, and an antibody subjected to amidation (for example, a heavy chain in which a proline residue at the carboxyl terminal site is amidated). Note that, as long as the binding ability to an antigen and the function of activating signal-related molecules located downstream of CD147 are maintained, a heavy chain carboxyl terminal-deficient antibody according to the present invention is not limited to the above types. The two heavy chains which compose the antibody of the present invention may be any one type of heavy chain selected from the group consisting of full-length heavy chains and the above-deficient heavy chains, or a combination of two types thereof. The ratio of carboxyl terminal-deficient heavy chains can be affected by the type and culture conditions of the cultured mammalian cells producing the antibody according to the present invention, and an example thereof can be a case in which each of the two heavy chains, as major components of the antibody of the present invention, has a deletion of one amino acid residue at the carboxyl terminus.

Homology between two types of amino acid sequence can be determined using default parameters of Blast algorithm version 2.2.2 (Altschul, Stephen F., Thomas L. Madden, Alejandro A. Schaffer, Jinghui Zhang, Zheng Zhang, Webb Miller, and David J. Lipman (1997), "Gapped BLAST and PSI-BLAST: a new generation of protein database search programs", Nucleic Acids Res. 25: 3389-3402). The Blast algorithm can also be used by accessing the Internet, www.ncbi.nlm.nih.gov/blast. Note that the two types of percentage of Identity (or Identities) and Positivity (or Positivities) are calculated by the Blast algorithm. The former percentage is a value derived from when amino acid residues match when comparing two types of amino acid sequence in which homology is expected to be found, and the latter is a numerical value found when amino acid residues analogous to each other in chemical structure are also taken into consideration. The value of identity when amino acid residues match is designated as the value of homology in the application.

As modified products of an antibody, antibodies bound to various molecules such as polyethylene glycol (PEG) can also be used.

The antibody of the present invention may also be an immunoconjugate formed between such an antibody and another drug. Examples of such an antibody can include the antibody bound to a radioactive substance or a compound having pharmacologic effects (Nature Biotechnology (2005) 23, p. 1137-1146).

The thus obtained antibody can be purified to a homogenous state. For separation and purification of an antibody, separation and purification methods used for general proteins may be employed. For example, an antibody can be separated and purified by adequately selecting or combining column chromatography, filter filtration, ultrafiltration, salting-out, dialysis, polyacrylamide gel electrophoresis for preparation, isoelectric focusing (Strategies for Protein Purification and Characterization: A Laboratory Course Manual, Daniel R. Marshak et al. eds., Cold Spring Harbor Laboratory Press (1996); Antibodies: A Laboratory Manual. Ed Harlow and David Lane, Cold Spring Harbor Laboratory (1988)), but separation and purification methods therefor are not limited to these examples.

Examples of chromatography can include affinity chromatography, ion exchange chromatography, hydrophobic chromatography, gel filtration chromatography, reverse phase chromatography, and adsorption chromatography.

These chromatographies can be performed using liquid chromatography such as HPLC and FPLC.

Examples of a column to be used for affinity chromatography can include a protein A column and a protein G column.

Examples of a column using the protein A column can include Hyper D, POROS, Sepharose F. F. (GE Healthcare).

An antibody can also be purified using a carrier to which an antigen is immobilized and the binding activity to the antigen.

(Drug Comprising Anti-CD147 Antibody)

The anti-CD147 antibody of the present invention can be obtained from among anti-CD147 antibodies obtained by a method described in the above section "Production of anti-CD147 antibody". The thus obtained antibody can be used as an agent for treating and/or preventing tumor and/or cancer. The anti-CD147 antibody of the present invention has excellent antitumor efficacy, and is useful as a remedy for treating tumor or cancer. The anti-CD147 antibody of the present invention exhibited excellent antitumor efficacy on gemcitabine-resistant cancer cells and cancer cells having low sensitivity to sorafenib. The anti-CD147 antibody of the present invention exhibited significantly stronger efficacy on chronic myeloid leukemia cells, than those of imatinib.

Examples of tumors that can be treated using the anti-CD147 antibody of the present invention or a drug comprising the antibody are not particularly limited, as long as they are tumors expressing CD147, and include preferably, pancreatic cancer, liver cancer, gastric cancer, colon cancer, renal cancer, breast cancer, uterine cancer, ovarian cancer, lung cancer, thyroid cancer, skin cancer, head and neck cancer, sarcoma, prostate cancer, bladder cancer, brain tumor, gastrointestinal stromal tumor (GIST), leukemia (for example, acute myeloid leukemia (AML), chronic myeloid leukemia (CML), or chronic lymphocytic leukemia (CLL) or acute lymphocytic leukemia (ALL)), lymphoma or malignant lymphoma (for example, B-cell lymphoma, non-Hodgkin's lymphoma or diffuse large B-cell lymphoma (DLBCL)), and more preferably, pancreatic cancer, liver cancer, gastric cancer, colon cancer, renal cancer, leukemia, acute myeloid leukemia (AML), chronic myeloid leukemia (CML), chronic lymphocytic leukemia (CLL), acute lymphocytic leukemia (ALL), malignant lymphoma, B-cell lymphoma, non-Hodgkin's lymphoma or diffuse large B-cell lymphoma (DLBCL).

Examples of tumors that can be treated using the antibody of the present invention or a drug comprising the antibody include SMAD-positive CD147-expressing tumors. Examples of SMAD-positive CD147-expressing tumors include SMAD-positive CD147-expressing liver cancer and pancreatic cancer. The anti-CD147 antibody of the present invention or a drug comprising the antibody is administered to, preferably, patients confirmed for the expression of CD147 and/or SMAD. Examples of SMAD include, preferably, SMAD2, SMAD3 and/or SMAD4, and more preferably SMAD4. Preferably, together with confirmation of the expression of SMAD4, the expression of at least one of SMAD2 and SMAD3 is confirmed.

Alternatively, examples of a tumor that can be treated with the antibody of the present invention or a drug comprising the antibody include a tumor exhibiting decreased expression of KLF5 or lacking the expression of KLF5. Examples of a tumor exhibiting decreased expression of KLF5 or lacking the expression of KLF5 include liver cancer, ALL, lymphoma, gastrointestinal stromal tumor (GIST), skin cancer, sarcoma, AML and renal cancer. The anti-CD147 antibody of the present invention or a drug comprising the antibody is preferably administered to a patient confirmed to exhibit decreased expression of KLF5 or lack the expression of KLF5.

The anti-CD147 antibody of the present invention can also be administered with 2, 3 or more other therapeutic agents depending on the purpose of treatment. These other therapeutic agents can be encapsulated in the same preparation and administered simultaneously. Other therapeutic agents and the anti-CD147 antibody may also be encapsulated in the same preparation and thus can be administered simultaneously. The anti-CD147 antibody and other therapeutic agents may be separately encapsulated in preparations and can then be administered simultaneously. Further, other drugs and the anti-CD147 antibody can also be administered separately, specifically the drugs can be administered before or after the administration of the anti-CD147 antibody. Specifically, after administration of other therapeutic agents, a therapeutic agent comprising the anti-CD147 antibody or an antigen-binding fragment of the antibody as an active component is administered, or, after administration of a therapeutic agent comprising the anti-CD147 antibody or an antigen-binding fragment of the antibody as an active component, other therapeutic agents may be administered.

The present invention also provides a pharmaceutical composition comprising a therapeutically and/or prophylactically effective amount of the anti-CD147 antibody, and a pharmaceutically acceptable diluent, carrier, solubilizer, emulsifier, preservative and/or adjuvant.

The present invention also provides a pharmaceutical composition comprising a therapeutically and/or prophylactically effective amount of the anti-CD147 antibody, a therapeutically and/or prophylactically effective amount of at least one antitumor therapeutic agent, and a pharmaceutically acceptable diluent, carrier, solubilizer, emulsifier, preservative and/or adjuvant.

Substances to be used for a preparation that are acceptable in the pharmaceutical composition of the present invention are preferably nontoxic to a subject to which the pharmaceutical composition is administered in terms of preferably dosage and concentration for administration.

The pharmaceutical composition of the present invention can contain substances for a preparation in order to vary or maintain the pH, osmotic pressure, viscosity, transparency, color, isotonicity, sterility, stability, solubility, sustained release rate, absorptivity, permeability, and the like. Examples of substances for a preparation can include the following, but are not limited to: amino acids such as glycine, alanine, glutamine, asparagine, arginine or lysine, antimicrobial agents, antioxidants such as ascorbic acid, sodium sulfate or sodium hydrogen sulfite, buffering agents such as a phosphate, citrate, or borate buffer, sodium hydrogen carbonate, and tris-hydrochloric acid (Tris-Hcl) solution, fillers such as mannitol and glycine, chelating agents such as ethylenediaminetetraacetic acid (EDTA), complexing agents such as caffeine, polyvinyl pyrrolysine, β-cyclodextrin, and hydroxypropyl-β-cyclodextrin, extending agents such as glucose, mannose or dextrin, carbohydrates such as monosaccharide and disaccharide, colorants, flavors, diluents, emulsifiers, hydrophilic polymers such as polyvinyl pyrrolysine, low-molecular-weight polypeptides, salt-forming counter ions, benzalkonium chloride, benzoic acid, salicylic acid, thimerosal, phenethyl alcohol, methylparaben, propylparaben, chlorhexidine, antiseptics such as sorbic acid or hydrogen peroxide, glycerin, solvents such as propylene and glycol or polyethylene glycol, sugar alcohols such as mannitol or sorbitol, suspensions, sorbitan esters, polysorbates such as polysorbate 20 and polysorbate 80, triton, tromethamine, surfactants such as lecithin or cholesterol, stabilization enhancers such as sucrose and sorbitol, sodium chloride, potassium chloride, elasticity enhancers such as mannitol and sorbitol, transporting agents, excipients, and/or pharmaceutical adjuvants. The amount of such a substance for a preparation is preferably added in an amount 0.01 to 100 times, and particularly 0.1 to 10 times the weight of the anti-CD147 antibody. The composition of a suitable pharmaceutical composition in a preparation can be adequately determined by persons skilled in the art according to its applicable disease, applicable route of administration, and the like.

An excipient and a carrier in a pharmaceutical composition may be liquid or solid. An appropriate excipient and an appropriate carrier may be water or saline for injection, an artificial cerebrospinal fluid, or other substances that are generally used for parenteral administration. Neutral saline or saline containing serum albumin can also be used as a carrier. A pharmaceutical composition can contain a Tris buffer of pH7.0-8.5, an acetate buffer of pH4.0-5.5, or a citrate buffer of pH3.0-6.2. These buffers may contain sorbitol and other compounds. Examples of the pharmaceutical composition of the present invention can include a pharmaceutical composition comprising the anti-CD147 antibody and a pharmaceutical composition comprising the anti-CD147 antibody and at least one antitumor therapeutic agent. The pharmaceutical composition of the present invention is prepared as a drug having the selected composition and purity as required, a freeze-dried product or a liquid. A pharmaceutical composition comprising the anti-CD147 antibody and a pharmaceutical composition comprising the anti-CD147 antibody and at least one anticancer therapeutic agent can also be formulated as a freeze-dried product in which an appropriate excipient such as sucrose is used.

The pharmaceutical composition of the present invention can also be prepared for parenteral administration, or for oral administration for gastrointestinal absorption. The composition and the concentration of a preparation can be determined depending on the method of administration. When the antibody of the present invention is administered to a human, about 0.1 to 100 mg/kg of the antibody may be administered once or several times during 1 to 180 days. However, the dosage and the frequency of administration should be generally determined in consideration of the gender, body weight, and age of a patient, symptoms, severity, adverse reaction, and the like, and thus doses and methods therefor are not limited to the above examples.

Examples of the form of the pharmaceutical composition of the present invention can include injection preparations including preparations for infusion, suppositories, nasal agents, sublingual agents, and transdermal absorbents. Examples of the route of administration include oral administration or parenteral administration. Examples of parenteral administration include intravenous, intraarterial, intramuscular, rectal, transmucosal or intramucosal, and intradermal administrations.

The antibody of the present invention or an antigen-binding fragment of the antibody, a drug complex comprising them, a bispecific antibody comprising them or a pharmaceutical composition comprising them can be provided in combination with a biomarker for selecting patients to which they are administered. Such an antibody or a pharmaceutical composition may also be provided as a kit in combination with a means for detecting a biomarker, or, such an antibody or a pharmaceutical composition may be provided separately with a biomarker. Through the use of a biomarker, the antibody or the pharmaceutical composition of the present invention can be administered to a patient group for whom the antibody of the present invention is expected to be highly effective.

The present invention relates to: a method for predicting responsiveness to cancer treatment, comprising using cancer patient-derived biological samples, measuring the expression of SMAD4 or the expression of KLF5 contained in the biological samples, and determining patients in whom SMAD4 is detected or patients in whom decreased expression of KLF5 or the lack of the expression of KLF5 is detected as having responsiveness to cancer treatment with the antibody of the present invention or a functional fragment of the antibody, or, the pharmaceutical composition of the present invention; a method for selecting subjects of cancer treatment, comprising using cancer patient-derived biological samples, detecting the expression of SMAD4 or the expression of KLF5 in the biological samples, and selecting patients in whom SMAD4 is detected or patients in whom decreased expression of KLF5 or the lack of the expression of KLF5 is detected as subjects of cancer treatment with the antibody of the present invention or a functional fragment of the antibody, or, the pharmaceutical composition of the present invention; a method for treating cancer, comprising using cancer patient-derived biological samples, detecting the expression of SMAD4 or the expression of KLF5 in the biological samples, and administering the antibody of the present invention or a functional fragment of the antibody, or, the pharmaceutical composition of the present invention to patients in whom SMAD4 is detected or patients in whom decreased expression of KLF5 or the lack of the expression of KLF5 is detected; or, a kit for determining responsiveness to cancer treatment with the antibody of the present invention or a functional fragment of the antibody, or, the pharmaceutical composition of the present invention, comprising at least a means for detecting the expression of SMAD4 or the expression of KLF5 in the cancer patient-derived biological samples.

The term “biological sample(s)” as used herein refers to a tissue, a liquid, and cells isolated from an individual and a mixture thereof, and examples thereof can include, but are not limited to, a tumor biopsy, spinal fluids, pleural fluids, intraperitoneal fluids, lymph, skin sections, blood, urine, feces, sputum, respiratory organs, intestinal tract, genitourinary organs, saliva, breast milk, digestive organs, and cells collected therefrom. Examples of the “biological sample(s)” include preferably a sample containing cancer cells, more preferably a tissue or cells obtained by excision or biopsy, or cells derived from a pleural fluid or an intraperitoneal fluid. Further preferred biological samples are samples containing cancer cells or cancerous tissue.

The “expression of SMAD4” can be detected or measured using the genome sequence, the gene expression or the protein expression of SMAD4 according to a method known by persons skilled in the art. Examples of such a method include RNA sequencing, microarray, genome sequencing, and immunoassay.

The “expression of KLF5” can be detected or measured using the genome sequence, the gene expression or the protein expression of KLF5 according to a method known by persons skilled in the art. Examples of such a method include IHC, RNA sequencing, microarray, genome sequencing, and immunoassay. The term “decreased expression of KLF5” means that when compared with a control (for example, the expression level in a healthy subject or the expression level in a non-cancerous tissue of the same patient), the expression level is found to be lower than that of the control. Alternatively, the degree of the decreased expression of KLF5 at which the responsiveness to cancer treatment resulting from the use of the antibody or the pharmaceutical composition of the present invention can be confirmed, can be determined by performing a method known by persons skilled in the art and appropriate clinical trials. For example, patients for which an effect can be obtained and patients for which no effect can be obtained are compared for KLF5 expression levels, thereby setting an appropriate threshold. Therefore, the term "decreased expression of KLF5" refers to an expression level lower than the thus determined threshold, for example.

EXAMPLES

Hereinafter, the present invention will be described specifically by way of examples, but the present invention is not limited to the following examples. Moreover, these are not to be interpreted in a limited manner in any sense. In the following examples, procedures relating to genetic engineering were performed according to the methods described in "Molecular Cloning" (Authors: Sambrook, J., Fritsch, E. F., and Maniatis, T., published by Cold SpringHarbor Laboratory Press in 1989), other methods described in experimental manuals and used by those skilled in the art, or instructions of commercially available products in the case of using commercially available reagents or kits, unless otherwise stated. Further, reagents, solvents, and starting materials which are not specifically mentioned in this description can be easily obtained from commercial supply sources. In these examples, ATCC, Cat. CRL-1420 was used as a human pancreatic line MIA PaCa-2, and ATCC, Cat. CRL-1469 was used as a human pancreatic cancer cell line PANC-1.

Example 1

Production of Mouse and Rat Antibodies by Cell Immunization

1)-1 Production of CD147 Expression Vector

A clone IOH3378 (Invitrogen, Thermo Fisher Scientific K.K.) of a commercially available human CD147 gene (BSG variant2/CD147v2) was cloned into an expression vector for mammalian cells pcDNA-DEST40 (Invitrogen, Thermo Fisher Scientific K.K.) using Gateway LR Clonase to produce a human CD147v2 expression vector (pcDNA-DEST40-CD147v2).

An expression vector for mammalian cells pCMV6-XL5-hBSGv1 (OriGene Technologies, Inc., Cat. SC303059) of a commercially available human CD147 gene (BSG variant1/CD147v1) was purchased and used as a human CD147v1 expression vector.

As a cynomolgus monkey CD147 expression vector, pCMV3-cynoBSG (Sino Biological Inc., Cat. CG90636-UT) was purchased.

As a mouse CD147v2 expression vector, pCMV3-mBSGv2 (Sino Biological Inc., Cat. MG50332-UT) was purchased.

1)-2 Production of Mouse Hybridomas 4 to 6 week-old BALB/cAnNCrlCrlj mice (CHARLES RIVER LABORATORIES JAPAN, INC.) were used. $5\times10^6$ LNCaP cells (ATCC, CRL-1740) separated using Versene (available from Thermo Fisher SCIENTIFIC K.K.) on day 0, 7, 15, and 24 were suspended in PBS, and the suspension was administered subcutaneously in the back. The same $5\times10^6$ cells were intravenously administered on day 31, and the spleen was collected on the same day and used for producing hybridomas. The spleen cells were fused with mouse myeloma P3X63Ag8U.1 cells (ATCC, CRL-1597) using PEG4000 (Immuno-Biological Laboratories Co., Ltd.) to produce hybridomas. For isolating and culturing hybridomas, ClonaCell-HY MediumD (STEMCELL Technologies Inc.) and ClonaCell-HY MediumE (STEMCELL Technologies Inc.) were used.

1)-3 Production of Rat Hybridomas 7 week-old WKY/Izm rats (Japan SLC, Inc.) were used. 13 days after immunization with $1\times10^7$ cells of a human pancreatic cancer cell line PANC-1 in the buttocks, iliac lymph node cells were collected and used for generation of hybridomas. Rat spleen cells were fused with mouse myeloma SP2/0-Ag14 cells (ATCC, CRL-1581) using a LF301 cell fusion device (BEX CO., LTD.) to produce hybridomas. For isolating and culturing hybridomas, ClonaCell-HY MediumD (STEMCELL Technologies Inc.) and ClonaCell-HY MediumE (STEMCELL Technologies Inc.) were used.

1)-4 Identification of Antigen by ELISA

A human CD147-Fc fusion protein (Sino Biological Inc., Cat. 10186-H02H) and a mouse CD147-Fc fusion protein (Sino Biological Inc., Cat.50332-M03H) were used. The human CD147-Fc fusion protein and the mouse CD147-Fc fusion protein were prepared by adding a PBS buffer solution and dissolving on ice to 1 μg/ml. 100 μl of the protein solution was added to a 96-well plate (Nunc, Thermo Fisher Scientific K.K., Cat. 442404), followed by storage overnight at 4° C., and the wells were coated with a CD147-Fc fusion protein. The protein solution was removed, and the wells were blocked with a PBS buffer solution containing 1% BSA (Research Organics, Inc., Cat. 1334A) at 4° C. for two hours. The wells were washed three times with a PBS buffer solution containing 0.05% Tween20 (ATTO CORPORATION, Cat. WSE-7235). Thereafter, the hybridoma culture supernatants prepared in Examples 1)-2 and 1)-3 were diluted 20 times with a PBS buffer solution and were each added to wells, followed by incubation at room temperature for one hour. The wells were washed with a PBS buffer solution containing 0.05% Tween20 (ATTO CORPORATION, Cat.WSE-7235) three times. Thereafter, 100 μl of anti-rat-Fab2-igG-HRP (Jackson ImmunoResearch Inc., Cat. 112-036-072) diluted 50000 times with a PBS buffer solution containing 1% BSA was added thereto, followed by shaking at room temperature for 30 minutes. The wells were washed 5 times with a PBS buffer solution containing 0.05% Tween20 (ATTO CORPORATION, Cat. WSE-7235). Thereafter, 100 μl of HRP enzyme coloring reagent (eBioscience, Thermo Fisher SCIENTIFIC K.K., Super AquaBlue ELISA substrate, Cat. 00-4203) was added thereto, followed by heating at room temperature for 10 to 20 minutes, and the absorbance at 405 nm was measured with a plate reader (Envision, PerkinElmer, Inc). An average of the measured values for absorbance of two to three wells was calculated, and antibodies having an absorbance twice or more the measured value of the control well without primary antibodies were determined to have a binding activity (+), and those having an absorbance less than twice were determined to have no binding activity (−). Table 1 summarizes the results. Color development specific to wells coated with the human CD147-Fc fusion protein was observed in the culture supernatants of LN22R8, 2P1A6, 2P3A9, 2P8C12, 2P10F2, 2P2D7, 2P2D10, and 2P1B7. Color development specific to wells coated with the human and mouse CD147-Fc fusion proteins was observed in LN24R7, 2P5F5, 2P6A2, and 2P3G8.

TABLE 1

| | BSA | hCD147 | mCD147 |
|---|---|---|---|
| LN22R8 | − | + | − |
| LN24R7 | − | + | + |
| 2P1A6 | − | + | − |
| 2P3A7 | − | − | − |
| 2P3A9 | − | + | − |
| 2P3E12 | − | − | − |
| 2P3G5 | − | − | − |
| 2P5E2 | − | − | − |
| 2P5F5 | − | + | + |
| 2P6A2 | − | + | + |
| 2P6C9 | − | − | − |
| 2P6H2 | − | − | − |
| 2P7B8 | + | + | − |
| 2P7D6 | − | − | − |
| 2P8B12 | − | − | − |
| 2P8C12 | − | + | − |
| 2P9A12 | + | + | + |
| 2P9B10 | − | − | − |
| 2P10E6 | − | − | − |
| 2P10F2 | − | + | − |
| 2P10H2 | + | + | + |
| 2P2D7 | − | + | − |
| 2P2D10 | − | + | − |
| 2P2E6 | − | − | − |
| 2P2H8 | − | − | − |
| 2P1B7 | − | + | − |
| 2P3A9 | − | − | − |
| 2P3G8 | − | + | + |

1)-5 Preparation of Monoclonal Antibodies and Determination of Antibody Isotypes For hybridomas in which production of anti-human CD147 antibodies was observed in Example 1)-4 and which could be stably cultured, isotypes of the antibodies contained in culture supernatants were determined using a commercially available isotyping kit, and Table 2 shows the results. Using a CL-1000 flask (Becton, Dickinson and Company), these hybridomas were cultured to prepare hybridoma culture supernatants containing monoclonal antibodies.

TABLE 2

CD147 antibodies obtained from cell immunization

| Antibody | Isotype |
|---|---|
| LN22R8 | Mouse IgG3 |
| 2P1A6 | Rat IgG2a/κ |
| 2P1B7 | Rat IgG2a/κ |
| 2P2D6 | Rat IgG2a/κ |
| 2P3G8 | Rat IgG2b/κ |
| 2P2D7 | Rat IgG2a/κ |
| 2P2D10 | Rat IgG2b/κ |
| 2P8C12 | Rat IgG2a/κ |
| 2P10F2 | Rat IgG2b/κ |

1)-6 Purification of Monoclonal Antibodies

Each antibody was purified from the culture supernatant prepared in Example 1)-5. The anti-human CD147 mouse monoclonal antibody was purified by a one-step process of rProtein A affinity chromatography (at 4 to 6° C.). A buffer replacement step was performed at 4 to 6° C. after the rProtein A affinity chromatographic purification. First, the culture supernatant was applied to a column equilibrated with PBS and filled with MabSelectSuRe (available from GE Healthcare Bioscience). After the culture solution was fully put into the column, the column was washed with PBS in an amount twice or more the column volume. Next, elution with a 2M arginine hydrochloride solution (pH 4.0) was performed to collect a fraction containing the antibody. The fraction was subjected to liquid replacement with HBSor (25 mM Histidine/5% Sorbitol/pH 6.0) by dialysis (Thermo Scientific, Slide-A-Lyzer Dialysis Cassette). After concentration using a Centrifugal UF Filter Device VIVASPIN20 (fraction molecular weight UF10K, Sartorius AG, at 4° C.), the IgG concentration was adjusted to 4.9 mg/ml. Finally, filtration was performed using a Minisart-Plus filter (Sartorius AG) to give a purified sample.

The anti-human CD147 rat monoclonal antibody was purified by a one-step process of Protein G affinity chromatography (at 4 to 6° C.). A buffer replacement step was performed at 4 to 6° C. after the Protein G affinity chromatographic purification. First, the hybridoma culture supernatant was applied to a column equilibrated with PBS and filled with ProteinG (GE Healthcare Bioscience). After the culture supernatant solution was fully put into the column, the column was washed with PBS in an amount twice or more the column volume. Next, elution with a 0.1M glycine/aqueous hydrochloric acid solution (pH 2.7) was performed to collect a fraction containing the antibody. After 1M Tris-HCl (pH 9.0) was added to the collected fraction to adjust the pH to 7.0 to 7.5, buffer replacement with HBSor (25 mM Histidine/5% Sorbitol/pH 6.0) was performed together with concentration using a Centrifugal UF Filter Device VIVASPIN20 (fraction molecular weight UF30K, Sartorius AG, at 4 to 6° C.) to adjust the antibody concentration to 1 mg/mL or more. Finally, filtration was performed using a Minisart-Plus filter (Sartorius AG) to give a purified sample.

1)-7 Antibody Screening by Measurement of In-Vivo Antitumor Efficacy $1\times10^7$ cells of human pancreatic line PANC-1 were suspended in PBS, and the suspension was inoculated subcutaneously into the axilla of NOD-scid mice (CHARLES RIVER LABORATORIES JAPAN, INC., NOD. CB17-Prkdc<scid>/J). Grouping was performed based on tumor volume, and the mouse anti-CD147 antibody (LN22R8) or the rat anti-CD147 antibody (2P1A6, 2P1B7, 2P3G8, 2P2D10, 2P8C12, or 2P10F2) was administered intraperitoneally to cancer-bearing mice at 10 mg/kg on the 27th, 34th, and 41st day after the inoculation (n=6). The rat anti-CD147 antibody (2P2D6) was administered intraperitoneally to cancer-bearing mice at 10 mg/kg on the 27th and 34th day after the inoculation (n=6). The major axis and the minor axis of the inoculated tumor were measured twice a week using an electronic digital caliper (available from MITUTOYO CORPORATION) to calculate the tumor volume by the following formula.

$$\text{Tumor volume (mm}^3\text{)}=1/2\times\text{minor axis(mm)}\times\text{minor axis(mm)}\times\text{major axis(mm)}$$

FIGS. 1(*a*) to (*c*) show the results. The graphs also show the averages and the standard errors of changes in tumor volume. FIG. 1(*a*) shows the results of the 2P2D6 antibody, the 2P3G8 antibody, and the 2P2D10 antibody. The tumor growth inhibition rate on the 48th day after the inoculation, which was the final measurement date, was 10%, 45%, and 40%, respectively, in the 10 mg/kg administration group. FIG. 1(*b*) shows the results of the LN22R8 antibody, the 2P1A6 antibody, and the 2P1B7 antibody. The tumor growth inhibition rate on the 48th day after the inoculation, which was the final measurement date, was 50%, 26%, and 24%, respectively, in the 10 mg/kg administration group. FIG. 1(*c*)

shows the results of the 2P8C12 antibody and the 2P10F2 antibody. The tumor growth inhibition rate on the 48th day after the inoculation, which was the final measurement date, was −2% and 62%, respectively, in the 10 mg/kg administration group.

1)-8 Analysis of Species Cross Reactivity of CD147 Antibody

Using Lipofectamine 2000 (Thermo Fisher SCIENTIFIC K.K., Cat. 11668-019), pcDNA-DEST40-CD147v2 or pCMV3-cynoBSG produced in Example 1)-1 was transfected into CHO-K1 cells (ATCC, CCL-61), and the cells were treated with mouse anti-human CD147 antibody (LN22R8) or rat anti-human CD147 antibody (2P1A6, 2P1B7, 2P3G8, 2P2D10, 2P8C12, 2P10F2, or 2P2D6) at 10 μg/ml one day later, thereby enabling fluorescence detection of binding of each antibody to CD147 expressing CHO-K1 cells using anti-mouse IgG-FITC (MP Biomedicals, Inc., Cat. 554936) or anti-rat IgG-PE (BD Biosciences, Cat. 550767). Fluorescence detection of human and cynomolgus monkey CD147 expression in CHO-K1 cells was enabled by binding of commercially available anti-CD147 antibody (MEM-M6/1, AbD Serotec, Cat. MCA28822). The aforementioned cells were measured using a flow cytometer (CantoII, BD Biosciences), and FIGS. 2-1 to 2-3 summarize the results. In the graphs, the vertical axis represents the number of cells, and the horizontal axis represents the intensity of fluorescence signals.

A commercially available anti-CD147 antibody (MEM-M6/1), a mouse anti-human CD147 antibody (LN22R8), and rat anti-CD147 antibodies (2P1A6, 2P1B7, 2P3G8, 2P2D10, 2P8C12, 2P10F2, and 2P2D6) all exhibited a binding activity to human CD147 expressing CHO-K1 cells (FIGS. 2-1 to 2-3).

The commercially available anti-CD147 antibody (MEM-M6/1) exhibited a binding activity to cynomolgus monkey CD147 expressing CHO-K1 cells, but none of the mouse anti-human CD147 antibody (LN22R8) and the rat anti-human CD147 antibodies (2P1A6, 2P1B7, 2P3G8, 2P2D10, 2P8C12, 2P10F2, and 2P2D6) exhibited a binding activity to cynomolgus monkey CD147 expressing CHO-K1 cells (FIGS. 2-1 to 2-3).

None of the anti-CD147 antibodies exhibited a binding activity to mouse CD147 expressing CHO-K1 cells (data not shown).

1)-9 Epitope Analysis

Production of Mutated Human CD147 Expressing Vectors for Epitope Analysis

As a result of a BLAST search (https://blast.ncbi.nlm.nih.gov/Blast.cgi), the amino acid sequences of cynomolgus monkey and human CD147 were calculated to be 81% identical. Therefore, estimation of antitumor epitopes using mutants in which different amino sequences were partially grafted between the species was performed, as it was assumed that limited differences in the amino acid sequences would directly affect recognition of CD147 antibody binding epitopes. Amino acid sequences contained in hCD147v1 and v2 which were in common were subjected to a sequence comparison between cynomolgus monkey and human CD147 and were classified into 9 different amino acid regions between the species to form mu1 to mu9 (FIG. 3). To produce CD147 mutant expression vectors and to confirm the expression on a cell surface, a cDNA sequence of human CD147 variant2 with a FLAG sequence introduced into the N-terminus was artificially synthesized in order to produce a plasmid which was then introduced into a pcDNA3.1 vector, Signal-N-Flag-hCD147v2 pcDNA3.1 (by GenScript Biotech Corporation). Further, 9 types of human-cynomolgus monkey chimeric CD147 expression vectors, hCD147-mu1_pcDNA3.1, hCD147-mu2_pcDNA3.1, hCD147-mu3_pcDNA3.1, hCD147-mu4_pcDNA3.1, hCD147-mu5_pcDNA3.1, hCD147-mu6_pcDNA3.1, hCD147-mu7_pcDNA3.1, hCD147-mu8_pcDNA3.1, and hCD147-mu9_pcDNA3.1, which were formed by introducing DNA encoding cynomolgus monkey CD147 amino acid sequences mu1 to mu9 as amino acid substitution mutations by DNA replacement into the human CD147 gene of the same plasmid, were produced (by GenScript Biotech Corporation).

1)-10 Identification of Antitumor Epitope Regions Using Mutants

The 9 types of expression vectors of human CD147, cynomolgus monkey CD147, or human-cynomolgus monkey chimeric CD147 expression vectors were introduced into CHO-K1 cells (ATCC, CCL-61) using Lipofectamine 2000 (Thermo Scientific, Cat. 11668-019), followed by treatment with an anti-human CD147 mouse antibody (LN22R8) or a rat anti-human CD147 antibody (2P1A6, 2P1B7, 2P3G8, 2P2D10, 2P8C12, 2P10F2, or 2P2D6) at 10 μg/ml one day later, and binding of the anti-CD147 antibody to CD147 expressing CHO-K1 cells was investigated using anti-mouse IgG-PE (DAKO, Cat. R480) or anti-rat IgG-PE (Becton, Dickinson and Company, #550767). Expression of CD147 protein was confirmed using a commercially available anti-FLAG antibody (anti-Flag M2, SIGMA, Cat. F4049-.2MG). Measurements using a flow cytometer (CantoII, BD Biosciences) were taken, and Table 3 summarizes the results. Samples with an increase in fluorescence signals of 10 times or more as compared with those in the control cells that were not treated with primary antibodies were determined to be binding positive (+). Samples with a partial increase in fluorescence signals of less than 10 times were determined to be binding slightly positive (±). Samples with no increase in fluorescence signals as compared with those in the control cells that were not treated with primary antibodies were determined to be binding negative (−).

All the antibodies 2P3G8, 2P10F2, 2P2D10, and LN22R8 having an antitumor efficacy of 40% or more observed in Example 1)-7 had lost the binding activity to CD147 with mu3 mutation. This suggested that an important epitope for the antitumor efficacy was the m3 region.

TABLE 3

| | in vivo anti-tumor effect | mock | pCMV3-cyno BSG | Signal-N-Flag-hCD147 v2_pcDNA3.1 | hCD 147-mu1_pcDNA3.1 | hCD 147-mu2_pcDNA3.1 | hCD 147-mu3_pcDNA3.1 | hCD 147-mu4_pcDNA3.1 | hCD 147-mu5_pcDNA3.1 | hCD 147-mu6_pcDNA3.1 | hCD 147-mu7_pcDNA3.1 | hCD 147-mu8_pcDNA3.1 | hCD 147-mu9_pcDNA3.1 |
|---|---|---|---|---|---|---|---|---|---|---|---|---|---|
| anti-Flag M2 | ND | − | − | + | + | + | + | + | + | + | + | + | + |
| 2P1A6 | 26% | − | ± | + | − | + | + | + | + | + | + | + | + |
| 2P1B7 | 24% | − | − | + | − | + | ± | + | + | + | + | + | + |

TABLE 3-continued

| | in vivo anti-tumor effect | mock | pCMV3-cynoBSG | Signal-N-Flag-hCD147 v2_pcDNA3.1 | hCD147-mu1_pcDNA3.1 | hCD147-mu2_pcDNA3.1 | hCD147-mu3_pcDNA3.1 | hCD147-mu4_pcDNA3.1 | hCD147-mu5_pcDNA3.1 | hCD147-mu6_pcDNA3.1 | hCD147-mu7_pcDNA3.1 | hCD147-mu8_pcDNA3.1 | hCD147-mu9_pcDNA3.1 |
|---|---|---|---|---|---|---|---|---|---|---|---|---|---|
| 2P3G8 | 45% | − | − | + | + | + | − | + | + | + | + | + | + |
| 2P10F2 | 58% | − | − | + | + | + | − | + | + | + | + | + | + |
| 2P8C12 | 8% | − | − | + | − | + | + | + | + | + | + | + | + |
| 2P2D10 | 40% | − | − | + | + | + | − | + | + | + | + | + | + |
| LN22R8 | 50% | − | − | + | ± | + | − | − | + | + | + | + | ± |
| MEM-M6/1 | ND | − | + | + | + | + | ± | + | + | + | + | + | + |

1)-11 Determination of the Nucleotide Sequence of cDNA Encoding the Variable Region of LN22R8 and 2P10F2 Antibodies 1)-11-1 Determination of the Nucleotide Sequence of cDNA Encoding the Variable Region of the LN22R8 Antibody 1)-11-1-1 Preparation of Total RNA of LN22R8 Antibody Producing Hybridoma For amplifying a cDNA encoding the variable region of the LN22R8 antibody, total RNA was prepared using a TRIzol Reagent (Ambion) from hybridomas producing LN22R8 antibody.

1)-11-1-2 Amplification of cDNA Encoding the LN22R8 Antibody Light Chain Variable Region by 5'-RACE PCR and Determination of its Sequence A cDNA encoding the light chain variable region was amplified using about 1 μg of the total RNA prepared in Example 1)-11-1-1 and a SMARTer RACE 5'/3' Kit (Clontech Laboratories, Inc). As primers for amplifying the cDNA encoding the variable region of the light chain gene of the LN22R8 antibody by PCR, UPM (Universal Primer A Mix: attached to the SMARTer RACE 5'/3' Kit) and a primer designed from the sequence of the constant region of a known mouse light chain were used.

The cDNA encoding the light chain variable region amplified by 5'-RACE PCR was cloned into a plasmid, and then the nucleotide sequence of the cDNA encoding the light chain variable region was analyzed.

SEQ ID NO: 7 represents the nucleotide sequence of the cDNA encoding the LN22R8 antibody light chain variable region thus determined, and SEQ ID NO: 8 represents the amino acid sequence thereof. SEQ ID NOs: 11, 12, and 13 respectively represent CDRL1, CDRL2, and CDRL3 of the LN22R8 antibody light chain variable region.

1)-11-1-3 Amplification of cDNA Encoding the LN22R8 Antibody Heavy Chain Variable Region by 5'-RACE PCR and Determination of its Sequence A cDNA encoding the heavy chain variable region was amplified using about 1 μg of the total RNA prepared in Example 1)-11-1-1 and a SMARTer RACE 5'/3' Kit (Clontech Laboratories, Inc.). As primers for amplifying the cDNA encoding the variable region of the heavy chain gene of the LN22R8 antibody by PCR, UPM (Universal Primer A Mix: attached to the SMARTer RACE 5'/3' Kit) and a primer designed from the sequence of the constant region of a known mouse heavy chain were used.

The cDNA encoding the heavy chain variable region amplified by 5'-RACE PCR was cloned into a plasmid, and then the nucleotide sequence of the cDNA encoding the heavy chain variable region was analyzed.

SEQ ID NO: 9 represents the nucleotide sequence of the cDNA encoding the LN22R8 antibody heavy chain variable region thus determined, and SEQ ID NO: 10 represents the amino acid sequence thereof. SEQ ID NOs: 14, 15, and 16 respectively represent CDRH1, CDRH2, and CDRH3 of the LN22R8 antibody heavy chain variable region.

1)-11-2 Determination of the Nucleotide Sequence of cDNA Encoding the Variable Region of the 2P10F2 Antibody The same methods as in Example 1)-11-1 were employed. However, UPM (Universal Primer A Mix: attached to the SMARTer RACE 5'/3' Kit) and a primer designed from the sequence of the constant region of a known rat light chain were used as primers for amplifying the cDNA encoding the variable region of the light chain gene by PCR, and UPM (Universal Primer A Mix: attached to the SMARTer RACE 5'/3' Kit) and a primer designed from the sequence of the constant region of a known rat heavy chain were used as primers for amplifying the cDNA encoding the variable region of the heavy chain gene by PCR.

SEQ ID NO: 17 represents the nucleotide sequence of the cDNA encoding the 2P10F2 antibody light chain variable region thus determined, and SEQ ID NO: 18 represents the amino acid sequence thereof. SEQ ID NOs: 21, 22, and 23 respectively represent CDRL1, CDRL2, and CDRL3 of the 2P10F2 antibody light chain variable region. SEQ ID NO: 19 represents the nucleotide sequence of the cDNA encoding the heavy chain variable region, and SEQ ID NO: 20 represents the amino acid sequence thereof. SEQ ID NOs: 24, 25, and 26 respectively represent CDRH1, CDRH2, and CDRH3 of the 2P10F2 antibody heavy chain variable region.

1)-12 Production of Human Chimeric Antibody Expression Vectors of LN22R8

1)-12-1 Construction of Human Chimeric and Humanized Light Chain Expression Vector pCMA-LK About 5.4 kb of a fragment obtained by digesting a plasmid pcDNA3.3-TOPO/LacZ (Invitrogen Corp.) with restriction enzymes XbaI and PmeI was bound to a DNA fragment containing the human light chain signal sequence represented by SEQ ID NO: 27 and the DNA sequence encoding the human κ chain constant region using an In-Fusion HD PCR cloning kit (Clontech Laboratories, Inc.) to produce pcDNA3.3/LK.

Neomycin expressing units were removed from pcDNA 3.3/LK, thereby constructing pCMA-LK.

1)-12-2 Construction of Human Chimeric and Humanized IgG1-Type Heavy Chain Expression Vector pCMA-G1

A DNA fragment from which the light chain signal sequence and the human κ chain constant region were removed by digesting pCMA-LK with XbaI and PmeI was bound to a DNA fragment containing the human heavy chain signal sequence represented by SEQ ID NO: 28 and the DNA sequence encoding the amino acids in the human IgG1 constant region using an In-Fusion HD PCR cloning kit (Clontech Laboratories, Inc.) to construct pCMA-G1.

1)-12-3 Construction of Human Chimeric and Humanized IgG2-Type Heavy Chain Expression Vector pCMA-G2

Using a DNA fragment containing the human heavy chain signal sequence represented by SEQ ID NO: 29 and the DNA sequence encoding the amino acids in the human IgG2 constant region, pCMA-G2 was constructed in the same manner as in Example 1)-12-2.

1)-12-4 Construction of Human Chimeric LN22R8 Light Chain Expression Vector

Using the cDNA encoding the LN22R8 light chain variable region obtained in Example 1)-11-1-2 as a template, PCR was performed using a primer designed for In-fusion cloning, thereby amplifying a DNA fragment containing the cDNA encoding the light chain variable region. The amplified DNA fragment was inserted at the site where pCMA-LK was digested with restriction enzyme BsiWI, using an In-Fusion HD PCR cloning kit (Clontech Laboratories, Inc.), thereby constructing a human chimeric LN22R8 light chain expression vector. SEQ ID NO: 30 and SEQ ID NO: 31 respectively represent the nucleotide sequence of human chimeric LN22R8 light chain and the amino acid sequence of the light chain.

1)-12-5 Construction of IgG1-Type Human Chimeric LN22R8 Heavy Chain Expression Vector Using the cDNA encoding the LN22R8 heavy chain variable region obtained in 1)-11-1-3 as a template, PCR was performed using a primer designed for In-fusion cloning, thereby amplifying a DNA fragment containing the cDNA encoding the heavy chain variable region. Using an In-Fusion HD PCR cloning kit (Clontech Laboratories, Inc.), the amplified DNA fragment was inserted at the site where pCMA-G1 was digested with restriction enzyme BlpI, thereby constructing an IgG1-type human chimeric LN22R8 heavy chain expression vector. SEQ ID NO: 32 and SEQ ID NO: 33 respectively represent the nucleotide sequence of the IgG1-type human chimeric LN22R8 heavy chain and the amino acid sequence of the heavy chain.

1)-12-6 Construction of IgG2-Type Human Chimeric LN22R8 Heavy Chain Expression Vector Using the cDNA encoding the LN22R8 heavy chain variable region obtained in Example 1)-11-1-3 as a template, PCR was performed using a primer designed for In-fusion cloning, thereby amplifying a DNA fragment containing the cDNA encoding the heavy chain variable region. Using an In-Fusion HD PCR cloning kit (Clontech Laboratories, Inc.), the amplified DNA fragment was inserted at the site where pCMA-G2 was digested with restriction enzyme BlpI, thereby constructing an IgG2-type human chimeric LN22R8 heavy chain expression vector. SEQ ID NO: 34 and SEQ ID NO: 35 respectively represent the nucleotide sequence of the IgG2-type heavy chain of human chimeric LN22R8 and the amino acid sequence of the heavy chain.

1)-12-7 Construction of IgG4P-Type Human Chimeric LN22R8 Heavy Chain Expression Vector A DNA fragment containing the DNA sequence encoding the amino acid sequence of the IgG4P-type heavy chain of human chimeric LN22R8 represented by SEQ ID NO: 36 was synthesized (Geneart AG). Using the synthesized DNA fragment, an IgG4P-type human chimeric LN22R8 heavy chain expression vector was constructed in the same manner as in Example 1)-12-2. SEQ ID NO: 37 represents the amino acid sequence of the IgG4P-type heavy chain of human chimeric LN22R8.

1)-13 Production of Human Chimeric Antibody Expression Vectors of 2P10F2

1)-13-1 Construction of Human Chimeric and Humanized IgG1LALA-Type Heavy Chain Expression Vector pCMA-G1LALA Using the human heavy chain signal sequence represented by SEQ ID NO: 38 and a DNA fragment containing the DNA sequence encoding the amino acids of the human IgG1LALA constant region, pCMA-G1LALA was constructed in the same manner as in Example 1)-12-2.

1)-13-2 Construction of Human Chimeric and Humanized IgG4P-Type Heavy Chain Expression Vector pCMA-G4P Using the human heavy chain signal sequence represented by SEQ ID NO: 39 and a DNA fragment containing the DNA sequence encoding the amino acids of the human IgG4P constant region, pCMA-G4P was constructed in the same manner as in Example 1)-12-2.

1)-13-3 Construction of Human Chimeric 2P10F2 Light Chain Expression Vector

Using the cDNA encoding the 2P10F2 light chain variable region obtained in Example 1)-11-2 as a template, a human chimeric 2P10F2 light chain expression vector was constructed in the same manner as in Example 1)-12-4. SEQ ID NO: 40 and SEQ ID NO: 41 respectively represent the nucleotide sequence of the human chimeric 2P10F2 light chain and the amino acid sequence of the light chain.

1)-13-4 Construction of IgG1LALA-Type Human Chimeric 2P10F2 Heavy Chain Expression Vector Using the cDNA encoding the 2P10F2 heavy chain variable region obtained in Example 1)-11-2 as a template, PCR was performed using a primer designed for In-fusion cloning, thereby amplifying a DNA fragment containing the cDNA encoding the heavy chain variable region. Using an In-Fusion HD PCR cloning kit (Clontech Laboratories, Inc.), the amplified DNA fragment was inserted at the site where pCMA-G1LALA was digested with restriction enzyme BlpI, thereby constructing an IgG1LALA-type human chimeric 2P10F2 heavy chain expression vector. SEQ ID NO: 42 and SEQ ID NO: 43 respectively represent the nucleotide sequence of the IgG1LALA-type heavy chain of human chimeric 2P10F2 and the amino acid sequence of the heavy chain.

1)-13-5 Construction of IgG2-Type Human Chimeric 2P10F2 Heavy Chain Expression Vector Using the cDNA encoding the 2P10F2 heavy chain variable region obtained in Example 1)-11-2 as a template, an IgG2-type human chimeric 2P10F2 heavy chain expression vector was constructed in the same manner as in Example 1)-12-6. SEQ ID NO: 44 and SEQ ID NO: 45 respectively represent the nucleotide sequence of the IgG2-type heavy chain of human chimeric 2P10F2 and the amino acid sequence of the heavy chain.

1)-13-6 Construction of IgG4P-Type Human Chimeric 2P10F2 Heavy Chain Expression Vector Using the cDNA encoding the 2P10F2 heavy chain variable region obtained in Example 1)-11-2 as a template, PCR was performed using a primer designed for In-fusion cloning, thereby amplifying a DNA fragment containing the cDNA encoding the heavy chain variable region. Using an In-Fusion HD PCR cloning kit (Clontech Laboratories, Inc.), the amplified DNA fragment was inserted at the site where pCMA-G4P was digested with restriction enzyme BlpI, thereby constructing an IgG4P-type human chimeric 2P10F2 heavy chain expression vector. SEQ ID NO: 46 and SEQ ID NO: 47 respectively represent the nucleotide sequence of the IgG4P-type heavy chain of human chimeric 2P10F2 and the amino acid sequence of the heavy chain.

1)-14 Production and Preparation of Human Chimeric Antibodies of LN22R8 and 2P10F2

1)-14-1 Production of Human Chimeric Antibodies of LN22R8 and 2P10F2

FreeStyle 293F cells (Invitrogen Corp.) were subcultured and cultured according to the manual. The $1.2\times10^9$ FreeStyle 293F cells (Invitrogen Corp.) in the logarithmic growth phase were seeded in a 3-L Fernbach Erlenmeyer Flask (Corning Incorporated) and diluted with a FreeStyle293 expression medium (Invitrogen Corp.) to $2.0\times10^6$ cells/mL. 0.24 mg of a heavy chain expression vector, 0.36 mg of a light chain expression vector, and 1.8 mg of Polyethyleneimine (Polyscience #24765) were added to 40 mL of an Opti-Pro SFM medium (Invitrogen Corp.), followed by gentle stirring and further standing for 5 minutes. Thereafter, the mixture was added to FreeStyle 293F cells. After shaking culture at 90 rpm in an incubator at 37° C. and 8% $CO_2$ for 4 hours, 600 mL of an EX-CELL VPRO medium (SAFC Biosciences, Sigma-Aldrich Corporation), 18 mL of GlutaMAX I (Gibco), and 30 mL of Yeastolate Ultrafiltrate (Gibco) were added thereto, followed by shaking the culture at 90 rpm in an incubator at 37° C. and 8% $CO_2$ for 7 days, and the obtained culture supernatant was filtered with a Disposable Capsule Filter (Advantec #CCS-045-E1H).

A human chimeric antibody of LN22R8 obtained by the combination of the IgG1-type human chimeric LN22R8 heavy chain expression vector and the human chimeric LN22R8 light chain expression vector was named "LN22R8chIgG1". A human chimeric antibody of LN22R8 obtained by the combination of the IgG2-type human chimeric LN22R8 heavy chain expression vector and the human chimeric LN22R8 light chain expression vector was named "LN22R8chIgG2". A human chimeric antibody of LN22R8 obtained by the combination of the IgG4P-type human chimeric LN22R8 heavy chain expression vector and the human chimeric LN22R8 light chain expression vector was named "LN22R8chIgG4P". A human chimeric antibody of L2P10F2 obtained by the combination of the IgG1LALA-type human chimeric 2P10F2 heavy chain expression vector and the human chimeric 2P10F2 light chain expression vector was named "2P10F2chIgG1LALA". A human chimeric antibody of L2P10F2 obtained by the combination of the IgG2-type human chimeric 2P10F2 heavy chain expression vector and the human chimeric 2P10F2 light chain expression vector was named "2P10F2chIgG2". A human chimeric antibody of L2P10F2 obtained by the combination of the IgG4P-type human chimeric 2P10F2 heavy chain expression vector and the human chimeric 2P10F2 light chain expression vector was named "2P10F2chIgG4P".

1)-14-2 Purification of Human Chimeric Antibodies of LN22R8 and 2P10F2

Each antibody was purified from the obtained culture supernatant in Example 1)-14-1 by a one-step process of rProtein A affinity chromatography. After the culture supernatant was applied to a column equilibrated with PBS and filled with MabSelectSuRe (available from GE Healthcare Bioscience), the column was washed with PBS an amount twice or more the column volume. Next, elution with a 2M arginine hydrochloride solution (pH 4.0) was performed to collect a fraction containing the antibody. The fraction was subjected to buffer replacement with HBSor buffer (25 mM Histidine/5% Sorbitol/pH 6.0) by dialysis (Thermo Scientific, Slide-A-Lyzer Dialysis Cassette). The antibody was concentrated using a Centrifugal UF Filter Device VIVASPIN20 (fraction molecular weight UF10K, Sartorius AG) to adjust the IgG concentration to 1 mg/mL or more. Finally, filtration was performed using a Minisart-Plus filter (Sartorius AG) to give a purified sample.

1)-15 ADCC Activity of Human Chimeric Antibodies

The ADCC activity of each human chimeric antibody was evaluated using human peripheral blood mononuclear cells (PBMC) as effector cells and human pancreatic line MIA PaCa-2 as ADCC target cells. After MIA PaCa-2 cells labeled with radioisotope $^{51}Cr$ were treated with mouse antibody (LN22R8), rat antibody (2P10F2), or human chimeric antibodies (LN22R8chIgG1, LN22R8chIgG2, LN22R8chIgG4P, 2P10F2chIgG1LALA, or 2P10F2chIgG4P) at a concentration of 0.5 or 5 μg/ml at 4° C. for 30 minutes, PBMC separated from human peripheral blood was added thereto in a proportion of 20 times that of the MIA PaCa-2 cells, followed by culture for 4 hours at 37° C. in the presence of 5% $CO_2$. Using TopCount NXT v2.53, $^{51}Cr$ released into the supernatant was measured to obtain a total release value. Using the measured value of $^{51}Cr$ released when MIA PaCa-2 cells labeled with $^{51}Cr$ were treated with Triton-100, as a maximum release value, and the measured value of $^{51}Cr$ released when antibody treated cells without the addition of PBMC were treated, as a spontaneous release value, a % specific release was calculated from the following formula. FIG. 6 summarizes the results. As a negative control sample, a sample obtained by treating human IgG (hIgG, ChromPure Human IgG, Jackson ImmunoResearch Laboratories, Inc., Cat. 009-000-003) was measured in the same manner, and the results are shown together. The measurement was performed three times, and the averages and the standard deviations were calculated and shown.

% specific release=(Total release−Spontaneous release)/Maximum release

While human IgG (hIgG) and mouse antibody of LN22R8 exhibited no ADCC activity, LN22R8chIgG1 exhibited an ADCC activity of 17.4% at 0.5 μg/ml and 18.1% at 5 μg/ml. The ADCC activities of LN22R8chIgG2 and LN22R8chIgG4P were lower than that of LN22R8chIgG1 and were respectively 3.0% and 2.2% even at 5 μg/ml.

2P10F2 rat antibody exhibited an ADCC activity of 4.8% at 0.5 μg/ml and 8.4% at 5 μg/ml. 2P10F2chIgG1LALA exhibited the ADCC activities of 4.7% at 0.5 μg/ml and 2.9% at 5 μg/ml. 2P10F2chIgG4P exhibited the ADCC activities of 3.4% at 0.5 μg/ml and 1.1% at 5 μg/ml, which were lower than those of 2P10F2 rat antibody and 2P10F2chIgG1LALA. As reported in the literature (Bruggemann et al., J. Exp. Med., 1351-1361, 1987), human chimeric antibodies using an IgG1 subtype exhibited the highest ADCC activity.

1)-16 CDC Activity of Human Chimeric Antibodies

The complement-dependent cell killing activity (CDC activity) of each anti-human CD147 antibody was evaluated using human pancreatic line MIA PaCa-2 as target cells. A commercially available rabbit complement (Low Tox-M Rabbit Complement, CEDARLANE LABORATORIES LIMITED, Cat. CL3051) was used as a complement. A mouse antibody (LN22R8), a rat antibody (2P10F2), or a human chimeric antibodies (LN22R8chIgG1, LN22R8chIgG2, LN22R8chIgG4P, 2P10F2chIgG1LALA, or 2P10F2chIgG4P) were used as the anti-human CD147 antibody. As a CDC activity negative control antibody, human IgG (hIgG, ChromPure Human IgG, Jackson ImmunoResearch Laboratories, Inc., Cat. 009-000-003) was used. After the antibody was treated at 4° C. and at a concentration of 0, 0.1, 1, or 10 μg/ml for one hour, the rabbit complement was added therein to a final concentration of 7.5%, followed by heating at 37° C. in the presence of 5% $CO_2$ for three hours. Thereafter, intercellular ATP contained in living cells was measured using a CellTiter-Glo Lumimescent Cell Viability Assay (Promega Corp., Cat. G7572). Luminescence signals obtained using CellTiter-Glo Lumimescent Cell Viability Assay were quantified using an EnVision 2104 Multilabel Reader (PerkinElmer Co., Ltd). The measurement was performed three times, and the averages and the standard deviations were calculated. Luminescence signals obtained from non-treated cells were taken as 100%, and any antibody- and complement-dependent reduced luminescence signals were taken as CDC activity. FIG. 7 summarizes the results.

Only in the mouse antibody (LN22R8) and the rat antibody (2P10F2), was a concentration-dependent CDC activity observed as compared with the negative control hIgG. In LN22R8, living cells at 10 μg/ml decreased to 41.1% at maximum. In 2P10F2, living cells at 10 μg/ml decreased to 53.5% at maximum.

In the human chimeric antibodies (LN22R8chIgG1, LN22R8chIgG2, LN22R8chIgG4P, 2P10F2chIgG1LALA, and 2P10F2chIgG4P), no clear CDC activity was observed as compared with the negative control hIgG.

1)-17 ADCP Activity of Human Chimeric Antibodies

Figure 8A:
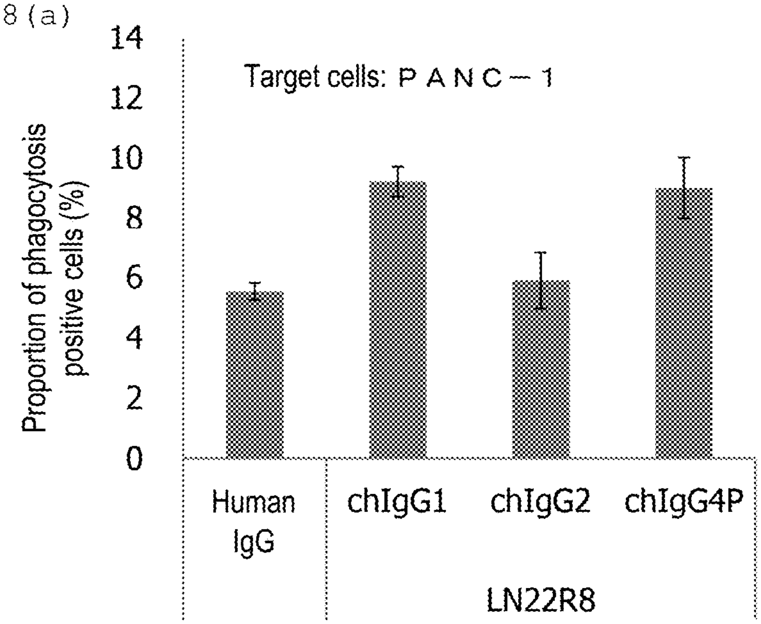
FIG. 8 shows the ADCP activities of human chimeric antibodies.
Figure 8B:
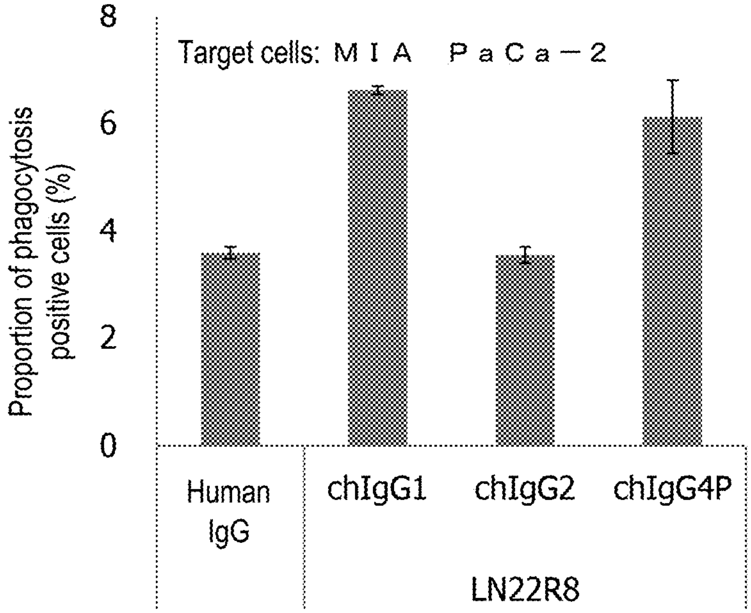

It has been reported that human IgG antibodies exhibit a cell killing activity of cancer cells by inducing phagocytosis (ADCP) by antibody-dependent monocytes or macrophages via interaction with mouse Fcγ receptors (Overdijk et al., Journal of Immunology, 1-9, 2012). The ADCP activity of each human chimeric antibody was evaluated using RAW264.7 (ATCC, TIB-71) as effector cells and human pancreatic line PANC-1 or MIA PaCa-2 as ADCP target cells. After ADCP target cells labeled with a PKH67 Green Fluorescent Cell Linker Mini Kit for General Cell Membrane Labeling (SIGMA, Cat. MINI67-1KIT) and the human chimeric antibodies (LN22R8chIgG1, LN22R8chIgG2, or LN22R8chIgG4P) were treated at a concentration of 20 μg/ml at 4° C. for one hour, RAW264.7 cells labeled with a PKH26 Red Fluorescent Cell Linker Kit for General Cell Membrane Labeling (SIGMA, Cat. PKH26GL-1KT) were added thereto at 5 times the amount of the ADCP target cells, followed by heating at 37° C. in the presence of 5% $CO_2$ for three hours. Using a flow cytometer (Becton, Dickinson and Company, CantoII), the ratio of PKH26-positive cells that transferred to PKH67 signal-positive cells by phagocytosis was measured. As a negative control sample, a sample obtained by treating human IgG (hIgG, ChromPure Human IgG, Jackson ImmunoResearch Laboratories, Inc., Cat. 009-000-003) was measured in the same manner. The measurement was performed three times, and the averages and the standard deviations were calculated. FIG. 8(*a*) shows the results for PANC-1, and FIG. 8(*b*) shows the results for MIA PaCa-2, respectively.

In the case of using PANC-1 cells as ADCP target cells, LN22R8chIgG1 exhibited a high ADCP activity of 9.2%, and LN22R8chIgG4P exhibited a high ADCP activity of 9.0%, as compared with human IgG (5.5%). LN22R8chIgG2 did not exhibit ADCP activity at 5.9%.

Also in the case of using MIA PaCa-2 cells as ADCP target cells, a similar tendency was shown, in which LN22R8chIgG1 exhibited a high ADCP activity of 6.6%, and LN22R8chIgG4P exhibited a high ADCP activity of 6.1%, as compared with human IgG (3.6%). LN22R8chIgG2 did not exhibit ADCP activity at 3.6%.

1)-18 Measurement of In-Vivo Antitumor Efficacy of Human Chimeric Antibodies $5\times10^6$ cells of human pancreatic line MIA PaCa-2 were suspended in PBS containing 50% GFR-Matrigel (Corning Inc., Cat. 354230), and the suspension was inoculated subcutaneously into the axilla of 4 to 5 week-old female NOD-scid mice (NOD. CB17-Prkdc<scid>/J, purchased from CHARLES RIVER LABORATORIES JAPAN, INC). Grouping was performed based on tumor volume 5 to 7 days after the inoculation, and the mouse antibody (LN22R8) and the three types of human chimeric antibodies (LN22R8chIgG1, LN22R8chIgG2, and LN22R8chIgG4P) of the anti-human CD147 antibody LN22R8 were administered intraperitoneally to cancer-bearing mice at 1 mg/kg, 3 mg/kg, or 10 mg/kg (n=5). The rat antibody (2P10F2) and the two types of human chimeric antibodies (2P10F2chIgG2 and 2P10F2chIgG4P) of the anti-human CD147 antibody 2P10F2 were administered intraperitoneally to cancer-bearing mice at 10 mg/kg (n=5 to 6). The major axis and the minor axis of the inoculated tumor were measured twice a week using an electronic digital caliper (available from MITUTOYO CORPORATION) to calculate the tumor volume by the following formula.

$$\text{Tumor volume (mm}^3\text{)}=1/2\times\text{minor axis(mm)}\times\text{minor axis(mm)}\times\text{major axis(mm)}$$

Figures 1A, 9:
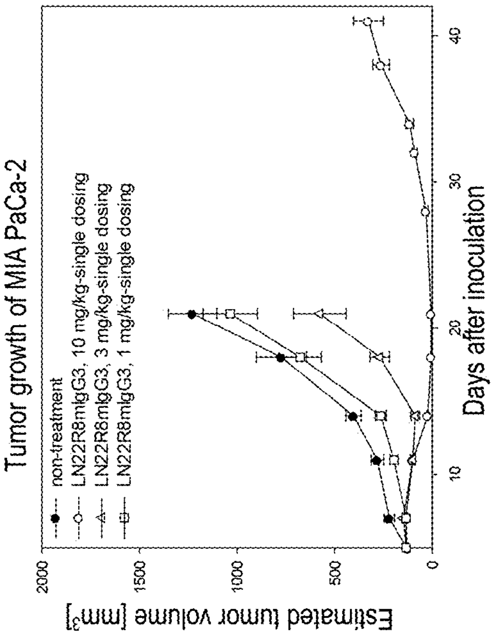
Figures 1B, 9:
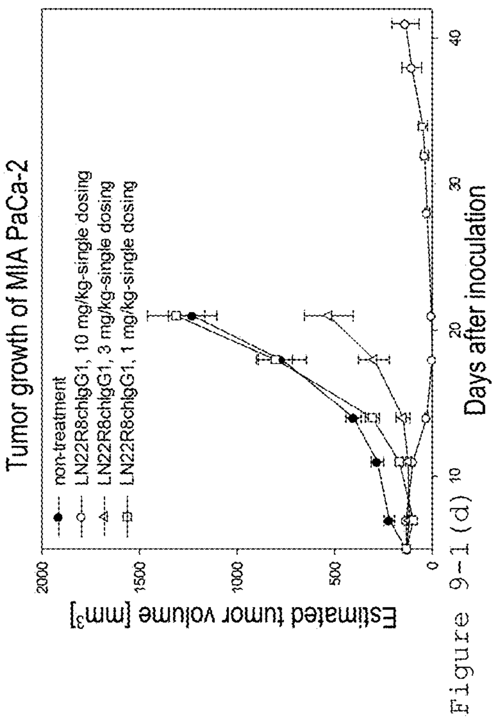
Figures 1C, 9:
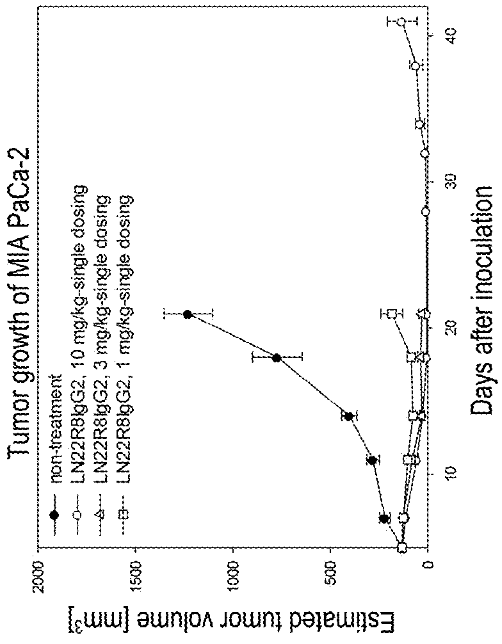
Figures 1D, 9:
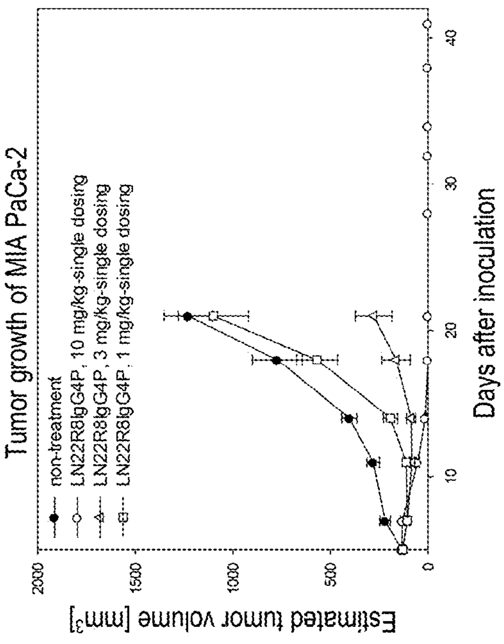
Figures 2F, 9:
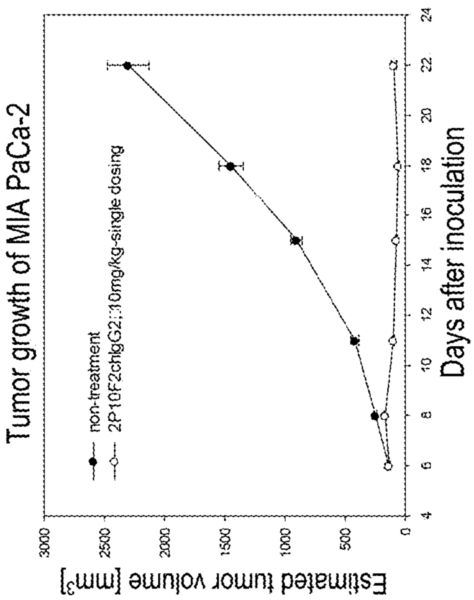
Figures 2E, 9:
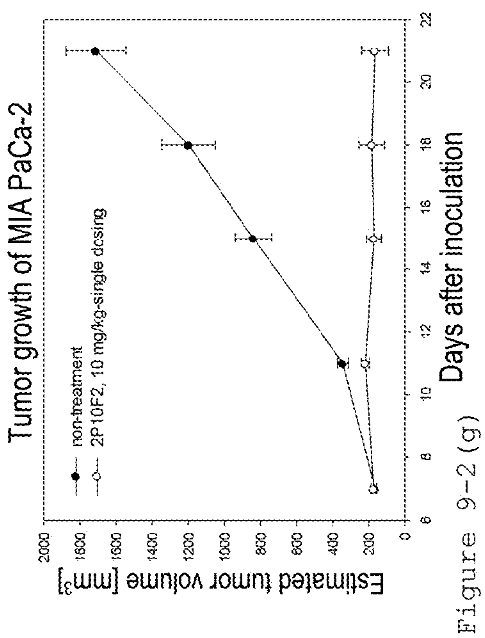
Figures 2G, 9:
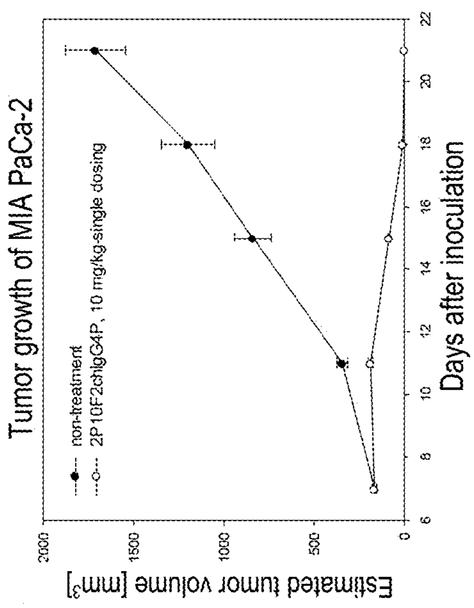
Figure 11A:
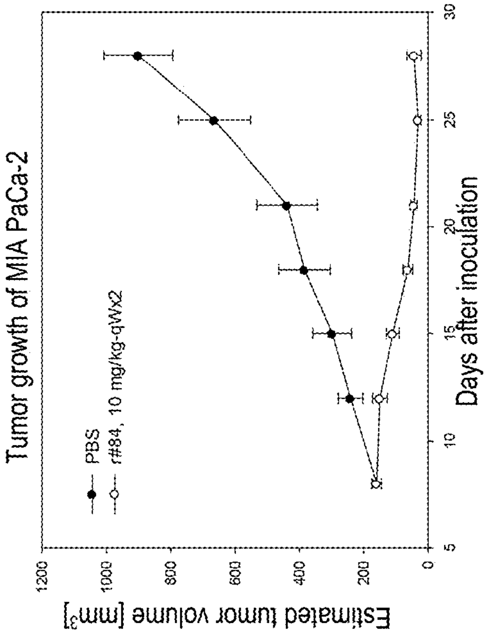
FIGS. 11(*a*) to (*d*) show the antitumor efficacy of r #84, r #101, r #110, and r #131 in a MIA PaCa-2 subcutaneous implantation model using NOD-scid mice.
Figure 11B:
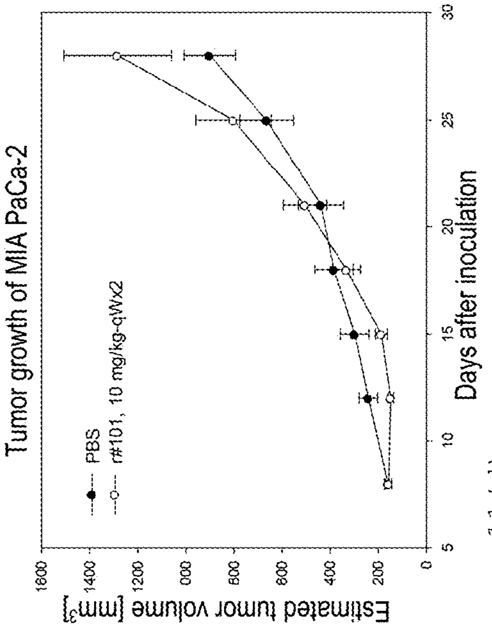
Figure 11C:
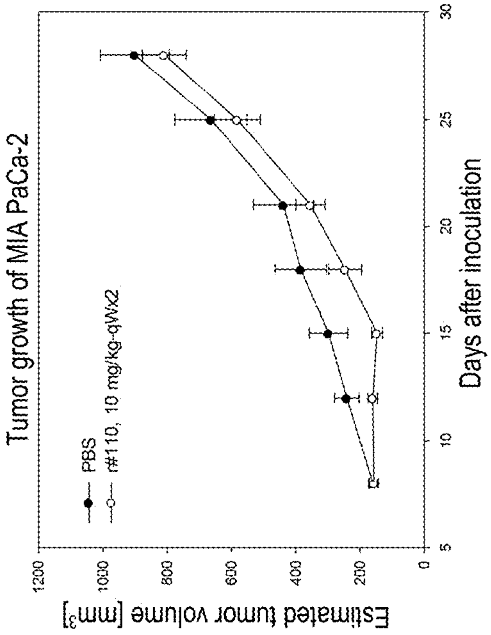
Figure 11D:
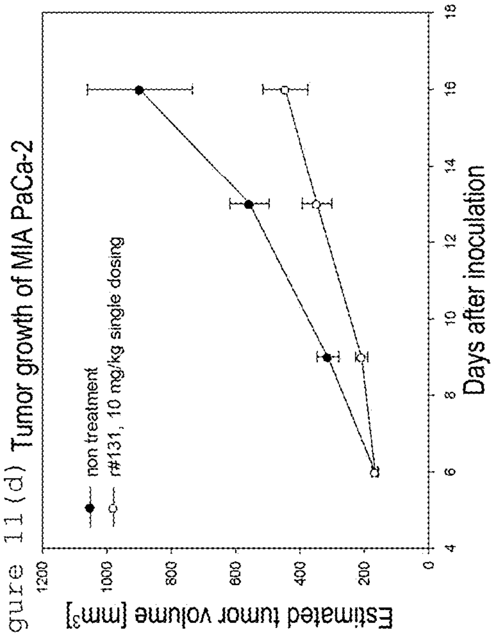

FIGS. 9-1(*a*) to (*d*) and FIGS. 9-2(*e*) to (*g*) show the results. The graphs also show the averages and the standard errors of changes in tumor volume.

In both the mouse antibody and the three types of human chimeric antibodies, LN22R8 exhibited a dose-dependent antitumor efficacy. In the human chimeric antibody LN22R8chIgG4P 10 mg/kg administration group, complete tumor regression was observed 18 days after the inoculation in 5 mice out of 5 mice, and tumor regrowth was not found even at 41 days after the inoculation at the time of the completion of the experiment. In the other LN22R8 antibody administration groups, tumor regrowth was observed in some or all of the mice.

In the rat antibody and the two types of human chimeric antibodies, the antitumor efficacy of 2P10F2 were observed. In the 2P10F2chIgG4P 10 mg/kg administration group, complete tumor regression was observed 21 days after the inoculation in 6 mice out of 6 mice.

It was suggested that the antitumor efficacy was exerted by a new mechanism of action on CD147, independent of the mouse immunity, because the mouse antibody LN22R8 and the rat antibody 2P10F2 that are anti-human CD147 antibodies configured to recognize the same epitope site maintain an antitumor efficacy of 90% or more not only in human chimeric antibody chIgG1 having effector functions dependent on the mouse immune system, such as ADCC activity, ADCP, and CDC activity, or human chimeric antibody chIgG4P having ADCP activity but also in human chimeric antibody chIgG2 that hardly shows any effector functions.

1)-19 Antitumor Efficacy of CD147 Human Chimeric Antibody in NOG Mice

NOG (NOD/Shi-scid, IL-2Rγnull) mice obtained by crossbreeding a IL-2 receptor γ chain knockout, which is a common cytokine receptor domain, with NOD-scid mice lacking mouse T cells and B cells lack the activities of NK cells and complement in addition to mouse T and B cells and have reduced functions of macrophages and dendritic cells, thus being in an exceptionally severe state of immune failure (Ito, Blood, 3175-3182, 2002). Whether the antitumor efficacy of the CD147 antibody is affected by such a severe state of failure of the mouse immune system was examined using a MIA PaCa-2 subcutaneous implantation model.

$5\times10^6$ cells of human pancreatic line MIA PaCa-2 were suspended in PBS containing 50% GFR-Matrigel (Corning Inc., Cat. 354230), and the suspension was inoculated subcutaneously into the axilla of 7 week-old female NOG mice (NOD/Shi-scid, IL-2RγKO Jic, purchased from In-Vivo Science Inc.). Grouping was performed based on tumor volume 6 days after the inoculation, and the anti-CD147 human chimeric antibody (LN22R8chIgG4P) was administered intraperitoneally to cancer-bearing mice at 10 mg/kg (n=5). The major axis and the minor axis of the inoculated tumor were measured twice a week using an electronic digital caliper (available from MITUTOYO CORPORATION) to calculate the tumor volume by the following formula.

$$\text{Tumor volume } (mm^3)=1/2\times\text{minor axis}(mm)\times\text{minor axis}(mm)\times\text{major axis}(mm)$$

FIG. 10 shows the results. The graphs also show the averages and the standard errors of changes in tumor volume.

According to the results of the human chimeric antibody LN22R8chIgG4P shown in FIG. 10, the tumor growth inhibition rate 17 days after the inoculation was 99% in the 10 mg/kg administration group, and complete tumor regression was observed in 3 mice out of 5 mice.

A possibility of exhibiting an antitumor efficacy independent of mouse immune cells was suggested, because the anti-CD147 human chimeric antibody (LN22R8chIgG4P) exhibited a strong antitumor efficacy also against pancreatic cancer tumors formed in NOG mice, which lack activities of NK cells and complement in addition to mouse T and B cells.

Example 2

Production of Monkey-Cross-Reactive Rat Antibody by Immunization with CD147 Protein The anti-human CD147 antibodies exhibiting a strong antitumor efficacy obtained in Example 1 did not exhibit cross-reactivity with mouse, rat, and cynomolgus monkey CD147s. An attempt to obtain a CD147 antibody exhibiting cross-reactivity with cynomolgus monkey CD147 was made using each antibody obtained in Example 1.

2)-1 Immunization

Female WKY/Izm rats (Japan SLC, Inc.) were used for immunization. A mixture of a Recombinant Human BSG, His tagged (available from Creative BioMart) antigen protein and a Freund's Complete Adjuvant (available from Wako Pure Chemical Industries, Ltd.) was administered to the base of the tail of the rat, and the lymph nodes and spleen of the rat were collected and used for producing hybridomas.

2)-2 Production of Hybridomas

The lymph node cells or spleen cells were electrofused with mouse myeloma SP2/0-ag14 cells (ATCC, No. CRL-1581) using a LF301 Cell Fusion Unit (BEX CO., LTD.), and the fused cells were diluted with a ClonaCell-HY Selection Medium D (StemCell Technologies Inc.) and cultured. Emerging hybridoma colonies were collected, thereby producing monoclonal hybridomas. The hybridoma colonies collected were each cultured, and anti-CD147 antibody producing hybridomas were screened using the obtained hybridoma culture supernatant.

2)-3 Antibody Screening by Flow Cytometry

In order to select antibody producing hybridomas configured to bind to human cancer cells and exhibiting a binding activity to human CD147 and cynomolgus monkey CD147, screening for antibody binding activity was performed using a flow cytometer. A CD147 positive human pancreatic line MIA PaCa-2 was used as human cancer cells. CHO-K1 cells (CHO-K1-hCD147v2 and CHO-K1-cynoCD147) expressing human or cynomolgus monkey CD147 were used in the same manner as in Example 1)-8 for confirming the binding activity to human or cynomolgus monkey CD147. An equal amount of the hybridoma culture supernatant was added to the suspension of MIA PaCa-2, CHO-K1-hCD147v2, or CHO-K1-cynoCD147, followed by reaction at 4° C. for one hour or more. Thereafter, the cells were washed with PBS containing 5% FBS to enable fluorescence detection of binding of each antibody to the cells using anti-rat IgG-PE (BD Biosciences, Cat. 550767). Fluorescence signals of the cells were measured using a flow cytometer (CantoII, BD Biosciences), and the ratio of the fluorescence signals to those in the negative control sample (cells without addition of the hybridoma culture solution) was calculated. Table 4 summarizes a part of the results.

Using a commercially available rat antibody isotyping kit (Bio-Rad Laboratories, RMT1), the isotype of the antibody contained in the culture supernatant was determined. Table 4 shows the results.

The 2P10F2 obtained in Example 1 exhibited a binding activity to MIA PaCa-2 and CHO-K1-hCD147v2, and exhibited no binding activity to CHO-K1-cynoCD147. Rat_CD147_#84 (which may be referred to as r #84 in this description), rat_CD147_#131 (which may be referred to as r #131 in this description), rat_CD147_#110 (which may be referred to as r #110 in this description), and rat_CD147_#101 (which may be referred to as r #101 in this description) exhibited a binding activity to MIA PaCa-2, CHO-K1-hCD147v2, and CHO-K1-cynoCD147. Thus, anti-human CD147 rat antibodies exhibiting cross-reactivity with cynomolgus monkey CD147 have been obtained.

TABLE 4

| Clone ID | Isotype | MIA PaCa-2 | CHO-K1-hCD147 v2 | CHO-K1-cyno CD147 |
|---|---|---|---|---|
| 2P10F2 | Rat IgG2b/κ | 17.3 | 33.0 | 0.0 |
| r#84 | Rat IgG2b/κ | 9.1 | 9.9 | 19.0 |
| r#131 | Rat IgG1/κ | 4.3 | 7.8 | 7.3 |
| r#110 | Rat IgG1/κ | 2.7 | 4.9 | 4.6 |
| r#101 | Rat IgG2a/κ | 10.2 | 23.1 | 8.8 |

2)-4 Preparation of Rat Monoclonal Antibody Using Low IgG Serum

Anti-human CD147 monoclonal antibodies exhibiting cross-reactivity with cynomolgus monkey CD147 were purified from the hybridoma culture supernatant. First, antibody producing hybridomas of rat_CD147_#131 were grown to a sufficient amount with a ClonaCell-HY Selection Medium E, and thereafter the medium was replaced with a Hybridoma SFM (Life Technologies) to which Ultra Low IgG FBS (Life Technologies) was added at 20%, followed by culture for 7 days. This culture supernatant was collected and passed through a 0.45 μm filter for sterilization.

2)-5 Preparation of Rat Monoclonal Antibody by High-Density Culture

The hybridomas of rat_CD147_#84, rat_CD147_#101, or rat_CD147_#110 were cultured using a CL-1000 flask (Becton, Dickinson and Company) to prepare a hybridoma culture supernatant containing each monoclonal antibody.

2)-6 Purification of Monoclonal Antibody

In the same manner as in Example 1)-6, the antibody was purified from the culture supernatant produced in Example 2)-4 and Example 2)-5.

2)-7 Screening for Antibody by Measuring In-Vivo Antitumor Efficacy $5\times10^6$ cells of human pancreatic line MIA PaCa-2 were suspended in PBS containing 50% GFR-Matrigel (Corning Inc., Cat. 354230), and the suspension was inoculated subcutaneously into the axilla of 5 week-old female NOD-scid mice (NOD. CB17-Prkdc<scid>/J, purchased from CHARLES RIVER LABORATORIES JAPAN, INC.). Grouping was performed based on tumor volume 6 to 8 days after the inoculation, and the cynomolgus monkey-cross-reactive anti-CD147 rat antibody #84, #101, or #110 was administered intraperitoneally to cancer-bearing mice at 10 mg/kg 8 days and 15 days after the inoculation (n=5). In the same manner, PBS was administered intraperitoneally to the mice of the control group. The cynomolgus monkey-cross-reactive anti-CD147 rat antibody #131 was administered intraperitoneally to cancer-bearing mice at 10 mg/kg 6 days after the inoculation (n=5). The major axis and the minor axis of the inoculated tumor were measured twice a week using an electronic digital caliper (available from MITUTOYO CORPORATION) to calculate the tumor volume by the following formula.

$$\text{Tumor volume } (mm^3)=1/2\times\text{minor axis(mm)}\times\text{minor axis(mm)}\times\text{major axis(mm)}$$

FIGS. 11(*a*) to (*d*) show the results. The graphs also show the averages and the standard errors of changes in tumor volume. The tumor growth inhibition rate 28 days after the inoculation of r #84 was 95% in the 10 mg/kg administration group (FIG. 11(*a*)). The tumor growth inhibition rate 15 days after the inoculation of r #101 was 37% in the 10 mg/kg administration group, but tumor regrowth was observed 28 days after the inoculation (FIG. 11(*b*)). The tumor growth inhibition rate 15 days after the inoculation of r #110 was 51% in the 10 mg/kg administration group, but tumor regrowth was observed 28 days after the inoculation (FIG. 11(*c*)). The tumor growth inhibition rate 16 days after the inoculation of r #131 was 50% in the 10 mg/kg administration group (FIG. 11(*d*)). Thus rat antibody r #84 that strongly inhibits tumor growth in MIA PaCa-2 and rat antibodies r #101, r #110, and r #131 that partially inhibit the tumor growth were obtained.

2)-8 Epitope Analysis: 2P10F2chIgG4P-Competitive ELISA

For the purpose of epitope analysis of the monkey-cross-reactive rat CD147 antibodies, whether each antibody inhibited the binding activity to a CD147 recombinant protein of 2P10F2chIgG4P was investigated by competitive ELISA. A human CD147-Fc fusion protein (Sino Biological Inc., 10186-H02H) was dissolved in PBS to 2 μg/ml, and 50 μl of the solution was added to a 96-well plate (Thermo Fisher SCIENTIFIC K.K., Cat. 43454), followed by storage at 4° C. After the protein solution was removed, 300 μl of PBS containing 1% BSA was added thereto, followed by heating at room temperature for one hour. Twenty five μl of the CD147 rat antibodies r #84, r #101, r #110, r #131, or 2P10F2 diluted with PBS containing 1% BSA at 20 or 60 μg/ml, or PBS containing 1% BSA were added as competitive antibodies to the 96-well plate, followed by heating at room temperature for two hours. Twenty five μl of 2P10F2chIgG4P diluted with PBS containing 1% BSA at 20 ng/ml was added to the 96-well plate, followed by heating at room temperature for two hours. The 96-well plate was washed with PBS containing 0.05% Tween 20 (BIO RAD, Cat. 170-6531) twice. 50 μl of Mouse monoclonal HP6025 Anti-Human IgG4 Fc (HRP) (Abcam plc., Cat. ab99823) diluted 2000 times with PBS containing 1% BSA was added to the 96-well plate, followed by heating at room temperature for one hour. The 96-well plate was washed with PBS containing 0.05% Tween 20 (BIO RAD, Cat. 170-6531) three times. 50 μl of Super AquaBlue ELISA Substrate (eBioscience, Thermo Fisher SCIENTIFIC K.K., 00-4203-58) was added to the 96-well plate, followed by heating at room temperature for 20 minutes. The absorbance at 405 nm of the 96-well plate was measured using an EnVision 2104 Multilabel Reader (PerkinElmer Co., Ltd). The measured value of a well containing no competitive antibodies was used as the control, and the absorbance decreased by each competitive antibody was calculated in terms of %. FIG. 12 shows the results. The measurement was performed for three wells, and the average was shown.

Similarly to the 2P10F2 rat antibody, r #84, r #101, and r #131 inhibited the binding activity of 2P10F2chIgG4P by 90% or more, and thus it was suggested that their antibody recognition sites were close to that of 2P10F2chIgG4P. Meanwhile, r #110 did not inhibit the binding of the 2P10F2chIgG4P antibody. It is conceivable that the binding of the 2P10F2chIgG4P antibody could not be inhibited because its antibody recognition site was distant from that of r #110, or the binding activity of r #110 was weak.

Example 3

Cloning of Monkey-Cross-Reactive Rat Antibody and Production of Human Chimeric Antibody 3)-1 Determination of the Cloning Nucleotide Sequence of cDNA Encoding the Variable Region of Rat Anti-CD147 Antibodies 3)-1-1 Determination of the Nucleotide Sequence of cDNA Encoding the Variable Region of the rat_CD147_#84 Antibody The determination was conducted in the same manner as in Example 1)-11-2. SEQ ID NO: 48 represents the nucleotide sequence of the cDNA encoding the determined rat_CD147_#84 antibody light chain variable region, and SEQ ID NO: 49 represents the amino acid sequence thereof. SEQ ID NO: 50 represents the nucleotide sequence of the cDNA encoding the heavy chain variable region thereof, and SEQ ID NO: 51 represents the amino acid sequence thereof. SEQ ID NOs: 52, 53, and 54 respectively represent CDRL1, CDRL2 and CDRL3 of the rat_CD147_#84 antibody light chain variable region. SEQ ID NOs: 55, 56, and 57 respectively represent CDRH1, CDRH2, and CDRH3 of the rat_CD147_#84 antibody heavy chain variable region.

3)-1-2 Determination of the Nucleotide Sequence of cDNA Encoding the Variable Region of the rat_CD147_#101 Antibody The determination was conducted in the same manner as in Example 1)-11-2. SEQ ID NO: 58 represents the nucleotide sequence of the cDNA encoding the determined rat_CD147_#101 antibody light chain variable region, and SEQ ID NO: 59 represents the amino acid sequence thereof. SEQ ID NO: 60 represents the nucleotide sequence of the cDNA encoding the heavy chain variable region, and SEQ ID NO: 61 represents the amino acid sequence thereof. SEQ ID NOs: 62, 63, and 64 respectively represent CDRL1, CDRL2 and CDRL3 of the rat_CD147_#101 antibody light chain variable region. SEQ ID NOs: 65, 66, and 67 respectively represent CDRH1, CDRH2, and CDRH3 of the rat_CD147_#101 antibody heavy chain variable region.

3)-1-3 Determination of the Nucleotide Sequence of cDNA Encoding the Variable Region of the rat_CD147_#110 Antibody The determination was conducted in the same manner as in Example 1)-11-2. SEQ ID NO: 68 represents the nucleotide sequence of the cDNA encoding the determined rat_CD147_#110 antibody light chain variable region, and SEQ ID NO: 69 represents the amino acid sequence thereof. SEQ ID NO: 70 represents the nucleotide sequence of the cDNA encoding the heavy chain variable region, and SEQ ID NO: 71 represents the amino acid sequence thereof. SEQ ID NOs: 72, 73, and 74 respectively represent CDRL1, CDRL2 and CDRL3 of the rat_CD147_#110 antibody light chain variable region. SEQ ID NOs: 75, 76, and 77 respectively represent CDRH1, CDRH2, and CDRH3 of the rat_CD147_#110 antibody heavy chain variable region.

3)-1-4 Determination of the Nucleotide Sequence of cDNA Encoding the Variable Region of the rat_CD147_#131 Antibody The determination was conducted in the same manner as in Example 1)-11-2. SEQ ID NO: 78 represents the nucleotide sequence of the cDNA encoding the determined rat_CD147_#131 antibody light chain variable region, and SEQ ID NO: 79 represents the amino acid sequence thereof. SEQ ID NO: 80 represents the nucleotide sequence of the cDNA encoding the heavy chain variable region, and SEQ ID NO: 81 represents the amino acid sequence thereof. SEQ ID NOs: 82, 83, and 84 respectively represent CDRL1, CDRL2 and CDRL3 of the rat_CD147_#131 antibody light chain variable region. SEQ ID NOs: 85, 86, and 87 respectively represent CDRH1, CDRH2, and CDRH3 of the rat_CD147_#131 antibody heavy chain variable region.

3)-2 Production of Human Chimeric Antibody Expression Vectors

3)-2-1 Production of Human Chimeric Antibody Expression Vector of rat_CD147_#84

3)-2-1-1 Construction of Human Chimeric and Humanized IgG4PFALA-Type Heavy Chain Expression Vector pCMA-G4PFALA Using the human heavy chain signal sequence represented by SEQ ID NO: 88 and a DNA fragment containing the DNA sequence encoding the amino acids in the human IgG4PFALA constant region, pCMA-G4PFALA was constructed in the same manner as in Example 1)-12-2.

3)-2-1-2 Construction of Human Chimeric rat_CD147_#84 Light Chain Expression Vector Using the cDNA encoding the rat_CD147_#84 light chain variable region obtained in Example 3)-1-1 as a template, a human chimeric rat_CD147_#84 light chain expression vector was constructed in the same manner as in Example 1)-12-4. SEQ ID NO: 89 and SEQ ID NO: 90 respectively represent the nucleotide sequence of the human chimeric rat_CD147_#84 light chain and the amino acid sequence of the light chain.

3)-2-1-3 Construction of IgG1-Type Human Chimeric rat_CD147_#84 Heavy Chain Expression Vector Using the cDNA encoding the rat_CD147_#84 heavy chain variable region obtained in Example 3)-1-1 as a template, an IgG1-type human chimeric rat_CD147_#84 heavy chain expression vector was constructed in the same manner as in Example 1)-12-5. SEQ ID NO: 91 and SEQ ID NO: 92 respectively represent the nucleotide sequence of the IgG1-type heavy chain of human chimeric rat_CD147_#84 and the amino acid sequence of the heavy chain.

3)-2-1-4 Construction of IgG2-Type Human Chimeric rat_CD147_#84 Heavy Chain Expression Vector Using the cDNA encoding the rat_CD147_#84 heavy chain variable region obtained in Example 3)-1-1 as a template, an IgG2-type human chimeric rat_CD147_#84 heavy chain expression vector was constructed in the same manner as in Example 1)-12-6. SEQ ID NO: 93 and SEQ ID NO: 94 respectively represent the nucleotide sequence of the IgG2-type heavy chain of human chimeric rat_CD147_#84 and the amino acid sequence of the heavy chain.

3)-2-1-5 Construction of IgG4P-Type Human Chimeric rat_CD147_#84 Heavy Chain Expression Vector Using the cDNA encoding the rat_CD147_#84 heavy chain variable region obtained in Example 3)-1-1 as a template, an IgG4P-type human chimeric rat_CD147_#84 heavy chain expression vector was constructed in the same manner as in Example 1)-13-6. SEQ ID NO: 95 and SEQ ID NO: 96 respectively represent the nucleotide sequence of the IgG4P-type heavy chain of human chimeric rat_CD147_#84 and the amino acid sequence of the heavy chain.

3)-2-1-6 Construction of IgG1LALA-Type Human Chimeric rat_CD147_#84 Heavy Chain Expression Vector Using the cDNA encoding the rat_CD147_#84 heavy chain variable region obtained in Example 3)-1-1 as a template, an IgG1LALA-type human chimeric rat_CD147_#84 heavy chain expression vector was constructed in the same manner as in Example 1)-13-4. SEQ ID NO: 97 and SEQ ID NO: 98 respectively represent the nucleotide sequence of the IgG1LALA-type heavy chain of human chimeric rat_CD147_#84 and the amino acid sequence of the heavy chain.

3)-2-1-7 Construction of IgG4PFALA-Type Human Chimeric rat_CD147_#84 Heavy Chain Expression Vector Using the cDNA encoding the rat_CD147_#84 heavy chain variable region obtained in Example 3)-1-1 as a template, PCR was performed using a primer designed for In-fusion cloning, thereby amplifying a DNA fragment containing the cDNA encoding the heavy chain variable region. Using an In-Fusion HD PCR cloning kit (Clontech Laboratories, Inc.), the amplified DNA fragment was inserted at the site where pCMA-G4PFALA was digested with restriction enzyme BlpI, thereby constructing an IgG4PFALA-type human chimeric rat_CD147_#84 heavy chain expression vector. SEQ ID NO: 99 and SEQ ID NO: 100 respectively represent the nucleotide sequence of the IgG4PFALA-type heavy chain of human chimeric rat_CD147_#84 and the amino acid sequence of the heavy chain.

3)-2-2 Production of Human Chimeric Antibody Expression Vector of rat_CD147_#101

3)-2-2-1 Construction of Human Chimeric rat_CD147_#101 Light Chain Expression Vector Using the cDNA encoding the rat_CD147_#101 light chain variable region obtained in Example 3)-1-2 as a template, a human chimeric rat_CD147_#101 light chain expression vector was constructed in the same manner as in Example 1)-12-4. SEQ ID NO: 101 and SEQ ID NO: 102 respectively represent the nucleotide sequence of the human chimeric rat_CD147_#101 light chain and the amino acid sequence of the light chain.

3)-2-2-2 Construction of IgG2-Type Human Chimeric rat_CD147_#101 Heavy Chain Expression Vector Using the cDNA encoding the rat_CD147_#101 heavy chain variable region obtained in Example 3)-1-2 as a template, an IgG2-type human chimeric rat_CD147_#101 heavy chain expression vector was constructed in the same manner as in Example 1)-12-6. SEQ ID NO: 103 and SEQ ID NO: 104 respectively represent the nucleotide sequence of the IgG2-type heavy chain of human chimeric rat_CD147_#101 and the amino acid sequence of the heavy chain.

3)-2-2-3 Construction of IgG4P-Type Human Chimeric rat_CD147_#101 Heavy Chain Expression Vector Using the cDNA encoding the rat_CD147_#101 heavy chain variable region obtained in Example 3)-1-2 as a template, an IgG4P-type human chimeric rat_CD147_#101 heavy chain expression vector was constructed in the same manner as in Example 1)-13-6. SEQ ID NO: 105 and SEQ ID NO: 106 respectively represent the nucleotide sequence of the IgG4P-type heavy chain of human chimeric rat_CD147_#101 and the amino acid sequence of the heavy chain.

3)-2-2-4 Construction of IgG4PFALA-Type Human Chimeric rat_CD147_#101 Heavy Chain Expression Vector Using the cDNA encoding the rat_CD147_#101 heavy chain variable region obtained in Example 3)-1-2 as a template, an IgG4PFALA-type human chimeric rat_CD147_#101 heavy chain expression vector was constructed in the same manner as in Example 3)-2-1-7. SEQ ID NO: 107 and SEQ ID NO: 108 respectively represent the nucleotide sequence of the IgG4PFALA-type heavy chain of human chimeric rat_CD147_#101 and the amino acid sequence of the heavy chain.

3)-2-3 Production of Human Chimeric Antibody Expression Vector of rat_CD147_#110

3)-2-3-1 Construction of Human Chimeric rat_CD147_#110 Light Chain Expression Vector Using the cDNA encoding the rat_CD147_#110 light chain variable region obtained in Example 3)-1-3 as a template, a human chimeric rat_CD147_#110 light chain expression vector was constructed in the same manner as in Example 1)-12-4. SEQ ID NO: 109 and SEQ ID NO: 110 respectively represent the nucleotide sequence of the human chimeric rat_CD147_#110 light chain and the amino acid sequence of the light chain.

3)-2-3-2 Construction of IgG2-Type Human Chimeric rat_CD147_#110 Heavy Chain Expression Vector Using the cDNA encoding the rat_CD147_#110 heavy chain variable region obtained in Example 3)-1-3 as a template, an IgG2-type human chimeric rat_CD147_#110 heavy chain expression vector was constructed in the same manner as in Example 1)-12-6. SEQ ID NO: 111 and SEQ ID NO: 112 respectively represent the nucleotide sequence of the IgG2-type heavy chain of human chimeric rat_CD147_#110 and the amino acid sequence of the heavy chain.

3)-2-3-3 Construction of IgG4P-Type Human Chimeric rat_CD147_#110 Heavy Chain Expression Vector Using the cDNA encoding the rat_CD147_#110 heavy chain variable region obtained in Example 3)-1-3 as a template, an IgG4P-type human chimeric rat_CD147_#110 heavy chain expression vector was constructed in the same manner as in Example 1)-13-6. SEQ ID NO: 113 and SEQ ID NO: 114 respectively represent the nucleotide sequence of the IgG4P-type heavy chain of human chimeric rat_CD147_#110 and the amino acid sequence of the heavy chain.

3)-2-3-4 Construction of IgG4PFALA-Type Human Chimeric rat_CD147_#110 Heavy Chain Expression Vector Using the cDNA encoding the rat_CD147_#110 heavy chain variable region obtained in Example 3)-1-3 as a template, an IgG4PFALA-type human chimeric rat_CD147_#110 heavy chain expression vector was constructed in the same manner as in Example 3)-2-1-7. SEQ ID NO: 115 and SEQ ID NO: 116 respectively represent the nucleotide sequence of the IgG4PFALA-type heavy chain of human chimeric rat_CD147_#110 and the amino acid sequence of the heavy chain.

3)-2-4 Production of Human Chimeric Antibody Expression Vector of rat_CD147_#131

3)-2-4-1 Construction of Human Chimeric rat_CD147_#131 Light Chain Expression Vector Using the cDNA encoding the rat_CD147_#131 light chain variable region obtained in Example 3)-1-4 as a template, a human chimeric rat_CD147_#131 light chain expression vector was constructed in the same manner as in Example 1)-12-4. SEQ ID NO: 117 and SEQ ID NO: 118 respectively represent the nucleotide sequence of the human chimeric rat_CD147_#131 light chain and the amino acid sequence of the light chain.

3)-2-4-2 Construction of IgG2-Type Human Chimeric rat_CD147_#131 Heavy Chain Expression Vector Using the cDNA encoding the rat_CD147_#131 heavy chain variable region obtained in Example 3)-1-4 as a template, an IgG2-type human chimeric rat_CD147_#131 heavy chain expression vector was constructed in the same manner as in Example 1)-12-6. SEQ ID NO: 119 and SEQ ID NO: 120 respectively represent the nucleotide sequence of the IgG2-type heavy chain of human chimeric rat_CD147_#131 and the amino acid sequence of the heavy chain.

3)-2-4-3 Construction of IgG4P-Type Human Chimeric rat_CD147_#131 Heavy Chain Expression Vector Using the cDNA encoding the rat_CD147_#131 heavy chain variable region obtained in Example 3)-1-4 as a template, an IgG4P-type human chimeric rat_CD147_#131 heavy chain expression vector was constructed in the same manner as in Example 1)-13-6. SEQ ID NO: 121 and SEQ ID NO: 122 respectively represent the nucleotide sequence of the IgG4P-type heavy chain of human chimeric rat_CD147_#131 and the amino acid sequence of the heavy chain.

3)-3 Preparation of Human Chimeric Antibody

3)-3-1 Production of Human Chimeric Antibody from Monkey-Cross-Reactive Rat Antibody The antibody was produced in the same manner as in Example 1)-14-1.

A human chimeric antibody of rat_CD147_#84 obtained by the combination of the IgG1-type human chimeric rat_CD147_#84 heavy chain expression vector and the human chimeric rat_CD147_#84 light chain expression vector was named "#84chIgG1". A human chimeric antibody of rat_CD147_#84 obtained by the combination of the IgG2-type human chimeric rat_CD147_#84 heavy chain expression vector and the human chimeric rat_CD147_#84 light chain expression vector was named "#84chIgG2". A human chimeric antibody of rat_CD147_#84 obtained by the combination of the IgG4P-type human chimeric rat_CD147_#84 heavy chain expression vector and the human chimeric rat_CD147_#84 light chain expression vector was named "#84chIgG4P". A human chimeric antibody of rat_CD147_#84 obtained by the combination of the IgG1LALA-type human chimeric rat_CD147_#84 heavy chain expression vector and the human chimeric rat_CD147_#84 light chain expression vector was named "#84chIgG1LALA". A human chimeric antibody of rat_CD147_#84 obtained by the combination of the IgG4PFALA-type human chimeric rat_CD147_#84 heavy chain expression vector and the human chimeric rat_CD147_#84 light chain expression vector was named "#84chIgG4PFALA".

A human chimeric antibody of rat_CD147_#101 obtained by the combination of the IgG2-type human chimeric rat_CD147_#101 heavy chain expression vector and the human chimeric rat_CD147_#101 light chain expression vector was named "#101chIgG2". A human chimeric antibody of rat_CD147_#101 obtained by the combination of the IgG4P-type human chimeric rat_CD147_#101 heavy chain expression vector and the human chimeric rat_CD147_#101 light chain expression vector was named "#101chIgG4P". A human chimeric antibody of rat_CD147_#101 obtained by the combination of the IgG4PFALA-type human chimeric rat_CD147_#101 heavy chain expression vector and the human chimeric rat_CD147_#101 light chain expression vector was named "#101chIgG4PFALA".

A human chimeric antibody of rat_CD147_#110 obtained by the combination of the IgG2-type human chimeric rat_CD147_#110 heavy chain expression vector and the human chimeric rat_CD147_#110 light chain expression vector was named "#101chIgG2". A human chimeric antibody of rat_CD147_#110 obtained by the combination of the IgG4P-type human chimeric rat_CD147_#110 heavy chain expression vector and the human chimeric rat_CD147_#110 light chain expression vector was named "#110chIgG4P". A human chimeric antibody of rat_CD147_#110 obtained by the combination of the IgG4PFALA-type human chimeric rat_CD147_#110 heavy chain expression vector and the human chimeric rat_CD147_#110 light chain expression vector was named "#110chIgG4PFALA".

A human chimeric antibody of rat_CD147_#131 obtained by the combination of the IgG2-type human chimeric rat_CD147_#131 heavy chain expression vector and the human chimeric rat_CD147_#131 light chain expression vector was named "#131chIgG2". A human chimeric antibody of rat_CD147_#131 obtained by the combination of the IgG4P-type human chimeric rat_CD147_#131 heavy chain expression vector and the human chimeric rat_CD147_#131 light chain expression vector was named "#131chIgG4P".

3)-3-2 Purification of Human Chimeric Antibody of Monkey-Cross-Reactive Rat Antibodies The antibodies were purified from the culture supernatant obtained in Example 3)-3-1 in the same manner as in Example 1)-14-2.

Example 4

In-Vivo Antitumor Efficacy of Human Chimeric Antibodies $5\times10^6$ cells of human pancreatic line MIA PaCa-2 were suspended in PBS containing 50% GFR-Matrigel (Corning Inc., Cat. 354230), and the suspension was inoculated subcutaneously into the axilla of 5 to 6 week-old female NOD-scid mice (NOD. CB17-Prkdc<scid>/J, purchased from CHARLES RIVER LABORATORIES JAPAN, INC). Grouping was performed based on tumor volume 5 to 6 days after the inoculation, and the cynomolgus monkey-cross-reactive anti-CD147 human chimeric antibody (#84chIgG1, #84chIgG1LALA, #84chIgG2, #84chIgG4P, or #84chIgG4PFALA) was administered intraperitoneally to cancer-bearing mice at 1, 3, or 10 mg/kg on the day after the grouping (n=5). The cynomolgus monkey-cross-reactive anti-CD147 human chimeric antibody (#101chIgG2, #101chIgG4P, #101chIgG4PFALA, #110chIgG2, #110chIgG4P, #110chIgG4PFALA, #131chIgG2, or #131chIgG4P) was administered intraperitoneally to cancer-bearing mice at 3 or 10 mg/kg on the day after the grouping (n=5). The major axis and the minor axis of the inoculated tumor were measured twice a week using an electronic digital caliper (available from MITUTOYO CORPORATION) to calculate the tumor volume by the following formula.

$$\text{Tumor volume (mm}^3\text{)}=1/2\times\text{minor axis(mm)}\times\text{minor axis(mm)}\times\text{major axis(mm)}$$

Figures 1A, 13:
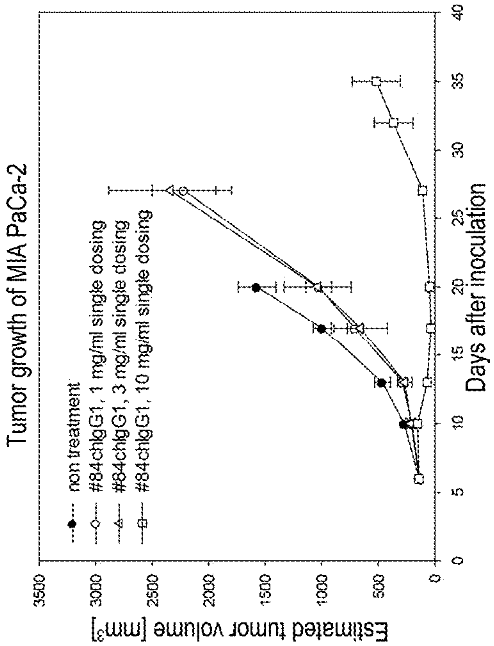
Figures 1B, 13:
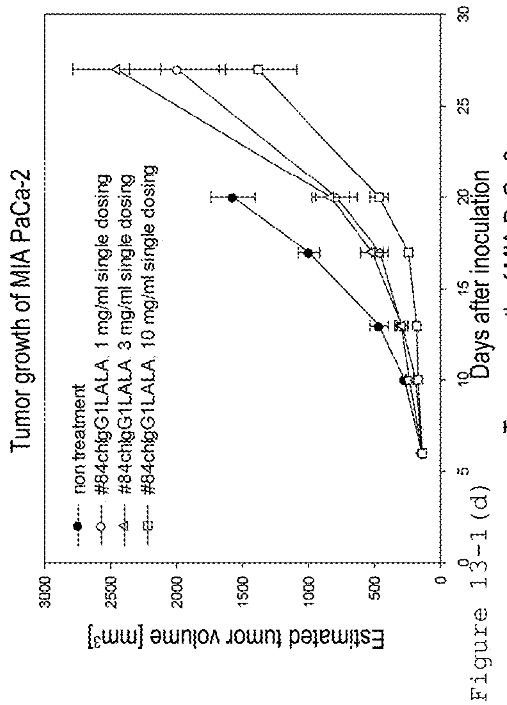
Figures 1C, 13:
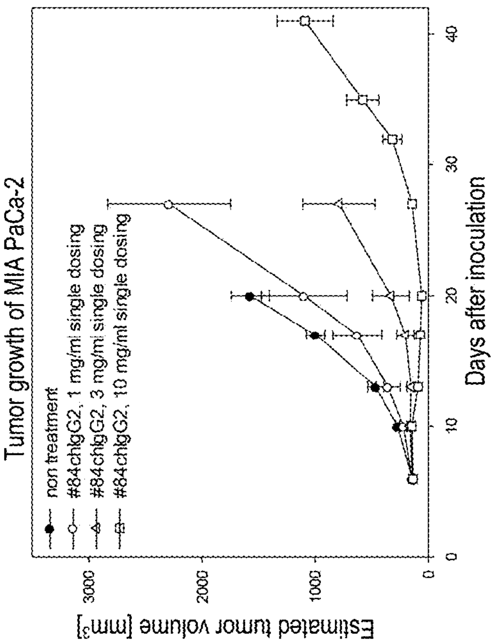
Figures 1D, 13:
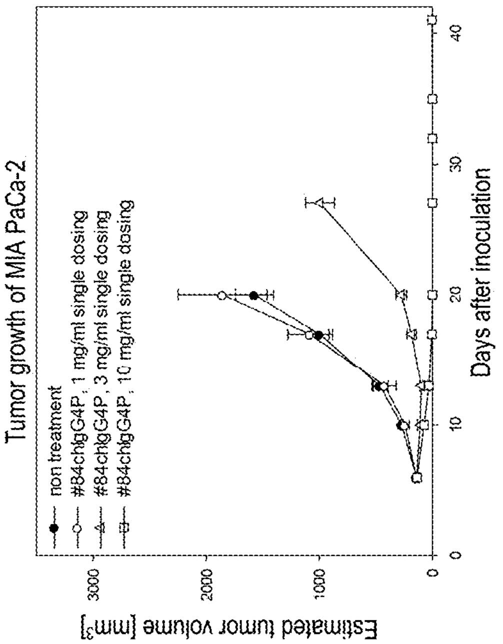
Figures 2E, 13:
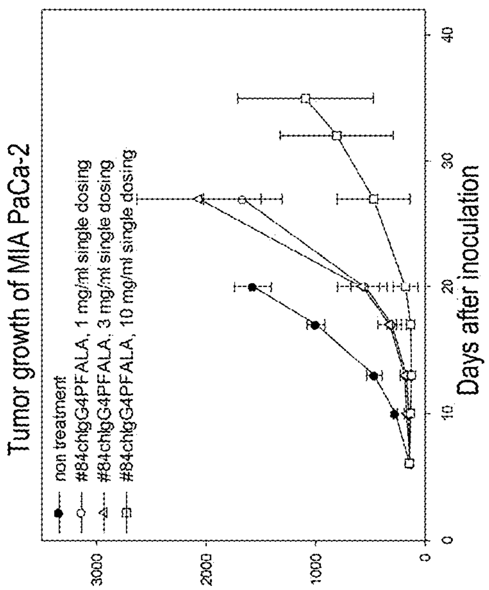
Figures 2F, 13:
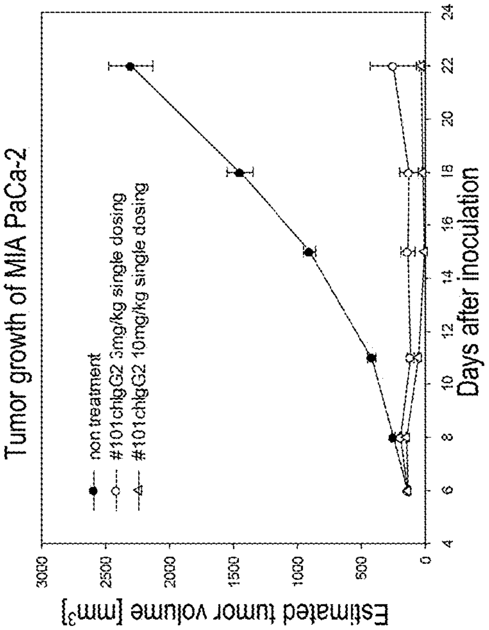
Figures 2G, 13:
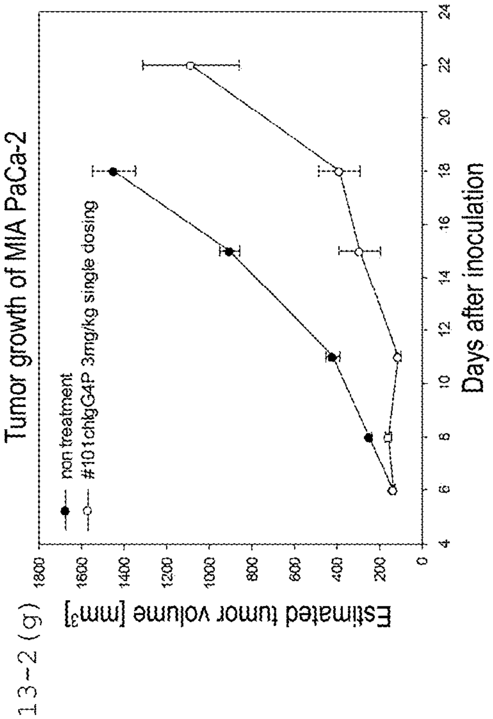
Figures 2H, 13:
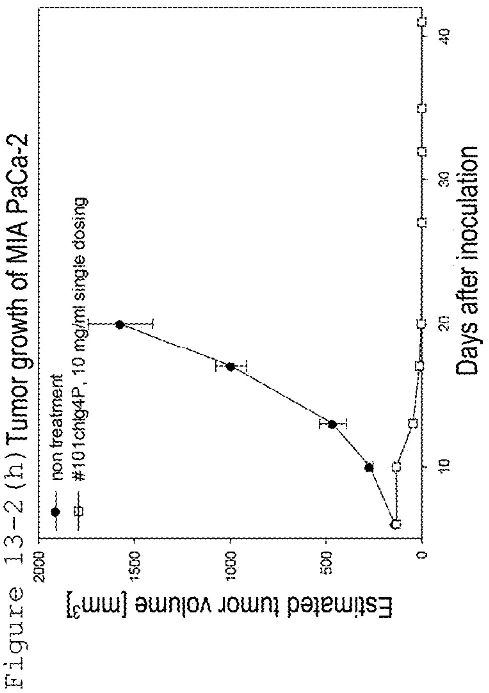
Figures 3I, 13:
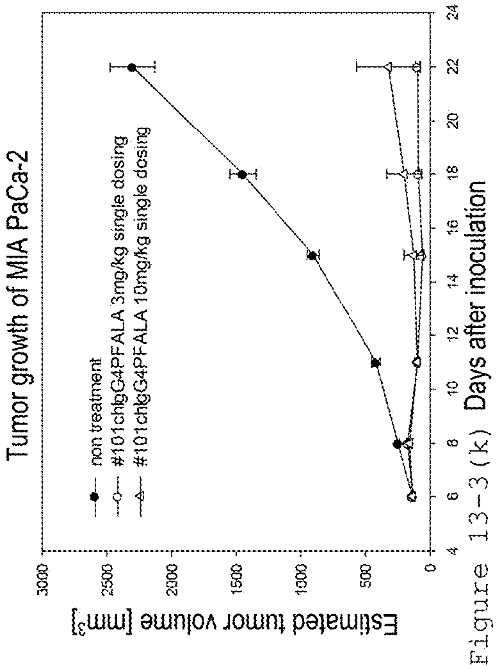
Figures 3J, 13:
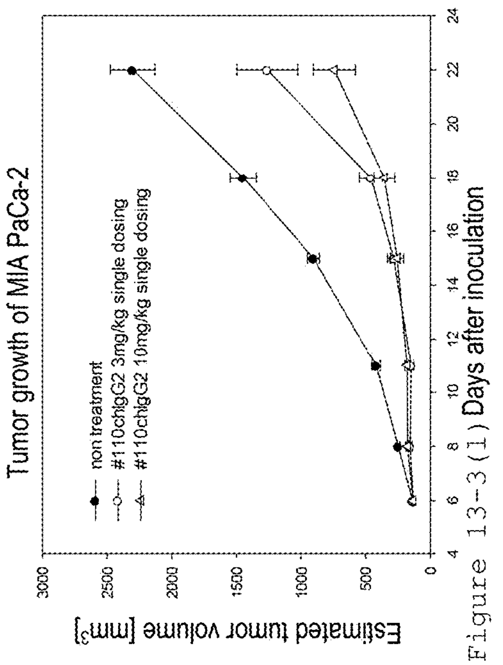
Figures 3K, 13:
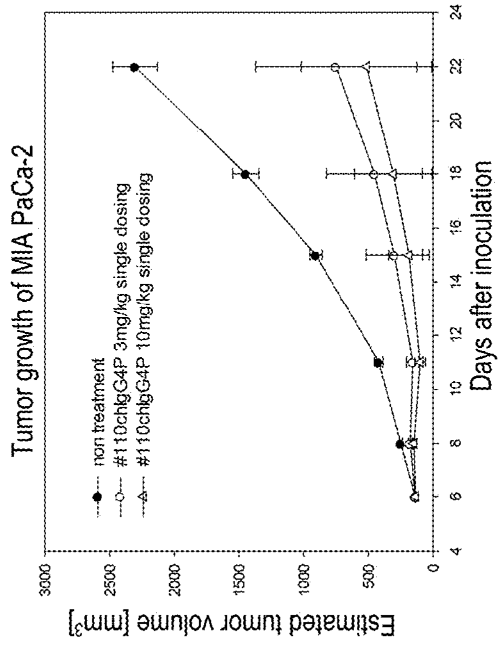
Figures 3L, 13:
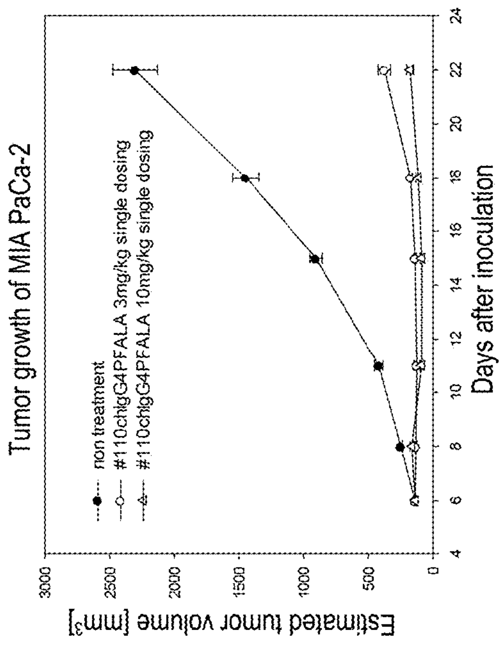
Figures 4M, 13:
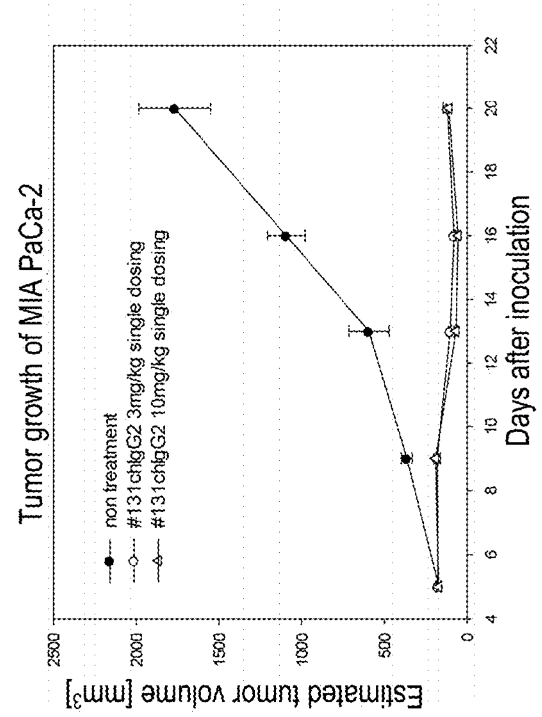
Figures 4N, 13:
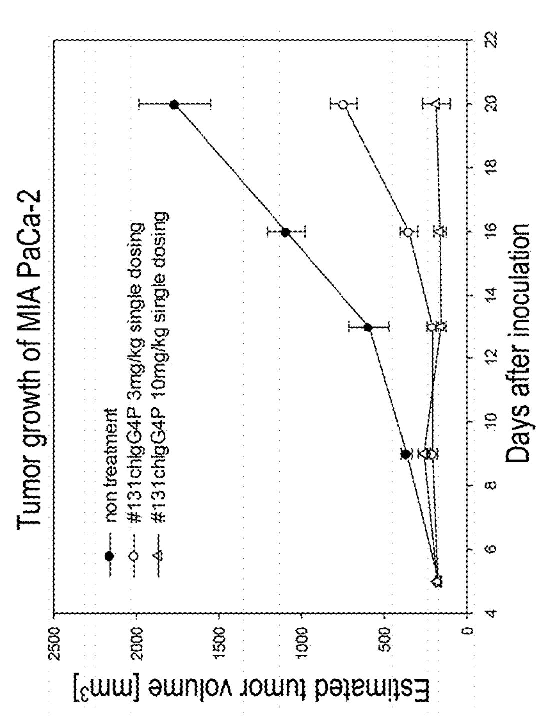
Figure 18A:
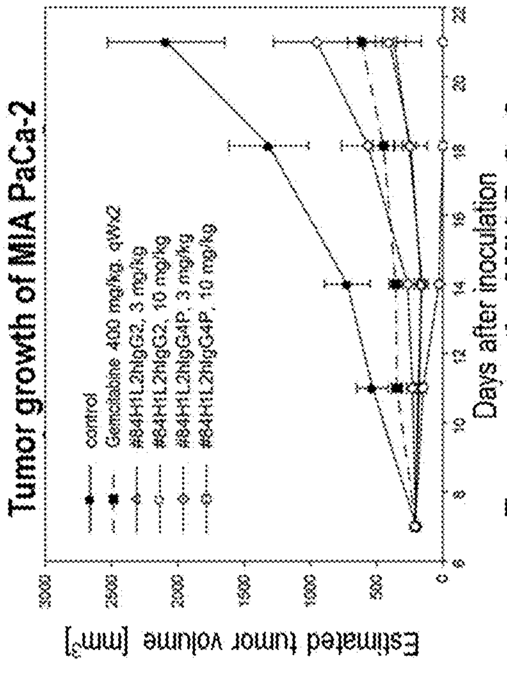
FIGS. 18(*a*) to (*d*) show the antitumor efficacy of humanized antibodies in a MIA PaCa-2 subcutaneous implantation model.
Figure 18B:
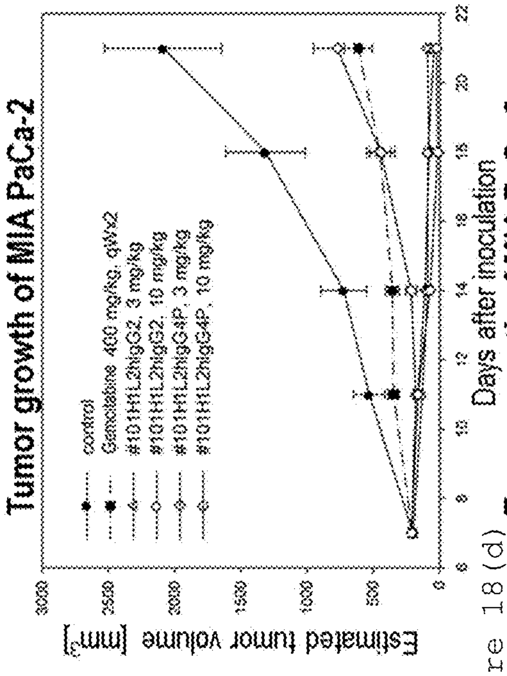
Figure 18C:
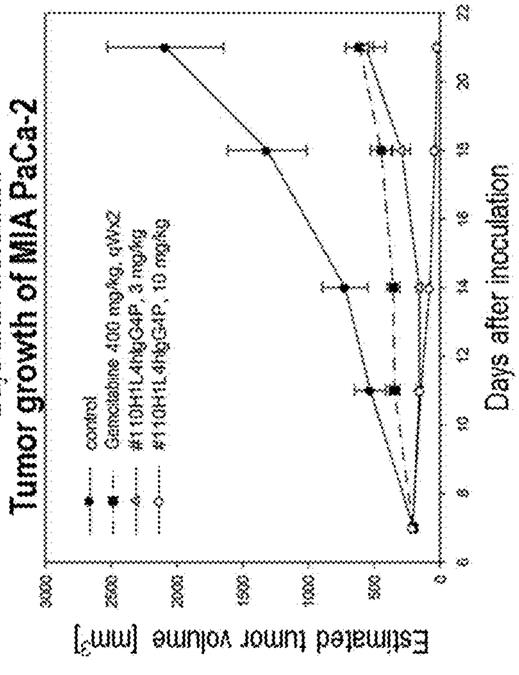
Figure 18D:
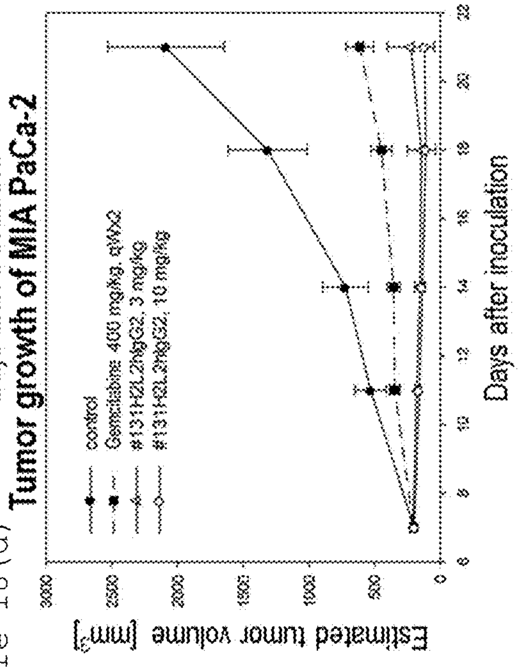

FIGS. 13-1(*a*) to (*d*), FIGS. 13-2(*e*) to (*h*), FIGS. 13-3(*i*) to (*l*), and FIGS. 13-4(*m*) and (*n*) show the results. The graphs also show the averages and the standard errors of changes in tumor volume.

Human chimeric antibody #84 exhibited a dose-dependent antitumor efficacy in all IgG subtypes. In the #84chIgG4P 10 mg/kg administration group in which the strongest antitumor efficacy was observed, complete tumor regression was observed 20 days after the inoculation in 5 mice out of 5 mice.

Human chimeric antibody #101 exhibited a dose-dependent antitumor efficacy in all IgG subtypes. In the 101chIgG4P 10 mg/kg administration group in which the strongest antitumor efficacy was observed, complete tumor regression was observed 20 days after the inoculation in 4 mice out of 5 mice.

Human chimeric antibody #110 exhibited a dose-dependent antitumor efficacy in all IgG subtypes. In the 110chIgG4P 10 mg/kg administration group in which the strongest antitumor efficacy was observed, complete tumor regression was observed 22 days after the inoculation in 3 mice out of 5 mice.

Human chimeric antibody #131 exhibited a dose-dependent antitumor efficacy in the IgG4P subtype. There was no difference in antitumor efficacy observed in the 3 mg/kg and 10 mg/kg administration groups of #131chIgG2.

All human chimeric antibodies exhibited tumor growth inhibition effects of 68 to 100% at a dose of 10 mg/kg, irrespective of the human IgG subtype of each antibody. It was suggested that the cynomolgus monkey-cross-reactive anti-human CD147 human chimeric antibodies #084, #101, #110, and #131 were also independent of the mouse immune system, similar to the anti-human CD147 antibody LN22R8 or 2P10F2 obtained from cell immunization, and exhibited antitumor efficacy by a new mechanism of action on CD147.

Example 5

Evaluation of Binding Activity of Human Chimeric Antibody to CD147

The dissociation constant for binding of #84chIgG1, #84chIgG2, #84chIgG4P, #84chIgG1LALA, #84chIgG4PFALA, #101chIgG4P, or #110chIgG4P produced in Example 3)-3-1 to human CD147 was measured using a Biacore T200 (available from GE Healthcare Bioscience). Anti-Human IgG (Fc) antibody was immobilized on a sensor chip by using a Human Antibody Capture Kit (available from GE Healthcare Bioscience) followed by capturing human chimeric antibody as a ligand and associating an antigen as an analyte. HBS-EP+ (available from GE Healthcare Bioscience) as a running buffer and CM5 (available from GE Healthcare Bioscience) as a sensor chip were used. After 1 μg/mL or 2 μg/mL of the human chimeric antibody was added onto the chip at 10 μL/minute over 60 seconds, a serial dilution of a CD147 protein as an antigen (0.25 to 4 μg/mL with respect to #131chIgG4P or 0.5 to 8

μg/mL with respect to #84chIgG1, #84chIgG2, #84chIgG4P, #84chIgG1LALA, #84chIgG4PFALA, #101chIgG4P, or #110chIgG4P) was associated at a flow rate of 30 μL/minute over 120 seconds, followed by subsequent monitoring for a dissociation phase of 120 seconds, 300 seconds, or 600 seconds. Here, the CD147 protein used was expressed in *Escherichia coli*, purified in 2 steps of Ni affinity and SEC, and then the tag was cleaved. 3M magnesium chloride (available from GE Healthcare Bioscience) was added at a flow rate 20 μL/minute over 30 seconds as a regenerating solution. Using a 1:1 binding model, the binding rate constant ka, the dissociation rate constant kd, and the dissociation constant (KD; KD=kd/ka) were calculated. Table 5 shows the results.

TABLE 5

Dissociation constant for binding of human chimeric antibody to human CD147

| | Name | KD (nM) |
|---|---|---|
| 1 | #84chIgG1 | 393 |
| 2 | #84chIgG2 | 334 |
| 3 | #84chIgG4P | 381 |
| 4 | #84chIgG1LALA | 371 |
| 5 | #84chIgG4PFALA | 358 |
| 6 | #101chIgG4P | 10.5 |
| 7 | #110chIgG4P | 9.94 |
| 8 | #131chIgG4P | 3.45 |

Example 6

Production of Humanized Antibody

6)-1 Design of Humanized Antibody

6)-1-1 Molecular Modeling of Variable Region

A method known as homology modeling (Methods in Enzymology, 203, 121-153, (1991)) was used. Using a commercially available protein three-dimensional structure analysis program, Discovery Studio (available from Dassault Systemes), the homologous sequences of the variable regions were identified from the registered structures in Protein Data Bank (Nuc. Acids Res. 35, D301-D303 (2007)). Three-dimensional models were created using the identified heavy chains, light chains, and heavy and light chain interface structures as templates.

6)-1-2 Method for Designing Humanized Antibody

The antibody was humanized by CDR grafting (Proc. Natl. Acad. Sci. USA 86, 10029-10033 (1989)). Having a high homology, the consensus sequence of the human kappa chain subgroup 1 and the consensus sequence of the human gamma chain subgroup 3 defined in KABAT et al. (Sequences of Proteins of Immunological Interest, 5th Ed. Public Health Service, available from Panasonic Corporation Institutes of Health, Bethesda, Md. (1991)) were selected as acceptors for the framework regions of light and heavy chains of rat_CD147_#84, respectively. Having a high homology, the consensus sequence of the human kappa chain subgroup 1 defined in KABAT et al., and IGHV3-30*05 and IGHJ3*01 of the human gamma chain defined in IMGT (THE INTERNATIONAL IMMUNOGENETICS INFORMATION SYSTEM (R)) were selected as acceptors for the framework regions of light chain and heavy chains of rat_CD147_#101, respectively. Having a high homology, IGKV1-39*01 and IGKJ4*01 of the human kappa chain defined in IMGT and IGHV1-2*02 and IGHJ6*01 of the human gamma chain defined in IMGT were selected as acceptors for the light and heavy chains of rat_CD147_#110, respectively. Having a high homology, IGKV1-39*01 and IGKJ2*01 of the human kappa chain defined in IMGT and IGHV3-30*05 and IGHJ6*01 of the human gamma chain defined in IMGT were selected as acceptors for the light and heavy chains of rat_CD147_#131, respectively. Donor residues to be imported into the acceptors were selected by analyzing the three-dimensional models while referring to the criteria given by Queen et al. (Proc. Natl. Acad. Sci. USA 86, 10029-10033 (1989)) or others.

6)-1-3 Humanization of rat_CD147_#84 Heavy Chain

The amino acid residues of the acceptor shown in FIG. 14(*a*) were imported into the variable region of the rat_CD147_#84 heavy chain, thereby designing the variable region of humanized antibody heavy chain #84H1h.

Humanized antibody heavy chains were designed by connecting the variable region designed above with the gamma chain constant regions of human IgG2 and IgG4P, and named #84H1hIgG2 and #84H1hIgG4P, respectively. SEQ ID NO: 123 represents the full-length amino acid sequence of #84H1hIgG2. SEQ ID NO: 124 represents a nucleotide sequence encoding the amino acid sequence of SEQ ID NO: 123. SEQ ID NO: 125 represents the full-length amino acid sequence of #84H1hIgG4P. SEQ ID NO: 126 represents a nucleotide sequence encoding the amino acid sequence of SEQ ID NO: 125.

6)-1-4 Humanization of rat_CD147_#84 Light Chain

The amino acid residues of the acceptor shown in FIG. 14(*b*) were imported into the variable region of the rat_CD147_#84 light chain, thereby designing a variable region of humanized antibody light chain #84L2h.

A humanized antibody light chain was constructed by connecting the variable region designed above with the human κ chain constant region, and named #84L2h. SEQ ID NO: 127 represents the full-length amino acid sequence of the light chain #84L2h. SEQ ID NO: 128 represents a nucleotide sequence encoding the amino acid sequence of SEQ ID NO: 127.

6)-1-5 Humanized Antibody #84

A humanized antibody #84H1L2hIgG2 was designed by combining the heavy chain #84H1hIgG2 and the light chain #84L2h designed as above. Further, a humanized antibody #84H1L2hIgG4P was designed by combining the heavy chain #84H1hIgG4P and the light chain #84L2h.

6)-1-6 Humanization of rat_CD147_#101 Heavy Chain

The amino acid residues of the acceptor shown in FIG. 15(*a*) were imported into the variable region of the rat_CD147_#101 heavy chain, thereby designing a variable region of humanized antibody heavy chain #101H1h. Humanized antibody heavy chains were constructed by connecting the variable region designed above with the gamma chain constant regions of human IgG2 and IgG4P and named #101H1hIgG2 and #101H1hIgG4P, respectively. SEQ ID NO: 129 represents the full-length amino acid sequence of #101H1hIgG2. SEQ ID NO: 130 represents a nucleotide sequence encoding the amino acid sequence of SEQ ID NO: 129. SEQ ID NO: 131 represents the full-length amino acid sequence of #101H1hIgG4P. SEQ ID NO: 132 represents a nucleotide sequence encoding the amino acid sequence of SEQ ID NO: 131.

6)-1-7 Humanization of rat_CD147_#101 Light Chain

The amino acid residues of the acceptor shown in FIG. 15(*b*) were imported into the variable region of the rat_CD147_#101 light chain, thereby designing a variable region of humanized antibody light chain #101L2h. In the variable region designed above, a humanized antibody light chain connected with human κ chain constant region was designed and named #101L2h. SEQ ID NO: 133 represents the full-length amino acid sequence of light chain #101L2h. SEQ ID NO: 134 represents a nucleotide sequence encoding the amino acid sequence of SEQ ID NO: 133.

6)-1-8 Humanized Antibody #101

A humanized antibody #101H1L2hIgG2 was designed by combining the heavy chain #101H1hIgG2 and the light chain #101L2h designed as above. Further, a humanized antibody #101H1L2hIgG4P was designed by combining the heavy chain #101H1hIgG4P and the light chain #101L2h.

6)-1-9 Humanization of rat_CD147_#110 Heavy Chain

The amino acid residues of the acceptors shown in FIGS. 16(*a*) and (*b*) were each imported into the variable region of rat_CD147_#110 heavy chain, thereby designing variable regions of humanized antibody heavy chains #110H1h and #110H13h.

Humanized antibody heavy chains were constructed by connecting the variable region designed above with the human gamma chain constant region of IgG4P and named #110H1hIgG4P and #110H13hIgG4P, respectively. SEQ ID NO: 135 represents the full-length amino acid sequence of #110H1hIgG4P, and SEQ ID NO: 147 represents the full-length amino acid sequence of #110H13hIgG4P. SEQ ID NO: 136 represents a nucleotide sequence encoding the amino acid sequence of SEQ ID NO: 135, and SEQ ID NO: 148 represents a nucleotide sequence encoding the amino acid sequence of SEQ ID NO: 147.

6)-1-10 Humanization of rat_CD147_#110 Light Chain

The amino acid residues of the acceptors shown in FIGS. 16(*c*), (*d*), and (*e*) were each imported into the variable region of the rat_CD147_#110 light chain, thereby designing variable regions of humanized antibody light chains #110L4h, #110L2h, and #110L12h.

Humanized antibody light chains were constructed by connecting the variable region designed above with the human κ chain constant region and named #110L4h, #110L2h, and #110L12h, respectively. SEQ ID NO: 137 represents the full-length amino acid sequence of light chain #110L4h, SEQ ID NO: 149 represents the full-length amino acid sequence of light chain #110L2h, and SEQ ID NO: 151 represents the full-length amino acid sequence of light chain #110L12h. SEQ ID NO: 138 represents a nucleotide sequence encoding the amino acid sequence of SEQ ID NO: 137, SEQ ID NO: 150 represents a nucleotide sequence encoding the amino acid sequence of SEQ ID NO: 149, and SEQ ID NO: 152 represents a nucleotide sequence encoding the amino acid sequence of SEQ ID NO: 151.

6)-1-11 Humanized Antibody #110

A humanized antibody #110H1L4hIgG4P was designed by combining the heavy chain #110H1hIgG4P and the light chain #110L4h designed as above. Further, a humanized antibody #110H13L2hIgG4P was designed by combining the heavy chain #110H13hIgG4P and the light chain #110L2h, and a humanized antibody #110H13L12hIgG4P was designed by combining the heavy chain #110H13hIgG4P and the light chain #110L12h.

6)-1-12 Humanization of rat_CD147_#131 Heavy Chain

The amino acid residues of the acceptor shown in FIG. 17(*a*) were imported into the variable region of the rat_CD147_#131 heavy chain, thereby designing a variable region of humanized antibody heavy chain #131H2h.

A humanized antibody heavy chain was constructed by connection the variable region designed above with the gamma chain constant region of human IgG2 and named #131H2hIgG2. SEQ ID NO: 139 represents the full-length amino acid sequence of #131H2hIgG2. SEQ ID NO: 140 represents a nucleotide sequence encoding the amino acid sequence of SEQ ID NO: 139.

6)-1-13 Humanization of rat_CD147_#131 Light Chain

The amino acid residues of the acceptor shown in FIG. 17(*b*) were imported into the variable region of the rat_CD147_#131 light chain, thereby designing a variable region of humanized antibody light chain #131L2h.

A humanized antibody light chain was constructed by connecting the variable region designed above with the human κ chain constant region and named #131L2h. SEQ ID NO: 141 represents the full-length amino acid sequence of light chain #131L2h. SEQ ID NO: 142 represents a nucleotide sequence encoding the amino acid sequence of SEQ ID NO: 141.

6)-1-14 Humanized Antibody #131

A humanized antibody #131H2L2hIgG2 was designed by combining the heavy chain #131H2hIgG2 and the light chain #131L2h as designed above.

6)-2 Construction of Humanized Antibody Light Chain Expression Vectors

6)-2-1 Construction of #84L2h Expression Vector

A DNA fragment represented by nucleotide positions 37 to 402 of the nucleotide sequence of #84L2h represented by SEQ ID NO: 128 was synthesized (Geneart AG). Using an In-Fusion HD PCR cloning kit (Clontech Laboratories, Inc.), the synthesized DNA fragment was inserted into the site where pCMA-LK was digested with restriction enzyme BsiWI, thereby constructing a #84L2h expression vector.

6)-2-2 Construction of #101L2h Expression Vector

A DNA fragment represented by nucleotide positions 37 to 402 of the nucleotide sequence of #101L2h represented by SEQ ID NO: 134 was synthesized (Geneart AG). A #101L2h expression vector was constructed in the same manner as in Example 6)-2-1.

6)-2-3 Construction of #110L4h, #110L2h, and #110L12h Expression Vectors

DNA fragments represented by nucleotide positions 37 to 402 of the nucleotide sequences of #110L4h, #110L2h, and #110L12h represented by SEQ ID NO: 138, SEQ ID NO: 150 and SEQ ID NO: 152 were synthesized (GeneArt AG). #110L4h, #110L2h, and #110L12h expression vectors were constructed in the same manner as in Example 6)-2-1.

6)-2-4 Construction of #131L2h Expression Vector

A DNA fragment represented by nucleotide positions 37 to 402 of the nucleotide sequence of #131L2h represented by SEQ ID NO: 142 was synthesized (GeneArt AG). A #131L2h expression vector was constructed in the same manner as in Example 6)-2-1.

6)-3 Construction of Humanized Antibody Heavy Chain Expression Vectors

6)-3-1 Construction of #84H1hIgG2 Expression Vector

A DNA fragment represented by nucleotide positions 36 to 437 of the nucleotide sequence of #84H1hIgG2 represented by SEQ ID NO: 124 was synthesized (GeneArt AG). Using an In-Fusion HD PCR cloning kit (Clontech Laboratories, Inc.), the synthesized DNA fragment was inserted into the site where pCMA-G2 was digested with restriction enzyme BlpI, thereby constructing a #84H1hIgG2 expression vector.

6)-3-2 Construction of #84H1hIgG4P Expression Vector

A DNA fragment represented by nucleotide positions 36 to 437 of the nucleotide sequence of #84H1hIgG4P represented by SEQ ID NO: 126 was synthesized (GeneArt AG). Using an In-Fusion HD PCR cloning kit (Clontech Laboratories, Inc.), the synthesized DNA fragment was inserted into the site where pCMA-G4P was digested with restriction enzyme BlpI, thereby constructing a #84H1hIgG4P expression vector.

6)-3-3 Construction of #101H1hIgG2 Expression Vector

A DNA fragment represented by nucleotide positions 36 to 428 of the nucleotide sequence of #101H1hIgG2 represented by SEQ ID NO: 130 was synthesized (GeneArt AG). A #101H1hIgG2 expression vector was constructed in the same manner as in Example 6)-3-1.

6)-3-4 Construction of #101H1hIgG4P Expression Vector

A DNA fragment represented by nucleotide positions 36 to 428 of the nucleotide sequence of #101H1hIgG4P represented by SEQ ID NO: 132 was synthesized (GeneArt AG). A #101H1hIgG4P expression vector was constructed in the same manner as in Example 6)-3-2.

6)-3-5 Construction of #110H1hIgG4P and #110H13hIgG4P Expression Vectors

DNA fragments represented by nucleotide positions 36 to 425 of the nucleotide sequences of #110H1hIgG4P and #110H13hIgG4P represented by SEQ ID NO: 136 and SEQ ID NO: 148 were synthesized (GeneArt AG). #110H1hIgG4P and #110H13hIgG4P expression vectors were constructed in the same manner as in Example 6)-3-2.

6)-3-6 Construction of #131H2hIgG2 Expression Vector

A DNA fragment represented by nucleotide positions 36 to 431 of the nucleotide sequence of #131H2hIgG2 represented by SEQ ID NO: 140 was synthesized (GeneArt AG). A #131H2hIgG2 expression vector was constructed in the same manner as in Example 6)-3-1.

6)-4 Preparation of Humanized Antibody

6)-4-1 Production of Humanized Antibody

The antibody was produced in the same manner as in Example 1)-14-1. A series of humanized antibodies was obtained by combining an H chain expression vector and an L chain expression vector corresponding to the combinations of an H chain and an L chain shown in Example 6)-1-5, Example 6)-1-8, Example 6)-1-11, and Example 6)-1-14.

6)-4-2 One-Step Purification of Humanized Antibody

An antibody was purified from the culture supernatant obtained in Example 6)-4-1 by a one-step process of rProtein A affinity chromatography. After the culture supernatant was applied to a column equilibrated with PBS and filled with MabSelectSuRe (available from GE Healthcare Bioscience), the column was washed with PBS an amount twice or more the column volume. Next, elution with a 2M arginine hydrochloride solution (pH 4.0) was performed to collect a fraction containing the antibody. The fraction was subjected to buffer replacement with PBS by dialysis (Thermo Scientific, Slide-A-Lyzer Dialysis Cassette). The antibody was concentrated using a Centrifugal UF Filter Device VIVASPIN20 (fraction molecular weight UF10K, Sartorius AG) to adjust the IgG concentration to 1 mg/mL or more. Finally, filtration was performed using a Minisart-Plus filter (Sartorius AG) to give a purified sample.

6)-4-3 Two-Step Purification of Humanized Antibody

The culture supernatant obtained in Example 6)-4-1 was purified by a two-step process of rProtein A affinity chromatography and ceramic hydroxyapatite. After the culture supernatant was applied to a column equilibrated with PBS and filled with MabSelectSuRe (available from GE Healthcare Bioscience), the column was washed with PBS in an amount twice or more the column volume. Next, the antibody was eluted with a 2M arginine hydrochloride solution (pH 4.0). A fraction containing the antibody was subjected to buffer replacement with PBS by dialysis (Thermo Scientific, Slide-A-Lyzer Dialysis Cassette), followed by 5-fold dilution with a 5 mM sodium phosphate/50 mM MES/pH 7.0 buffer, and was applied to a ceramic hydroxyapatite column (Japan Bio-Rad Laboratories, Inc., Bio-Scale CHT Type-1 Hydroxyapatite Column) equilibrated with a 5 mM NaPi/50 mM MES/30 mM NaCl/pH 7.0 buffer. Linear gradient elution with sodium chloride was performed to collect a fraction containing the antibody. The fraction was subjected to buffer replacement with HBSor buffer (25 mM Histidine/5% Sorbitol/pH 6.0) by dialysis (Thermo Scientific, Slide-A-Lyzer Dialysis Cassette). The antibody was concentrated using a Centrifugal UF Filter Device VIVASPIN20 (fraction molecular weight UF10K, Sartorius AG) to adjust the IgG concentration to 25 mg/mL. Finally, filtration was performed using a Minisart-Plus filter (Sartorius AG) to give a purified sample.

Example 7

Measurement of Activities of Humanized Antibody

7)-1 Evaluation of the Binding Activity of Humanized Antibody to CD147

The dissociation constant for binding of humanized anti-human CD147 antibody #84H1L2hIgG2, #84H1L2hIgG4P, #101H1L2hIgG2, #101H1L2hIgG4P, #110H1L4hIgG4P, or #131H2L2hIgG2 produced in Example 6)-4-3 to human CD147 was measured using a Biacore T200 (available from GE Healthcare Bioscience). Anti-Human IgG (Fc) antibody was immobilized on a sensor chip by using a Human Antibody Capture Kit (available from GE Healthcare Bioscience) followed by capturing humanized antibody as a ligand and associating an antigen as an analyte. HBS-EP+ (available from GE Healthcare Bioscience) as a running buffer and CM5 (available from GE Healthcare Bioscience) as a sensor chip were used. After 1 μg/mL of a humanized antibody was added onto the chip at 10 μL/minute over 60 seconds, the serial dilution of the antigen used in Example 5) was associated at a flow rate of 30 μL/minute over 120 seconds (0.0625 to 1 μg/mL with respect to #101H1L2hIgG2 and #101H1L2hIgG4P, and 0.25 to 4 μg/mL with respect to #84H1L2hIgG2, #84H1L2hIgG4P, #110H1L4hIgG4P, #110H13L2hIgG4P, #110H13L12hIgG4P, and #131H2L2hIgG2), followed by subsequent monitoring for a dissociation phase of 300 seconds. 3M magnesium chloride (available from GE Healthcare Bioscience) as a regenerating solution was added thereto at a flow rate of 20 μL/minute over 30 seconds. The binding rate constant ka, the dissociation rate constant kd, and the dissociation constant (KD; KD=kd/ka) were calculated using a 1:1 binding model.

Table 6 shows the results.

TABLE 6

Dissociation constant for binding of humanized antibody to human CD147

| Name | KD (nM) |
|---|---|
| #84H1L2hIgG2 | 227 |
| #84H1L2hIgG4P | 242 |
| #101H1L2hIgG2 | 10.5 |
| #101H1L2hIgG4P | 10.5 |
| #110H1L4hIgG4P | 8.60 |
| #110H13L2hIgG4P | 58.9 |
| #110H13L12hIgG4P | 154 |
| #131H2L2hIgG2 | 5.84 |

7)-2 Antitumor Effect of Humanized CD147 Antibodies in Pancreatic Xenograft Model $5\times10^6$ cells of human pancreatic line MIA PaCa-2 were suspended in PBS containing 50% GFR-Matrigel (Corning Inc., Cat. 354230), and the suspension was inoculated subcutaneously into the axilla of 4 week-old female NOD-scid mice (NOD. CB17-Prkdc<scid>/J, purchased from CHARLES RIVER LABORATORIES JAPAN, INC). Grouping was performed based on tumor volume, the humanized CD147 antibody (#84H1L2hIgG2, #84H1L2IgG4P, #101H1L2hIgG2, #101H1L2hIgG4P, #110H1L4hIgG4P, or #131H2L2hIgG2) produced in Example 6)-4-2 was administered intraperitoneally to mice bearing tumor at 3 mg/kg or 10 mg/kg 7 days after the inoculation (n=5). As a control drug, gemcitabine (purchased from Eli Lilly Japan K.K.) that is a standard therapeutic agent for pancreatic cancer was administered intraperitoneally to cancer-bearing mice at 400 mg/kg 7 and 14 days after the inoculation (n=5). The major axis and the minor axis of the inoculated tumor were measured twice a week using an electronic digital caliper (available from MITUTOYO CORPORATION) to calculate the tumor volume by the following formula.

FIGS. 18(*a*) to (*d*) show the results. The graphs also show the averages and the standard errors of changes in tumor volume.

While the tumor growth inhibition rate of the control drug was 71%, and no tumor disappearance was recognized, all the humanized CD147 antibodies exhibited a more potent antitumor efficacy in the 3 or 10 mg/kg administration group than gemcitabine. In the 10 mg/kg administration group of #84H1L2hIgG4P, #101H1L2hIgG2, #101H1L2hIgG4P, or #110H1L4hIgG4P, a potent antitumor efficacy with tumor disappearance was observed.

Example 8

In-Vitro Activation of p38MAPK Signal by CD147 Antibody

8)-1 Induction of p38MAPK Phosphorylation by Anti-Human CD147 Human Chimeric Antibody in Pancreatic Cancer Cells PANC-1

It has been reported that CD147 activation promotes p38MAPK phosphorylation (Lim et al., FEBS Letters, 88-92, 1998) (Li et., al. J. Hepatology, 1378-1389, 2015). In order to investigate the influence of an anti-CD147 antibody exhibiting an antitumor efficacy on the p38MAPK signal, p38MAPK phosphorylation in PANC-1 cells treated with the CD147 human chimeric antibody LN22R8chIgG4P at 10 μg/ml for 15 minutes was evaluated using Simple Western assays (ProteinSimple Japan K.K., Wes). As a control sample, PANC-1 cells treated with human IgG (Jackson ImmunoResearch Inc., Cat. 009-000-003) at 10 μg/ml in the same manner were analyzed. In order to detect p38MAPK, p38 MAPK rabbit mAb (Cell Signaling Technology, Inc., Cat. #9212) was used. In order to detect phosphorylated p38MAPK, P-p38 MAPK (T180/Y182) (D3F9) XP rabbit mAb (Cell Signaling Technology, Inc., Cat. #4511S) was used. FIG. 19 shows the ratio of the phosphorylated p38MAPK signal to the detected p38MAPK signal. The antibody treated samples were measured twice, and the graph shows the averages.

In the LN22R8chIgG4P antibody treated group, an increase in the phosphorylated MAPK signal was observed.

8)-2 Anti-CD147 Antibody Mediated Phosphorylation of HSP27 Which is a Molecule Downstream of the p38 Signal It has been reported that HSP27 is phosphorylated by activation of p38MAPK (Landry et al., Biochem. Cell Biol., 703-707, 1995). In order to investigate whether p38 phosphorylation induced by the CD147 human chimeric antibody LN22R8 in fact promotes activation of the p38 signal, phosphorylation in the antibody treated samples of 8)-1 was evaluated using Simple Western assays (ProteinSimple Japan K.K., Wes). In order to detect HSP27, an anti-HSP27 antibody (R&D systems, Cat. AF15801) was used. In order to detect phosphorylated HSP27, a Phospho-HSP27 (Ser82) antibody (Cell Signaling Technology, Inc., Cat. 2401S) or an Anti-HSP27 (phospho Ser15) antibody (Abcam plc., Cat. ab76313) was used.

Figure 20A:
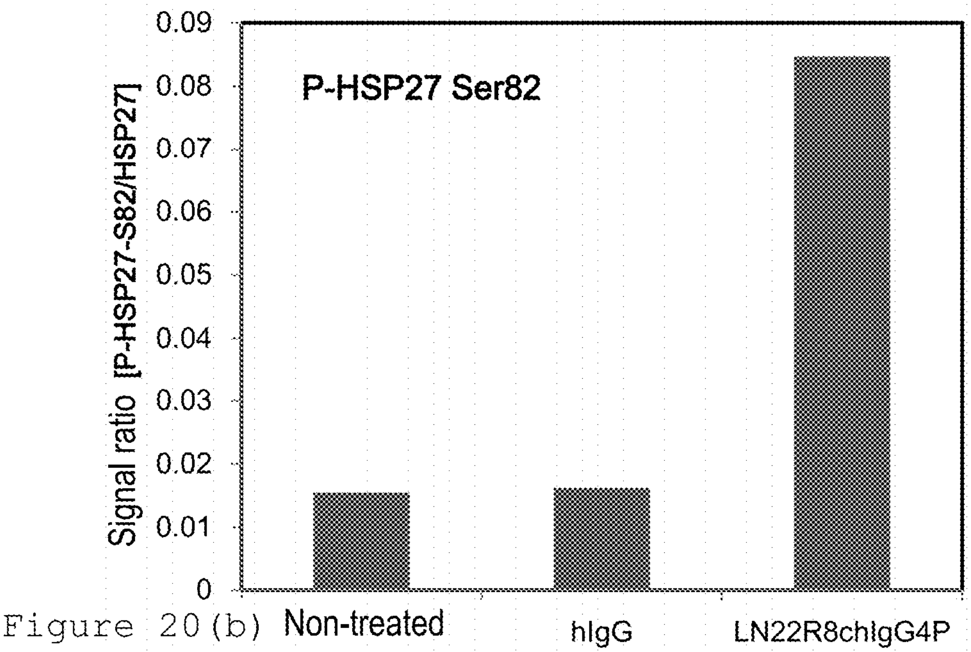
FIGS. 20(*a*) and (*b*) show HSP27 phosphorylation by an anti-human CD147 human chimeric antibody.
Figure 20B:
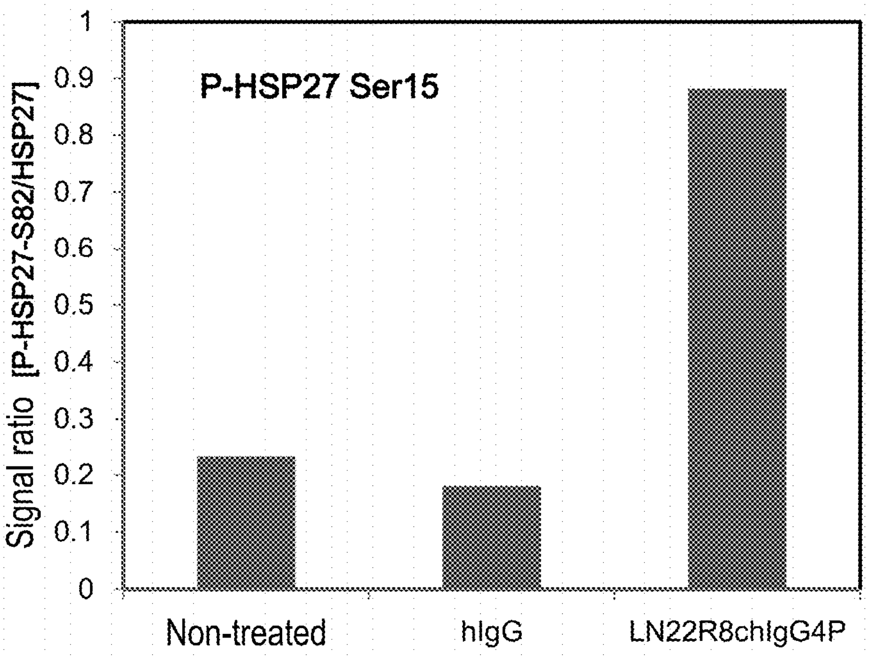

FIG. 20(*a*) or FIG. 20(*b*) shows the ratio of the Ser82 or Ser15 phosphorylated HSP27 signal to the detected HSP27 signal, respectively. The antibody treated samples were evaluated in duplicate, and the graphs show the averages.

In the LN22R8chIgG4P antibody treated group, an increase in phosphorylated HSP27 signal was observed. Since the phosphorylation and activation of HSP27 is downstream and is induced by p38 phosphorylation, which in turn is induced by the CD147 human chimeric antibody, it was found that the anti-human CD147 human chimeric antibody LN22R8IgG4P induced the activation of p38MAPK signal. Likewise, the activation of p38MAPK signal was observed also in pancreatic cancer cells MIA PaCa-2.

Example 9

Activation of the p38 Signal by CD147 Antibody in Xenograft Tumor Tissue

Whether the activation of the p38MAPK signal by the CD147 antibody observed in vitro also occurs within tumors formed subcutaneously in mice was investigated in the subcutaneous tumors of MIA PaCa-2 mice. $5\times10^6$ cells of human pancreatic line MIA PaCa-2 were suspended in PBS containing 50% GFR-Matrigel (Corning Inc., Cat. 354230), and the suspension was inoculated subcutaneously into the axilla of 5 week-old female NOD-scid mice (NOD. CB17-Prkdc<scid>/J, purchased from CHARLES RIVER LABORATORIES JAPAN, INC). Grouping was performed based on tumor volume 5 days after the inoculation, and the anti-human CD147 human chimeric antibody LN22R8chIgG4P was administered intraperitoneally to mice bearing tumor at 10 mg/kg on the day after the grouping. Tumors were sampled 6, 24, 48, 72 hours after the antibody administration, frozen using dry ice, and stored frozen. In order to prepare samples from the frozen tumor tissues (n=3), a gentleMACS Octo Dissociator with Heaters (Miltenyi Biotec K.K.) was used. The prepared tumor lysates were analyzed using Simple Western assays (ProteinSimple Japan K.K., Wes).

FIG. 21(*a*) shows the averages of the detected p38MAPK signal together with the standard errors. FIG. 21(*b*) shows the averages of the detected phosphorylated p38MAPK signal together with the standard errors. FIG. 21(*c*) shows the averages of the ratio of the phosphorylated p38MAPK signal to the p38MAPK signal together with the standard errors. In LN22R8chIgG4P, phosphorylated P38MAPK increased from 6 hours to 72 hours after the administration. The ratio of the phosphorylated p38MAPK signal was at its peak at 6 hours after administration and then decreased as p38MAPK increased from 24 hours to 72 hours.

Since an increase in p38 phosphorylation and an increase in HSP27 phosphorylation due to administration of the CD147 chimeric antibody were also observed in the subcutaneous tumors of mice, it was found that the p38 signal was activated.

Example 10

Induction of Molecules Such as CXCL8 Downstream of p38MAPK

It has been reported that activation of p38MAPK causes induction of CXCL8 via mRNA stabilization (Hoffmann et al., J. Leukoc. Biol., 847-855, 2002) and activation of the SMAD3/4 signal (Leovonen et al., PLOS ONE, e57474, 2013). RNA extracted from mouse subcutaneous tumors after administration of the antibody was investigated by quantitative PCR to determine whether CXCL8 gene expression was induced within MIA PaCa-2 tumors after administration of the antibody. Likewise, the RHOB gene (Vasilaki et al., FASEB Journal, 891-905, 2010) which has been reported to be induced by activation of SMAD signaling was also investigated for changes due to administration of the CD147 antibody. As endogenous control genes, expression of the importin (ipo8) gene and the TATA box binding protein (tbp) gene were measured. After the anti-human CD147 human chimeric antibody was administered, and MIA PaCa-2 tumors were sampled 72 hours later and treated with RNA later (Qiagen N.V., Cat. 76104), RNA was extracted using an RNeasy Mini Kit (250) (Qiagen N.V., Cat. 74106). As the anti-human CD147 human chimeric antibody, LN22R8chIgG1, LN22R8chIgG2, or LN22R8chIgG4P produced in Example 1)-14 was used. For quantitative RT-PCR, an EXPRESS One-Step SuperScript qRT-PCR kit Universal (Thermofisher scienticic, Cat. 11781-01K) was used, and importin (ipo8) (Thermo Fisher Scientific, Cat. Hs00183533_m1), TATA box binding protein (tbp) (Thermo Fisher Scientific, Cat. Hs00427621_m1), rashomolog family member B (rhoB) (Thermo Fisher Scientific, Cat. h500269660_s1), and interleukin 8 (Thermo Fisher Scientific, Cat. Hs00174103_m1) were used as gene quantitative probes. Gene-specific increases in fluorescence signals following PCR reaction were measured using ABI-Prism 7500 (Applied Biosystems). FIG. 22(*a*) shows the averages (n=3) of the ipo8/tbp gene expression ratio together with the standard deviations. FIG. 22(*b*) shows the averages (n=3) of the cxcl8/tbp gene expression ratio together with the standard deviations. FIG. 22(*c*) shows the averages (n=3) of the rhoB/tbp gene expression ratio together with the standard deviations.

After the administration of LN22R8chIgG1, LN22R8chIgG2, or LN22R8chIgG4P, ipo8 gene expression did not vary, but induction of cxcl8 and rhoB expression in the anti-human CD147 human chimeric antibody administration group was observed. The induction of cxcl8 and rhoB expression was in keeping with the magnitude of the antitumor efficacy of the human chimeric antibody shown in Example 1)-18, suggesting that the induction of expression of both genes may possibly correlate with the antitumor efficacy.

Example 11

Induction of cxcl8 and rhoB Genes by Enhancing Antitumor Efficacy Through Conversion of Anti-Human CD147 Rat Antibody Into Human Chimeric Antibody The antitumor efficacy of the anti-human CD147 rat antibody rat_CD147_#110 was enhanced by human chimerization as shown in Example 2 and Example 7. For the induction of cxcl8 and rhoB observed in tumors after the administration of the human chimeric antibody LN22R8chIgG1, LN22R8chIgG2, or LN22R8chIgG4P, rat_CD147_#110 was compared with the chimeric antibody #110chIgG4P in the same manner as in Example 10.

FIG. 23(*a*) shows the averages (n=3) of the ipo8/tbp gene expression ratio together with the standard deviations.

FIG. 23(*b*) shows the averages (n=3) of the cxcl8/tbp gene expression ratio together with the standard deviations.

FIG. 23(*c*) shows the averages (n=3) of the rhoB/tbp gene expression ratio together with the standard deviations.

The ipo8 gene expression did not vary due to the administration of the antibody. While no change was observed in cxcl8 and rhoB gene expression due to the administration of rat_CD147_#110, as in the antibody non-administered group, induction of cxcl8 and rhoB by #110chIgG4P was observed. It was suggested that the induction of both genes was a parameter correlated with the antitumor efficacy by the CD147 antibody.

Example 12

Evaluation Using SMAD4-Negative Pancreatic Cancer-Bearing Model

The transcription factor, SMAD4, is known as one of the molecules important for activation of SMAD signaling (Zang, et al., Current Biology, 270-276, 1997). It is known that SMAD signaling is partially impaired due to genetic defects of SMAD4 in some pancreatic cancers (Hahn, et al., Science, 350-353, 1996). Whether the CD147 antibody exhibits an antitumor efficacy in pancreatic cancer cell line BxPC-3 lacking SMAD4 and with SMAD signaling partially inhibited (Yasutome et al., Clin. Exp. Metastasis, 461-473, 2005) was investigated. $2.5\times10^6$ cells of human pancreatic line BxPC-3 (ATCC, Cat. CRL-1687) were suspended in PBS containing 100% Matrigel (Corning Inc., Cat. 354234), and the suspension was inoculated subcutaneously into the axilla of 6 week-old female BALB/c-nu mouse (CAnN. Cg-Foxn1nu/CrlCrlj, purchased from CHARLES RIVER LABORATORIES JAPAN, INC). Grouping was performed based on tumor volume 8 days after the inoculation, and the mouse anti-human CD147 antibody LN22R8 or the rat anti-human CD147 antibody 2P10F2 was administered intraperitoneally to cancer-bearing mice at 10 mg/kg 8, 15, and 22 days after the inoculation (n=5). As a control drug, gemcitabine (Eli Lilly Japan K.K., Gemzar (R)) that is a therapeutic agent for pancreatic cancer was administered to mice bearing tumor via the tail vein at 200 mg/kg 8, 15, 22 days after the inoculation (n=5). The major axis and the minor axis of the inoculated tumor were measured twice a week using an electronic digital caliper (available from MITUTOYO CORPORATION) to calculate the tumor volume by the following formula.

$$\text{Tumor volume (mm}^3\text{)}=1/2\times\text{minor axis(mm)}\times\text{minor axis(mm)}\times\text{major axis(mm)}$$

FIG. 24 shows the results. The graphs also show the averages and the standard errors of changes in tumor volume. The BxPC-3 tumor was resistant to LN22R8 antibody, 2P10F2 antibody, and gemcitabine.

Example 13

Acquisition of CD147 Antibody Sensitivity by Sestoration of SMAD4

It has been reported that the SMAD signal recovers by restoration of SMAD4 in some pancreatic cancer cell lines.

Whether the SMAD signal which was recovered by restoration of SMAD4 causes an increase in CD147 antibody sensitivity was investigated.

13)-1 Generation of SMAD4 Stably Expressing Cells

Using a Retro-X™ Q vector kit, SMAD4 stably expressing cell line BxPC-3 was generated. A human SMAD4 gene produced by artificial synthesis was introduced into a cloning site of pQCXIP plasmid contained in the kit as a retroviral vector (Takara Bio Inc., Retro-X™ Q Vector Set, Cat. 631516) to form a SMAD4 expressing retroviral vector. Using a Retro-X Universal Packaging System (Takara Bio Inc., Cat. 631530), the SMAD4 expressing retroviral vector was introduced into BxPC-3, and BxPC-3 cells in which a retrovirus was incorporated into a chromosome by viral infection and which thus became puromycin resistant and SMAD4 positive were selected using puromycin (Takara Bio Inc., Cat. 631306) to serve as SMAD4-positive BxPC-3 cells, BxPC-3-SMAD4. The retroviral vector pQCXIP plasmid was introduced in the same manner, and BxPC-3 cells which became puromycin resistant served as BxPC-3-mock. The retrovirus infection experiment was performed twice to produce lot. 1 and lot. 2 of BxPC-3-mock and BxPC-3-SMAD4.

13)-2 Confirmation of CD147 and SMAD4 Expression

BxPC-3 (ATCC, Cat. CRL-1687), and BxPC-3-mock and BxPC-3-SMAD4 produced in Example 13)-1 were analyzed using Simple Western assays (ProteinSimple Japan K.K., Wes). As a SMAD4-positive control sample, MIA PaCa-2 was used. For detecting SMAD4, an anti-SMAD4 antibody (R&D systems, Cat. AF2097) was used. For detecting GAPDH, an anti-GAPDH antibody (Abfrontier, Cat. LF-MA0026) was used. For detecting CD147, an anti-CD147 antibody (Abcam, Cat. Ab108317) was used.

Figure 25A:
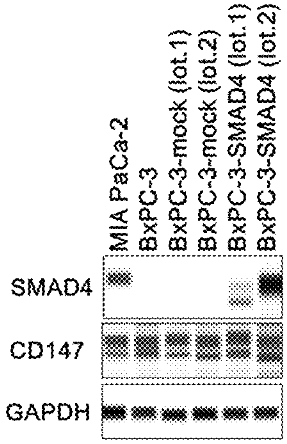
FIGS. 25(*a*) to (*c*) show the results of evaluating the antitumor efficacy of anti-CD147 human chimeric antibodies using BxPC-3 stably expressing SMAD4.
Figure 25B:
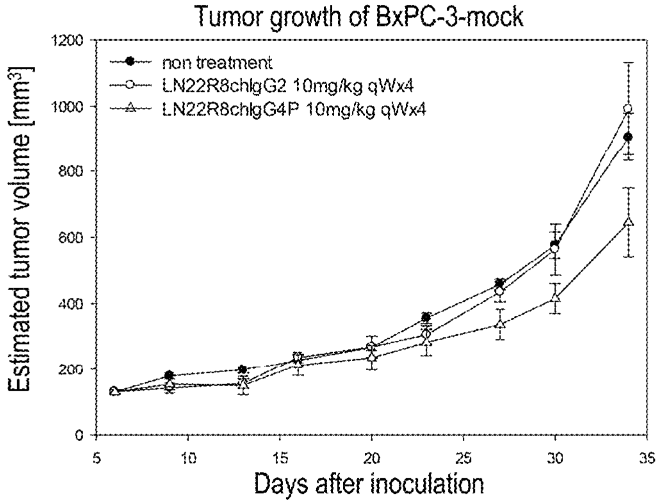
Figure 25C:
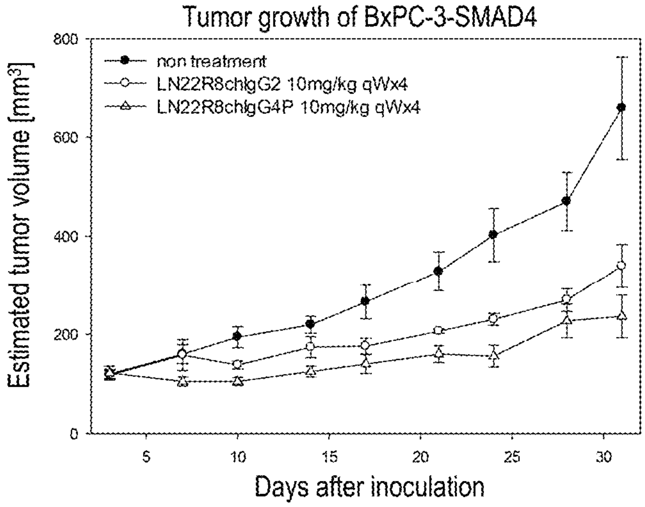

FIG. 25(*a*) shows the results. MIA PaCa-2 was SMAD4 positive and CD147 positive. BxPC-3 was SMAD4 negative and CD147 positive. BxPC-3-mock was SMAD4 negative and CD147 positive with no influence of retrovirus infection observed. Both lot. 1 and lot. 2 of BxPC-3-SMAD4 with the SMAD4 expressing retroviral vector introduced were SMAD4 positive. The SMAD4 expression of Lot. 2 was high, and thus lot. 2 was used as BxPC-3-SMAD4 in the subsequent experiments.

13)-3 Sensitivity of SMAD4 Stably Expressing BxPC-3 Tumor to CD147 Human Chimeric Antibody $2.5\times10^6$ cells of BxPC-3-mock or BxPC-3-SMAD4 were suspended in PBS containing 100% Matrigel (Corning Inc., Cat. 354234), and the suspension was inoculated subcutaneously into the axilla of 5 week-old female BALB/c-nu mice (CAnN. Cg-Foxn1nu/CrlCrlj, purchased from CHARLES RIVER LABORATORIES JAPAN, INC). Grouping was performed based on tumor volume 6 days after the inoculation of BxPC-3-mock, and grouping of BxPC-3-SMAD4 was performed 3 days after the inoculation, respectively, the human chimeric anti-human CD147 antibody LN22R8chIgG2 or LN22R8chIgG4P was administered intraperitoneally to cancer-bearing mice at 10 mg/kg on the day, and 7, 14, 21, 28 days after the grouping (n=5). The major axis and the minor axis of the inoculated tumor were measured twice a week using an electronic digital caliper (available from MITUTOYO CORPORATION) to calculate the tumor volume by the following formula.

$$\text{Tumor volume } (mm^3)=1/2\times\text{minor axis}(mm)\times\text{minor axis}(mm)\times\text{major axis}(mm)$$

FIG. 25(*b*) and FIG. 25(*c*) show the results. The graphs also show the averages and the standard errors of changes in tumor volume. The BxPC-3-mock tumor was resistant or exhibited low sensitivity to the LN22R8chIgG2 or LN22R8chIgG4P antibody. The BxPC-3-SMAD4 tumor exhibited a partial sensitivity to the LN22R8chIgG2 or LN22R8chIgG4P antibody.

13)-4 Intratumoral Changes in p38 Signal Due to SMAD4 Expression

It has been reported that the p38 signal is enhanced by expressing SMAD4 in SMAD4-negative pancreatic cancer cells (Chen et al., B. M. C., 1471-2407, 2014). Changes in p38MAPK and phosphorylated p38MAPK in the BxPC-3-SMAD4 tumor due to the administration of the anti-human CD147 human chimeric antibody (72 hours after the administration of the antibody) were analyzed using Simple Western assays (ProteinSimple Japan K.K., Wes) in the same manner as in Example 13)-1. In the same manner as in Example 1)-18, LN22R8chIgG4P as the anti-human CD147 human chimeric antibody was administered to mice bearing a MIA PaCa-2 subcutaneous tumor at 10 mg/kg. For sample preparation (n=3) from tumor tissues, a gentleMACS Octo Dissociator with Heaters (Miltenyi Biotec K.K.) was used.

Figure 26A:
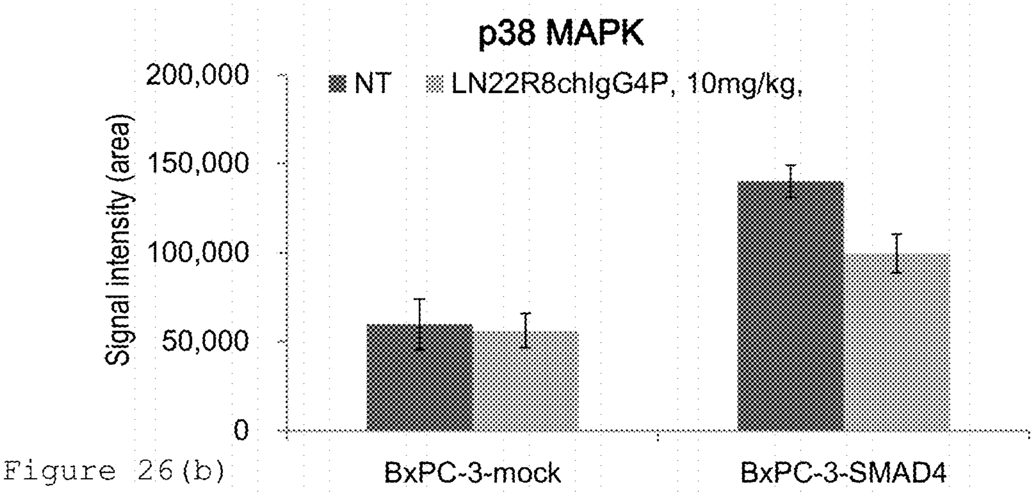
FIGS. 26(*a*) and (*b*) show p38MAPK phosphorylation by an anti-CD147 human chimeric antibody in a subcutaneous implantation model with pancreatic cancer cells BxPC-3 expressing SMAD4.
Figure 26B:
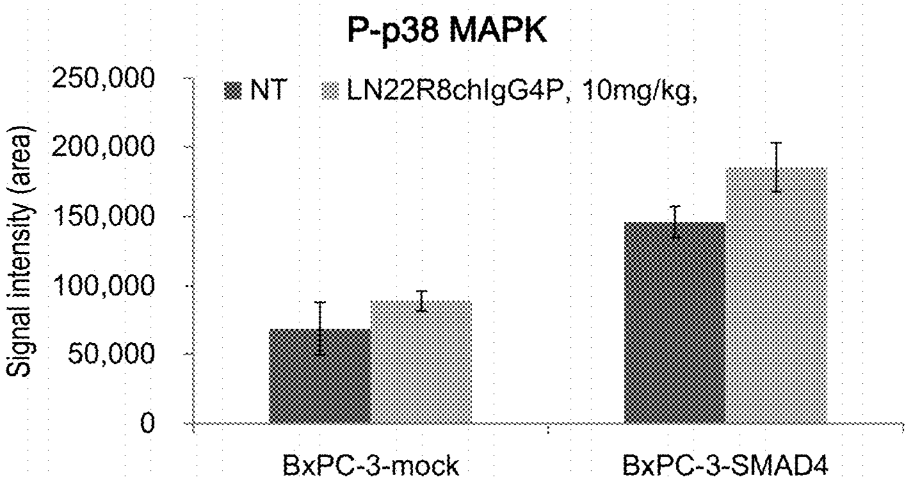

FIG. 26(*a*) shows the averages of the measured values of three tumor samples together with the standard errors of the measured values of p38 MAPK in the form of graphs. FIG. 26(*b*) shows the averages of the measured values of three tumor samples together with the standard errors of the measured values of phosphorylated p38 MAPK in the form of graphs.

In the BxPC-3-SMAD4 tumors, p38 and phosphorylated p38 increased twofold. 72 hours after the administration of the CD147 human chimeric antibody, a partial reduction in p38 and a partial increase in phosphorylated p38 were observed.

It was found that the p38 signal was increased due to SMAD4 expression in the tumors of pancreatic cancer cells BxPC-3. There is a possibility that the increase in the SMAD4-dependent p38 signal contributed to the increase in sensitivity to the CD147 human chimeric antibody LN22R8chIgG4P.

Example 14

Antitumor Efficacy of Chimeric CD147 Antibody in Gemcitabine-Resistant Pancreatic Cancer The antitumor efficacy of the CD147 antibody in a gemcitabine-resistant pancreatic cancer tumor model was investigated. $5\times10^6$ cells of human pancreatic line MIA PaCa-2 were suspended in PBS containing 50% GFR-Matrigel (Corning Inc., Cat. 354230), and the suspension was inoculated subcutaneously into the axilla of 5 week-old female NOD-scid mice (NOD. CB17-Prkdc<scid>/J, CHARLES RIVER LABORATORIES JAPAN, INC). Gemcitabine (Eli Lilly Japan K.K.), which is a standard therapeutic agent for pancreatic cancer, was intraperitoneally administered at 400 mg/kg 6 days after the inoculation, and grouping of mice in which gemcitabine-resistant tumors were confirmed to grow was performed based on tumor size one week later. Gemcitabine was intraperitoneally administered to the control group at 400 mg/kg (n=5) 13 days (grouping date) and 20 days after the inoculation. As a CD147 antibody and gemcitabine combined administration group (n=5), the CD147 human chimeric antibody LN22R8chIgG4P was intraperitoneally administered at 10 mg/kg 13 days (grouping date) and 20 days after the inoculation, in addition to gemcitabine intraperitoneally administered at 400 mg/kg 13 days (grouping date) and 20 days after the inoculation. The major axis and the minor axis of the inoculated tumor were measured twice a week using an electronic digital caliper (available from MITUTOYO CORPORATION) to calculate the tumor volume by the following formula.

$$\text{Tumor volume } (\text{mm}^3)=1/2\times\text{minor axis(mm)}\times\text{minor axis(mm)}\times\text{major axis(mm)}$$

The graph of FIG. 27 showing the results shows the averages and the standard errors of changes in tumor volume. The graph also shows the tumor growth of the non-administered group (non treatment) without administration of gemcitabine and antibody (n=5).

While the average tumor size of the gemcitabine administration group, as the control drug, was 1269 $mm^3$ 28 days after the inoculation, and no regressing tumors were observed, the average tumor size of the group to which the CD147 human chimeric antibody LN22R8chIgG4P was administered in combination was 15 $mm^3$, and tumor regression was observed in 3 out of 5 mice. These results showed that there was a possibility for CD147 antibody sensitivity to be exhibited in growing pancreatic cancer tumors resistant to gemcitabine.

Example 15

Antitumor Efficacy of Humanized CD147 Antibody in a Liver Cancer Model

15)-1 Expression of CD147 and SMAD4 in Hep G2 Cells

CD147 and SMAD4 expression in liver cancer cell line HepG2 cells (ATCC, Cat. HB-8065) was investigated in the same manner as in Example 13)-2. As to the control specimens that were CD147 positive, MIA PaCa-2 and BxPC-3 (ATCC, Cat. CRL-1687) were used. MIA PaCa-2 was used as the control specimen that was SMAD4 positive, and BxPC-3 was used as the control specimen that was SMAD4 negative.

The ratio of the detected signal to GAPDH was determined, and the results are summarized as follows. The Hep G2 cells were found to be CD147 and SMAD4 positive.

Signal Ratio of CD147/GAPDH

| | |
|---|---|
| MIA PaCa-2 | 0.481 |
| BxPC-3 | 0.481 |
| Hep G2 | 2.944 |

Signal Ratio of SMAD4/GAPDH

| | |
|---|---|
| MIA PaCa-2 | 0.329 |
| BxPC-3 | 0.003 |
| Hep G2 | 0.723 |

Figure 28A:
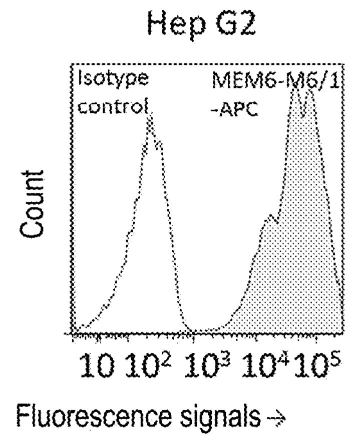
FIG. 28(*a*) shows the confirmation of CD147 expression in Hep G2 cells using a flow cytometer.
Figure 28B:
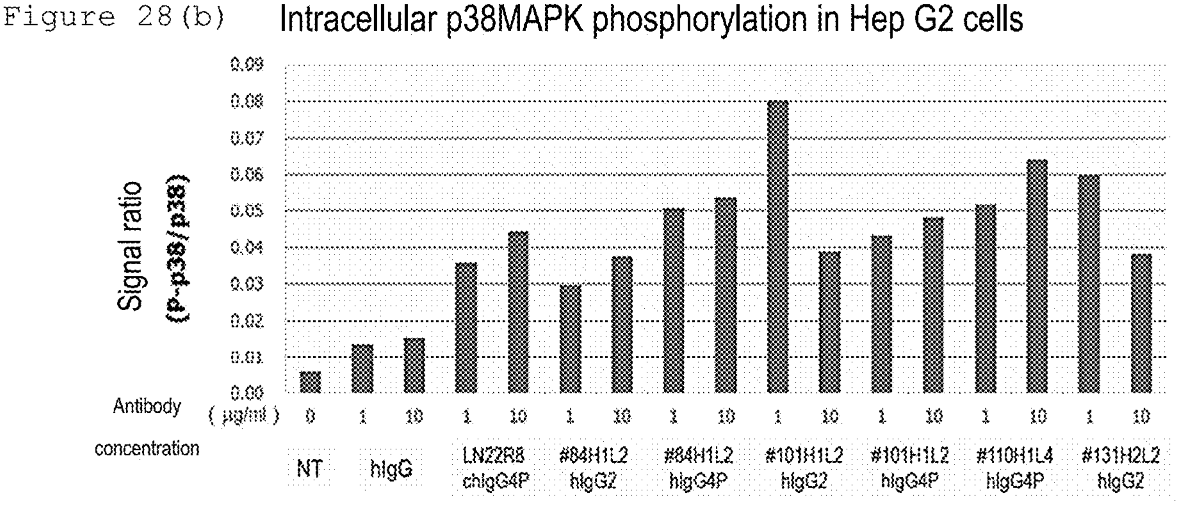
Figure 29A:
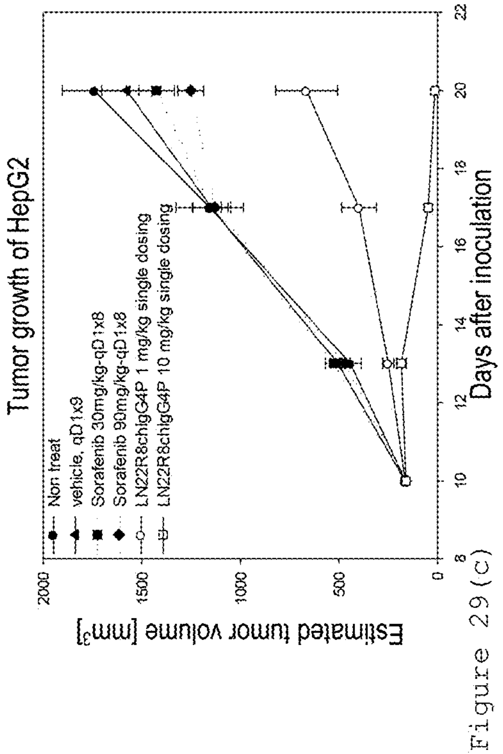
FIGS. 29(*a*) to (*d*) show comparisons of the antitumor efficacy of CD147 antibodies with sorafenib in liver cancer.
Figure 29B:
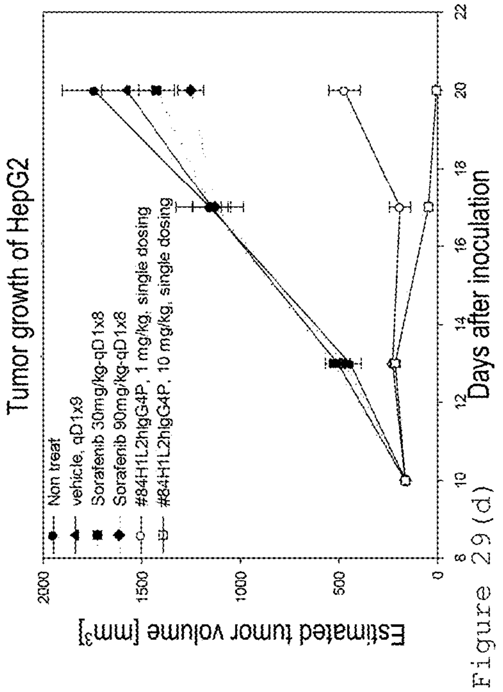
Figure 29C:
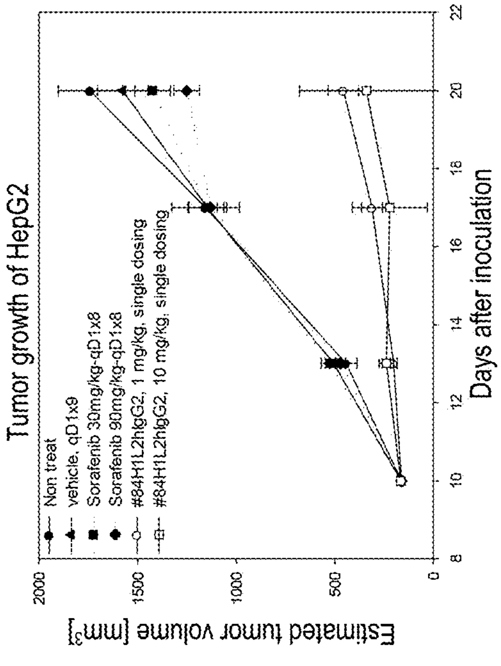
Figure 29D:
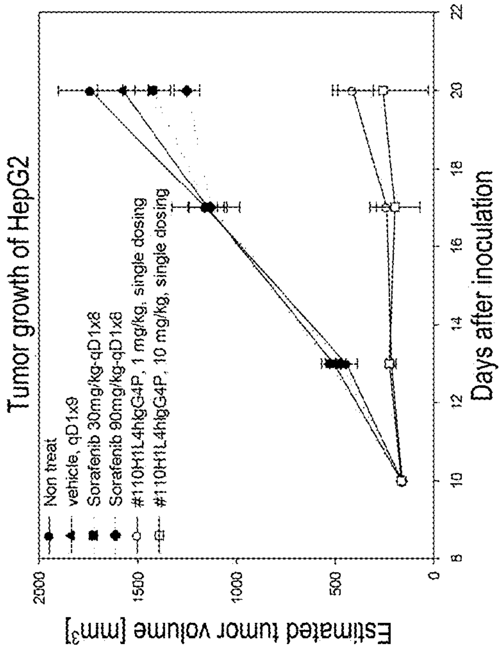

15)-2 Confirmation of Expression of CD147 in Hep G2 Cells Using a Flow Cytometer CD147 expressed on the cell surface of HepG2 cells (ATCC, Cat. HB-8065) was analyzed using a flow cytometer. In order to confirm human CD147 expression, an anti-human CD147 mouse IgG1 antibody MEM-M6/1-APC labeled with APC (Thermofisher, Cat. MA1-10104) was used as a commercially available anti-human CD147 antibody. As a mouse IgG1 Isotype control antibody, mIgG1-APC (Miltenyi Biotec K.K., Cat. 130-092-214) was used. MEM-M6/1-APC was added to a suspension of HepG2 cells in an amount of 1/10, followed by treatment at 4° C. for 30 minutes. The cells were washed with a PBS buffer solution containing 5% FBS, followed by measurement using a flow cytometer (CantoII, BD Biosciences). FIG. 28(*a*) summarizes the results.

It was found that the Hep G2 cells stained with MEM-M6/1-APC exhibited a strong fluorescence signal, thus they expressed CD147.

15)-3 Activation of p38 by Humanized CD147 Antibody in Liver Cancer Cells

In order to investigate the influence of the anti-CD147 antibody on p38MAPK in liver cancer cells HepG2, P38 phosphorylation in HepG2 cells (ATCC, Cat. HB-8065) treated with the anti-human CD147 human chimeric antibody (LN22R8chIgG4P) or the anti-human CD147 humanized antibody (#84H1L2hIgG2, #84H1L2hIgG4P, #101H1L2hIgG2, #101H1L2hIgG4P, #110H1L4hIgG4P, or #131H2L2hIgG2) produced in Example 6)-4-2 at 10 μg/ml for 15 minutes were evaluated using Simple Western assays (ProteinSimple Japan K.K., Wes). As a control sample, HepG2 cells treated with human IgG (hIgG, Jackson ImmunoResearch Inc., 009-000-003) at 10 μg/ml in the same manner were analyzed. For detecting p38MAPK, p38 MAPK rabbit mAb (Cell Signaling Technology, Inc., Cat. #9212) was used. For detecting phosphorylated p38MAPK, P-p38 MAPK (T180/Y182) (D3F9) XP rabbit mAb (Cell Signaling Technology, Inc., #4511S) was used. FIG. 28(*b*) shows the ratio of the phosphorylated p38MAPK signal to the detected p38MAPK signal.

An increase in the phosphorylated p38 MAPK signal twice or more that of the human IgG treated group due to the treatment with LN22R8chIgG4P, #84H1L2hIgG2, #84H1L2hIgG4P, #101H1L2hIgG2, #101H1L2hIgG4P, #110H1L4hIgG4P or #131H2L2hIgG2 was observed, and it was found that p38MAPK phosphorylation was induced by the anti-human CD147 antibody in liver cancer cells, as well as in pancreatic cancer cells.

15)-4 Comparison of Antitumor Efficacy Between Humanized CD147 Antibody and Sorafenib in Liver Cancer The antitumor efficacy of the anti-human CD147 human chimeric antibody and the humanized antibody in a human liver cell line HepG2 (ATCC, Cat. HB-8065) which was CD147 and SMAD4 positive and in which p38 phosphorylation due to the anti-human CD147 antibody was observed were examined.

$5\times10^6$ cells of the human liver cell line HepG2 were suspended in PBS containing 50% Matrigel (Corning Inc., Cat. 354234), and the suspension was inoculated subcutaneously into the axilla of 4 week-old female NOD-scid mice (NOD. CB17-Prkdc<scid>/J, purchased from CHARLES RIVER LABORATORIES JAPAN, INC). Grouping was performed based on tumor volume 9 days after the inoculation, and the human chimeric CD147 antibody (LN22R8chIgG4P) or the humanized CD147 antibody (#84H1L2hIgG2, #84H1L2hIgG4P, or #110H1L4hIgG4P) produced in Example 6)-4-2 was administered intraperitoneally to cancer-bearing mice at 1 mg/kg or 10 mg/kg (n=5). As a control drug, sorafenib (Nexavar tablets 200 mg, Bayer AG), which is a therapeutic agent for liver cancer, was dissolved in a PEG-35 castor oil (Cremophor EL, NACALAI TESQUE, INC., Cat. 09727-14) ethanol solvent according to the reference (Chang et. al., Cancer Chem. Thera. Pharm., 2007) attached to Nexavar tablets, and the solution was orally administered to cancer-bearing mice at 30 mg/kg or 90 mg/kg 9, 10, 11, 12, 13, 16, 17, and 18 days after the inoculation (n=5). The major axis and the minor axis of the inoculated tumor were measured twice a week using an electronic digital caliper (available from MITUTOYO CORPORATION) to calculate the tumor volume by the following formula.

Tumor volume ($mm^3$)=1/2×minor axis(mm)×minor axis(mm)×major axis(mm)

Table 7 and FIGS. 29(*a*) to (*d*) show the results. The graphs also show the averages and the standard errors of changes in tumor volume. As a result of the administration of sorafenib, partial inhibition of tumor growth was observed, but tumor disappearance was not observed. All of LN22R8chIgG4P, #84H1L2hIgG2, #84H1L2hIgG4P, and #110H1L4hIgG4P exhibited potent antitumor efficacy with tumor disappearance.

TABLE 7

| Group configuration/ Administration (n = 5) | Average tumor volume ($mm^3$) | Tumor growth inhibition rate (%) | Number of examples of complete tumor regression |
|---|---|---|---|
| Non-treated | 1740 | 0 | 0/5 |
| Vehicle, qD1x9 po | 1576 | 9 | 0/5 |
| Sorafenib 30 mg/kg, qD1x9 po | 1425 | 18 | 0/5 |
| Sorafenib 90 mg/kg, qD1x9 po | 1252 | 28 | 0/5 |
| LN22R8chIgG4P, 1 mg/kg, Single dose ip | 664 | 62 | 0/5 |
| LN22R8chIgG4P, 10 mg/kg, Single dose ip | 13 | 99 | 2/5 |
| #84H1L2hIgG2, 1 mg/kg, Single dose ip | 456 | 74 | 0/5 |
| #84H1L2hIgG2, 10 mg/kg, Single dose ip | 339 | 81 | 4/5 |
| #84H1L2hIgG4P, 1 mg/kg, Single dose ip | 471 | 73 | 0/5 |
| #84H1L2hIgG4P, 10 mg/kg, Single dose ip | 6 | 100 | 4/5 |
| #110H1L4hIgG4P, 1 mg/kgSingle dose ip | 410 | 76 | 0/5 |
| #110H1L4hIgG4P, 10 mg/kg, Single dose ip | 257 | 85 | 2/5 |

Example 16

Effect on T Cells and PBMC

It has been reported that expression of CD147 increases in CD4 positive and CD8 positive T cells with T cell activation (Hu et al., J. Cell. Mol. Med., 2132-2143, 2010), and some CD147 antibodies have an effect of inducing T cell activation and inhibiting growth (Koch et al., Int. Immunology, 777-786, 1999; Chiampanichayakul et al., Immunology 167-178, 2006). The influence of the anti-human CD147 antibody, exhibiting a potent antitumor efficacy that is independent of an effector function, on peripheral blood lymphocytes (PBL) containing T cells was investigated.

16)-1 Increase in CD147 Expression by CD3/CD28 Stimulation of PBMC

Whether CD147 expression increases with T cell activation was investigated using human PBMC. Human PBMC was cultured in an RPMI1640 medium containing 10% FBS at 37° C. in the presence of 5% $CO_2$. Growth was induced by adding Dynabeads Human T-Activator CD3/CD28 (CD3/CD28 beads, Thermo Fisher SCIENTIFIC K.K., Cat. 1131D) during culture, and analysis was performed using a flow cytometer 4 days later to investigate changes in CD147 expression. In order to confirm human CD147 expression, anti-human CD147 mouse IgG1 antibody MEM-M6/1-APC labeled with APC (CD147-APC, Thermofisher, Cat. MA1-10104) was used as a commercially available anti-human CD147 antibody. As a mouse IgG1 Isotype control antibody, mIgG1-APC (Miltenyi Biotec K.K., Cat. 130-092-214) was used. In order to detect CD3, CD4, and CD8 T cells contained in human PBMC, APC/Fire™ 750 anti-human CD3 Antibody (available from BioLegend, Inc., Cat. 344840), PerCP/Cy5.5 anti-human CD4 (available from BioLegend, Inc., Cat. 344608), and Brilliant Violet 510 anti-human CD8 (available from BioLegend, Inc., Cat. 344732) were used.

FIG. 30 summarizes the results of CD147-APC binding in CD3 and CD4-positive cells and CD3 and CD8-positive cells. In the case where the CD3 and CD4-positive cells and CD3 and CD8-positive cells were stimulated by CD3/CD28 beads, an increase in CD147 expression was confirmed, and an increase in CD147 expression on the membrane surface of T cells with T cell activation was confirmed.

16)-2 Evaluation of the Action of Anti-Human CD147 Antibody on the Growth of Human Peripheral Blood Mononuclear Cells The action of anti-human CD147 antibody on the growth of human peripheral blood mononuclear cells (PBMC) was analyzed. As an anti-human CD147 antibody, 2P10F2chIgG4P was used. After fluorescence labeling of PBMC using a CellVue Claret Far Red Fluorescent Cell Linker Kit (sigma, Cat. MIDCLARET-1KT), cells were cultured in an RPMI1640 medium containing 10% FBS at 37° C. in the presence of 5% $CO_2$. 2P10F2chIgG4P (10 μg/ml) was added during culture when growth was induced by adding IL-2 and Dynabeads Human T-Activator CD3/CD28 (CD3/CD28 beads, Thermo Fisher SCIENTIFIC K.K., Cat. 1131D) to investigate the influence on the growth. PBMC cell fluorescence signals that decreased due to cell division were measured using a flow cytometer (CantoII, BD Biosciences) 3 days and 5 days after the culture. FIG. 31 summarizes the results.

PBMC cell fluorescence signals that decreased due to cell division were observed 3 days and 5 days after the culture because of the addition of CD3/CD28 beads. In the case of adding IL-2, 2P10F2chIgG4P, or IL-2 and 2P10F2chIgG4P during culture, there was no change in the decrease of the fluorescence signals observed. It was suggested that the anti-human CD147 human chimeric antibody 2P10F2chIgG4P that exhibited a potent antitumor efficacy in the mouse tumor model of human pancreatic cancer shown in Example 1)-18 has no influence on the growth of PBMC.

16)-3 Evaluation of Anti-Human CD147 Antibody on Cytokine Production by Human Peripheral Blood Lymphocytes As an anti-human CD147 antibody, the human chimeric antibody #84chIgG1, #84chIgG2, #84chIgG4P, #84chIgG1LALA, #84chIgG4PFALA, #101chIgG4P, or #110chIgG4P was used. PBL was prepared from human peripheral blood using Ficoll-Paque PLUS (GE Healthcare Japan). A 96-well plate was coated with 10 μg/ml of the human chimeric antibody. Human IgG (hIgG, Jackson ImmunoResearch Inc., Cat. 009-000-003) as a negative control antibody and a Dynabeads Human T-Activator CD3/CD28 (CD3/CD28-beads, Thermo Fisher SCIENTIFIC K.K., Cat. 1131D) as a positive control antibody that induces T cell activation and cytokine induction were used. $1\times10^6$ cells of PBL were added to the wells coated with the antibody, and cytokines (IL2, TNFα, and INFγ) in the medium were measured 24 hours later. A Dynabeads Human T-Activator CD3/CD28 was directly added to the wells with PBL added, and cytokines (IL2, TNFα, and INFγ) in the medium were measured 24 hours later in the same manner.

Quantikine ELISA Human IL-2 (R&D systems, Cat. D2050) was used for measuring IL2. Amersham TNF-α Human, Biotrak Easy ELISA (GE Healthcare Japan, Cat. RPN5967) was used for measuring TNFα. A Human IFN-γ ELISA development kit (Mabtech, Cat. 3420-1H-6) was used for measuring INFγ. Each measurement was performed three times, and the averages and the standard deviations of the detected absorbance were calculated. FIG. 32 summarizes the results.

It was confirmed that all cytokines (IL2, TNFα, and INFγ) measured and produced from PBL increased only in culture in the wells with CD3/CD28-beads serving as a positive control added, and cytokines did not increase in culture in the wells coated with any one of the anti-human CD147 human chimeric antibodies, as per hIgG which was serving as a negative control.

Example 17

X-Ray Crystal Structure Analysis of Humanized #110Fab'-CD147 Complex

17)-1 Crystallization of Complex

Humanized #110H1L4hIgG4P was cleaved by Pepsin, and the obtained Fab'2 was reduced with Dithiothreitol, followed by alkylation with Iodoacetamide to obtain a Fab' fragment. A mixture of the Fab' fragment and hCD147v2 (22-205) used in Example 5) was subjected to gel filtration chromatography using a Superdex 10/300GL Increase column (GE Healthcare) to obtain a complex fraction. The complex was replaced with a buffer solution (10 mM Tris HCl pH 7.5, 50 mM NaCl) using AmiconUltra15 MWCO 10K (available from Millipore Corporation) to be concentrated to 13 g/L. The complex solution was crystallized by vapor diffusion. A solution formed by adding an equal amount of a precipitant solution (0.1 M NaMalonate, pH 7.0, 12% (w/v) Polyethylene Glycol 3350) to 0.5 μL of a protein solution was put into a closed container containing 0.05 mL of a precipitant solution so that the two solutions were not in contact with each other, followed by standing at 25° C. A crystal of 0.15 mm×0.15 mm×0.3 mm obtained about one week later was immersed in a precipitant solution with Polyethylene Glycol 400 added to give 30% (w/v), followed by freezing with liquid nitrogen. X-ray diffraction data was collected using beam line PF-BL17A of Photon Factory, High Energy Accelerator Research Organization (KEK) (Ibaraki, Japan). The diffraction intensity was quantified from the diffraction image obtained using the software, mosflm (CCP4: Collaborative Computational Project No. 4) to determine the crystal structure factor. The crystal space group was P21, and the crystal unit cell was (a=64.96 Å, b=93.37 Å, c=98.31 Å, alpha=gamma=90, and beta=90.89).

17)-2 Structural Analysis of Complex

Molecular replacement was performed using the three-dimensional structure coordinate of the obtained structure factor and the homology model of the Fab' fragment, and a known structure of the human CD147 (PDBID: 3b5h) to determine the phase. For calculation, a software phaser (CCP4: Collaborative Computational Project No. 4) was used. The crystal contained two complexes in the asymmetric unit. The structure was refined using the software, Refmac5 (CCP4: Collaborative Computational Project No. 4), and the model was corrected using the software, coot. This operation was repeated to obtain a final R value of 23% and a free R value of 28% with a resolution of 2.3 Å. The final model included two Fab' fragments of humanized #110H1L4, and hCD147v2 binding to each of them. For one hCD147v2, an electronic density corresponding to amino acid residues 23-203 was observed, but for the other, an electronic density corresponding to domain 1 was not clear, and only an electronic density corresponding to amino acid residues 103-202 was observed.

17)-3 Identification of Epitope

Amino acid residues of hCD147v2 that were present within 4 Å from the Fab' fragment binding surface of humanized #110H1L4 in the two complexes contained in the asymmetric unit in common were as follows: Arg106, Lys108, Ala109, Val110, Lys127, Ser128, Glu129, Ser130, Val131, Pro132, Pro133, Val134, Gln164, and Gly165. FIG. 41 shows the ribbon model and the entire surface of the complexes, and FIG. 42 shows the interaction between hCD147v2 and humanized #110H1L4.

Example 18

Antitumor Effect of Humanized CD147 Antibody in a Gastric Cancer Model

The antitumor efficacy of the anti-human CD147 human chimeric antibody and the humanized antibody on human gastric cancer cell line KATO III cells (ATCC, Cat. HTB-103) confirmed to be CD147 positive by a flow cytometer were evaluated.

$5\times10^6$ cells of human gastric cancer cell line KATO III were suspended in 100% Matrigel (Corning Inc., Cat. 354234), and the suspension was inoculated subcutaneously into the axilla of 5-week old female NOD-scid mice (NOD. CB17-Prkdc<scid>/J, purchased from CLEA Japan, Inc). Grouping was performed based on tumor volume 3 days after the inoculation, and the human chimeric CD147 antibody (LN22R8chIgG4P) or the humanized CD147 antibody (#110H1L4hIgG4P) produced in Example 6)-4-2 was administered intraperitoneally to cancer-bearing mice at 10 mg/kg every 7 days after the grouping (n=6). The major axis and the minor axis of the inoculated tumor were measured twice a week using an electronic digital caliper (available from MITUTOYO CORPORATION) to calculate the tumor volume by the following formula.

$$\text{Tumor volume } (mm^3)=1/2\times\text{minor axis}(mm)\times\text{minor axis}(mm)\times\text{major axis}(mm)$$

FIG. 43 shows the results. The graphs also show the averages and the standard errors of changes in tumor volume. While the average tumor volume of the mice 24 days after the inoculation was 290 $mm^3$ in the untreated group, it was 199 $mm^3$ in the LN22R8chIgG4p administration group and 134 $mm^3$ in the #110H1L4hIgG4P administration group. The calculated antitumor efficacy was 31% in the LN22R8chIgG4p administration group and 54% in the #110H1L4hIgG4P administration group.

Example 19

Antitumor Effect of Humanized CD147 Antibody in a Chronic Myeloid Leukemia Model The antitumor efficacy of anti-human CD147 humanized antibody on human chronic myeloid leukemia cell line KU812 cells (ATCC, Cat. CRL-2099) confirmed to be CD147 positive by a flow cytometer was examined.

$5\times10^6$ cells of chronic myeloid leukemia cell line KU812 were suspended in PBS containing 50% Matrigel (Corning Inc., Cat. 354234), and the suspension was inoculated subcutaneously into the axilla of 5-week old female NOD-scid mice (NOD. CB17-Prkdc<scid>/J, purchased from CLEA Japan, Inc). Grouping was performed based on tumor volume 3 days after the inoculation, and the humanized CD147 antibody (#110H1L4hIgG4P) produced in Example 6)-4-2 was administered intraperitoneally to mice bearing tumor at 10 mg/kg every 7 days after the grouping (n=5). As a control drug, imatinib (AstaTech, Inc., Cat. #63168), which is a standard therapeutic agent for chronic myeloid leukemia, adjusted with distilled water to a 9 mg/ml solution was orally administered to cancer-bearing mice at 90 mg/kg (daily administration except Saturdays and Sundays; administration 4, 7, 8, 9, 10, 11, 14, 15, 16, 17, 18, 21, 22, 23, 24 days after the inoculation). The major axis and the minor axis of the inoculated tumor were measured twice a week using an electronic digital caliper (available from MITUTOYO CORPORATION) to calculate the tumor volume by the following formula.

Tumor volume ($mm^3$)=1/2×minor axis(mm)×minor axis(mm)×major axis(mm)

FIG. 44 shows the results. The graph shows the averages and the standard errors of changes in tumor volume. While the average tumor volume of the mice in the untreated group was 627 $mm^3$ 25 days after the inoculation, it was 328 $mm^3$ in the imatinib administration group and 6 $mm^3$ in the #110H1L4hIgG4P administration group. The calculated antitumor efficacy was 48% in the imatinib administration group and 97% in the #110H1L4hIgG4P administration group. In the #110H1L4hIgG4P administration group alone, complete tumor regression was observed in 4 examples out of 5 examples.

Example 20

Antitumor Effect of Humanized CD147 Antibody in a Colon Cancer Model

The antitumor efficacy of each humanized antibody on human colon cancer cell line SW620 cells (ATCC, Cat. CCL-227) confirmed to be CD147 positive by a flow cytometer was evaluated.

5×$10^6$ cells of human colon cancer cell line SW620 were suspended in 100% Matrigel (Corning Inc., Cat. 354234), and the suspension was inoculated subcutaneously into the axilla of 5-week old female NOD-scid mice (NOD. CB17-Prkdc<scid>/J, purchased from CLEA Japan, Inc). Grouping was performed based on tumor volume 3 days after the inoculation, and the human chimeric CD147 antibody (LN22R8chIgG4P) or the humanized CD147 antibody (#084H1L2hIgG4P or #110H1L4hIgG4P) produced in Example 6)-4-2 was administered intraperitoneally to cancer-bearing mice at 10 mg/kg every 7 days after the grouping (n=5). The major axis and the minor axis of the inoculated tumor were measured twice a week using an electronic digital caliper (available from MITUTOYO CORPORATION) to calculate the tumor volume by the following formula.

Tumor volume ($mm^3$)=1/2×minor axis(mm)×minor axis(mm)×major axis(mm)

FIG. 45 shows the results. The graph shows the averages and the standard errors of changes in tumor volume. While the average tumor volume of the mice in the untreated group 21 days after the inoculation was 1302 $mm^3$, it was 709 $mm^3$ in the #084H1L2hIgG4P administration group and 403 $mm^3$ in the #110H1L4hIgG4P administration group. The calculated antitumor efficacy was 46% in the #084H1L2hIgG4P administration group and 69% in the #110H1L4hIgG4P administration group.

Example 21

Antitumor Efficacy of Humanized CD147 Antibody in the Renal Cancer 786-O Model The antitumor efficacy of each humanized antibody on human renal cancer 786-O confirmed to be CD147 positive by a flow cytometer was evaluated. 5×$10^6$ cells of human renal cancer 786-O were suspended in 50% Matrigel (Corning Inc., Cat. 354234), and the suspension was inoculated subcutaneously into the axilla of 5-week old female NOD-scid mice (NOD. CB17-Prkdc<scid>/J, purchased from CLEA Japan, Inc). Grouping was performed based on tumor volume 3 days after the inoculation, and the human chimeric CD147 antibody (LN22R8chIgG4P) or the humanized CD147 antibody (#084H1L2hIgG4P or #110H1L4hIgG4P) produced in Example 6)-4-2 was administered intraperitoneally to cancer-bearing mice at 10 mg/kg every 7 days after the grouping a total of 4 times (n=6). The major axis and the minor axis of the inoculated tumor were measured twice a week using an electronic digital caliper (available from MITUTOYO CORPORATION) to calculate the tumor volume by the following formula.

Tumor volume ($mm^3$)=1/2×minor axis(mm)×minor axis(mm)×major axis(mm)

FIG. 46 shows the results. The graph shows the averages and the standard errors of changes in tumor volume. While the average tumor volume of the mice in the untreated group 31 days after the inoculation was 918 $mm^3$, it was 224 $mm^3$ in the #084H1L2hIgG4P administration group and 379 $mm^3$ in the #110H1L4hIgG4P administration group. The calculated antitumor efficacy was 76% in the #084H1L2hIgG4P administration group and 59% in the #110H1L4hIgG4P administration group.

Example 22

Antitumor Effect of Humanized CD147 Antibody in an Acute Myeloid Leukemia (AML) Model The antitumor efficacy of the humanized antibody on human AML cell line OCI-AML3 cells (DSMZ, Cat. ACC 582) confirmed to be CD147 positive by a flow cytometer was evaluated.

5×$10^6$ cells of human AML cell line OCI-AML3 cell were suspended in 50% GFR-Matrigel (Corning Inc., Cat. 354230), and the suspension was inoculated subcutaneously into the axilla of 5-week old female NOD-scid mice (NOD. CB17-Prkdc<scid>/J, purchased from CLEA Japan, Inc). Grouping was performed based on tumor volume 3 days after the inoculation, and the humanized CD147 antibody (#110H1L4hIgG4P) produced in Example 6)-4-2 was administered via a tail vein injection to mice bearing tumor at 10 mg/kg every 7 days after the grouping (n=6). The major axis and the minor axis of the inoculated tumor were measured twice a week using an electronic digital caliper (available from MITUTOYO CORPORATION) to calculate the tumor volume by the following formula.

Tumor volume ($mm^3$)=1/2×minor axis(mm)×minor axis(mm)×major axis(mm)

FIG. 47 shows the results. The graph shows the averages and the standard errors of changes in tumor volume. While the average tumor volume of the mice in the untreated group 21 days after the inoculation was 1533 $mm^3$, it was 394 $mm^3$ in the #110H1L4hIgG4P administration group. The calculated antitumor efficacy was 74% in the #110H1L4hIgG4P administration group.

Example 23

Measurement of Efficacies of Humanized Anti-CD147 Antibodies Having Different Binding Activities $5\times10^6$ cells of human pancreatic line MIA PaCa-2 were suspended in PBS containing 50% GFR-Matrigel (Corning Inc., Cat. 354230), and the suspension was inoculated subcutaneously into the axilla of 4-week old female Nude mice (BALB/c Slc-nu/nu, purchased from Japan SLC, Inc). Grouping was performed based on tumor volume, and three types of humanized CD147 antibodies (#110H1L4hIgG4P, #110H13L02hIgG4P, and #110H13L12hIgG4P; Table 6 shows their binding activities) having different binding activities to the CD147 protein produced in Example 6)-4-2 were each administered to mice bearing tumor via the tail vein at 10 mg/kg 7 days after the inoculation (n=6). As a control drug, gemcitabine (purchased from Eli Lilly Japan K.K.), which is a standard therapeutic agent for pancreatic cancer, was administered to cancer-bearing mice via the tail vein at 400 mg/kg 3 and 10 days after the inoculation (n=6). The major axis and the minor axis of the inoculated tumor were measured twice a week using an electronic digital caliper (available from MITUTOYO CORPORATION) to calculate the tumor volume by the following formula.

$$\text{Tumor volume } (mm^3)=1/2\times\text{minor axis(mm)}\times\text{minor axis(mm)}\times\text{major axis(mm)}$$

FIG. 48 shows the results. The graph shows the averages and the standard errors of changes in tumor volume.

While the tumor growth inhibition rate of gemcitabine as a control drug was 66%, all the humanized CD147 antibodies exhibited a more potent antitumor efficacy in the 10 mg/kg administration group than gemcitabine.

Example 24

Comparison of CD147 Antibodies

24)-1 Evaluation of Binding Activity of Existing Anti-CD147 Antibodies to Antigen Purified antibodies were prepared based on the sequences of 4A5, 5F6 of WO2010/036460 and PPAT-082-03 of WO2017/061602. The dissociation constant for binding of 4A5, 5F6 or PPAT-082-03 to the CD147 protein was measured using a Biacore T200 (available from GE Healthcare Bioscience). Anti-Human IgG (Fc) antibody was immobilized on a sensor chip by using a Human Antibody Capture Kit (available from GE Healthcare Bioscience) followed by capturing human chimeric antibody as a ligand and associating an antigen as an analyte. HBS-EP+ (available from GE Healthcare Bioscience) as a running buffer and CM5 (available from GE Healthcare Bioscience) as a sensor chip were used. After 1 μg/mL of a competitive antibody was added onto the chip at 10 μL/minute over 60 seconds, a serial dilution of the antigen used in Example 5 (0.5 to 8 μg/mL) was added thereto at a flow rate of 30 μL/minute over 120 seconds, followed by subsequent monitoring for a dissociation phase of 300 seconds. 3M magnesium chloride (available from GE Healthcare Bioscience) as a regenerating solution was added thereto at a flow rate of 20 μL/minute over 30 seconds. The binding rate constant ka, the dissociation rate constant kd, and the dissociation constant (KD; KD=kd/ka) were calculated using a 1:1 binding model for analyzing data. The dissociation constant for binding of the humanized CD147 antibody (#084H1L2hIgG4P or #110H1L4hIgG4P) to CD147 protein was calculated by the method of Example 7)-1.

Table 8 shows information on the calculated dissociation constant, the effector function, and the epitope region.

TABLE 8

| Antibody | Antibody format | KD (nM) | Effector function | Epitope region |
|---|---|---|---|---|
| #110H1L4h | Human IgG4P | 8.60 | ADCC(−) CDC(−) ADCP(±) | Arg106 to Gly165 of SEQ ID NO: 3 (variant 2 of human CD147) |
| #084H1L2h | Human IgG4P | 242 | ADCC(−) CDC(−) ADCP(+) | In the vicinity from Asp65 to Gln81 of SEQ ID NO: 3 (variant 2 of human CD147) |
| 4A5 | Mouse IgG2a | 132 | ADCC(+) CDC(+) ADCP(+) | Competing with #084H1L2h |
| 5F6 | Human IgG1 | 71.9 | ADCC(+) CDC(−) ADCP(+) | Competing with #084H1L2h |
| PPAT-082-03 | Human IgG1 | 33.2 | ADCC(+) CDC(−) ADCP(+) | Competing with #084H1L2h |

24)-2 Competitive ELISA with Existing CD147 Antibody

Using humanized CD147 antibody (#084H1L2hIgG4P or #110H1L4hIgG4P) produced in Example 6)-4-2, the binding activity to Recombinant Human CD147/Fc (Sino Biological Inc., Cat. 10186-H02H) was evaluated by competitive ELISA. As competitive antibodies, 4A5 and 5F6 antibodies prepared in 24)-1 and PPAT-082-03 antibody were used. As a competition negative control antibody, human IgG (Jackson ImmunoResearch Inc., Cat. 130093) was used. As a competition positive control antibody, the #84H1L2hIgG2 antibody was used with respect to the #084H1L2hIgG4P antibody and the #110chIgG2 antibody was used with respect to #110H1L4hIgG4P.

Recombinant Human CD147/Fc diluted with PBS at 2 μg/ml was added to a 96-well plate (Thermo Scientific, Cat. 43454) at 50 μl/well, followed by overnight storage at 4° C. After removing the protein solution, 300 μl of PBS containing 1% BSA was added thereto, followed by heating at room temperature for one hour. After removing the solution, 25 μl of an existing antibody solution (0, 0.2, 2, or 20 μg/ml) was added thereto, followed by heating at room temperature for two hours. 25 μl of the humanized CD147 antibody (#084H1L2hIgG4P or #110H1L4hIgG4P) at a concentration of 20 ng/ml was added to each well, followed by heating at room temperature for two hours. After washing with PBS containing 0.05% Tween20 (Bio-Rad Laboratories, Inc., Cat. 170-6531) twice, 50 μl of anti-human IgG4-HRP (Abcam plc., Cat.ab99823) diluted 2000 times with PBS containing 1% BSA was added thereto, followed by heating at room temperature for one hour. After washing with PBS containing 0.05% Tween20 (Bio-Rad Laboratories, Inc., Cat. 170-6531) three times, the washing solution was sufficiently drained, and 50 μl of an HRP substrate solution (eBioscience, Thermo Fisher SCIENTIFIC K.K., Cat.00-4203-58) was added thereto, followed by heating at room temperature for 15 to 20 minutes. Thereafter, the absorbance at 405 nm was measured using a plate reader (model name: EnVision2104, available from PerkinElmer, Inc).

Figure 49A:
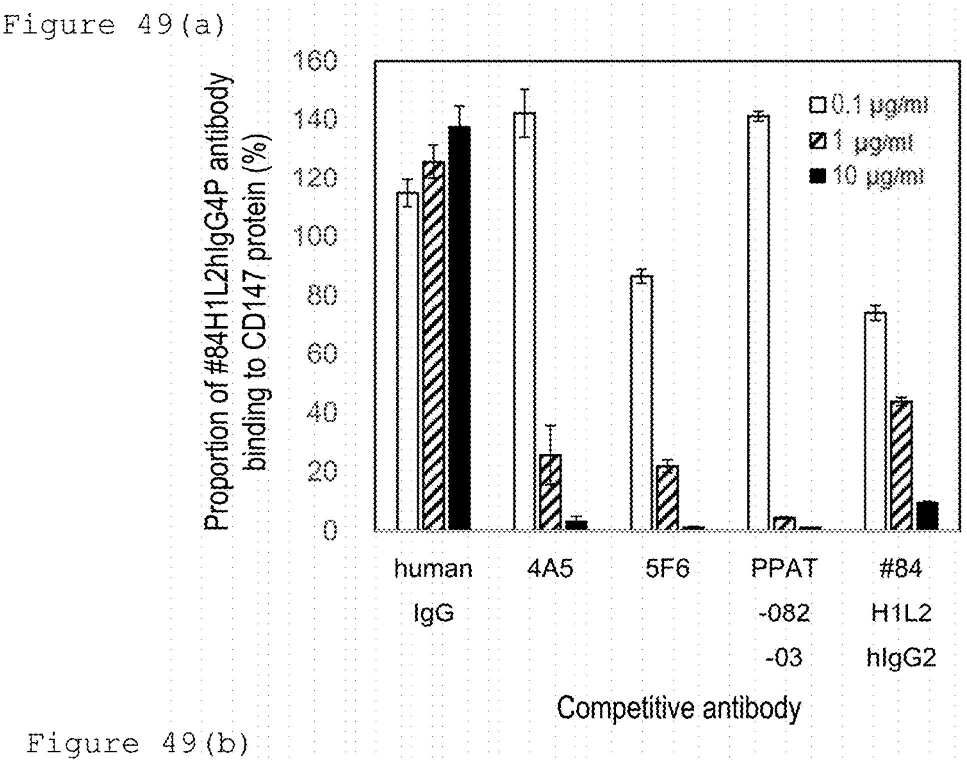
FIG. 49 shows the results of competitive ELISA.
Figure 49B:
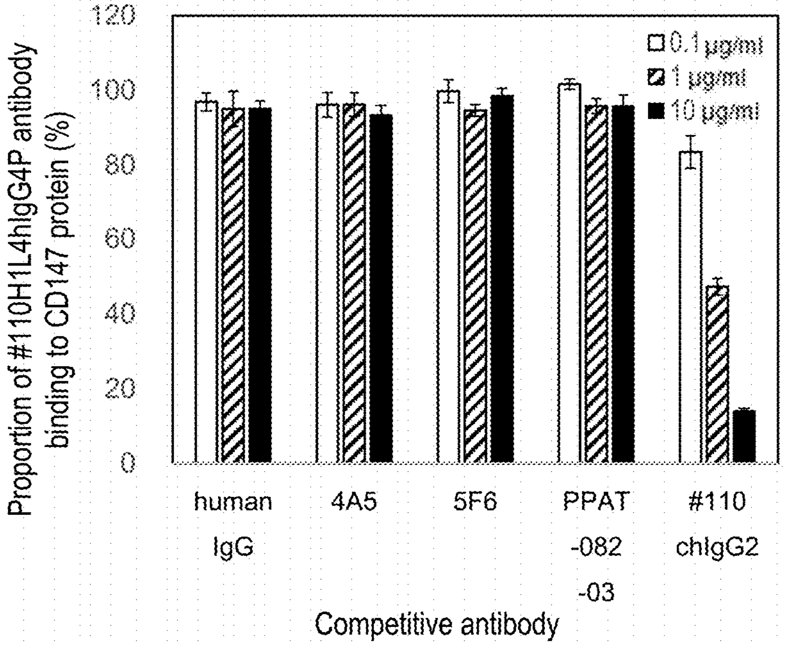

Table 8 and FIGS. 49(*a*) and (*b*) show the results.

The binding of #084H1L2hIgG4P to Recombinant Human CD147/Fc was inhibited by the presence of an existing CD147 antibody at 1 to 10 μg/ml in the presence of hIgG. The binding of #110H1L4hIgG4P to Recombinant Human CD147/Fc was not inhibited by the presence of an existing CD147 antibody at 0.1 to 10 μg/ml in the presence of hIgG but was inhibited by the presence of #110chIgG2 antibody. It was found that the epitope of #084H1L2hIgG4P competed with the binding of the existing anti-CD147 antibody, but the epitope of #110H1L4hIgG4P was not affected by the binding of the existing anti-CD147 antibody. Table 8 shows the epitope information of the H110H1L4h antibody represented by Example 17)-3. The epitope region of #084H1L2h was estimated from the test results of the competitive binding (Example 2)-8) with the 2P10F2 antibody, the epitope of which was estimated by analysis using CD147 mutants of Example 1)-9. Table 8 shows the results.

24)-3 Evaluation of ADCC of Anti-CD147 Antibodies

According to the method of Example 1)-15, the ADCC activity of anti-CD147 antibody was evaluated. Different conditions from those in the method of Example 1)-15 included, evaluation being performed using HepG2 cells (ATCC, Cat. HB-8065) as ADCC target cells and #110H1L4hIgG4P, #084H1L2hIgG4P, 4A5, 5F6, and PPAT-082-03 being used as CD147 antibodies at a concentration of 1 μg/ml. The measurement was performed in triplicate, and the averages and the standard deviations were calculated. In the case where $^{51}Cr$ was detected in 5% or more of the cells, the ADCC was determined to be positive (+). In the case of less than 5%, the ADCC activity was determined to be negative (−). Table 8 shows the results.

The ADCC activity was not detected in #110H1L4hIgG4P and #084H1L2hIgG4P, and thus ADCC was determined to be (−). In 4A5, 5F6, and PPAT-082-03, $^{51}Cr$ was detected in 5% or more of cells, and thus ADCC was determined to be positive (+). #110H1L4hIgG4P and #084H1L2hIgG4P were negative for ADCC and so are expected to induce potentially a lower level of cell death of normal cells, such as blood cells expressing CD147, in the human body than 4A5, 5F6, and PPAT-082-03, which were positive for ADCC activity.

24)-4 Evaluation of CDC of Anti-CD147 Antibodies

According to the method of Example 1)-16, the complement-dependent cell killing activity (CDC activity) by anti-human CD147 antibody was evaluated. Different conditions from those in the method of Example 1)-16 included, measurement being performed by using human liver cell line HepG2 cells (ATCC, Cat. HB-8065) as target cells and #110H1L4hIgG4P, #084H1L2hIgG4P, 4A5, 5F6, and PPAT-082-03 as anti-human CD147 antibodies and adding a rabbit complement to a final concentration of 10%. The measurement was performed in triplicate, and the averages and the standard deviations were calculated. Antibodies in which 30% or more of antibody-dependent CDC activity was observed were determined to have a positive CDC activity and were shown as CDC (+) in the table. Table 8 shows the results. Only 4A5 out of the anti-human CD147 antibodies exhibited a positive CDC activity. #110H1L4hIgG4P, #084H1L2hIgG4P, 5F6, and PPAT-082-03 were negative for CDC and are expected to induce potentially a lower level of cell death of normal cells, such as blood cells expressing CD147, in the human body than 4A5, which had a positive CDC activity.

24)-5 Evaluation of ADCP of Anti-CD147 Antibodies

According to the method of Example 1)-17, the ADCP activity of anti-CD147 antibody was measured. Different conditions from those in the method of Example 1)-17 included, the ADCP activity being measured by using human liver cell line HepG2 cells (ATCC, Cat. HB-8065) as target cells and adding #110H1L4hIgG4P, #084H1L2hIgG4P, 4A5, 5F6, and PPAT-082-03 as anti-CD147 antibodies at a concentration of 1 μg/ml and an equal amount of labeled RAW264.7 cells to ADCP target cells. The measurement was performed in triplicate, and the averages and the standard deviations were calculated. An increase in ADCP activity of less than 10% of the human IgG treated group was determined to be slightly positive (±), and an increase in activity of 10% or more was determined to be positive (+). Table 8 shows the results.

#110H1L4hIgG4P had an ADCP activity of less than 10%, and the ADCP activity was determined to be ±. #084H1L2hIgG4P, 4A5, 5F6, and PPAT-082-03 antibodies had an ADCP activity of 10% or more, and the ADCP activity was determined to be +. #110H1L4hIgG4P that recognizes CD147-D2 had a lower ADCP activity than other CD147 antibodies that recognize CD147-D1. After CD147 antibody is bound to CD147, the FC portion of the antibody needs to be recognized by Fcγ receptor expressed on macrophages or mononuclear cells for ADCP. However, there is a possibility that the ADCP activity is low because the epitope of the #110 antibody is close to the surface of the cells, and it is more difficult for Fcγ receptor to recognize the FC portion of the antibody bound to CD147 serving as an antigen than other antibodies that recognize CD147-D1. It is expected that #110H1L4hIgG4P having a slightly positive ADCP activity is less likely to induce cell death of normal cells, such as blood cells expressing CD147, in the human body than #084H1L2hIgG4P, 4A5, 5F6, and PPAT-082-03, which have a positive ADCP activity.

Example 25

25)-1 Blood System Cell Aggregation by Anti-CD147 Antibody

It has been reported that some anti-CD147 antibodies induce aggregation of blood cells (Kasinrerk, et al., Immunology 1999, 96 (2) p184-192). Aggregation of blood cells could potentially cause a serious blood toxicity (Doll, C., et al., 1994, Curr. Opin. Oncol., 345-350) and is a property that is not desirable for a therapeutic antibody. Differences in cell aggregation activity between anti-CD147 antibodies were investigated. As CD147 antibodies, #110H1L4hIgG4P, #084H1L2hIgG4P, 4A5, 5F6, and PPAT-082-03 were evaluated. As a negative control antibody, human IgG (hIgG, ChromPure Human IgG, Jackson ImmunoResearch Laboratories, Inc., Cat. 009-000-003) was used. HEL92.1.7 cells (purchased from ATCC, Cat. #TIB-180) with RPMI1640 medium (Thermo Fisher SCIENTIFIC K.K., Cat. 11875-093) containing 10% FBS (HyClone, GE Healthcare, Cat. SH30084.03) were added to a 96-well U bottom plate (Sumitomo Bakelite Co., Ltd., Cat. MS-9096U) at 1600 cells/80 μl per well, followed by culture for 4 hours under conditions of 5% $CO_2$, a humidity of 95%, and 37° C. 20 μl of an anti-CD147 antibody solution (150 μg/ml, 50 μg/ml) was added to each well to a final concentration of 30 or 10 μg/ml. After culture for 2 days under conditions of 5% $CO_2$, a humidity of 95%, and 37° C., microscopic observation was conducted.

While cell aggregation due to the addition of human IgG or #110H1L4hIgG4P was not observed, cells aggregated in the presence of #084H1L2hIgG4P, 4A5, 5F6, or PPAT-082-03 antibody, and cell masses overlapping at the center of the plate were observed. It was revealed that #110H1L4hIgG4P that recognizes CD147-D2 has no blood cell aggregation activity and so was different from other CD147 antibodies that recognize the CD147-D1 domain. Since CD147 antibodies including #084 that have a cell aggregation activity may potentially cause toxicity such as a thrombus via aggregation of blood cells when administered to humans, it is desirable to avoid or reduce such side effects by the combined use of a subcutaneous injection of heparin at a dose used for treating a thrombus or low-molecular weight heparin or anti-platelet drugs.

25)-2 Evaluation of the Risk of Cytokine Release Syndrome

In some antibodies such as OKT3 and TGN1412, administration of the therapeutic antibodies causes an increase in cytokines in the blood by activating immune cells, thereby causing serious cytokine release syndrome (Gaston, R., Kidney International, 1991, 141-148; Suntharalingam, G., et al., N. Engl. J. Med. 2006, 1018-1028). It has been reported that some CD147 antibodies act on immune cells, having an action of increasing production of interferon gamma or interleukin-4 (Hu, J., et al., J. Cell. Mol. Med., 2010, 2132-2143). The toxicity of antibody drugs due to cytokine release syndrome can be predicted by a cytokine release assay using peripheral blood (Vessillier, S. et al., J. Immunolol. Methods, 2015, 43-52). Thus, the risk of cytokine release syndrome was evaluated by a cytokine release assay using human peripheral blood. #110H1L4hIgG4P, #110chIgG4PFALA, #084H1L2hIgG4P, and #084H1L2hIgG2 were used as CD147 antibodies, and bevacizumab (Genentech, Inc.), trastuzumab (Roche Pharma AG), alemtuzumab (Sanofi K.K.), and anti-human CD3 antibody (BioLegend Cat. No 317326) were used as comparative antibodies. For all evaluated CD147 antibodies, acceleration of cell growth was not observed in human peripheral blood mononuclear cells (6 donors were evaluated for each), and the influence on cytokine release (TNFα, INF-γ, IL-2, IL-6, IL-8, IL-10, and MIP-1α) was less than in bevacizumab, which has a low risk of cytokine release syndrome. For anti-human CD3 antibody (OKT3), acceleration of cell growth and acceleration of cytokine release (TNFα, INF-γ, IL-2, IL-6, IL-8, IL-10, and MIP-1α) were observed. It was demonstrated that #110H1L4hIgG4P, #110chIgG4PFALA, #084H1L2hIgG4P, and #084H1L2hIgG2 do not induce cytokine release that could potentially cause cytokine release syndrome.

25)-3 Evaluation of the Safety of Anti-CD147 Antibody in Monkeys

It has been reported that some mouse anti-CD147 antibodies, when administered to mice, inhibit the functions of CD147, induce aggregation of red blood cells in the spleen, and reduce the amount of red blood cells in the peripheral blood, thereby causing anemia (Coste, I. et al., Blood, 2001, 3984-3988). Since the CD147 antibodies obtained in the present invention such as #110H1L4hIgG4P do not exhibit binding to mouse CD147, the safety is not appropriately evaluated in mice. Therefore, the safety was evaluated by administering #110H1L4hIgG4P, which is an anti-CD147 antibody confirmed to have a binding activity to human and monkey CD147 by experiments using a flow cytometer, to cynomolgus monkeys. #110H1L4hIgG4P was intravenously administered to cynomolgus monkeys (one male and one female) at a single dose of 99.2 mg/kg that is the maximum dose. As a result, serious toxicity (changes in body weight and food intake or histopathological changes) was not observed either in the observation period of 15 days from the administration or by histopathological examination at the completion of the observation period. #110H1L4hIgG4P exhibited no toxicity to cynomolgus monkeys, thus indicating that it may be used for human cancer treatment.

Example 26

Influence of KLF5 on Sensitivity to CD147 Antibody

A lethal EMT signal is known as a signal of SMAD2/SMAD3/SMAD4-dependent cell death in cancer cells, and it has been reported that, in SMAD4-negative cancer cells, there is an increased expression of transcription factor KLF5 protein, which is normally reduced by SMAD signaling, and this reduces the lethal EMT signal in SMAD4-negative cancer cells (David, C., Cell, 2016, 1015-1030). Since the CD147 antibody of the present invention activates SMAD signaling and exhibits an antitumor efficacy on SMAD4-positive cells, it was considered to induce a SMAD signal-dependent cell death. Whether KLF5 is involved in the sensitivity to the CD147 antibody-dependent antitumor efficacy was investigated.

26)-1 Production of KLF5 Expressing Cell Line

According to the method of Example 13, KLF5 stably expressing cell line MIA PaCa-2 cells were produced. SEQ ID NOs: 145 and 146 respectively represent the amino acid sequence and the nucleotide sequence of human KLF5. A retroviral vector pQCXIP with a sequence (Ref seq. ID: NM_001730.4) of the KLF5 gene contained in it (GenScript Biotech Corporation, Cat. OHu21278C) was produced and the retroviral vector was used for the production of the retrovirus. The retrovirus was incorporated into a chromosome by viral infection, and MIA PaCa-2 cells that became resistant to puromycin and positive for KLF5 were selected to form KLF5 positive MIA PaCa-2 cells, MIA PaCa-2-KLF5. A retroviral vector pQCXIP was infected in the same manner to form puromycin resistant MIA PaCa-2 cells, MIA PaCa-2-mock.

26)-2 Confirmation of KLF5 Expression

KLF5 expressions of MIA PaCa-2-mock and MIA PaCa-2-KLF5 were confirmed using a flow cytometer. According to the method of Example 13-2, it was confirmed that the KLF5 expression level in MIA PaCa-2-KLF5 increased from that in MIA PaCa-2-mock. For detecting KLF5, a KLF5 antibody (Cell Signaling Technology, Inc., Cat. #51586) was used.

Figure 50A:
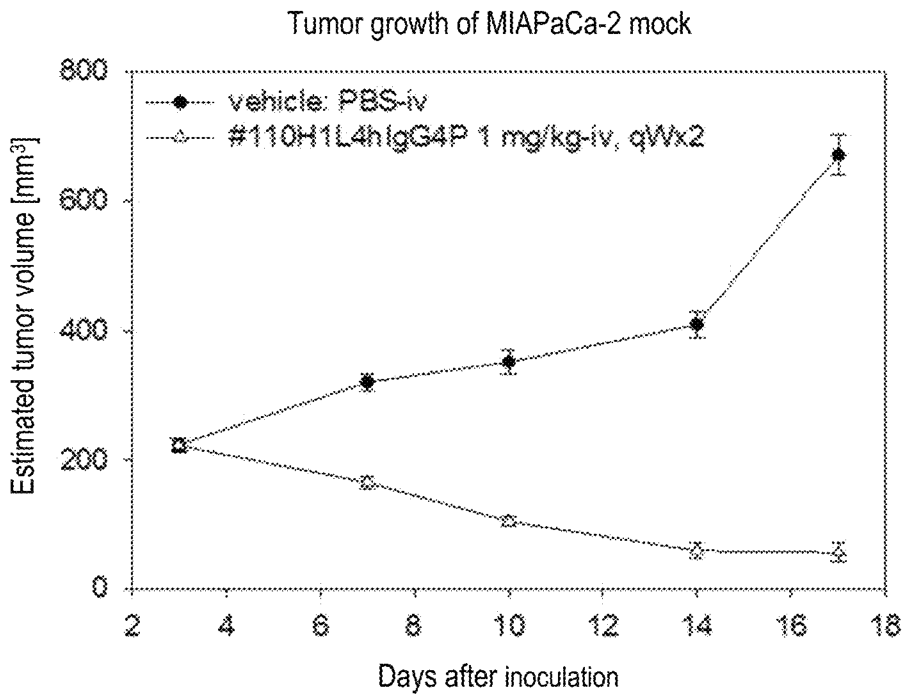
FIG. 50(*a*) shows the antitumor efficacy of a humanized CD147 antibody using MIA PaCa-2 cells, and FIG. 50(*b*) shows the antitumor efficacy of the humanized CD147 antibody using MIA PaCa-2 cells expressing KLF5 for comparison.
Figure 50B:
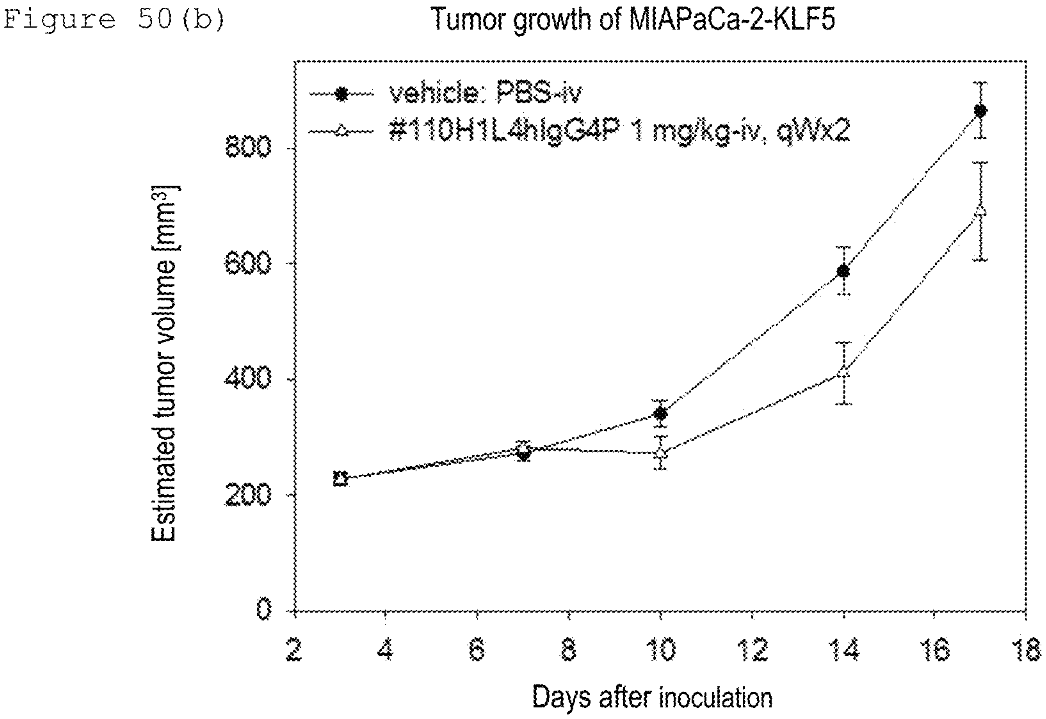

26)-3 Sensitivity of MIA PaCa-2 Tumor Expressing KLF5 to Humanized CD147 Antibody According to the method of Example 7)-2, the sensitivities of tumors of MIA PaCa-2-KLF5 and MIA PaCa-2-mock to the humanized CD147 antibody #110H1L4hIgG4P were compared. The humanized CD147 antibody (#110H1L4hIgG4P) produced in Example 6)-4-2 was administered to mice bearing tumor via the tail vein at 1 mg/kg 3 days after the cell inoculation (n=6). The antibody was administered 7 days later in the same manner. A PBS buffer solution was administered to mice bearing tumor of the control group via the tail vein in the same manner (n=6). FIG. 50 shows the results.

The average volume of tumor of MIA PaCa-2-mock decreased to 9% of that in the control group 14 days after the administration of the humanized CD147 antibody, thus exhibiting a sensitivity to the CD147 antibody. The average tumor volume of MIA PaCa-2-KLF5 was 80% of the control group, thus exhibiting a low sensitivity to the CD147 antibody. It was found that the SMAD signal-dependent antitumor efficacy of the CD147 antibody is suppressed by KLF5 expression.

INDUSTRIAL APPLICABILITY

The present invention provides a CD147-specific antibody that activates CD147 and exhibits potent antitumor efficacy. The present invention provides an antibody exhibiting potent antitumor efficacy independent of effector functions. The antibody of the present invention exhibits efficacy in liver cancer cells that is clearly better than that of sorafenib that is used as one of the standard of care drugs for liver cancer. The antibody of the present invention exhibits efficacy in pancreatic cancer cells significantly stronger than that of gemcitabine that is used as one of the standard of care drugs for pancreatic cancer. The antibody of the present invention exhibits efficacy in chronic myeloid leukemia cells significantly stronger than that of imatinib that is used as one of the standard of care drugs for chronic myeloid leukemia. The antibody of the present invention has antitumor efficacy that is exhibited independent of effector functions and causes fewer concerns in terms of safety evaluation, and thus an anti-CD147 antibody with excellent safety is provided. CD147 is expressed not only in tumor cells, but also in blood cells. However, the antibody of the present invention does not act on T cells and PBMC and is independent of effector functions, so that the antibody has an advantage of causing fewer safety concerns in development thereof as an antitumor agent. The present invention provides a pharmaceutical composition comprising the above antibody, as well as a method for treating tumors using the antibody and/or the pharmaceutical composition.

Sequence Listing Free Text

SEQ ID NO: 1: Amino acid sequence of variant 1 of human CD147

SEQ ID NO: 2: Nucleotide sequence of variant 1 of human CD147

SEQ ID NO: 3: Amino acid sequence of variant 2 of human CD147

SEQ ID NO: 4: Nucleotide sequence of variant 2 of human CD147

SEQ ID NO: 5: Amino acid sequence of human SMAD4

SEQ ID NO: 6: Nucleotide sequence of human SMAD4

SEQ ID NO: 7: Nucleotide sequence of the light chain variable region of LN22R8

SEQ ID NO: 8: Amino acid sequence of the light chain variable region of LN22R8

SEQ ID NO: 9: Nucleotide sequence of the heavy chain variable region of LN22R8

SEQ ID NO: 10: Amino acid sequence of the heavy chain variable region of LN22R8

SEQ ID NO: 11: Amino acid sequence of CDRL1 of LN22R8

SEQ ID NO: 12: Amino acid sequence of CDRL2 of LN22R8

SEQ ID NO: 13: Amino acid sequence of CDRL3 of LN22R8

SEQ ID NO: 14: Amino acid sequence of CDRH1 of LN22R8

SEQ ID NO: 15: Amino acid sequence of CDRH2 of LN22R8

SEQ ID NO: 16: Amino acid sequence of CDRH3 of LN22R8

SEQ ID NO: 17: Nucleotide sequence of the light chain variable region of 2P10F2

SEQ ID NO: 18: Amino acid sequence of the light chain variable region of 2P10F2

SEQ ID NO: 19: Nucleotide sequence of the heavy chain variable region of 2P10F2

SEQ ID NO: 20: Amino acid sequence of the heavy chain variable region of 2P10F2

SEQ ID NO: 21: Amino acid sequence of CDRL1 of 2P10F2

SEQ ID NO: 22: Amino acid sequence of CDRL2 of 2P10F2

SEQ ID NO: 23: Amino acid sequence of CDRL3 of 2P10F2

SEQ ID NO: 24: Amino acid sequence of CDRH1 of 2P10F2

SEQ ID NO: 25: Amino acid sequence of CDRH2 of 2P10F2

SEQ ID NO: 26: Amino acid sequence of CDRH3 of 2P10F2

SEQ ID NO: 27: DNA comprising DNA sequence coding for human light chain signal sequence and human kappa chain constant region SEQ ID NO: 28: DNA comprising DNA sequence coding for amino acid of human heavy chain signal sequence and human IgG1 constant region SEQ ID NO: 29: DNA comprising DNA sequence coding for amino acid of human heavy chain signal sequence and human IgG2 constant region SEQ ID NO: 30: Nucleotide sequence of the light chain of human chimeric LN22R8

SEQ ID NO: 31: Amino acid sequence of the light chain of human chimeric LN22R8

SEQ ID NO: 32: Nucleotide sequence of the heavy chain IgG1 type of human chimeric LN22R8

SEQ ID NO: 33: Amino acid sequence of the heavy chain IgG1 type of human chimeric LN22R8

SEQ ID NO: 34: Nucleotide sequence of the heavy chain IgG2 type of human chimeric LN22R8

SEQ ID NO: 35: Amino acid sequence of the heavy chain IgG2 type of human chimeric LN22R8

SEQ ID NO: 36: DNA comprising DNA sequence coding for amino acid sequence of human chimera LN22R8_heavy chain_IgG4P type SEQ ID NO: 37: Amino acid sequence of the heavy chain IgG4P type of human chimeric LN22R8

SEQ ID NO: 38: DNA comprising DNA sequence coding for amino acid of human heavy chain signal sequence and human IgG1LALA constant region SEQ ID NO: 39: DNA comprising DNA sequence coding for amino acid of human heavy chain signal sequence and human IgG4P constant region SEQ ID NO: 40: Nucleotide sequence of the light chain of human chimeric 2P10F2

SEQ ID NO: 41: Amino acid sequence of the light chain of human chimeric 2P10F2

SEQ ID NO: 42: Nucleotide sequence of the heavy chain IgG1LALA type of human chimeric 2P10F2

SEQ ID NO: 43: Amino acid sequence of the heavy chain IgG1LALA type of human chimeric 2P10F2

SEQ ID NO: 44: Nucleotide sequence of the heavy chain IgG2 type of human chimeric 2P10F2

SEQ ID NO: 45: Amino acid sequence of the heavy chain IgG2 type of human chimeric 2P10F2

SEQ ID NO: 46: Nucleotide sequence of the heavy chain IgG4P type of human chimeric 2P10F2

SEQ ID NO: 47: Amino acid sequence of the heavy chain IgG4P type of human chimeric 2P10F2

SEQ ID NO: 48: Nucleotide sequence of the light chain variable region of rat_CD147_#84(r #84)

SEQ ID NO: 49: Amino acid sequence of the light chain variable region of rat_CD147_#84(r #84)

SEQ ID NO: 50: Nucleotide sequence of the heavy chain variable region of rat_CD147_#84(r #84)

SEQ ID NO: 51: Amino acid sequence of the heavy chain variable region of rat_CD147_#84(r #84)

SEQ ID NO: 52: Amino acid sequence of CDRL1 of rat_CD147_#84(r #84)

SEQ ID NO: 53: Amino acid sequence of CDRL2 of rat_CD147_#84(r #84)

SEQ ID NO: 54: Amino acid sequence of CDRL3 of rat_CD147_#84(r #84)

SEQ ID NO: 55: Amino acid sequence of CDRH1 of rat_CD147_#84(r #84)

SEQ ID NO: 56: Amino acid sequence of CDRH2 of rat_CD147_#84(r #84)

SEQ ID NO: 57: Amino acid sequence of CDRH3 of rat_CD147_#84(r #84)

SEQ ID NO: 58: Nucleotide sequence of the light chain variable region of rat_CD147_#101(r #101)

SEQ ID NO: 59: Amino acid sequence of the light chain variable region of rat_CD147_#101(r #101)

SEQ ID NO: 60: Nucleotide sequence of the heavy chain variable region of rat_CD147_#101(r #101)

SEQ ID NO: 61: Amino acid sequence of the heavy chain variable region of rat_CD147_#101(r #101)

SEQ ID NO: 62: Amino acid sequence of CDRL1 of rat_CD147_#101(r #101)

SEQ ID NO: 63: Amino acid sequence of CDRL2 of rat_CD147_#101(r #101)

SEQ ID NO: 64: Amino acid sequence of CDRL3 of rat_CD147_#101(r #101)

SEQ ID NO: 65: Amino acid sequence of CDRH1 of rat_CD147_#101(r #101)

SEQ ID NO: 66: Amino acid sequence of CDRH2 of rat_CD147_#101(r #101)

SEQ ID NO: 67: Amino acid sequence of CDRH3 of rat_CD147_#101(r #101)

SEQ ID NO: 68: Nucleotide sequence of the light chain variable region of rat_CD147_#110(r #110)

SEQ ID NO: 69: Amino acid sequence of the light chain variable region of rat_CD147_#110(r #110)

SEQ ID NO: 70: Nucleotide sequence of the heavy chain variable region of rat_CD147_#110(r #110)

SEQ ID NO: 71: Amino acid sequence of the heavy chain variable region of rat_CD147_#110(r #110)

SEQ ID NO: 72: Amino acid sequence of CDRL1 of rat_CD147_#110(r #110)

SEQ ID NO: 73: Amino acid sequence of CDRL2 of rat_CD147_#110(r #110)

SEQ ID NO: 74: Amino acid sequence of CDRL3 of rat_CD147_#110(r #110)

SEQ ID NO: 75: Amino acid sequence of CDRH1 of rat_CD147_#110(r #110)

SEQ ID NO: 76: Amino acid sequence of CDRH2 of rat_CD147_#110(r #110)

SEQ ID NO: 77: Amino acid sequence of CDRH3 of rat_CD147_#110(r #110)

SEQ ID NO: 78: Nucleotide sequence of the light chain variable region of rat_CD147_#131(r #131)

SEQ ID NO: 79: Amino acid sequence of the light chain variable region of rat_CD147_#131(r #131)

SEQ ID NO: 80: Nucleotide sequence of the heavy chain variable region of rat_CD147_#131(r #131)

SEQ ID NO: 81: Amino acid sequence of the heavy chain variable region of rat_CD147_#131(r #131)

SEQ ID NO: 82: Amino acid sequence of CDRL1 of rat_CD147_#131(r #131)

SEQ ID NO: 83: Amino acid sequence of CDRL2 of rat_CD147_#131(r #131)

SEQ ID NO: 84: Amino acid sequence of CDRL3 of rat_CD147_#131(r #131)

SEQ ID NO: 85: Amino acid sequence of CDRH1 of rat_CD147_#131(r #131)

SEQ ID NO: 86: Amino acid sequence of CDRH2 of rat_CD147_#131(r #131)

SEQ ID NO: 87: Amino acid sequence of CDRH3 of rat_CD147_#131(r #131)

SEQ ID NO: 88: DNA comprising DNA sequence coding for amino acid of human heavy chain signal sequence and human IgG4PFALA constant region SEQ ID NO: 89: Nucleotide sequence of the light chain of human chimeric rat_CD147_#84

SEQ ID NO: 90: Amino acid sequence of the light chain of human chimeric rat_CD147_#84

SEQ ID NO: 91: Nucleotide sequence of the heavy chain IgG1 type of human chimeric rat_CD147_#84

SEQ ID NO: 92: Amino acid sequence of the heavy chain IgG1 type of human chimeric rat_CD147_#84

SEQ ID NO: 93: Nucleotide sequence of the heavy chain IgG2 type of human chimeric rat_CD147_#84

SEQ ID NO: 94: Amino acid sequence of the heavy chain IgG2 type of human chimeric rat_CD147_#84

SEQ ID NO: 95: Nucleotide sequence of the heavy chain IgG4P type of human chimeric rat_CD147_#84

SEQ ID NO: 96: Amino acid sequence of the heavy chain IgG4P type of human chimeric rat_CD147_#84

SEQ ID NO: 97: Nucleotide sequence of the heavy chain IgG1LALA type of human chimeric rat_CD147_#84

SEQ ID NO: 98: Amino acid sequence of the heavy chain IgG1LALA type of human chimeric rat_CD147_#84

SEQ ID NO: 99: Nucleotide sequence of the heavy chain IgG4PFALA type of human chimeric rat_CD147_#84

SEQ ID NO: 100: Amino acid sequence of the heavy chain IgG4PFALA type of human chimeric rat_CD147_#84

SEQ ID NO: 101: Nucleotide sequence of the light chain of human chimeric rat_CD147_#101

SEQ ID NO: 102: Amino acid sequence of the light chain of human chimeric rat_CD147_#101

SEQ ID NO: 103: Nucleotide sequence of the heavy chain IgG2 of human chimeric rat_CD147_#101

SEQ ID NO: 104: Amino acid sequence of the heavy chain IgG2 of human chimeric rat_CD147_#101

SEQ ID NO: 105: Nucleotide sequence of the heavy chain IgG4P of human chimeric rat_CD147_#101

SEQ ID NO: 106: Amino acid sequence of the heavy chain IgG4P of human chimeric rat_CD147_#101

SEQ ID NO: 107: Nucleotide sequence of the heavy chain IgG4PFALA of human chimeric rat_CD147_#101

SEQ ID NO: 108: Amino acid sequence of the heavy chain IgG4PFALA of human chimeric rat_CD147_#101

SEQ ID NO: 109: Nucleotide sequence of the light chain of human chimeric rat_CD147_#110
SEQ ID NO: 110: Amino acid sequence of the light chain of human chimeric rat_CD147_#110
SEQ ID NO: 111: Nucleotide sequence of the heavy chain IgG2 of human chimeric rat_CD147_#110
SEQ ID NO: 112: Amino acid sequence of the heavy chain IgG2 of human chimeric rat_CD147_#110
SEQ ID NO: 113: Nucleotide sequence of the heavy chain IgG4P of human chimeric rat_CD147_#110
SEQ ID NO: 114: Amino acid sequence of the heavy chain IgG4P of human chimeric rat_CD147_#110
SEQ ID NO: 115: Nucleotide sequence of the heavy chain IgG4PFALA of human chimeric rat_CD147_#110
SEQ ID NO: 116: Amino acid sequence of the heavy chain IgG4PFALA of human chimeric rat_CD147_#110
SEQ ID NO: 117: Nucleotide sequence of the light chain of human chimeric rat_CD147_#131
SEQ ID NO: 118: Amino acid sequence of the light chain of human chimeric rat_CD147_#131
SEQ ID NO: 119: Nucleotide sequence of the heavy chain IgG2 of human chimeric rat_CD147_#131
SEQ ID NO: 120: Amino acid sequence of the heavy chain IgG2 of human chimeric rat_CD147_#131
SEQ ID NO: 121: Nucleotide sequence of the heavy chain IgG4P of human chimeric rat_CD147_#131
SEQ ID NO: 122: Amino acid sequence of the heavy chain IgG4P of human chimeric rat_CD147_#131
SEQ ID NO: 123: Amino acid sequence of #84H1hIgG2
SEQ ID NO: 124: Nucleotide sequence of #84H1hIgG2
SEQ ID NO: 125: Amino acid sequence of #84H1hIgG4P
SEQ ID NO: 126: Nucleotide sequence of #84H1hIgG4P
SEQ ID NO: 127: Amino acid sequence of #84L2h
SEQ ID NO: 128: Nucleotide sequence of #84L2h
SEQ ID NO: 129: Amino acid sequence of #101H1hIgG2
SEQ ID NO: 130: Nucleotide sequence of #101H1hIgG2
SEQ ID NO: 131: Amino acid sequence of #101H1hIgG4P
SEQ ID NO: 132: Nucleotide sequence of #101H1hIgG4P
SEQ ID NO: 133: Amino acid sequence of #101L2h
SEQ ID NO: 134: Nucleotide sequence of #101L2h
SEQ ID NO: 135: Amino acid sequence of #110H1hIgG4P
SEQ ID NO: 136: Nucleotide sequence of #110H1hIgG4P
SEQ ID NO: 137: Amino acid sequence of #110L4h
SEQ ID NO: 138: Nucleotide sequence of #110L4h
SEQ ID NO: 139: Amino acid sequence of #131H2hIgG2
SEQ ID NO: 140: Nucleotide sequence of #131H2hIgG2
SEQ ID NO: 141: Amino acid sequence of #131L2h
SEQ ID NO: 142: Nucleotide sequence of #131L2h
SEQ ID NO: 143: mu3 region of human CD147v1
SEQ ID NO: 144: mu3 region of cynomolgus monkey CD147
SEQ ID NO: 145: Amino acid sequence of human KLF5
SEQ ID NO: 146: Nucleotide sequence of human KLF5
SEQ ID NO: 147: Amino acid sequence of #110H13hIgG4P
SEQ ID NO: 148: Nucleotide sequence of #110H13hIgG4P
SEQ ID NO: 149: Amino acid sequence of #110L2h
SEQ ID NO: 150: Nucleotide sequence of #110L2h
SEQ ID NO: 151: Amino acid sequence of #110L12h
SEQ ID NO: 152: Nucleotide sequence of #110L12h

The invention claimed is:

1. An antibody against human CD147 or an antigen-binding fragment thereof, comprising:

(i) a heavy chain sequence, which comprises a variable region having CDRH1, CDRH2 and CDRH3, the CDRH1 comprises SEQ ID NO: 75, the CDRH2 comprises SEQ ID NO: 76, and the CDRH3 comprises SEQ ID NO: 77, and a light chain sequence, which comprises a variable region having CDRL1, CDRL2 and CDRL3, the CDRL1 comprises SEQ ID NO: 72, the CDRL2 comprises SEQ ID NO: 73, and the CDRL3 comprises SEQ ID NO: 74:

(ii) a heavy chain sequence, which comprises a variable region having CDRH1, CDRH2 and CDRH3, the CDRH1 comprises SEQ ID NO: 55, the CDRH2 comprises SEQ ID NO: 56, and the CDRH3 comprises SEQ ID NO: 57, and a light chain sequence, which comprises a variable region having CDRL1, CDRL2 and CDRL3, the CDRL1 comprises SEQ ID NO: 52, the CDRL2 comprises SEQ ID NO: 53, and the CDRL3 comprises SEQ ID NO: 54;

(iii) a heavy chain sequence, which comprises a variable region having CDRH1, CDRH2 and CDRH3, the CDRH1 comprises SEQ ID NO: 65, the CDRH2 comprises SEQ ID NO: 66, and the CDRH3 comprises SEQ ID NO: 67, and a light chain sequence, which comprises a variable region having CDRL1, CDRL2 and CDRL3, the CDRL1 comprises SEQ ID NO: 62, the CDRL2 comprises SEQ ID NO: 63, and the CDRL3 comprises SEQ ID NO: 64; or (iv) a heavy chain sequence, which comprises a variable region having CDRH1, CDRH2 and CDRH3, the CDRH1 comprises SEQ ID NO: 85, the CDRH2 comprises SEQ ID NO: 86, and the CDRH3 comprises SEQ ID NO: 87, and a light chain sequence, which comprises a variable region having CDRL1, CDRL2 and CDRL3, the CDRL1 comprises SEQ ID NO: 82, the CDRL2 comprises SEQ ID NO: 83, and the CDRL3 comprises SEQ ID NO: 84:

wherein the antibody or antigen-binding fragment thereof competes with at least one antibody selected from the group consisting of the following (A) to (F) for binding to human CD 147 and which activates signal transduction through CD147:

(A) an antibody comprising a heavy chain variable region consisting of an amino acid sequence comprises SEQ ID NO: 71 and a light chain variable region consisting of an amino acid sequence comprises SEQ ID NO: 69;

(B) an antibody comprising a heavy chain variable region consisting of an amino acid sequence comprises SEQ ID NO: 51 and a light chain variable region consisting of an amino acid sequence comprises SEQ ID NO: 49;

(C) an antibody comprising a heavy chain variable region consisting of an amino acid sequence comprises SEQ ID NO: 61 and a light chain variable region consisting of an amino acid sequence comprises SEQ ID NO: 59;

(D) an antibody comprising a heavy chain variable region consisting of an amino acid sequence comprises SEQ ID NO: 81 and a light chain variable region consisting of an amino acid sequence comprises SEQ ID NO: 79;

(E) an antibody comprising a heavy chain variable region consisting of an amino acid sequence comprises SEQ ID NO: 10 and a light chain variable region consisting of an amino acid sequence comprises SEQ ID NO: 8; and (F) an antibody comprising a heavy chain variable region consisting of an amino acid sequence comprises SEQ ID NO: 20 and a light chain variable region consisting of an amino acid sequence comprises SEQ ID NO: 18.

2. An antibody against human CD147 or an antigen-binding fragment thereof, comprising:

(i) a heavy chain sequence, which comprises a variable region having CDRH1, CDRH2 and CDRH3, the CDRH1 comprises SEQ ID NO: 75, the CDRH2 comprises SEQ ID NO: 76, and the CDRH3 comprises SEQ ID NO: 77, and a light chain sequence, which comprises a variable region having CDRL1, CDRL2 and CDRL3, the CDRL1 comprises SEQ ID NO: 72, the CDRL2 comprises SEQ ID NO: 73, and the CDRL3 comprises SEQ ID NO: 74:

(ii) a heavy chain sequence, which comprises a variable region having CDRH1, CDRH2 and CDRH3, the CDRH1 comprises SEQ ID NO: 55, the CDRH2 comprises SEQ ID NO: 56, and the CDRH3 comprises SEQ ID NO: 57, and a light chain sequence, which comprises a variable region having CDRL1, CDRL2 and CDRL3, the CDRL1 comprises SEQ ID NO: 52, the CDRL2 comprises SEQ ID NO: 53, and the CDRL3 comprises SEQ ID NO: 54, (iii) a heavy chain sequence, which comprises a variable region having CDRH1, CDRH2 and CDRH3, the CDRH1 comprises SEQ ID NO: 65, the CDRH2 comprises SEQ ID NO: 66, and the CDRH3 comprises SEQ ID NO: 67, and a light chain sequence, which comprises a variable region having CDRL1, CDRL2 and CDRL3, the CDRL1 comprises SEQ ID NO: 62, the CDRL2 comprises SEQ ID NO: 63, and the CDRL3 comprises SEQ ID NO: 64, or (iv) a heavy chain sequence, which comprises a variable region having CDRH1, CDRH2 and CDRH3, the CDRH1 comprises SEQ ID NO: 85, the CDRH2 comprises SEQ ID NO: 86, and the CDRH3 SEQ ID NO: 87, and a light chain sequence, which comprises a variable region having CDRL1, CDRL2 and CDRL3, the CDRL1 comprises SEQ ID NO: 82, the CDRL2 comprises SEQ ID NO: 83, and the CDRL3 comprises SEQ ID NO: 84:

wherein the antibody or antigen-binding fragment thereof binds to an epitope to which at least one antibody selected from the group consisting of the following (A) to (F) binds, and which activates signal transduction through CD147:

(A) an antibody comprising a heavy chain variable region consisting of an amino acid sequence comprises SEQ ID NO: 71 and a light chain variable region consisting of an amino acid sequence comprises SEQ ID NO: 69;

(B) an antibody comprising a heavy chain variable region consisting of an amino acid sequence comprises SEQ ID NO: 51 and a light chain variable region consisting of an amino acid sequence comprises SEQ ID NO: 49;

(C) an antibody comprising a heavy chain variable region consisting of an amino acid sequence comprises SEQ ID NO: 61 and a light chain variable region consisting of an amino acid sequence comprises SEQ ID NO: 59;

(D) an antibody comprising a heavy chain variable region consisting of an amino acid sequence comprises SEQ ID NO: 81 and a light chain variable region consisting of an amino acid sequence comprises SEQ ID NO: 79;

(E) an antibody comprising a heavy chain variable region consisting of an amino acid sequence comprises SEQ ID NO: 10 and a light chain variable region consisting of an amino acid sequence comprises SEQ ID NO: 8; and (F) an antibody comprising a heavy chain variable region consisting of an amino acid sequence comprises SEQ ID NO: 20 and a light chain variable region consisting of an amino acid sequence comprises SEQ ID NO: 18.

3. The antibody against human CD147 or the antigen-binding fragment thereof according to claim 1, which has decreased ADCC activity or lacks ADCC activity.

4. The antibody against human CD147 or the antigen-binding fragment thereof according to claim 1, which has decreased CDC activity or lacks CDC activity.

5. The antibody against human CD147 or the antigen-binding fragment thereof according to claim 1, which has decreased ADCP activity or lacks ADCP activity.

6. The antibody or the antigen-binding fragment thereof according to claim 1, which binds to an epitope comprising residues of arginine (Arg) at position 106 to glycine (Gly) at position 165 in SEQ ID NO: 3.

7. The antibody or the antigen-binding fragment thereof according to claim 1, which binds to an epitope comprising residues of arginine (Arg) at position 106, lysine (Lys) at position 108, alanine (Ala) at position 109, valine (Val) at position 110, lysine (Lys) at position 127, serine (Ser) at position 128, glutamic acid (Glu) at position 129, serine (Ser) at position 130, valine (Val) at position 131, proline (Pro) at position 132, proline (Pro) at position 133, valine (Val) at position 134, glutamine (Gln) at position 164 and glycine (Gly) at position 165 in the amino acid sequence set forth in SEQ ID NO: 3.

8. The antibody or the antigen-binding fragment thereof according to claim 1, wherein:

in the heavy chain sequence, which comprises a variable region having CDRH1, CDRH2 and CDRH3, the CDRH1 comprises SEQ ID NO: 75, the CDRH2 comprises SEQ ID NO: 76, and the CDRH3 comprises SEQ ID NO: 77; and in the light chain sequence, which comprises a variable region having CDRL1, CDRL2 and CDRL3, the CDRL1 comprises SEQ ID NO: 72, the CDRL2 comprises SEQ ID NO: 73, and the CDRL3 comprises SEQ ID NO: 74.

9. The antibody or the antigen-binding fragment thereof according to claim 1, which binds to an epitope comprising an amino acid sequence set forth in SEQ ID NO: 143 or an amino acid sequence in which one or several amino acids are deleted, substituted or added in the sequence of SEQ ID NO: 143.

10. The antibody or the antigen-binding fragment thereof according to claim 1, wherein:

in the heavy chain sequence, which comprises a variable region having CDRH1, CDRH2 and CDRH3, the CDRH1 comprises SEQ ID NO: 55, the CDRH2 comprises SEQ ID NO: 56, and the CDRH3 comprises SEQ ID NO: 57; and in the light chain sequence, which comprises a variable region having CDRL1, CDRL2 and CDRL3, the CDRL1 comprises SEQ ID NO: 52, the CDRL2 comprises SEQ ID NO: 53, and the CDRL3 comprises SEQ ID NO: 54.

11. The antibody or the antigen-binding fragment thereof according to claim 1, wherein:

in the heavy chain sequence, which comprises a variable region having CDRH1, CDRH2 and CDRH3, the CDRH1 comprises SEQ ID NO: 65, the CDRH2 comprises SEQ ID NO: 66, and the CDRH3 comprises SEQ ID NO: 67; and in the light chain sequence, which comprises a variable region having CDRL1, CDRL2 and CDRL3, the CDRL1 comprises SEQ ID NO: 62, the CDRL2 comprises SEQ ID NO: 63, and the CDRL3 comprises SEQ ID NO: 64.

12. The antibody or the antigen-binding fragment thereof according to claim 1, wherein:

in the heavy chain sequence, which comprises a variable region having CDRH1, CDRH2 and CDRH3, the CDRH1 comprises SEQ ID NO: 85, the CDRH2 comprises SEQ ID NO: 86, and the CDRH3 comprises SEQ ID NO: 87; and in the light chain sequence, which comprises a variable region having CDRL1, CDRL2 and CDRL3, the CDRL1 comprises SEQ ID NO: 82, the CDRL2 comprises SEQ ID NO: 83, and the CDRL3 comprises SEQ ID NO: 84.

13. The antigen-binding fragment of the antibody according to claim 1, which is selected from the group consisting of Fab, F(ab')2, Fab' and Fv.

14. The antibody according to claim 1, which is scFv.

15. The antibody or the antigen-binding fragment thereof according to claim 1, which is a chimeric antibody.

16. The antibody or the antigen-binding fragment thereof according to claim 1, which is humanized.

17. The antibody according to claim 1, wherein the heavy chain comprises a human immunoglobulin G1 heavy chain constant region, a human immunoglobulin G2 heavy chain constant region or a human immunoglobulin G4 heavy chain constant region, and the light chain comprises a human immunoglobulin x light chain constant region.

18. The antibody according to claim 17, wherein the heavy chain comprises the human immunoglobulin G4 heavy chain constant region.

19. The antibody according to claim 18, wherein within the human immunoglobulin G4 heavy chain constant region, the serine (Ser) at position 228 as indicated by the EU index is substituted with a proline (Pro).

20. The antibody according to claim 18, wherein within the human immunoglobulin G4 heavy chain constant region, the phenylalanine (Phe) at position 234 as indicated by the EU index is substituted with an alanine (Ala), and the leucine (Leu) at position 235 as indicated by the EU index is substituted with an alanine (Ala).

21. The antibody according to claim 18, wherein within the human immunoglobulin G4 heavy chain constant region, the serine (Ser) at position 228 as indicated by the EU index is substituted with a proline (Pro), the phenylalanine (Phe) at position 234 as indicated by the EU index is substituted with an alanine (Ala), and the leucine (Leu) at position 235 as indicated by the EU index is substituted with an alanine (Ala).

22. The antibody according to claim 17, wherein the heavy chain comprises the human immunoglobulin G2 heavy chain constant region.

23. An antibody against human CD147 or an antigen-binding fragment thereof, which comprises the following (c) and (d), and activates signal transduction through CD147:

(c) a heavy chain variable region selected from the group consisting of the following (c1) to (c4):

(c1) a heavy chain variable region consisting of amino acid residues at positions 20 to 136 in an amino acid sequence comprising SEQ ID NO: 135;

(c2) a heavy chain variable region consisting of amino acid residues at positions 20 to 136 in an amino acid sequence comprising SEQ ID NO: 147;

(c3) an amino acid sequence having at least 95% or more sequence identity with the sequence of a framework region outside each CDR sequence in the sequence of (c1) or (c2); and (c4) an amino acid sequence in which one or several amino acids are deleted, substituted, or added in the sequence of a framework region outside each CDR sequence in the sequence according to any one of (c1) to (c3); and (d) a light chain variable region selected from the group consisting of the following (d1) to (d5):

(d1) a light chain variable region consisting of amino acid residues at positions 21 to 128 in an amino acid sequence comprising SEQ ID NO: 137;

(d2) a light chain variable region consisting of amino acid residues at positions 21 to 128 in an amino acid sequence comprising SEQ ID NO: 149;

(d3) a light chain variable region consisting of amino acid residues at positions 21 to 128 in an amino acid sequence comprising SEQ ID NO: 151;

(d4) an amino acid sequence having at least 95% or more sequence identity with the sequence of a framework region outside each CDR sequence in the sequence according to any one of (d1) to (d3); and (d5) an amino acid sequence in which one or several amino acids are deleted, substituted, or added in the sequence of a framework region outside each CDR sequence in the sequence according to any one of (d1) to (d4).

24. The antibody or the antigen-binding fragment thereof according to claim 23, which comprises:

the heavy chain variable region consisting of amino acid residues at positions 20 to 136 in the amino acid sequence comprising SEQ ID NO: 135; and the light chain variable region consisting of amino acid residues at positions 21 to 128 in the amino acid sequence comprising SEQ ID NO: 137.

25. The antibody or the antigen-binding fragment thereof according to claim 23, which comprises:

the heavy chain consisting of amino acid residues at positions 20 to 463 in the amino acid sequence comprising SEQ ID NO: 135; and the light chain consisting of amino acid residues at positions 21 to 234 in the amino acid sequence comprising SEQ ID NO: 137.

26. The antibody or the antigen-binding fragment thereof according to claim 23, which comprises:

the heavy chain variable region consisting of amino acid residues at positions 20 to 136 in the amino acid sequence comprising SEQ ID NO: 147; and the light chain variable region consisting of amino acid residues at positions 21 to 128 in the amino acid sequence comprising SEQ ID NO: 149.

27. The antibody or the antigen-binding fragment thereof according to claim 23, which comprises:

the heavy chain consisting of amino acid residues at positions 20 to 463 in the amino acid sequence comprising SEQ ID NO: 147; and the light chain consisting of amino acid residues at positions 21 to 234 in the amino acid sequence comprising SEQ ID NO: 149.

28. The antibody or the antigen-binding fragment thereof according to claim 23, which comprises:

the heavy chain variable region consisting of amino acid residues at positions 20 to 136 in the amino acid sequence comprising SEQ ID NO: 147; and the light chain variable region consisting of amino acid residues at positions 21 to 128 in the amino acid sequence comprising SEQ ID NO: 151.

29. The antibody or the antigen-binding fragment thereof according to claim 23, which comprises:

the heavy chain consisting of amino acid residues at positions 20 to 463 in the amino acid sequence comprising SEQ ID NO: 147; and the light chain consisting of amino acid residues at positions 21 to 234 in the amino acid sequence comprising SEQ ID NO: 151.

30. An antibody against human CD147 or an antigen-binding fragment thereof, which comprises the following (a) and (b), and activates signal transduction through CD147:

(a) a heavy chain variable region selected from the group consisting of the following (a1) to (a4):

(a1) a heavy chain variable region consisting of amino acid residues at positions 20 to 140 in an amino acid sequence comprising SEQ ID NO: 123;

(a2) a heavy chain variable region consisting of amino acid residues at positions 20 to 140 in an amino acid sequence comprising SEQ ID NO: 125;

(a3) an amino acid sequence having at least 95% or more sequence identity with the sequence of a framework region outside each CDR sequence in the sequence of (a1) or (a2); and (a4) an amino acid sequence in which one or several amino acids are deleted, substituted, or added in the sequence of a framework region outside each CDR sequence in the sequence according to any one of (a1) to (a3); and (b) a light chain variable region selected from the group consisting of the following (b1) to (b3):

(b1) a light chain variable region consisting of amino acid residues at positions 21 to 128 in an amino acid sequence comprising SEQ ID NO: 127;

(b2) an amino acid sequence having at least 95% or more sequence identity with the sequence of a framework region outside each CDR sequence in the sequence of (b1); and (b3) an amino acid sequence in which one or several amino acids are deleted, substituted, or added in the sequence of a framework region outside each CDR sequence in the sequence of (b1) or (b2).

31. The antibody or the antigen-binding fragment thereof according to claim 30, which comprises:

the heavy chain variable region consisting of amino acid residues at positions 20 to 140 in the amino acid sequence comprising SEQ ID NO: 123 or the heavy chain variable region consisting of amino acid residues at positions 20 to 140 in the amino acid sequence comprising SEQ ID NO: 125; and the light chain variable region consisting of amino acid residues at positions 21 to 128 in the amino acid sequence comprising SEQ ID NO: 127.

32. The antibody or the antigen-binding fragment thereof according to claim 30, which comprises:

the heavy chain consisting of amino acid residues at positions 20 to 466 in the amino acid sequence comprising SEQ ID NO: 123 or the heavy chain consisting of amino acid residues at positions 20 to 467 in the amino acid sequence comprising SEQ ID NO: 125; and the light chain consisting of amino acid residues at positions 21 to 234 in the amino acid sequence comprising SEQ ID NO: 127.

33. An antibody against human CD147 or an antigen-binding fragment thereof, which comprises the following (e) and (f), and activates signal transduction through CD147:

(e) a heavy chain variable region selected from the group consisting of the following (e1) to (e4):

(e1) a heavy chain variable region consisting of amino acid residues at positions 20 to 137 in an amino acid sequence comprising SEQ ID NO: 129;

(e2) a heavy chain variable region consisting of amino acid residues at positions 20 to 137 in an amino acid sequence comprising SEQ ID NO: 131;

(e3) an amino acid sequence having at least 95% or more sequence identity with the sequence of a framework region outside each CDR sequence in the sequence of (e1) or (2); and (e4) an amino acid sequence in which one or several amino acids are deleted, substituted, or added in the sequence of a framework region outside each CDR sequence in the sequence according to any one of (e1) to (e3); and (f) a light chain variable region selected from the group consisting of the following (f1) to (f3):

(f1) a light chain variable region consisting of amino acid residues at positions 21 to 128 in an amino acid sequence comprising SEQ ID NO: 133;

(f2) an amino acid sequence having at least 95% or more sequence identity with the sequence of a framework region outside each CDR sequence in the sequence of (f1); and (f3) an amino acid sequence in which one or several amino acids are deleted, substituted, or added in the sequence of a framework region outside each CDR sequence in the sequence of (f1) or (f2).

34. The antibody or the antigen-binding fragment thereof according to claim 33, which comprises:

the heavy chain variable region consisting of amino acid residues at positions 20 to 137 in the amino acid sequence comprising SEQ ID NO: 129 or the heavy chain variable region consisting of amino acid residues at positions 20 to 137 in the amino acid sequence comprising SEQ ID NO: 131; and the light chain variable region consisting of amino acid residues at positions 21 to 128 in the amino acid sequence comprising SEQ ID NO: 133.

35. The antibody or the antigen-binding fragment thereof according to claim 33, which comprises:

the heavy chain consisting of amino acid residues at positions 20 to 463 in the amino acid sequence comprising SEQ ID NO: 129 or the heavy chain consisting of amino acid residues at positions 20 to 464 in the amino acid sequence comprising SEQ ID NO: 131; and the light chain consisting of amino acid residues at positions 21 to 234 in the amino acid sequence comprising SEQ ID NO: 133.

36. An antibody against human CD147 or an antigen-binding fragment thereof, which comprises the following (g) and (h), and activates signal transduction through CD147:

(g) a heavy chain variable region selected from the group consisting of the following (g1) to (g3):

(g1) a heavy chain variable region consisting of amino acid residues at positions 20 to 138 in an amino acid sequence comprising SEQ ID NO: 139;

(g2) an amino acid sequence having at least 95% or more sequence identity with the sequence of a framework region outside each CDR sequence in the sequence of (g1); and (g3) an amino acid sequence in which one or several amino acids are deleted, substituted, or added in the sequence of a framework region outside each CDR sequence in the sequence of (g1) or (g2); and (h) a light chain variable region selected from the group consisting of the following (h1) to (h3):

(h1) a light chain variable region consisting of amino acid residues at positions 21 to 128 in an amino acid sequence comprising SEQ ID NO: 141;

(h2) an amino acid sequence having at least 95% or more sequence identity with the sequence of a framework region outside each CDR sequence in the sequence of (h1); and (h3) an amino acid sequence in which one or several amino acids are deleted, substituted, or added in the sequence of a framework region outside each CDR sequence in the sequence of (h1) or (h2).

37. The antibody or the antigen-binding fragment thereof according to claim 36, which comprises:

the heavy chain variable region consisting of amino acid residues at positions 20 to 138 in the amino acid sequence comprising SEQ ID NO: 139; and the light chain variable region consisting of amino acid residues at positions 21 to 128 in the amino acid sequence comprising SEQ ID NO: 141.

38. The antibody or the antigen-binding fragment thereof according to claim 36, which comprises:

the heavy chain consisting of amino acid residues at positions 20 to 464 in the amino acid sequence comprising SEQ ID NO: 139; and the light chain consisting of amino acid residues at positions 21 to 234 in the amino acid sequence comprising SEQ ID NO: 141.

39. The antibody against human CD147 or the antigen-binding fragment thereof according to claim 23, which has decreased ADCC activity or lacks ADCC activity.

40. The antibody against human CD147 or the antigen-binding fragment thereof according to claim 23, which has decreased CDC activity or lacks CDC activity.

41. The antibody against human CD147 or the antigen-binding fragment thereof according to claim 23, which has decreased ADCP activity or lacks ADCP activity.

42. A pharmaceutical composition comprising at least one of the antibodies or antigen-binding fragments thereof according to claim 1.

43. The pharmaceutical composition according to claim 42, which is an antitumor agent.

44. The pharmaceutical composition according to claim 43, wherein the tumor is a tumor expressing CD147.

45. The pharmaceutical composition according to claim 43, wherein the tumor is pancreatic cancer, liver cancer, gastric cancer, colon cancer, renal cancer, breast cancer, uterine cancer, ovarian cancer, lung cancer, lymphoma, thyroid cancer, skin cancer, head and neck cancer, sarcoma, prostate cancer, bladder cancer, brain tumor, gastrointestinal stromal tumor (GIST), leukemia, acute myeloid leukemia (AML), chronic myeloid leukemia (CML), chronic lymphocytic leukemia (CLL), acute lymphocytic leukemia (ALL), malignant lymphoma, B-cell lymphoma, non-Hodgkin's lymphoma or diffuse large B-cell lymphoma (DLBCL).

46. The pharmaceutical composition according to claim 43, wherein the tumor is pancreatic cancer, liver cancer, gastric cancer, colon cancer, renal cancer, leukemia, acute myeloid leukemia (AML), chronic myeloid leukemia (CIVIL), chronic lymphocytic leukemia (CLL), acute lymphocytic leukemia (ALL), malignant lymphoma, B-cell lymphoma, non-Hodgkin's lymphoma or diffuse large B-cell lymphoma (DLBCL).

47. The pharmaceutical composition according to claim 43, wherein the tumor is a SMAD4-positive tumor or a tumor having a decreased expression level of or lacking the expression of KLF5.

48. The pharmaceutical composition according to claim 42, further comprising another antitumor agent.

49. A method for treating a CD147-expressing tumor, comprising administering the antibody or the antigen-binding fragment thereof according to claim 1 or a pharmaceutical composition thereof.

50. The method according to claim 49, wherein the tumor is pancreatic cancer, liver cancer, gastric cancer, colon cancer, renal cancer, breast cancer, uterine cancer, ovarian cancer, lung cancer, lymphoma, thyroid cancer, skin cancer, head and neck cancer, sarcoma, prostate cancer, bladder cancer, brain tumor, gastrointestinal stromal tumor (GIST), leukemia, acute myeloid leukemia (AML), chronic myeloid leukemia (CML), chronic lymphocytic leukemia (CLL), acute lymphocytic leukemia (ALL), malignant lymphoma, B-cell lymphoma, non-Hodgkin's lymphoma or diffuse large B-cell lymphoma (DLBCL).

51. The method according to claim 49, wherein the tumor is pancreatic cancer, liver cancer, gastric cancer, colon cancer, renal cancer, leukemia, acute myeloid leukemia (AML), chronic myeloid leukemia (CIVIL), chronic lymphocytic leukemia (CLL), acute lymphocytic leukemia (ALL), malignant lymphoma, B-cell lymphoma, non-Hodgkin's lymphoma or diffuse large B-cell lymphoma (DLBCL).

52. The method according to claim 49, wherein the tumor is a SMAD4-positive tumor or a tumor having a decreased expression level of or lacking the expression of KLF5.

53. The method according to claim 49, wherein the antibody or the antigen-binding fragment thereof, or the pharmaceutical composition is administered in combination with another antitumor agent.

54. A method for producing the antibody or the antigen-binding fragment thereof, comprising a step of culturing a host cell with an expression vector comprising a nucleotide that encodes the antibody or antigen-binding fragment thereof according to claim 1 and collecting the target antibody or the antigen-binding fragment thereof from a culture supernatant.

55. The antibody or the antigen-binding fragment thereof according to claim 1, wherein the activation of signal transduction through CD147 is an activation of p38MAPK and/or an activation of SMAD4.

56. The antibody or the antigen-binding fragment thereof according to claim 55, wherein the activation of p38MAPK and/or the activation of SMAD4 is an increase in p38MAPK expression level, the phosphorylation of p38MAPK, the phosphorylation of HSP27, an increase in CXCL8 expression level, an increase in rhoB expression level, a decrease in KLF5 mRNA or a decrease in KLF5 protein expression level.

57. A method for treating a CD147-expressing tumor, comprising administering the antibody or the antigen-binding fragment thereof according to claim 55.

58. A kit for determining responsiveness to cancer treatment with the antibody or the antigen-binding fragment thereof according to claim 1 or a pharmaceutical composition thereof, the kit comprising at least one means for detecting the expression of SMAD4 or the expression of KLF5 in a biological sample derived from a cancer patient.

59. An antibody-drug complex comprising the antibody or the antigen-binding fragment thereof according to claim 1 conjugated to another drug.

60. A bispecific antibody comprising: the antigen-binding fragment of the antibody according to claim 1; and an antigen-binding fragment which binds to an antigen other than CD147.

* * * * *

UNITED STATES PATENT AND TRADEMARK OFFICE

CERTIFICATE OF CORRECTION

PATENT NO. : 11,661,451 B2
APPLICATION NO. : 16/633565
DATED : May 30, 2023
INVENTOR(S) : Keisuke Fukuchi et al.

It is certified that error appears in the above-identified patent and that said Letters Patent is hereby corrected as shown below:

In the Claims

Claim 17, Column 280, Line 43:
Please delete:
"immunoglobulin x light chain constant region."
Please replace with:
immunoglobulin κ light chain constant region.

Signed and Sealed this
First Day of October, 2024

Katherine Kelly Vidal
*Director of the United States Patent and Trademark Office*

SEQUENCE LISTING

<160> NUMBER OF SEQ ID NOS: 152

<210> SEQ ID NO 1
<211> LENGTH: 385
<212> TYPE: PRT
<213> ORGANISM: Homo sapiens

<400> SEQUENCE: 1

Met Ala Ala Ala Leu Phe Val Leu Leu Gly Phe Ala Leu Leu Gly Thr
1 5 10 15

His Gly Ala Ser Gly Ala Ala Gly Phe Val Gln Ala Pro Leu Ser Gln
20 25 30

Gln Arg Trp Val Gly Gly Ser Val Glu Leu His Cys Glu Ala Val Gly
35 40 45

Ser Pro Val Pro Glu Ile Gln Trp Trp Phe Glu Gly Gln Gly Pro Asn
50 55 60

Asp Thr Cys Ser Gln Leu Trp Asp Gly Ala Arg Leu Asp Arg Val His
65 70 75 80

Ile His Ala Thr Tyr His Gln His Ala Ala Ser Thr Ile Ser Ile Asp
85 90 95

Thr Leu Val Glu Glu Asp Thr Gly Thr Tyr Glu Cys Arg Ala Ser Asn
100 105 110

Asp Pro Asp Arg Asn His Leu Thr Arg Ala Pro Arg Val Lys Trp Val
115 120 125

Arg Ala Gln Ala Val Val Leu Val Leu Glu Pro Gly Thr Val Phe Thr
130 135 140

Thr Val Glu Asp Leu Gly Ser Lys Ile Leu Leu Thr Cys Ser Leu Asn
145 150 155 160

```
Asp Ser Ala Thr Glu Val Thr Gly His Arg Trp Leu Lys Gly Gly Val
                165                 170                 175

Val Leu Lys Glu Asp Ala Leu Pro Gly Gln Lys Thr Glu Phe Lys Val
            180                 185                 190

Asp Ser Asp Asp Gln Trp Gly Glu Tyr Ser Cys Val Phe Leu Pro Glu
        195                 200                 205

Pro Met Gly Thr Ala Asn Ile Gln Leu His Gly Pro Pro Arg Val Lys
    210                 215                 220

Ala Val Lys Ser Ser Glu His Ile Asn Glu Gly Glu Thr Ala Met Leu
225                 230                 235                 240

Val Cys Lys Ser Glu Ser Val Pro Pro Val Thr Asp Trp Ala Trp Tyr
                245                 250                 255

Lys Ile Thr Asp Ser Glu Asp Lys Ala Leu Met Asn Gly Ser Glu Ser
            260                 265                 270

Arg Phe Phe Val Ser Ser Ser Gln Gly Arg Ser Glu Leu His Ile Glu
        275                 280                 285

Asn Leu Asn Met Glu Ala Asp Pro Gly Gln Tyr Arg Cys Asn Gly Thr
    290                 295                 300

Ser Ser Lys Gly Ser Asp Gln Ala Ile Ile Thr Leu Arg Val Arg Ser
305                 310                 315                 320

His Leu Ala Ala Leu Trp Pro Phe Leu Gly Ile Val Ala Glu Val Leu
                325                 330                 335

Val Leu Val Thr Ile Ile Phe Ile Tyr Glu Lys Arg Arg Lys Pro Glu
            340                 345                 350

Asp Val Leu Asp Asp Asp Asp Ala Gly Ser Ala Pro Leu Lys Ser Ser
        355                 360                 365

Gly Gln His Gln Asn Asp Lys Gly Lys Asn Val Arg Gln Arg Asn Ser
    370                 375                 380

Ser
385


<210> SEQ ID NO 2
<211> LENGTH: 1158
<212> TYPE: DNA
<213> ORGANISM: Homo sapiens

<400> SEQUENCE: 2

atggcggctg cgctgttcgt gctgctggga ttcgcgctgc tgggcaccca cggagcctcc      60

ggggctgccg gcttcgtcca ggcgccgctg tcccagcaga ggtgggtggg gggcagtgtg     120

gagctgcact gcgaggccgt gggcagcccg gtgcccgaga tccagtggtg gtttgaaggg     180

cagggtccca acgacacctg ctcccagctc tgggacggcg cccggctgga ccgcgtccac     240

atccacgcca cctaccacca gcacgcggcc agcaccatct ccatcgacac gctcgtggag     300

gaggacacgg gcacttacga gtgccgggcc agcaacgacc cggatcgcaa ccacctgacc     360

cgggcgccca gggtcaagtg ggtccgcgcc caggcagtcg tgctagtcct ggaacccggc     420

acagtcttca ctaccgtaga agaccttggc tccaagatac tcctcacctg ctccttgaat     480

gacagcgcca cagaggtcac agggcaccgc tggctgaagg ggggcgtggt gctgaaggag     540

gacgcgctgc ccggccagaa aacggagttc aaggtggact ccgacgacca gtggggagag     600

tactcctgcg tcttcctccc cgagcccatg ggcacggcca acatccagct ccacgggcct     660

cccagagtga aggctgtgaa gtcgtcagaa cacatcaacg agggggagac ggccatgctg     720

gtctgcaagt cagagtccgt gccacctgtc actgactggg cctggtacaa gatcactgac     780
```

-continued

```
tctgaggaca aggccctcat gaacggctcc gagagcaggt tcttcgtgag ttcctcgcag    840

ggccggtcag agctacacat tgagaacctg aacatggagg ccgaccccgg ccagtaccgg    900

tgcaacggca ccagctccaa gggctccgac caggccatca tcacgctccg cgtgcgcagc    960

cacctggccg ccctctggcc cttcctgggc atcgtggctg aggtgctggt gctggtcacc   1020

atcatcttca tctacgagaa gcgccggaag cccgaggacg tcctggatga tgacgacgcc   1080

ggctctgcac ccctgaagag cagcgggcag caccagaatg acaaaggcaa gaacgtccgc   1140

cagaggaact cttcctga                                                 1158
```

```
<210> SEQ ID NO 3
<211> LENGTH: 269
<212> TYPE: PRT
<213> ORGANISM: Homo sapiens

<400> SEQUENCE: 3

Met Ala Ala Ala Leu Phe Val Leu Leu Gly Phe Ala Leu Leu Gly Thr
1               5                   10                  15

His Gly Ala Ser Gly Ala Ala Gly Thr Val Phe Thr Thr Val Glu Asp
            20                  25                  30

Leu Gly Ser Lys Ile Leu Leu Thr Cys Ser Leu Asn Asp Ser Ala Thr
        35                  40                  45

Glu Val Thr Gly His Arg Trp Leu Lys Gly Gly Val Val Leu Lys Glu
    50                  55                  60

Asp Ala Leu Pro Gly Gln Lys Thr Glu Phe Lys Val Asp Ser Asp Asp
65                  70                  75                  80

Gln Trp Gly Glu Tyr Ser Cys Val Phe Leu Pro Glu Pro Met Gly Thr
                85                  90                  95

Ala Asn Ile Gln Leu His Gly Pro Pro Arg Val Lys Ala Val Lys Ser
            100                 105                 110

Ser Glu His Ile Asn Glu Gly Glu Thr Ala Met Leu Val Cys Lys Ser
        115                 120                 125

Glu Ser Val Pro Pro Val Thr Asp Trp Ala Trp Tyr Lys Ile Thr Asp
    130                 135                 140

Ser Glu Asp Lys Ala Leu Met Asn Gly Ser Glu Ser Arg Phe Phe Val
145                 150                 155                 160

Ser Ser Ser Gln Gly Arg Ser Glu Leu His Ile Glu Asn Leu Asn Met
                165                 170                 175

Glu Ala Asp Pro Gly Gln Tyr Arg Cys Asn Gly Thr Ser Ser Lys Gly
            180                 185                 190

Ser Asp Gln Ala Ile Ile Thr Leu Arg Val Arg Ser His Leu Ala Ala
        195                 200                 205

Leu Trp Pro Phe Leu Gly Ile Val Ala Glu Val Leu Val Leu Val Thr
    210                 215                 220

Ile Ile Phe Ile Tyr Glu Lys Arg Arg Lys Pro Glu Asp Val Leu Asp
225                 230                 235                 240

Asp Asp Asp Ala Gly Ser Ala Pro Leu Lys Ser Ser Gly Gln His Gln
                245                 250                 255

Asn Asp Lys Gly Lys Asn Val Arg Gln Arg Asn Ser Ser
            260                 265

<210> SEQ ID NO 4
<211> LENGTH: 810
<212> TYPE: DNA
<213> ORGANISM: Homo sapiens
```

-continued

<400> SEQUENCE: 4

```
atggcggctg cgctgttcgt gctgctggga ttcgcgctgc tgggcaccca cggagcctcc      60
ggggctgccg gcacagtctt cactaccgta gaagaccttg gctccaagat actcctcacc     120
tgctccttga atgacagcgc cacagaggtc acagggcacc gctggctgaa gggggggcgtg    180
gtgctgaagg aggacgcgct gcccggccag aaaacggagt tcaaggtgga ctccgacgac     240
cagtggggag agtactcctg cgtcttcctc cccgagccca tgggcacggc caacatccag     300
ctccacgggc ctcccagagt gaaggctgtg aagtcgtcag aacacatcaa cgagggggag     360
acggccatgc tggtctgcaa gtcagagtcc gtgccacctg tcactgactg ggcctggtac     420
aagatcactg actctgagga caaggccctc atgaacggct ccgagagcag gttcttcgtg     480
agttcctcgc agggccggtc agagctacac attgagaacc tgaacatgga ggccgacccc     540
ggccagtacc ggtgcaacgg caccagctcc aagggctccg accaggccat catcacgctc     600
cgcgtgcgca gccacctggc cgccctctgg cccttcctgg gcatcgtggc tgaggtgctg     660
gtgctggtca ccatcatctt catctacgag aagcgccgga agcccgagga cgtcctggat     720
gatgacgacg ccggctctgc acccctgaag agcagcgggc agcaccagaa tgacaaaggc     780
aagaacgtcc gccagaggaa ctcttcctga                                      810
```

<210> SEQ ID NO 5
<211> LENGTH: 552
<212> TYPE: PRT
<213> ORGANISM: Homo sapiens

<400> SEQUENCE: 5

```
Met Asp Asn Met Ser Ile Thr Asn Thr Pro Thr Ser Asn Asp Ala Cys
1               5                   10                  15

Leu Ser Ile Val His Ser Leu Met Cys His Arg Gln Gly Gly Glu Ser
            20                  25                  30

Glu Thr Phe Ala Lys Arg Ala Ile Glu Ser Leu Val Lys Lys Leu Lys
        35                  40                  45

Glu Lys Lys Asp Glu Leu Asp Ser Leu Ile Thr Ala Ile Thr Thr Asn
    50                  55                  60

Gly Ala His Pro Ser Lys Cys Val Thr Ile Gln Arg Thr Leu Asp Gly
65                  70                  75                  80

Arg Leu Gln Val Ala Gly Arg Lys Gly Phe Pro His Val Ile Tyr Ala
                85                  90                  95

Arg Leu Trp Arg Trp Pro Asp Leu His Lys Asn Glu Leu Lys His Val
            100                 105                 110

Lys Tyr Cys Gln Tyr Ala Phe Asp Leu Lys Cys Asp Ser Val Cys Val
        115                 120                 125

Asn Pro Tyr His Tyr Glu Arg Val Val Ser Pro Gly Ile Asp Leu Ser
    130                 135                 140

Gly Leu Thr Leu Gln Ser Asn Ala Pro Ser Ser Met Met Val Lys Asp
145                 150                 155                 160

Glu Tyr Val His Asp Phe Glu Gly Gln Pro Ser Leu Ser Thr Glu Gly
                165                 170                 175

His Ser Ile Gln Thr Ile Gln His Pro Pro Ser Asn Arg Ala Ser Thr
            180                 185                 190

Glu Thr Tyr Ser Thr Pro Ala Leu Leu Ala Pro Ser Glu Ser Asn Ala
        195                 200                 205

Thr Ser Thr Ala Asn Phe Pro Asn Ile Pro Val Ala Ser Thr Ser Gln
    210                 215                 220
```

-continued

Pro Ala Ser Ile Leu Gly Gly Ser His Ser Glu Gly Leu Leu Gln Ile
225 230 235 240

Ala Ser Gly Pro Gln Pro Gly Gln Gln Gln Asn Gly Phe Thr Gly Gln
245 250 255

Pro Ala Thr Tyr His His Asn Ser Thr Thr Thr Trp Thr Gly Ser Arg
260 265 270

Thr Ala Pro Tyr Thr Pro Asn Leu Pro His His Gln Asn Gly His Leu
275 280 285

Gln His His Pro Pro Met Pro Pro His Pro Gly His Tyr Trp Pro Val
290 295 300

His Asn Glu Leu Ala Phe Gln Pro Pro Ile Ser Asn His Pro Ala Pro
305 310 315 320

Glu Tyr Trp Cys Ser Ile Ala Tyr Phe Glu Met Asp Val Gln Val Gly
325 330 335

Glu Thr Phe Lys Val Pro Ser Ser Cys Pro Ile Val Thr Val Asp Gly
340 345 350

Tyr Val Asp Pro Ser Gly Gly Asp Arg Phe Cys Leu Gly Gln Leu Ser
355 360 365

Asn Val His Arg Thr Glu Ala Ile Glu Arg Ala Arg Leu His Ile Gly
370 375 380

Lys Gly Val Gln Leu Glu Cys Lys Gly Glu Gly Asp Val Trp Val Arg
385 390 395 400

Cys Leu Ser Asp His Ala Val Phe Val Gln Ser Tyr Tyr Leu Asp Arg
405 410 415

Glu Ala Gly Arg Ala Pro Gly Asp Ala Val His Lys Ile Tyr Pro Ser
420 425 430

Ala Tyr Ile Lys Val Phe Asp Leu Arg Gln Cys His Arg Gln Met Gln
435 440 445

Gln Gln Ala Ala Thr Ala Gln Ala Ala Ala Ala Ala Gln Ala Ala Ala
450 455 460

Val Ala Gly Asn Ile Pro Gly Pro Gly Ser Val Gly Gly Ile Ala Pro
465 470 475 480

Ala Ile Ser Leu Ser Ala Ala Ala Gly Ile Gly Val Asp Asp Leu Arg
485 490 495

Arg Leu Cys Ile Leu Arg Met Ser Phe Val Lys Gly Trp Gly Pro Asp
500 505 510

Tyr Pro Arg Gln Ser Ile Lys Glu Thr Pro Cys Trp Ile Glu Ile His
515 520 525

Leu His Arg Ala Leu Gln Leu Leu Asp Glu Val Leu His Thr Met Pro
530 535 540

Ile Ala Asp Pro Gln Pro Leu Asp
545 550

<210> SEQ ID NO 6
<211> LENGTH: 1659
<212> TYPE: DNA
<213> ORGANISM: Homo sapiens

<400> SEQUENCE: 6
atggacaata tgtctattac gaatacacca acaagtaatg atgcctgtct gagcattgtg 60
catagtttga tgtgccatag acaaggtgga gagagtgaaa catttgcaaa aagagcaatt 120
gaaagtttgg taaagaagct gaaggagaaa aaagatgaat tggattcttt aataacagct 180

```
ataactacaa atggagctca tcctagtaaa tgtgttacca tacagagaac attggatggg    240

aggcttcagg tggctggtcg gaaaggattt cctcatgtga tctatgcccg tctctggagg    300

tggcctgatc ttcacaaaaa tgaactaaaa catgttaaat attgtcagta tgcgtttgac    360

ttaaaatgtg atagtgtctg tgtgaatcca tatcactacg aacgagttgt atcacctgga    420

attgatctct caggattaac actgcagagt aatgctccat caagtatgat ggtgaaggat    480

gaatatgtgc atgactttga gggacagcca tcgttgtcca ctgaaggaca ttcaattcaa    540

accatccagc atccaccaag taatcgtgca tcgacagaga catacagcac cccagctctg    600

ttagccccat ctgagtctaa tgctaccagc actgccaact ttcccaacat tcctgtggct    660

tccacaagtc agcctgccag tatactgggg ggcagccata gtgaaggact gttgcagata    720

gcatcagggc ctcagccagg acagcagcag aatggattta ctggtcagcc agctacttac    780

catcataaca gcactaccac ctggactgga agtaggactg caccatacac acctaatttg    840

cctcaccacc aaaacggcca tcttcagcac cacccgccta tgccgcccca tcccggacat    900

tactggcctg ttcacaatga gcttgcattc cagcctccca tttccaatca tcctgctcct    960

gagtattggt gttccattgc ttactttgaa atggatgttc aggtaggaga gacatttaag   1020

gttccttcaa gctgccctat tgttactgtt gatggatacg tggacccttc tggaggagat   1080

cgcttttgtt tgggtcaact ctccaatgtc cacaggacag aagccattga gagagcaagg   1140

ttgcacatag gcaaaggtgt gcagttggaa tgtaaaggtg aaggtgatgt ttgggtcagg   1200

tgccttagtg accacgcggt ctttgtacag agttactact tagacagaga agctgggcgt   1260

gcacctggag atgctgttca taagatctac ccaagtgcat atataaaggt ctttgatttg   1320

cgtcagtgtc atcgacagat gcagcagcag gcggctactg cacaagctgc agcagctgcc   1380

caggcagcag ccgtggcagg aaacatccct ggcccaggat cagtaggtgg aatagctcca   1440

gctatcagtc tgtcagctgc tgctggaatt ggtgttgatg accttcgtcg cttatgcata   1500

ctcaggatga gttttgtgaa aggctgggga ccggattacc caagacagag catcaaagaa   1560

acaccttgct ggattgaaat tcacttacac cgggccctcc agctcctaga cgaagtactt   1620

cataccatgc cgattgcaga cccacaacct ttagactga                          1659
```

<210> SEQ ID NO 7
<211> LENGTH: 324
<212> TYPE: DNA
<213> ORGANISM: Mus musculus

<400> SEQUENCE: 7

```
gacatccaga tgacccagtc tccatcctcc ttatctgcct ctctgggaga aagagtcagt     60

ctcacttgtc gggcaagtct ggaaattagt ggtttcttaa gttggcttca gcagaaacca    120

gatggaacta ttaaacgcct gatctacgcc gcatccattt tagattctgg tgtcccaaaa    180

aggttcagtg gcagtaggtc tgggtcagat tattctctca ccatcagcag ccttgagtct    240

gaagattttg cagactatta ctgtctacaa tatgctagtt atccgtggac gttcggtgga    300

ggcaccaagc tggaaatcaa acgg                                           324
```

<210> SEQ ID NO 8
<211> LENGTH: 108
<212> TYPE: PRT
<213> ORGANISM: Mus musculus

<400> SEQUENCE: 8

```
Asp Ile Gln Met Thr Gln Ser Pro Ser Ser Leu Ser Ala Ser Leu Gly
1               5                   10                  15

Glu Arg Val Ser Leu Thr Cys Arg Ala Ser Leu Glu Ile Ser Gly Phe
            20                  25                  30

Leu Ser Trp Leu Gln Gln Lys Pro Asp Gly Thr Ile Lys Arg Leu Ile
        35                  40                  45

Tyr Ala Ala Ser Ile Leu Asp Ser Gly Val Pro Lys Arg Phe Ser Gly
    50                  55                  60

Ser Arg Ser Gly Ser Asp Tyr Ser Leu Thr Ile Ser Ser Leu Glu Ser
65                  70                  75                  80

Glu Asp Phe Ala Asp Tyr Tyr Cys Leu Gln Tyr Ala Ser Tyr Pro Trp
                85                  90                  95

Thr Phe Gly Gly Gly Thr Lys Leu Glu Ile Lys Arg
            100                 105
```

<210> SEQ ID NO 9
<211> LENGTH: 366
<212> TYPE: DNA
<213> ORGANISM: Mus musculus

<400> SEQUENCE: 9

```
cagatccagt tggtgcagtc tggacctgag ctgaagaagc ctggagagac agtcaagatc      60

tcctgcaagg cttctgggta taccttcaca aactatggaa tgaactgggt gaagcaggct     120

ccaggaaagg gtttaaagtg gatgggctgg ataaacacct acactggaga gccaacatat     180

gctgatgact tcaagggacg gtttgccttc tctttggaaa cctctgccag cactgcctat     240

ttgcagatca acaacctcaa aaatgaggac acggctacat atttctgtgc aagagggggg     300

tatggtaact acggggcggg ggctatggac tactggggtc aaggtacctc agtcaccgtc     360

tcctca                                                                366
```

<210> SEQ ID NO 10
<211> LENGTH: 122
<212> TYPE: PRT
<213> ORGANISM: Mus musculus

<400> SEQUENCE: 10

```
Gln Ile Gln Leu Val Gln Ser Gly Pro Glu Leu Lys Lys Pro Gly Glu
1               5                   10                  15

Thr Val Lys Ile Ser Cys Lys Ala Ser Gly Tyr Thr Phe Thr Asn Tyr
            20                  25                  30

Gly Met Asn Trp Val Lys Gln Ala Pro Gly Lys Gly Leu Lys Trp Met
        35                  40                  45

Gly Trp Ile Asn Thr Tyr Thr Gly Glu Pro Thr Tyr Ala Asp Asp Phe
    50                  55                  60

Lys Gly Arg Phe Ala Phe Ser Leu Glu Thr Ser Ala Ser Thr Ala Tyr
65                  70                  75                  80

Leu Gln Ile Asn Asn Leu Lys Asn Glu Asp Thr Ala Thr Tyr Phe Cys
                85                  90                  95

Ala Arg Gly Gly Tyr Gly Asn Tyr Gly Ala Gly Ala Met Asp Tyr Trp
            100                 105                 110

Gly Gln Gly Thr Ser Val Thr Val Ser Ser
        115                 120
```

<210> SEQ ID NO 11
<211> LENGTH: 11
<212> TYPE: PRT
<213> ORGANISM: Mus musculus

<400> SEQUENCE: 11

Arg Ala Ser Leu Glu Ile Ser Gly Phe Leu Ser
1 5 10

<210> SEQ ID NO 12
<211> LENGTH: 7
<212> TYPE: PRT
<213> ORGANISM: Mus musculus

<400> SEQUENCE: 12

Ala Ala Ser Ile Leu Asp Ser
1 5

<210> SEQ ID NO 13
<211> LENGTH: 9
<212> TYPE: PRT
<213> ORGANISM: Mus musculus

<400> SEQUENCE: 13

Leu Gln Tyr Ala Ser Tyr Pro Trp Thr
1 5

<210> SEQ ID NO 14
<211> LENGTH: 10
<212> TYPE: PRT
<213> ORGANISM: Mus musculus

<400> SEQUENCE: 14

Gly Tyr Thr Phe Thr Asn Tyr Gly Met Asn
1 5 10

<210> SEQ ID NO 15
<211> LENGTH: 10
<212> TYPE: PRT
<213> ORGANISM: Mus musculus

<400> SEQUENCE: 15

Trp Ile Asn Thr Tyr Thr Gly Glu Pro Thr
1 5 10

<210> SEQ ID NO 16
<211> LENGTH: 13
<212> TYPE: PRT
<213> ORGANISM: Mus musculus

<400> SEQUENCE: 16

Gly Gly Tyr Gly Asn Tyr Gly Ala Gly Ala Met Asp Tyr
1 5 10

<210> SEQ ID NO 17
<211> LENGTH: 324
<212> TYPE: DNA
<213> ORGANISM: Rattus norvegicus

<400> SEQUENCE: 17
gacatccaga tgacacagtc tccagcttcc ctgtctgcat ctctgggaga aactgtctcc 60
atcgaatgtc ttgcaagtga gggcatttcc aatagtttag cgtggtatca gcagaagcca 120
gggaaatctc ctcagctcct gatctatggt gcaagtagct tgcaagacgg ggtcccatca 180

```
cggttcagtg gcagtggatc tggcacacag tattctctca agatcagcgg catgcaacct    240

gaagatgaag ggtttatta ctgtcaacag ggttacaagt atccattcac gttcggctca     300

gggacgaagt tggaaataaa acgg                                           324


<210> SEQ ID NO 18
<211> LENGTH: 108
<212> TYPE: PRT
<213> ORGANISM: Rattus norvegicus

<400> SEQUENCE: 18

Asp Ile Gln Met Thr Gln Ser Pro Ala Ser Leu Ser Ala Ser Leu Gly
1               5                   10                  15

Glu Thr Val Ser Ile Glu Cys Leu Ala Ser Glu Gly Ile Ser Asn Ser
            20                  25                  30

Leu Ala Trp Tyr Gln Gln Lys Pro Gly Lys Ser Pro Gln Leu Leu Ile
        35                  40                  45

Tyr Gly Ala Ser Ser Leu Gln Asp Gly Val Pro Ser Arg Phe Ser Gly
    50                  55                  60

Ser Gly Ser Gly Thr Gln Tyr Ser Leu Lys Ile Ser Gly Met Gln Pro
65                  70                  75                  80

Glu Asp Glu Gly Val Tyr Tyr Cys Gln Gln Gly Tyr Lys Tyr Pro Phe
                85                  90                  95

Thr Phe Gly Ser Gly Thr Lys Leu Glu Ile Lys Arg
            100                 105


<210> SEQ ID NO 19
<211> LENGTH: 351
<212> TYPE: DNA
<213> ORGANISM: Rattus norvegicus

<400> SEQUENCE: 19

gaggtgcagc ttcaggagtc aggacctggc cttgtgaaac cctcacagtc actctccctc     60

acctgttctg tcactggtta ctccatcact agtaattact ggggctggat ccggaagttc    120

ccaggaaata aaatggagtg gatgggatgc ataacctaca gtggtggcac tagctacaac    180

ccatctctca aaagtcgaat ctccattact agagacacat caaagaatca gttcttcctg    240

cagttgaact ctgtaactac tgaggacaca gccacatatt actgtgcaag ttcctatacc    300

agtggtgacg tcgattactg gggccaagga gtcatggtca cagtctcctc a             351


<210> SEQ ID NO 20
<211> LENGTH: 117
<212> TYPE: PRT
<213> ORGANISM: Rattus norvegicus

<400> SEQUENCE: 20

Glu Val Gln Leu Gln Glu Ser Gly Pro Gly Leu Val Lys Pro Ser Gln
1               5                   10                  15

Ser Leu Ser Leu Thr Cys Ser Val Thr Gly Tyr Ser Ile Thr Ser Asn
            20                  25                  30

Tyr Trp Gly Trp Ile Arg Lys Phe Pro Gly Asn Lys Met Glu Trp Met
        35                  40                  45

Gly Cys Ile Thr Tyr Ser Gly Gly Thr Ser Tyr Asn Pro Ser Leu Lys
    50                  55                  60

Ser Arg Ile Ser Ile Thr Arg Asp Thr Ser Lys Asn Gln Phe Phe Leu
65                  70                  75                  80
```

-continued

```
Gln Leu Asn Ser Val Thr Thr Glu Asp Thr Ala Thr Tyr Tyr Cys Ala
                85                  90                  95

Ser Ser Tyr Thr Ser Gly Asp Val Asp Tyr Trp Gly Gln Gly Val Met
            100                 105                 110

Val Thr Val Ser Ser
        115


<210> SEQ ID NO 21
<211> LENGTH: 11
<212> TYPE: PRT
<213> ORGANISM: Rattus norvegicus

<400> SEQUENCE: 21

Leu Ala Ser Glu Gly Ile Ser Asn Ser Leu Ala
1               5                   10


<210> SEQ ID NO 22
<211> LENGTH: 7
<212> TYPE: PRT
<213> ORGANISM: Rattus norvegicus

<400> SEQUENCE: 22

Gly Ala Ser Ser Leu Gln Asp
1               5


<210> SEQ ID NO 23
<211> LENGTH: 9
<212> TYPE: PRT
<213> ORGANISM: Rattus norvegicus

<400> SEQUENCE: 23

Gln Gln Gly Tyr Lys Tyr Pro Phe Thr
1               5


<210> SEQ ID NO 24
<211> LENGTH: 10
<212> TYPE: PRT
<213> ORGANISM: Rattus norvegicus

<400> SEQUENCE: 24

Gly Tyr Ser Ile Thr Ser Asn Tyr Trp Gly
1               5                   10


<210> SEQ ID NO 25
<211> LENGTH: 9
<212> TYPE: PRT
<213> ORGANISM: Rattus norvegicus

<400> SEQUENCE: 25

Cys Ile Thr Tyr Ser Gly Gly Thr Ser
1               5


<210> SEQ ID NO 26
<211> LENGTH: 9
<212> TYPE: PRT
<213> ORGANISM: Rattus norvegicus

<400> SEQUENCE: 26

Ser Tyr Thr Ser Gly Asp Val Asp Tyr
1               5
```

<210> SEQ ID NO 27
<211> LENGTH: 449
<212> TYPE: DNA
<213> ORGANISM: Artificial Sequence
<220> FEATURE:
<223> OTHER INFORMATION: DNA comprising DNA sequence coding for human light chain signal sequence and human kappa chain constant region

<400> SEQUENCE: 27
gcctccggac tctagagcca ccatggtgct gcagacccag gtgttcatct ccctgctgct 60
gtggatctcc ggcgcgtacg gcgatatcgt gatgattaaa cgtacggtgg ccgccccctc 120
cgtgttcatc ttccccccct ccgacgagca gctgaagtcc ggcaccgcct ccgtggtgtg 180
cctgctgaat aacttctacc ccagagaggc caaggtgcag tggaaggtgg acaacgccct 240
gcagtccggg aactcccagg agagcgtgac cgagcaggac agcaaggaca gcacctacag 300
cctgagcagc accctgaccc tgagcaaagc cgactacgag aagcacaagg tgtacgcctg 360
cgaggtgacc caccagggcc tgagctcccc cgtcaccaag agcttcaaca ggggggagtg 420
ttaggggccc gtttaaacgg gggaggcta 449

<210> SEQ ID NO 28
<211> LENGTH: 1132
<212> TYPE: DNA
<213> ORGANISM: Artificial Sequence
<220> FEATURE:
<223> OTHER INFORMATION: DNA comprising DNA sequence coding for amino acid of human heavy chain signal sequence and human IgG1 constant region

<400> SEQUENCE: 28
gcctccggac tctagagcca ccatgaaaca cctgtggttc ttcctcctgc tggtggcagc 60
tcccagatgg gtgctgagcc aggtgcaatt gtgcaggcgg ttagctcagc ctccaccaag 120
ggcccaagcg tcttccccct ggcaccctcc tccaagagca cctctggcgg cacagccgcc 180
ctgggctgcc tggtcaagga ctacttcccc gaacccgtga ccgtgagctg gaactcaggc 240
gccctgacca gcggcgtgca caccttcccc gctgtcctgc agtcctcagg actctactcc 300
ctcagcagcg tggtgaccgt gccctccagc agcttgggca cccagaccta catctgcaac 360
gtgaatcaca agcccagcaa caccaaggtg gacaagagag ttgagcccaa atcttgtgac 420
aaaactcaca catgcccacc ctgcccagca cctgaactcc tggggggacc ctcagtcttc 480
ctcttccccc caaaacccaa ggacaccctc atgatctccc ggacccctga ggtcacatgc 540
gtggtggtgg acgtgagcca cgaagaccct gaggtcaagt tcaactggta cgtggacggc 600
gtggaggtgc ataatgccaa gacaaagccc cgggaggagc agtacaacag cacgtaccgg 660
gtggtcagcg tcctcaccgt cctgcaccag gactggctga atggcaagga gtacaagtgc 720
aaggtctcca acaaagccct cccagccccc atcgagaaaa ccatctccaa agccaaaggc 780
cagccccggg aaccacaggt gtacaccctg cccccatccc gggaggagat gaccaagaac 840
caggtcagcc tgacctgcct ggtcaaaggc ttctatccca gcgacatcgc cgtggagtgg 900
gagagcaatg gccagcccga gaacaactac aagaccaccc ctcccgtgct ggactccgac 960
ggctccttct tcctctacag caagctcacc gtggacaaga gcaggtggca gcagggcaac 1020
gtcttctcat gctccgtgat gcatgaggct ctgcacaacc actacaccca gaagagcctc 1080
tccctgtctc ccggcaaatg agatatcggg cccgtttaaa cgggggaggc ta 1132

<210> SEQ ID NO 29
<211> LENGTH: 1114
<212> TYPE: DNA
<213> ORGANISM: Artificial Sequence
<220> FEATURE:
<223> OTHER INFORMATION: DNA comprising DNA sequence coding for amino acid of human heavy chain signal sequence and human IgG2 constant region

<400> SEQUENCE: 29
ccagcctccg gactctagag ccaccatgaa acacctgtgg ttcttcctcc tgctggtggc 60
agctcccaga tgggtgctga gccaggtgca attgtgcagg cggttagctc agcctccacc 120
aagggccctt ccgtgttccc tctggcccct tgtagccgtt ccaccagcga gtccaccgcc 180
gcccttggct gtctggtgaa ggactacttc cctgagcctg tgaccgtgag ctggaactcc 240
ggagccctta ccagcggcgt gcacaccttc cctgccgtgc tgcagtccag cggcctttac 300
tccctgagct ccgtggtgac cgtgcctagc tccaacttcg gcacccaaac ctacacctgt 360
aacgtggacc acaagcctag caacaccaag gtggacaaga ccgtggagcg taagtgttgt 420
gtggagtgtc ctccttgtcc tgcccctcct gtggccggac cttccgtgtt cctttttccct 480 cctaagccta aggacaccct gatgatcagc cgtacccctg aggtgacctg tgtggtggtg 540
gacgtgtccc acgaggaccc tgaggtgcag ttcaactggt acgtggacgg cgtggaggtg 600
cacaacgcca agaccaagcc tcgtgaggag caattcaaca gcaccttccg tgtggtgtcc 660
gtgcttaccg tggtgcacca agactggctg aacggcaagg agtacaagtg taaggtgagc 720
aacaagggac ttcctgcccc tatcgagaag accatctcca agaccaaggg ccaacctcgt 780
gagcctcaag tgtacaccct tcctcctagc cgtgaggaga tgaccaagaa ccaagtgtcc 840
cttacctgtc tggtgaaggg cttctaccct agcgacatcg ccgtggagtg ggagtccaac 900
ggacaacctg agaacaacta caagaccacc cctcctatgc ttgacagcga cggctccttc 960
ttcctgtaca gcaagctgac cgtggacaag tcccgttggc aacaaggcaa cgtgttcagc 1020
tgttccgtga tgcacgaggc cctgcacaac cactacaccc aaaagagcct ttccctgagc 1080
cctggaaagt gagtttaaac gggggaggct aact 1114

<210> SEQ ID NO 30
<211> LENGTH: 702
<212> TYPE: DNA
<213> ORGANISM: Artificial Sequence
<220> FEATURE:
<223> OTHER INFORMATION: Light chain of human chimeric LN22R8

<400> SEQUENCE: 30
atggtgctgc agacccaggt gttcatctcc ctgctgctgt ggatctccgg cgcgtacggc 60
gacatccaga tgacccagtc tccatcctcc ttatctgcct ctctgggaga aagagtcagt 120
ctcacttgtc gggcaagtct ggaaattagt ggtttcttaa gttggcttca gcagaaacca 180
gatggaacta ttaaacgcct gatctacgcc gcatccattt tagattctgg tgtcccaaaa 240
aggttcagtg gcagtaggtc tgggtcagat tattctctca ccatcagcag ccttgagtct 300
gaagattttg cagactatta ctgtctacaa tatgctagtt atccgtggac gttcggtgga 360
ggcaccaagc tggaaatcaa acgggctgtg gccgcccccct ccgtgttcat cttccccccc 420
tccgacgagc agctgaagtc cggcaccgcc tccgtggtgt gcctgctgaa taacttctac 480
cccagagagg ccaaggtgca gtggaaggtg gacaacgccc tgcagtccgg gaactcccag 540
gagagcgtga ccgagcagga cagcaaggac agcacctaca gcctgagcag caccctgacc 600
ctgagcaaag ccgactacga gaagcacaag gtgtacgcct gcgaggtgac ccaccagggc 660
ctgagctccc ccgtcaccaa gagcttcaac aggggggagt gt 702

<210> SEQ ID NO 31
<211> LENGTH: 234
<212> TYPE: PRT
<213> ORGANISM: Artificial Sequence
<220> FEATURE:
<223> OTHER INFORMATION: Light chain of human chimeric LN22R8

<400> SEQUENCE: 31

Met Val Leu Gln Thr Gln Val Phe Ile Ser Leu Leu Leu Trp Ile Ser
1 5 10 15

Gly Ala Tyr Gly Asp Ile Gln Met Thr Gln Ser Pro Ser Ser Leu Ser
20 25 30

Ala Ser Leu Gly Glu Arg Val Ser Leu Thr Cys Arg Ala Ser Leu Glu
35 40 45

Ile Ser Gly Phe Leu Ser Trp Leu Gln Gln Lys Pro Asp Gly Thr Ile
50 55 60

Lys Arg Leu Ile Tyr Ala Ala Ser Ile Leu Asp Ser Gly Val Pro Lys
65 70 75 80

Arg Phe Ser Gly Ser Arg Ser Gly Ser Asp Tyr Ser Leu Thr Ile Ser
85 90 95

Ser Leu Glu Ser Glu Asp Phe Ala Asp Tyr Tyr Cys Leu Gln Tyr Ala
100 105 110

Ser Tyr Pro Trp Thr Phe Gly Gly Gly Thr Lys Leu Glu Ile Lys Arg
115 120 125

Ala Val Ala Ala Pro Ser Val Phe Ile Phe Pro Pro Ser Asp Glu Gln
130 135 140

Leu Lys Ser Gly Thr Ala Ser Val Val Cys Leu Leu Asn Asn Phe Tyr
145 150 155 160

Pro Arg Glu Ala Lys Val Gln Trp Lys Val Asp Asn Ala Leu Gln Ser
165 170 175

Gly Asn Ser Gln Glu Ser Val Thr Glu Gln Asp Ser Lys Asp Ser Thr
180 185 190

Tyr Ser Leu Ser Ser Thr Leu Thr Leu Ser Lys Ala Asp Tyr Glu Lys
195 200 205

His Lys Val Tyr Ala Cys Glu Val Thr His Gln Gly Leu Ser Ser Pro
210 215 220

Val Thr Lys Ser Phe Asn Arg Gly Glu Cys
225 230

<210> SEQ ID NO 32
<211> LENGTH: 1413
<212> TYPE: DNA
<213> ORGANISM: Artificial Sequence
<220> FEATURE:
<223> OTHER INFORMATION: Heavy chain IgG1 type of human chimeric LN22R8

<400> SEQUENCE: 32
atgaaacacc tgtggttctt cctcctgctg gtggcagctc ccagatgggt gctgagccag 60
atccagttgg tgcagtctgg acctgagctg aagaagcctg gagagacagt caagatctcc 120
tgcaaggctt ctgggtatac cttcacaaac tatggaatga actgggtgaa gcaggctcca 180
ggaaagggtt taaagtggat gggctggata aacacctaca ctggagagcc aacatatgct 240
gatgacttca agggacggtt tgccttctct ttggaaacct ctgccagcac tgcctatttg 300

-continued cagatcaaca acctcaaaaa tgaggacacg gctacatatt tctgtgcaag agggggggtat 360 ggtaactacg gggcgggggc tatggactac tggggtcaag gtacctcagt caccgtcagc 420
tcagcctcca ccaagggccc aagcgtcttc cccctggcac cctcctccaa gagcacctct 480
ggcggcacag ccgccctggg ctgcctggtc aaggactact tccccgaacc cgtgaccgtg 540
agctggaact caggcgccct gaccagcggc gtgcacacct tccccgctgt cctgcagtcc 600
tcaggactct actccctcag cagcgtggtg accgtgccct ccagcagctt gggcacccag 660
acctacatct gcaacgtgaa tcacaagccc agcaacacca aggtggacaa gagagttgag 720
cccaaatctt gtgacaaaac tcacacatgc ccaccctgcc cagcacctga actcctgggg 780
ggaccctcag tcttcctctt ccccccaaaa cccaaggaca ccctcatgat ctcccggacc 840
cctgaggtca catgcgtggt ggtggacgtg agccacgaag accctgaggt caagttcaac 900
tggtacgtgg acggcgtgga ggtgcataat gccaagacaa agccccggga ggagcagtac 960
aacagcacgt accgggtggt cagcgtcctc accgtcctgc accaggactg gctgaatggc 1020
aaggagtaca agtgcaaggt ctccaacaaa gccctcccag cccccatcga gaaaaccatc 1080
tccaaagcca aaggccagcc ccgggaacca caggtgtaca ccctgccccc atcccgggag 1140
gagatgacca agaaccaggt cagcctgacc tgcctggtca aaggcttcta tcccagcgac 1200
atcgccgtgg agtgggagag caatggccag cccgagaaca actacaagac cacccctccc 1260
gtgctggact ccgacggctc cttcttcctc tacagcaagc tcaccgtgga caagagcagg 1320
tggcagcagg gcaacgtctt ctcatgctcc gtgatgcatg aggctctgca caaccactac 1380
acccagaaga gcctctccct gtctcccggc aaa 1413

<210> SEQ ID NO 33
<211> LENGTH: 471
<212> TYPE: PRT
<213> ORGANISM: Artificial Sequence
<220> FEATURE:
<223> OTHER INFORMATION: Heavy chain IgG1 type of human chimeric LN22R8

<400> SEQUENCE: 33

Met Lys His Leu Trp Phe Phe Leu Leu Leu Val Ala Ala Pro Arg Trp
1 5 10 15

Val Leu Ser Gln Ile Gln Leu Val Gln Ser Gly Pro Glu Leu Lys Lys
20 25 30

Pro Gly Glu Thr Val Lys Ile Ser Cys Lys Ala Ser Gly Tyr Thr Phe
35 40 45

Thr Asn Tyr Gly Met Asn Trp Val Lys Gln Ala Pro Gly Lys Gly Leu
50 55 60

Lys Trp Met Gly Trp Ile Asn Thr Tyr Thr Gly Glu Pro Thr Tyr Ala
65 70 75 80

Asp Asp Phe Lys Gly Arg Phe Ala Phe Ser Leu Glu Thr Ser Ala Ser
85 90 95

Thr Ala Tyr Leu Gln Ile Asn Asn Leu Lys Asn Glu Asp Thr Ala Thr
100 105 110

Tyr Phe Cys Ala Arg Gly Gly Tyr Gly Asn Tyr Gly Ala Gly Ala Met
115 120 125

Asp Tyr Trp Gly Gln Gly Thr Ser Val Thr Val Ser Ser Ala Ser Thr
130 135 140

Lys Gly Pro Ser Val Phe Pro Leu Ala Pro Ser Ser Lys Ser Thr Ser
145 150 155 160

-continued

```
Gly Gly Thr Ala Ala Leu Gly Cys Leu Val Lys Asp Tyr Phe Pro Glu
                165                 170                 175

Pro Val Thr Val Ser Trp Asn Ser Gly Ala Leu Thr Ser Gly Val His
            180                 185                 190

Thr Phe Pro Ala Val Leu Gln Ser Ser Gly Leu Tyr Ser Leu Ser Ser
        195                 200                 205

Val Val Thr Val Pro Ser Ser Ser Leu Gly Thr Gln Thr Tyr Ile Cys
    210                 215                 220

Asn Val Asn His Lys Pro Ser Asn Thr Lys Val Asp Lys Arg Val Glu
225                 230                 235                 240

Pro Lys Ser Cys Asp Lys Thr His Thr Cys Pro Pro Cys Pro Ala Pro
                245                 250                 255

Glu Leu Leu Gly Gly Pro Ser Val Phe Leu Phe Pro Pro Lys Pro Lys
            260                 265                 270

Asp Thr Leu Met Ile Ser Arg Thr Pro Glu Val Thr Cys Val Val Val
        275                 280                 285

Asp Val Ser His Glu Asp Pro Glu Val Lys Phe Asn Trp Tyr Val Asp
    290                 295                 300

Gly Val Glu Val His Asn Ala Lys Thr Lys Pro Arg Glu Glu Gln Tyr
305                 310                 315                 320

Asn Ser Thr Tyr Arg Val Val Ser Val Leu Thr Val Leu His Gln Asp
                325                 330                 335

Trp Leu Asn Gly Lys Glu Tyr Lys Cys Lys Val Ser Asn Lys Ala Leu
            340                 345                 350

Pro Ala Pro Ile Glu Lys Thr Ile Ser Lys Ala Lys Gly Gln Pro Arg
        355                 360                 365

Glu Pro Gln Val Tyr Thr Leu Pro Pro Ser Arg Glu Glu Met Thr Lys
    370                 375                 380

Asn Gln Val Ser Leu Thr Cys Leu Val Lys Gly Phe Tyr Pro Ser Asp
385                 390                 395                 400

Ile Ala Val Glu Trp Glu Ser Asn Gly Gln Pro Glu Asn Asn Tyr Lys
                405                 410                 415

Thr Thr Pro Pro Val Leu Asp Ser Asp Gly Ser Phe Phe Leu Tyr Ser
            420                 425                 430

Lys Leu Thr Val Asp Lys Ser Arg Trp Gln Gln Gly Asn Val Phe Ser
        435                 440                 445

Cys Ser Val Met His Glu Ala Leu His Asn His Tyr Thr Gln Lys Ser
    450                 455                 460

Leu Ser Leu Ser Pro Gly Lys
465                 470
```

<210> SEQ ID NO 34
<211> LENGTH: 1401
<212> TYPE: DNA
<213> ORGANISM: Artificial Sequence
<220> FEATURE:
<223> OTHER INFORMATION: Heavy chain IgG2 type of human chimeric LN22R8

<400> SEQUENCE: 34

```
atgaaacacc tgtggttctt cctcctgctg gtggcagctc ccagatgggt gctgagccag      60

atccagttgg tgcagtctgg acctgagctg aagaagcctg gagagacagt caagatctcc     120

tgcaaggctt ctgggtatac cttcacaaac tatggaatga actgggtgaa gcaggctcca     180

ggaaagggtt taaagtggat gggctggata aacacctaca ctggagagcc aacatatgct     240

gatgacttca agggacggtt tgccttctct ttggaaacct ctgccagcac tgcctatttg     300
```

-continued

```
cagatcaaca acctcaaaaa tgaggacacg gctacatatt tctgtgcaag agggggggtat    360

ggtaactacg gggcgggggc tatggactac tggggtcaag gtacctcagt caccgtcagc    420

tcagcctcca ccaagggccc ttccgtgttc cctctggccc cttgtagccg ttccaccagc    480

gagtccaccg ccgcccttgg ctgtctggtg aaggactact tccctgagcc tgtgaccgtg    540

agctggaact ccggagccct taccagcggc gtgcacacct tccctgccgt gctgcagtcc    600

agcggccttt actccctgag ctccgtggtg accgtgccta gctccaactt cggcacccaa    660

acctacacct gtaacgtgga ccacaagcct agcaacacca aggtggacaa gaccgtggag    720

cgtaagtgtt gtgtggagtg tcctccttgt cctgcccctc ctgtggccgg accttccgtg    780

ttccttttcc ctcctaagcc taaggacacc ctgatgatca gccgtacccc tgaggtgacc    840

tgtgtggtgg tggacgtgtc ccacgaggac cctgaggtgc agttcaactg gtacgtggac    900

ggcgtggagg tgcacaacgc caagaccaag cctcgtgagg agcaattcaa cagcaccttc    960

cgtgtggtgt ccgtgcttac cgtggtgcac caagactggc tgaacggcaa ggagtacaag   1020

tgtaaggtga gcaacaaggg acttcctgcc cctatcgaga agaccatctc caagaccaag   1080

ggccaacctc gtgagcctca agtgtacacc cttcctccta gccgtgagga gatgaccaag   1140

aaccaagtgt cccttacctg tctggtgaag ggcttctacc ctagcgacat cgccgtggag   1200

tgggagtcca acggacaacc tgagaacaac tacaagacca cccctcctat gcttgacagc   1260

gacggctcct tcttcctgta cagcaagctg accgtggaca agtcccgttg gcaacaaggc   1320

aacgtgttca gctgttccgt gatgcacgag gccctgcaca accactacac ccaaaagagc   1380

ctttccctga gccctggaaa g                                              1401
```

<210> SEQ ID NO 35
<211> LENGTH: 467
<212> TYPE: PRT
<213> ORGANISM: Artificial Sequence
<220> FEATURE:
<223> OTHER INFORMATION: Heavy chain IgG2 type of human chimeric LN22R8

<400> SEQUENCE: 35

```
Met Lys His Leu Trp Phe Phe Leu Leu Leu Val Ala Ala Pro Arg Trp
1               5                   10                  15

Val Leu Ser Gln Ile Gln Leu Val Gln Ser Gly Pro Glu Leu Lys Lys
            20                  25                  30

Pro Gly Glu Thr Val Lys Ile Ser Cys Lys Ala Ser Gly Tyr Thr Phe
        35                  40                  45

Thr Asn Tyr Gly Met Asn Trp Val Lys Gln Ala Pro Gly Lys Gly Leu
    50                  55                  60

Lys Trp Met Gly Trp Ile Asn Thr Tyr Thr Gly Glu Pro Thr Tyr Ala
65                  70                  75                  80

Asp Asp Phe Lys Gly Arg Phe Ala Phe Ser Leu Glu Thr Ser Ala Ser
                85                  90                  95

Thr Ala Tyr Leu Gln Ile Asn Asn Leu Lys Asn Glu Asp Thr Ala Thr
            100                 105                 110

Tyr Phe Cys Ala Arg Gly Gly Tyr Gly Asn Tyr Gly Ala Gly Ala Met
        115                 120                 125

Asp Tyr Trp Gly Gln Gly Thr Ser Val Thr Val Ser Ser Ala Ser Thr
    130                 135                 140

Lys Gly Pro Ser Val Phe Pro Leu Ala Pro Cys Ser Arg Ser Thr Ser
145                 150                 155                 160
```

-continued

```
Glu Ser Thr Ala Ala Leu Gly Cys Leu Val Lys Asp Tyr Phe Pro Glu
                165                 170                 175

Pro Val Thr Val Ser Trp Asn Ser Gly Ala Leu Thr Ser Gly Val His
            180                 185                 190

Thr Phe Pro Ala Val Leu Gln Ser Ser Gly Leu Tyr Ser Leu Ser Ser
        195                 200                 205

Val Val Thr Val Pro Ser Ser Asn Phe Gly Thr Gln Thr Tyr Thr Cys
    210                 215                 220

Asn Val Asp His Lys Pro Ser Asn Thr Lys Val Asp Lys Thr Val Glu
225                 230                 235                 240

Arg Lys Cys Cys Val Glu Cys Pro Pro Cys Pro Ala Pro Pro Val Ala
                245                 250                 255

Gly Pro Ser Val Phe Leu Phe Pro Pro Lys Pro Lys Asp Thr Leu Met
            260                 265                 270

Ile Ser Arg Thr Pro Glu Val Thr Cys Val Val Val Asp Val Ser His
        275                 280                 285

Glu Asp Pro Glu Val Gln Phe Asn Trp Tyr Val Asp Gly Val Glu Val
    290                 295                 300

His Asn Ala Lys Thr Lys Pro Arg Glu Glu Gln Phe Asn Ser Thr Phe
305                 310                 315                 320

Arg Val Val Ser Val Leu Thr Val Val His Gln Asp Trp Leu Asn Gly
                325                 330                 335

Lys Glu Tyr Lys Cys Lys Val Ser Asn Lys Gly Leu Pro Ala Pro Ile
            340                 345                 350

Glu Lys Thr Ile Ser Lys Thr Lys Gly Gln Pro Arg Glu Pro Gln Val
        355                 360                 365

Tyr Thr Leu Pro Pro Ser Arg Glu Glu Met Thr Lys Asn Gln Val Ser
    370                 375                 380

Leu Thr Cys Leu Val Lys Gly Phe Tyr Pro Ser Asp Ile Ala Val Glu
385                 390                 395                 400

Trp Glu Ser Asn Gly Gln Pro Glu Asn Asn Tyr Lys Thr Thr Pro Pro
                405                 410                 415

Met Leu Asp Ser Asp Gly Ser Phe Phe Leu Tyr Ser Lys Leu Thr Val
            420                 425                 430

Asp Lys Ser Arg Trp Gln Gln Gly Asn Val Phe Ser Cys Ser Val Met
        435                 440                 445

His Glu Ala Leu His Asn His Tyr Thr Gln Lys Ser Leu Ser Leu Ser
    450                 455                 460

Pro Gly Lys
465


<210> SEQ ID NO 36
<211> LENGTH: 1454
<212> TYPE: DNA
<213> ORGANISM: Artificial Sequence
<220> FEATURE:
<223> OTHER INFORMATION: DNA comprising DNA sequence coding for amino
      acid sequence of human chimera LN22R8_heavy chain_ IgG4P type

<400> SEQUENCE: 36

ccagcctccg gactctagag ccaccatgaa gcacctgtgg ttctttctgc tgctggtggc      60

cgctcccaga tgggtgctgt ctcagatcca gctggtgcag agcggccctg agctgaagaa     120

acccggcgag acagtgaaga tcagctgcaa ggccagcggc tacaccttca ccaactacgg     180

catgaactgg gtcaagcagg cccctggcaa gggcctgaag tggatgggct ggatcaacac     240
```

-continued

```
ctacaccggc gagcccacct acgccgacga cttcaagggc agattcgcct tcagcctgga    300

aaccagcgcc agcaccgcct acctgcagat caacaacctg aagaacgagg acaccgccac    360

ctacttttgc gccagaggcg gctacggcaa ttacggcgct ggcgccatgg attactgggg    420

ccagggaaca agcgtgaccg tgtccagcgc ctctaccaag ggccctagcg tgttccctct    480

ggccccttgc agcagaagca ccagcgaatc tacagccgcc ctgggctgcc tcgtgaagga    540

ctactttccc gagcccgtga cagtgtcctg gaactctggc gccctgacaa gcggcgtgca    600

cacctttcca gccgtgctgc agagcagcgg cctgtactct ctgagcagcg tcgtgactgt    660

gcccagcagc tctctgggca ccaagaccta cacctgtaac gtggaccaca agcccagcaa    720

caccaaggtg gacaagcggg tggaatctaa gtacggccct ccctgccctc cttgcccagc    780

ccctgaattt ctgggcggac cctccgtgtt cctgttcccc ccaaagccca aggacaccct    840

gatgatcagc cggacccccg aagtgacctg cgtggtggtg gatgtgtccc aggaagatcc    900

cgaggtgcag ttcaattggt acgtggacgg cgtggaagtg cacaacgcca agaccaagcc    960

tagagaggaa cagttcaaca gcacctaccg ggtggtgtcc gtgctgacag tgctgcacca   1020

ggactggctg aacggcaaag agtacaagtg caaggtgtcc aacaagggac tgcccagctc   1080

catcgagaaa accatcagca aggccaaggg ccagccccgc gaaccccagg tgtacacact   1140

gcctccaagc caggaagaga tgaccaagaa ccaggtgtcc ctgacctgtc tcgtgaaagg   1200

cttctacccc tccgatatcg ccgtggaatg ggagagcaac ggccagcccg agaacaacta   1260

caagaccacc ccccctgtgc tggacagcga cggctcattc ttcctgtaca gcagactgac   1320

cgtggacaag agccggtggc aggaaggcaa cgtgttcagc tgcagcgtga tgcacgaggc   1380

cctgcacaac cactacaccc agaagtccct gtctctgagc ctgggcaaat gagtttaaac   1440

gggggaggct aact                                                     1454


<210> SEQ ID NO 37
<211> LENGTH: 468
<212> TYPE: PRT
<213> ORGANISM: Artificial Sequence
<220> FEATURE:
<223> OTHER INFORMATION: Heavy chain IgG4P type of human chimeric LN22R8

<400> SEQUENCE: 37

Met Lys His Leu Trp Phe Phe Leu Leu Leu Val Ala Ala Pro Arg Trp
1               5                   10                  15

Val Leu Ser Gln Ile Gln Leu Val Gln Ser Gly Pro Glu Leu Lys Lys
            20                  25                  30

Pro Gly Glu Thr Val Lys Ile Ser Cys Lys Ala Ser Gly Tyr Thr Phe
        35                  40                  45

Thr Asn Tyr Gly Met Asn Trp Val Lys Gln Ala Pro Gly Lys Gly Leu
    50                  55                  60

Lys Trp Met Gly Trp Ile Asn Thr Tyr Thr Gly Glu Pro Thr Tyr Ala
65                  70                  75                  80

Asp Asp Phe Lys Gly Arg Phe Ala Phe Ser Leu Glu Thr Ser Ala Ser
                85                  90                  95

Thr Ala Tyr Leu Gln Ile Asn Asn Leu Lys Asn Glu Asp Thr Ala Thr
            100                 105                 110

Tyr Phe Cys Ala Arg Gly Gly Tyr Gly Asn Tyr Gly Ala Gly Ala Met
        115                 120                 125

Asp Tyr Trp Gly Gln Gly Thr Ser Val Thr Val Ser Ser Ala Ser Thr
    130                 135                 140
```

-continued

Lys Gly Pro Ser Val Phe Pro Leu Ala Pro Cys Ser Arg Ser Thr Ser
145 150 155 160

Glu Ser Thr Ala Ala Leu Gly Cys Leu Val Lys Asp Tyr Phe Pro Glu
165 170 175

Pro Val Thr Val Ser Trp Asn Ser Gly Ala Leu Thr Ser Gly Val His
180 185 190

Thr Phe Pro Ala Val Leu Gln Ser Ser Gly Leu Tyr Ser Leu Ser Ser
195 200 205

Val Val Thr Val Pro Ser Ser Ser Leu Gly Thr Lys Thr Tyr Thr Cys
210 215 220

Asn Val Asp His Lys Pro Ser Asn Thr Lys Val Asp Lys Arg Val Glu
225 230 235 240

Ser Lys Tyr Gly Pro Pro Cys Pro Pro Cys Pro Ala Pro Glu Phe Leu
245 250 255

Gly Gly Pro Ser Val Phe Leu Phe Pro Pro Lys Pro Lys Asp Thr Leu
260 265 270

Met Ile Ser Arg Thr Pro Glu Val Thr Cys Val Val Val Asp Val Ser
275 280 285

Gln Glu Asp Pro Glu Val Gln Phe Asn Trp Tyr Val Asp Gly Val Glu
290 295 300

Val His Asn Ala Lys Thr Lys Pro Arg Glu Glu Gln Phe Asn Ser Thr
305 310 315 320

Tyr Arg Val Val Ser Val Leu Thr Val Leu His Gln Asp Trp Leu Asn
325 330 335

Gly Lys Glu Tyr Lys Cys Lys Val Ser Asn Lys Gly Leu Pro Ser Ser
340 345 350

Ile Glu Lys Thr Ile Ser Lys Ala Lys Gly Gln Pro Arg Glu Pro Gln
355 360 365

Val Tyr Thr Leu Pro Pro Ser Gln Glu Glu Met Thr Lys Asn Gln Val
370 375 380

Ser Leu Thr Cys Leu Val Lys Gly Phe Tyr Pro Ser Asp Ile Ala Val
385 390 395 400

Glu Trp Glu Ser Asn Gly Gln Pro Glu Asn Asn Tyr Lys Thr Thr Pro
405 410 415

Pro Val Leu Asp Ser Asp Gly Ser Phe Phe Leu Tyr Ser Arg Leu Thr
420 425 430

Val Asp Lys Ser Arg Trp Gln Glu Gly Asn Val Phe Ser Cys Ser Val
435 440 445

Met His Glu Ala Leu His Asn His Tyr Thr Gln Lys Ser Leu Ser Leu
450 455 460

Ser Leu Gly Lys
465

<210> SEQ ID NO 38
<211> LENGTH: 1137
<212> TYPE: DNA
<213> ORGANISM: Artificial Sequence
<220> FEATURE:
<223> OTHER INFORMATION: DNA comprising DNA sequence coding for amino acid of human heavy chain signal sequence and human IgG1LALA constant region

<400> SEQUENCE: 38
ccagcctccg gactctagag ccaccatgaa acacctgtgg ttcttcctcc tgctggtggc 60
agctcccaga tgggtgctga gccaggtgca attgtgcagg cggttagctc agcctccacc 120

```
aagggcccaa gcgtcttccc cctggcaccc tcctccaaga gcacctctgg cggcacagcc    180

gccctgggct gcctggtcaa ggactacttc cccgaacccg tgaccgtgag ctggaactca    240

ggcgccctga ccagcggcgt gcacaccttc cccgctgtcc tgcagtcctc aggactctac    300

tccctcagca gcgtggtgac cgtgccctcc agcagcttgg gcacccagac ctacatctgc    360

aacgtgaatc acaagcccag caacaccaag gtggacaaga gagttgagcc caaatcttgt    420

gacaaaactc acacatgccc accctgccca gcacctgaag ccgcgggggg accctcagtc    480

ttcctcttcc ccccaaaacc caaggacacc ctcatgatct cccggacccc tgaggtcaca    540

tgcgtggtgg tggacgtgag ccacgaagac cctgaggtca agttcaactg gtacgtggac    600

ggcgtggagg tgcataatgc caagacaaag ccccgggagg agcagtacaa cagcacgtac    660

cgggtggtca gcgtcctcac cgtcctgcac caggactggc tgaatggcaa ggagtacaag    720

tgcaaggtct ccaacaaagc cctcccagcc cccatcgaga aaaccatctc caaagccaaa    780

ggccagcccc gggaaccaca ggtgtacacc ctgcccccat cccgggagga gatgaccaag    840

aaccaggtca gcctgacctg cctggtcaaa ggcttctatc ccagcgacat cgccgtggag    900

tgggagagca atggccagcc cgagaacaac tacaagacca cccctcccgt gctggactcc    960

gacggctcct tcttcctcta cagcaagctc accgtggaca agagcaggtg gcagcagggc   1020

aacgtcttct catgctccgt gatgcatgag gctctgcaca accactacac ccagaagagc   1080

ctctccctgt ctcccggcaa atgagatatc gggcccgttt aaacggggga ggctaac      1137
```

<210> SEQ ID NO 39
<211> LENGTH: 1117
<212> TYPE: DNA
<213> ORGANISM: Artificial Sequence
<220> FEATURE:
<223> OTHER INFORMATION: DNA comprising DNA sequence coding for amino acid of human heavy chain signal sequence and human IgG4P constant region

<400> SEQUENCE: 39

```
ccagcctccg gactctagag ccaccatgaa acacctgtgg ttcttcctcc tgctggtggc     60

agctcccaga tgggtgctga gccaggtgca attgtgcagg cggttagctc agcctccacc    120

aagggcccta gcgtgttccc tctggcccct tgtagcagaa gcaccagcga gtctacagcc    180

gccctgggct gcctcgtgaa ggactacttt cccgagcccg tgaccgtgtc ctggaactct    240

ggcgctctga caagcggcgt gcacaccttt ccagccgtgc tgcagagcag cggcctgtac    300

tctctgtcca gcgtcgtgac tgtgcccagc agctctctgg gcaccaagac ctacacctgt    360

aacgtggacc acaagcccag caacaccaag gtggacaagc gggtggaatc taagtacggc    420

cctccctgcc ctccttgccc agcccctgaa tttctgggcg gaccctccgt gttcctgttc    480

cccccaaagc ccaaggacac cctgatgatc agccggaccc ccgaagtgac ctgcgtggtg    540

gtggatgtgt cccaggaaga tcccgaggtg cagttcaatt ggtacgtgga cggcgtggaa    600

gtgcacaacg ccaagaccaa gcctagagag gaacagttca acagcaccta ccgggtggtg    660

tccgtgctga cagtgctgca ccaggactgg ctgaacggca aagagtacaa gtgcaaggtg    720

tccaacaagg gcctgcccag ctccatcgag aaaaccatca gcaaggccaa gggccagccc    780

cgcgaacccc aggtgtacac actgcctcca agccaggaag agatgaccaa gaatcaggtg    840

tccctgacct gtctcgtgaa aggcttctac ccctccgata tcgccgtgga atgggagagc    900

aacggccagc ccgagaacaa ctacaagacc acccccccctg tgctggactc cgatggctca    960

ttcttcctgt acagcagact gaccgtggac aagagccggt ggcaggaagg caacgtgttc   1020
```

-continued agctgctccg tgatgcacga ggccctgcac aaccactaca cccagaagtc cctgtctctg 1080
agcctgggca aatgagttta aacgggggag gctaact 1117

<210> SEQ ID NO 40
<211> LENGTH: 702
<212> TYPE: DNA
<213> ORGANISM: Artificial Sequence
<220> FEATURE:
<223> OTHER INFORMATION: Light chain of human chimeric 2P10F2

<400> SEQUENCE: 40
atggtgctgc agacccaggt gttcatctcc ctgctgctgt ggatctccgg cgcgtacggc 60
gacatccaga tgacacagtc tccagcttcc ctgtctgcat ctctgggaga aactgtctcc 120
atcgaatgtc ttgcaagtga gggcatttcc aatagtttag cgtggtatca gcagaagcca 180
gggaaatctc ctcagctcct gatctatggt gcaagtagct tgcaagacgg ggtcccatca 240
cggttcagtg gcagtggatc tggcacacag tattctctca agatcagcgg catgcaacct 300
gaagatgaag ggtttatta ctgtcaacag ggttacaagt atccattcac gttcggctca 360
gggacgaagt tggaaataaa acgggctgtg gccgcccccct ccgtgttcat cttccccccc 420
tccgacgagc agctgaagtc cggcaccgcc tccgtggtgt gcctgctgaa taacttctac 480
cccagagagg ccaaggtgca gtggaaggtg gacaacgccc tgcagtccgg gaactcccag 540
gagagcgtga ccgagcagga cagcaaggac agcacctaca gcctgagcag caccctgacc 600
ctgagcaaag ccgactacga gaagcacaag gtgtacgcct gcgaggtgac ccaccagggc 660
ctgagctccc ccgtcaccaa gagcttcaac aggggggagt gt 702

<210> SEQ ID NO 41
<211> LENGTH: 234
<212> TYPE: PRT
<213> ORGANISM: Artificial Sequence
<220> FEATURE:
<223> OTHER INFORMATION: Light chain of human chimeric 2P10F2

<400> SEQUENCE: 41

Met Val Leu Gln Thr Gln Val Phe Ile Ser Leu Leu Leu Trp Ile Ser
1 5 10 15

Gly Ala Tyr Gly Asp Ile Gln Met Thr Gln Ser Pro Ala Ser Leu Ser
20 25 30

Ala Ser Leu Gly Glu Thr Val Ser Ile Glu Cys Leu Ala Ser Glu Gly
35 40 45

Ile Ser Asn Ser Leu Ala Trp Tyr Gln Gln Lys Pro Gly Lys Ser Pro
50 55 60

Gln Leu Leu Ile Tyr Gly Ala Ser Ser Leu Gln Asp Gly Val Pro Ser
65 70 75 80

Arg Phe Ser Gly Ser Gly Ser Gly Thr Gln Tyr Ser Leu Lys Ile Ser
85 90 95

Gly Met Gln Pro Glu Asp Glu Gly Val Tyr Tyr Cys Gln Gln Gly Tyr
100 105 110

Lys Tyr Pro Phe Thr Phe Gly Ser Gly Thr Lys Leu Glu Ile Lys Arg
115 120 125

Ala Val Ala Ala Pro Ser Val Phe Ile Phe Pro Pro Ser Asp Glu Gln
130 135 140

Leu Lys Ser Gly Thr Ala Ser Val Val Cys Leu Leu Asn Asn Phe Tyr
145 150 155 160

-continued

```
Pro Arg Glu Ala Lys Val Gln Trp Lys Val Asp Asn Ala Leu Gln Ser
                165                 170                 175

Gly Asn Ser Gln Glu Ser Val Thr Glu Gln Asp Ser Lys Asp Ser Thr
            180                 185                 190

Tyr Ser Leu Ser Ser Thr Leu Thr Leu Ser Lys Ala Asp Tyr Glu Lys
        195                 200                 205

His Lys Val Tyr Ala Cys Glu Val Thr His Gln Gly Leu Ser Ser Pro
    210                 215                 220

Val Thr Lys Ser Phe Asn Arg Gly Glu Cys
225                 230
```

<210> SEQ ID NO 42
<211> LENGTH: 1398
<212> TYPE: DNA
<213> ORGANISM: Artificial Sequence
<220> FEATURE:
<223> OTHER INFORMATION: Heavy chain IgG1LALA type of human chimeric 2P10F2

<400> SEQUENCE: 42

```
atgaaacacc tgtggttctt cctcctgctg gtggcagctc ccagatgggt gctgagcgag     60

gtgcagcttc aggagtcagg acctggcctt gtgaaaccct cacagtcact ctccctcacc    120

tgttctgtca ctggttactc catcactagt aattactggg gctggatccg gaagttccca    180

ggaaataaaa tggagtggat gggatgcata acctacagtg gtggcactag ctacaaccca    240

tctctcaaaa gtcgaatctc cattactaga gacacatcaa agaatcagtt cttcctgcag    300

ttgaactctg taactactga ggacacagcc acatattact gtgcaagttc ctataccagt    360

ggtgacgtcg attactgggg ccaaggagtc atggtcacag tcagctcagc ctccaccaag    420

ggcccaagcg tcttcccct ggcaccctcc tccaagagca cctctggcgg cacagccgcc    480

ctgggctgcc tggtcaagga ctacttcccc gaacccgtga ccgtgagctg gaactcaggc    540

gccctgacca gcggcgtgca caccttcccc gctgtcctgc agtcctcagg actctactcc    600

ctcagcagcg tggtgaccgt gccctccagc agcttgggca cccagaccta catctgcaac    660

gtgaatcaca agcccagcaa caccaaggtg gacaagagag ttgagcccaa atcttgtgac    720

aaaactcaca catgcccacc ctgcccagca cctgaagccg cgggggggacc ctcagtcttc    780

ctcttccccc caaaacccaa ggacaccctc atgatctccc ggacccctga ggtcacatgc    840

gtggtggtgg acgtgagcca cgaagaccct gaggtcaagt tcaactggta cgtggacggc    900

gtggaggtgc ataatgccaa gacaaagccc cgggaggagc agtacaacag cacgtaccgg    960

gtggtcagcg tcctcaccgt cctgcaccag gactggctga atggcaagga gtacaagtgc   1020

aaggtctcca acaaagccct cccagccccc atcgagaaaa ccatctccaa agccaaaggc   1080

cagccccggg aaccacaggt gtacaccctg cccccatccc gggaggagat gaccaagaac   1140

caggtcagcc tgacctgcct ggtcaaaggc ttctatccca gcgacatcgc cgtggagtgg   1200

gagagcaatg gccagcccga gaacaactac aagaccaccc ctcccgtgct ggactccgac   1260

ggctccttct tcctctacag caagctcacc gtggacaaga gcaggtggca gcagggcaac   1320

gtcttctcat gctccgtgat gcatgaggct ctgcacaacc actacaccca gaagagcctc   1380

tccctgtctc ccggcaaa                                                 1398
```

<210> SEQ ID NO 43
<211> LENGTH: 466
<212> TYPE: PRT
<213> ORGANISM: Artificial Sequence
<220> FEATURE:
<223> OTHER INFORMATION: Heavy chain IgG1LALA type of human chimeric 2P10F2

<400> SEQUENCE: 43

Met Lys His Leu Trp Phe Phe Leu Leu Leu Val Ala Ala Pro Arg Trp
1 5 10 15

Val Leu Ser Glu Val Gln Leu Gln Glu Ser Gly Pro Gly Leu Val Lys
20 25 30

Pro Ser Gln Ser Leu Ser Leu Thr Cys Ser Val Thr Gly Tyr Ser Ile
35 40 45

Thr Ser Asn Tyr Trp Gly Trp Ile Arg Lys Phe Pro Gly Asn Lys Met
50 55 60

Glu Trp Met Gly Cys Ile Thr Tyr Ser Gly Gly Thr Ser Tyr Asn Pro
65 70 75 80

Ser Leu Lys Ser Arg Ile Ser Ile Thr Arg Asp Thr Ser Lys Asn Gln
85 90 95

Phe Phe Leu Gln Leu Asn Ser Val Thr Thr Glu Asp Thr Ala Thr Tyr
100 105 110

Tyr Cys Ala Ser Ser Tyr Thr Ser Gly Asp Val Asp Tyr Trp Gly Gln
115 120 125

Gly Val Met Val Thr Val Ser Ser Ala Ser Thr Lys Gly Pro Ser Val
130 135 140

Phe Pro Leu Ala Pro Ser Ser Lys Ser Thr Ser Gly Gly Thr Ala Ala
145 150 155 160

Leu Gly Cys Leu Val Lys Asp Tyr Phe Pro Glu Pro Val Thr Val Ser
165 170 175

Trp Asn Ser Gly Ala Leu Thr Ser Gly Val His Thr Phe Pro Ala Val
180 185 190

Leu Gln Ser Ser Gly Leu Tyr Ser Leu Ser Ser Val Val Thr Val Pro
195 200 205

Ser Ser Ser Leu Gly Thr Gln Thr Tyr Ile Cys Asn Val Asn His Lys
210 215 220

Pro Ser Asn Thr Lys Val Asp Lys Arg Val Glu Pro Lys Ser Cys Asp
225 230 235 240

Lys Thr His Thr Cys Pro Pro Cys Pro Ala Pro Glu Ala Ala Gly Gly
245 250 255

Pro Ser Val Phe Leu Phe Pro Pro Lys Pro Lys Asp Thr Leu Met Ile
260 265 270

Ser Arg Thr Pro Glu Val Thr Cys Val Val Val Asp Val Ser His Glu
275 280 285

Asp Pro Glu Val Lys Phe Asn Trp Tyr Val Asp Gly Val Glu Val His
290 295 300

Asn Ala Lys Thr Lys Pro Arg Glu Glu Gln Tyr Asn Ser Thr Tyr Arg
305 310 315 320

Val Val Ser Val Leu Thr Val Leu His Gln Asp Trp Leu Asn Gly Lys
325 330 335

Glu Tyr Lys Cys Lys Val Ser Asn Lys Ala Leu Pro Ala Pro Ile Glu
340 345 350

Lys Thr Ile Ser Lys Ala Lys Gly Gln Pro Arg Glu Pro Gln Val Tyr
355 360 365

Thr Leu Pro Pro Ser Arg Glu Glu Met Thr Lys Asn Gln Val Ser Leu
370 375 380

-continued

```
Thr Cys Leu Val Lys Gly Phe Tyr Pro Ser Asp Ile Ala Val Glu Trp
385                 390                 395                 400

Glu Ser Asn Gly Gln Pro Glu Asn Asn Tyr Lys Thr Thr Pro Pro Val
                405                 410                 415

Leu Asp Ser Asp Gly Ser Phe Phe Leu Tyr Ser Lys Leu Thr Val Asp
            420                 425                 430

Lys Ser Arg Trp Gln Gln Gly Asn Val Phe Ser Cys Ser Val Met His
        435                 440                 445

Glu Ala Leu His Asn His Tyr Thr Gln Lys Ser Leu Ser Leu Ser Pro
    450                 455                 460

Gly Lys
465


<210> SEQ ID NO 44
<211> LENGTH: 1386
<212> TYPE: DNA
<213> ORGANISM: Artificial Sequence
<220> FEATURE:
<223> OTHER INFORMATION: Heavy chain IgG2 type of human chimeric 2P10F2

<400> SEQUENCE: 44

atgaaacacc tgtggttctt cctcctgctg gtggcagctc ccagatgggt gctgagcgag     60

gtgcagcttc aggagtcagg acctggcctt gtgaaaccct cacagtcact ctccctcacc    120

tgttctgtca ctggttactc catcactagt aattactggg gctggatccg gaagttccca    180

ggaaataaaa tggagtggat gggatgcata acctacagtg gtggcactag ctacaaccca    240

tctctcaaaa gtcgaatctc cattactaga gacacatcaa agaatcagtt cttcctgcag    300

ttgaactctg taactactga ggacacagcc acatattact gtgcaagttc ctataccagt    360

ggtgacgtcg attactgggg ccaaggagtc atggtcacag tcagctcagc ctccaccaag    420

ggcccttccg tgttccctct ggccccttgt agccgttcca ccagcgagtc caccgccgcc    480

cttggctgtc tggtgaagga ctacttccct gagcctgtga ccgtgagctg gaactccgga    540

gcccttacca gcggcgtgca caccttccct gccgtgctgc agtccagcgg cctttactcc    600

ctgagctccg tggtgaccgt gcctagctcc aacttcggca cccaaaccta cacctgtaac    660

gtggaccaca agcctagcaa caccaaggtg gacaagaccg tggagcgtaa gtgttgtgtg    720

gagtgtcctc cttgtcctgc ccctcctgtg gccggacctt ccgtgttcct tttccctcct    780

aagcctaagg acaccctgat gatcagccgt acccctgagg tgacctgtgt ggtggtggac    840

gtgtcccacg aggaccctga ggtgcagttc aactggtacg tggacggcgt ggaggtgcac    900

aacgccaaga ccaagcctcg tgaggagcaa ttcaacagca ccttccgtgt ggtgtccgtg    960

cttaccgtgg tgcaccaaga ctggctgaac ggcaaggagt acaagtgtaa ggtgagcaac   1020

aagggacttc ctgcccctat cgagaagacc atctccaaga ccaagggcca acctcgtgag   1080

cctcaagtgt acacccttcc tcctagccgt gaggagatga ccaagaacca agtgtccctt   1140

acctgtctgg tgaagggctt ctaccctagc gacatcgccg tggagtggga gtccaacgga   1200

caacctgaga acaactacaa gaccacccct cctatgcttg acagcgacgg ctccttcttc   1260

ctgtacagca agctgaccgt ggacaagtcc cgttggcaac aaggcaacgt gttcagctgt   1320

tccgtgatgc acgaggccct gcacaaccac tacacccaaa agagcctttc cctgagccct   1380

ggaaag                                                              1386
```

<210> SEQ ID NO 45
<211> LENGTH: 462
<212> TYPE: PRT
<213> ORGANISM: Artificial Sequence
<220> FEATURE:
<223> OTHER INFORMATION: Heavy chain IgG2 type of human chimeric 2P10F2

<400> SEQUENCE: 45

```
Met Lys His Leu Trp Phe Phe Leu Leu Leu Val Ala Ala Pro Arg Trp
1               5                   10                  15

Val Leu Ser Glu Val Gln Leu Gln Glu Ser Gly Pro Gly Leu Val Lys
            20                  25                  30

Pro Ser Gln Ser Leu Ser Leu Thr Cys Ser Val Thr Gly Tyr Ser Ile
        35                  40                  45

Thr Ser Asn Tyr Trp Gly Trp Ile Arg Lys Phe Pro Gly Asn Lys Met
    50                  55                  60

Glu Trp Met Gly Cys Ile Thr Tyr Ser Gly Gly Thr Ser Tyr Asn Pro
65                  70                  75                  80

Ser Leu Lys Ser Arg Ile Ser Ile Thr Arg Asp Thr Ser Lys Asn Gln
                85                  90                  95

Phe Phe Leu Gln Leu Asn Ser Val Thr Thr Glu Asp Thr Ala Thr Tyr
            100                 105                 110

Tyr Cys Ala Ser Ser Tyr Thr Ser Gly Asp Val Asp Tyr Trp Gly Gln
        115                 120                 125

Gly Val Met Val Thr Val Ser Ser Ala Ser Thr Lys Gly Pro Ser Val
    130                 135                 140

Phe Pro Leu Ala Pro Cys Ser Arg Ser Thr Ser Glu Ser Thr Ala Ala
145                 150                 155                 160

Leu Gly Cys Leu Val Lys Asp Tyr Phe Pro Glu Pro Val Thr Val Ser
                165                 170                 175

Trp Asn Ser Gly Ala Leu Thr Ser Gly Val His Thr Phe Pro Ala Val
            180                 185                 190

Leu Gln Ser Ser Gly Leu Tyr Ser Leu Ser Ser Val Val Thr Val Pro
        195                 200                 205

Ser Ser Asn Phe Gly Thr Gln Thr Tyr Thr Cys Asn Val Asp His Lys
    210                 215                 220

Pro Ser Asn Thr Lys Val Asp Lys Thr Val Glu Arg Lys Cys Cys Val
225                 230                 235                 240

Glu Cys Pro Pro Cys Pro Ala Pro Pro Val Ala Gly Pro Ser Val Phe
                245                 250                 255

Leu Phe Pro Pro Lys Pro Lys Asp Thr Leu Met Ile Ser Arg Thr Pro
            260                 265                 270

Glu Val Thr Cys Val Val Val Asp Val Ser His Glu Asp Pro Glu Val
        275                 280                 285

Gln Phe Asn Trp Tyr Val Asp Gly Val Glu Val His Asn Ala Lys Thr
    290                 295                 300

Lys Pro Arg Glu Glu Gln Phe Asn Ser Thr Phe Arg Val Val Ser Val
305                 310                 315                 320

Leu Thr Val Val His Gln Asp Trp Leu Asn Gly Lys Glu Tyr Lys Cys
                325                 330                 335

Lys Val Ser Asn Lys Gly Leu Pro Ala Pro Ile Glu Lys Thr Ile Ser
            340                 345                 350

Lys Thr Lys Gly Gln Pro Arg Glu Pro Gln Val Tyr Thr Leu Pro Pro
        355                 360                 365
```

Ser Arg Glu Glu Met Thr Lys Asn Gln Val Ser Leu Thr Cys Leu Val
    370                 375                 380

Lys Gly Phe Tyr Pro Ser Asp Ile Ala Val Glu Trp Glu Ser Asn Gly
385                 390                 395                 400

Gln Pro Glu Asn Asn Tyr Lys Thr Thr Pro Pro Met Leu Asp Ser Asp
                405                 410                 415

Gly Ser Phe Phe Leu Tyr Ser Lys Leu Thr Val Asp Lys Ser Arg Trp
            420                 425                 430

Gln Gln Gly Asn Val Phe Ser Cys Ser Val Met His Glu Ala Leu His
        435                 440                 445

Asn His Tyr Thr Gln Lys Ser Leu Ser Leu Ser Pro Gly Lys
    450                 455                 460

<210> SEQ ID NO 46
<211> LENGTH: 1389
<212> TYPE: DNA
<213> ORGANISM: Artificial Sequence
<220> FEATURE:
<223> OTHER INFORMATION: Heavy chain IgG4P type of human chimeric 2P10F2

<400> SEQUENCE: 46
atgaaacacc tgtggttctt cctcctgctg gtggcagctc ccagatgggt gctgagcgag 60
gtgcagcttc aggagtcagg acctggcctt gtgaaaccct cacagtcact ctccctcacc 120
tgttctgtca ctggttactc catcactagt aattactggg gctggatccg gaagttccca 180
ggaaataaaa tggagtggat gggatgcata acctacagtg gtggcactag ctacaaccca 240
tctctcaaaa gtcgaatctc cattactaga gacacatcaa agaatcagtt cttcctgcag 300
ttgaactctg taactactga ggacacagcc acatattact gtgcaagttc ctataccagt 360
ggtgacgtcg attactgggg ccaaggagtc atggtcacag tcagctcagc ctccaccaag 420
ggccctagcg tgttccctct ggccccttgt agcagaagca ccagcgagtc tacagccgcc 480
ctgggctgcc tcgtgaagga ctactttccc gagcccgtga ccgtgtcctg gaactctggc 540
gctctgacaa gcggcgtgca cacctttcca gccgtgctgc agagcagcgg cctgtactct 600
ctgtccagcg tcgtgactgt gcccagcagc tctctgggca ccaagaccta cacctgtaac 660
gtggaccaca agcccagcaa caccaaggtg gacaagcggg tggaatctaa gtacggccct 720
ccctgccctc cttgcccagc ccctgaattt ctgggcggac cctccgtgtt cctgttcccc 780
ccaaagccca aggacaccct gatgatcagc cggacccccg aagtgacctg cgtggtggtg 840
gatgtgtccc aggaagatcc cgaggtgcag ttcaattggt acgtggacgg cgtggaagtg 900
cacaacgcca agaccaagcc tagagaggaa cagttcaaca gcacctaccg ggtggtgtcc 960
gtgctgacag tgctgcacca ggactggctg aacggcaaag agtacaagtg caaggtgtcc 1020
aacaagggcc tgcccagctc catcgagaaa accatcagca aggccaaggg ccagccccgc 1080
gaaccccagg tgtacacact gcctccaagc caggaagaga tgaccaagaa tcaggtgtcc 1140
ctgacctgtc tcgtgaaagg cttctacccc tccgatatcg ccgtggaatg ggagagcaac 1200
ggccagcccg agaacaacta caagaccacc ccccctgtgc tggactccga tggctcattc 1260
ttcctgtaca gcagactgac cgtggacaag agccggtggc aggaaggcaa cgtgttcagc 1320
tgctccgtga tgcacgaggc cctgcacaac cactacaccc agaagtccct gtctctgagc 1380
ctgggcaaa 1389

<210> SEQ ID NO 47
<211> LENGTH: 463
<212> TYPE: PRT
<213> ORGANISM: Artificial Sequence
<220> FEATURE:
<223> OTHER INFORMATION: Heavy chain IgG4P type of human chimeric 2P10F2

<400> SEQUENCE: 47

```
Met Lys His Leu Trp Phe Phe Leu Leu Leu Val Ala Ala Pro Arg Trp
1               5                   10                  15

Val Leu Ser Glu Val Gln Leu Gln Glu Ser Gly Pro Gly Leu Val Lys
            20                  25                  30

Pro Ser Gln Ser Leu Ser Leu Thr Cys Ser Val Thr Gly Tyr Ser Ile
        35                  40                  45

Thr Ser Asn Tyr Trp Gly Trp Ile Arg Lys Phe Pro Gly Asn Lys Met
    50                  55                  60

Glu Trp Met Gly Cys Ile Thr Tyr Ser Gly Gly Thr Ser Tyr Asn Pro
65                  70                  75                  80

Ser Leu Lys Ser Arg Ile Ser Ile Thr Arg Asp Thr Ser Lys Asn Gln
                85                  90                  95

Phe Phe Leu Gln Leu Asn Ser Val Thr Thr Glu Asp Thr Ala Thr Tyr
            100                 105                 110

Tyr Cys Ala Ser Ser Tyr Thr Ser Gly Asp Val Asp Tyr Trp Gly Gln
        115                 120                 125

Gly Val Met Val Thr Val Ser Ser Ala Ser Thr Lys Gly Pro Ser Val
    130                 135                 140

Phe Pro Leu Ala Pro Cys Ser Arg Ser Thr Ser Glu Ser Thr Ala Ala
145                 150                 155                 160

Leu Gly Cys Leu Val Lys Asp Tyr Phe Pro Glu Pro Val Thr Val Ser
                165                 170                 175

Trp Asn Ser Gly Ala Leu Thr Ser Gly Val His Thr Phe Pro Ala Val
            180                 185                 190

Leu Gln Ser Ser Gly Leu Tyr Ser Leu Ser Ser Val Val Thr Val Pro
        195                 200                 205

Ser Ser Ser Leu Gly Thr Lys Thr Tyr Thr Cys Asn Val Asp His Lys
    210                 215                 220

Pro Ser Asn Thr Lys Val Asp Lys Arg Val Glu Ser Lys Tyr Gly Pro
225                 230                 235                 240

Pro Cys Pro Pro Cys Pro Ala Pro Glu Phe Leu Gly Gly Pro Ser Val
                245                 250                 255

Phe Leu Phe Pro Pro Lys Pro Lys Asp Thr Leu Met Ile Ser Arg Thr
            260                 265                 270

Pro Glu Val Thr Cys Val Val Val Asp Val Ser Gln Glu Asp Pro Glu
        275                 280                 285

Val Gln Phe Asn Trp Tyr Val Asp Gly Val Glu Val His Asn Ala Lys
    290                 295                 300

Thr Lys Pro Arg Glu Glu Gln Phe Asn Ser Thr Tyr Arg Val Val Ser
305                 310                 315                 320

Val Leu Thr Val Leu His Gln Asp Trp Leu Asn Gly Lys Glu Tyr Lys
                325                 330                 335

Cys Lys Val Ser Asn Lys Gly Leu Pro Ser Ser Ile Glu Lys Thr Ile
            340                 345                 350

Ser Lys Ala Lys Gly Gln Pro Arg Glu Pro Gln Val Tyr Thr Leu Pro
        355                 360                 365
```

```
Pro Ser Gln Glu Glu Met Thr Lys Asn Gln Val Ser Leu Thr Cys Leu
    370                 375                 380

Val Lys Gly Phe Tyr Pro Ser Asp Ile Ala Val Glu Trp Glu Ser Asn
385                 390                 395                 400

Gly Gln Pro Glu Asn Asn Tyr Lys Thr Thr Pro Pro Val Leu Asp Ser
                405                 410                 415

Asp Gly Ser Phe Phe Leu Tyr Ser Arg Leu Thr Val Asp Lys Ser Arg
            420                 425                 430

Trp Gln Glu Gly Asn Val Phe Ser Cys Ser Val Met His Glu Ala Leu
        435                 440                 445

His Asn His Tyr Thr Gln Lys Ser Leu Ser Leu Ser Leu Gly Lys
    450                 455                 460
```

<210> SEQ ID NO 48
<211> LENGTH: 324
<212> TYPE: DNA
<213> ORGANISM: Rattus norvegicus

<400> SEQUENCE: 48

```
gatgtccaga tgacccagtc tccatcttat cttgctgcgt ctcctggaga aagtgtttcc      60

atcagttgca aggcaagtaa gagcattagc aataatttag cctggtatca ggagaaacct     120

gggaaagcaa ataagcttct tattcactct gggtcaactt tgcaatctgg aactccatcg     180

aggttcagtg gcagtggatc tggtacagat ttcacgctca ccatcagaag cctggagttt     240

gaagattttg cagtctatta ctgtcaacag tataatgaat acccactcac gttcggttct     300

gggaccaagc tggagatcaa acgg                                            324
```

<210> SEQ ID NO 49
<211> LENGTH: 108
<212> TYPE: PRT
<213> ORGANISM: Rattus norvegicus

<400> SEQUENCE: 49

```
Asp Val Gln Met Thr Gln Ser Pro Ser Tyr Leu Ala Ala Ser Pro Gly
1               5                   10                  15

Glu Ser Val Ser Ile Ser Cys Lys Ala Ser Lys Ser Ile Ser Asn Asn
            20                  25                  30

Leu Ala Trp Tyr Gln Glu Lys Pro Gly Lys Ala Asn Lys Leu Leu Ile
        35                  40                  45

His Ser Gly Ser Thr Leu Gln Ser Gly Thr Pro Ser Arg Phe Ser Gly
    50                  55                  60

Ser Gly Ser Gly Thr Asp Phe Thr Leu Thr Ile Arg Ser Leu Glu Phe
65                  70                  75                  80

Glu Asp Phe Ala Val Tyr Tyr Cys Gln Gln Tyr Asn Glu Tyr Pro Leu
                85                  90                  95

Thr Phe Gly Ser Gly Thr Lys Leu Glu Ile Lys Arg
            100                 105
```

<210> SEQ ID NO 50
<211> LENGTH: 363
<212> TYPE: DNA
<213> ORGANISM: Rattus norvegicus

<400> SEQUENCE: 50

```
gaggtgcagc tggtggagtc tgggggaggc ctagtgcagc ctggaaggtc cctgaaactc      60

tcctgtgcag cctcaggatt cactttcagt aactattaca tggcctgggt ccgccaggct     120
```

-continued

```
ccaaagaagg gtctggagtg ggtcgcaacc attactacca gtggtagcag accttactat    180

ccagactccg tgaaaggccg attcactatc tccagagata atgcaaaaag cagcctatac    240

ctgcaaatga acagtctgaa gtctgaggac acggccactt attactgtgc aagacatatt    300

tattactatg atggttaccc ctttgcttac tggggccaag gcactctggt cactgtctct    360

tca                                                                   363


<210> SEQ ID NO 51
<211> LENGTH: 121
<212> TYPE: PRT
<213> ORGANISM: Rattus norvegicus

<400> SEQUENCE: 51

Glu Val Gln Leu Val Glu Ser Gly Gly Gly Leu Val Gln Pro Gly Arg
1               5                   10                  15

Ser Leu Lys Leu Ser Cys Ala Ala Ser Gly Phe Thr Phe Ser Asn Tyr
            20                  25                  30

Tyr Met Ala Trp Val Arg Gln Ala Pro Lys Lys Gly Leu Glu Trp Val
        35                  40                  45

Ala Thr Ile Thr Thr Ser Gly Ser Arg Pro Tyr Tyr Pro Asp Ser Val
    50                  55                  60

Lys Gly Arg Phe Thr Ile Ser Arg Asp Asn Ala Lys Ser Ser Leu Tyr
65                  70                  75                  80

Leu Gln Met Asn Ser Leu Lys Ser Glu Asp Thr Ala Thr Tyr Tyr Cys
                85                  90                  95

Ala Arg His Ile Tyr Tyr Tyr Asp Gly Tyr Pro Phe Ala Tyr Trp Gly
            100                 105                 110

Gln Gly Thr Leu Val Thr Val Ser Ser
        115                 120


<210> SEQ ID NO 52
<211> LENGTH: 11
<212> TYPE: PRT
<213> ORGANISM: Rattus norvegicus

<400> SEQUENCE: 52

Lys Ala Ser Lys Ser Ile Ser Asn Asn Leu Ala
1               5                   10


<210> SEQ ID NO 53
<211> LENGTH: 7
<212> TYPE: PRT
<213> ORGANISM: Rattus norvegicus

<400> SEQUENCE: 53

Ser Gly Ser Thr Leu Gln Ser
1               5


<210> SEQ ID NO 54
<211> LENGTH: 9
<212> TYPE: PRT
<213> ORGANISM: Rattus norvegicus

<400> SEQUENCE: 54

Gln Gln Tyr Asn Glu Tyr Pro Leu Thr
1               5
```

-continued

<210> SEQ ID NO 55
<211> LENGTH: 10
<212> TYPE: PRT
<213> ORGANISM: Rattus norvegicus

<400> SEQUENCE: 55

Gly Phe Thr Phe Ser Asn Tyr Tyr Met Ala
1               5                   10

<210> SEQ ID NO 56
<211> LENGTH: 10
<212> TYPE: PRT
<213> ORGANISM: Rattus norvegicus

<400> SEQUENCE: 56

Thr Ile Thr Thr Ser Gly Ser Arg Pro Tyr
1               5                   10

<210> SEQ ID NO 57
<211> LENGTH: 12
<212> TYPE: PRT
<213> ORGANISM: Rattus norvegicus

<400> SEQUENCE: 57

His Ile Tyr Tyr Tyr Asp Gly Tyr Pro Phe Ala Tyr
1               5                   10

<210> SEQ ID NO 58
<211> LENGTH: 324
<212> TYPE: DNA
<213> ORGANISM: Rattus norvegicus

<400> SEQUENCE: 58
gacatccaga tgacccagtc tccttcactc ctgtctgcat ctgtgggagg cagaatcact      60
ctcaactgca aagcaagtca gaatctctat aagaacttag cctggtatca gcagaagctt     120
ggagaagctc ccaaactcct gattgataat gcaaacagtt tgcaaacggg catcccatca     180
aggttcagtg gcagtggatc tggtacagat ttcacactca ccatcagcag cctgcagcct     240
gaagatgttg ccacatattt ctgccagcag tattatagcg ggtcgtacac gtttggagct     300
gggaccaagc tggaactgaa acgg                                            324

<210> SEQ ID NO 59
<211> LENGTH: 108
<212> TYPE: PRT
<213> ORGANISM: Rattus norvegicus

<400> SEQUENCE: 59

Asp Ile Gln Met Thr Gln Ser Pro Ser Leu Leu Ser Ala Ser Val Gly
1               5                   10                  15

Gly Arg Ile Thr Leu Asn Cys Lys Ala Ser Gln Asn Leu Tyr Lys Asn
            20                  25                  30

Leu Ala Trp Tyr Gln Gln Lys Leu Gly Glu Ala Pro Lys Leu Leu Ile
        35                  40                  45

Asp Asn Ala Asn Ser Leu Gln Thr Gly Ile Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Val Ala Thr Tyr Phe Cys Gln Gln Tyr Tyr Ser Gly Ser Tyr
85 90 95

Thr Phe Gly Ala Gly Thr Lys Leu Glu Leu Lys Arg
100 105

<210> SEQ ID NO 60
<211> LENGTH: 354
<212> TYPE: DNA
<213> ORGANISM: Rattus norvegicus

<400> SEQUENCE: 60
gaggtgcagc tggtggagtc tgatggaggc ttagtgcagc ctggaaggtc cctaaaactc 60
tcctgtgcag cctcaggatt cactttcagt gactattaca tggcctgggt ccgccaggct 120
ccaacgaagg ggctggagtg ggtcgcaacc attagttatg atggtagtaa cacttactat 180
cgagactccg tgaagggccg attcactatc tccagagata atgcaaaaag caccctatac 240
ctgcaaatgg acagtctgag gtctggggac acggccactt attactgtgc aagattttac 300
aacaactact actttgatta ctggggccaa ggagtcatgg tcacagtctc ctca 354

<210> SEQ ID NO 61
<211> LENGTH: 118
<212> TYPE: PRT
<213> ORGANISM: Rattus norvegicus

<400> SEQUENCE: 61

Glu Val Gln Leu Val Glu Ser Asp Gly Gly Leu Val Gln Pro Gly Arg
1 5 10 15

Ser Leu Lys Leu Ser Cys Ala Ala Ser Gly Phe Thr Phe Ser Asp Tyr
20 25 30

Tyr Met Ala Trp Val Arg Gln Ala Pro Thr Lys Gly Leu Glu Trp Val
35 40 45

Ala Thr Ile Ser Tyr Asp Gly Ser Asn Thr Tyr Tyr Arg Asp Ser Val
50 55 60

Lys Gly Arg Phe Thr Ile Ser Arg Asp Asn Ala Lys Ser Thr Leu Tyr
65 70 75 80

Leu Gln Met Asp Ser Leu Arg Ser Gly Asp Thr Ala Thr Tyr Tyr Cys
85 90 95

Ala Arg Phe Tyr Asn Asn Tyr Tyr Phe Asp Tyr Trp Gly Gln Gly Val
100 105 110

Met Val Thr Val Ser Ser
115

<210> SEQ ID NO 62
<211> LENGTH: 11
<212> TYPE: PRT
<213> ORGANISM: Rattus norvegicus

<400> SEQUENCE: 62

Lys Ala Ser Gln Asn Leu Tyr Lys Asn Leu Ala
1 5 10

<210> SEQ ID NO 63
<211> LENGTH: 7
<212> TYPE: PRT
<213> ORGANISM: Rattus norvegicus

<400> SEQUENCE: 63

Asn Ala Asn Ser Leu Gln Thr
1 5

<210> SEQ ID NO 64
<211> LENGTH: 9
<212> TYPE: PRT
<213> ORGANISM: Rattus norvegicus

<400> SEQUENCE: 64

Gln Gln Tyr Tyr Ser Gly Ser Tyr Thr
1 5

<210> SEQ ID NO 65
<211> LENGTH: 10
<212> TYPE: PRT
<213> ORGANISM: Rattus norvegicus

<400> SEQUENCE: 65

Gly Phe Thr Phe Ser Asp Tyr Tyr Met Ala
1 5 10

<210> SEQ ID NO 66
<211> LENGTH: 10
<212> TYPE: PRT
<213> ORGANISM: Rattus norvegicus

<400> SEQUENCE: 66

Thr Ile Ser Tyr Asp Gly Ser Asn Thr Tyr
1 5 10

<210> SEQ ID NO 67
<211> LENGTH: 9
<212> TYPE: PRT
<213> ORGANISM: Rattus norvegicus

<400> SEQUENCE: 67

Phe Tyr Asn Asn Tyr Tyr Phe Asp Tyr
1 5

<210> SEQ ID NO 68
<211> LENGTH: 324
<212> TYPE: DNA
<213> ORGANISM: Rattus norvegicus

<400> SEQUENCE: 68
gacatccaga tgacccagac tccatcctcc atgcctgcat ctctgggaga gagagtcacc 60
atcagttgca gagcaagtca gggtattagc aattatctaa actggtatca gcagaaacca 120
gatggaacga ttaaacccct gatctactac acatccaatt tacaatctgg tgtcccatca 180
aggttcagtg gcagtgggtc tgggacagat tattctctca ccatcagcag cctggagcct 240
gaagattttg caatgtattt ctgccaacag tatgatagtt ctcctcggac gttcggtgga 300
ggcaccaagc tggaattgaa acgg 324

<210> SEQ ID NO 69
<211> LENGTH: 108
<212> TYPE: PRT
<213> ORGANISM: Rattus norvegicus

<400> SEQUENCE: 69

Asp Ile Gln Met Thr Gln Thr Pro Ser Ser Met Pro Ala Ser Leu Gly
1 5 10 15

Glu Arg Val Thr Ile Ser Cys Arg Ala Ser Gln Gly Ile Ser Asn Tyr
20 25 30

Leu Asn Trp Tyr Gln Gln Lys Pro Asp Gly Thr Ile Lys Pro Leu Ile
35 40 45

```
Tyr Tyr Thr Ser Asn Leu Gln Ser Gly Val Pro Ser Arg Phe Ser Gly
    50                  55                  60

Ser Gly Ser Gly Thr Asp Tyr Ser Leu Thr Ile Ser Ser Leu Glu Pro
65                  70                  75                  80

Glu Asp Phe Ala Met Tyr Phe Cys Gln Gln Tyr Asp Ser Ser Pro Arg
                85                  90                  95

Thr Phe Gly Gly Gly Thr Lys Leu Glu Leu Lys Arg
            100                 105


<210> SEQ ID NO 70
<211> LENGTH: 351
<212> TYPE: DNA
<213> ORGANISM: Rattus norvegicus

<400> SEQUENCE: 70

caggtacagc tgcagcaatc tggggctgaa ctggtgaagc ctgggtcctc agtgaaaatt      60

tcctgcaagg cttctggcta caccttcacc agtgacttta tgcactggat aaaacagcag     120

cctggaaatg gccttgagtg gattgggtgg atttatcctg gagatggtga tacagagtac     180

aatcaaaagt tcaatgggaa ggcaacactc actgcagaca aatcctccag cacagcctat     240

atgcagctca gcagcctgac atctgaggac tctgcagtct atttctgtgc aaggggacgg     300

gggtatgtta tggatgcctg gggtcaagga gcttcagtca ctgtctcctc a              351


<210> SEQ ID NO 71
<211> LENGTH: 117
<212> TYPE: PRT
<213> ORGANISM: Rattus norvegicus

<400> SEQUENCE: 71

Gln Val Gln Leu Gln Gln Ser Gly Ala Glu Leu Val Lys Pro Gly Ser
1               5                   10                  15

Ser Val Lys Ile Ser Cys Lys Ala Ser Gly Tyr Thr Phe Thr Ser Asp
            20                  25                  30

Phe Met His Trp Ile Lys Gln Gln Pro Gly Asn Gly Leu Glu Trp Ile
        35                  40                  45

Gly Trp Ile Tyr Pro Gly Asp Gly Asp Thr Glu Tyr Asn Gln Lys Phe
    50                  55                  60

Asn Gly Lys Ala Thr Leu Thr Ala Asp Lys Ser Ser Ser Thr Ala Tyr
65                  70                  75                  80

Met Gln Leu Ser Ser Leu Thr Ser Glu Asp Ser Ala Val Tyr Phe Cys
                85                  90                  95

Ala Arg Gly Arg Gly Tyr Val Met Asp Ala Trp Gly Gln Gly Ala Ser
            100                 105                 110

Val Thr Val Ser Ser
        115


<210> SEQ ID NO 72
<211> LENGTH: 11
<212> TYPE: PRT
<213> ORGANISM: Rattus norvegicus

<400> SEQUENCE: 72

Arg Ala Ser Gln Gly Ile Ser Asn Tyr Leu Asn
1               5                   10
```

<210> SEQ ID NO 73
<211> LENGTH: 7
<212> TYPE: PRT
<213> ORGANISM: Rattus norvegicus

<400> SEQUENCE: 73

Tyr Thr Ser Asn Leu Gln Ser
1               5

<210> SEQ ID NO 74
<211> LENGTH: 9
<212> TYPE: PRT
<213> ORGANISM: Rattus norvegicus

<400> SEQUENCE: 74

Gln Gln Tyr Asp Ser Ser Pro Arg Thr
1               5

<210> SEQ ID NO 75
<211> LENGTH: 10
<212> TYPE: PRT
<213> ORGANISM: Rattus norvegicus

<400> SEQUENCE: 75

Gly Tyr Thr Phe Thr Ser Asp Phe Met His
1               5                   10

<210> SEQ ID NO 76
<211> LENGTH: 10
<212> TYPE: PRT
<213> ORGANISM: Rattus norvegicus

<400> SEQUENCE: 76

Trp Ile Tyr Pro Gly Asp Gly Asp Thr Glu
1               5                   10

<210> SEQ ID NO 77
<211> LENGTH: 8
<212> TYPE: PRT
<213> ORGANISM: Rattus norvegicus

<400> SEQUENCE: 77

Gly Arg Gly Tyr Val Met Asp Ala
1               5

<210> SEQ ID NO 78
<211> LENGTH: 324
<212> TYPE: DNA
<213> ORGANISM: Rattus norvegicus

<400> SEQUENCE: 78
gatgtccaga tgacccagtc tccatcttat cttgctgcgt ctcctggaga aagtgtttcc     60
atcagttgca aggcaagtaa aagcattaac acatacttag cctggtatca ggagaaacct    120
gggaaaacga ataagcttct tatctactct gggtcaactt tgcaatctgg aactccatcg    180
agattcagtg gcagtggatc tggtacagat ttcacgctca ccatcagaag cctggagcct    240
gaagattttg cagtctacta ctgtcaacag cataatgaat accccttcac gttcggctca    300
gggacgaagt tggaaataaa acgg                                           324

<210> SEQ ID NO 79
<211> LENGTH: 108
<212> TYPE: PRT
<213> ORGANISM: Rattus norvegicus

<400> SEQUENCE: 79

```
Asp Val Gln Met Thr Gln Ser Pro Ser Tyr Leu Ala Ala Ser Pro Gly
1               5                   10                  15

Glu Ser Val Ser Ile Ser Cys Lys Ala Ser Lys Ser Ile Asn Thr Tyr
            20                  25                  30

Leu Ala Trp Tyr Gln Glu Lys Pro Gly Lys Thr Asn Lys Leu Leu Ile
        35                  40                  45

Tyr Ser Gly Ser Thr Leu Gln Ser Gly Thr Pro Ser Arg Phe Ser Gly
    50                  55                  60

Ser Gly Ser Gly Thr Asp Phe Thr Leu Thr Ile Arg Ser Leu Glu Pro
65                  70                  75                  80

Glu Asp Phe Ala Val Tyr Tyr Cys Gln Gln His Asn Glu Tyr Pro Phe
                85                  90                  95

Thr Phe Gly Ser Gly Thr Lys Leu Glu Ile Lys Arg
            100                 105
```

<210> SEQ ID NO 80
<211> LENGTH: 357
<212> TYPE: DNA
<213> ORGANISM: Rattus norvegicus

<400> SEQUENCE: 80

```
gaggtgcagc tggtggagtc tggggggaggc ctagtgcagc ctggaaggtc tctgaaacta      60

tcctgtggag cctctggatt cacattcaat aactactgga tgacctgggt ccgccaggct     120

ccagggaagg ggctggagtg ggttgcatcc attactaaag ctggtggtag cacttactat     180

cgagactctg tgaagggccg attcactatc tccagagata atgcaaaaag caccctatat     240

ctgcaaatga acagtctgag gtctgaggac acggccactt attactgtac aagagaactg     300

ggagagttct atgttatgga tgcctggggt caaggagctt cagtcactgt ctcctca        357
```

<210> SEQ ID NO 81
<211> LENGTH: 119
<212> TYPE: PRT
<213> ORGANISM: Rattus norvegicus

<400> SEQUENCE: 81

```
Glu Val Gln Leu Val Glu Ser Gly Gly Gly Leu Val Gln Pro Gly Arg
1               5                   10                  15

Ser Leu Lys Leu Ser Cys Gly Ala Ser Gly Phe Thr Phe Asn Asn Tyr
            20                  25                  30

Trp Met Thr Trp Val Arg Gln Ala Pro Gly Lys Gly Leu Glu Trp Val
        35                  40                  45

Ala Ser Ile Thr Lys Ala Gly Gly Ser Thr Tyr Tyr Arg Asp Ser Val
    50                  55                  60

Lys Gly Arg Phe Thr Ile Ser Arg Asp Asn Ala Lys Ser Thr Leu Tyr
65                  70                  75                  80

Leu Gln Met Asn Ser Leu Arg Ser Glu Asp Thr Ala Thr Tyr Tyr Cys
                85                  90                  95

Thr Arg Glu Leu Gly Glu Phe Tyr Val Met Asp Ala Trp Gly Gln Gly
            100                 105                 110

Ala Ser Val Thr Val Ser Ser
        115
```

<210> SEQ ID NO 82
<211> LENGTH: 11
<212> TYPE: PRT
<213> ORGANISM: Rattus norvegicus

<400> SEQUENCE: 82

```
Lys Ala Ser Lys Ser Ile Asn Thr Tyr Leu Ala
1               5                   10
```

<210> SEQ ID NO 83
<211> LENGTH: 7
<212> TYPE: PRT
<213> ORGANISM: Rattus norvegicus

<400> SEQUENCE: 83

```
Ser Gly Ser Thr Leu Gln Ser
1               5
```

<210> SEQ ID NO 84
<211> LENGTH: 9
<212> TYPE: PRT
<213> ORGANISM: Rattus norvegicus

<400> SEQUENCE: 84

```
Gln Gln His Asn Glu Tyr Pro Phe Thr
1               5
```

<210> SEQ ID NO 85
<211> LENGTH: 10
<212> TYPE: PRT
<213> ORGANISM: Rattus norvegicus

<400> SEQUENCE: 85

```
Gly Phe Thr Phe Asn Asn Tyr Trp Met Thr
1               5                   10
```

<210> SEQ ID NO 86
<211> LENGTH: 10
<212> TYPE: PRT
<213> ORGANISM: Rattus norvegicus

<400> SEQUENCE: 86

```
Ser Ile Thr Lys Ala Gly Gly Ser Thr Tyr
1               5                   10
```

<210> SEQ ID NO 87
<211> LENGTH: 10
<212> TYPE: PRT
<213> ORGANISM: Rattus norvegicus

<400> SEQUENCE: 87

```
Glu Leu Gly Glu Phe Tyr Val Met Asp Ala
1               5                   10
```

<210> SEQ ID NO 88
<211> LENGTH: 1117
<212> TYPE: DNA
<213> ORGANISM: Artificial Sequence
<220> FEATURE:
<223> OTHER INFORMATION: DNA comprising DNA sequence coding for amino
      acid of human heavy chain signal sequence and human IgG4PFALA
      constant region

<400> SEQUENCE: 88
ccagcctccg gactctagag ccaccatgaa acacctgtgg ttcttcctcc tgctggtggc 60
agctcccaga tgggtgctga gccaggtgca attgtgcagg cggttagctc agcctccacc 120
aagggcccta gcgtgttccc tctggcccct tgtagcagaa gcaccagcga gtctacagcc 180
gccctgggct gcctcgtgaa ggactacttt cccgagcccg tgaccgtgtc ctggaactct 240
ggcgctctga caagcggcgt gcacaccttt ccagccgtgc tgcagagcag cggcctgtac 300
tctctgtcca gcgtcgtgac tgtgcccagc agctctctgg gcaccaagac ctacacctgt 360
aacgtggacc acaagcccag caacaccaag gtggacaagc gggtggaatc taagtacggc 420
cctccctgcc ctccttgccc agcccctgaa gccgcgggcg gaccctccgt gttcctgttc 480
cccccaaagc ccaaggacac cctgatgatc agccggaccc ccgaagtgac ctgcgtggtg 540
gtggatgtgt cccaggaaga tcccgaggtg cagttcaatt ggtacgtgga cggcgtggaa 600
gtgcacaacg ccaagaccaa gcctagagag gaacagttca acagcaccta ccgggtggtg 660
tccgtgctga cagtgctgca ccaggactgg ctgaacggca aagagtacaa gtgcaaggtg 720
tccaacaagg gcctgcccag ctccatcgag aaaaccatca gcaaggccaa gggccagccc 780
cgcgaacccc aggtgtacac actgcctcca agccaggaag agatgaccaa gaatcaggtg 840
tccctgacct gtctcgtgaa aggcttctac ccctccgata tcgccgtgga atgggagagc 900
aacggccagc ccgagaacaa ctacaagacc acccccccctg tgctggactc cgatggctca 960
ttcttcctgt acagcagact gaccgtggac aagagccggt ggcaggaagg caacgtgttc 1020
agctgctccg tgatgcacga ggccctgcac aaccactaca cccagaagtc cctgtctctg 1080
agcctgggca aatgagttta aacgggggag gctaact 1117

<210> SEQ ID NO 89
<211> LENGTH: 702
<212> TYPE: DNA
<213> ORGANISM: Artificial Sequence
<220> FEATURE:
<223> OTHER INFORMATION: Light chain of human chimeric rat_CD147_#84

<400> SEQUENCE: 89
atggtgctgc agacccaggt gttcatctcc ctgctgctgt ggatctccgg cgcgtacggc 60
gatgtccaga tgacccagtc tccatcttat cttgctgcgt ctcctggaga aagtgtttcc 120
atcagttgca aggcaagtaa gagcattagc aataatttag cctggtatca ggagaaacct 180
gggaaagcaa ataagcttct tattcactct gggtcaactt tgcaatctgg aactccatcg 240
aggttcagtg gcagtggatc tggtacagat ttcacgctca ccatcagaag cctggagttt 300
gaagattttg cagtctatta ctgtcaacag tataatgaat acccactcac gttcggttct 360
gggaccaagc tggagatcaa acggacggtg gccgcccccct ccgtgttcat cttccccccc 420
tccgacgagc agctgaagtc cggcaccgcc tccgtggtgt gcctgctgaa taacttctac 480
cccagagagg ccaaggtgca gtggaaggtg gacaacgccc tgcagtccgg gaactcccag 540
gagagcgtga ccgagcagga cagcaaggac agcacctaca gcctgagcag caccctgacc 600
ctgagcaaag ccgactacga gaagcacaag gtgtacgcct gcgaggtgac ccaccagggc 660
ctgagctccc ccgtcaccaa gagcttcaac aggggggagt gt 702

<210> SEQ ID NO 90
<211> LENGTH: 234
<212> TYPE: PRT
<213> ORGANISM: Artificial Sequence
<220> FEATURE:
<223> OTHER INFORMATION: Light chain of human chimeric rat_CD147_#84

<400> SEQUENCE: 90

```
Met Val Leu Gln Thr Gln Val Phe Ile Ser Leu Leu Leu Trp Ile Ser
1               5                   10                  15

Gly Ala Tyr Gly Asp Val Gln Met Thr Gln Ser Pro Ser Tyr Leu Ala
            20                  25                  30

Ala Ser Pro Gly Glu Ser Val Ser Ile Ser Cys Lys Ala Ser Lys Ser
        35                  40                  45

Ile Ser Asn Asn Leu Ala Trp Tyr Gln Glu Lys Pro Gly Lys Ala Asn
    50                  55                  60

Lys Leu Leu Ile His Ser Gly Ser Thr Leu Gln Ser Gly Thr Pro Ser
65                  70                  75                  80

Arg Phe Ser Gly Ser Gly Ser Gly Thr Asp Phe Thr Leu Thr Ile Arg
                85                  90                  95

Ser Leu Glu Phe Glu Asp Phe Ala Val Tyr Tyr Cys Gln Gln Tyr Asn
            100                 105                 110

Glu Tyr Pro Leu Thr Phe Gly Ser Gly Thr Lys Leu Glu Ile Lys Arg
        115                 120                 125

Thr Val Ala Ala Pro Ser Val Phe Ile Phe Pro Pro Ser Asp Glu Gln
    130                 135                 140

Leu Lys Ser Gly Thr Ala Ser Val Val Cys Leu Leu Asn Asn Phe Tyr
145                 150                 155                 160

Pro Arg Glu Ala Lys Val Gln Trp Lys Val Asp Asn Ala Leu Gln Ser
                165                 170                 175

Gly Asn Ser Gln Glu Ser Val Thr Glu Gln Asp Ser Lys Asp Ser Thr
            180                 185                 190

Tyr Ser Leu Ser Ser Thr Leu Thr Leu Ser Lys Ala Asp Tyr Glu Lys
        195                 200                 205

His Lys Val Tyr Ala Cys Glu Val Thr His Gln Gly Leu Ser Ser Pro
    210                 215                 220

Val Thr Lys Ser Phe Asn Arg Gly Glu Cys
225                 230
```

<210> SEQ ID NO 91
<211> LENGTH: 1410
<212> TYPE: DNA
<213> ORGANISM: Artificial Sequence
<220> FEATURE:
<223> OTHER INFORMATION: Heavy chain IgG1 type of human chimeric
      rat_CD147_#84

<400> SEQUENCE: 91

```
atgaaacacc tgtggttctt cctcctgctg gtggcagctc ccagatgggt gctgagcgag      60

gtgcagctgg tggagtctgg gggaggccta gtgcagcctg gaaggtccct gaaactctcc     120

tgtgcagcct caggattcac tttcagtaac tattacatgg cctgggtccg ccaggctcca     180

aagaagggtc tggagtgggt cgcaaccatt actaccagtg gtagcagacc ttactatcca     240

gactccgtga aaggccgatt cactatctcc agagataatg caaaaagcag cctatacctg     300

caaatgaaca gtctgaagtc tgaggacacg gccacttatt actgtgcaag acatatttat     360

tactatgatg gttacccctt tgcttactgg ggccaaggca ctctggtcac tgtcagctca     420

gcctccacca agggcccaag cgtcttcccc ctggcaccct cctccaagag cacctctggc     480

ggcacagccg ccctgggctg cctggtcaag gactacttcc ccgaacccgt gaccgtgagc     540
```

-continued

```
tggaactcag gcgccctgac cagcggcgtg cacaccttcc ccgctgtcct gcagtcctca    600

ggactctact ccctcagcag cgtggtgacc gtgccctcca gcagcttggg cacccagacc    660

tacatctgca acgtgaatca caagcccagc aacaccaagg tggacaagag agttgagccc    720

aaatcttgtg acaaaactca cacatgccca ccctgcccag cacctgaact cctgggggga    780

ccctcagtct tcctcttccc cccaaaaccc aaggacaccc tcatgatctc ccggacccct    840

gaggtcacat gcgtggtggt ggacgtgagc cacgaagacc ctgaggtcaa gttcaactgg    900

tacgtggacg gcgtggaggt gcataatgcc aagacaaagc cccgggagga gcagtacaac    960

agcacgtacc gggtggtcag cgtcctcacc gtcctgcacc aggactggct gaatggcaag   1020

gagtacaagt gcaaggtctc caacaaagcc ctcccagccc ccatcgagaa aaccatctcc   1080

aaagccaaag gccagccccg ggaaccacag gtgtacaccc tgcccccatc ccgggaggag   1140

atgaccaaga accaggtcag cctgacctgc ctggtcaaag gcttctatcc cagcgacatc   1200

gccgtggagt gggagagcaa tggccagccc gagaacaact acaagaccac ccctcccgtg   1260

ctggactccg acggctcctt cttcctctac agcaagctca ccgtggacaa gagcaggtgg   1320

cagcagggca acgtcttctc atgctccgtg atgcatgagg ctctgcacaa ccactacacc   1380

cagaagagcc tctccctgtc tcccggcaaa                                    1410
```

```
<210> SEQ ID NO 92
<211> LENGTH: 470
<212> TYPE: PRT
<213> ORGANISM: Artificial Sequence
<220> FEATURE:
<223> OTHER INFORMATION: Heavy chain IgG1 type of human chimeric
      rat_CD147_#84

<400> SEQUENCE: 92

Met Lys His Leu Trp Phe Phe Leu Leu Leu Val Ala Ala Pro Arg Trp
1               5                   10                  15

Val Leu Ser Glu Val Gln Leu Val Glu Ser Gly Gly Gly Leu Val Gln
            20                  25                  30

Pro Gly Arg Ser Leu Lys Leu Ser Cys Ala Ala Ser Gly Phe Thr Phe
        35                  40                  45

Ser Asn Tyr Tyr Met Ala Trp Val Arg Gln Ala Pro Lys Lys Gly Leu
    50                  55                  60

Glu Trp Val Ala Thr Ile Thr Thr Ser Gly Ser Arg Pro Tyr Tyr Pro
65                  70                  75                  80

Asp Ser Val Lys Gly Arg Phe Thr Ile Ser Arg Asp Asn Ala Lys Ser
                85                  90                  95

Ser Leu Tyr Leu Gln Met Asn Ser Leu Lys Ser Glu Asp Thr Ala Thr
            100                 105                 110

Tyr Tyr Cys Ala Arg His Ile Tyr Tyr Tyr Asp Gly Tyr Pro Phe Ala
        115                 120                 125

Tyr Trp Gly Gln Gly Thr Leu Val Thr Val Ser Ser Ala Ser Thr Lys
    130                 135                 140

Gly Pro Ser Val Phe Pro Leu Ala Pro Ser Ser Lys Ser Thr Ser Gly
145                 150                 155                 160

Gly Thr Ala Ala Leu Gly Cys Leu Val Lys Asp Tyr Phe Pro Glu Pro
                165                 170                 175

Val Thr Val Ser Trp Asn Ser Gly Ala Leu Thr Ser Gly Val His Thr
            180                 185                 190

Phe Pro Ala Val Leu Gln Ser Ser Gly Leu Tyr Ser Leu Ser Ser Val
        195                 200                 205
```

Val Thr Val Pro Ser Ser Ser Leu Gly Thr Gln Thr Tyr Ile Cys Asn
    210                 215                 220

Val Asn His Lys Pro Ser Asn Thr Lys Val Asp Lys Arg Val Glu Pro
225                 230                 235                 240

Lys Ser Cys Asp Lys Thr His Thr Cys Pro Pro Cys Pro Ala Pro Glu
                245                 250                 255

Leu Leu Gly Gly Pro Ser Val Phe Leu Phe Pro Pro Lys Pro Lys Asp
            260                 265                 270

Thr Leu Met Ile Ser Arg Thr Pro Glu Val Thr Cys Val Val Val Asp
        275                 280                 285

Val Ser His Glu Asp Pro Glu Val Lys Phe Asn Trp Tyr Val Asp Gly
    290                 295                 300

Val Glu Val His Asn Ala Lys Thr Lys Pro Arg Glu Glu Gln Tyr Asn
305                 310                 315                 320

Ser Thr Tyr Arg Val Val Ser Val Leu Thr Val Leu His Gln Asp Trp
                325                 330                 335

Leu Asn Gly Lys Glu Tyr Lys Cys Lys Val Ser Asn Lys Ala Leu Pro
            340                 345                 350

Ala Pro Ile Glu Lys Thr Ile Ser Lys Ala Lys Gly Gln Pro Arg Glu
        355                 360                 365

Pro Gln Val Tyr Thr Leu Pro Pro Ser Arg Glu Glu Met Thr Lys Asn
    370                 375                 380

Gln Val Ser Leu Thr Cys Leu Val Lys Gly Phe Tyr Pro Ser Asp Ile
385                 390                 395                 400

Ala Val Glu Trp Glu Ser Asn Gly Gln Pro Glu Asn Asn Tyr Lys Thr
                405                 410                 415

Thr Pro Pro Val Leu Asp Ser Asp Gly Ser Phe Phe Leu Tyr Ser Lys
            420                 425                 430

Leu Thr Val Asp Lys Ser Arg Trp Gln Gln Gly Asn Val Phe Ser Cys
        435                 440                 445

Ser Val Met His Glu Ala Leu His Asn His Tyr Thr Gln Lys Ser Leu
    450                 455                 460

Ser Leu Ser Pro Gly Lys
465                 470

<210> SEQ ID NO 93
<211> LENGTH: 1398
<212> TYPE: DNA
<213> ORGANISM: Artificial Sequence
<220> FEATURE:
<223> OTHER INFORMATION: Heavy chain IgG2 type of human chimeric
      rat_CD147_#84

<400> SEQUENCE: 93
atgaaacacc tgtggttctt cctcctgctg gtggcagctc ccagatgggt gctgagcgag 60
gtgcagctgg tggagtctgg gggaggccta gtgcagcctg gaaggtccct gaaactctcc 120
tgtgcagcct caggattcac tttcagtaac tattacatgg cctgggtccg ccaggctcca 180
aagaagggtc tggagtgggt cgcaaccatt actaccagtg gtagcagacc ttactatcca 240
gactccgtga aaggccgatt cactatctcc agagataatg caaaaagcag cctatacctg 300
caaatgaaca gtctgaagtc tgaggacacg gccacttatt actgtgcaag acatatttat 360
tactatgatg gttacccctt tgcttactgg ggccaaggca ctctggtcac tgtcagctca 420
gcctccacca agggcccttc cgtgttccct ctggcccctt gtagccgttc caccagcgag 480
tccaccgccg cccttggctg tctggtgaag gactacttcc ctgagcctgt gaccgtgagc 540

-continued

```
tggaactccg gagcccttac cagcggcgtg cacaccttcc ctgccgtgct gcagtccagc    600

ggcctttact ccctgagctc cgtggtgacc gtgcctagct ccaacttcgg cacccaaacc    660

tacacctgta acgtggacca caagcctagc aacaccaagg tggacaagac cgtggagcgt    720

aagtgttgtg tggagtgtcc tccttgtcct gcccctcctg tggccggacc ttccgtgttc    780

cttttccctc ctaagcctaa ggacaccctg atgatcagcc gtacccctga ggtgacctgt    840

gtggtggtgg acgtgtccca cgaggaccct gaggtgcagt tcaactggta cgtggacggc    900

gtggaggtgc acaacgccaa gaccaagcct cgtgaggagc aattcaacag caccttccgt    960

gtggtgtccg tgcttaccgt ggtgcaccaa gactggctga acggcaagga gtacaagtgt   1020

aaggtgagca acaagggact tcctgcccct atcgagaaga ccatctccaa gaccaagggc   1080

caacctcgtg agcctcaagt gtacaccctt cctcctagcc gtgaggagat gaccaagaac   1140

caagtgtccc ttacctgtct ggtgaagggc ttctacccta gcgacatcgc cgtggagtgg   1200

gagtccaacg gacaacctga gaacaactac aagaccaccc ctcctatgct tgacagcgac   1260

ggctccttct tcctgtacag caagctgacc gtggacaagt cccgttggca acaaggcaac   1320

gtgttcagct gttccgtgat gcacgaggcc ctgcacaacc actacaccca aaagagcctt   1380

tccctgagcc ctggaaag                                                 1398
```

<210> SEQ ID NO 94
<211> LENGTH: 466
<212> TYPE: PRT
<213> ORGANISM: Artificial Sequence
<220> FEATURE:
<223> OTHER INFORMATION: Heavy chain IgG2 type of human chimeric rat_CD147_#84

<400> SEQUENCE: 94

```
Met Lys His Leu Trp Phe Phe Leu Leu Leu Val Ala Ala Pro Arg Trp
1               5                   10                  15

Val Leu Ser Glu Val Gln Leu Val Glu Ser Gly Gly Gly Leu Val Gln
            20                  25                  30

Pro Gly Arg Ser Leu Lys Leu Ser Cys Ala Ala Ser Gly Phe Thr Phe
        35                  40                  45

Ser Asn Tyr Tyr Met Ala Trp Val Arg Gln Ala Pro Lys Lys Gly Leu
    50                  55                  60

Glu Trp Val Ala Thr Ile Thr Thr Ser Gly Ser Arg Pro Tyr Tyr Pro
65                  70                  75                  80

Asp Ser Val Lys Gly Arg Phe Thr Ile Ser Arg Asp Asn Ala Lys Ser
                85                  90                  95

Ser Leu Tyr Leu Gln Met Asn Ser Leu Lys Ser Glu Asp Thr Ala Thr
            100                 105                 110

Tyr Tyr Cys Ala Arg His Ile Tyr Tyr Tyr Asp Gly Tyr Pro Phe Ala
        115                 120                 125

Tyr Trp Gly Gln Gly Thr Leu Val Thr Val Ser Ser Ala Ser Thr Lys
    130                 135                 140

Gly Pro Ser Val Phe Pro Leu Ala Pro Cys Ser Arg Ser Thr Ser Glu
145                 150                 155                 160

Ser Thr Ala Ala Leu Gly Cys Leu Val Lys Asp Tyr Phe Pro Glu Pro
                165                 170                 175

Val Thr Val Ser Trp Asn Ser Gly Ala Leu Thr Ser Gly Val His Thr
            180                 185                 190

Phe Pro Ala Val Leu Gln Ser Ser Gly Leu Tyr Ser Leu Ser Ser Val
        195                 200                 205
```

Val Thr Val Pro Ser Ser Asn Phe Gly Thr Gln Thr Tyr Thr Cys Asn
    210                 215                 220

Val Asp His Lys Pro Ser Asn Thr Lys Val Asp Lys Thr Val Glu Arg
225                 230                 235                 240

Lys Cys Cys Val Glu Cys Pro Pro Cys Pro Ala Pro Pro Val Ala Gly
                245                 250                 255

Pro Ser Val Phe Leu Phe Pro Pro Lys Pro Lys Asp Thr Leu Met Ile
            260                 265                 270

Ser Arg Thr Pro Glu Val Thr Cys Val Val Val Asp Val Ser His Glu
        275                 280                 285

Asp Pro Glu Val Gln Phe Asn Trp Tyr Val Asp Gly Val Glu Val His
    290                 295                 300

Asn Ala Lys Thr Lys Pro Arg Glu Glu Gln Phe Asn Ser Thr Phe Arg
305                 310                 315                 320

Val Val Ser Val Leu Thr Val Val His Gln Asp Trp Leu Asn Gly Lys
                325                 330                 335

Glu Tyr Lys Cys Lys Val Ser Asn Lys Gly Leu Pro Ala Pro Ile Glu
            340                 345                 350

Lys Thr Ile Ser Lys Thr Lys Gly Gln Pro Arg Glu Pro Gln Val Tyr
        355                 360                 365

Thr Leu Pro Pro Ser Arg Glu Glu Met Thr Lys Asn Gln Val Ser Leu
    370                 375                 380

Thr Cys Leu Val Lys Gly Phe Tyr Pro Ser Asp Ile Ala Val Glu Trp
385                 390                 395                 400

Glu Ser Asn Gly Gln Pro Glu Asn Asn Tyr Lys Thr Thr Pro Pro Met
                405                 410                 415

Leu Asp Ser Asp Gly Ser Phe Phe Leu Tyr Ser Lys Leu Thr Val Asp
            420                 425                 430

Lys Ser Arg Trp Gln Gln Gly Asn Val Phe Ser Cys Ser Val Met His
        435                 440                 445

Glu Ala Leu His Asn His Tyr Thr Gln Lys Ser Leu Ser Leu Ser Pro
    450                 455                 460

Gly Lys
465

<210> SEQ ID NO 95
<211> LENGTH: 1401
<212> TYPE: DNA
<213> ORGANISM: Artificial Sequence
<220> FEATURE:
<223> OTHER INFORMATION: Heavy chain IgG4P type of human chimeric rat_CD147_#84

<400> SEQUENCE: 95
atgaaacacc tgtggttctt cctcctgctg gtggcagctc ccagatgggt gctgagcgag 60
gtgcagctgg tggagtctgg gggaggccta gtgcagcctg gaaggtccct gaaactctcc 120
tgtgcagcct caggattcac tttcagtaac tattacatgg cctgggtccg ccaggctcca 180
aagaagggtc tggagtgggt cgcaaccatt actaccagtg gtagcagacc ttactatcca 240
gactccgtga aaggccgatt cactatctcc agagataatg caaaaagcag cctatacctg 300
caaatgaaca gtctgaagtc tgaggacacg gccacttatt actgtgcaag acatatttat 360
tactatgatg gttacccctt tgcttactgg ggccaaggca ctctggtcac tgtcagctca 420
gcctccacca agggccctag cgtgttccct ctggcccctt gtagcagaag caccagcgag 480
tctacagccg ccctgggctg cctcgtgaag gactactttc ccgagcccgt gaccgtgtcc 540
tggaactctg gcgctctgac aagcggcgtg cacacctttc cagccgtgct gcagagcagc 600
ggcctgtact ctctgtccag cgtcgtgact gtgcccagca gctctctggg caccaagacc 660
tacacctgta acgtggacca caagcccagc aacaccaagg tggacaagcg ggtggaatct 720
aagtacggcc ctccctgccc tccttgccca gcccctgaat ttctgggcgg accctccgtg 780
ttcctgttcc ccccaaagcc caaggacacc ctgatgatca gccggacccc cgaagtgacc 840
tgcgtggtgg tggatgtgtc ccaggaagat cccgaggtgc agttcaattg gtacgtggac 900
ggcgtggaag tgcacaacgc caagaccaag cctagagagg aacagttcaa cagcacctac 960
cgggtggtgt ccgtgctgac agtgctgcac caggactggc tgaacggcaa agagtacaag 1020
tgcaaggtgt ccaacaaggg cctgcccagc tccatcgaga aaaccatcag caaggccaag 1080
ggccagcccc gcgaacccca ggtgtacaca ctgcctccaa gccaggaaga gatgaccaag 1140
aatcaggtgt ccctgacctg tctcgtgaaa ggcttctacc cctccgatat cgccgtggaa 1200
tgggagagca acggccagcc cgagaacaac tacaagacca cccccccctgt gctggactcc 1260 gatggctcat tcttcctgta cagcagactg accgtggaca agagccggtg gcaggaaggc 1320
aacgtgttca gctgctccgt gatgcacgag gccctgcaca accactacac ccagaagtcc 1380
ctgtctctga gcctgggcaa a 1401

<210> SEQ ID NO 96
<211> LENGTH: 467
<212> TYPE: PRT
<213> ORGANISM: Artificial Sequence
<220> FEATURE:
<223> OTHER INFORMATION: Heavy chain IgG4P type of human chimeric rat_CD147_#84

<400> SEQUENCE: 96

Met Lys His Leu Trp Phe Phe Leu Leu Leu Val Ala Ala Pro Arg Trp
1 5 10 15

Val Leu Ser Glu Val Gln Leu Val Glu Ser Gly Gly Gly Leu Val Gln
20 25 30

Pro Gly Arg Ser Leu Lys Leu Ser Cys Ala Ala Ser Gly Phe Thr Phe
35 40 45

Ser Asn Tyr Tyr Met Ala Trp Val Arg Gln Ala Pro Lys Lys Gly Leu
50 55 60

Glu Trp Val Ala Thr Ile Thr Thr Ser Gly Ser Arg Pro Tyr Tyr Pro
65 70 75 80

Asp Ser Val Lys Gly Arg Phe Thr Ile Ser Arg Asp Asn Ala Lys Ser
85 90 95

Ser Leu Tyr Leu Gln Met Asn Ser Leu Lys Ser Glu Asp Thr Ala Thr
100 105 110

Tyr Tyr Cys Ala Arg His Ile Tyr Tyr Tyr Asp Gly Tyr Pro Phe Ala
115 120 125

Tyr Trp Gly Gln Gly Thr Leu Val Thr Val Ser Ser Ala Ser Thr Lys
130 135 140

Gly Pro Ser Val Phe Pro Leu Ala Pro Cys Ser Arg Ser Thr Ser Glu
145 150 155 160

Ser Thr Ala Ala Leu Gly Cys Leu Val Lys Asp Tyr Phe Pro Glu Pro
165 170 175

Val Thr Val Ser Trp Asn Ser Gly Ala Leu Thr Ser Gly Val His Thr
180 185 190

Phe Pro Ala Val Leu Gln Ser Ser Gly Leu Tyr Ser Leu Ser Ser Val
195 200 205

```
Val Thr Val Pro Ser Ser Ser Leu Gly Thr Lys Thr Tyr Thr Cys Asn
    210                 215                 220

Val Asp His Lys Pro Ser Asn Thr Lys Val Asp Lys Arg Val Glu Ser
225                 230                 235                 240

Lys Tyr Gly Pro Pro Cys Pro Pro Cys Pro Ala Pro Glu Phe Leu Gly
                245                 250                 255

Gly Pro Ser Val Phe Leu Phe Pro Pro Lys Pro Lys Asp Thr Leu Met
            260                 265                 270

Ile Ser Arg Thr Pro Glu Val Thr Cys Val Val Val Asp Val Ser Gln
        275                 280                 285

Glu Asp Pro Glu Val Gln Phe Asn Trp Tyr Val Asp Gly Val Glu Val
    290                 295                 300

His Asn Ala Lys Thr Lys Pro Arg Glu Glu Gln Phe Asn Ser Thr Tyr
305                 310                 315                 320

Arg Val Val Ser Val Leu Thr Val Leu His Gln Asp Trp Leu Asn Gly
                325                 330                 335

Lys Glu Tyr Lys Cys Lys Val Ser Asn Lys Gly Leu Pro Ser Ser Ile
            340                 345                 350

Glu Lys Thr Ile Ser Lys Ala Lys Gly Gln Pro Arg Glu Pro Gln Val
        355                 360                 365

Tyr Thr Leu Pro Pro Ser Gln Glu Glu Met Thr Lys Asn Gln Val Ser
    370                 375                 380

Leu Thr Cys Leu Val Lys Gly Phe Tyr Pro Ser Asp Ile Ala Val Glu
385                 390                 395                 400

Trp Glu Ser Asn Gly Gln Pro Glu Asn Asn Tyr Lys Thr Thr Pro Pro
                405                 410                 415

Val Leu Asp Ser Asp Gly Ser Phe Phe Leu Tyr Ser Arg Leu Thr Val
            420                 425                 430

Asp Lys Ser Arg Trp Gln Glu Gly Asn Val Phe Ser Cys Ser Val Met
        435                 440                 445

His Glu Ala Leu His Asn His Tyr Thr Gln Lys Ser Leu Ser Leu Ser
    450                 455                 460

Leu Gly Lys
465
```

<210> SEQ ID NO 97
<211> LENGTH: 1410
<212> TYPE: DNA
<213> ORGANISM: Artificial Sequence
<220> FEATURE:
<223> OTHER INFORMATION: Heavy chain IgG1LALA type of human chimeric rat_CD147_#84

<400> SEQUENCE: 97

```
atgaaacacc tgtggttctt cctcctgctg gtggcagctc ccagatgggt gctgagcgag     60

gtgcagctgg tggagtctgg gggaggccta gtgcagcctg gaaggtccct gaaactctcc    120

tgtgcagcct caggattcac tttcagtaac tattacatgg cctgggtccg ccaggctcca    180

aagaagggtc tggagtgggt cgcaaccatt actaccagtg gtagcagacc ttactatcca    240

gactccgtga aaggccgatt cactatctcc agagataatg caaaaagcag cctatacctg    300

caaatgaaca gtctgaagtc tgaggacacg gccacttatt actgtgcaag acatatttat    360

tactatgatg gttacccctt tgcttactgg ggccaaggca ctctggtcac tgtcagctca    420

gcctccacca agggcccaag cgtcttcccc ctggcaccct cctccaagag cacctctggc    480

ggcacagccg ccctgggctg cctggtcaag gactacttcc ccgaacccgt gaccgtgagc    540
```

-continued

```
tggaactcag gcgccctgac cagcggcgtg cacaccttcc ccgctgtcct gcagtcctca    600

ggactctact ccctcagcag cgtggtgacc gtgccctcca gcagcttggg cacccagacc    660

tacatctgca acgtgaatca caagcccagc aacaccaagg tggacaagag agttgagccc    720

aaatcttgtg acaaaactca cacatgccca ccctgcccag cacctgaagc cgcgggggga    780

ccctcagtct tcctcttccc cccaaaaccc aaggacaccc tcatgatctc ccggacccct    840

gaggtcacat gcgtggtggt ggacgtgagc cacgaagacc ctgaggtcaa gttcaactgg    900

tacgtggacg gcgtggaggt gcataatgcc aagacaaagc cccgggagga gcagtacaac    960

agcacgtacc gggtggtcag cgtcctcacc gtcctgcacc aggactggct gaatggcaag   1020

gagtacaagt gcaaggtctc caacaaagcc ctcccagccc ccatcgagaa aaccatctcc   1080

aaagccaaag gccagccccg ggaaccacag gtgtacaccc tgcccccatc ccgggaggag   1140

atgaccaaga accaggtcag cctgacctgc ctggtcaaag gcttctatcc cagcgacatc   1200

gccgtggagt gggagagcaa tggccagccc gagaacaact acaagaccac ccctcccgtg   1260

ctggactccg acggctcctt cttcctctac agcaagctca ccgtggacaa gagcaggtgg   1320

cagcagggca acgtcttctc atgctccgtg atgcatgagg ctctgcacaa ccactacacc   1380

cagaagagcc tctccctgtc tcccggcaaa                                      1410


<210> SEQ ID NO 98
<211> LENGTH: 470
<212> TYPE: PRT
<213> ORGANISM: Artificial Sequence
<220> FEATURE:
<223> OTHER INFORMATION: Heavy chain IgG1LALA type of human chimeric
      rat_CD147_#84

<400> SEQUENCE: 98

Met Lys His Leu Trp Phe Phe Leu Leu Leu Val Ala Ala Pro Arg Trp
1               5                   10                  15

Val Leu Ser Glu Val Gln Leu Val Glu Ser Gly Gly Gly Leu Val Gln
            20                  25                  30

Pro Gly Arg Ser Leu Lys Leu Ser Cys Ala Ala Ser Gly Phe Thr Phe
        35                  40                  45

Ser Asn Tyr Tyr Met Ala Trp Val Arg Gln Ala Pro Lys Lys Gly Leu
    50                  55                  60

Glu Trp Val Ala Thr Ile Thr Thr Ser Gly Ser Arg Pro Tyr Tyr Pro
65                  70                  75                  80

Asp Ser Val Lys Gly Arg Phe Thr Ile Ser Arg Asp Asn Ala Lys Ser
                85                  90                  95

Ser Leu Tyr Leu Gln Met Asn Ser Leu Lys Ser Glu Asp Thr Ala Thr
            100                 105                 110

Tyr Tyr Cys Ala Arg His Ile Tyr Tyr Tyr Asp Gly Tyr Pro Phe Ala
        115                 120                 125

Tyr Trp Gly Gln Gly Thr Leu Val Thr Val Ser Ser Ala Ser Thr Lys
    130                 135                 140

Gly Pro Ser Val Phe Pro Leu Ala Pro Ser Ser Lys Ser Thr Ser Gly
145                 150                 155                 160

Gly Thr Ala Ala Leu Gly Cys Leu Val Lys Asp Tyr Phe Pro Glu Pro
                165                 170                 175

Val Thr Val Ser Trp Asn Ser Gly Ala Leu Thr Ser Gly Val His Thr
            180                 185                 190

Phe Pro Ala Val Leu Gln Ser Ser Gly Leu Tyr Ser Leu Ser Ser Val
        195                 200                 205
```

-continued

```
Val Thr Val Pro Ser Ser Ser Leu Gly Thr Gln Thr Tyr Ile Cys Asn
    210                 215                 220

Val Asn His Lys Pro Ser Asn Thr Lys Val Asp Lys Arg Val Glu Pro
225                 230                 235                 240

Lys Ser Cys Asp Lys Thr His Thr Cys Pro Pro Cys Pro Ala Pro Glu
                245                 250                 255

Ala Ala Gly Gly Pro Ser Val Phe Leu Phe Pro Pro Lys Pro Lys Asp
            260                 265                 270

Thr Leu Met Ile Ser Arg Thr Pro Glu Val Thr Cys Val Val Val Asp
        275                 280                 285

Val Ser His Glu Asp Pro Glu Val Lys Phe Asn Trp Tyr Val Asp Gly
    290                 295                 300

Val Glu Val His Asn Ala Lys Thr Lys Pro Arg Glu Glu Gln Tyr Asn
305                 310                 315                 320

Ser Thr Tyr Arg Val Val Ser Val Leu Thr Val Leu His Gln Asp Trp
                325                 330                 335

Leu Asn Gly Lys Glu Tyr Lys Cys Lys Val Ser Asn Lys Ala Leu Pro
            340                 345                 350

Ala Pro Ile Glu Lys Thr Ile Ser Lys Ala Lys Gly Gln Pro Arg Glu
        355                 360                 365

Pro Gln Val Tyr Thr Leu Pro Pro Ser Arg Glu Glu Met Thr Lys Asn
    370                 375                 380

Gln Val Ser Leu Thr Cys Leu Val Lys Gly Phe Tyr Pro Ser Asp Ile
385                 390                 395                 400

Ala Val Glu Trp Glu Ser Asn Gly Gln Pro Glu Asn Asn Tyr Lys Thr
                405                 410                 415

Thr Pro Pro Val Leu Asp Ser Asp Gly Ser Phe Phe Leu Tyr Ser Lys
            420                 425                 430

Leu Thr Val Asp Lys Ser Arg Trp Gln Gln Gly Asn Val Phe Ser Cys
        435                 440                 445

Ser Val Met His Glu Ala Leu His Asn His Tyr Thr Gln Lys Ser Leu
    450                 455                 460

Ser Leu Ser Pro Gly Lys
465                 470


<210> SEQ ID NO 99
<211> LENGTH: 1401
<212> TYPE: DNA
<213> ORGANISM: Artificial Sequence
<220> FEATURE:
<223> OTHER INFORMATION: Heavy chain IgG4PFALA type of human chimeric
      rat_CD147_#84

<400> SEQUENCE: 99

atgaaacacc tgtggttctt cctcctgctg gtggcagctc ccagatgggt gctgagcgag     60

gtgcagctgg tggagtctgg gggaggccta gtgcagcctg gaaggtccct gaaactctcc    120

tgtgcagcct caggattcac tttcagtaac tattacatgg cctgggtccg ccaggctcca    180

aagaagggtc tggagtgggt cgcaaccatt actaccagtg gtagcagacc ttactatcca    240

gactccgtga aaggccgatt cactatctcc agagataatg caaaaagcag cctatacctg    300

caaatgaaca gtctgaagtc tgaggacacg gccacttatt actgtgcaag acatatttat    360

tactatgatg gttacccctt tgcttactgg ggccaaggca ctctggtcac tgtcagctca    420

gcctccacca agggccctag cgtgttccct ctggcccctt gtagcagaag caccagcgag    480

tctacagccg ccctgggctg cctcgtgaag gactactttc ccgagcccgt gaccgtgtcc    540
```

-continued

```
tggaactctg gcgctctgac aagcggcgtg cacacctttc cagccgtgct gcagagcagc    600

ggcctgtact ctctgtccag cgtcgtgact gtgcccagca gctctctggg caccaagacc    660

tacacctgta acgtggacca caagcccagc aacaccaagg tggacaagcg ggtggaatct    720

aagtacggcc ctccctgccc tccttgccca gcccctgaag ccgcgggcgg accctccgtg    780

ttcctgttcc ccccaaagcc caaggacacc ctgatgatca gccggacccc cgaagtgacc    840

tgcgtggtgg tggatgtgtc ccaggaagat cccgaggtgc agttcaattg gtacgtggac    900

ggcgtggaag tgcacaacgc caagaccaag cctagagagg aacagttcaa cagcacctac    960

cgggtggtgt ccgtgctgac agtgctgcac caggactggc tgaacggcaa agagtacaag   1020

tgcaaggtgt ccaacaaggg cctgcccagc tccatcgaga aaaccatcag caaggccaag   1080

ggccagcccc gcgaacccca ggtgtacaca ctgcctccaa gccaggaaga gatgaccaag   1140

aatcaggtgt ccctgacctg tctcgtgaaa ggcttctacc cctccgatat cgccgtggaa   1200

tgggagagca acggccagcc cgagaacaac tacaagacca ccccccctgt gctggactcc   1260

gatggctcat tcttcctgta cagcagactg accgtggaca agagccggtg gcaggaaggc   1320

aacgtgttca gctgctccgt gatgcacgag gccctgcaca accactacac ccagaagtcc   1380

ctgtctctga gcctgggcaa a                                              1401
```

<210> SEQ ID NO 100
<211> LENGTH: 467
<212> TYPE: PRT
<213> ORGANISM: Artificial Sequence
<220> FEATURE:
<223> OTHER INFORMATION: Heavy chain IgG4PFALA type of human chimeric rat_CD147_#84

<400> SEQUENCE: 100

```
Met Lys His Leu Trp Phe Phe Leu Leu Leu Val Ala Ala Pro Arg Trp
1               5                   10                  15

Val Leu Ser Glu Val Gln Leu Val Glu Ser Gly Gly Gly Leu Val Gln
            20                  25                  30

Pro Gly Arg Ser Leu Lys Leu Ser Cys Ala Ala Ser Gly Phe Thr Phe
        35                  40                  45

Ser Asn Tyr Tyr Met Ala Trp Val Arg Gln Ala Pro Lys Lys Gly Leu
    50                  55                  60

Glu Trp Val Ala Thr Ile Thr Thr Ser Gly Ser Arg Pro Tyr Tyr Pro
65                  70                  75                  80

Asp Ser Val Lys Gly Arg Phe Thr Ile Ser Arg Asp Asn Ala Lys Ser
                85                  90                  95

Ser Leu Tyr Leu Gln Met Asn Ser Leu Lys Ser Glu Asp Thr Ala Thr
            100                 105                 110

Tyr Tyr Cys Ala Arg His Ile Tyr Tyr Tyr Asp Gly Tyr Pro Phe Ala
        115                 120                 125

Tyr Trp Gly Gln Gly Thr Leu Val Thr Val Ser Ser Ala Ser Thr Lys
    130                 135                 140

Gly Pro Ser Val Phe Pro Leu Ala Pro Cys Ser Arg Ser Thr Ser Glu
145                 150                 155                 160

Ser Thr Ala Ala Leu Gly Cys Leu Val Lys Asp Tyr Phe Pro Glu Pro
                165                 170                 175

Val Thr Val Ser Trp Asn Ser Gly Ala Leu Thr Ser Gly Val His Thr
            180                 185                 190

Phe Pro Ala Val Leu Gln Ser Ser Gly Leu Tyr Ser Leu Ser Ser Val
        195                 200                 205
```

```
Val Thr Val Pro Ser Ser Ser Leu Gly Thr Lys Thr Tyr Thr Cys Asn
    210                 215                 220

Val Asp His Lys Pro Ser Asn Thr Lys Val Asp Lys Arg Val Glu Ser
225                 230                 235                 240

Lys Tyr Gly Pro Pro Cys Pro Pro Cys Pro Ala Pro Glu Ala Ala Gly
                245                 250                 255

Gly Pro Ser Val Phe Leu Phe Pro Pro Lys Pro Lys Asp Thr Leu Met
            260                 265                 270

Ile Ser Arg Thr Pro Glu Val Thr Cys Val Val Val Asp Val Ser Gln
        275                 280                 285

Glu Asp Pro Glu Val Gln Phe Asn Trp Tyr Val Asp Gly Val Glu Val
    290                 295                 300

His Asn Ala Lys Thr Lys Pro Arg Glu Glu Gln Phe Asn Ser Thr Tyr
305                 310                 315                 320

Arg Val Val Ser Val Leu Thr Val Leu His Gln Asp Trp Leu Asn Gly
                325                 330                 335

Lys Glu Tyr Lys Cys Lys Val Ser Asn Lys Gly Leu Pro Ser Ser Ile
            340                 345                 350

Glu Lys Thr Ile Ser Lys Ala Lys Gly Gln Pro Arg Glu Pro Gln Val
        355                 360                 365

Tyr Thr Leu Pro Pro Ser Gln Glu Glu Met Thr Lys Asn Gln Val Ser
    370                 375                 380

Leu Thr Cys Leu Val Lys Gly Phe Tyr Pro Ser Asp Ile Ala Val Glu
385                 390                 395                 400

Trp Glu Ser Asn Gly Gln Pro Glu Asn Asn Tyr Lys Thr Thr Pro Pro
                405                 410                 415

Val Leu Asp Ser Asp Gly Ser Phe Phe Leu Tyr Ser Arg Leu Thr Val
            420                 425                 430

Asp Lys Ser Arg Trp Gln Glu Gly Asn Val Phe Ser Cys Ser Val Met
        435                 440                 445

His Glu Ala Leu His Asn His Tyr Thr Gln Lys Ser Leu Ser Leu Ser
    450                 455                 460

Leu Gly Lys
465


<210> SEQ ID NO 101
<211> LENGTH: 702
<212> TYPE: DNA
<213> ORGANISM: Artificial Sequence
<220> FEATURE:
<223> OTHER INFORMATION: Light chain of human chimeric rat_CD147_#101

<400> SEQUENCE: 101

atggtgctgc agacccaggt gttcatctcc ctgctgctgt ggatctccgg cgcgtacggc     60

gacatccaga tgacccagtc tccttcactc ctgtctgcat ctgtgggagg cagaatcact    120

ctcaactgca aagcaagtca gaatctctat aagaacttag cctggtatca gcagaagctt    180

ggagaagctc ccaaactcct gattgataat gcaaacagtt tgcaaacggg catcccatca    240

aggttcagtg gcagtggatc tggtacagat ttcacactca ccatcagcag cctgcagcct    300

gaagatgttg ccacatattt ctgccagcag tattatagcg ggtcgtacac gtttggagct    360

gggaccaagc tggaactgaa acggacggtg gccgcccct ccgtgttcat cttcccccc    420

tccgacgagc agctgaagtc cggcaccgcc tccgtggtgt gcctgctgaa taacttctac    480

cccagagagg ccaaggtgca gtggaaggtg gacaacgccc tgcagtccgg gaactcccag    540
```

gagagcgtga ccgagcagga cagcaaggac agcacctaca gcctgagcag caccctgacc 600
ctgagcaaag ccgactacga gaagcacaag gtgtacgcct gcgaggtgac ccaccagggc 660
ctgagctccc ccgtcaccaa gagcttcaac aggggggagt gt 702

<210> SEQ ID NO 102
<211> LENGTH: 234
<212> TYPE: PRT
<213> ORGANISM: Artificial Sequence
<220> FEATURE:
<223> OTHER INFORMATION: Light chain of human chimeric rat_CD147_#101

<400> SEQUENCE: 102

Met Val Leu Gln Thr Gln Val Phe Ile Ser Leu Leu Leu Trp Ile Ser
1 5 10 15

Gly Ala Tyr Gly Asp Ile Gln Met Thr Gln Ser Pro Ser Leu Leu Ser
20 25 30

Ala Ser Val Gly Gly Arg Ile Thr Leu Asn Cys Lys Ala Ser Gln Asn
35 40 45

Leu Tyr Lys Asn Leu Ala Trp Tyr Gln Gln Lys Leu Gly Glu Ala Pro
50 55 60

Lys Leu Leu Ile Asp Asn Ala Asn Ser Leu Gln Thr Gly Ile Pro Ser
65 70 75 80

Arg Phe Ser Gly Ser Gly Ser Gly Thr Asp Phe Thr Leu Thr Ile Ser
85 90 95

Ser Leu Gln Pro Glu Asp Val Ala Thr Tyr Phe Cys Gln Gln Tyr Tyr
100 105 110

Ser Gly Ser Tyr Thr Phe Gly Ala Gly Thr Lys Leu Glu Leu Lys Arg
115 120 125

Thr Val Ala Ala Pro Ser Val Phe Ile Phe Pro Pro Ser Asp Glu Gln
130 135 140

Leu Lys Ser Gly Thr Ala Ser Val Val Cys Leu Leu Asn Asn Phe Tyr
145 150 155 160

Pro Arg Glu Ala Lys Val Gln Trp Lys Val Asp Asn Ala Leu Gln Ser
165 170 175

Gly Asn Ser Gln Glu Ser Val Thr Glu Gln Asp Ser Lys Asp Ser Thr
180 185 190

Tyr Ser Leu Ser Ser Thr Leu Thr Leu Ser Lys Ala Asp Tyr Glu Lys
195 200 205

His Lys Val Tyr Ala Cys Glu Val Thr His Gln Gly Leu Ser Ser Pro
210 215 220

Val Thr Lys Ser Phe Asn Arg Gly Glu Cys
225 230

<210> SEQ ID NO 103
<211> LENGTH: 1389
<212> TYPE: DNA
<213> ORGANISM: Artificial Sequence
<220> FEATURE:
<223> OTHER INFORMATION: Heavy chain IgG2 of human chimeric
rat_CD147_#101

<400> SEQUENCE: 103
atgaaacacc tgtggttctt cctcctgctg gtggcagctc ccagatgggt gctgagcgag 60
gtgcagctgg tggagtctga tggaggctta gtgcagcctg gaaggtccct aaaactctcc 120
tgtgcagcct caggattcac tttcagtgac tattacatgg cctgggtccg ccaggctcca 180
acgaaggggc tggagtgggt cgcaaccatt agttatgatg gtagtaacac ttactatcga 240

-continued

```
gactccgtga agggccgatt cactatctcc agagataatg caaaaagcac cctatacctg    300

caaatggaca gtctgaggtc tggggacacg gccacttatt actgtgcaag attttacaac    360

aactactact ttgattactg gggccaagga gtcatggtca cagtcagctc agcctccacc    420

aagggccctt ccgtgttccc tctggcccct tgtagccgtt ccaccagcga gtccaccgcc    480

gcccttggct gtctggtgaa ggactacttc cctgagcctg tgaccgtgag ctggaactcc    540

ggagccctta ccagcggcgt gcacaccttc cctgccgtgc tgcagtccag cggcctttac    600

tccctgagct ccgtggtgac cgtgcctagc tccaacttcg gcacccaaac ctacacctgt    660

aacgtggacc acaagcctag caacaccaag gtggacaaga ccgtggagcg taagtgttgt    720

gtggagtgtc ctccttgtcc tgcccctcct gtggccggac cttccgtgtt cctttttccct    780

cctaagccta aggacaccct gatgatcagc cgtacccctg aggtgacctg tgtggtggtg    840

gacgtgtccc acgaggaccc tgaggtgcag ttcaactggt acgtggacgg cgtggaggtg    900

cacaacgcca agaccaagcc tcgtgaggag caattcaaca gcaccttccg tgtggtgtcc    960

gtgcttaccg tggtgcacca agactggctg aacggcaagg agtacaagtg taaggtgagc   1020

aacaagggac ttcctgcccc tatcgagaag accatctcca agaccaaggg ccaacctcgt   1080

gagcctcaag tgtacaccct tcctcctagc cgtgaggaga tgaccaagaa ccaagtgtcc   1140

cttacctgtc tggtgaaggg cttctaccct agcgacatcg ccgtggagtg ggagtccaac   1200

ggacaacctg agaacaacta caagaccacc cctcctatgc ttgacagcga cggctccttc   1260

ttcctgtaca gcaagctgac cgtggacaag tcccgttggc aacaaggcaa cgtgttcagc   1320

tgttccgtga tgcacgaggc cctgcacaac cactacaccc aaaagagcct ttccctgagc   1380

cctggaaag                                                           1389
```

<210> SEQ ID NO 104
<211> LENGTH: 463
<212> TYPE: PRT
<213> ORGANISM: Artificial Sequence
<220> FEATURE:
<223> OTHER INFORMATION: Heavy chain IgG2 of human chimeric rat_CD147_#101

<400> SEQUENCE: 104

```
Met Lys His Leu Trp Phe Phe Leu Leu Leu Val Ala Ala Pro Arg Trp
1               5                   10                  15

Val Leu Ser Glu Val Gln Leu Val Glu Ser Asp Gly Gly Leu Val Gln
            20                  25                  30

Pro Gly Arg Ser Leu Lys Leu Ser Cys Ala Ala Ser Gly Phe Thr Phe
        35                  40                  45

Ser Asp Tyr Tyr Met Ala Trp Val Arg Gln Ala Pro Thr Lys Gly Leu
    50                  55                  60

Glu Trp Val Ala Thr Ile Ser Tyr Asp Gly Ser Asn Thr Tyr Tyr Arg
65                  70                  75                  80

Asp Ser Val Lys Gly Arg Phe Thr Ile Ser Arg Asp Asn Ala Lys Ser
                85                  90                  95

Thr Leu Tyr Leu Gln Met Asp Ser Leu Arg Ser Gly Asp Thr Ala Thr
            100                 105                 110

Tyr Tyr Cys Ala Arg Phe Tyr Asn Asn Tyr Tyr Phe Asp Tyr Trp Gly
        115                 120                 125

Gln Gly Val Met Val Thr Val Ser Ser Ala Ser Thr Lys Gly Pro Ser
    130                 135                 140
```

-continued

```
Val Phe Pro Leu Ala Pro Cys Ser Arg Ser Thr Ser Glu Ser Thr Ala
145                 150                 155                 160

Ala Leu Gly Cys Leu Val Lys Asp Tyr Phe Pro Glu Pro Val Thr Val
                165                 170                 175

Ser Trp Asn Ser Gly Ala Leu Thr Ser Gly Val His Thr Phe Pro Ala
            180                 185                 190

Val Leu Gln Ser Ser Gly Leu Tyr Ser Leu Ser Ser Val Val Thr Val
        195                 200                 205

Pro Ser Ser Asn Phe Gly Thr Gln Thr Tyr Thr Cys Asn Val Asp His
    210                 215                 220

Lys Pro Ser Asn Thr Lys Val Asp Lys Thr Val Glu Arg Lys Cys Cys
225                 230                 235                 240

Val Glu Cys Pro Pro Cys Pro Ala Pro Pro Val Ala Gly Pro Ser Val
                245                 250                 255

Phe Leu Phe Pro Pro Lys Pro Lys Asp Thr Leu Met Ile Ser Arg Thr
            260                 265                 270

Pro Glu Val Thr Cys Val Val Val Asp Val Ser His Glu Asp Pro Glu
        275                 280                 285

Val Gln Phe Asn Trp Tyr Val Asp Gly Val Glu Val His Asn Ala Lys
    290                 295                 300

Thr Lys Pro Arg Glu Glu Gln Phe Asn Ser Thr Phe Arg Val Val Ser
305                 310                 315                 320

Val Leu Thr Val Val His Gln Asp Trp Leu Asn Gly Lys Glu Tyr Lys
                325                 330                 335

Cys Lys Val Ser Asn Lys Gly Leu Pro Ala Pro Ile Glu Lys Thr Ile
            340                 345                 350

Ser Lys Thr Lys Gly Gln Pro Arg Glu Pro Gln Val Tyr Thr Leu Pro
        355                 360                 365

Pro Ser Arg Glu Glu Met Thr Lys Asn Gln Val Ser Leu Thr Cys Leu
    370                 375                 380

Val Lys Gly Phe Tyr Pro Ser Asp Ile Ala Val Glu Trp Glu Ser Asn
385                 390                 395                 400

Gly Gln Pro Glu Asn Asn Tyr Lys Thr Thr Pro Pro Met Leu Asp Ser
                405                 410                 415

Asp Gly Ser Phe Phe Leu Tyr Ser Lys Leu Thr Val Asp Lys Ser Arg
            420                 425                 430

Trp Gln Gln Gly Asn Val Phe Ser Cys Ser Val Met His Glu Ala Leu
        435                 440                 445

His Asn His Tyr Thr Gln Lys Ser Leu Ser Leu Ser Pro Gly Lys
    450                 455                 460
```

<210> SEQ ID NO 105
<211> LENGTH: 1392
<212> TYPE: DNA
<213> ORGANISM: Artificial Sequence
<220> FEATURE:
<223> OTHER INFORMATION: Heavy chain IgG4P of human chimeric rat_CD147_#101

<400> SEQUENCE: 105

```
atgaaacacc tgtggttctt cctcctgctg gtggcagctc ccagatgggt gctgagcgag     60

gtgcagctgg tggagtctga tggaggctta gtgcagcctg gaaggtccct aaaactctcc    120

tgtgcagcct caggattcac tttcagtgac tattacatgg cctgggtccg ccaggctcca    180
```

```
acgaaggggc tggagtgggt cgcaaccatt agttatgatg gtagtaacac ttactatcga    240

gactccgtga agggccgatt cactatctcc agagataatg caaaaagcac cctatacctg    300

caaatggaca gtctgaggtc tggggacacg gccacttatt actgtgcaag attttacaac    360

aactactact ttgattactg gggccaagga gtcatggtca cagtcagctc agcctccacc    420

aagggcccta gcgtgttccc tctggcccct tgtagcagaa gcaccagcga gtctacagcc    480

gccctgggct gcctcgtgaa ggactacttt cccgagcccg tgaccgtgtc ctggaactct    540

ggcgctctga caagcggcgt gcacaccttt ccagccgtgc tgcagagcag cggcctgtac    600

tctctgtcca gcgtcgtgac tgtgcccagc agctctctgg gcaccaagac ctacacctgt    660

aacgtggacc acaagcccag caacaccaag gtggacaagc gggtggaatc taagtacggc    720

cctccctgcc ctccttgccc agcccctgaa tttctgggcg gaccctccgt gttcctgttc    780

cccccaaagc ccaaggacac cctgatgatc agccggaccc ccgaagtgac ctgcgtggtg    840

gtggatgtgt cccaggaaga tcccgaggtg cagttcaatt ggtacgtgga cggcgtggaa    900

gtgcacaacg ccaagaccaa gcctagagag gaacagttca acagcaccta ccgggtggtg    960

tccgtgctga cagtgctgca ccaggactgg ctgaacggca aagagtacaa gtgcaaggtg   1020

tccaacaagg gcctgcccag ctccatcgag aaaaccatca gcaaggccaa gggccagccc   1080

cgcgaacccc aggtgtacac actgcctcca agccaggaag agatgaccaa gaatcaggtg   1140

tccctgacct gtctcgtgaa aggcttctac ccctccgata tcgccgtgga atgggagagc   1200

aacggccagc ccgagaacaa ctacaagacc acccccccctg tgctggactc cgatggctca   1260

ttcttcctgt acagcagact gaccgtggac aagagccggt ggcaggaagg caacgtgttc   1320

agctgctccg tgatgcacga ggccctgcac aaccactaca cccagaagtc cctgtctctg   1380

agcctgggca aa                                                       1392
```

<210> SEQ ID NO 106
<211> LENGTH: 464
<212> TYPE: PRT
<213> ORGANISM: Artificial Sequence
<220> FEATURE:
<223> OTHER INFORMATION: Heavy chain IgG4P of human chimeric rat_CD147_#101

<400> SEQUENCE: 106

```
Met Lys His Leu Trp Phe Phe Leu Leu Leu Val Ala Ala Pro Arg Trp
1               5                   10                  15

Val Leu Ser Glu Val Gln Leu Val Glu Ser Asp Gly Gly Leu Val Gln
            20                  25                  30

Pro Gly Arg Ser Leu Lys Leu Ser Cys Ala Ala Ser Gly Phe Thr Phe
        35                  40                  45

Ser Asp Tyr Tyr Met Ala Trp Val Arg Gln Ala Pro Thr Lys Gly Leu
    50                  55                  60

Glu Trp Val Ala Thr Ile Ser Tyr Asp Gly Ser Asn Thr Tyr Tyr Arg
65                  70                  75                  80

Asp Ser Val Lys Gly Arg Phe Thr Ile Ser Arg Asp Asn Ala Lys Ser
                85                  90                  95

Thr Leu Tyr Leu Gln Met Asp Ser Leu Arg Ser Gly Asp Thr Ala Thr
            100                 105                 110

Tyr Tyr Cys Ala Arg Phe Tyr Asn Asn Tyr Tyr Phe Asp Tyr Trp Gly
        115                 120                 125

Gln Gly Val Met Val Thr Val Ser Ser Ala Ser Thr Lys Gly Pro Ser
    130                 135                 140
```

-continued

Val Phe Pro Leu Ala Pro Cys Ser Arg Ser Thr Ser Glu Ser Thr Ala
145 150 155 160

Ala Leu Gly Cys Leu Val Lys Asp Tyr Phe Pro Glu Pro Val Thr Val
165 170 175

Ser Trp Asn Ser Gly Ala Leu Thr Ser Gly Val His Thr Phe Pro Ala
180 185 190

Val Leu Gln Ser Ser Gly Leu Tyr Ser Leu Ser Ser Val Val Thr Val
195 200 205

Pro Ser Ser Ser Leu Gly Thr Lys Thr Tyr Thr Cys Asn Val Asp His
210 215 220

Lys Pro Ser Asn Thr Lys Val Asp Lys Arg Val Glu Ser Lys Tyr Gly
225 230 235 240

Pro Pro Cys Pro Pro Cys Pro Ala Pro Glu Phe Leu Gly Gly Pro Ser
245 250 255

Val Phe Leu Phe Pro Pro Lys Pro Lys Asp Thr Leu Met Ile Ser Arg
260 265 270

Thr Pro Glu Val Thr Cys Val Val Val Asp Val Ser Gln Glu Asp Pro
275 280 285

Glu Val Gln Phe Asn Trp Tyr Val Asp Gly Val Glu Val His Asn Ala
290 295 300

Lys Thr Lys Pro Arg Glu Glu Gln Phe Asn Ser Thr Tyr Arg Val Val
305 310 315 320

Ser Val Leu Thr Val Leu His Gln Asp Trp Leu Asn Gly Lys Glu Tyr
325 330 335

Lys Cys Lys Val Ser Asn Lys Gly Leu Pro Ser Ser Ile Glu Lys Thr
340 345 350

Ile Ser Lys Ala Lys Gly Gln Pro Arg Glu Pro Gln Val Tyr Thr Leu
355 360 365

Pro Pro Ser Gln Glu Glu Met Thr Lys Asn Gln Val Ser Leu Thr Cys
370 375 380

Leu Val Lys Gly Phe Tyr Pro Ser Asp Ile Ala Val Glu Trp Glu Ser
385 390 395 400

Asn Gly Gln Pro Glu Asn Asn Tyr Lys Thr Thr Pro Pro Val Leu Asp
405 410 415

Ser Asp Gly Ser Phe Phe Leu Tyr Ser Arg Leu Thr Val Asp Lys Ser
420 425 430

Arg Trp Gln Glu Gly Asn Val Phe Ser Cys Ser Val Met His Glu Ala
435 440 445

Leu His Asn His Tyr Thr Gln Lys Ser Leu Ser Leu Ser Leu Gly Lys
450 455 460

<210> SEQ ID NO 107
<211> LENGTH: 1392
<212> TYPE: DNA
<213> ORGANISM: Artificial Sequence
<220> FEATURE:
<223> OTHER INFORMATION: Heavy chain IgG4PFALA of human chimeric
rat_CD147_#101

<400> SEQUENCE: 107
atgaaacacc tgtggttctt cctcctgctg gtggcagctc ccagatgggt gctgagcgag 60
gtgcagctgg tggagtctga tggaggctta gtgcagcctg gaaggtccct aaaactctcc 120
tgtgcagcct caggattcac tttcagtgac tattacatgg cctgggtccg ccaggctcca 180
acgaaggggc tggagtgggt cgcaaccatt agttatgatg gtagtaacac ttactatcga 240

```
gactccgtga agggccgatt cactatctcc agagataatg caaaaagcac cctatacctg    300

caaatggaca gtctgaggtc tggggacacg gccacttatt actgtgcaag attttacaac    360

aactactact ttgattactg gggccaagga gtcatggtca cagtcagctc agcctccacc    420

aagggcccta gcgtgttccc tctggcccct tgtagcagaa gcaccagcga gtctacagcc    480

gccctgggct gcctcgtgaa ggactacttt cccgagcccg tgaccgtgtc ctggaactct    540

ggcgctctga caagcggcgt gcacaccttt ccagccgtgc tgcagagcag cggcctgtac    600

tctctgtcca gcgtcgtgac tgtgcccagc agctctctgg gcaccaagac ctacacctgt    660

aacgtggacc acaagcccag caacaccaag gtggacaagc gggtggaatc taagtacggc    720

cctccctgcc ctccttgccc agcccctgaa gccgcgggcg gaccctccgt gttcctgttc    780

cccccaaagc ccaaggacac cctgatgatc agccggaccc ccgaagtgac ctgcgtggtg    840

gtggatgtgt cccaggaaga tcccgaggtg cagttcaatt ggtacgtgga cggcgtggaa    900

gtgcacaacg ccaagaccaa gcctagagag gaacagttca acagcaccta ccgggtggtg    960

tccgtgctga cagtgctgca ccaggactgg ctgaacggca aagagtacaa gtgcaaggtg   1020

tccaacaagg gcctgcccag ctccatcgag aaaaccatca gcaaggccaa gggccagccc   1080

cgcgaacccc aggtgtacac actgcctcca agccaggaag agatgaccaa gaatcaggtg   1140

tccctgacct gtctcgtgaa aggcttctac ccctccgata tcgccgtgga atgggagagc   1200

aacggccagc ccgagaacaa ctacaagacc acccccccctg tgctggactc cgatggctca   1260

ttcttcctgt acagcagact gaccgtggac aagagccggt ggcaggaagg caacgtgttc   1320

agctgctccg tgatgcacga ggccctgcac aaccactaca cccagaagtc cctgtctctg   1380

agcctgggca aa                                                        1392
```

```
<210> SEQ ID NO 108
<211> LENGTH: 464
<212> TYPE: PRT
<213> ORGANISM: Artificial Sequence
<220> FEATURE:
<223> OTHER INFORMATION: Heavy chain IgG4PFALA of human chimeric
      rat_CD147_#101

<400> SEQUENCE: 108

Met Lys His Leu Trp Phe Phe Leu Leu Leu Val Ala Ala Pro Arg Trp
1               5                   10                  15

Val Leu Ser Glu Val Gln Leu Val Glu Ser Asp Gly Gly Leu Val Gln
            20                  25                  30

Pro Gly Arg Ser Leu Lys Leu Ser Cys Ala Ala Ser Gly Phe Thr Phe
        35                  40                  45

Ser Asp Tyr Tyr Met Ala Trp Val Arg Gln Ala Pro Thr Lys Gly Leu
    50                  55                  60

Glu Trp Val Ala Thr Ile Ser Tyr Asp Gly Ser Asn Thr Tyr Tyr Arg
65                  70                  75                  80

Asp Ser Val Lys Gly Arg Phe Thr Ile Ser Arg Asp Asn Ala Lys Ser
                85                  90                  95

Thr Leu Tyr Leu Gln Met Asp Ser Leu Arg Ser Gly Asp Thr Ala Thr
            100                 105                 110

Tyr Tyr Cys Ala Arg Phe Tyr Asn Asn Tyr Tyr Phe Asp Tyr Trp Gly
        115                 120                 125

Gln Gly Val Met Val Thr Val Ser Ser Ala Ser Thr Lys Gly Pro Ser
    130                 135                 140
```

```
Val Phe Pro Leu Ala Pro Cys Ser Arg Ser Thr Ser Glu Ser Thr Ala
145                 150                 155                 160

Ala Leu Gly Cys Leu Val Lys Asp Tyr Phe Pro Glu Pro Val Thr Val
                165                 170                 175

Ser Trp Asn Ser Gly Ala Leu Thr Ser Gly Val His Thr Phe Pro Ala
            180                 185                 190

Val Leu Gln Ser Ser Gly Leu Tyr Ser Leu Ser Ser Val Val Thr Val
        195                 200                 205

Pro Ser Ser Ser Leu Gly Thr Lys Thr Tyr Thr Cys Asn Val Asp His
    210                 215                 220

Lys Pro Ser Asn Thr Lys Val Asp Lys Arg Val Glu Ser Lys Tyr Gly
225                 230                 235                 240

Pro Pro Cys Pro Pro Cys Pro Ala Pro Glu Ala Ala Gly Gly Pro Ser
                245                 250                 255

Val Phe Leu Phe Pro Pro Lys Pro Lys Asp Thr Leu Met Ile Ser Arg
            260                 265                 270

Thr Pro Glu Val Thr Cys Val Val Val Asp Val Ser Gln Glu Asp Pro
        275                 280                 285

Glu Val Gln Phe Asn Trp Tyr Val Asp Gly Val Glu Val His Asn Ala
    290                 295                 300

Lys Thr Lys Pro Arg Glu Glu Gln Phe Asn Ser Thr Tyr Arg Val Val
305                 310                 315                 320

Ser Val Leu Thr Val Leu His Gln Asp Trp Leu Asn Gly Lys Glu Tyr
                325                 330                 335

Lys Cys Lys Val Ser Asn Lys Gly Leu Pro Ser Ser Ile Glu Lys Thr
            340                 345                 350

Ile Ser Lys Ala Lys Gly Gln Pro Arg Glu Pro Gln Val Tyr Thr Leu
        355                 360                 365

Pro Pro Ser Gln Glu Glu Met Thr Lys Asn Gln Val Ser Leu Thr Cys
    370                 375                 380

Leu Val Lys Gly Phe Tyr Pro Ser Asp Ile Ala Val Glu Trp Glu Ser
385                 390                 395                 400

Asn Gly Gln Pro Glu Asn Asn Tyr Lys Thr Thr Pro Pro Val Leu Asp
                405                 410                 415

Ser Asp Gly Ser Phe Phe Leu Tyr Ser Arg Leu Thr Val Asp Lys Ser
            420                 425                 430

Arg Trp Gln Glu Gly Asn Val Phe Ser Cys Ser Val Met His Glu Ala
        435                 440                 445

Leu His Asn His Tyr Thr Gln Lys Ser Leu Ser Leu Ser Leu Gly Lys
    450                 455                 460


<210> SEQ ID NO 109
<211> LENGTH: 702
<212> TYPE: DNA
<213> ORGANISM: Artificial Sequence
<220> FEATURE:
<223> OTHER INFORMATION: Light chain of human chimeric rat_CD147_#110

<400> SEQUENCE: 109

atggtgctgc agacccaggt gttcatctcc ctgctgctgt ggatctccgg cgcgtacggc      60

gacatccaga tgacccagac tccatcctcc atgcctgcat ctctgggaga gagagtcacc     120

atcagttgca gagcaagtca gggtattagc aattatctaa actggtatca gcagaaacca     180

gatggaacga ttaaacccct gatctactac acatccaatt tacaatctgg tgtcccatca     240

aggttcagtg gcagtgggtc tgggacagat tattctctca ccatcagcag cctggagcct     300
```

-continued

```
gaagattttg caatgtattt ctgccaacag tatgatagtt ctcctcggac gttcggtgga    360

ggcaccaagc tggaattgaa acggacggtg gccgcccccct ccgtgttcat cttccccccc    420

tccgacgagc agctgaagtc cggcaccgcc tccgtggtgt gcctgctgaa taacttctac    480

cccagagagg ccaaggtgca gtggaaggtg gacaacgccc tgcagtccgg gaactcccag    540

gagagcgtga ccgagcagga cagcaaggac agcacctaca gcctgagcag caccctgacc    600

ctgagcaaag ccgactacga gaagcacaag gtgtacgcct gcgaggtgac ccaccagggc    660

ctgagctccc ccgtcaccaa gagcttcaac aggggggagt gt                        702


<210> SEQ ID NO 110
<211> LENGTH: 234
<212> TYPE: PRT
<213> ORGANISM: Artificial Sequence
<220> FEATURE:
<223> OTHER INFORMATION: Light chain of human chimeric rat_CD147_#110

<400> SEQUENCE: 110

Met Val Leu Gln Thr Gln Val Phe Ile Ser Leu Leu Leu Trp Ile Ser
1               5                   10                  15

Gly Ala Tyr Gly Asp Ile Gln Met Thr Gln Thr Pro Ser Ser Met Pro
            20                  25                  30

Ala Ser Leu Gly Glu Arg Val Thr Ile Ser Cys Arg Ala Ser Gln Gly
        35                  40                  45

Ile Ser Asn Tyr Leu Asn Trp Tyr Gln Gln Lys Pro Asp Gly Thr Ile
    50                  55                  60

Lys Pro Leu Ile Tyr Tyr Thr Ser Asn Leu Gln Ser Gly Val Pro Ser
65                  70                  75                  80

Arg Phe Ser Gly Ser Gly Ser Gly Thr Asp Tyr Ser Leu Thr Ile Ser
                85                  90                  95

Ser Leu Glu Pro Glu Asp Phe Ala Met Tyr Phe Cys Gln Gln Tyr Asp
            100                 105                 110

Ser Ser Pro Arg Thr Phe Gly Gly Gly Thr Lys Leu Glu Leu Lys Arg
        115                 120                 125

Thr Val Ala Ala Pro Ser Val Phe Ile Phe Pro Pro Ser Asp Glu Gln
    130                 135                 140

Leu Lys Ser Gly Thr Ala Ser Val Val Cys Leu Leu Asn Asn Phe Tyr
145                 150                 155                 160

Pro Arg Glu Ala Lys Val Gln Trp Lys Val Asp Asn Ala Leu Gln Ser
                165                 170                 175

Gly Asn Ser Gln Glu Ser Val Thr Glu Gln Asp Ser Lys Asp Ser Thr
            180                 185                 190

Tyr Ser Leu Ser Ser Thr Leu Thr Leu Ser Lys Ala Asp Tyr Glu Lys
        195                 200                 205

His Lys Val Tyr Ala Cys Glu Val Thr His Gln Gly Leu Ser Ser Pro
    210                 215                 220

Val Thr Lys Ser Phe Asn Arg Gly Glu Cys
225                 230


<210> SEQ ID NO 111
<211> LENGTH: 1386
<212> TYPE: DNA
<213> ORGANISM: Artificial Sequence
<220> FEATURE:
<223> OTHER INFORMATION: Heavy chain IgG2 of human chimeric
      rat_CD147_#110
```

<400> SEQUENCE: 111

```
atgaaacacc tgtggttctt cctcctgctg gtggcagctc ccagatgggt gctgagccag     60
gtacagctgc agcaatctgg ggctgaactg gtgaagcctg ggtcctcagt gaaaatttcc    120
tgcaaggctt ctggctacac cttcaccagt gactttatgc actggataaa acagcagcct    180
ggaaatggcc ttgagtggat tgggtggatt tatcctggag atggtgatac agagtacaat    240
caaaagttca atgggaaggc aacactcact gcagacaaat cctccagcac agcctatatg    300
cagctcagca gcctgacatc tgaggactct gcagtctatt tctgtgcaag gggacggggg    360
tatgttatgg atgcctgggg tcaaggagct tcagtcactg tcagctcagc ctccaccaag    420
ggcccttccg tgttccctct ggccccttgt agccgttcca ccagcgagtc caccgccgcc    480
cttggctgtc tggtgaagga ctacttccct gagcctgtga ccgtgagctg gaactccgga    540
gcccttacca gcggcgtgca caccttccct gccgtgctgc agtccagcgg cctttactcc    600
ctgagctccg tggtgaccgt gcctagctcc aacttcggca cccaaaccta cacctgtaac    660
gtggaccaca agcctagcaa caccaaggtg gacaagaccg tggagcgtaa gtgttgtgtg    720
gagtgtcctc cttgtcctgc ccctcctgtg gccggacctt ccgtgttcct tttccctcct    780
aagcctaagg acaccctgat gatcagccgt acccctgagg tgacctgtgt ggtggtggac    840
gtgtcccacg aggaccctga ggtgcagttc aactggtacg tggacggcgt ggaggtgcac    900
aacgccaaga ccaagcctcg tgaggagcaa ttcaacagca ccttccgtgt ggtgtccgtg    960
cttaccgtgg tgcaccaaga ctggctgaac ggcaaggagt acaagtgtaa ggtgagcaac   1020
aagggacttc ctgcccctat cgagaagacc atctccaaga ccaagggcca acctcgtgag   1080
cctcaagtgt acacccttcc tcctagccgt gaggagatga ccaagaacca agtgtccctt   1140
acctgtctgg tgaagggctt ctaccctagc gacatcgccg tggagtggga gtccaacgga   1200
caacctgaga acaactacaa gaccacccct cctatgcttg acagcgacgg ctccttcttc   1260
ctgtacagca agctgaccgt ggacaagtcc cgttggcaac aaggcaacgt gttcagctgt   1320
tccgtgatgc acgaggccct gcacaaccac tacacccaaa agagcctttc cctgagccct   1380
ggaaag                                                              1386
```

<210> SEQ ID NO 112
<211> LENGTH: 462
<212> TYPE: PRT
<213> ORGANISM: Artificial Sequence
<220> FEATURE:
<223> OTHER INFORMATION: Heavy chain IgG2 of human chimeric rat_CD147_#110

<400> SEQUENCE: 112

```
Met Lys His Leu Trp Phe Phe Leu Leu Leu Val Ala Ala Pro Arg Trp
1               5                   10                  15

Val Leu Ser Gln Val Gln Leu Gln Gln Ser Gly Ala Glu Leu Val Lys
            20                  25                  30

Pro Gly Ser Ser Val Lys Ile Ser Cys Lys Ala Ser Gly Tyr Thr Phe
        35                  40                  45

Thr Ser Asp Phe Met His Trp Ile Lys Gln Gln Pro Gly Asn Gly Leu
    50                  55                  60

Glu Trp Ile Gly Trp Ile Tyr Pro Gly Asp Gly Asp Thr Glu Tyr Asn
65                  70                  75                  80

Gln Lys Phe Asn Gly Lys Ala Thr Leu Thr Ala Asp Lys Ser Ser Ser
                85                  90                  95
```

-continued

```
Thr Ala Tyr Met Gln Leu Ser Ser Leu Thr Ser Glu Asp Ser Ala Val
            100                 105                 110

Tyr Phe Cys Ala Arg Gly Arg Gly Tyr Val Met Asp Ala Trp Gly Gln
        115                 120                 125

Gly Ala Ser Val Thr Val Ser Ser Ala Ser Thr Lys Gly Pro Ser Val
    130                 135                 140

Phe Pro Leu Ala Pro Cys Ser Arg Ser Thr Ser Glu Ser Thr Ala Ala
145                 150                 155                 160

Leu Gly Cys Leu Val Lys Asp Tyr Phe Pro Glu Pro Val Thr Val Ser
                165                 170                 175

Trp Asn Ser Gly Ala Leu Thr Ser Gly Val His Thr Phe Pro Ala Val
            180                 185                 190

Leu Gln Ser Ser Gly Leu Tyr Ser Leu Ser Ser Val Val Thr Val Pro
        195                 200                 205

Ser Ser Asn Phe Gly Thr Gln Thr Tyr Thr Cys Asn Val Asp His Lys
    210                 215                 220

Pro Ser Asn Thr Lys Val Asp Lys Thr Val Glu Arg Lys Cys Cys Val
225                 230                 235                 240

Glu Cys Pro Pro Cys Pro Ala Pro Pro Val Ala Gly Pro Ser Val Phe
                245                 250                 255

Leu Phe Pro Pro Lys Pro Lys Asp Thr Leu Met Ile Ser Arg Thr Pro
            260                 265                 270

Glu Val Thr Cys Val Val Val Asp Val Ser His Glu Asp Pro Glu Val
        275                 280                 285

Gln Phe Asn Trp Tyr Val Asp Gly Val Glu Val His Asn Ala Lys Thr
    290                 295                 300

Lys Pro Arg Glu Glu Gln Phe Asn Ser Thr Phe Arg Val Val Ser Val
305                 310                 315                 320

Leu Thr Val Val His Gln Asp Trp Leu Asn Gly Lys Glu Tyr Lys Cys
                325                 330                 335

Lys Val Ser Asn Lys Gly Leu Pro Ala Pro Ile Glu Lys Thr Ile Ser
            340                 345                 350

Lys Thr Lys Gly Gln Pro Arg Glu Pro Gln Val Tyr Thr Leu Pro Pro
        355                 360                 365

Ser Arg Glu Glu Met Thr Lys Asn Gln Val Ser Leu Thr Cys Leu Val
    370                 375                 380

Lys Gly Phe Tyr Pro Ser Asp Ile Ala Val Glu Trp Glu Ser Asn Gly
385                 390                 395                 400

Gln Pro Glu Asn Asn Tyr Lys Thr Thr Pro Pro Met Leu Asp Ser Asp
                405                 410                 415

Gly Ser Phe Phe Leu Tyr Ser Lys Leu Thr Val Asp Lys Ser Arg Trp
            420                 425                 430

Gln Gln Gly Asn Val Phe Ser Cys Ser Val Met His Glu Ala Leu His
        435                 440                 445

Asn His Tyr Thr Gln Lys Ser Leu Ser Leu Ser Pro Gly Lys
    450                 455                 460
```

<210> SEQ ID NO 113
<211> LENGTH: 1389
<212> TYPE: DNA
<213> ORGANISM: Artificial Sequence
<220> FEATURE:
<223> OTHER INFORMATION: Heavy chain IgG4P of human chimeric rat_CD147_#110

<400> SEQUENCE: 113
atgaaacacc tgtggttctt cctcctgctg gtggcagctc ccagatgggt gctgagccag 60
gtacagctgc agcaatctgg ggctgaactg gtgaagcctg ggtcctcagt gaaaatttcc 120
tgcaaggctt ctggctacac cttcaccagt gactttatgc actggataaa acagcagcct 180
ggaaatggcc ttgagtggat tgggtggatt tatcctggag atggtgatac agagtacaat 240
caaaagttca atgggaaggc aacactcact gcagacaaat cctccagcac agcctatatg 300
cagctcagca gcctgacatc tgaggactct gcagtctatt tctgtgcaag gggacggggg 360
tatgttatgg atgcctgggg tcaaggagct tcagtcactg tcagctcagc ctccaccaag 420
ggccctagcg tgttccctct ggccccttgt agcagaagca ccagcgagtc tacagccgcc 480
ctgggctgcc tcgtgaagga ctactttccc gagcccgtga ccgtgtcctg gaactctggc 540
gctctgacaa gcggcgtgca cacctttcca gccgtgctgc agagcagcgg cctgtactct 600
ctgtccagcg tcgtgactgt gcccagcagc tctctgggca ccaagaccta cacctgtaac 660
gtggaccaca agcccagcaa caccaaggtg gacaagcggg tggaatctaa gtacggccct 720
ccctgccctc cttgcccagc ccctgaattt ctgggcggac cctccgtgtt cctgttcccc 780
ccaaagccca aggacaccct gatgatcagc cggacccccg aagtgacctg cgtggtggtg 840
gatgtgtccc aggaagatcc cgaggtgcag ttcaattggt acgtggacgg cgtggaagtg 900
cacaacgcca agaccaagcc tagagaggaa cagttcaaca gcacctaccg ggtggtgtcc 960
gtgctgacag tgctgcacca ggactggctg aacggcaaag agtacaagtg caaggtgtcc 1020
aacaagggcc tgcccagctc catcgagaaa accatcagca aggccaaggg ccagccccgc 1080
gaaccccagg tgtacacact gcctccaagc caggaagaga tgaccaagaa tcaggtgtcc 1140
ctgacctgtc tcgtgaaagg cttctacccc tccgatatcg ccgtggaatg ggagagcaac 1200
ggccagcccg agaacaacta caagaccacc ccccctgtgc tggactccga tggctcattc 1260
ttcctgtaca gcagactgac cgtggacaag agccggtggc aggaaggcaa cgtgttcagc 1320
tgctccgtga tgcacgaggc cctgcacaac cactacaccc agaagtccct gtctctgagc 1380
ctgggcaaa 1389

<210> SEQ ID NO 114
<211> LENGTH: 463
<212> TYPE: PRT
<213> ORGANISM: Artificial Sequence
<220> FEATURE:
<223> OTHER INFORMATION: Heavy chain IgG4P of human chimeric rat_CD147_#110

<400> SEQUENCE: 114

Met Lys His Leu Trp Phe Phe Leu Leu Leu Val Ala Ala Pro Arg Trp
1 5 10 15

Val Leu Ser Gln Val Gln Leu Gln Gln Ser Gly Ala Glu Leu Val Lys
20 25 30

Pro Gly Ser Ser Val Lys Ile Ser Cys Lys Ala Ser Gly Tyr Thr Phe
35 40 45

Thr Ser Asp Phe Met His Trp Ile Lys Gln Gln Pro Gly Asn Gly Leu
50 55 60

Glu Trp Ile Gly Trp Ile Tyr Pro Gly Asp Gly Asp Thr Glu Tyr Asn
65 70 75 80

Gln Lys Phe Asn Gly Lys Ala Thr Leu Thr Ala Asp Lys Ser Ser Ser
85 90 95

-continued

```
Thr Ala Tyr Met Gln Leu Ser Ser Leu Thr Ser Glu Asp Ser Ala Val
            100                 105                 110

Tyr Phe Cys Ala Arg Gly Arg Gly Tyr Val Met Asp Ala Trp Gly Gln
        115                 120                 125

Gly Ala Ser Val Thr Val Ser Ser Ala Ser Thr Lys Gly Pro Ser Val
    130                 135                 140

Phe Pro Leu Ala Pro Cys Ser Arg Ser Thr Ser Glu Ser Thr Ala Ala
145                 150                 155                 160

Leu Gly Cys Leu Val Lys Asp Tyr Phe Pro Glu Pro Val Thr Val Ser
                165                 170                 175

Trp Asn Ser Gly Ala Leu Thr Ser Gly Val His Thr Phe Pro Ala Val
            180                 185                 190

Leu Gln Ser Ser Gly Leu Tyr Ser Leu Ser Ser Val Val Thr Val Pro
        195                 200                 205

Ser Ser Ser Leu Gly Thr Lys Thr Tyr Thr Cys Asn Val Asp His Lys
    210                 215                 220

Pro Ser Asn Thr Lys Val Asp Lys Arg Val Glu Ser Lys Tyr Gly Pro
225                 230                 235                 240

Pro Cys Pro Pro Cys Pro Ala Pro Glu Phe Leu Gly Gly Pro Ser Val
                245                 250                 255

Phe Leu Phe Pro Pro Lys Pro Lys Asp Thr Leu Met Ile Ser Arg Thr
            260                 265                 270

Pro Glu Val Thr Cys Val Val Val Asp Val Ser Gln Glu Asp Pro Glu
        275                 280                 285

Val Gln Phe Asn Trp Tyr Val Asp Gly Val Glu Val His Asn Ala Lys
    290                 295                 300

Thr Lys Pro Arg Glu Glu Gln Phe Asn Ser Thr Tyr Arg Val Val Ser
305                 310                 315                 320

Val Leu Thr Val Leu His Gln Asp Trp Leu Asn Gly Lys Glu Tyr Lys
                325                 330                 335

Cys Lys Val Ser Asn Lys Gly Leu Pro Ser Ser Ile Glu Lys Thr Ile
            340                 345                 350

Ser Lys Ala Lys Gly Gln Pro Arg Glu Pro Gln Val Tyr Thr Leu Pro
        355                 360                 365

Pro Ser Gln Glu Glu Met Thr Lys Asn Gln Val Ser Leu Thr Cys Leu
    370                 375                 380

Val Lys Gly Phe Tyr Pro Ser Asp Ile Ala Val Glu Trp Glu Ser Asn
385                 390                 395                 400

Gly Gln Pro Glu Asn Asn Tyr Lys Thr Thr Pro Pro Val Leu Asp Ser
                405                 410                 415

Asp Gly Ser Phe Phe Leu Tyr Ser Arg Leu Thr Val Asp Lys Ser Arg
            420                 425                 430

Trp Gln Glu Gly Asn Val Phe Ser Cys Ser Val Met His Glu Ala Leu
        435                 440                 445

His Asn His Tyr Thr Gln Lys Ser Leu Ser Leu Ser Leu Gly Lys
    450                 455                 460
```

<210> SEQ ID NO 115
<211> LENGTH: 1389
<212> TYPE: DNA
<213> ORGANISM: Artificial Sequence
<220> FEATURE:
<223> OTHER INFORMATION: Heavy chain IgG4PFALA of human chimeric
rat_CD147_#110

<400> SEQUENCE: 115

```
atgaaacacc tgtggttctt cctcctgctg gtggcagctc ccagatgggt gctgagccag      60
gtacagctgc agcaatctgg ggctgaactg gtgaagcctg ggtcctcagt gaaaatttcc     120
tgcaaggctt ctggctacac cttcaccagt gactttatgc actggataaa acagcagcct     180
ggaaatggcc ttgagtggat tgggtggatt tatcctggag atggtgatac agagtacaat     240
caaaagttca atgggaaggc aacactcact gcagacaaat cctccagcac agcctatatg     300
cagctcagca gcctgacatc tgaggactct gcagtctatt tctgtgcaag gggacggggg     360
tatgttatgg atgcctgggg tcaaggagct tcagtcactg tcagctcagc ctccaccaag     420
ggccctagcg tgttccctct ggccccttgt agcagaagca ccagcgagtc tacagccgcc     480
ctgggctgcc tcgtgaagga ctactttccc gagcccgtga ccgtgtcctg gaactctggc     540
gctctgacaa gcggcgtgca cacctttcca gccgtgctgc agagcagcgg cctgtactct     600
ctgtccagcg tcgtgactgt gcccagcagc tctctgggca ccaagaccta cacctgtaac     660
gtggaccaca agcccagcaa caccaaggtg gacaagcggg tggaatctaa gtacggccct     720
ccctgccctc cttgcccagc ccctgaagcc gcgggcggac cctccgtgtt cctgttcccc     780
ccaaagccca aggacaccct gatgatcagc cggacccccg aagtgacctg cgtggtggtg     840
gatgtgtccc aggaagatcc cgaggtgcag ttcaattggt acgtggacgg cgtggaagtg     900
cacaacgcca agaccaagcc tagagaggaa cagttcaaca gcacctaccg ggtggtgtcc     960
gtgctgacag tgctgcacca ggactggctg aacggcaaag agtacaagtg caaggtgtcc    1020
aacaagggcc tgcccagctc catcgagaaa accatcagca aggccaaggg ccagccccgc    1080
gaaccccagg tgtacacact gcctccaagc caggaagaga tgaccaagaa tcaggtgtcc    1140
ctgacctgtc tcgtgaaagg cttctacccc tccgatatcg ccgtggaatg ggagagcaac    1200
ggccagcccg agaacaacta caagaccacc ccccctgtgc tggactccga tggctcattc    1260
ttcctgtaca gcagactgac cgtggacaag agccggtggc aggaaggcaa cgtgttcagc    1320
tgctccgtga tgcacgaggc cctgcacaac cactacaccc agaagtccct gtctctgagc    1380
ctgggcaaa                                                            1389
```

<210> SEQ ID NO 116
<211> LENGTH: 463
<212> TYPE: PRT
<213> ORGANISM: Artificial Sequence
<220> FEATURE:
<223> OTHER INFORMATION: Heavy chain IgG4PFALA of human chimeric rat_CD147_#110

<400> SEQUENCE: 116

```
Met Lys His Leu Trp Phe Phe Leu Leu Leu Val Ala Ala Pro Arg Trp
1               5                   10                  15

Val Leu Ser Gln Val Gln Leu Gln Gln Ser Gly Ala Glu Leu Val Lys
            20                  25                  30

Pro Gly Ser Ser Val Lys Ile Ser Cys Lys Ala Ser Gly Tyr Thr Phe
        35                  40                  45

Thr Ser Asp Phe Met His Trp Ile Lys Gln Gln Pro Gly Asn Gly Leu
    50                  55                  60

Glu Trp Ile Gly Trp Ile Tyr Pro Gly Asp Gly Asp Thr Glu Tyr Asn
65                  70                  75                  80

Gln Lys Phe Asn Gly Lys Ala Thr Leu Thr Ala Asp Lys Ser Ser Ser
                85                  90                  95
```

-continued

```
Thr Ala Tyr Met Gln Leu Ser Ser Leu Thr Ser Glu Asp Ser Ala Val
            100                 105                 110

Tyr Phe Cys Ala Arg Gly Arg Gly Tyr Val Met Asp Ala Trp Gly Gln
        115                 120                 125

Gly Ala Ser Val Thr Val Ser Ser Ala Ser Thr Lys Gly Pro Ser Val
    130                 135                 140

Phe Pro Leu Ala Pro Cys Ser Arg Ser Thr Ser Glu Ser Thr Ala Ala
145                 150                 155                 160

Leu Gly Cys Leu Val Lys Asp Tyr Phe Pro Glu Pro Val Thr Val Ser
                165                 170                 175

Trp Asn Ser Gly Ala Leu Thr Ser Gly Val His Thr Phe Pro Ala Val
            180                 185                 190

Leu Gln Ser Ser Gly Leu Tyr Ser Leu Ser Ser Val Val Thr Val Pro
        195                 200                 205

Ser Ser Ser Leu Gly Thr Lys Thr Tyr Thr Cys Asn Val Asp His Lys
    210                 215                 220

Pro Ser Asn Thr Lys Val Asp Lys Arg Val Glu Ser Lys Tyr Gly Pro
225                 230                 235                 240

Pro Cys Pro Pro Cys Pro Ala Pro Glu Ala Ala Gly Gly Pro Ser Val
                245                 250                 255

Phe Leu Phe Pro Pro Lys Pro Lys Asp Thr Leu Met Ile Ser Arg Thr
            260                 265                 270

Pro Glu Val Thr Cys Val Val Val Asp Val Ser Gln Glu Asp Pro Glu
        275                 280                 285

Val Gln Phe Asn Trp Tyr Val Asp Gly Val Glu Val His Asn Ala Lys
    290                 295                 300

Thr Lys Pro Arg Glu Glu Gln Phe Asn Ser Thr Tyr Arg Val Val Ser
305                 310                 315                 320

Val Leu Thr Val Leu His Gln Asp Trp Leu Asn Gly Lys Glu Tyr Lys
                325                 330                 335

Cys Lys Val Ser Asn Lys Gly Leu Pro Ser Ser Ile Glu Lys Thr Ile
            340                 345                 350

Ser Lys Ala Lys Gly Gln Pro Arg Glu Pro Gln Val Tyr Thr Leu Pro
        355                 360                 365

Pro Ser Gln Glu Glu Met Thr Lys Asn Gln Val Ser Leu Thr Cys Leu
    370                 375                 380

Val Lys Gly Phe Tyr Pro Ser Asp Ile Ala Val Glu Trp Glu Ser Asn
385                 390                 395                 400

Gly Gln Pro Glu Asn Asn Tyr Lys Thr Thr Pro Pro Val Leu Asp Ser
                405                 410                 415

Asp Gly Ser Phe Phe Leu Tyr Ser Arg Leu Thr Val Asp Lys Ser Arg
            420                 425                 430

Trp Gln Glu Gly Asn Val Phe Ser Cys Ser Val Met His Glu Ala Leu
        435                 440                 445

His Asn His Tyr Thr Gln Lys Ser Leu Ser Leu Ser Leu Gly Lys
    450                 455                 460
```

<210> SEQ ID NO 117
<211> LENGTH: 702
<212> TYPE: DNA
<213> ORGANISM: Artificial Sequence
<220> FEATURE:
<223> OTHER INFORMATION: Light chain of human chimeric rat_CD147_#131

<400> SEQUENCE: 117
atggtgctgc agacccaggt gttcatctcc ctgctgctgt ggatctccgg cgcgtacggc 60
gatgtccaga tgacccagtc tccatcttat cttgctgcgt ctcctggaga aagtgtttcc 120
atcagttgca aggcaagtaa aagcattaac acatacttag cctggtatca ggagaaacct 180
gggaaaacga ataagcttct tatctactct gggtcaactt tgcaatctgg aactccatcg 240
agattcagtg gcagtggatc tggtacagat ttcacgctca ccatcagaag cctggagcct 300
gaagattttg cagtctacta ctgtcaacag cataatgaat accccttcac gttcggctca 360
gggacgaagt tggaaataaa acggacggtg gccgcccct ccgtgttcat cttcccccc 420 tccgacgagc agctgaagtc cggcaccgcc tccgtggtgt gcctgctgaa taacttctac 480
cccagagagg ccaaggtgca gtggaaggtg gacaacgccc tgcagtccgg gaactcccag 540
gagagcgtga ccgagcagga cagcaaggac agcacctaca gcctgagcag caccctgacc 600
ctgagcaaag ccgactacga gaagcacaag gtgtacgcct gcgaggtgac ccaccagggc 660
ctgagctccc ccgtcaccaa gagcttcaac aggggggagt gt 702

<210> SEQ ID NO 118
<211> LENGTH: 234
<212> TYPE: PRT
<213> ORGANISM: Artificial Sequence
<220> FEATURE:
<223> OTHER INFORMATION: Light chain of human chimeric rat_CD147_#131

<400> SEQUENCE: 118

Met Val Leu Gln Thr Gln Val Phe Ile Ser Leu Leu Leu Trp Ile Ser
1               5                   10                  15

Gly Ala Tyr Gly Asp Val Gln Met Thr Gln Ser Pro Ser Tyr Leu Ala
            20                  25                  30

Ala Ser Pro Gly Glu Ser Val Ser Ile Ser Cys Lys Ala Ser Lys Ser
        35                  40                  45

Ile Asn Thr Tyr Leu Ala Trp Tyr Gln Glu Lys Pro Gly Lys Thr Asn
    50                  55                  60

Lys Leu Leu Ile Tyr Ser Gly Ser Thr Leu Gln Ser Gly Thr Pro Ser
65                  70                  75                  80

Arg Phe Ser Gly Ser Gly Ser Gly Thr Asp Phe Thr Leu Thr Ile Arg
                85                  90                  95

Ser Leu Glu Pro Glu Asp Phe Ala Val Tyr Tyr Cys Gln Gln His Asn
            100                 105                 110

Glu Tyr Pro Phe Thr Phe Gly Ser Gly Thr Lys Leu Glu Ile Lys Arg
        115                 120                 125

Thr Val Ala Ala Pro Ser Val Phe Ile Phe Pro Pro Ser Asp Glu Gln
    130                 135                 140

Leu Lys Ser Gly Thr Ala Ser Val Val Cys Leu Leu Asn Asn Phe Tyr
145                 150                 155                 160

Pro Arg Glu Ala Lys Val Gln Trp Lys Val Asp Asn Ala Leu Gln Ser
                165                 170                 175

Gly Asn Ser Gln Glu Ser Val Thr Glu Gln Asp Ser Lys Asp Ser Thr
            180                 185                 190

Tyr Ser Leu Ser Ser Thr Leu Thr Leu Ser Lys Ala Asp Tyr Glu Lys
        195                 200                 205

-continued

His Lys Val Tyr Ala Cys Glu Val Thr His Gln Gly Leu Ser Ser Pro
    210                 215                 220

Val Thr Lys Ser Phe Asn Arg Gly Glu Cys
225                 230

<210> SEQ ID NO 119
<211> LENGTH: 1392
<212> TYPE: DNA
<213> ORGANISM: Artificial Sequence
<220> FEATURE:
<223> OTHER INFORMATION: Heavy chain IgG2 of human chimeric
      rat_CD147_#131

<400> SEQUENCE: 119
atgaaacacc tgtggttctt cctcctgctg gtggcagctc ccagatgggt gctgagcgag 60
gtgcagctgg tggagtctgg gggaggccta gtgcagcctg gaaggtctct gaaactatcc 120
tgtggagcct ctggattcac attcaataac tactggatga cctgggtccg ccaggctcca 180
gggaaggggc tggagtgggt tgcatccatt actaaagctg gtggtagcac ttactatcga 240
gactctgtga agggccgatt cactatctcc agagataatg caaaaagcac cctatatctg 300
caaatgaaca gtctgaggtc tgaggacacg gccacttatt actgtacaag agaactggga 360
gagttctatg ttatggatgc ctggggtcaa ggagcttcag tcactgtcag ctcagcctcc 420
accaagggcc cttccgtgtt ccctctggcc ccttgtagcc gttccaccag cgagtccacc 480
gccgcccttg gctgtctggt gaaggactac ttccctgagc ctgtgaccgt gagctggaac 540
tccggagccc ttaccagcgg cgtgcacacc ttccctgccg tgctgcagtc cagcggcctt 600
tactccctga gctccgtggt gaccgtgcct agctccaact tcggcaccca aacctacacc 660
tgtaacgtgg accacaagcc tagcaacacc aaggtggaca agaccgtgga gcgtaagtgt 720
tgtgtggagt gtcctccttg tcctgcccct cctgtggccg gaccttccgt gttccttttc 780
cctcctaagc ctaaggacac cctgatgatc agccgtaccc ctgaggtgac ctgtgtggtg 840
gtggacgtgt cccacgagga ccctgaggtg cagttcaact ggtacgtgga cggcgtggag 900
gtgcacaacg ccaagaccaa gcctcgtgag gagcaattca acagcacctt ccgtgtggtg 960
tccgtgctta ccgtggtgca ccaagactgg ctgaacggca aggagtacaa gtgtaaggtg 1020
agcaacaagg gacttcctgc ccctatcgag aagaccatct ccaagaccaa gggccaacct 1080
cgtgagcctc aagtgtacac ccttcctcct agccgtgagg agatgaccaa gaaccaagtg 1140
tcccttacct gtctggtgaa gggcttctac cctagcgaca tcgccgtgga gtgggagtcc 1200
aacggacaac ctgagaacaa ctacaagacc acccctccta tgcttgacag cgacggctcc 1260
ttcttcctgt acagcaagct gaccgtggac aagtcccgtt ggcaacaagg caacgtgttc 1320
agctgttccg tgatgcacga ggccctgcac aaccactaca cccaaaagag cctttccctg 1380
agccctggaa ag 1392

<210> SEQ ID NO 120
<211> LENGTH: 464
<212> TYPE: PRT
<213> ORGANISM: Artificial Sequence
<220> FEATURE:
<223> OTHER INFORMATION: Heavy chain IgG2 of human chimeric
      rat_CD147_#131

<400> SEQUENCE: 120

```
Met Lys His Leu Trp Phe Phe Leu Leu Leu Val Ala Ala Pro Arg Trp
1               5                   10                  15

Val Leu Ser Glu Val Gln Leu Val Glu Ser Gly Gly Gly Leu Val Gln
            20                  25                  30

Pro Gly Arg Ser Leu Lys Leu Ser Cys Gly Ala Ser Gly Phe Thr Phe
        35                  40                  45

Asn Asn Tyr Trp Met Thr Trp Val Arg Gln Ala Pro Gly Lys Gly Leu
    50                  55                  60

Glu Trp Val Ala Ser Ile Thr Lys Ala Gly Gly Ser Thr Tyr Tyr Arg
65                  70                  75                  80

Asp Ser Val Lys Gly Arg Phe Thr Ile Ser Arg Asp Asn Ala Lys Ser
                85                  90                  95

Thr Leu Tyr Leu Gln Met Asn Ser Leu Arg Ser Glu Asp Thr Ala Thr
            100                 105                 110

Tyr Tyr Cys Thr Arg Glu Leu Gly Glu Phe Tyr Val Met Asp Ala Trp
        115                 120                 125

Gly Gln Gly Ala Ser Val Thr Val Ser Ser Ala Ser Thr Lys Gly Pro
    130                 135                 140

Ser Val Phe Pro Leu Ala Pro Cys Ser Arg Ser Thr Ser Glu Ser Thr
145                 150                 155                 160

Ala Ala Leu Gly Cys Leu Val Lys Asp Tyr Phe Pro Glu Pro Val Thr
                165                 170                 175

Val Ser Trp Asn Ser Gly Ala Leu Thr Ser Gly Val His Thr Phe Pro
            180                 185                 190

Ala Val Leu Gln Ser Ser Gly Leu Tyr Ser Leu Ser Ser Val Val Thr
        195                 200                 205

Val Pro Ser Ser Asn Phe Gly Thr Gln Thr Tyr Thr Cys Asn Val Asp
    210                 215                 220

His Lys Pro Ser Asn Thr Lys Val Asp Lys Thr Val Glu Arg Lys Cys
225                 230                 235                 240

Cys Val Glu Cys Pro Pro Cys Pro Ala Pro Pro Val Ala Gly Pro Ser
                245                 250                 255

Val Phe Leu Phe Pro Pro Lys Pro Lys Asp Thr Leu Met Ile Ser Arg
            260                 265                 270

Thr Pro Glu Val Thr Cys Val Val Val Asp Val Ser His Glu Asp Pro
        275                 280                 285

Glu Val Gln Phe Asn Trp Tyr Val Asp Gly Val Glu Val His Asn Ala
    290                 295                 300

Lys Thr Lys Pro Arg Glu Glu Gln Phe Asn Ser Thr Phe Arg Val Val
305                 310                 315                 320

Ser Val Leu Thr Val Val His Gln Asp Trp Leu Asn Gly Lys Glu Tyr
                325                 330                 335

Lys Cys Lys Val Ser Asn Lys Gly Leu Pro Ala Pro Ile Glu Lys Thr
            340                 345                 350

Ile Ser Lys Thr Lys Gly Gln Pro Arg Glu Pro Gln Val Tyr Thr Leu
        355                 360                 365

Pro Pro Ser Arg Glu Glu Met Thr Lys Asn Gln Val Ser Leu Thr Cys
    370                 375                 380

Leu Val Lys Gly Phe Tyr Pro Ser Asp Ile Ala Val Glu Trp Glu Ser
385                 390                 395                 400

Asn Gly Gln Pro Glu Asn Asn Tyr Lys Thr Thr Pro Pro Met Leu Asp
                405                 410                 415
```

```
Ser Asp Gly Ser Phe Phe Leu Tyr Ser Lys Leu Thr Val Asp Lys Ser
            420                 425                 430

Arg Trp Gln Gln Gly Asn Val Phe Ser Cys Ser Val Met His Glu Ala
        435                 440                 445

Leu His Asn His Tyr Thr Gln Lys Ser Leu Ser Leu Ser Pro Gly Lys
    450                 455                 460
```

<210> SEQ ID NO 121
<211> LENGTH: 1395
<212> TYPE: DNA
<213> ORGANISM: Artificial Sequence
<220> FEATURE:
<223> OTHER INFORMATION: Heavy chain IgG4P of human chimeric rat_CD147_#131

<400> SEQUENCE: 121

```
atgaaacacc tgtggttctt cctcctgctg gtggcagctc ccagatgggt gctgagcgag     60

gtgcagctgg tggagtctgg gggaggccta gtgcagcctg gaaggtctct gaaactatcc    120

tgtggagcct ctggattcac attcaataac tactggatga cctgggtccg ccaggctcca    180

gggaaggggc tggagtgggt tgcatccatt actaaagctg gtggtagcac ttactatcga    240

gactctgtga agggccgatt cactatctcc agagataatg caaaaagcac cctatatctg    300

caaatgaaca gtctgaggtc tgaggacacg gccacttatt actgtacaag agaactggga    360

gagttctatg ttatggatgc ctggggtcaa ggagcttcag tcactgtcag ctcagcctcc    420

accaagggcc ctagcgtgtt ccctctggcc ccttgtagca gaagcaccag cgagtctaca    480

gccgccctgg gctgcctcgt gaaggactac tttcccgagc ccgtgaccgt gtcctggaac    540

tctggcgctc tgacaagcgg cgtgcacacc tttccagccg tgctgcagag cagcggcctg    600

tactctctgt ccagcgtcgt gactgtgccc agcagctctc tgggcaccaa gacctacacc    660

tgtaacgtgg accacaagcc cagcaacacc aaggtggaca agcgggtgga atctaagtac    720

ggccctccct gccctccttg cccagcccct gaatttctgg gcggaccctc cgtgttcctg    780

ttccccccaa agcccaagga caccctgatg atcagccgga cccccgaagt gacctgcgtg    840

gtggtggatg tgtcccagga agatcccgag gtgcagttca attggtacgt ggacggcgtg    900

gaagtgcaca acgccaagac caagcctaga gaggaacagt tcaacagcac ctaccgggtg    960

gtgtccgtgc tgacagtgct gcaccaggac tggctgaacg gcaaagagta caagtgcaag   1020

gtgtccaaca agggcctgcc cagctccatc gagaaaacca tcagcaaggc caagggccag   1080

ccccgcgaac cccaggtgta cacactgcct ccaagccagg aagagatgac caagaatcag   1140

gtgtccctga cctgtctcgt gaaaggcttc taccccctccg atatcgccgt ggaatgggag   1200

agcaacggcc agcccgagaa caactacaag accacccccc ctgtgctgga ctccgatggc   1260

tcattcttcc tgtacagcag actgaccgtg gacaagagcc ggtggcagga aggcaacgtg   1320

ttcagctgct ccgtgatgca cgaggccctg cacaaccact acacccagaa gtccctgtct   1380

ctgagcctgg gcaaa                                                    1395
```

<210> SEQ ID NO 122
<211> LENGTH: 465
<212> TYPE: PRT
<213> ORGANISM: Artificial Sequence
<220> FEATURE:
<223> OTHER INFORMATION: Heavy chain IgG4P of human chimeric rat_CD147_#131

<400> SEQUENCE: 122

```
Met Lys His Leu Trp Phe Phe Leu Leu Leu Val Ala Ala Pro Arg Trp
1               5                   10                  15

Val Leu Ser Glu Val Gln Leu Val Glu Ser Gly Gly Gly Leu Val Gln
            20                  25                  30

Pro Gly Arg Ser Leu Lys Leu Ser Cys Gly Ala Ser Gly Phe Thr Phe
        35                  40                  45

Asn Asn Tyr Trp Met Thr Trp Val Arg Gln Ala Pro Gly Lys Gly Leu
    50                  55                  60

Glu Trp Val Ala Ser Ile Thr Lys Ala Gly Gly Ser Thr Tyr Tyr Arg
65                  70                  75                  80

Asp Ser Val Lys Gly Arg Phe Thr Ile Ser Arg Asp Asn Ala Lys Ser
                85                  90                  95

Thr Leu Tyr Leu Gln Met Asn Ser Leu Arg Ser Glu Asp Thr Ala Thr
            100                 105                 110

Tyr Tyr Cys Thr Arg Glu Leu Gly Glu Phe Tyr Val Met Asp Ala Trp
        115                 120                 125

Gly Gln Gly Ala Ser Val Thr Val Ser Ser Ala Ser Thr Lys Gly Pro
    130                 135                 140

Ser Val Phe Pro Leu Ala Pro Cys Ser Arg Ser Thr Ser Glu Ser Thr
145                 150                 155                 160

Ala Ala Leu Gly Cys Leu Val Lys Asp Tyr Phe Pro Glu Pro Val Thr
                165                 170                 175

Val Ser Trp Asn Ser Gly Ala Leu Thr Ser Gly Val His Thr Phe Pro
            180                 185                 190

Ala Val Leu Gln Ser Ser Gly Leu Tyr Ser Leu Ser Ser Val Val Thr
        195                 200                 205

Val Pro Ser Ser Ser Leu Gly Thr Lys Thr Tyr Thr Cys Asn Val Asp
    210                 215                 220

His Lys Pro Ser Asn Thr Lys Val Asp Lys Arg Val Glu Ser Lys Tyr
225                 230                 235                 240

Gly Pro Pro Cys Pro Pro Cys Pro Ala Pro Glu Phe Leu Gly Gly Pro
                245                 250                 255

Ser Val Phe Leu Phe Pro Pro Lys Pro Lys Asp Thr Leu Met Ile Ser
            260                 265                 270

Arg Thr Pro Glu Val Thr Cys Val Val Val Asp Val Ser Gln Glu Asp
        275                 280                 285

Pro Glu Val Gln Phe Asn Trp Tyr Val Asp Gly Val Glu Val His Asn
    290                 295                 300

Ala Lys Thr Lys Pro Arg Glu Glu Gln Phe Asn Ser Thr Tyr Arg Val
305                 310                 315                 320

Val Ser Val Leu Thr Val Leu His Gln Asp Trp Leu Asn Gly Lys Glu
                325                 330                 335

Tyr Lys Cys Lys Val Ser Asn Lys Gly Leu Pro Ser Ser Ile Glu Lys
            340                 345                 350

Thr Ile Ser Lys Ala Lys Gly Gln Pro Arg Glu Pro Gln Val Tyr Thr
        355                 360                 365

Leu Pro Pro Ser Gln Glu Glu Met Thr Lys Asn Gln Val Ser Leu Thr
    370                 375                 380

Cys Leu Val Lys Gly Phe Tyr Pro Ser Asp Ile Ala Val Glu Trp Glu
385                 390                 395                 400

Ser Asn Gly Gln Pro Glu Asn Asn Tyr Lys Thr Thr Pro Pro Val Leu
                405                 410                 415
```

```
Asp Ser Asp Gly Ser Phe Phe Leu Tyr Ser Arg Leu Thr Val Asp Lys
            420                 425                 430

Ser Arg Trp Gln Glu Gly Asn Val Phe Ser Cys Ser Val Met His Glu
        435                 440                 445

Ala Leu His Asn His Tyr Thr Gln Lys Ser Leu Ser Leu Ser Leu Gly
    450                 455                 460

Lys
465
```

<210> SEQ ID NO 123
<211> LENGTH: 466
<212> TYPE: PRT
<213> ORGANISM: Artificial Sequence
<220> FEATURE:
<223> OTHER INFORMATION: #84H1hIgG2

<400> SEQUENCE: 123

```
Met Lys His Leu Trp Phe Phe Leu Leu Leu Val Ala Ala Pro Arg Trp
1               5                   10                  15

Val Leu Ser Glu Val Gln Leu Val Glu Ser Gly Gly Gly Leu Val Gln
            20                  25                  30

Pro Gly Gly Ser Leu Arg Leu Ser Cys Ala Ala Ser Gly Phe Thr Phe
        35                  40                  45

Ser Asn Tyr Tyr Met Ala Trp Val Arg Gln Ala Pro Gly Lys Gly Leu
    50                  55                  60

Glu Trp Val Ser Thr Ile Thr Thr Ser Gly Ser Arg Pro Tyr Tyr Ala
65                  70                  75                  80

Asp Ser Val Lys Gly Arg Phe Thr Ile Ser Arg Asp Asn Ser Lys Asn
                85                  90                  95

Thr Leu Tyr Leu Gln Met Asn Ser Leu Arg Ala Glu Asp Thr Ala Val
            100                 105                 110

Tyr Tyr Cys Ala Arg His Ile Tyr Tyr Tyr Asp Gly Tyr Pro Phe Ala
        115                 120                 125

Tyr Trp Gly Gln Gly Thr Leu Val Thr Val Ser Ser Ala Ser Thr Lys
    130                 135                 140

Gly Pro Ser Val Phe Pro Leu Ala Pro Cys Ser Arg Ser Thr Ser Glu
145                 150                 155                 160

Ser Thr Ala Ala Leu Gly Cys Leu Val Lys Asp Tyr Phe Pro Glu Pro
                165                 170                 175

Val Thr Val Ser Trp Asn Ser Gly Ala Leu Thr Ser Gly Val His Thr
            180                 185                 190

Phe Pro Ala Val Leu Gln Ser Ser Gly Leu Tyr Ser Leu Ser Ser Val
        195                 200                 205

Val Thr Val Pro Ser Ser Asn Phe Gly Thr Gln Thr Tyr Thr Cys Asn
    210                 215                 220

Val Asp His Lys Pro Ser Asn Thr Lys Val Asp Lys Thr Val Glu Arg
225                 230                 235                 240

Lys Cys Cys Val Glu Cys Pro Pro Cys Pro Ala Pro Pro Val Ala Gly
                245                 250                 255

Pro Ser Val Phe Leu Phe Pro Pro Lys Pro Lys Asp Thr Leu Met Ile
            260                 265                 270

Ser Arg Thr Pro Glu Val Thr Cys Val Val Val Asp Val Ser His Glu
        275                 280                 285

Asp Pro Glu Val Gln Phe Asn Trp Tyr Val Asp Gly Val Glu Val His
    290                 295                 300
```

-continued

```
Asn Ala Lys Thr Lys Pro Arg Glu Glu Gln Phe Asn Ser Thr Phe Arg
305                 310                 315                 320

Val Val Ser Val Leu Thr Val Val His Gln Asp Trp Leu Asn Gly Lys
                325                 330                 335

Glu Tyr Lys Cys Lys Val Ser Asn Lys Gly Leu Pro Ala Pro Ile Glu
            340                 345                 350

Lys Thr Ile Ser Lys Thr Lys Gly Gln Pro Arg Glu Pro Gln Val Tyr
        355                 360                 365

Thr Leu Pro Pro Ser Arg Glu Glu Met Thr Lys Asn Gln Val Ser Leu
    370                 375                 380

Thr Cys Leu Val Lys Gly Phe Tyr Pro Ser Asp Ile Ala Val Glu Trp
385                 390                 395                 400

Glu Ser Asn Gly Gln Pro Glu Asn Asn Tyr Lys Thr Thr Pro Pro Met
                405                 410                 415

Leu Asp Ser Asp Gly Ser Phe Phe Leu Tyr Ser Lys Leu Thr Val Asp
            420                 425                 430

Lys Ser Arg Trp Gln Gln Gly Asn Val Phe Ser Cys Ser Val Met His
        435                 440                 445

Glu Ala Leu His Asn His Tyr Thr Gln Lys Ser Leu Ser Leu Ser Pro
    450                 455                 460

Gly Lys
465


<210> SEQ ID NO 124
<211> LENGTH: 1398
<212> TYPE: DNA
<213> ORGANISM: Artificial Sequence
<220> FEATURE:
<223> OTHER INFORMATION: #84H1hIgG2

<400> SEQUENCE: 124

atgaaacacc tgtggttctt cctcctgctg gtggcagctc ccagatgggt gctgagcgaa      60

gtgcagctgg ttgagtctgg cggaggactg gttcaacctg gcggaagcct gagactgtct     120

tgtgccgcca gcggcttcac cttcagcaac tactatatgg cctgggtccg acaggcccct     180

ggcaaaggac ttgaatgggt gtccaccatc accaccagcg gcagcagacc ttactacgcc     240

gatagcgtga agggcagatt caccatcagc cgggacaaca gcaagaacac cctgtacctg     300

cagatgaaca gcctgagagc cgaggacacc gccgtgtact attgcgccag acacatctac     360

tactacgacg gctacccctt cgcctattgg ggccagggaa cactggtcac agttagctca     420

gcctccacca agggcccttc cgtgttccct ctggcccctt gtagccgttc caccagcgag     480

tccaccgccg cccttggctg tctggtgaag gactacttcc ctgagcctgt gaccgtgagc     540

tggaactccg gagcccttac cagcggcgtg cacaccttcc ctgccgtgct gcagtccagc     600

ggcctttact ccctgagctc cgtggtgacc gtgcctagct ccaacttcgg cacccaaacc     660

tacacctgta acgtggacca caagcctagc aacaccaagg tggacaagac cgtggagcgt     720

aagtgttgtg tggagtgtcc tccttgtcct gcccctcctg tggccggacc ttccgtgttc     780

cttttccctc ctaagcctaa ggacaccctg atgatcagcc gtacccctga ggtgacctgt     840

gtggtggtgg acgtgtccca cgaggaccct gaggtgcagt tcaactggta cgtggacggc     900

gtggaggtgc acaacgccaa gaccaagcct cgtgaggagc aattcaacag caccttccgt     960

gtggtgtccg tgcttaccgt ggtgcaccaa gactggctga acggcaagga gtacaagtgt    1020

aaggtgagca acaagggact tcctgcccct atcgagaaga ccatctccaa gaccaagggc    1080
```

-continued

```
caacctcgtg agcctcaagt gtacaccctt cctcctagcc gtgaggagat gaccaagaac   1140

caagtgtccc ttacctgtct ggtgaagggc ttctacccta gcgacatcgc cgtggagtgg   1200

gagtccaacg gacaacctga gaacaactac aagaccaccc ctcctatgct tgacagcgac   1260

ggctccttct tcctgtacag caagctgacc gtggacaagt cccgttggca acaaggcaac   1320

gtgttcagct gttccgtgat gcacgaggcc ctgcacaacc actacaccca aaagagcctt   1380

tccctgagcc ctggaaag                                                 1398


<210> SEQ ID NO 125
<211> LENGTH: 467
<212> TYPE: PRT
<213> ORGANISM: Artificial Sequence
<220> FEATURE:
<223> OTHER INFORMATION: #84H1hIgG4P

<400> SEQUENCE: 125

Met Lys His Leu Trp Phe Phe Leu Leu Leu Val Ala Ala Pro Arg Trp
1               5                   10                  15

Val Leu Ser Glu Val Gln Leu Val Glu Ser Gly Gly Gly Leu Val Gln
            20                  25                  30

Pro Gly Gly Ser Leu Arg Leu Ser Cys Ala Ala Ser Gly Phe Thr Phe
        35                  40                  45

Ser Asn Tyr Tyr Met Ala Trp Val Arg Gln Ala Pro Gly Lys Gly Leu
    50                  55                  60

Glu Trp Val Ser Thr Ile Thr Thr Ser Gly Ser Arg Pro Tyr Tyr Ala
65                  70                  75                  80

Asp Ser Val Lys Gly Arg Phe Thr Ile Ser Arg Asp Asn Ser Lys Asn
                85                  90                  95

Thr Leu Tyr Leu Gln Met Asn Ser Leu Arg Ala Glu Asp Thr Ala Val
            100                 105                 110

Tyr Tyr Cys Ala Arg His Ile Tyr Tyr Tyr Asp Gly Tyr Pro Phe Ala
        115                 120                 125

Tyr Trp Gly Gln Gly Thr Leu Val Thr Val Ser Ser Ala Ser Thr Lys
    130                 135                 140

Gly Pro Ser Val Phe Pro Leu Ala Pro Cys Ser Arg Ser Thr Ser Glu
145                 150                 155                 160

Ser Thr Ala Ala Leu Gly Cys Leu Val Lys Asp Tyr Phe Pro Glu Pro
                165                 170                 175

Val Thr Val Ser Trp Asn Ser Gly Ala Leu Thr Ser Gly Val His Thr
            180                 185                 190

Phe Pro Ala Val Leu Gln Ser Ser Gly Leu Tyr Ser Leu Ser Ser Val
        195                 200                 205

Val Thr Val Pro Ser Ser Ser Leu Gly Thr Lys Thr Tyr Thr Cys Asn
    210                 215                 220

Val Asp His Lys Pro Ser Asn Thr Lys Val Asp Lys Arg Val Glu Ser
225                 230                 235                 240

Lys Tyr Gly Pro Pro Cys Pro Pro Cys Pro Ala Pro Glu Phe Leu Gly
                245                 250                 255

Gly Pro Ser Val Phe Leu Phe Pro Pro Lys Pro Lys Asp Thr Leu Met
            260                 265                 270

Ile Ser Arg Thr Pro Glu Val Thr Cys Val Val Val Asp Val Ser Gln
        275                 280                 285

Glu Asp Pro Glu Val Gln Phe Asn Trp Tyr Val Asp Gly Val Glu Val
    290                 295                 300
```

His Asn Ala Lys Thr Lys Pro Arg Glu Glu Gln Phe Asn Ser Thr Tyr
305 310 315 320

Arg Val Val Ser Val Leu Thr Val Leu His Gln Asp Trp Leu Asn Gly
325 330 335

Lys Glu Tyr Lys Cys Lys Val Ser Asn Lys Gly Leu Pro Ser Ser Ile
340 345 350

Glu Lys Thr Ile Ser Lys Ala Lys Gly Gln Pro Arg Glu Pro Gln Val
355 360 365

Tyr Thr Leu Pro Pro Ser Gln Glu Glu Met Thr Lys Asn Gln Val Ser
370 375 380

Leu Thr Cys Leu Val Lys Gly Phe Tyr Pro Ser Asp Ile Ala Val Glu
385 390 395 400

Trp Glu Ser Asn Gly Gln Pro Glu Asn Asn Tyr Lys Thr Thr Pro Pro
405 410 415

Val Leu Asp Ser Asp Gly Ser Phe Phe Leu Tyr Ser Arg Leu Thr Val
420 425 430

Asp Lys Ser Arg Trp Gln Glu Gly Asn Val Phe Ser Cys Ser Val Met
435 440 445

His Glu Ala Leu His Asn His Tyr Thr Gln Lys Ser Leu Ser Leu Ser
450 455 460

Leu Gly Lys
465

<210> SEQ ID NO 126
<211> LENGTH: 1401
<212> TYPE: DNA
<213> ORGANISM: Artificial Sequence
<220> FEATURE:
<223> OTHER INFORMATION: #84H1hIgG4P

<400> SEQUENCE: 126
atgaaacacc tgtggttctt cctcctgctg gtggcagctc ccagatgggt gctgagcgaa 60
gtgcagctgg ttgagtctgg cggaggactg gttcaacctg gcggaagcct gagactgtct 120
tgtgccgcca gcggcttcac cttcagcaac tactatatgg cctgggtccg acaggcccct 180
ggcaaaggac ttgaatgggt gtccaccatc accaccagcg gcagcagacc ttactacgcc 240
gatagcgtga agggcagatt caccatcagc cgggacaaca gcaagaacac cctgtacctg 300
cagatgaaca gcctgagagc cgaggacacc gccgtgtact attgcgccag acacatctac 360
tactacgacg gctacccctt cgcctattgg ggccagggaa cactggtcac agttagctca 420
gcctccacca agggccctag cgtgttccct ctggcccctt gtagcagaag caccagcgag 480
tctacagccg ccctgggctg cctcgtgaag gactactttc ccgagcccgt gaccgtgtcc 540
tggaactctg gcgctctgac aagcggcgtg cacacctttc cagccgtgct gcagagcagc 600
ggcctgtact ctctgtccag cgtcgtgact gtgcccagca gctctctggg caccaagacc 660
tacacctgta acgtggacca caagcccagc aacaccaagg tggacaagcg ggtggaatct 720
aagtacggcc ctccctgccc tccttgccca gcccctgaat ttctgggcgg accctccgtg 780
ttcctgttcc ccccaaagcc caaggacacc ctgatgatca gccggacccc cgaagtgacc 840
tgcgtggtgg tggatgtgtc ccaggaagat cccgaggtgc agttcaattg gtacgtggac 900
ggcgtggaag tgcacaacgc caagaccaag cctagagagg aacagttcaa cagcacctac 960
cgggtggtgt ccgtgctgac agtgctgcac caggactggc tgaacggcaa agagtacaag 1020
tgcaaggtgt ccaacaaggg cctgcccagc tccatcgaga aaaccatcag caaggccaag 1080
ggccagcccc gcgaacccca ggtgtacaca ctgcctccaa gccaggaaga gatgaccaag 1140
aatcaggtgt ccctgacctg tctcgtgaaa ggcttctacc cctccgatat cgccgtggaa 1200
tgggagagca acggccagcc cgagaacaac tacaagacca cccccccctgt gctggactcc 1260 gatggctcat tcttcctgta cagcagactg accgtggaca agagccggtg gcaggaaggc 1320
aacgtgttca gctgctccgt gatgcacgag gccctgcaca accactacac ccagaagtcc 1380
ctgtctctga gcctgggcaa a 1401

<210> SEQ ID NO 127
<211> LENGTH: 234
<212> TYPE: PRT
<213> ORGANISM: Artificial Sequence
<220> FEATURE:
<223> OTHER INFORMATION: #84L2h

<400> SEQUENCE: 127

Met Val Leu Gln Thr Gln Val Phe Ile Ser Leu Leu Leu Trp Ile Ser
1 5 10 15

Gly Ala Tyr Gly Asp Val Gln Met Thr Gln Ser Pro Ser Ser Leu Ser
20 25 30

Ala Ser Val Gly Asp Arg Val Thr Ile Thr Cys Lys Ala Ser Lys Ser
35 40 45

Ile Ser Asn Asn Leu Ala Trp Tyr Gln Gln Lys Pro Gly Lys Ala Asn
50 55 60

Lys Leu Leu Ile His Ser Gly Ser Thr Leu Gln Ser Gly Thr Pro Ser
65 70 75 80

Arg Phe Ser Gly Ser Gly Ser Gly Thr Asp Phe Thr Leu Thr Ile Ser
85 90 95

Ser Leu Gln Pro Glu Asp Phe Ala Thr Tyr Tyr Cys Gln Gln Tyr Asn
100 105 110

Glu Tyr Pro Leu Thr Phe Gly Gln Gly Thr Lys Val Glu Ile Lys Arg
115 120 125

Thr Val Ala Ala Pro Ser Val Phe Ile Phe Pro Pro Ser Asp Glu Gln
130 135 140

Leu Lys Ser Gly Thr Ala Ser Val Val Cys Leu Leu Asn Asn Phe Tyr
145 150 155 160

Pro Arg Glu Ala Lys Val Gln Trp Lys Val Asp Asn Ala Leu Gln Ser
165 170 175

Gly Asn Ser Gln Glu Ser Val Thr Glu Gln Asp Ser Lys Asp Ser Thr
180 185 190

Tyr Ser Leu Ser Ser Thr Leu Thr Leu Ser Lys Ala Asp Tyr Glu Lys
195 200 205

His Lys Val Tyr Ala Cys Glu Val Thr His Gln Gly Leu Ser Ser Pro
210 215 220

Val Thr Lys Ser Phe Asn Arg Gly Glu Cys
225 230

<210> SEQ ID NO 128
<211> LENGTH: 702
<212> TYPE: DNA
<213> ORGANISM: Artificial Sequence
<220> FEATURE:
<223> OTHER INFORMATION: #84L2h

<400> SEQUENCE: 128
atggtgctgc agacccaggt gttcatctcc ctgctgctgt ggatctccgg cgcgtacggc 60
gacgttcaga tgacacagag ccctagcagc ctgtctgcca gcgtgggaga cagagtgacc 120
atcacatgca aggccagcaa gagcatcagc aacaacctgg cctggtatca gcagaagccc 180
ggaaaggcca acaagctgct gatccacagc ggcagcacac tgcagtctgg cacccctagc 240
agattttccg gctctggcag cggcaccgat ttcaccctga ccatatctag cctgcagcct 300
gaggacttcg ccacctacta ctgccagcag tacaacgagt accctctgac ctttggccag 360
ggcaccaagg tggaaatcaa gcgtacggtg gccgcccct ccgtgttcat cttcccccc 420 tccgacgagc agctgaagtc cggcaccgcc tccgtggtgt gcctgctgaa taacttctac 480
cccagagagg ccaaggtgca gtggaaggtg gacaacgccc tgcagtccgg gaactcccag 540
gagagcgtga ccgagcagga cagcaaggac agcacctaca gcctgagcag caccctgacc 600
ctgagcaaag ccgactacga gaagcacaag gtgtacgcct gcgaggtgac ccaccagggc 660
ctgagctccc ccgtcaccaa gagcttcaac aggggggagt gt 702

<210> SEQ ID NO 129
<211> LENGTH: 463
<212> TYPE: PRT
<213> ORGANISM: Artificial Sequence
<220> FEATURE:
<223> OTHER INFORMATION: #101H1hIgG2

<400> SEQUENCE: 129

Met Lys His Leu Trp Phe Phe Leu Leu Leu Val Ala Ala Pro Arg Trp
1 5 10 15

Val Leu Ser Glu Val Gln Leu Val Glu Ser Gly Gly Gly Leu Val Gln
20 25 30

Pro Gly Arg Ser Leu Arg Leu Ser Cys Ala Ala Ser Gly Phe Thr Phe
35 40 45

Ser Asp Tyr Tyr Met Ala Trp Val Arg Gln Ala Pro Gly Lys Gly Leu
50 55 60

Glu Trp Val Ala Thr Ile Ser Tyr Asp Gly Ser Asn Thr Tyr Tyr Arg
65 70 75 80

Asp Ser Val Lys Gly Arg Phe Thr Ile Ser Arg Asp Asn Ser Lys Ser
85 90 95

Thr Leu Tyr Leu Gln Met Asn Ser Leu Arg Ala Gly Asp Thr Ala Val
100 105 110

Tyr Tyr Cys Ala Arg Phe Tyr Asn Asn Tyr Tyr Phe Asp Tyr Trp Gly
115 120 125

Gln Gly Thr Leu Val Thr Val Ser Ser Ala Ser Thr Lys Gly Pro Ser
130 135 140

Val Phe Pro Leu Ala Pro Cys Ser Arg Ser Thr Ser Glu Ser Thr Ala
145 150 155 160

Ala Leu Gly Cys Leu Val Lys Asp Tyr Phe Pro Glu Pro Val Thr Val
165 170 175

Ser Trp Asn Ser Gly Ala Leu Thr Ser Gly Val His Thr Phe Pro Ala
180 185 190

Val Leu Gln Ser Ser Gly Leu Tyr Ser Leu Ser Ser Val Val Thr Val
195 200 205

Pro Ser Ser Asn Phe Gly Thr Gln Thr Tyr Thr Cys Asn Val Asp His
210 215 220

Lys Pro Ser Asn Thr Lys Val Asp Lys Thr Val Glu Arg Lys Cys Cys
225 230 235 240

Val Glu Cys Pro Pro Cys Pro Ala Pro Pro Val Ala Gly Pro Ser Val
245 250 255

Phe Leu Phe Pro Pro Lys Pro Lys Asp Thr Leu Met Ile Ser Arg Thr
260 265 270

Pro Glu Val Thr Cys Val Val Val Asp Val Ser His Glu Asp Pro Glu
275 280 285

Val Gln Phe Asn Trp Tyr Val Asp Gly Val Glu Val His Asn Ala Lys
290 295 300

Thr Lys Pro Arg Glu Glu Gln Phe Asn Ser Thr Phe Arg Val Val Ser
305 310 315 320

Val Leu Thr Val Val His Gln Asp Trp Leu Asn Gly Lys Glu Tyr Lys
325 330 335

Cys Lys Val Ser Asn Lys Gly Leu Pro Ala Pro Ile Glu Lys Thr Ile
340 345 350

Ser Lys Thr Lys Gly Gln Pro Arg Glu Pro Gln Val Tyr Thr Leu Pro
355 360 365

Pro Ser Arg Glu Glu Met Thr Lys Asn Gln Val Ser Leu Thr Cys Leu
370 375 380

Val Lys Gly Phe Tyr Pro Ser Asp Ile Ala Val Glu Trp Glu Ser Asn
385 390 395 400

Gly Gln Pro Glu Asn Asn Tyr Lys Thr Thr Pro Pro Met Leu Asp Ser
405 410 415

Asp Gly Ser Phe Phe Leu Tyr Ser Lys Leu Thr Val Asp Lys Ser Arg
420 425 430

Trp Gln Gln Gly Asn Val Phe Ser Cys Ser Val Met His Glu Ala Leu
435 440 445

His Asn His Tyr Thr Gln Lys Ser Leu Ser Leu Ser Pro Gly Lys
450 455 460

<210> SEQ ID NO 130
<211> LENGTH: 1389
<212> TYPE: DNA
<213> ORGANISM: Artificial Sequence
<220> FEATURE:
<223> OTHER INFORMATION: #101H1hIgG2

<400> SEQUENCE: 130
atgaaacacc tgtggttctt cctcctgctg gtggcagctc ccagatgggt gctgagcgaa 60
gtgcagctgg ttgagtctgg cggaggactg gttcagcctg gcagaagcct gagactgtct 120
tgtgccgcca gcggcttcac cttcagcgac tactatatgg cctgggtccg acaggcccct 180
ggcaaaggac ttgaatgggt cgccaccatc agctacgacg gcagcaacac ctactaccgg 240
gacagcgtga agggcagatt caccatctcc agagacaaca gcaagagcac cctgtacctg 300
cagatgaaca gcctgagagc cggcgatacc gccgtgtact actgcgccag attctacaac 360
aactactact tcgactactg gggccagggc accctggtca cagttagctc agcctccacc 420
aagggccctt ccgtgttccc tctggcccct tgtagccgtt ccaccagcga gtccaccgcc 480
gcccttggct gtctggtgaa ggactacttc cctgagcctg tgaccgtgag ctggaactcc 540
ggagccctta ccagcggcgt gcacaccttc cctgccgtgc tgcagtccag cggcctttac 600
tccctgagct ccgtggtgac cgtgcctagc tccaacttcg gcacccaaac ctacacctgt 660
aacgtggacc acaagcctag caacaccaag gtggacaaga ccgtggagcg taagtgttgt 720

```
gtggagtgtc ctccttgtcc tgcccctcct gtggccggac cttccgtgtt ccttttccct    780

cctaagccta aggacaccct gatgatcagc cgtacccctg aggtgacctg tgtggtggtg    840

gacgtgtccc acgaggaccc tgaggtgcag ttcaactggt acgtggacgg cgtggaggtg    900

cacaacgcca agaccaagcc tcgtgaggag caattcaaca gcaccttccg tgtggtgtcc    960

gtgcttaccg tggtgcacca agactggctg aacggcaagg agtacaagtg taaggtgagc   1020

aacaagggac ttcctgcccc tatcgagaag accatctcca agaccaaggg ccaacctcgt   1080

gagcctcaag tgtacaccct tcctcctagc cgtgaggaga tgaccaagaa ccaagtgtcc   1140

cttacctgtc tggtgaaggg cttctaccct agcgacatcg ccgtggagtg ggagtccaac   1200

ggacaacctg agaacaacta caagaccacc cctcctatgc ttgacagcga cggctccttc   1260

ttcctgtaca gcaagctgac cgtggacaag tcccgttggc aacaaggcaa cgtgttcagc   1320

tgttccgtga tgcacgaggc cctgcacaac cactacaccc aaaagagcct ttccctgagc   1380

cctggaaag                                                           1389
```

```
<210> SEQ ID NO 131
<211> LENGTH: 464
<212> TYPE: PRT
<213> ORGANISM: Artificial Sequence
<220> FEATURE:
<223> OTHER INFORMATION: #101H1hIgG4P

<400> SEQUENCE: 131

Met Lys His Leu Trp Phe Phe Leu Leu Leu Val Ala Ala Pro Arg Trp
1               5                   10                  15

Val Leu Ser Glu Val Gln Leu Val Glu Ser Gly Gly Gly Leu Val Gln
            20                  25                  30

Pro Gly Arg Ser Leu Arg Leu Ser Cys Ala Ala Ser Gly Phe Thr Phe
        35                  40                  45

Ser Asp Tyr Tyr Met Ala Trp Val Arg Gln Ala Pro Gly Lys Gly Leu
    50                  55                  60

Glu Trp Val Ala Thr Ile Ser Tyr Asp Gly Ser Asn Thr Tyr Tyr Arg
65                  70                  75                  80

Asp Ser Val Lys Gly Arg Phe Thr Ile Ser Arg Asp Asn Ser Lys Ser
                85                  90                  95

Thr Leu Tyr Leu Gln Met Asn Ser Leu Arg Ala Gly Asp Thr Ala Val
            100                 105                 110

Tyr Tyr Cys Ala Arg Phe Tyr Asn Asn Tyr Tyr Phe Asp Tyr Trp Gly
        115                 120                 125

Gln Gly Thr Leu Val Thr Val Ser Ser Ala Ser Thr Lys Gly Pro Ser
    130                 135                 140

Val Phe Pro Leu Ala Pro Cys Ser Arg Ser Thr Ser Glu Ser Thr Ala
145                 150                 155                 160

Ala Leu Gly Cys Leu Val Lys Asp Tyr Phe Pro Glu Pro Val Thr Val
                165                 170                 175

Ser Trp Asn Ser Gly Ala Leu Thr Ser Gly Val His Thr Phe Pro Ala
            180                 185                 190

Val Leu Gln Ser Ser Gly Leu Tyr Ser Leu Ser Ser Val Val Thr Val
        195                 200                 205

Pro Ser Ser Ser Leu Gly Thr Lys Thr Tyr Thr Cys Asn Val Asp His
    210                 215                 220

Lys Pro Ser Asn Thr Lys Val Asp Lys Arg Val Glu Ser Lys Tyr Gly
225                 230                 235                 240
```

-continued

```
Pro Pro Cys Pro Pro Cys Pro Ala Pro Glu Phe Leu Gly Gly Pro Ser
            245                 250                 255

Val Phe Leu Phe Pro Pro Lys Pro Lys Asp Thr Leu Met Ile Ser Arg
            260                 265                 270

Thr Pro Glu Val Thr Cys Val Val Val Asp Val Ser Gln Glu Asp Pro
        275                 280                 285

Glu Val Gln Phe Asn Trp Tyr Val Asp Gly Val Glu Val His Asn Ala
    290                 295                 300

Lys Thr Lys Pro Arg Glu Glu Gln Phe Asn Ser Thr Tyr Arg Val Val
305                 310                 315                 320

Ser Val Leu Thr Val Leu His Gln Asp Trp Leu Asn Gly Lys Glu Tyr
            325                 330                 335

Lys Cys Lys Val Ser Asn Lys Gly Leu Pro Ser Ser Ile Glu Lys Thr
            340                 345                 350

Ile Ser Lys Ala Lys Gly Gln Pro Arg Glu Pro Gln Val Tyr Thr Leu
        355                 360                 365

Pro Pro Ser Gln Glu Glu Met Thr Lys Asn Gln Val Ser Leu Thr Cys
    370                 375                 380

Leu Val Lys Gly Phe Tyr Pro Ser Asp Ile Ala Val Glu Trp Glu Ser
385                 390                 395                 400

Asn Gly Gln Pro Glu Asn Asn Tyr Lys Thr Thr Pro Pro Val Leu Asp
            405                 410                 415

Ser Asp Gly Ser Phe Phe Leu Tyr Ser Arg Leu Thr Val Asp Lys Ser
            420                 425                 430

Arg Trp Gln Glu Gly Asn Val Phe Ser Cys Ser Val Met His Glu Ala
        435                 440                 445

Leu His Asn His Tyr Thr Gln Lys Ser Leu Ser Leu Ser Leu Gly Lys
    450                 455                 460
```

<210> SEQ ID NO 132
<211> LENGTH: 1392
<212> TYPE: DNA
<213> ORGANISM: Artificial Sequence
<220> FEATURE:
<223> OTHER INFORMATION: #101H1hIgG4P

<400> SEQUENCE: 132

```
atgaaacacc tgtggttctt cctcctgctg gtggcagctc ccagatgggt gctgagcgaa      60

gtgcagctgg ttgagtctgg cggaggactg gttcagcctg gcagaagcct gagactgtct     120

tgtgccgcca gcggcttcac cttcagcgac tactatatgg cctgggtccg acaggcccct     180

ggcaaaggac ttgaatgggt cgccaccatc agctacgacg gcagcaacac ctactaccgg     240

gacagcgtga agggcagatt caccatctcc agagacaaca gcaagagcac cctgtacctg     300

cagatgaaca gcctgagagc cggcgatacc gccgtgtact actgcgccag attctacaac     360

aactactact tcgactactg gggccagggc accctggtca cagttagctc agcctccacc     420

aagggcccta gcgtgttccc tctggcccct tgtagcagaa gcaccagcga gtctacagcc     480

gccctgggct gcctcgtgaa ggactacttt cccgagcccg tgaccgtgtc ctggaactct     540

ggcgctctga caagcggcgt gcacaccttt ccagccgtgc tgcagagcag cggcctgtac     600

tctctgtcca gcgtcgtgac tgtgcccagc agctctctgg gcaccaagac ctacacctgt     660

aacgtggacc acaagcccag caacaccaag gtggacaagc gggtggaatc taagtacggc     720

cctccctgcc ctccttgccc agcccctgaa tttctgggcg gaccctccgt gttcctgttc     780

cccccaaagc ccaaggacac cctgatgatc agccggaccc ccgaagtgac ctgcgtggtg     840
```

-continued

```
gtggatgtgt cccaggaaga tcccgaggtg cagttcaatt ggtacgtgga cggcgtggaa    900

gtgcacaacg ccaagaccaa gcctagagag gaacagttca acagcaccta ccgggtggtg    960

tccgtgctga cagtgctgca ccaggactgg ctgaacggca aagagtacaa gtgcaaggtg   1020

tccaacaagg gcctgcccag ctccatcgag aaaaccatca gcaaggccaa gggccagccc   1080

cgcgaacccc aggtgtacac actgcctcca agccaggaag agatgaccaa gaatcaggtg   1140

tccctgacct gtctcgtgaa aggcttctac ccctccgata tcgccgtgga atgggagagc   1200

aacggccagc ccgagaacaa ctacaagacc acccccccctg tgctggactc cgatggctca   1260

ttcttcctgt acagcagact gaccgtggac aagagccggt ggcaggaagg caacgtgttc   1320

agctgctccg tgatgcacga ggccctgcac aaccactaca cccagaagtc cctgtctctg   1380

agcctgggca aa                                                        1392
```

```
<210> SEQ ID NO 133
<211> LENGTH: 234
<212> TYPE: PRT
<213> ORGANISM: Artificial Sequence
<220> FEATURE:
<223> OTHER INFORMATION: #101L2h

<400> SEQUENCE: 133

Met Val Leu Gln Thr Gln Val Phe Ile Ser Leu Leu Leu Trp Ile Ser
1               5                   10                  15

Gly Ala Tyr Gly Asp Ile Gln Met Thr Gln Ser Pro Ser Ser Leu Ser
            20                  25                  30

Ala Ser Val Gly Asp Arg Val Thr Ile Asn Cys Lys Ala Ser Gln Asn
        35                  40                  45

Leu Tyr Lys Asn Leu Ala Trp Tyr Gln Gln Lys Pro Gly Lys Ala Pro
    50                  55                  60

Lys Leu Leu Ile Asp Asn Ala Asn Ser Leu Gln Thr Gly Ile Pro Ser
65                  70                  75                  80

Arg Phe Ser Gly Ser Gly Ser Gly Thr Asp Phe Thr Leu Thr Ile Ser
                85                  90                  95

Ser Leu Gln Pro Glu Asp Phe Ala Thr Tyr Phe Cys Gln Gln Tyr Tyr
            100                 105                 110

Ser Gly Ser Tyr Thr Phe Gly Gln Gly Thr Lys Val Glu Ile Lys Arg
        115                 120                 125

Thr Val Ala Ala Pro Ser Val Phe Ile Phe Pro Pro Ser Asp Glu Gln
    130                 135                 140

Leu Lys Ser Gly Thr Ala Ser Val Val Cys Leu Leu Asn Asn Phe Tyr
145                 150                 155                 160

Pro Arg Glu Ala Lys Val Gln Trp Lys Val Asp Asn Ala Leu Gln Ser
                165                 170                 175

Gly Asn Ser Gln Glu Ser Val Thr Glu Gln Asp Ser Lys Asp Ser Thr
            180                 185                 190

Tyr Ser Leu Ser Ser Thr Leu Thr Leu Ser Lys Ala Asp Tyr Glu Lys
        195                 200                 205

His Lys Val Tyr Ala Cys Glu Val Thr His Gln Gly Leu Ser Ser Pro
    210                 215                 220

Val Thr Lys Ser Phe Asn Arg Gly Glu Cys
225                 230
```

```
<210> SEQ ID NO 134
<211> LENGTH: 702
<212> TYPE: DNA
<213> ORGANISM: Artificial Sequence
<220> FEATURE:
<223> OTHER INFORMATION: #101L2h

<400> SEQUENCE: 134

atggtgctgc agacccaggt gttcatctcc ctgctgctgt ggatctccgg cgcgtacggc      60

gatatccaga tgacacagag ccctagcagc ctgtctgcca gcgtgggaga tagagtgacc     120

atcaactgca aggccagcca gaacctgtac aagaacctgg cctggtatca gcagaagccc     180

ggcaaggctc ctaagctgct gatcgacaac gccaacagcc tgcagaccgg cattcccagc     240

agatttctg gcagcggctc cggcaccgat ttcaccctga ccatatctag cctgcagcct     300

gaggacttcg ccacctactt ttgccagcag tactacagcg gcagctacac ctttggccag     360

ggcaccaagg tggaaatcaa gcgtacggtg gccgcccct ccgtgttcat cttccccccc     420

tccgacgagc agctgaagtc cggcaccgcc tccgtggtgt gcctgctgaa taacttctac     480

cccagagagg ccaaggtgca gtggaaggtg gacaacgccc tgcagtccgg gaactcccag     540

gagagcgtga ccgagcagga cagcaaggac agcacctaca gcctgagcag caccctgacc     600

ctgagcaaag ccgactacga gaagcacaag gtgtacgcct gcgaggtgac ccaccagggc     660

ctgagctccc ccgtcaccaa gagcttcaac aggggggagt gt                        702


<210> SEQ ID NO 135
<211> LENGTH: 463
<212> TYPE: PRT
<213> ORGANISM: Artificial Sequence
<220> FEATURE:
<223> OTHER INFORMATION: #110H1hIgG4P

<400> SEQUENCE: 135

Met Lys His Leu Trp Phe Phe Leu Leu Leu Val Ala Ala Pro Arg Trp
1               5                   10                  15

Val Leu Ser Gln Val Gln Leu Val Gln Ser Gly Ala Glu Val Lys Lys
            20                  25                  30

Pro Gly Ala Ser Val Lys Val Ser Cys Lys Ala Ser Gly Tyr Thr Phe
        35                  40                  45

Thr Ser Asp Phe Met His Trp Val Arg Gln Ala Pro Gly Gln Gly Leu
    50                  55                  60

Glu Trp Met Gly Trp Ile Tyr Pro Gly Asp Gly Asp Thr Glu Tyr Asn
65                  70                  75                  80

Gln Lys Phe Gln Gly Arg Val Thr Leu Thr Arg Asp Thr Ser Ile Ser
                85                  90                  95

Thr Ala Tyr Met Glu Leu Ser Arg Leu Arg Ser Asp Asp Thr Ala Val
            100                 105                 110

Tyr Tyr Cys Ala Arg Gly Arg Gly Tyr Val Met Asp Ala Trp Gly Gln
        115                 120                 125

Gly Thr Thr Val Thr Val Ser Ser Ala Ser Thr Lys Gly Pro Ser Val
    130                 135                 140

Phe Pro Leu Ala Pro Cys Ser Arg Ser Thr Ser Glu Ser Thr Ala Ala
145                 150                 155                 160

Leu Gly Cys Leu Val Lys Asp Tyr Phe Pro Glu Pro Val Thr Val Ser
                165                 170                 175

Trp Asn Ser Gly Ala Leu Thr Ser Gly Val His Thr Phe Pro Ala Val
            180                 185                 190
```

-continued

```
Leu Gln Ser Ser Gly Leu Tyr Ser Leu Ser Ser Val Val Thr Val Pro
        195                 200                 205

Ser Ser Ser Leu Gly Thr Lys Thr Tyr Thr Cys Asn Val Asp His Lys
    210                 215                 220

Pro Ser Asn Thr Lys Val Asp Lys Arg Val Glu Ser Lys Tyr Gly Pro
225                 230                 235                 240

Pro Cys Pro Pro Cys Pro Ala Pro Glu Phe Leu Gly Gly Pro Ser Val
                245                 250                 255

Phe Leu Phe Pro Pro Lys Pro Lys Asp Thr Leu Met Ile Ser Arg Thr
            260                 265                 270

Pro Glu Val Thr Cys Val Val Val Asp Val Ser Gln Glu Asp Pro Glu
        275                 280                 285

Val Gln Phe Asn Trp Tyr Val Asp Gly Val Glu Val His Asn Ala Lys
    290                 295                 300

Thr Lys Pro Arg Glu Glu Gln Phe Asn Ser Thr Tyr Arg Val Val Ser
305                 310                 315                 320

Val Leu Thr Val Leu His Gln Asp Trp Leu Asn Gly Lys Glu Tyr Lys
                325                 330                 335

Cys Lys Val Ser Asn Lys Gly Leu Pro Ser Ser Ile Glu Lys Thr Ile
            340                 345                 350

Ser Lys Ala Lys Gly Gln Pro Arg Glu Pro Gln Val Tyr Thr Leu Pro
        355                 360                 365

Pro Ser Gln Glu Glu Met Thr Lys Asn Gln Val Ser Leu Thr Cys Leu
    370                 375                 380

Val Lys Gly Phe Tyr Pro Ser Asp Ile Ala Val Glu Trp Glu Ser Asn
385                 390                 395                 400

Gly Gln Pro Glu Asn Asn Tyr Lys Thr Thr Pro Pro Val Leu Asp Ser
                405                 410                 415

Asp Gly Ser Phe Phe Leu Tyr Ser Arg Leu Thr Val Asp Lys Ser Arg
            420                 425                 430

Trp Gln Glu Gly Asn Val Phe Ser Cys Ser Val Met His Glu Ala Leu
        435                 440                 445

His Asn His Tyr Thr Gln Lys Ser Leu Ser Leu Ser Leu Gly Lys
    450                 455                 460
```

<210> SEQ ID NO 136
<211> LENGTH: 1389
<212> TYPE: DNA
<213> ORGANISM: Artificial Sequence
<220> FEATURE:
<223> OTHER INFORMATION: #110H1hIgG4P

<400> SEQUENCE: 136

```
atgaaacacc tgtggttctt cctcctgctg gtggcagctc ccagatgggt gctgagccag      60

gttcagctgg ttcagtctgg cgccgaagtg aagaaacctg gcgcctctgt gaaggtgtcc     120

tgcaaggcca gcggctacac ctttaccagc gacttcatgc actgggtccg acaggctcca     180

ggacagggac ttgaatggat gggctggatc tatcccggcg acggcgacac cgagtacaac     240

cagaaattcc agggcagagt gaccctgacc agagacacca gcatcagcac cgcctacatg     300

gaactgagcc ggctgagatc cgatgacacc gccgtgtact actgcgccag aggcagaggc     360

tatgtgatgg atgcttgggg ccagggcacc accgttacag ttagctcagc ctccaccaag     420

ggccctagcg tgttccctct ggccccttgt agcagaagca ccagcgagtc tacagccgcc     480

ctgggctgcc tcgtgaagga ctactttccc gagcccgtga ccgtgtcctg gaactctggc     540
```

```
gctctgacaa gcggcgtgca cacctttcca gccgtgctgc agagcagcgg cctgtactct    600

ctgtccagcg tcgtgactgt gcccagcagc tctctgggca ccaagaccta cacctgtaac    660

gtggaccaca agcccagcaa caccaaggtg gacaagcggg tggaatctaa gtacggccct    720

ccctgccctc cttgcccagc ccctgaattt ctgggcggac cctccgtgtt cctgttcccc    780

ccaaagccca aggacaccct gatgatcagc cggacccccg aagtgacctg cgtggtggtg    840

gatgtgtccc aggaagatcc cgaggtgcag ttcaattggt acgtggacgg cgtggaagtg    900

cacaacgcca agaccaagcc tagagaggaa cagttcaaca gcacctaccg ggtggtgtcc    960

gtgctgacag tgctgcacca ggactggctg aacggcaaag agtacaagtg caaggtgtcc   1020

aacaagggcc tgcccagctc catcgagaaa accatcagca aggccaaggg ccagccccgc   1080

gaaccccagg tgtacacact gcctccaagc caggaagaga tgaccaagaa tcaggtgtcc   1140

ctgacctgtc tcgtgaaagg cttctacccc tccgatatcg ccgtggaatg ggagagcaac   1200

ggccagcccg agaacaacta caagaccacc ccccctgtgc tggactccga tggctcattc   1260

ttcctgtaca gcagactgac cgtggacaag agccggtggc aggaaggcaa cgtgttcagc   1320

tgctccgtga tgcacgaggc cctgcacaac cactacaccc agaagtccct gtctctgagc   1380

ctgggcaaa                                                             1389


<210> SEQ ID NO 137
<211> LENGTH: 234
<212> TYPE: PRT
<213> ORGANISM: Artificial Sequence
<220> FEATURE:
<223> OTHER INFORMATION: #110L4h

<400> SEQUENCE: 137

Met Val Leu Gln Thr Gln Val Phe Ile Ser Leu Leu Leu Trp Ile Ser
1               5                   10                  15

Gly Ala Tyr Gly Asp Ile Gln Met Thr Gln Ser Pro Ser Ser Leu Ser
            20                  25                  30

Ala Ser Val Gly Asp Arg Val Thr Ile Thr Cys Arg Ala Ser Gln Gly
        35                  40                  45

Ile Ser Asn Tyr Leu Asn Trp Tyr Gln Gln Lys Pro Gly Lys Ala Ile
    50                  55                  60

Lys Pro Leu Ile Tyr Tyr Thr Ser Asn Leu Gln Ser Gly Val Pro Ser
65                  70                  75                  80

Arg Phe Ser Gly Ser Gly Ser Gly Thr Asp Tyr Thr Leu Thr Ile Ser
                85                  90                  95

Ser Leu Gln Pro Glu Asp Phe Ala Thr Tyr Phe Cys Gln Gln Tyr Asp
            100                 105                 110

Ser Ser Pro Arg Thr Phe Gly Gly Gly Thr Lys Val Glu Ile Lys Arg
        115                 120                 125

Thr Val Ala Ala Pro Ser Val Phe Ile Phe Pro Pro Ser Asp Glu Gln
    130                 135                 140

Leu Lys Ser Gly Thr Ala Ser Val Val Cys Leu Leu Asn Asn Phe Tyr
145                 150                 155                 160

Pro Arg Glu Ala Lys Val Gln Trp Lys Val Asp Asn Ala Leu Gln Ser
                165                 170                 175

Gly Asn Ser Gln Glu Ser Val Thr Glu Gln Asp Ser Lys Asp Ser Thr
            180                 185                 190

Tyr Ser Leu Ser Ser Thr Leu Thr Leu Ser Lys Ala Asp Tyr Glu Lys
        195                 200                 205
```

```
His Lys Val Tyr Ala Cys Glu Val Thr His Gln Gly Leu Ser Ser Pro
    210                 215                 220

Val Thr Lys Ser Phe Asn Arg Gly Glu Cys
225                 230


<210> SEQ ID NO 138
<211> LENGTH: 702
<212> TYPE: DNA
<213> ORGANISM: Artificial Sequence
<220> FEATURE:
<223> OTHER INFORMATION: #110L4h

<400> SEQUENCE: 138

atggtgctgc agacccaggt gttcatctcc ctgctgctgt ggatctccgg cgcgtacggc      60

gatatccaga tgacacagag ccctagcagc ctgtctgcca gcgtgggaga cagagtgacc     120

atcacctgta gagccagcca gggcatcagc aactacctga actggtatca gcagaagccc     180

ggcaaggcca tcaagcccct gatctactac accagcaacc tgcagagcgg cgtgcccagc     240

agatttctg gctctggcag cggcaccgac tacaccctga ccatatctag cctgcagcct     300

gaggacttcg ccacctactt ttgccagcag tacgacagca gccccagaac ctttggcggc     360

ggaacaaagg tggaaatcaa gcgtacggtg gccgccccct ccgtgttcat cttccccccc     420

tccgacgagc agctgaagtc cggcaccgcc tccgtggtgt gcctgctgaa taacttctac     480

cccagagagg ccaaggtgca gtggaaggtg gacaacgccc tgcagtccgg gaactcccag     540

gagagcgtga ccgagcagga cagcaaggac agcacctaca gcctgagcag caccctgacc     600

ctgagcaaag ccgactacga gaagcacaag gtgtacgcct gcgaggtgac ccaccagggc     660

ctgagctccc ccgtcaccaa gagcttcaac aggggggagt gt                        702


<210> SEQ ID NO 139
<211> LENGTH: 464
<212> TYPE: PRT
<213> ORGANISM: Artificial Sequence
<220> FEATURE:
<223> OTHER INFORMATION: #131H2hIgG2

<400> SEQUENCE: 139

Met Lys His Leu Trp Phe Phe Leu Leu Leu Val Ala Ala Pro Arg Trp
1               5                   10                  15

Val Leu Ser Gln Val Gln Leu Val Glu Ser Gly Gly Gly Val Val Gln
            20                  25                  30

Pro Gly Arg Ser Leu Arg Leu Ser Cys Ala Ala Ser Gly Phe Thr Phe
        35                  40                  45

Asn Asn Tyr Trp Met Thr Trp Val Arg Gln Ala Pro Gly Lys Gly Leu
    50                  55                  60

Glu Trp Val Ala Ser Ile Thr Lys Ala Gly Gly Ser Thr Tyr Tyr Ala
65                  70                  75                  80

Asp Ser Val Lys Gly Arg Phe Thr Ile Ser Arg Asp Asn Ser Lys Ser
                85                  90                  95

Thr Leu Tyr Leu Gln Met Asn Ser Leu Arg Ala Glu Gly Thr Ala Val
            100                 105                 110

Tyr Tyr Cys Thr Arg Glu Leu Gly Glu Phe Tyr Val Met Asp Ala Trp
        115                 120                 125

Gly Gln Gly Thr Thr Val Thr Val Ser Ser Ala Ser Thr Lys Gly Pro
    130                 135                 140

Ser Val Phe Pro Leu Ala Pro Cys Ser Arg Ser Thr Ser Glu Ser Thr
145                 150                 155                 160
```

-continued

```
Ala Ala Leu Gly Cys Leu Val Lys Asp Tyr Phe Pro Glu Pro Val Thr
                165                 170                 175

Val Ser Trp Asn Ser Gly Ala Leu Thr Ser Gly Val His Thr Phe Pro
            180                 185                 190

Ala Val Leu Gln Ser Ser Gly Leu Tyr Ser Leu Ser Ser Val Val Thr
        195                 200                 205

Val Pro Ser Ser Asn Phe Gly Thr Gln Thr Tyr Thr Cys Asn Val Asp
    210                 215                 220

His Lys Pro Ser Asn Thr Lys Val Asp Lys Thr Val Glu Arg Lys Cys
225                 230                 235                 240

Cys Val Glu Cys Pro Pro Cys Pro Ala Pro Pro Val Ala Gly Pro Ser
                245                 250                 255

Val Phe Leu Phe Pro Pro Lys Pro Lys Asp Thr Leu Met Ile Ser Arg
            260                 265                 270

Thr Pro Glu Val Thr Cys Val Val Val Asp Val Ser His Glu Asp Pro
        275                 280                 285

Glu Val Gln Phe Asn Trp Tyr Val Asp Gly Val Glu Val His Asn Ala
    290                 295                 300

Lys Thr Lys Pro Arg Glu Glu Gln Phe Asn Ser Thr Phe Arg Val Val
305                 310                 315                 320

Ser Val Leu Thr Val Val His Gln Asp Trp Leu Asn Gly Lys Glu Tyr
                325                 330                 335

Lys Cys Lys Val Ser Asn Lys Gly Leu Pro Ala Pro Ile Glu Lys Thr
            340                 345                 350

Ile Ser Lys Thr Lys Gly Gln Pro Arg Glu Pro Gln Val Tyr Thr Leu
        355                 360                 365

Pro Pro Ser Arg Glu Glu Met Thr Lys Asn Gln Val Ser Leu Thr Cys
    370                 375                 380

Leu Val Lys Gly Phe Tyr Pro Ser Asp Ile Ala Val Glu Trp Glu Ser
385                 390                 395                 400

Asn Gly Gln Pro Glu Asn Asn Tyr Lys Thr Thr Pro Pro Met Leu Asp
                405                 410                 415

Ser Asp Gly Ser Phe Phe Leu Tyr Ser Lys Leu Thr Val Asp Lys Ser
            420                 425                 430

Arg Trp Gln Gln Gly Asn Val Phe Ser Cys Ser Val Met His Glu Ala
        435                 440                 445

Leu His Asn His Tyr Thr Gln Lys Ser Leu Ser Leu Ser Pro Gly Lys
    450                 455                 460
```

<210> SEQ ID NO 140
<211> LENGTH: 1392
<212> TYPE: DNA
<213> ORGANISM: Artificial Sequence
<220> FEATURE:
<223> OTHER INFORMATION: #131H2hIgG2

<400> SEQUENCE: 140

```
atgaaacacc tgtggttctt cctcctgctg gtggcagctc ccagatgggt gctgagccag      60

gttcagctgg ttgaatctgg tggcggagtg gtgcagcctg gcagatctct gagactgtct     120

tgtgccgcca gcggcttcac cttcaacaac tactggatga cctgggtccg acaggcccct     180

ggcaaaggac ttgaatgggt cgccagcatc accaaggctg gcggctctac ctactacgcc     240

gatagcgtga agggcagatt caccatcagc cgggacaaca gcaagagcac cctgtacctg     300

cagatgaaca gcctgagagc cgagggcaca gccgtgtact actgtacaag agagctgggc     360
```

```
gagttctacg tgatggatgc ctggggccag ggcaccacag ttacagttag ctcagcctcc    420

accaagggcc cttccgtgtt ccctctggcc ccttgtagcc gttccaccag cgagtccacc    480

gccgcccttg gctgtctggt gaaggactac ttccctgagc ctgtgaccgt gagctggaac    540

tccggagccc ttaccagcgg cgtgcacacc ttccctgccg tgctgcagtc cagcggcctt    600

tactccctga gctccgtggt gaccgtgcct agctccaact tcggcaccca aacctacacc    660

tgtaacgtgg accacaagcc tagcaacacc aaggtggaca agaccgtgga gcgtaagtgt    720

tgtgtggagt gtcctccttg tcctgcccct cctgtggccg gaccttccgt gttccttttc    780

cctcctaagc ctaaggacac cctgatgatc agccgtaccc ctgaggtgac ctgtgtggtg    840

gtggacgtgt cccacgagga ccctgaggtg cagttcaact ggtacgtgga cggcgtggag    900

gtgcacaacg ccaagaccaa gcctcgtgag gagcaattca acagcacctt ccgtgtggtg    960

tccgtgctta ccgtggtgca ccaagactgg ctgaacggca aggagtacaa gtgtaaggtg   1020

agcaacaagg gacttcctgc ccctatcgag aagaccatct ccaagaccaa gggccaacct   1080

cgtgagcctc aagtgtacac ccttcctcct agccgtgagg agatgaccaa gaaccaagtg   1140

tcccttacct gtctggtgaa gggcttctac cctagcgaca tcgccgtgga gtgggagtcc   1200

aacggacaac ctgagaacaa ctacaagacc acccctccta tgcttgacag cgacggctcc   1260

ttcttcctgt acagcaagct gaccgtggac aagtcccgtt ggcaacaagg caacgtgttc   1320

agctgttccg tgatgcacga ggccctgcac aaccactaca cccaaaagag cctttccctg   1380

agccctggaa ag                                                       1392
```

```
<210> SEQ ID NO 141
<211> LENGTH: 234
<212> TYPE: PRT
<213> ORGANISM: Artificial Sequence
<220> FEATURE:
<223> OTHER INFORMATION: #131L2h

<400> SEQUENCE: 141

Met Val Leu Gln Thr Gln Val Phe Ile Ser Leu Leu Leu Trp Ile Ser
1               5                   10                  15

Gly Ala Tyr Gly Asp Val Gln Met Thr Gln Ser Pro Ser Ser Leu Ser
            20                  25                  30

Ala Ser Val Gly Asp Arg Val Thr Ile Thr Cys Lys Ala Ser Lys Ser
        35                  40                  45

Ile Asn Thr Tyr Leu Ala Trp Tyr Gln Glu Lys Pro Gly Lys Thr Asn
    50                  55                  60

Lys Leu Leu Ile Tyr Ser Gly Ser Thr Leu Gln Ser Gly Thr Pro Ser
65                  70                  75                  80

Arg Phe Ser Gly Ser Gly Ser Gly Thr Asp Phe Thr Leu Thr Ile Ser
                85                  90                  95

Ser Leu Gln Pro Glu Asp Phe Ala Thr Tyr Tyr Cys Gln Gln His Asn
            100                 105                 110

Glu Tyr Pro Phe Thr Phe Gly Gln Gly Thr Lys Leu Glu Ile Lys Arg
        115                 120                 125

Thr Val Ala Ala Pro Ser Val Phe Ile Phe Pro Pro Ser Asp Glu Gln
    130                 135                 140

Leu Lys Ser Gly Thr Ala Ser Val Val Cys Leu Leu Asn Asn Phe Tyr
145                 150                 155                 160

Pro Arg Glu Ala Lys Val Gln Trp Lys Val Asp Asn Ala Leu Gln Ser
                165                 170                 175
```

```
Gly Asn Ser Gln Glu Ser Val Thr Glu Gln Asp Ser Lys Asp Ser Thr
            180                 185                 190

Tyr Ser Leu Ser Ser Thr Leu Thr Leu Ser Lys Ala Asp Tyr Glu Lys
        195                 200                 205

His Lys Val Tyr Ala Cys Glu Val Thr His Gln Gly Leu Ser Ser Pro
    210                 215                 220

Val Thr Lys Ser Phe Asn Arg Gly Glu Cys
225                 230
```

```
<210> SEQ ID NO 142
<211> LENGTH: 702
<212> TYPE: DNA
<213> ORGANISM: Artificial Sequence
<220> FEATURE:
<223> OTHER INFORMATION: #131L2h

<400> SEQUENCE: 142

atggtgctgc agacccaggt gttcatctcc ctgctgctgt ggatctccgg cgcgtacggc      60

gacgttcaga tgacacagag ccctagcagc ctgtctgcca gcgtgggaga cagagtgacc     120

atcacatgca aggccagcaa gagcatcaac acctacctgg cctggtatca agagaagccc     180

ggcaagacca acaagctgct gatctacagc ggcagcacac tgcagagcgg caccccttct     240

agattttccg gctctggcag cggcaccgac ttcaccctga ccatatctag cctgcagcct     300

gaggacttcg ccacctacta ctgccagcag cacaacgagt accccttcac ctttggccag     360

ggcaccaagc tggaaatcaa gcgtacggtg gccgcccct ccgtgttcat cttccccccc      420

tccgacgagc agctgaagtc cggcaccgcc tccgtggtgt gcctgctgaa taacttctac     480

cccagagagg ccaaggtgca gtggaaggtg gacaacgccc tgcagtccgg gaactcccag     540

gagagcgtga ccgagcagga cagcaaggac agcacctaca gcctgagcag caccctgacc     600

ctgagcaaag ccgactacga gaagcacaag gtgtacgcct gcgaggtgac ccaccagggc     660

ctgagctccc ccgtcaccaa gagcttcaac aggggggagt gt                        702
```

```
<210> SEQ ID NO 143
<211> LENGTH: 17
<212> TYPE: PRT
<213> ORGANISM: Homo sapiens

<400> SEQUENCE: 143

Asp Ala Leu Pro Gly Gln Lys Thr Glu Phe Lys Val Asp Ser Asp Asp
1               5                   10                  15

Gln
```

```
<210> SEQ ID NO 144
<211> LENGTH: 17
<212> TYPE: PRT
<213> ORGANISM: Macaca fascicularis

<400> SEQUENCE: 144

Asp Thr Leu Pro Gly Gln Lys Thr Asp Phe Glu Val Asp Ser Asp Asp
1               5                   10                  15

Leu
```

```
<210> SEQ ID NO 145
<211> LENGTH: 457
<212> TYPE: PRT
<213> ORGANISM: Homo sapiens
```

<400> SEQUENCE: 145

Met Ala Thr Arg Val Leu Ser Met Ser Ala Arg Leu Gly Pro Val Pro
1               5                   10                  15

Gln Pro Pro Ala Pro Gln Asp Glu Pro Val Phe Ala Gln Leu Lys Pro
            20                  25                  30

Val Leu Gly Ala Ala Asn Pro Ala Arg Asp Ala Ala Leu Phe Pro Gly
        35                  40                  45

Glu Glu Leu Lys His Ala His His Arg Pro Gln Ala Gln Pro Ala Pro
    50                  55                  60

Ala Gln Ala Pro Gln Pro Ala Gln Pro Pro Ala Thr Gly Pro Arg Leu
65                  70                  75                  80

Pro Pro Glu Asp Leu Val Gln Thr Arg Cys Glu Met Glu Lys Tyr Leu
                85                  90                  95

Thr Pro Gln Leu Pro Pro Val Pro Ile Ile Pro Glu His Lys Lys Tyr
            100                 105                 110

Arg Arg Asp Ser Ala Ser Val Val Asp Gln Phe Phe Thr Asp Thr Glu
        115                 120                 125

Gly Leu Pro Tyr Ser Ile Asn Met Asn Val Phe Leu Pro Asp Ile Thr
    130                 135                 140

His Leu Arg Thr Gly Leu Tyr Lys Ser Gln Arg Pro Cys Val Thr His
145                 150                 155                 160

Ile Lys Thr Glu Pro Val Ala Ile Phe Ser His Gln Ser Glu Thr Thr
                165                 170                 175

Ala Pro Pro Pro Ala Pro Thr Gln Ala Leu Pro Glu Phe Thr Ser Ile
            180                 185                 190

Phe Ser Ser His Gln Thr Ala Ala Pro Glu Val Asn Asn Ile Phe Ile
        195                 200                 205

Lys Gln Glu Leu Pro Thr Pro Asp Leu His Leu Ser Val Pro Thr Gln
    210                 215                 220

Gln Gly His Leu Tyr Gln Leu Leu Asn Thr Pro Asp Leu Asp Met Pro
225                 230                 235                 240

Ser Ser Thr Asn Gln Thr Ala Ala Met Asp Thr Leu Asn Val Ser Met
                245                 250                 255

Ser Ala Ala Met Ala Gly Leu Asn Thr His Thr Ser Ala Val Pro Gln
            260                 265                 270

Thr Ala Val Lys Gln Phe Gln Gly Met Pro Pro Cys Thr Tyr Thr Met
        275                 280                 285

Pro Ser Gln Phe Leu Pro Gln Gln Ala Thr Tyr Phe Pro Pro Ser Pro
    290                 295                 300

Pro Ser Ser Glu Pro Gly Ser Pro Asp Arg Gln Ala Glu Met Leu Gln
305                 310                 315                 320

Asn Leu Thr Pro Pro Pro Ser Tyr Ala Ala Thr Ile Ala Ser Lys Leu
                325                 330                 335

Ala Ile His Asn Pro Asn Leu Pro Thr Thr Leu Pro Val Asn Ser Gln
            340                 345                 350

Asn Ile Gln Pro Val Arg Tyr Asn Arg Arg Ser Asn Pro Asp Leu Glu
        355                 360                 365

Lys Arg Arg Ile His Tyr Cys Asp Tyr Pro Gly Cys Thr Lys Val Tyr
    370                 375                 380

Thr Lys Ser Ser His Leu Lys Ala His Leu Arg Thr His Thr Gly Glu
385                 390                 395                 400

Lys Pro Tyr Lys Cys Thr Trp Glu Gly Cys Asp Trp Arg Phe Ala Arg
                405                 410                 415

-continued

```
Ser Asp Glu Leu Thr Arg His Tyr Arg Lys His Thr Gly Ala Lys Pro
            420                 425                 430

Phe Gln Cys Gly Val Cys Asn Arg Ser Phe Ser Arg Ser Asp His Leu
        435                 440                 445

Ala Leu His Met Lys Arg His Gln Asn
    450                 455


<210> SEQ ID NO 146
<211> LENGTH: 1374
<212> TYPE: DNA
<213> ORGANISM: Homo sapiens

<400> SEQUENCE: 146

atggctacaa gggtgctgag catgagcgcc cgcctgggac ccgtgcccca gccgccggcg      60

ccgcaggacg agccggtgtt cgcgcagctc aagccggtgc tgggcgccgc gaatccggcc     120

cgcgacgcgg cgctcttccc cggcgaggag ctgaagcacg cgcaccaccg cccgcaggcg     180

cagcccgcgc ccgcgcaggc ccccgcagccg gcccagccgc ccgccaccgg cccgcggctg     240

cctccagagg acctggtcca gacaagatgt gaaatggaga agtatctgac acctcagctt     300

cctccagttc ctataattcc agagcataaa aagtatagac gagacagtgc ctcagtcgta     360

gaccagttct tcactgacac tgaagggtta ccttacagta tcaacatgaa cgtcttcctc     420

cctgacatca ctcacctgag aactggcctc tacaaatccc agagaccgtg cgtaacacac     480

atcaagacag aacctgttgc cattttcagc caccagagtg aaacgactgc ccctcctccg     540

gccccgaccc aggccctccc tgagttcacc agtatattca gctcacacca gaccgcagct     600

ccagaggtga acaatatttt catcaaacaa gaacttccta caccagatct tcatcttttct     660

gtccctaccc agcagggcca cctgtaccag ctactgaata caccggatct agatatgccc     720

agttctacaa atcagacagc agcaatggac actcttaatg tttctatgtc agctgccatg     780

gcaggcctta acacacacac ctctgctgtt ccgcagactg cagtgaaaca attccagggc     840

atgccccctt gcacatacac aatgccaagt cagtttcttc cacaacaggc cacttacttt     900

cccccgtcac caccaagctc agagcctgga agtccagata gacaagcaga gatgctccag     960

aatttaaccc cacctccatc ctatgctgct acaattgctt ctaaactggc aattcacaat    1020

ccaaatttac ccaccaccct gccagttaac tcacaaaaca tccaacctgt cagatacaat    1080

agaaggagta accccgattt ggagaaacga cgcatccact actgcgatta ccctggttgc    1140

acaaaagttt ataccaagtc ttctcattta aaagctcacc tgaggactca cactggtgaa    1200

aagccataca agtgtacctg ggaaggctgc gactggaggt tcgcgcgatc ggatgagctg    1260

acccgccact accggaagca cacaggcgcc aagcccttcc agtgcggggt gtgcaaccgc    1320

agcttctcgc gctctgacca cctggccctg catatgaaga ggcaccagaa ctga          1374


<210> SEQ ID NO 147
<211> LENGTH: 463
<212> TYPE: PRT
<213> ORGANISM: Artificial Sequence
<220> FEATURE:
<223> OTHER INFORMATION: #110H13hIgG4P

<400> SEQUENCE: 147

Met Lys His Leu Trp Phe Phe Leu Leu Leu Val Ala Ala Pro Arg Trp
1               5                   10                  15

Val Leu Ser Gln Val Gln Leu Val Gln Ser Gly Ala Glu Val Lys Lys
            20                  25                  30
```

-continued

```
Pro Gly Ala Ser Val Lys Val Ser Cys Lys Ala Ser Gly Tyr Thr Phe
        35                  40                  45

Thr Ser Asp Phe Met His Trp Val Arg Gln Ala Pro Gly Gln Gly Leu
    50                  55                  60

Glu Trp Met Gly Trp Ile Tyr Pro Gly Asp Gly Asp Thr Glu Tyr Ala
65                  70                  75                  80

Gln Lys Phe Gln Gly Arg Val Thr Met Thr Arg Asp Thr Ser Ile Ser
                85                  90                  95

Thr Ala Tyr Met Glu Leu Ser Arg Leu Arg Ser Asp Asp Thr Ala Val
            100                 105                 110

Tyr Tyr Cys Ala Arg Gly Arg Gly Tyr Val Met Asp Ala Trp Gly Gln
        115                 120                 125

Gly Thr Thr Val Thr Val Ser Ser Ala Ser Thr Lys Gly Pro Ser Val
    130                 135                 140

Phe Pro Leu Ala Pro Cys Ser Arg Ser Thr Ser Glu Ser Thr Ala Ala
145                 150                 155                 160

Leu Gly Cys Leu Val Lys Asp Tyr Phe Pro Glu Pro Val Thr Val Ser
                165                 170                 175

Trp Asn Ser Gly Ala Leu Thr Ser Gly Val His Thr Phe Pro Ala Val
            180                 185                 190

Leu Gln Ser Ser Gly Leu Tyr Ser Leu Ser Ser Val Val Thr Val Pro
        195                 200                 205

Ser Ser Ser Leu Gly Thr Lys Thr Tyr Thr Cys Asn Val Asp His Lys
    210                 215                 220

Pro Ser Asn Thr Lys Val Asp Lys Arg Val Glu Ser Lys Tyr Gly Pro
225                 230                 235                 240

Pro Cys Pro Pro Cys Pro Ala Pro Glu Phe Leu Gly Gly Pro Ser Val
                245                 250                 255

Phe Leu Phe Pro Pro Lys Pro Lys Asp Thr Leu Met Ile Ser Arg Thr
            260                 265                 270

Pro Glu Val Thr Cys Val Val Val Asp Val Ser Gln Glu Asp Pro Glu
        275                 280                 285

Val Gln Phe Asn Trp Tyr Val Asp Gly Val Glu Val His Asn Ala Lys
    290                 295                 300

Thr Lys Pro Arg Glu Glu Gln Phe Asn Ser Thr Tyr Arg Val Val Ser
305                 310                 315                 320

Val Leu Thr Val Leu His Gln Asp Trp Leu Asn Gly Lys Glu Tyr Lys
                325                 330                 335

Cys Lys Val Ser Asn Lys Gly Leu Pro Ser Ser Ile Glu Lys Thr Ile
            340                 345                 350

Ser Lys Ala Lys Gly Gln Pro Arg Glu Pro Gln Val Tyr Thr Leu Pro
        355                 360                 365

Pro Ser Gln Glu Glu Met Thr Lys Asn Gln Val Ser Leu Thr Cys Leu
    370                 375                 380

Val Lys Gly Phe Tyr Pro Ser Asp Ile Ala Val Glu Trp Glu Ser Asn
385                 390                 395                 400

Gly Gln Pro Glu Asn Asn Tyr Lys Thr Thr Pro Pro Val Leu Asp Ser
                405                 410                 415

Asp Gly Ser Phe Phe Leu Tyr Ser Arg Leu Thr Val Asp Lys Ser Arg
            420                 425                 430
```

-continued

```
Trp Gln Glu Gly Asn Val Phe Ser Cys Ser Val Met His Glu Ala Leu
        435                 440                 445

His Asn His Tyr Thr Gln Lys Ser Leu Ser Leu Ser Leu Gly Lys
    450                 455                 460


<210> SEQ ID NO 148
<211> LENGTH: 1389
<212> TYPE: DNA
<213> ORGANISM: Artificial Sequence
<220> FEATURE:
<223> OTHER INFORMATION: #110H13hIgG4P

<400> SEQUENCE: 148

atgaaacacc tgtggttctt cctcctgctg gtggcagctc ccagatgggt gctgagccag     60

gttcagctgg ttcagtctgg cgccgaagtg aagaaacctg gcgcctctgt gaaggtgtcc    120

tgcaaggcca gcggctacac ctttaccagc gacttcatgc actgggtccg acaggctcca    180

ggacagggac ttgaatggat gggctggatc tatcccggcg acggcgatac agagtacgcc    240

cagaaattcc agggcagagt gaccatgacc agagacacca gcatcagcac cgcctacatg    300

gaactgagcc ggctgagatc cgatgacacc gccgtgtact actgcgccag aggcagaggc    360

tatgtgatgg atgcttgggg ccagggcacc accgttacag ttagctcagc ctccaccaag    420

ggccctagcg tgttccctct ggccccttgt agcagaagca ccagcgagtc tacagccgcc    480

ctgggctgcc tcgtgaagga ctactttccc gagcccgtga ccgtgtcctg gaactctggc    540

gctctgacaa gcggcgtgca cacctttcca gccgtgctgc agagcagcgg cctgtactct    600

ctgtccagcg tcgtgactgt gcccagcagc tctctgggca ccaagaccta cacctgtaac    660

gtggaccaca agcccagcaa caccaaggtg gacaagcggg tggaatctaa gtacggccct    720

ccctgccctc cttgcccagc ccctgaattt ctgggcggac cctccgtgtt cctgttcccc    780

ccaaagccca aggacaccct gatgatcagc cggacccccg aagtgacctg cgtggtggtg    840

gatgtgtccc aggaagatcc cgaggtgcag ttcaattggt acgtggacgg cgtggaagtg    900

cacaacgcca agaccaagcc tagagaggaa cagttcaaca gcacctaccg ggtggtgtcc    960

gtgctgacag tgctgcacca ggactggctg aacggcaaag agtacaagtg caaggtgtcc   1020

aacaagggcc tgcccagctc catcgagaaa accatcagca aggccaaggg ccagccccgc   1080

gaaccccagg tgtacacact gcctccaagc caggaagaga tgaccaagaa tcaggtgtcc   1140

ctgacctgtc tcgtgaaagg cttctacccc tccgatatcg ccgtggaatg ggagagcaac   1200

ggccagcccg agaacaacta caagaccacc ccccctgtgc tggactccga tggctcattc   1260

ttcctgtaca gcagactgac cgtggacaag agccggtggc aggaaggcaa cgtgttcagc   1320

tgctccgtga tgcacgaggc cctgcacaac cactacaccc agaagtccct gtctctgagc   1380

ctgggcaaa                                                          1389


<210> SEQ ID NO 149
<211> LENGTH: 234
<212> TYPE: PRT
<213> ORGANISM: Artificial Sequence
<220> FEATURE:
<223> OTHER INFORMATION: #110L2h

<400> SEQUENCE: 149

Met Val Leu Gln Thr Gln Val Phe Ile Ser Leu Leu Leu Trp Ile Ser
1               5                   10                  15

Gly Ala Tyr Gly Asp Ile Gln Met Thr Gln Ser Pro Ser Ser Leu Ser
            20                  25                  30
```

```
Ala Ser Val Gly Asp Arg Val Thr Ile Thr Cys Arg Ala Ser Gln Gly
        35                  40                  45

Ile Ser Asn Tyr Leu Asn Trp Tyr Gln Gln Lys Pro Gly Lys Ala Pro
    50                  55                  60

Lys Pro Leu Ile Tyr Tyr Thr Ser Asn Leu Gln Ser Gly Val Pro Ser
65                  70                  75                  80

Arg Phe Ser Gly Ser Gly Ser Gly Thr Asp Tyr Thr Leu Thr Ile Ser
                85                  90                  95

Ser Leu Gln Pro Glu Asp Phe Ala Thr Tyr Tyr Cys Gln Gln Tyr Asp
            100                 105                 110

Ser Ser Pro Arg Thr Phe Gly Gly Gly Thr Lys Val Glu Ile Lys Arg
        115                 120                 125

Thr Val Ala Ala Pro Ser Val Phe Ile Phe Pro Pro Ser Asp Glu Gln
    130                 135                 140

Leu Lys Ser Gly Thr Ala Ser Val Val Cys Leu Leu Asn Asn Phe Tyr
145                 150                 155                 160

Pro Arg Glu Ala Lys Val Gln Trp Lys Val Asp Asn Ala Leu Gln Ser
                165                 170                 175

Gly Asn Ser Gln Glu Ser Val Thr Glu Gln Asp Ser Lys Asp Ser Thr
            180                 185                 190

Tyr Ser Leu Ser Ser Thr Leu Thr Leu Ser Lys Ala Asp Tyr Glu Lys
        195                 200                 205

His Lys Val Tyr Ala Cys Glu Val Thr His Gln Gly Leu Ser Ser Pro
    210                 215                 220

Val Thr Lys Ser Phe Asn Arg Gly Glu Cys
225                 230
```

```
<210> SEQ ID NO 150
<211> LENGTH: 702
<212> TYPE: DNA
<213> ORGANISM: Artificial Sequence
<220> FEATURE:
<223> OTHER INFORMATION: #110L2h

<400> SEQUENCE: 150

atggtgctgc agacccaggt gttcatctcc ctgctgctgt ggatctccgg cgcgtacggc      60

gatatccaga tgacacagag ccctagcagc ctgtctgcca gcgtgggaga cagagtgacc     120

atcacctgta gagccagcca gggcatcagc aactacctga actggtatca gcagaagccc     180

ggcaaggccc ctaagcctct gatctactac accagcaacc tgcagagcgg cgtgcccagc     240

agattttctg gctctggcag cggcaccgac tacaccctga ccatatctag cctgcagcct     300

gaggacttcg ccacctacta ctgccagcag tacgacagca gccccagaac atttggcgga     360

ggcaccaagg tggaaatcaa gcgtacggtg gccgcccct ccgtgttcat cttcccccc     420

tccgacgagc agctgaagtc cggcaccgcc tccgtggtgt gcctgctgaa taacttctac     480

cccagagagg ccaaggtgca gtggaaggtg gacaacgccc tgcagtccgg gaactcccag     540

gagagcgtga ccgagcagga cagcaaggac agcacctaca gcctgagcag caccctgacc     600

ctgagcaaag ccgactacga gaagcacaag gtgtacgcct gcgaggtgac ccaccagggc     660

ctgagctccc ccgtcaccaa gagcttcaac aggggggagt gt                        702

<210> SEQ ID NO 151
<211> LENGTH: 234
<212> TYPE: PRT
<213> ORGANISM: Artificial Sequence
```

<220> FEATURE:
<223> OTHER INFORMATION: #110L12h

<400> SEQUENCE: 151

Met Val Leu Gln Thr Gln Val Phe Ile Ser Leu Leu Leu Trp Ile Ser
1               5                   10                  15

Gly Ala Tyr Gly Asp Ile Gln Met Thr Gln Ser Pro Ser Ser Leu Ser
            20                  25                  30

Ala Ser Val Gly Asp Arg Val Thr Ile Thr Cys Arg Ala Ser Gln Gly
        35                  40                  45

Ile Ser Asn Tyr Leu Asn Trp Tyr Gln Gln Lys Pro Gly Lys Ala Pro
    50                  55                  60

Lys Pro Leu Ile Tyr Tyr Thr Ser Asn Leu Gln Ser Gly Val Pro Ser
65                  70                  75                  80

Arg Phe Ser Gly Ser Gly Ser Gly Thr Asp Phe Thr Leu Thr Ile Ser
                85                  90                  95

Ser Leu Gln Pro Glu Asp Phe Ala Thr Tyr Tyr Cys Gln Gln Tyr Asp
            100                 105                 110

Ser Ser Pro Arg Thr Phe Gly Gly Gly Thr Lys Val Glu Ile Lys Arg
        115                 120                 125

Thr Val Ala Ala Pro Ser Val Phe Ile Phe Pro Pro Ser Asp Glu Gln
    130                 135                 140

Leu Lys Ser Gly Thr Ala Ser Val Val Cys Leu Leu Asn Asn Phe Tyr
145                 150                 155                 160

Pro Arg Glu Ala Lys Val Gln Trp Lys Val Asp Asn Ala Leu Gln Ser
                165                 170                 175

Gly Asn Ser Gln Glu Ser Val Thr Glu Gln Asp Ser Lys Asp Ser Thr
            180                 185                 190

Tyr Ser Leu Ser Ser Thr Leu Thr Leu Ser Lys Ala Asp Tyr Glu Lys
        195                 200                 205

His Lys Val Tyr Ala Cys Glu Val Thr His Gln Gly Leu Ser Ser Pro
    210                 215                 220

Val Thr Lys Ser Phe Asn Arg Gly Glu Cys
225                 230

<210> SEQ ID NO 152
<211> LENGTH: 702
<212> TYPE: DNA
<213> ORGANISM: Artificial Sequence
<220> FEATURE:
<223> OTHER INFORMATION: #110L12h

<400> SEQUENCE: 152
atggtgctgc agacccaggt gttcatctcc ctgctgctgt ggatctccgg cgcgtacggc 60
gatatccaga tgacacagag ccctagcagc ctgtctgcca gcgtgggaga cagagtgacc 120
atcacctgta gagccagcca gggcatcagc aactacctga actggtatca gcagaagccc 180
ggcaaggccc ctaagcctct gatctactac accagcaacc tgcagagcgg cgtgcccagc 240
agattttctg gctctggcag cggcaccgac ttcaccctga ccatatctag cctgcagcct 300
gaggacttcg ccacctacta ctgccagcag tacgacagca gccccagaac atttggcgga 360
ggcaccaagg tggaaatcaa gcgtacggtg gccgcccct ccgtgttcat cttcccccc 420 tccgacgagc agctgaagtc cggcaccgcc tccgtggtgt gcctgctgaa taacttctac 480
cccagagagg ccaaggtgca gtggaaggtg gacaacgccc tgcagtccgg gaactcccag 540
gagagcgtga ccgagcagga cagcaaggac agcacctaca gcctgagcag caccctgacc 600

-continued

```
ctgagcaaag ccgactacga gaagcacaag gtgtacgcct gcgaggtgac ccaccagggc    660

ctgagctccc ccgtcaccaa gagcttcaac aggggggagt gt                       702
```